United States Patent
Zhang et al.

(10) Patent No.: US 12,060,385 B2
(45) Date of Patent: Aug. 13, 2024

(54) COMPOUNDS FOR RNA CAPPING AND USES THEREOF

(71) Applicant: GUANGZHOU HENOVCOM BIOSCIENCE CO., LTD., Guangzhou (CN)

(72) Inventors: Jiancun Zhang, Guangzhou (CN); Lijun Zhang, Guangzhou (CN); Yiqian Zhou, Guangzhou (CN); Jiafeng Chen, Guangzhou (CN); Jufu Zhang, Guangzhou (CN); Suyong Li, Guangzhou (CN); Yanhui Liu, Guangzhou (CN); Chen Guo, Guangzhou (CN); Wanjun Tang, Guangzhou (CN); Feng Wu, Guangzhou (CN); Xiaoxi He, Guangzhou (CN); Qi Guo, Guangzhou (CN); Huixuan Chen, Guangzhou (CN); Kun Wang, Guangzhou (CN); Deyao Li, Guangzhou (CN)

(73) Assignee: GUANGZHOU HENOVCOM BIOSCIENCE CO., LTD., Guangzhou (CN)

( * ) Notice: Subject to any disclaimer, the term of this patent is extended or adjusted under 35 U.S.C. 154(b) by 0 days.

(21) Appl. No.: 18/217,783

(22) Filed: Jul. 3, 2023

(65) Prior Publication Data
US 2023/0340009 A1    Oct. 26, 2023

Related U.S. Application Data

(63) Continuation of application No. PCT/CN2022/120455, filed on Sep. 22, 2022.

(30) Foreign Application Priority Data

Feb. 28, 2022 (CN) .................. 202210188028.7
Apr. 14, 2022 (CN) .................. 202210388175.9
(Continued)

(51) Int. Cl.
C07H 21/02    (2006.01)
C07H 19/207   (2006.01)
C12P 19/34    (2006.01)

(52) U.S. Cl.
CPC .......... C07H 21/02 (2013.01); C07H 19/207 (2013.01); C12P 19/34 (2013.01)

(58) Field of Classification Search
CPC ..................................................... C07H 21/02
See application file for complete search history.

(56) References Cited

U.S. PATENT DOCUMENTS

2019/0211368 A1    7/2019  Butora et al.

FOREIGN PATENT DOCUMENTS

CN    105209633 A    12/2015
CN    108366604 A    8/2018
(Continued)

OTHER PUBLICATIONS

English machine translation of WO22/086140, downloaded from worldwide.espacenet.org (Year: 2022).*
(Continued)

Primary Examiner — Eric Olson
(74) Attorney, Agent, or Firm — Schmeiser, Olsen & Watts LLP

(57) ABSTRACT

The present disclosure relates to compounds for RNA capping and uses thereof, which belong to the technical field of genetic engineering. Compounds of formula I can result in
(Continued)

high levels of capping efficiency, and the capped mRNA exhibits a high transcription level and increased expression.

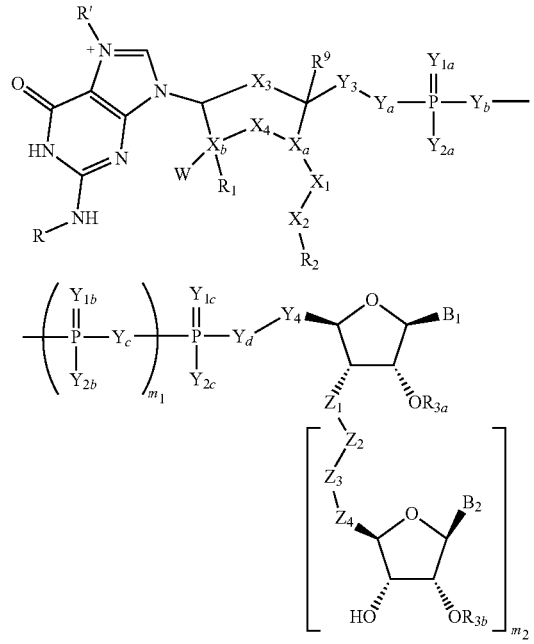

29 Claims, 1 Drawing Sheet

(30) Foreign Application Priority Data

Jul. 22, 2022 (CN) .......................... 202210870489.2
Aug. 15, 2022 (CN) .......................... 202210973168.5

(56) References Cited

FOREIGN PATENT DOCUMENTS

| CN | 111944864 | A | 11/2020 | |
|---|---|---|---|---|
| CN | 113507963 | A | 10/2021 | |
| CN | 113874502 | A | 12/2021 | |
| CN | 113957108 | A | 1/2022 | |
| WO | 2013130161 | A1 | 9/2013 | |
| WO | 2017/066782 | A1 | 4/2017 | |
| WO | 2018075827 | A1 | 4/2018 | |
| WO | 2021162566 | A1 | 8/2021 | |
| WO | 2021216776 | A2 | 10/2021 | |
| WO | WO-2022086140 | A1 * | 4/2022 | ......... A61K 31/7088 |

OTHER PUBLICATIONS

Product description for "CleanCap(R) Reagent AG (3'OMe)-(N-7413)" downloaded from www.trilinkbiotech.com/gmp-reagents (Year: 2024).*
International Search Report for PCT/CN2022/120455, issued on Dec. 27, 2022.
Annamalai Senthilvelan—Trinucleotide Cap Analogue Bearing a Locked Nucleic Acid Moiety: Synthesis, mRNA Modification, and Translation for Therapeutic Applications; 2021 American Chemical Society; Org. Lett. 2021, 23, 4133-4136.
Pawel J. Sikorski—The identity and methylation status of the first transcribed nucleotide in eukaryotic mRNA 5' cap modulates protein expression in living cells; Nucleic Acids Research, 2020, vol. 48, No. 4 1607-1626.

* cited by examiner

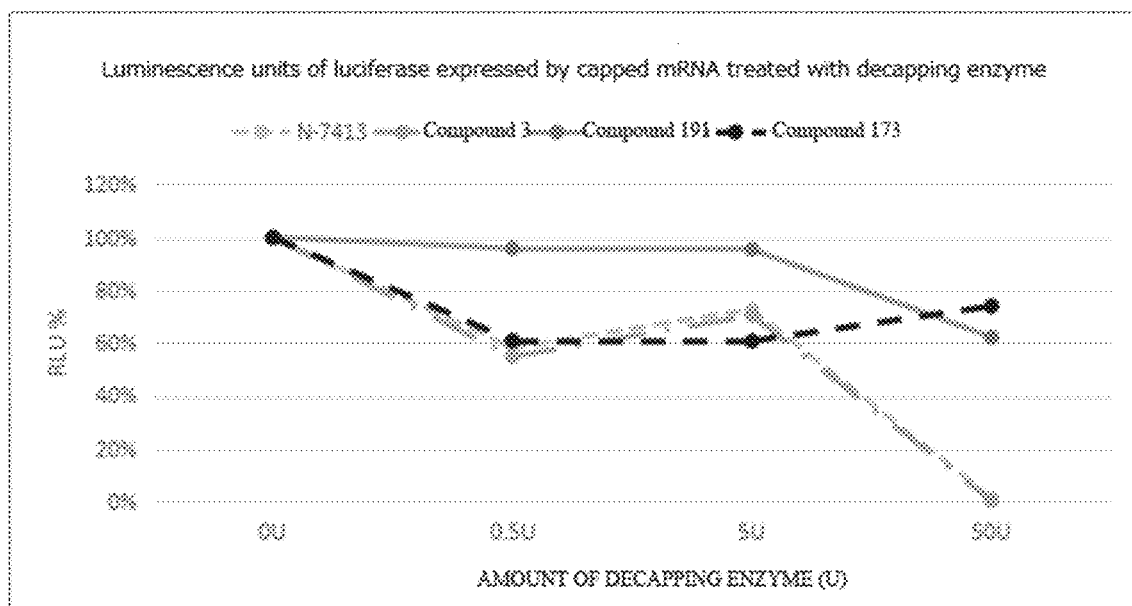

COMPOUNDS FOR RNA CAPPING AND USES THEREOF

CROSS-REFERENCE TO RELATED APPLICATIONS

This application is a continuation of PCT International Patent Application No. PCT/CN2022/120455, filed Sep. 22, 2022, which claims the benefit of Chinese Application No. 202210188028.7 filed Feb. 28, 2022, Chinese Application No. 202210388175.9 filed Apr. 14, 2022, Chinese Application No. 202210870489.2 filed Jul. 22, 2022 and Chinese Application No. 202210973168.5 filed Aug. 15, 2022, the disclosure of each of these applications are expressly incorporated herein by reference in their entireties.

FIELD OF TECHNOLOGY

The following relates to the technical field of genetic engineering, and particularly, it relates to compounds for RNA capping and uses thereof.

BACKGROUND

The five-prime cap (m7GpppN) structure of mRNA was discovered in 1970s, and its presence provides stability for mRNA and enables its efficient translation. There are usually three types of cap structures (m7G5'ppp5'Np, m7G5'ppp5'NmpNp, m7G5'ppp5'NmpNmpNp), named Type 0 (m7G5'ppp5'Np), Type 1 (m7G5'ppp5'NmpNp), and Type 2 (m7G5'ppp5'NmpNmpNp), respectively. Type 0 has an unmethylated ribose in the first nucleotide at the terminus, Type 1 has a methylated ribose in the first nucleotide at the terminus, Type 2 has a methylated ribose in both nucleotides at the terminus.

In eukaryote, in addition to recognizing the initiation of protein synthesis, the 5'-cap structure also functions as a protective group from 5' to 3' exonuclease cleavage, i.e., it is resistant to 5'-exonuclease degradation. It also serves as a unique identifier for recruiting protein factors for pre-RNA splicing, polyadenylation and nuclear export during protein synthesis, and acts as an anchor for recruitment of initiation factors, which helps the ribosome to recognize and bind mRNAs for proper translation initiation.

Studies have shown that the cap structure of mRNA is importantly linked to RNA quality control and intrinsic immunity of the organism, and therefore, it is important to provide a system that can improve the capping efficiency and can increase the mRNA expression after capping.

SUMMARY

Based on this, it is necessary to address the above problem and provide a compound for RNA capping. When the compound is used for capping 5' ends of mRNA, it can result in high levels of capping efficiency and the capped mRNA exhibits a high transcription level and increased expression.

An aspect relates to a compound of formula I, or a stereoisomer, or a pharmaceutically acceptable salt, or a solvate thereof:

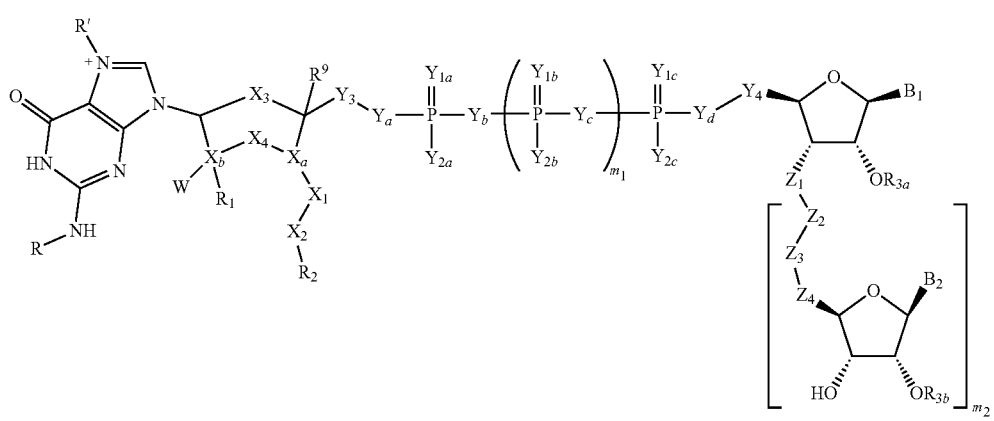

I wherein:
R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

$X_a$ is O, S, Se, CH, CHCN, $CHN_3$, or $NR_{10}$; when $X_a$ is O, S, Se, CHCN, $CHN_3$, or $NR_{10}$, $X_1$, $X_2$, and $R_2$ are absent;

$X_b$ is O, S, Se, C, or —$NR_{10}$; when $X_b$ is O, S, Se, or $NR_{10}$, W and $R_1$ are absent;

$X_1$ is absent, or $X_1$ is $(CH_2)_n$, or $NR_4$;

$X_2$ is absent, or $X_2$ is O, S, $NR_4$, CO, $CO_2$, $CONR_4$, $NR_4CO$, $NR_4CO_2$, $NR_4CONR_4$, $SO_2$, $SO_2NR_4$, or $CH_2$;

$X_3$ is O, S, $NR_4$, $CH_2$, $CF_2$, CHF, $CCH_2$, or $CCF_2$;

$X_4$ is O, S, $CH_2$, $NR_4$, or $NCOR_4$; —$X_4$—, in each instance, is a single bond or a double bond; when —$X_4$—, in each instance, is a double bond, W is absent;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_1$ is absent, or $R_1$ is H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, $R_5$-substituted $C_2$-$C_6$ alkynyl, or halogen;

or $R_2$ is $NR_5$, or $OR_5$;

$R_2$ is absent, or $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$;

each of $R_{3a}$ and $R_{3b}$ is absent; or each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is absent, or W is H, O, OH, $OR_4$, $NR_4R_4$, $NR_4COR_4$, F, Cl, $N_3$, or CN;

$R_1$ and W are connected to form a ring by chemical bonds;

W and $X_2$, or W and $R_2$, or W and $R_9$, or $R_9$ and $X_2$ are connected to form a ring by chemical bonds;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$ and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or P(O)V$CO_2$H; $Z_2$ forms a ring with oxygen atom linked to $R_{3a}$;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_5$;

$R_7$ is absent, or $R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

$R_9$ is H, $C_1$-$C_3$ alkyl, or $R_4$-substituted $C_1$-$C_3$ alkyl; when —$X_4$—, in each instance, is a single bond, $R_9$ and W are connected to form a ring by chemical bonds, or $R_9$ and $X_2$ are connected to form a ring by chemical bonds;

$R_{10}$ is H, $C_1$-$C_6$ alkyl, $C_2$-$C_6$ alkenyl, $C_2$-$C_6$ alkynyl, benzyl, aryl, $COR_8$, $CO_2R_8$, $CONR_8R_8$, or $SO_2R_8$;

V is $C_1$-$C_4$ alkyl;

$m_1$ is 1, 2, or 3;

$m_2$ is 0, 1, or 2; and n is 1, 2, or 3.

In some embodiments, $X_1$ is absent, or $X_1$ is $(CH_2)_n$, or $NR_4$;

$X_2$ is O, S, CO, $CO_2$, $CONR_4$, $NR_4CO$, $NR_4CO_2$, $NR_4CONR_4$, $SO_2$, or $SO_2NR_4$; and $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, or CN.

In some embodiments, $R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl; and $R_7$ is H, $C_1$-$C_4$ alkyl, $C_1$-$C_4$ alkenyl, or $C_1$-$C_4$ alkynyl.

In some embodiments, $Z_1$ is $CH_2$, or $NR_6$.

In some embodiments, $R_6$ is H, $C_1$-$C_4$ alkyl, $COR_8$, or $SO_2R_8$;

$R_8$ is H, $C_{1-4}$ alkyl, $C_2$-$C_5$ alkenyl, or $C_2$-$C_5$ alkynyl.

In some embodiments, $X_1$ is absent, or $X_4$ is $(CH_2)_n$, or $NR_4$;

$X_2$ is absent, or $X_2$ is O, S, CO, $CONR_4$, $NR_4CO$, $NR_4CO_2$, or $NR_4CONR_4$;

when $X_3$ is present, $X_3$ is O;

$X_4$ is absent, or $X_4$ is O, or $NCOR_4$; —$X_4$—, in each instance, is a single bond or a double bond; when —$X_4$—, in each instance, is a double bond, W is absent;

R is H;

$R_1$ is absent, or $R_1$ is H, or halogen;

$R_2$ is absent, or $R_2$ is $C_1$-$C_8$ alkyl, $C_2$-$C_8$ alkenyl, $R_5$-substituted $C_2$-$C_8$ alkyl, $R_5$-substituted aryl, heteroaryl, or $N_3$;

when $R_{3a}$ and $R_{3b}$ are present, each of $R_{3a}$ and $R_{3b}$ is H;

W is O, or OH;

each of $Y_a$, $Y_b$, $Y_c$, and $Y_d$ is independently selected from O, or $CH_2$;

each of $Y_{1a}$, $Y_{1b}$, and $Y_{1c}$ is independently selected from O, or S;

each of $Y_{2a}$, $Y_{2b}$, and $Y_{2c}$ is independently OH;

each of $Y_3$ and $Y_4$ is independently selected from $CH_2$, or O;

$Z_1$ is O, OH, $CH_2$, S, or $NR_6$;

each of $Z_2$ and $Z_3$ is independently selected from O, $NR_6$, $CHR_7$, $CHCOOR_7$, CO, $SO_2$, or PO(OH);

when $Z_4$ is present, $Z_4$ is O, or $CH_2$;

when $Z_1$ is O, $Z_2$ is PO(OH); when $Z_3$ is O, $X_1$ is absent; when —$X_4$—, in each instance, is a single bond, $X_2$ is not O;

when $m_2$ is 0, $Z_1$ is OH; and when X is absent and —$X_4$—, in each instance, is a single bond, $X_2$ is not O;

each of $B_1$ and $B_2$ is independently selected from natural or modified pyrimidine base, or natural or modified purine base;

$R_4$ is H, or $C_1$-$C_8$ alkyl;

$R_5$ is $OR_7$, $NR_7R_7$, $CONR_7R_7$, $OCONR_7R_7$, or halogen;

$R_6$ is H;

$R_7$ is H, or $C_1$-$C_8$ alkyl;

when $R_{10}$ is present, $R_{10}$ is H, or $C_1$-$C_3$ alkyl;

$m_1$ is 1;

m2 is 0, or 1; and n is 1, or 2.

In some embodiments, $X_1$ is absent, or $X_1$ is $(CH_2)_n$;

$X_2$ is O;

when $X_3$ is present, $X_3$ is O;

when $X_4$ is present, —$X_4$—, in each instance, is a single bond;

R is H;

when $R_1$ is present, $R_1$ is H;

$R_2$ is $C_1$-$C_{58}$ alkyl, or $R_5$-substituted $C_1$-$C_8$ alkyl;

when $R_{3a}$ and $R_{3b}$ are present, each of $R_{3a}$ and $R_{3b}$ is H;

W is OH;

each of $Y_a$, $Y_b$, $Y_c$, and $Y_d$ is independently selected from O, or $CH_2$;

each of $Y_{1a}$, $Y_{1b}$, and $Y_{1c}$ is independently selected from O, or S;

each of $Y_{2a}$, $Y_{2b}$, and $Y_{2c}$ is independently OH;

each of $Y_3$ and $Y_4$ is independently $CH_2$;

$Z_1$ is O, OH, or $NR_6$;

each of $Z_2$ and $Z_3$ is independently O, $CHR_7$, or PO(OH);

when $Z_4$ is present, $Z_4$ is $CH_2$;

when $Z_1$ is O, $Z_2$ is PO(OH), $Z_3$ is O, and $X_1$ is absent; when —$X_4$—, in each instance, is a single bond, $X_2$ is not O;

when $m_2$ is 0, $Z_1$ is OH; and when $X_1$ is absent and —$X_4$—, in each instance, is single bond, $X_2$ is not O;

each of $B_1$ and $B_2$ is independently selected from natural or modified pyrimidine base, or natural or modified purine base;

$R_5$ is aryl;

$R_6$ is H;

$R_7$ is H;

when $R_9$ is present, $R_9$ is H;

$m_1$ is 1;

m2 is 0, or 1; and n is 1.

In some embodiments, when $X_2$ is absent, or $X_2$ is S, or N, $R_2$ is $C_1$-$C_4$ alkyl, $C_2$-$C_6$ alkenyl, $C_1$-$C_4$ haloalkyl, $C_2$-$C_6$ haloalkenyl, CN, $N_3$, or morpholine.

In some embodiments, when $X_2$ is absent, or $X_2$ is S, $R_2$ is methyl, ethyl, propyl, halomethyl, haloethyl, halopropyl, CN, $N_3$, or morpholine.

In some embodiments, the compound has a structure of formula IV-A shown as follows:

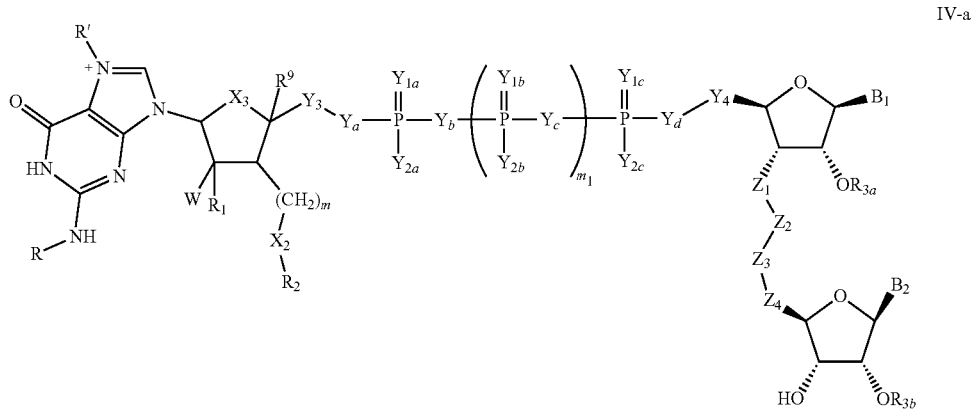

IV-a wherein, $X_2$ is absent, or $X_2$ is not $CH_2$; when $X_2$ is present, $X_2$ is O, S, $NR_4$, CO, $CO_2$, $CONR_4$, $NR_4CO$, $NR_4CO_2$, $NR_4CONR_4$, $SO_2$, or $SO_2NR_4$.

In some embodiments, the compound has a structure of formula IV shown as follows:

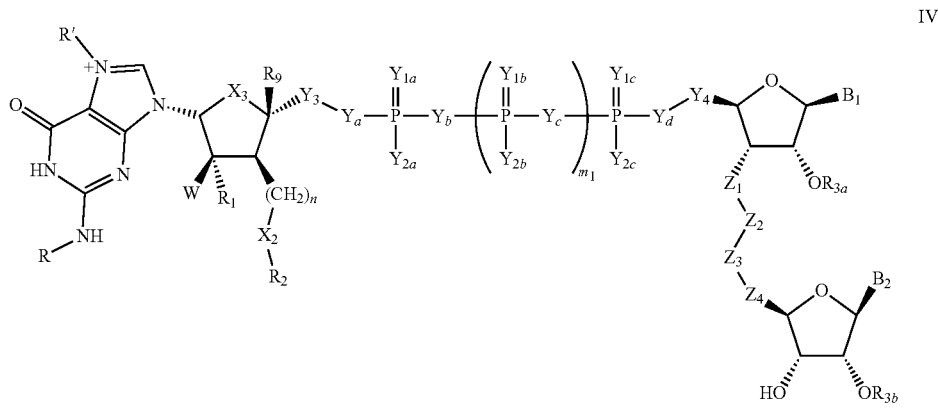

IV wherein, $X_2$ is absent, or $X_2$ is not $CH_2$; when $X_2$ is present, $X_2$ is O, S, $NR_4$, CO, $CO_2$, $CONR_4$, $NR_4CO$, $NR_4CO_2$, $NR_4CONR_4$, $SO_2$, or $SO_2NR_4$.

In some embodiments, $R_1$ is H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, $R_5$-substituted $C_2$-$C_6$ alkynyl, or halogen;

W is H, O, OH, $OR_4$, $NR_4R_4$, $NR_4COR_4$, F, Cl, $N_3$, or CN;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_7$ is absent, or $R_7$ is H, $C_1$-$C_8$ alkyl, $C_2$-$C_8$ alkenyl, or $C_2$-$C_8$ alkynyl; and $m_1$ is 1, or 2.

In some embodiments, when $R_1$ is H, W is H, OH, $OR_4$, $NR_4R_4$, $NR_4COR_4$, F, Cl, $N_3$, or CN;

$R_4$ is H, $C_1$-$C_4$ alkyl, $C_2$-$C_6$ alkenyl, or $C_2$-$C_6$ alkynyl.

In some embodiments, when $R_1$ is H, W is H, OH, $OR_4$, $NR_4R_4$, F, Cl, or CN; and $R_4$ is $C_1$-$C_4$ alkyl.

In some embodiments, when $R_1$ is H, W is OH, F, Cl, methoxy, trifluoromethoxy, ethoxy, or trifluoroethoxy.

In some embodiments, the compound has a structure of formula IV-1 shown as follows:

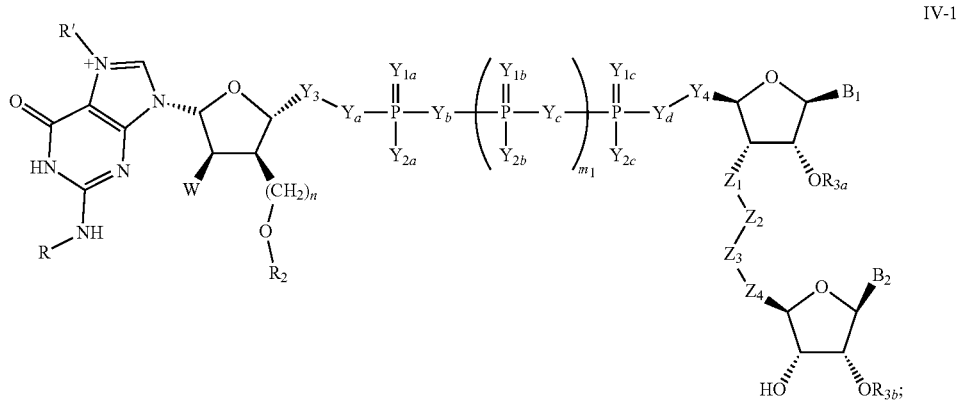

IV-1 wherein, R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_2$ is absent, or $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$;

each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is H, OH, $OR_4$, $NR_4R_4$, F, Cl, or CN;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$ and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or $P(O)VCO_2H$;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_8$;

$R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

V is $C_1$-$C_4$ alkyl;

$m_1$ is 1, or 2; and n is 1, 2, or 3.

In some embodiments, the compound has a structure of formula IV-2 shown as follows:

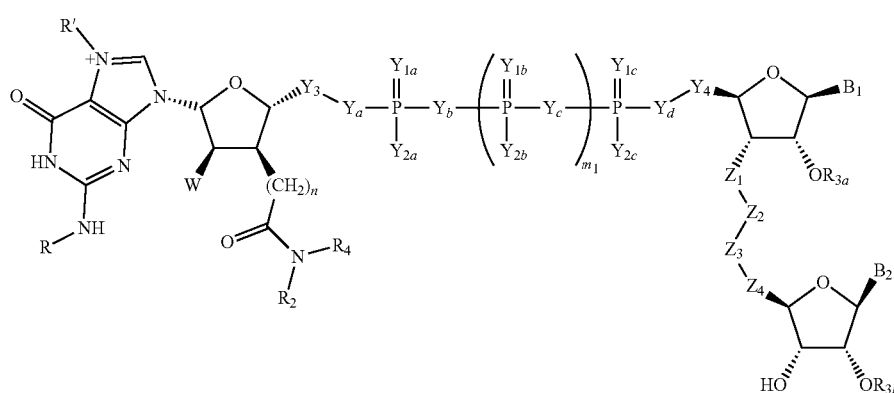

IV-2 wherein, R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_2$ is absent, or $R_2$ is H, $C_1$-$C_8$ alkyl, $C_2$-$C_8$ alkenyl, $C_2$-$C_8$ alkynyl, $R_5$-substituted $C_2$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$;

each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is H, OH, $OR_4$, $NR_4R_4$, F, Cl, or CN;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$ and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or P(O)$VCO_2$H;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_8$;

$R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

V is $C_1$-$C_4$ alkyl;

$m_1$ is 1, or 2; and n is 1, 2, or 3.

In some embodiments, the compound has a structure of formula IV-3 shown as follows:

wherein, R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_2$ is absent, or $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$; or $R_2$ is NRs, or $OR_5$;

each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is H, OH, $OR_4$, $NR_4R_4$, F, Cl, or CN;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$ and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or P(O)$VCO_2$H;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_8$;

$R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

V is $C_1$-$C_4$ alkyl;

$m_1$ is 1, or 2; and n is 1, 2, or 3.

IV-3

In some embodiments, the compound has a structure of formula IV-4 shown as follows:

IV-4

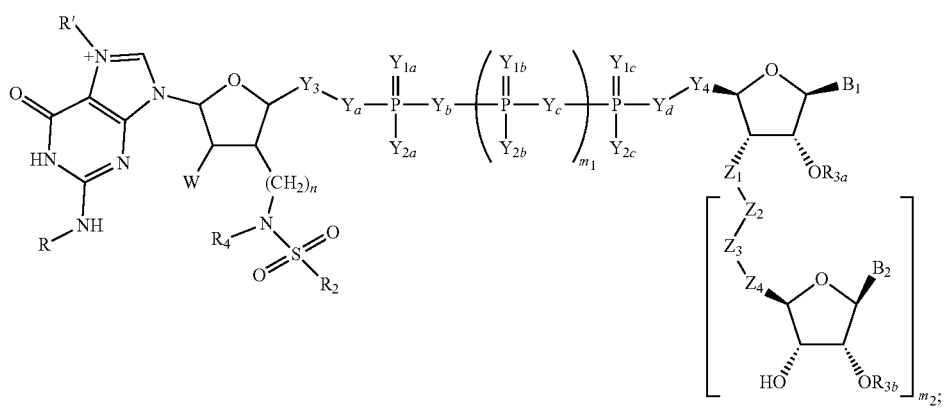

wherein, R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_2$ is absent, or $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$;

each of $R_{3a}$ and $R_{3b}$ is absent, or each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is H, O, OH, $OR_4$, $NR_4R_4$, $NR_4COR_4$, F, Cl, $N_3$, or CN;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$, and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or $P(O)VCO_2H$; or $Z_2$ forms a ring with oxygen atom linked to $R_{3a}$;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_5$;

$R_7$ is absent, or $R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

V is $C_1$-$C_4$ alkyl;

$m_1$ is 1, 2, or 3;

$m_2$ is 0, 1, or 2; and n is 1, 2, or 3.

In some embodiments, the compound has a structure of formula VI-5 shown as follows:

VI-5

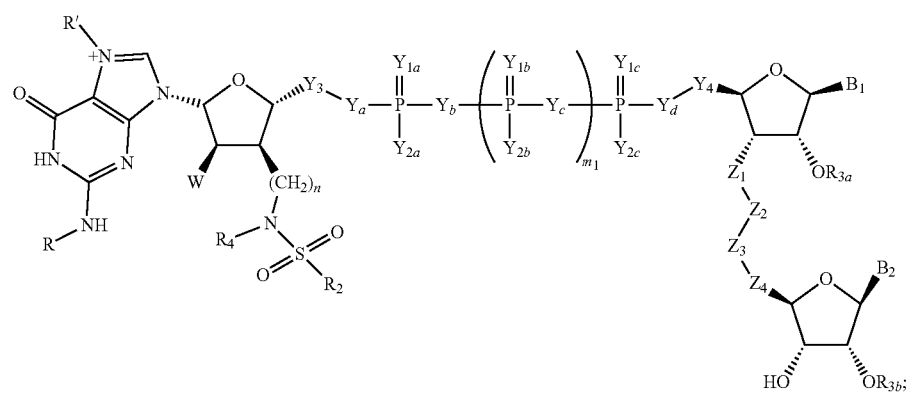

wherein $m_1$ is 1, or 2.

In some embodiments, the compound has a structure of formula VI-6 shown as follows:

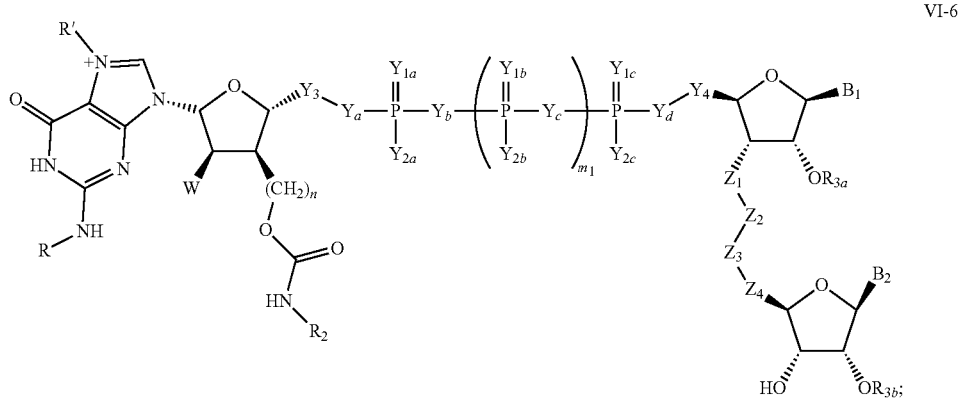

VI-6 wherein, R' is $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkene, benzyl, $R_5$-substituted $C_1$-$C_6$ alkyl, $R_5$-substituted $C_2$-$C_6$ alkenyl, $R_5$-substituted $C_2$-$C_6$ alkynyl, $R_5$-substituted $C_3$-$C_6$ cycloalkyl, $R_5$-substituted $C_3$-$C_6$ cycloalkene, or $R_5$-substituted benzyl;

R is H, $C_1$-$C_6$ alkyl, $C_2$-$C_6$ alkenyl, $C_2$-$C_6$ alkynyl, cycloalkyl, cycloalkene, benzyl, aryl, heteroaryl, $R_5$-substituted benzyl, $R_5$-substituted aryl, carbonylalkyl, carbonylalkoxy, or sulfanilamido;

$R_2$ is absent, or $R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, aryl, $R_5$-substituted aryl, heteroaryl, $R_5$-substituted heteroaryl, halogen, CN, or $N_3$;

each of $R_{3a}$ and $R_{3b}$ is absent, or each of $R_{3a}$ and $R_{3b}$ is independently selected from H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, or $R_5$-substituted $C_2$-$C_6$ alkynyl;

W is H, O, OH, $OR_4$, $NR_4R_4$, $NR_4COR_4$, F, Cl, $N_3$, or CN;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, SH, or $BH_3$;

each of $Y_3$, and $Y_4$ is independently selected from $CH_2$, or O;

$Z_1$ is O, OH, $CH_2$, S, $NR_6$, CO, or $SO_2$;

each of $Z_2$ and $Z_3$ is absent, or each of $Z_2$ and $Z_3$ is independently selected from O, $NR_6$, $CHR_7$, $CHCOOR_7$, $CHCONR_7R_7$, S, CO, $SO_2$, PO(OH), PO(SH), or $P(O)VCO_2H$; or $Z_2$ forms a ring with oxygen atom linked to $R_{3a}$;

$Z_4$ is absent, or $Z_4$ is O, $CH_2$, S, $NR_6$, CO, or $SO_2$;

each of $B_1$ and $B_2$ is independently selected from natural or modified pyrimidine base, or natural or modified purine base;

$R_4$ is H, $C_1$-$C_8$ alkyl, $C_2$-$C_8$ alkenyl, or $C_2$-$C_8$ alkynyl;

$R_5$ is substituted or unsubstituted alkyl, substituted or unsubstituted alkenyl, substituted or unsubstituted alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_6$ alkyl, $COR_8$, or $SO_2R_8$;

$R_7$ is absent, or $R_7$ is H, $C_1$-$C_8$ alkyl, $C_2$-$C_8$ alkenyl, or $C_2$-$C_8$ alkynyl;

$R_8$ is H, $C_1$-$C_8$ alkyl, $C_2$-$C_8$ alkenyl, or $C_2$-$C_8$ alkynyl;

V is $C_1$-$C_4$ alkyl;

$m_1$ is 1, 2, or 3;

$m_2$ is 0, 1, or 2; and n is 1, 2, or 3.

In some embodiments, $R_4$ is H, $C_1$-$C_4$ alkyl, $C_2$-$C_4$ alkenyl, or $C_2$-$C_4$ alkynyl;

$R_5$ is $C_1$-$C_4$ alkyl, $C_2$-$C_4$ alkenyl, $C_2$-$C_4$ alkynyl, $OR_7$, $SR_7$, $NR_7R_7$, $COR_7$, $COOR_7$, $OCOOR_7$, $CONR_7R_7$, $NHCOR_7$, $OCONR_7R_7$, halogen, CN, $SO_2$, $NO_2$, D, $N_3$, aryl, or heteroaryl;

$R_6$ is H, $C_1$-$C_4$ alkyl, $COR_8$, or $SO_2R_8$;

$R_7$ is H, $C_1$-$C_4$ alkyl, $C_2$-$C_4$ alkenyl, or $C_2$-$C_4$ alkynyl; and $R_8$ is H, $C_1$-$C_4$ alkyl, $C_2$-$C_5$ alkenyl, or $C_2$-$C_5$ alkynyl.

In some embodiments, $Z_1$ is O, $CH_2$, S, or NH;

each of $Z_2$ and $Z_3$ is absent, or each of $Z_2$ and $Z_3$ is independently selected from $NR_6$, $CHR_7$, $CHCOOR_7$, $CHCONR_7R_7$, S, CO, $SO_2$, PO(OH), or PO(SH);

$Z_4$ is absent, or $Z_4$ is O, $CH_2$, S, or NH;

each of $B_1$ and $B_2$ is independently selected from natural or modified cytosine base, natural or modified uracil base, natural or modified adenine base, or natural or modified guanine base;

$R_6$ is H, methyl, ethyl, propyl, or isopropyl; and $R_7$ is H, methyl, ethyl, propyl, or isopropyl.

In some embodiments, each of $Y_a$, $Y_b$, $Y_c$, and $Y_d$ is O, or at most one of $Y_a$, $Y_b$, $Y_c$, and $Y_d$ is S, $CH_2$, $CCl_2$, $CF_2$, or NH;

each of $Y_{1a}$, $Y_{1b}$, and $Y_{1c}$, is O, or at most one of $Y1_a$, $Y1_b$, or $Y1_c$ is S;

each of $Y_{2a}$, $Y_{2b}$, and $Y_{2c}$ is OH, or at most one of $Y_{2a}$, $Y_{2b}$, or $Y_{2c}$ is SH, or $BH_3$;

each of $Y_3$ and $Y_4$ is independently $CH_2$;

$Z_2$ is absent, or $Z_2$ is $CH_2$, $CH_2CH_2$, CO, $SO_2$, or PO(OH);

$Z_3$ is O, $CH_2$, or NH; and $Z_4$ is $CH_2$, or NH.

In some embodiments, each of $Y_a$ and $Y_d$ is O, or at most one of $Y_a$ and $Y_d$ is S, or $CH_2$.

In some embodiments, each of $Y_b$ and $Y_c$ is O, or at most one of $Y_b$ and $Y_c$ is S, $CH_2$, $CCl_2$, $CF_2$, or NH.

In some embodiments, $Z_2$ is $CH_2$, $SO_2$, or PO(OH).

In some embodiments, W is H, OH, OR$_4$, NR$_4$R$_4$, F, Cl, or CN;
- R' is C$_1$-C$_4$ alkyl, C$_2$-C$_4$ alkenyl, C$_2$-C$_4$ alkynyl, C$_3$-C$_6$ cycloalkyl, C$_3$-C$_6$ cycloalkene, benzyl, C$_1$-C$_4$ haloalkyl, C$_2$-C$_4$ haloalkenyl, C$_2$-C$_4$ haloalkynyl, C$_3$-C$_6$ halocycloalkyl, C$_3$-C$_6$ halocycloalkene, or halobenzyl;
- R is H, C$_1$-C$_4$ alkyl, C$_2$-C$_4$ alkenyl, C$_2$-C$_4$ alkynyl, C$_3$-C$_6$ cycloalkyl, C$_3$-C$_6$ cycloalkene, C$_1$-C$_4$ haloalkyl, C$_2$-C$_4$ haloalkenyl, C$_2$-C$_4$ haloalkynyl, C$_3$-C$_6$ halocycloalkyl, C$_3$-C$_6$ halocycloalkene, benzyl, or halobenzyl;
- R$_2$ is absent, or R$_2$ is H, C$_1$-C$_6$ alkyl, C$_2$-C$_6$ alkenyl, C$_2$-C$_6$ alkynyl, R$_5$-substituted C$_1$-C$_6$ alkyl, R$_5$-substituted C$_2$-C$_6$ alkenyl, R$_5$-substituted C$_2$-C$_6$ alkynyl, aryl, R$_5$-substituted aryl, heteroaryl, R$_5$-substituted heteroaryl, halogen, CN, or N$_3$;
- each of R$_{3a}$ and R$_{3b}$ is independently selected from H, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, or C$_2$-C$_4$ haloalkynyl;
- R$_4$ is H, methyl, ethyl, n-propyl, isopropyl, butyl, ethenyl, propenyl, butenyl, ethynyl, propynyl, or butynyl;
- R$_5$ is C$_1$-C$_4$ alkyl, C$_2$-C$_4$ alkenyl, C$_2$-C$_4$ alkynyl, OR$_7$, SR$_7$, NR$_7$R$_7$, COR$_7$, COOR$_7$, halogen, CN, D, N$_3$, pyridine, pyrimidine, or morpholine; and
- R$_7$ is H, methyl, ethyl, n-propyl, isopropyl, butyl, ethenyl, propenyl, butenyl, ethynyl, propynyl, or butynyl.

In some embodiments, W is OH, F, Cl, methoxy, or ethoxy.

In some embodiments, W is OH, or methoxy.

In some embodiments, each of R$_{3a}$ and R$_{3b}$ is independently H, methyl, ethyl, n-propyl, isopropyl, propenyl, propynyl, halomethyl, haloethyl, halopropyl, or haloisopropyl.

In some embodiments, each of R$_{3a}$ and R$_{3b}$ is independently H, methyl, ethyl, n-propyl, isopropyl, propenyl, propynyl, fluoromethyl, difluoromethyl, trifluoromethyl, trifluoroethyl, trifluoropropyl, or trifluoroisopropyl.

In some embodiments, each of R$_{3a}$ and R$_{3b}$ is independently H, methyl, ethyl, n-propyl, isopropyl, trifluoromethyl, or trifluoroethyl.

In some embodiments, R' is methyl, ethyl, n-propyl, isopropyl, butyl, ethenyl, propenyl, butenyl, ethynyl, propynyl, butynyl, benzyl, halomethyl, haloethyl, halopropyl, haloisopropyl, halobutyl, haloethenyl, halopropenyl, halobutenyl, haloethynyl, halopropynyl, halobutynyl, or halobenzyl.

In some embodiments, R' is methyl, ethyl, n-propyl, isopropyl, fluoromethyl, difluoromethyl, trifluoromethyl, trifluoroethyl, trifluoropropyl, trifluoroisopropyl, benzyl, p-fluorobenzyl, p-chlorobenzyl, difluorobenzyl, or dichlorobenzyl.

In some embodiments, R' is methyl, ethyl, n-propyl, isopropyl, difluoromethyl, trifluoromethyl, trifluoroethyl, trifluoropropyl, or trifluoroisopropyl.

In some embodiments, R' is methyl, ethyl, n-propyl, isopropyl, difluoromethyl, trifluoromethyl, or trifluoroethyl.

In some embodiments, R is H, methyl, ethyl, n-propyl, isopropyl, butyl, ethenyl, propenyl, butenyl, ethynyl, propynyl, butynyl, benzyl, halomethyl, haloethyl, halopropyl, haloisopropyl, halobutyl, haloethenyl, halopropenyl, halobutenyl, haloethynyl, halopropynyl, halobutynyl, or halobenzyl.

In some embodiments, R is methyl, ethyl, n-propyl, isopropyl, fluoromethyl, difluoromethyl, trifluoromethyl, trifluoroethyl, trifluoropropyl, or trifluoroisopropyl.

In some embodiments, R is methyl, ethyl, n-propyl, isopropyl, difluoromethyl, trifluoromethyl, or trifluoroethyl.

In some embodiments, R$_2$ is H, methyl, ethyl, n-propyl, isopropyl, butyl, hexyl, ethenyl, propenyl, butenyl, ethynyl, propynyl, butynyl, benzyl, halomethyl, haloethyl, halopropyl, haloisopropyl, halobutyl, halohexyl, haloethenyl, halopropenyl, halobutenyl, haloethynyl, halopropynyl, halobutynyl, halobenzyl, halogen, C$_1$-C$_4$ pyridinylalkyl, C$_1$-C$_4$ pyrimidinylalkyl, C$_1$-C$_4$ alkoxy-C$_1$-C$_4$ alkyl, C$_1$-C$_4$ amidoalkyl, or C$_1$-C$_4$ alkylamio-C$_1$-C$_4$ alkyl.

In some embodiments, R$_2$ is H, methyl, ethyl, n-propyl, isopropyl, butyl, ethenyl, propenyl, butenyl, ethynyl, propynyl, butynyl, benzyl, halomethyl, haloethyl, halopropyl, haloisopropyl, halobutyl, haloethenyl, halopropenyl, halobutenyl, haloethynyl, halopropynyl, halobutynyl, halobenzyl, pyridinylmethyl, pyridinylethyl, pyrimidinylmethyl, pyrimidinylethyl, methoxymethyl, ethoxymethyl, ethoxyethyl, amidomethyl, or methylaminomethyl.

In some embodiments, R$_2$ is H, methyl, ethyl, n-propyl, isopropyl, butyl, propenyl, butenyl, propynyl, butynyl, difluoromethly, trifluoromethyl, difluoroethyl, trifluoroethyl, benzyl, F, Cl, methoxymethyl, ethoxymethyl, ethoxyethyl, amidomethyl, or methylaminomethyl.

In some embodiments, R$_2$ is H, methyl, ethyl, n-propyl, isopropyl, butyl, propenyl, butenyl, propynyl, difluoromethly, trifluoromethyl, trifluoroethyl, benzyl, methoxymethyl, ethoxymethyl, or ethoxyethyl.

In some embodiments, the compound is selected from any one of the following compounds:

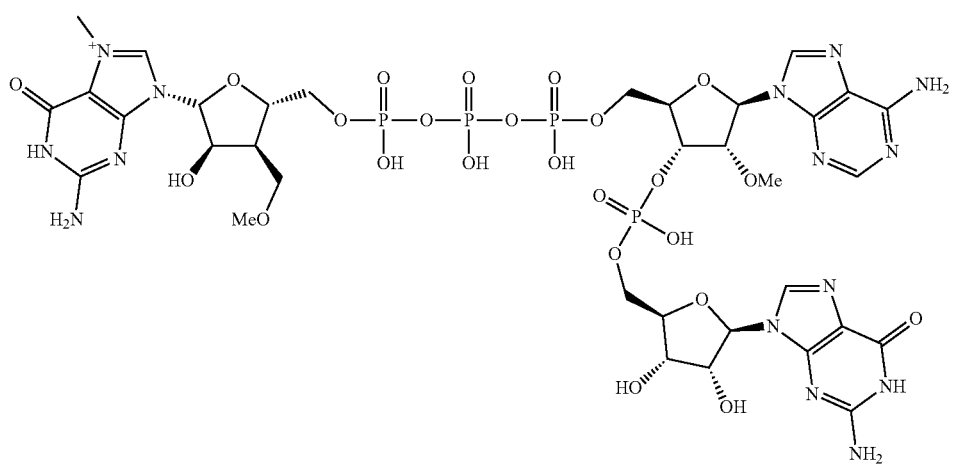

Compound 3

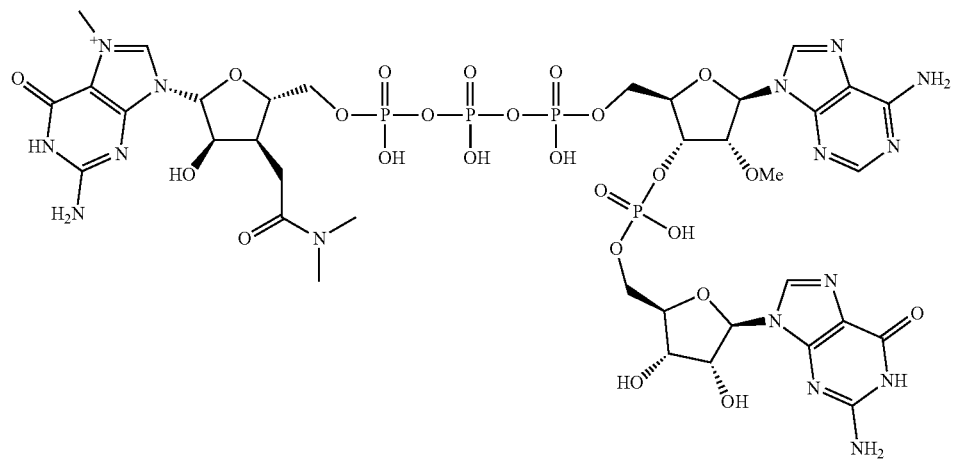
Compound 4
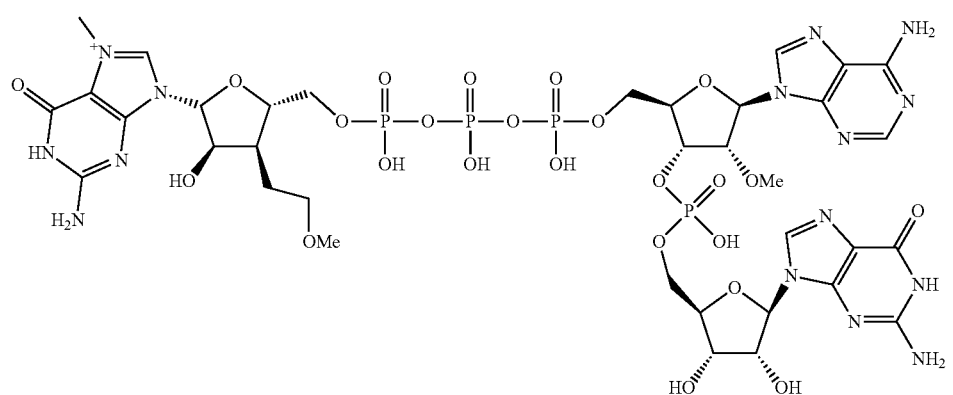
Compound 5
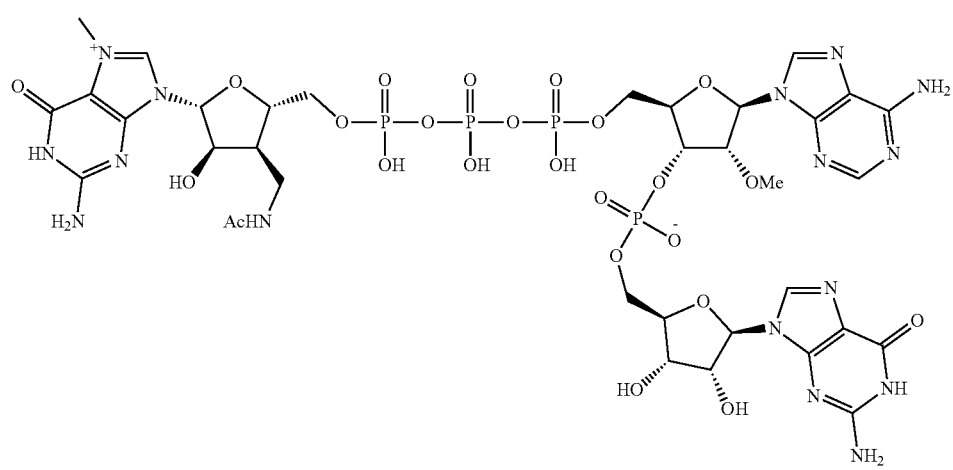
Compound 6

-continued
Compound 16
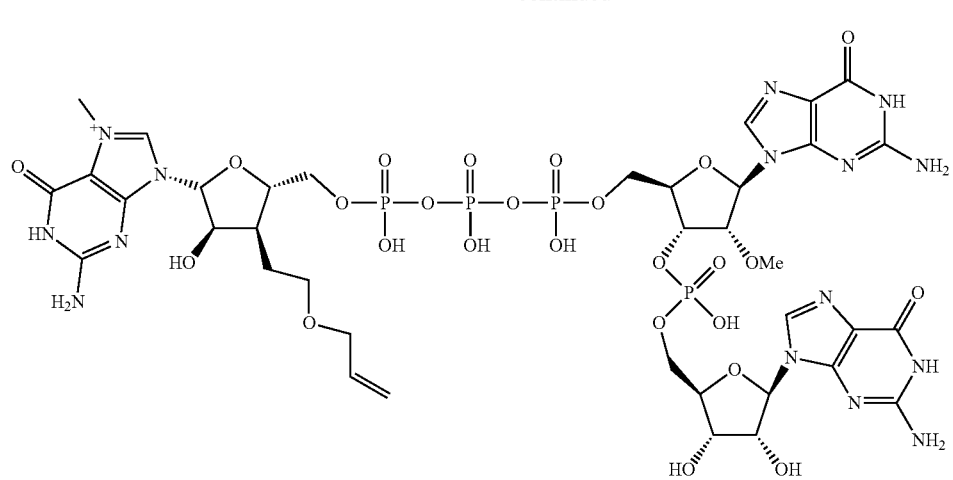
Compound 17
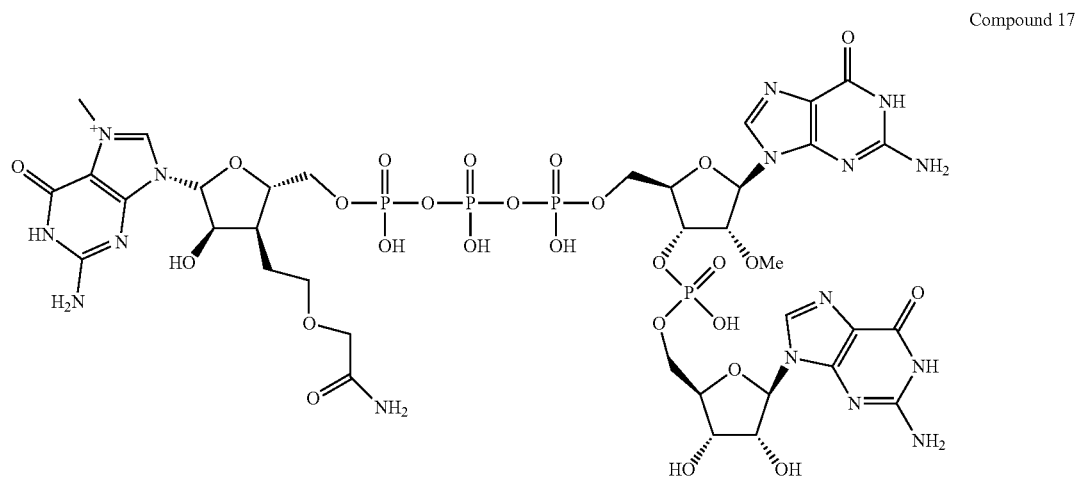
Compound 18
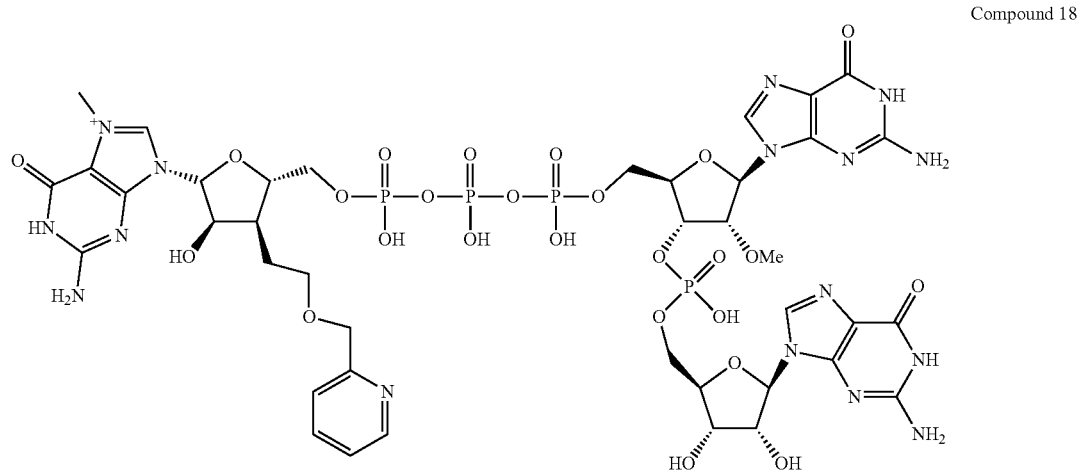

-continued
Compound 21
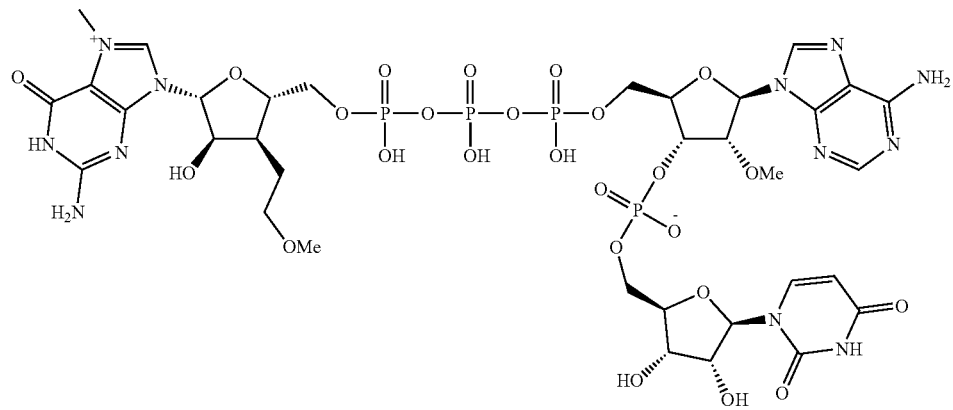
Compound 22
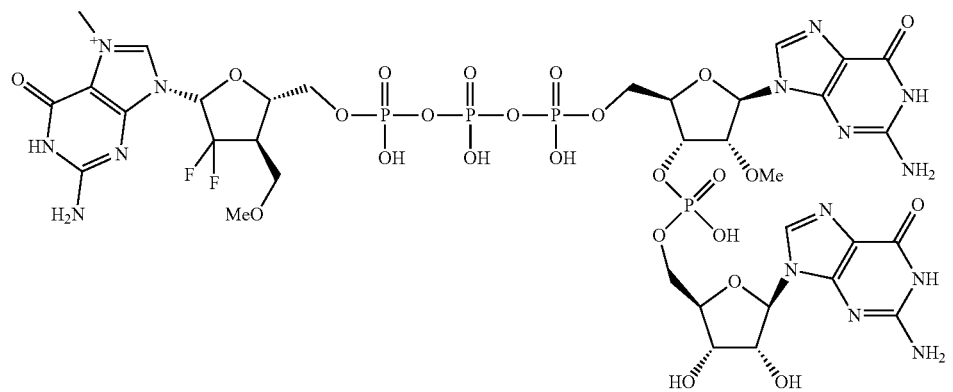
Compound 23
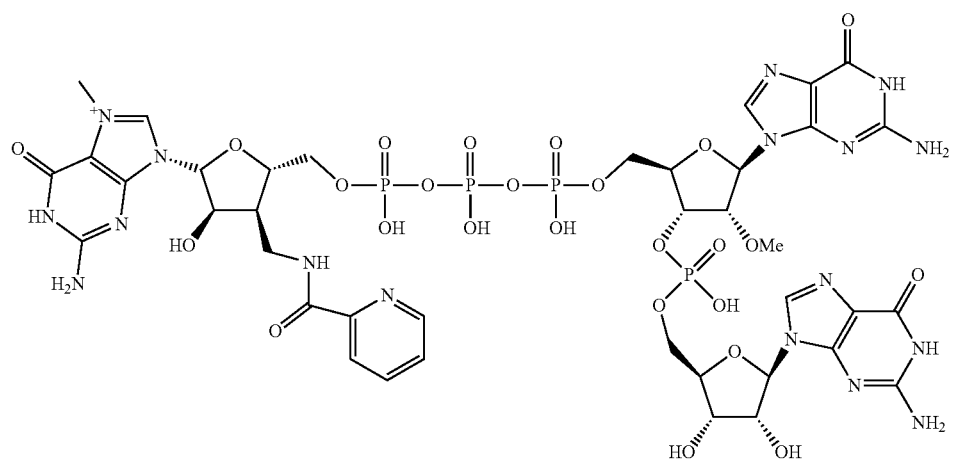
Compound 29
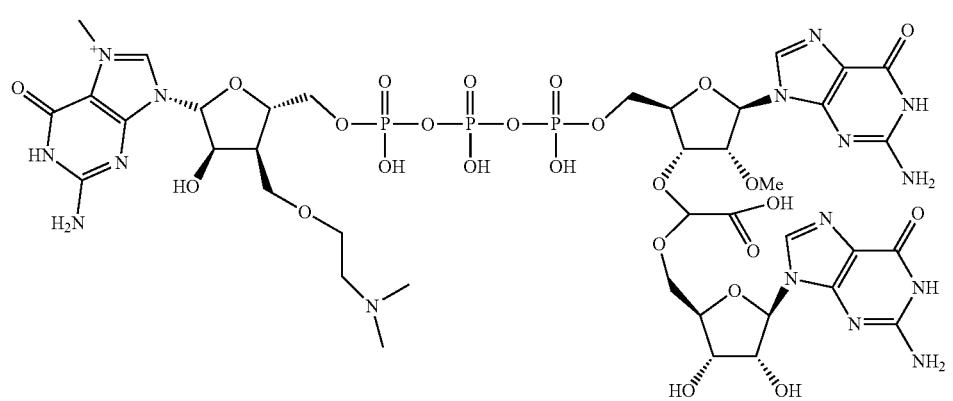

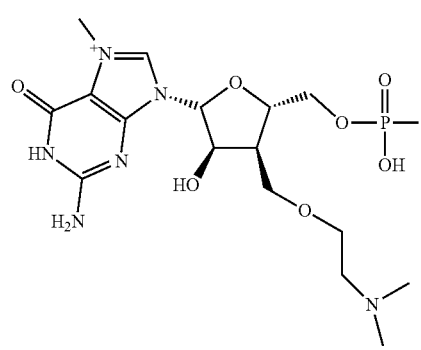 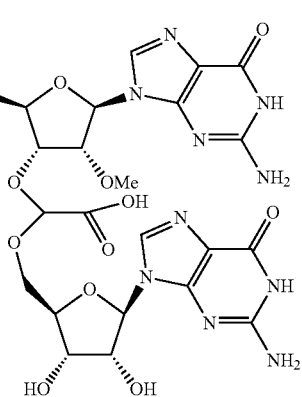
Compound 30
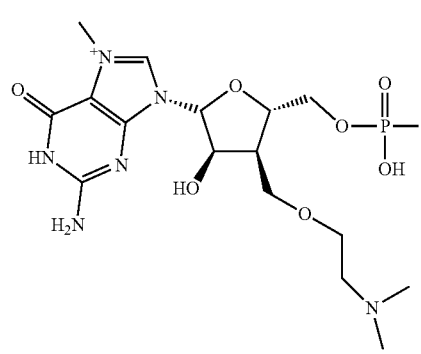 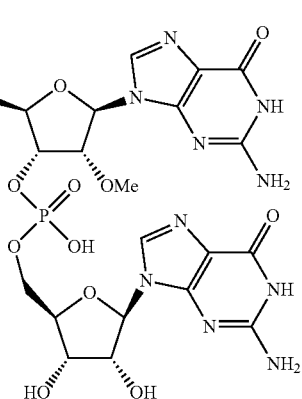
Compound 31
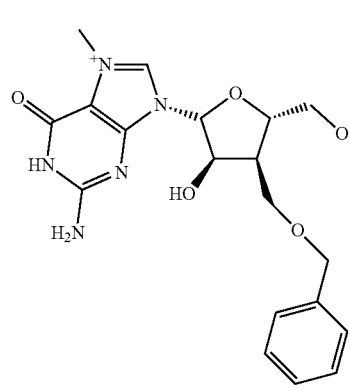 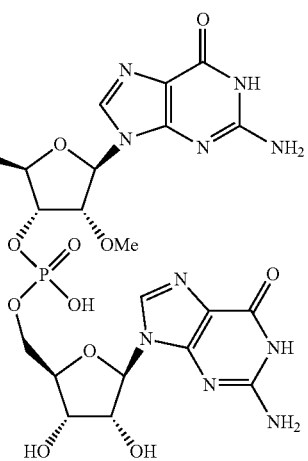
Compound 32

-continued
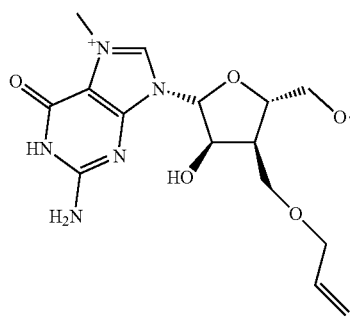 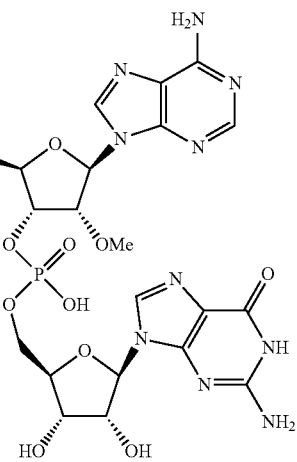
Compound 33
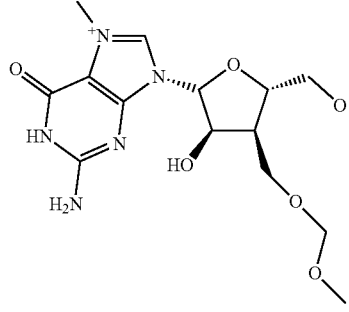 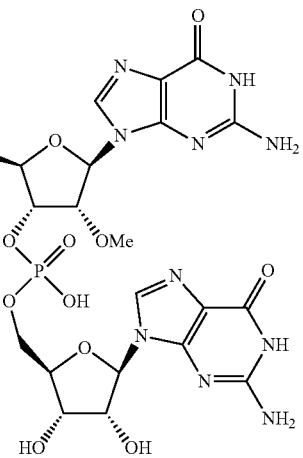
Compound 34
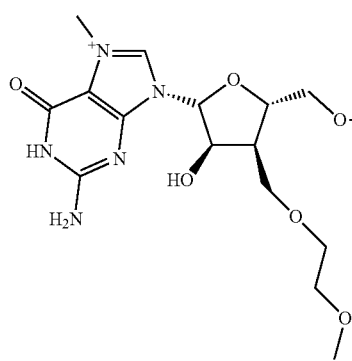 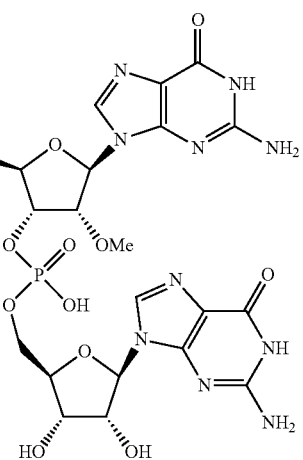
Compound 35

Compound 36
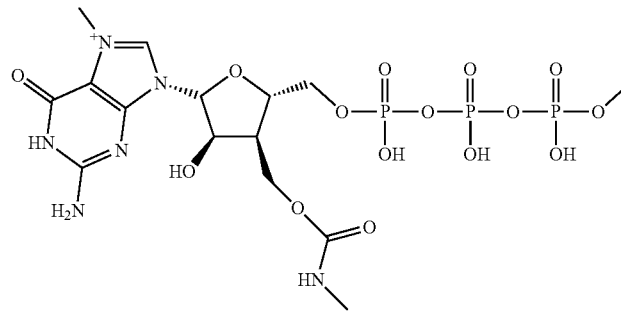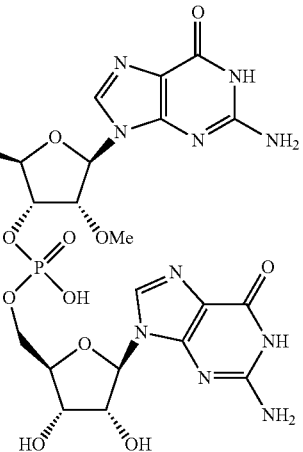
Compound 37
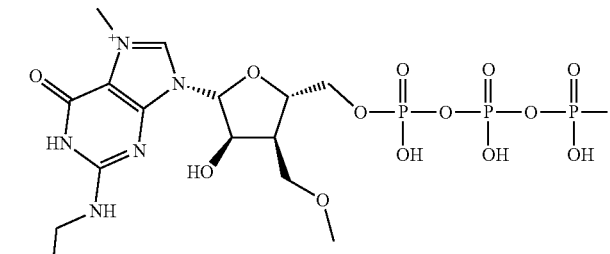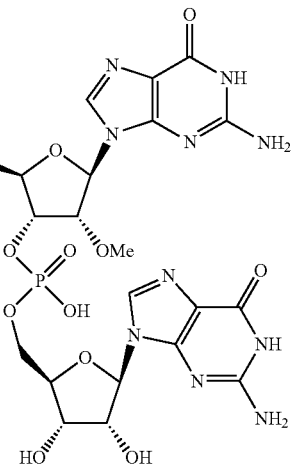
Compound 38
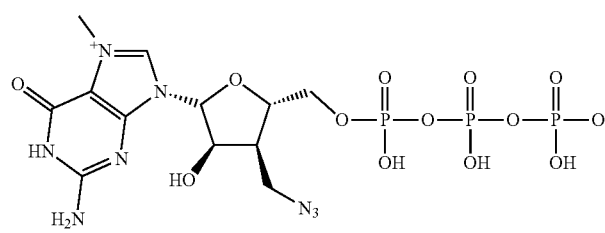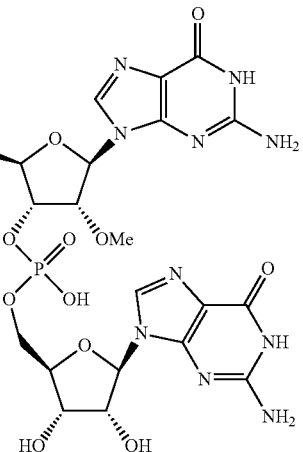

Compound 39
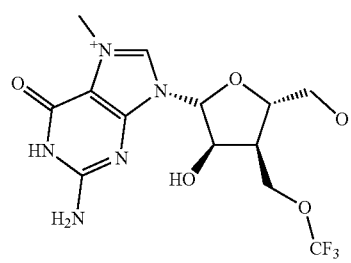 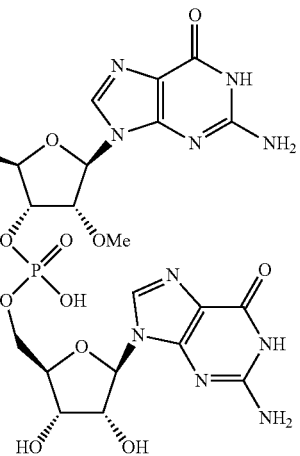
Compound 40
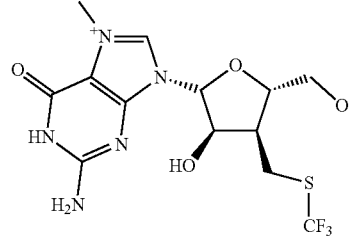 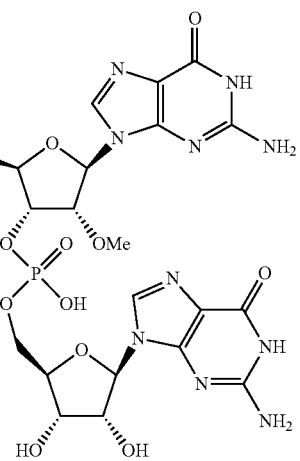
Compound 47
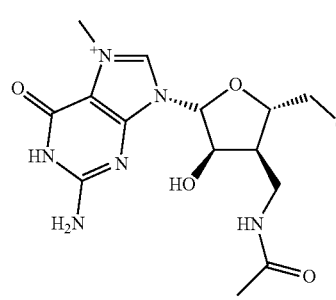 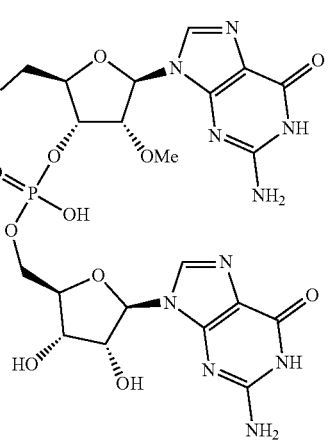

Compound 48
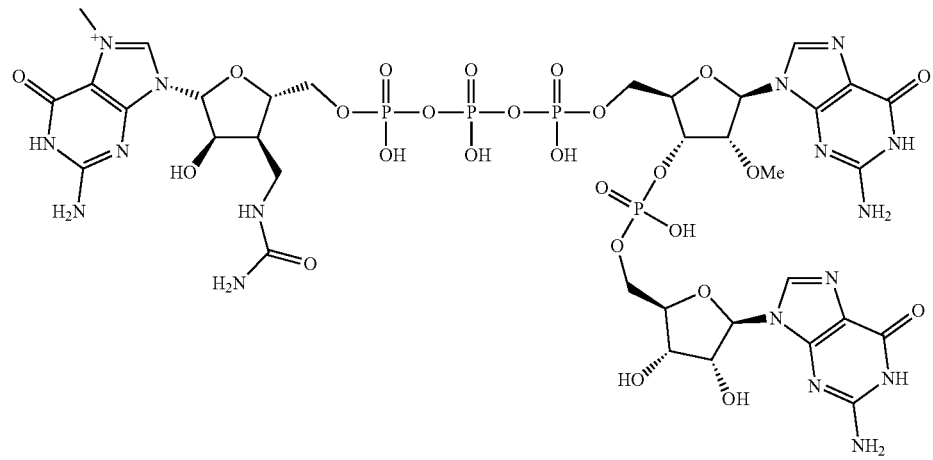
Compound 49
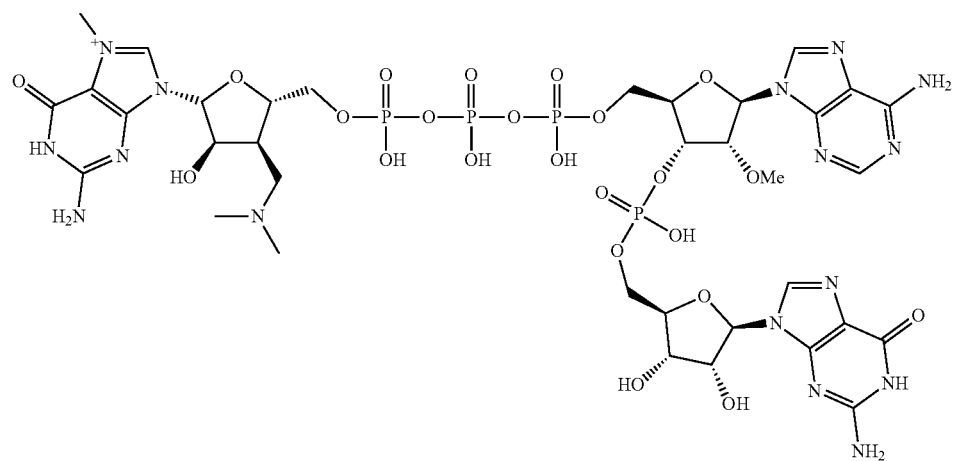
Compound 50
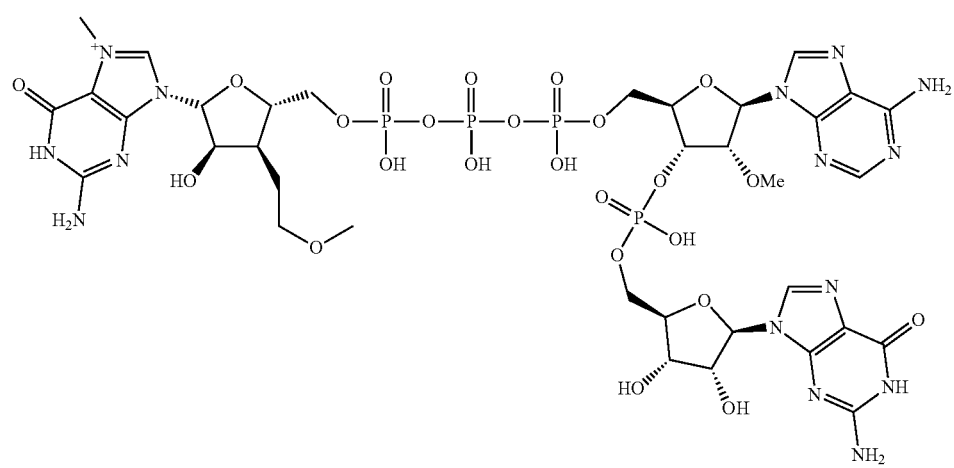

-continued
Compound 51
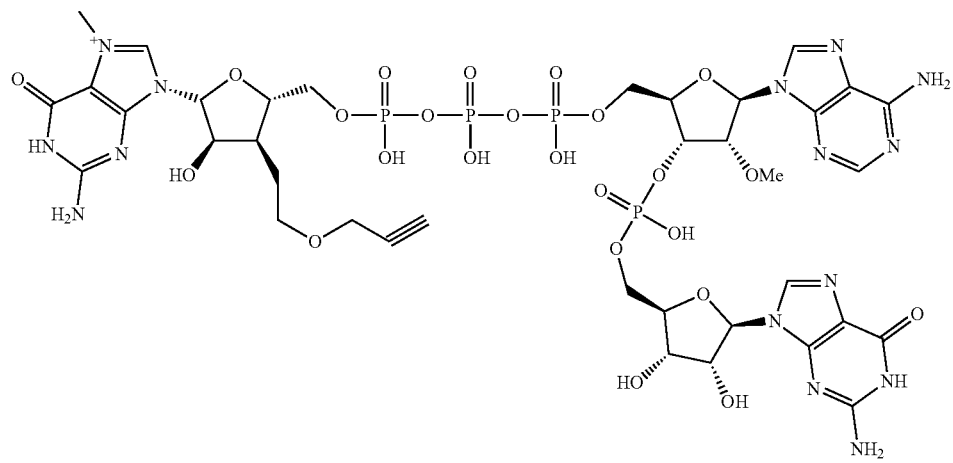
Compound 52
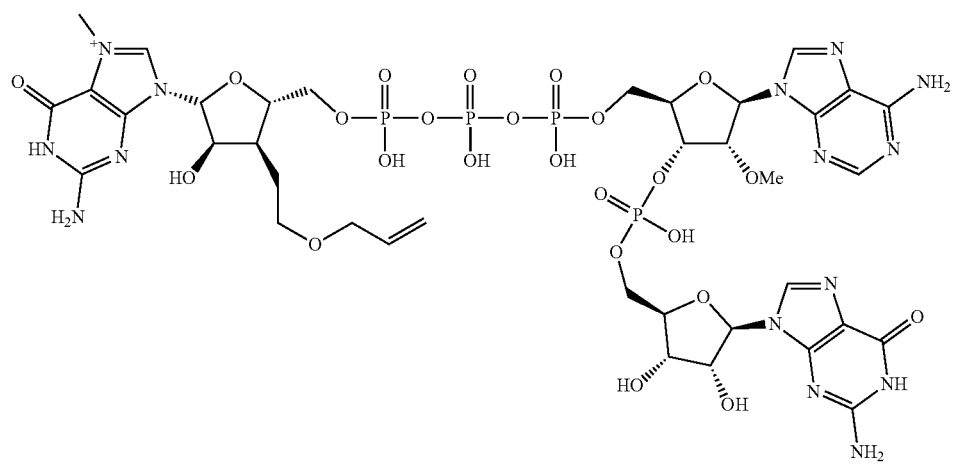
Compound 53
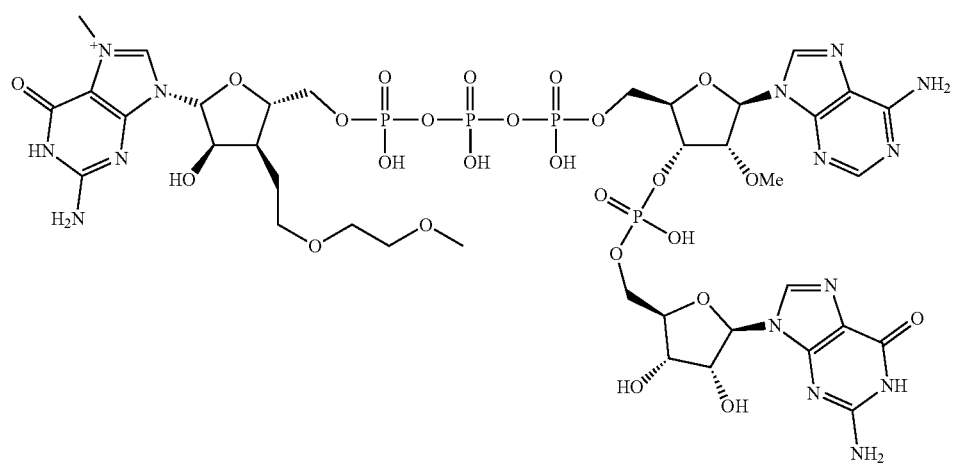

-continued
Compound 54
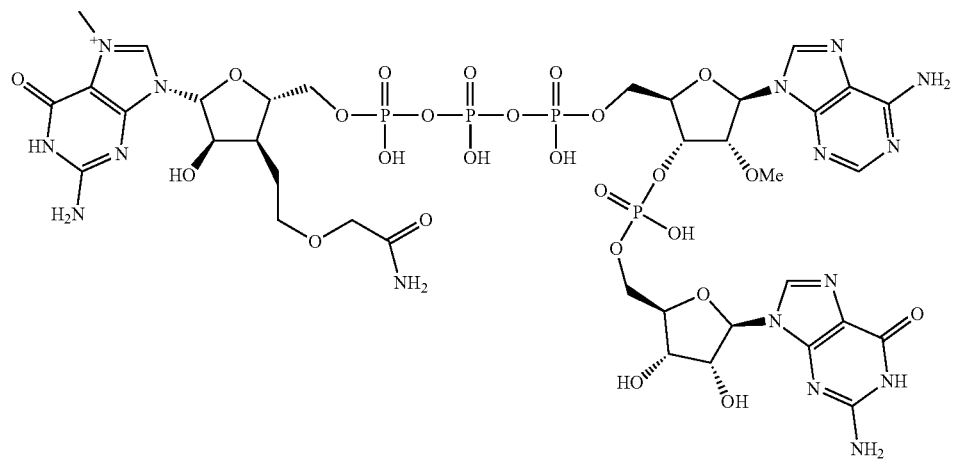
Compound 55
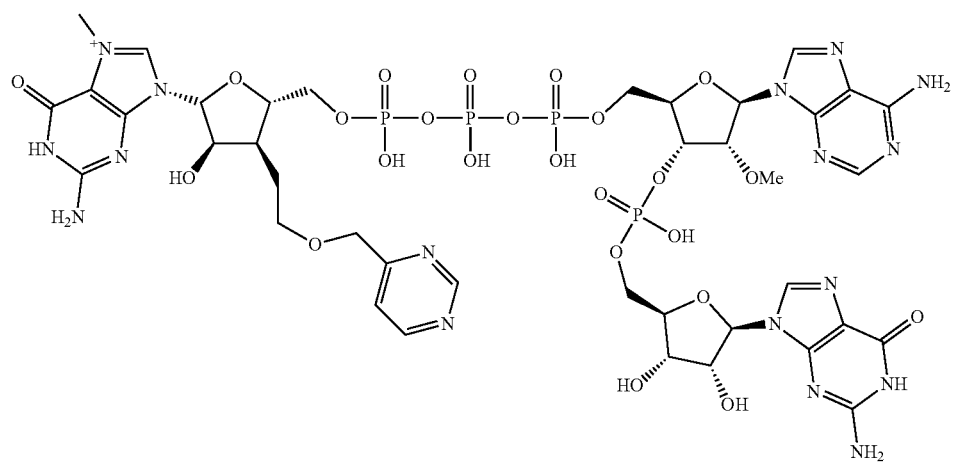
Compound 57
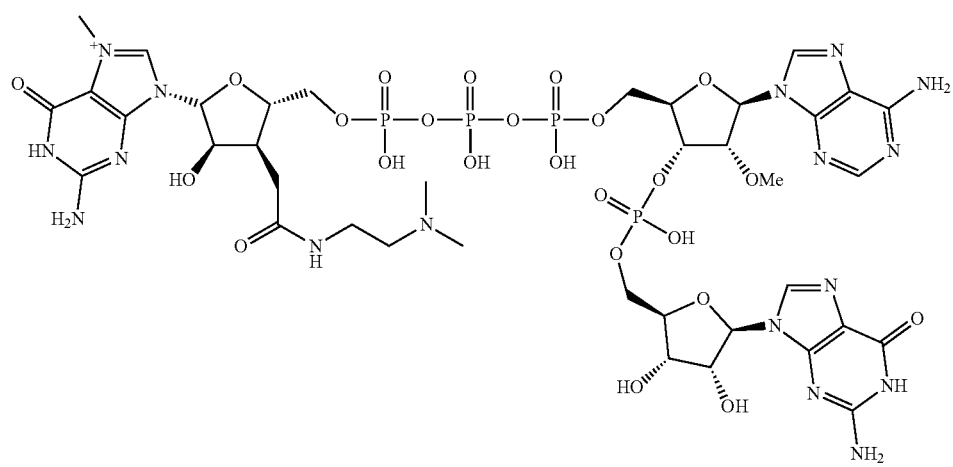

Compound 58
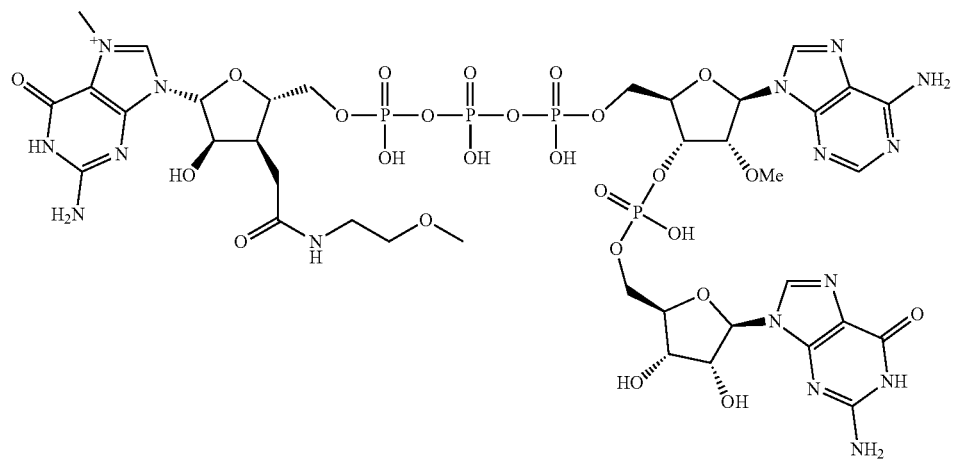
Compound 92
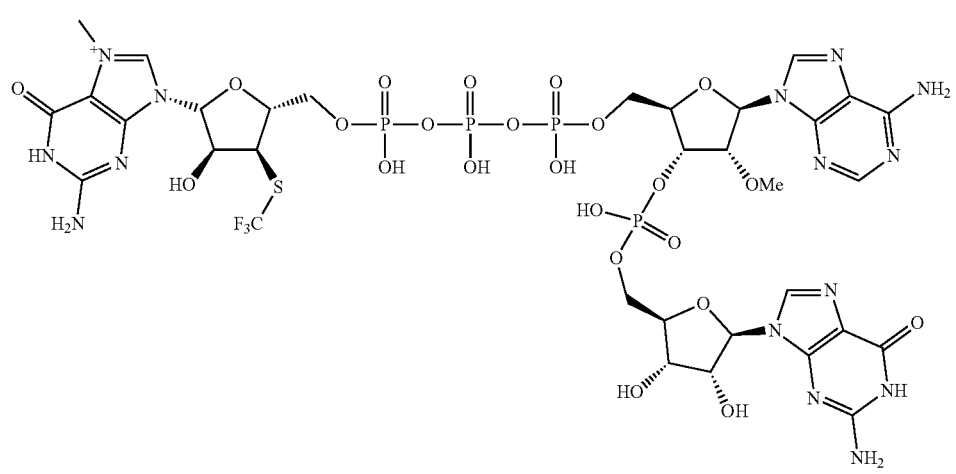
Compound 93
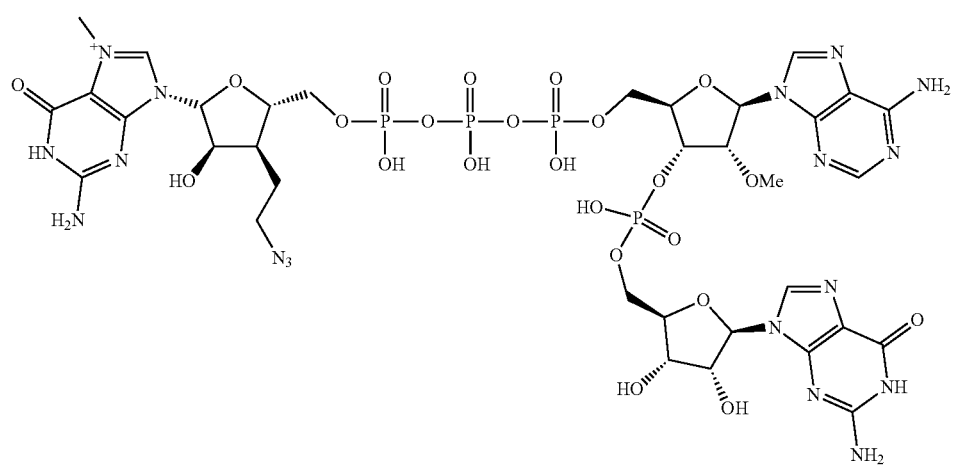

-continued
Compound 95
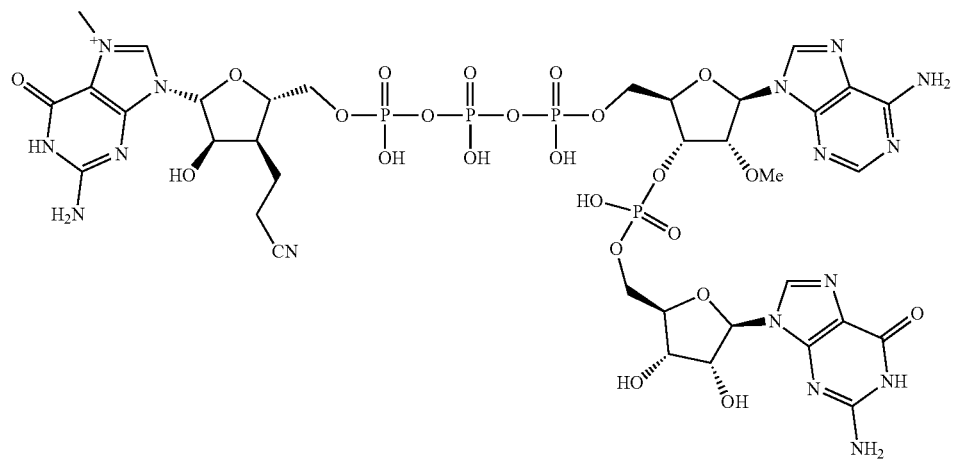
Compound 98
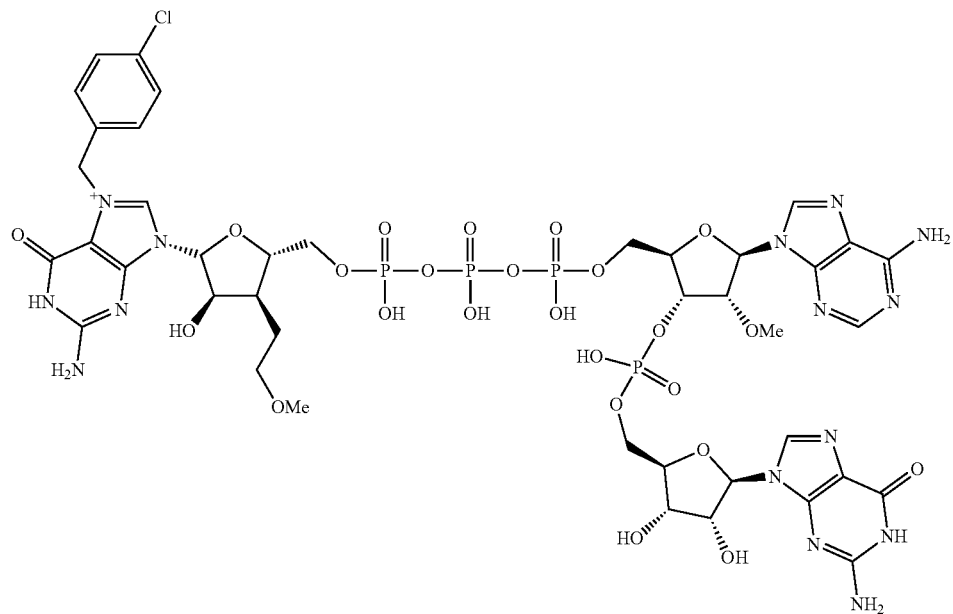
Compound 100
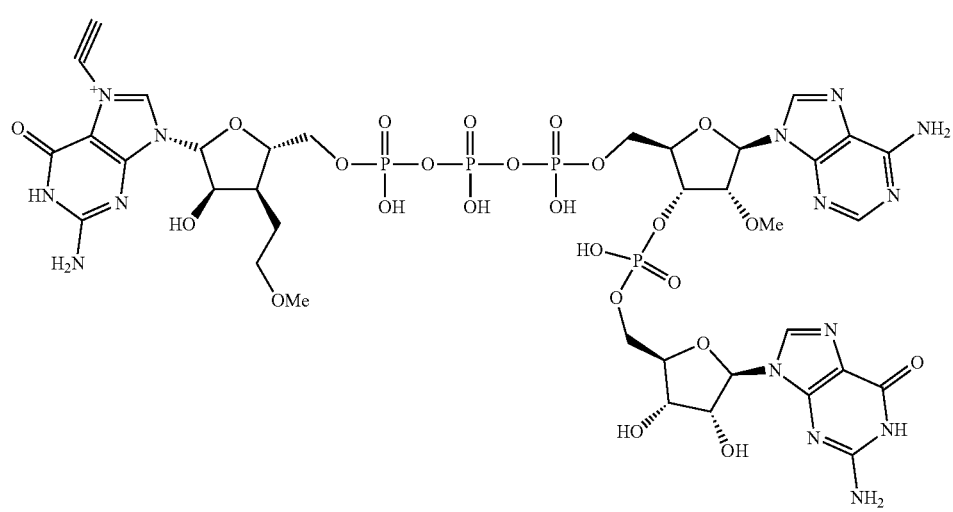

-continued
Compound 110
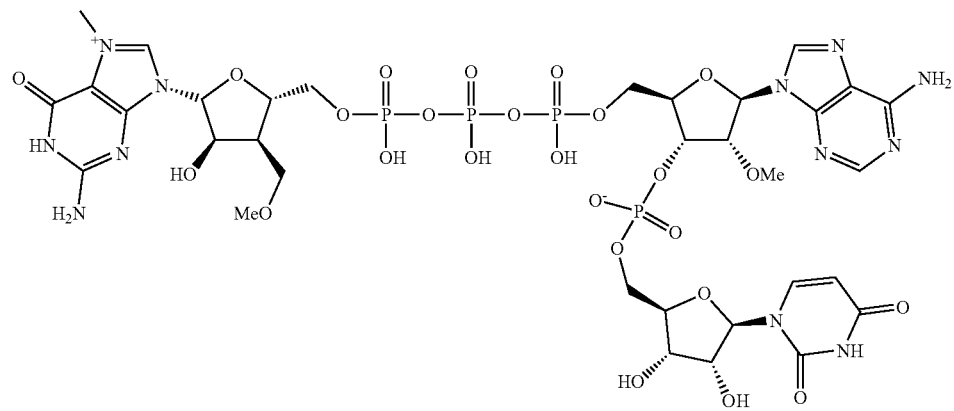
Compound 111
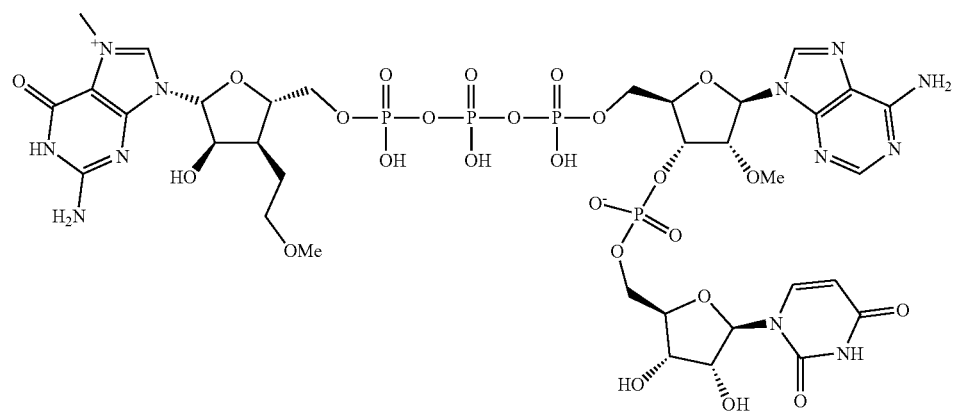
Compound 117
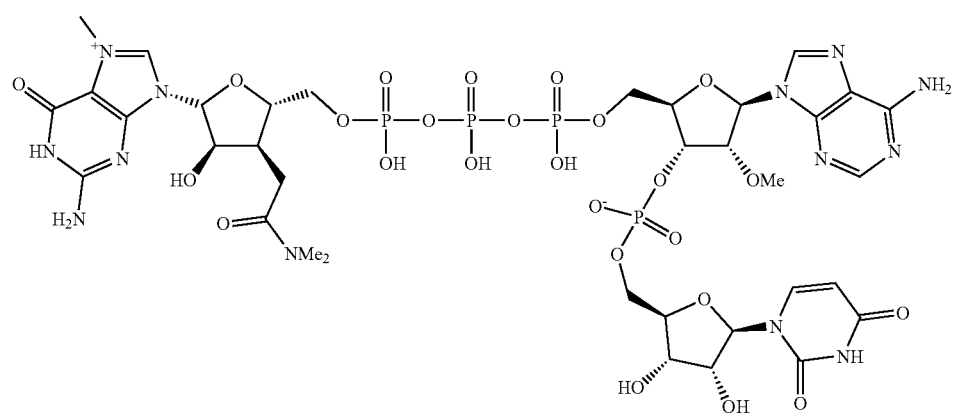
Compound 118
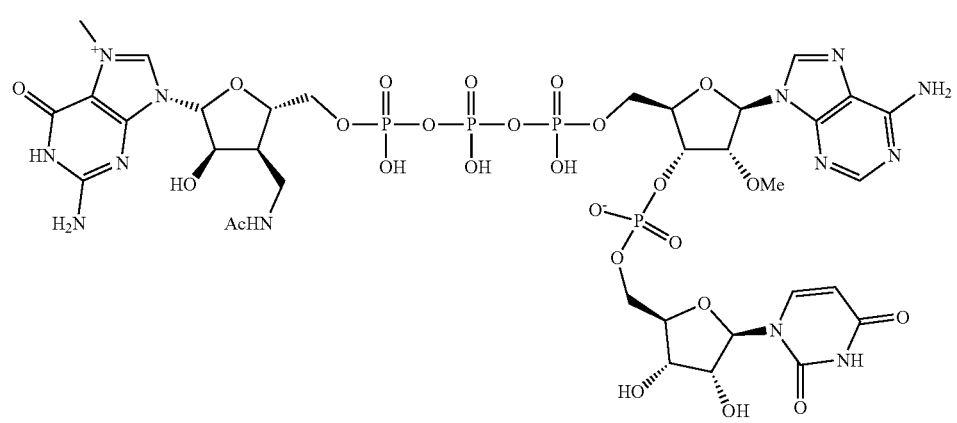

Compound 119
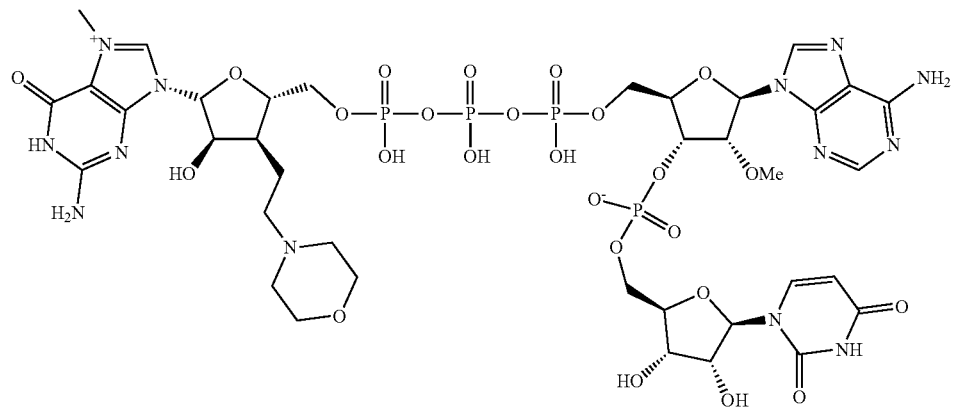
Compound 121
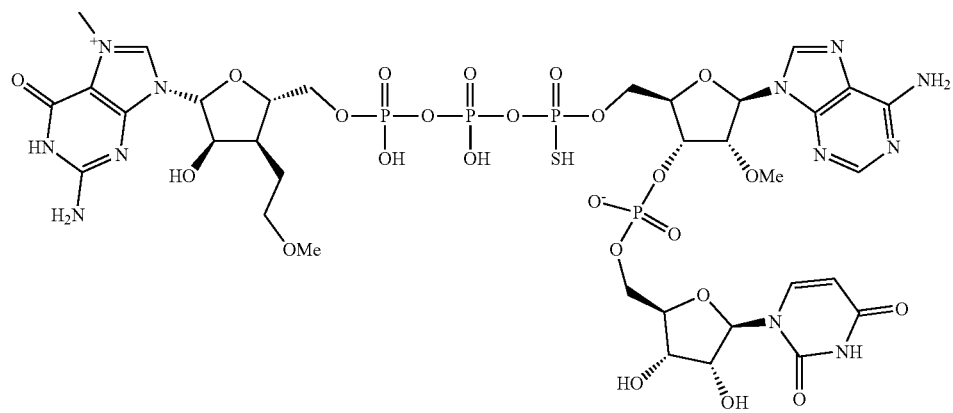
Compound 122
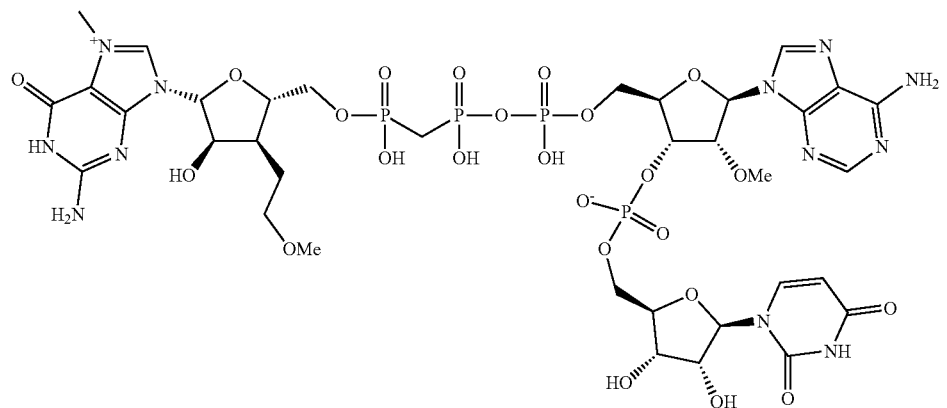
Compound 125
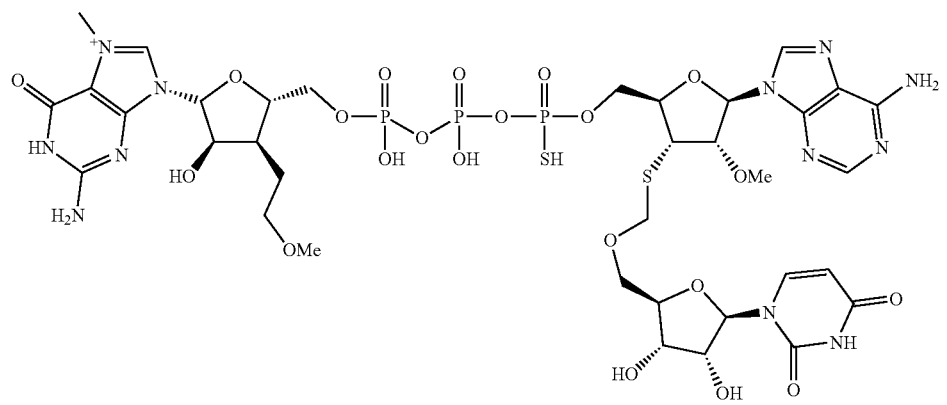

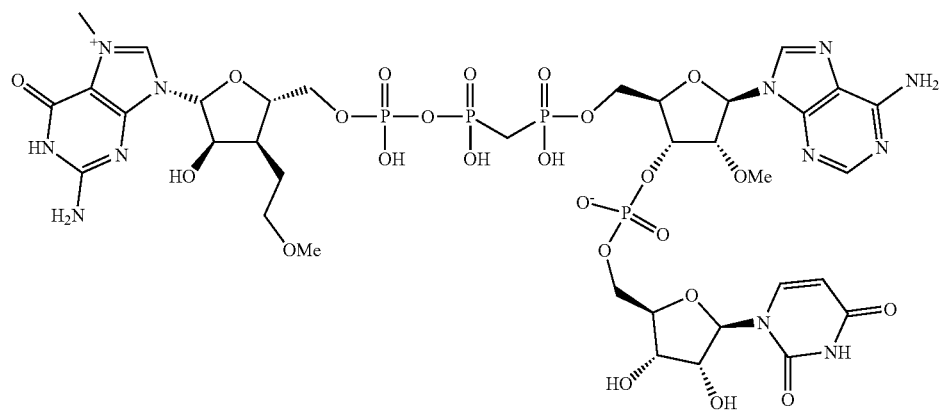
Compound 128
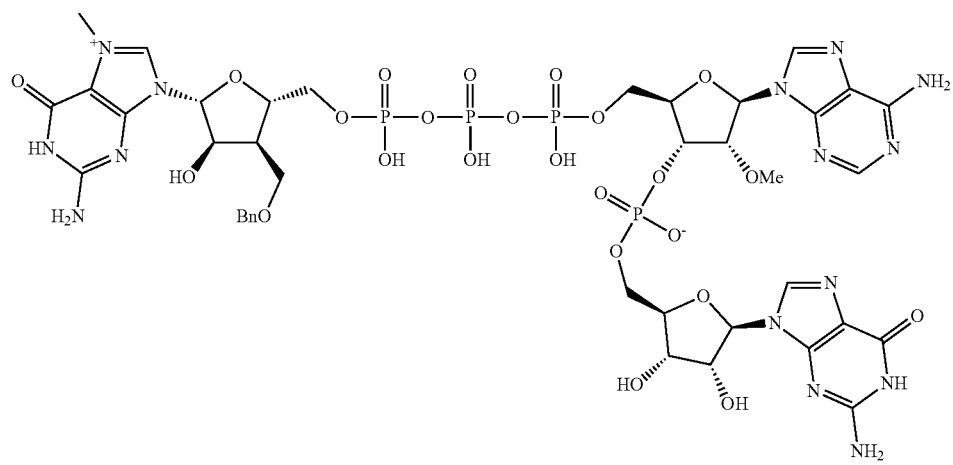
Compound 135
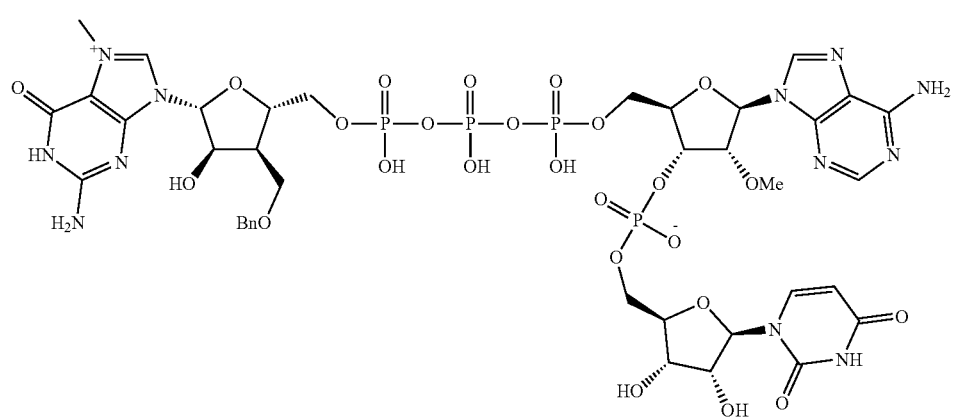
Compound 136

Compound 137
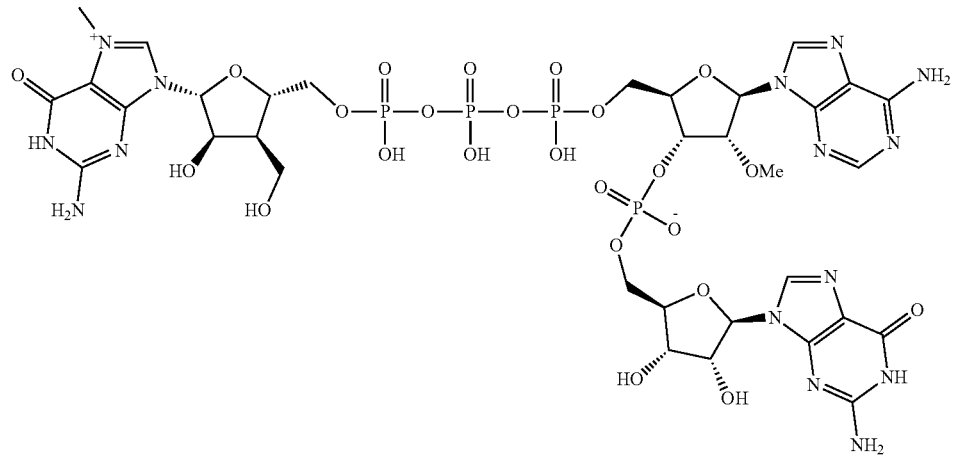
Compound 138
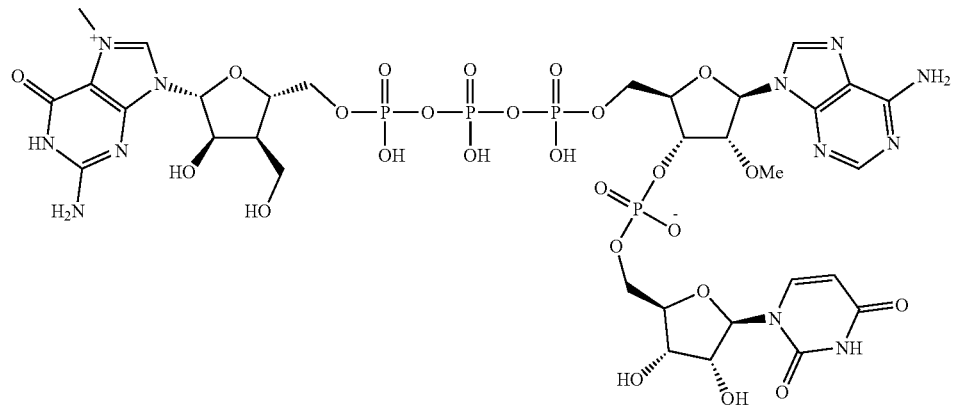
Compound 139
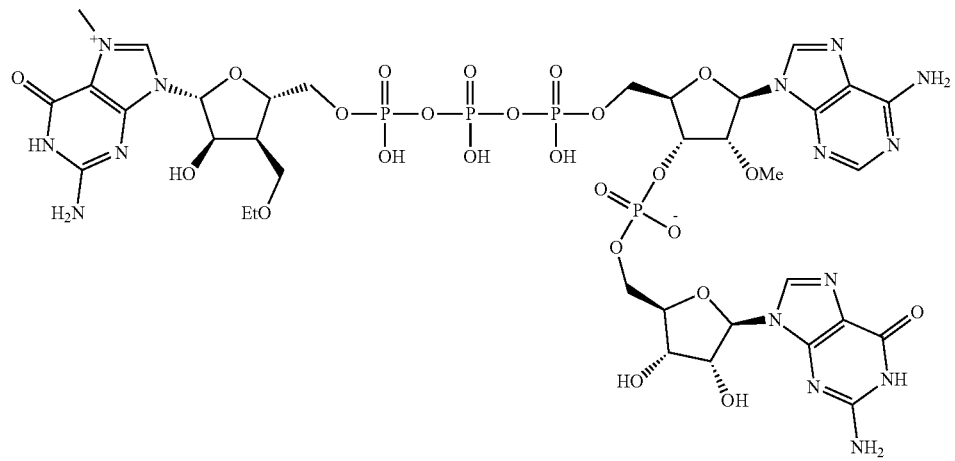

Compound 140
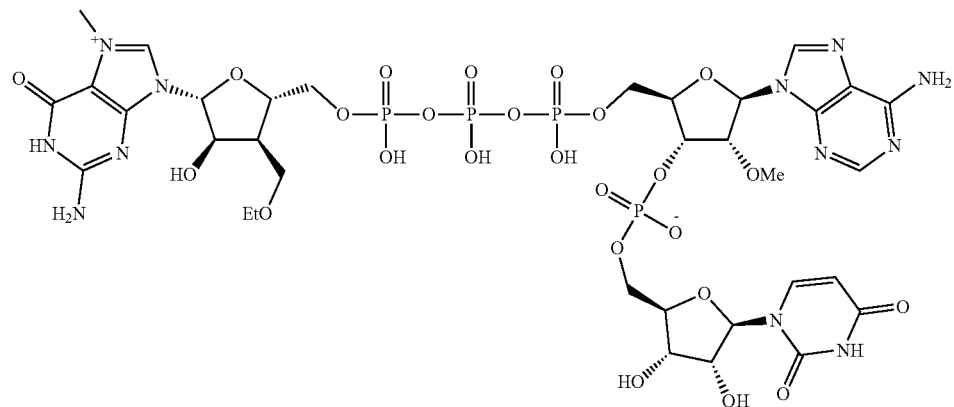
Compound 141
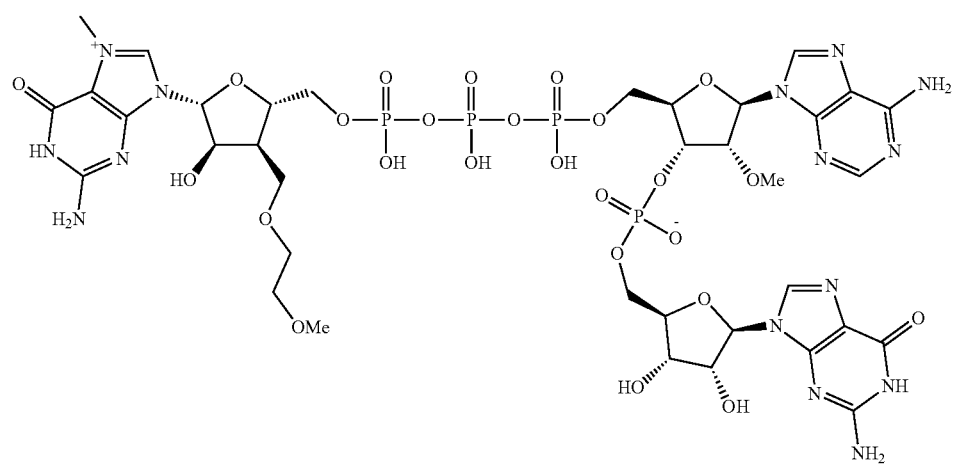
Compound 142
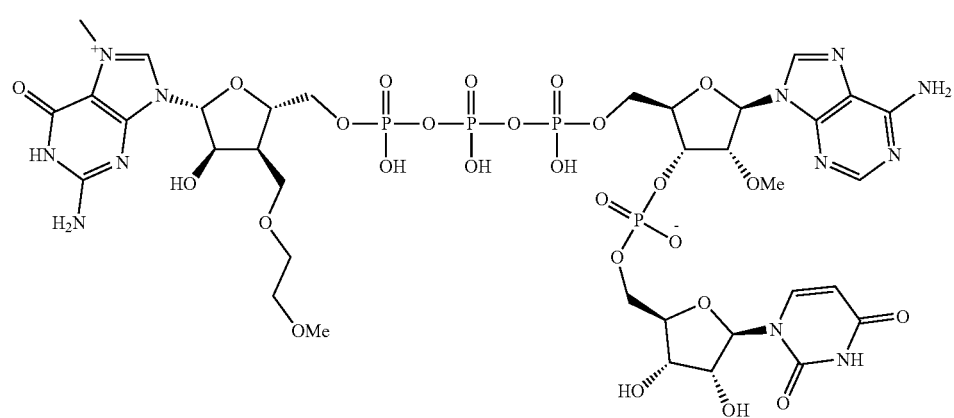

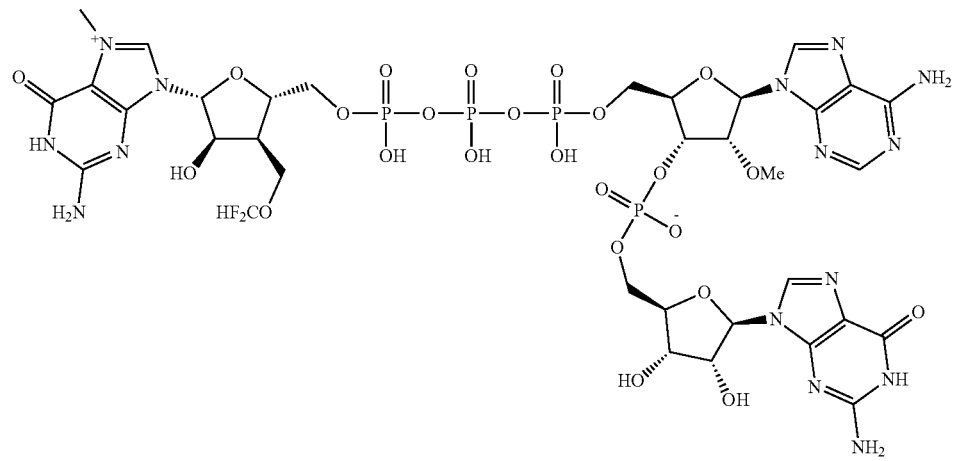
Compound 143
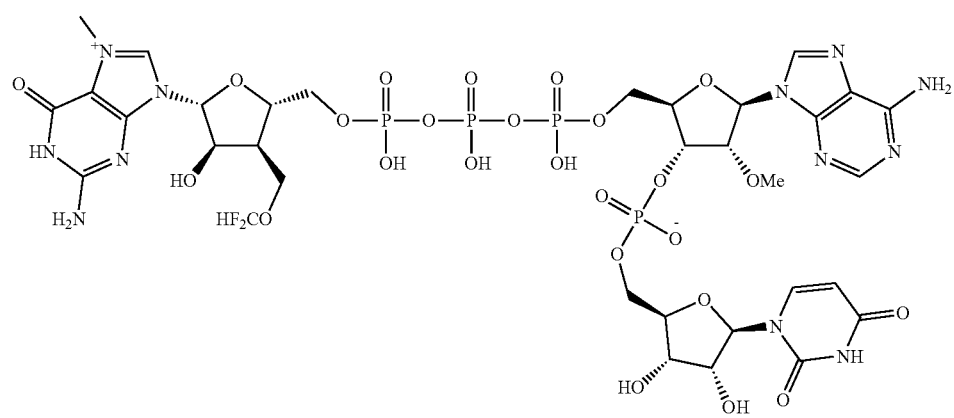
Compound 144
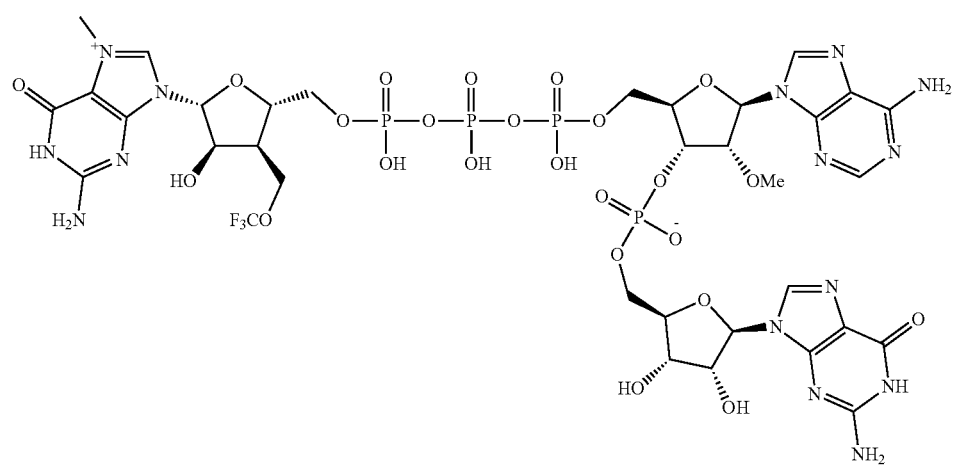
Compound 145

-continued
Compound 146
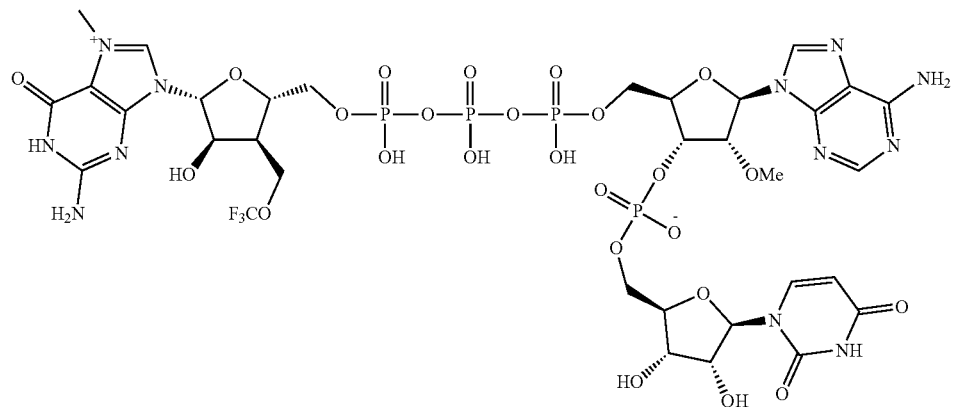
Compound 147
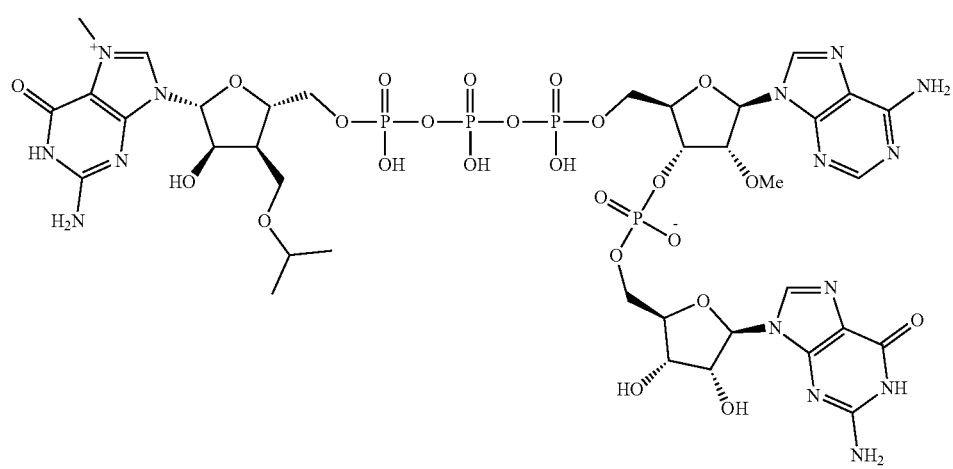
Compound 148
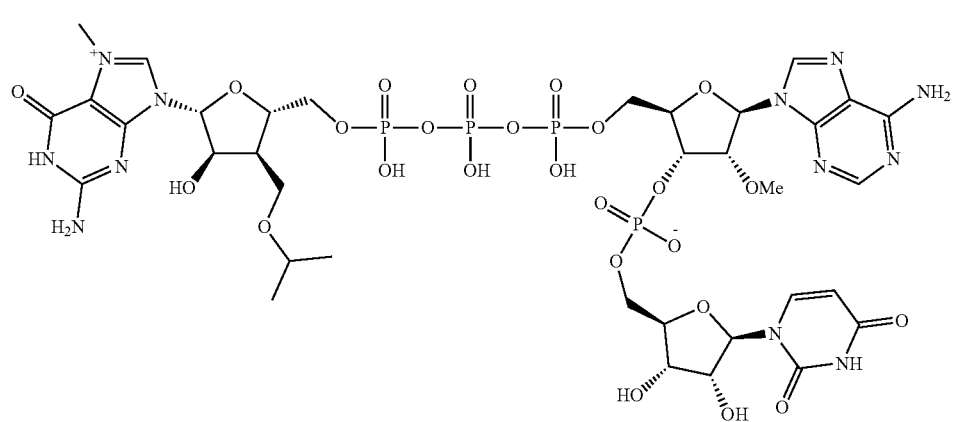

-continued
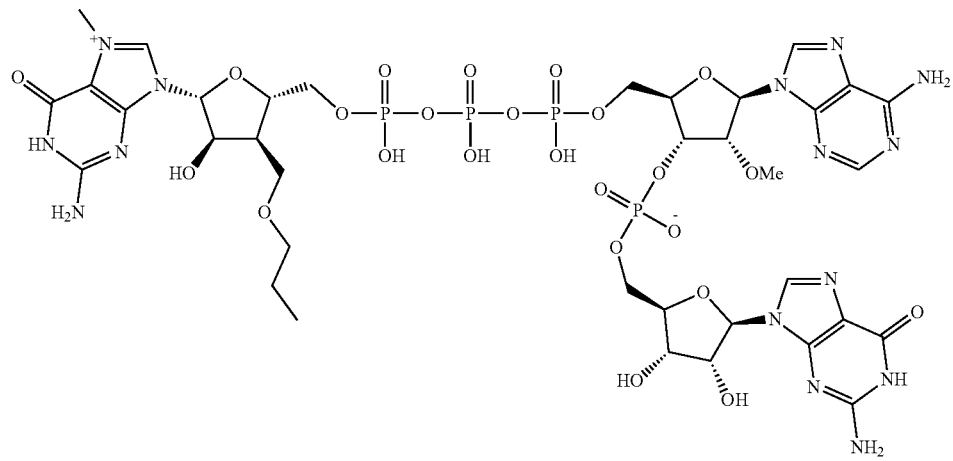
Compound 149
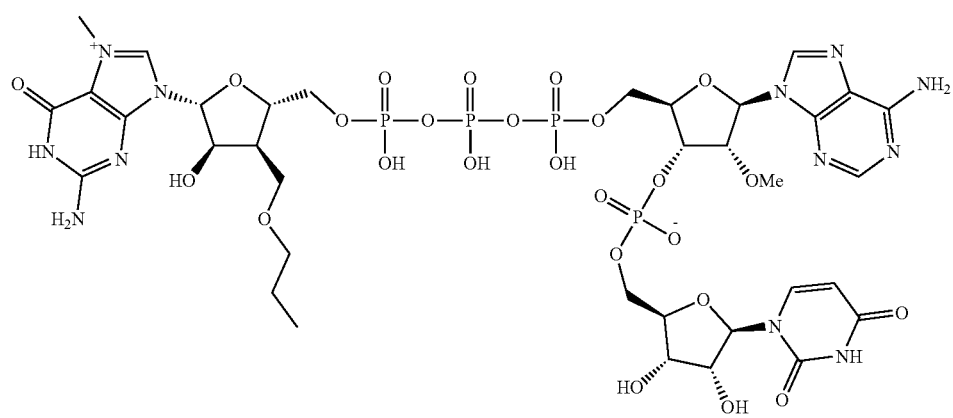
Compound 150
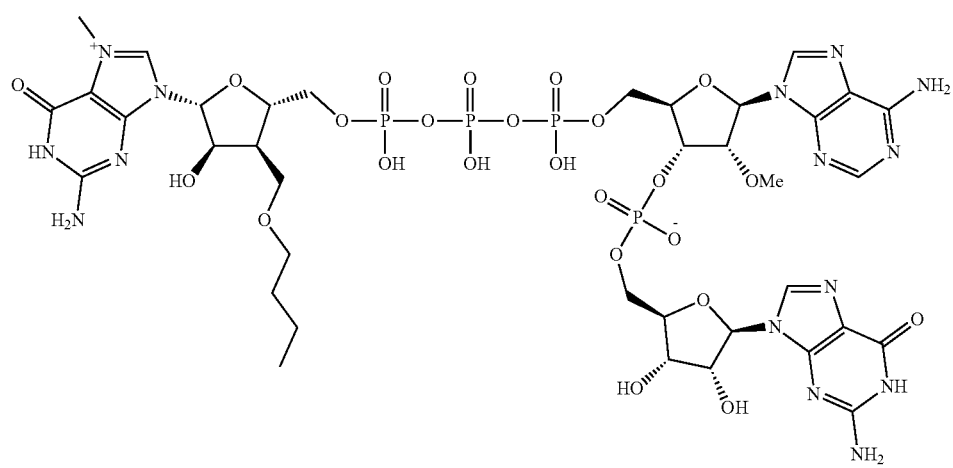
Compound 151

Compound 152
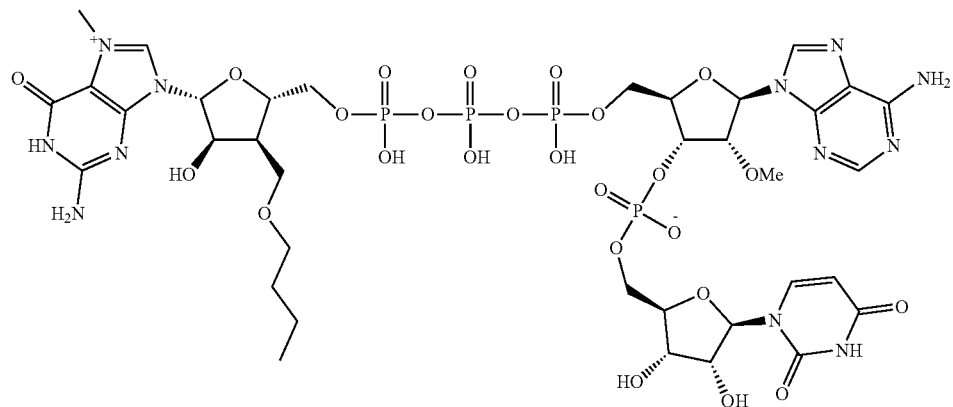
Compound 153
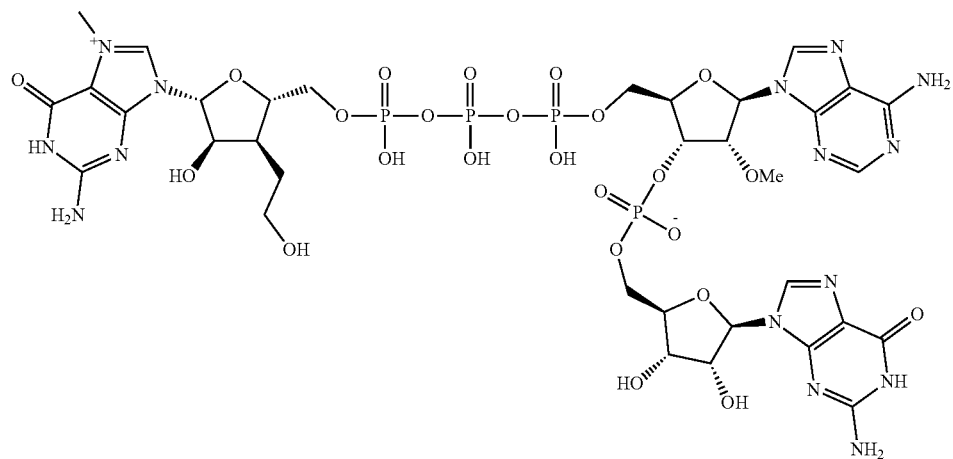
Compound 154
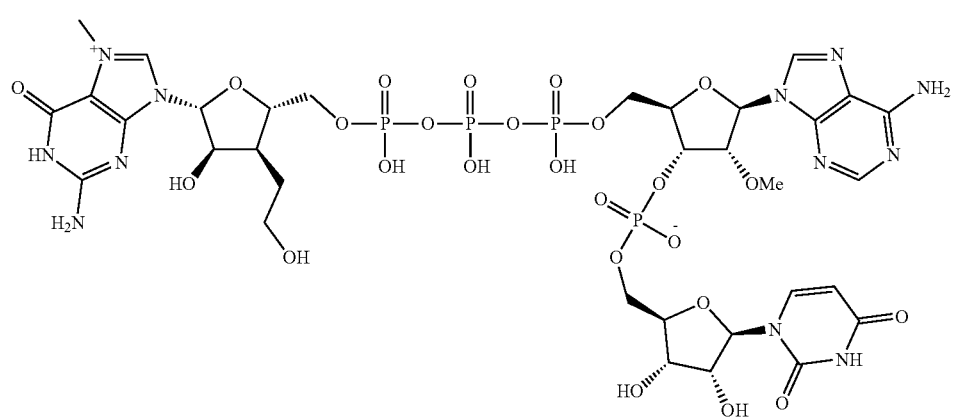

Compound 155
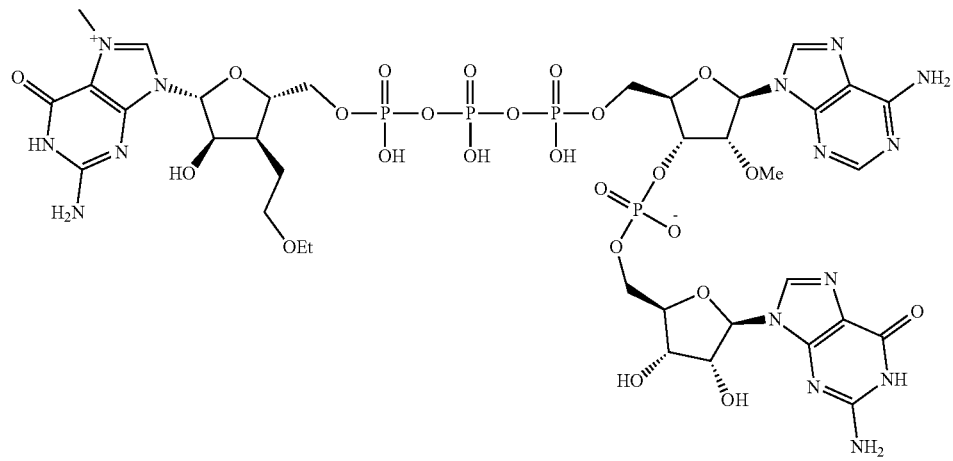
Compound 156
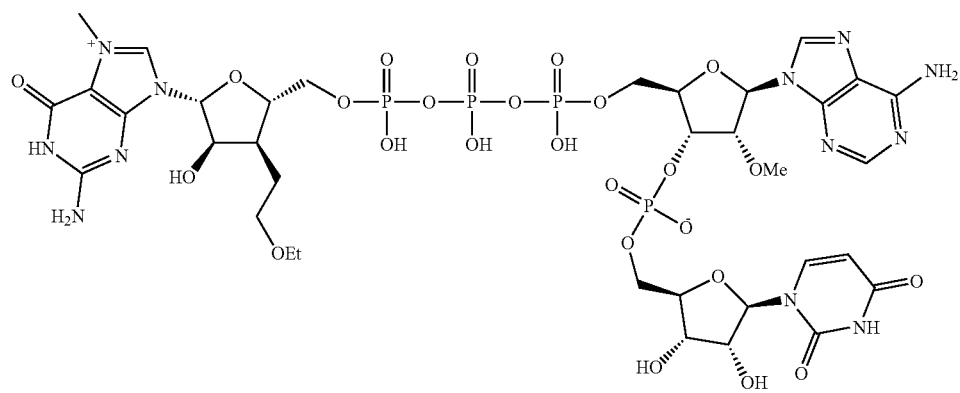
Compound 157
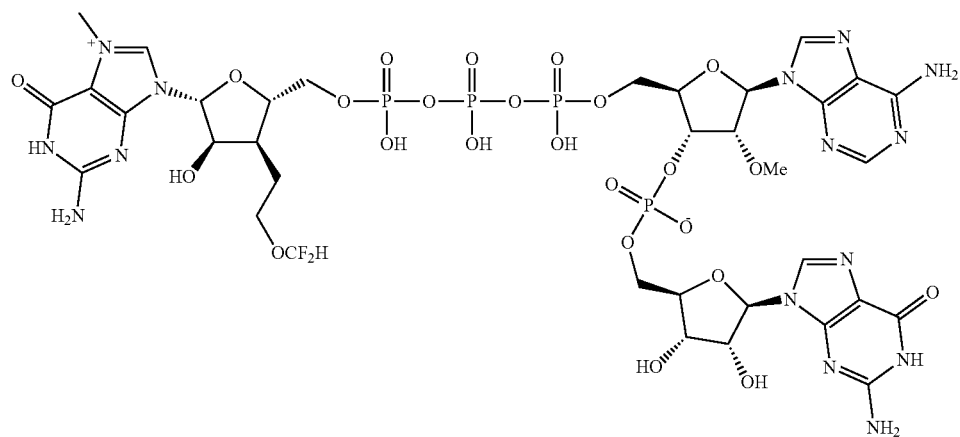

-continued
Compound 158
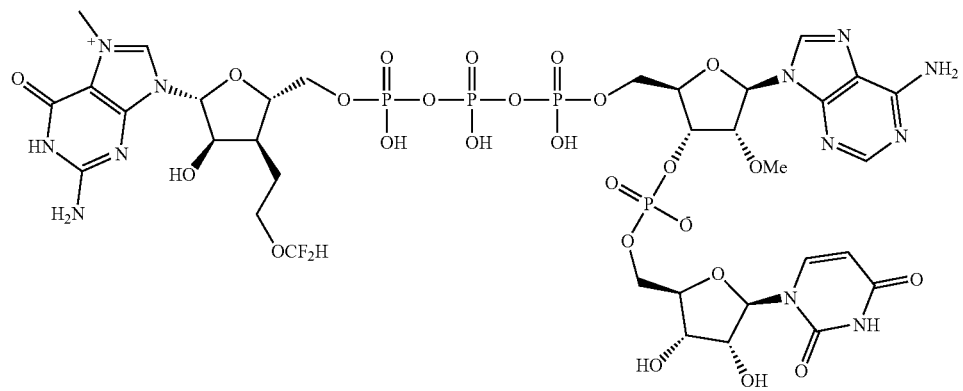
Compound 159
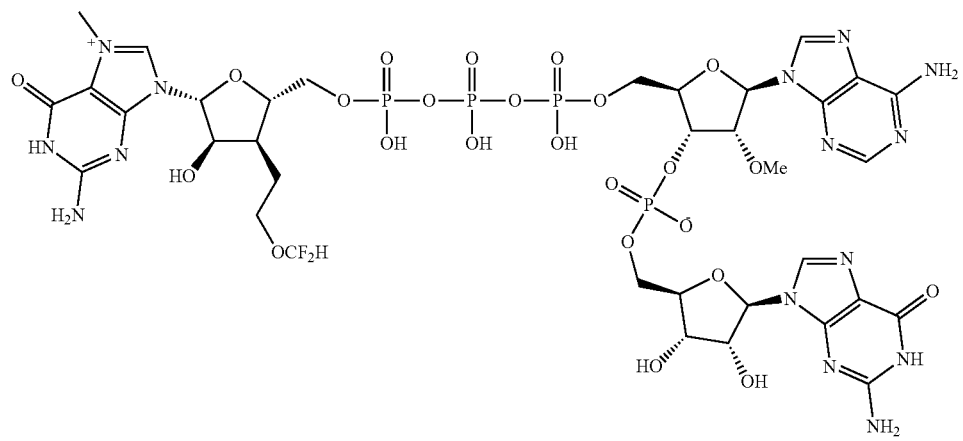
Compound 160
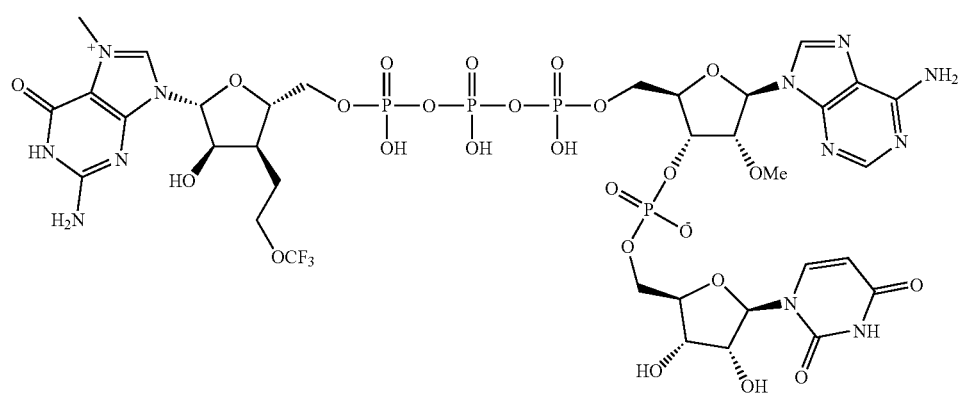
Compound 161
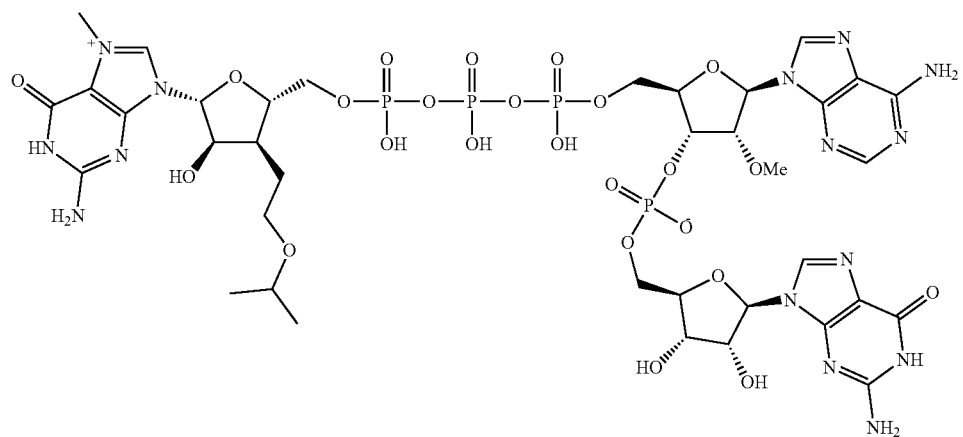

Compound 162
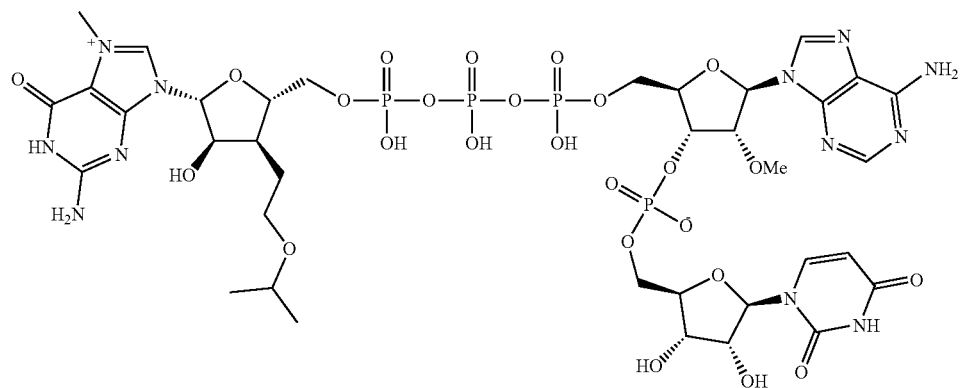
Compound 163
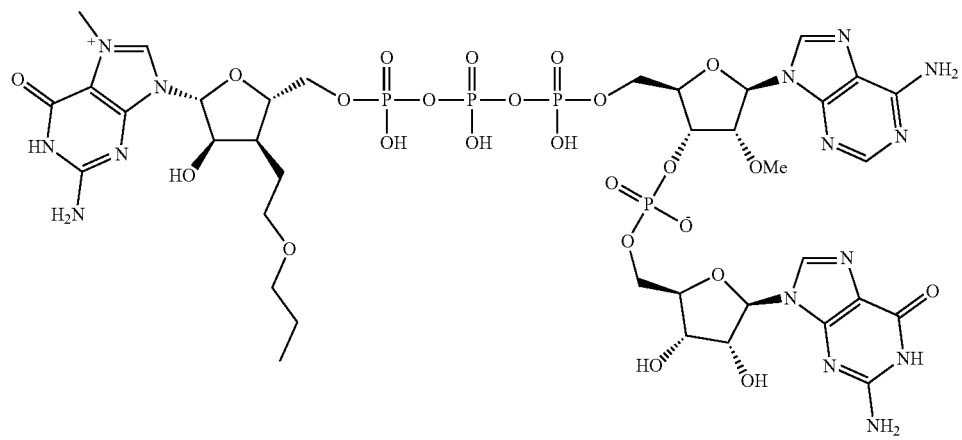
Compound 164
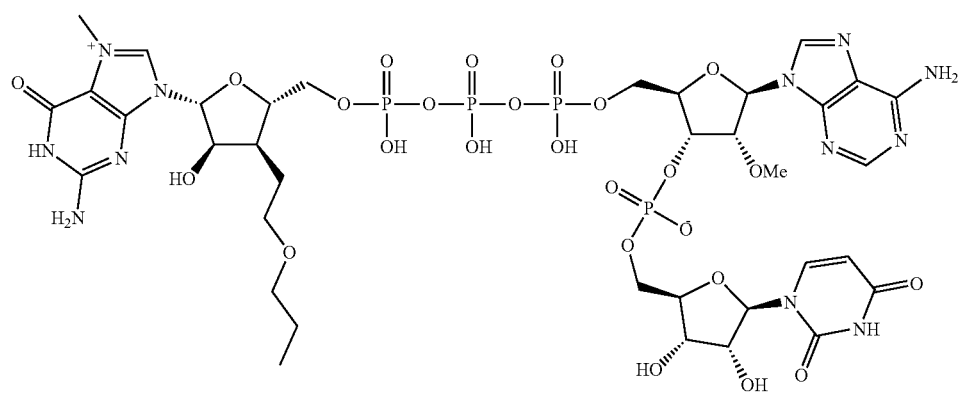
Compound 165
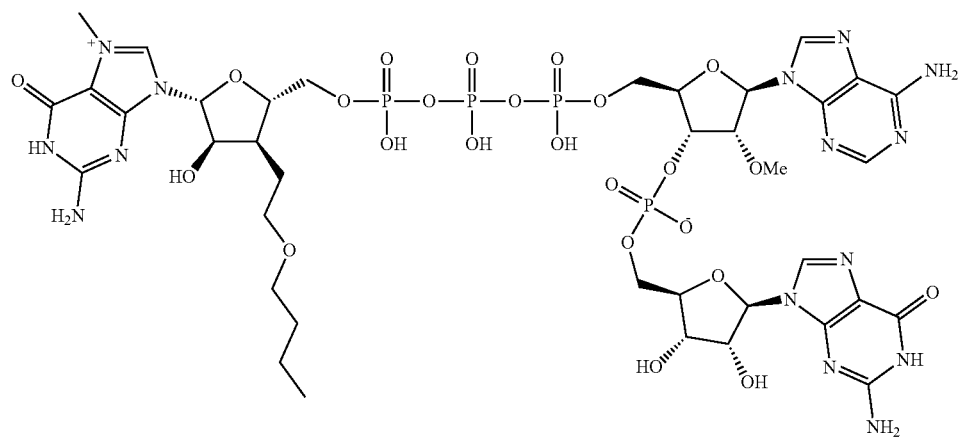

-continued
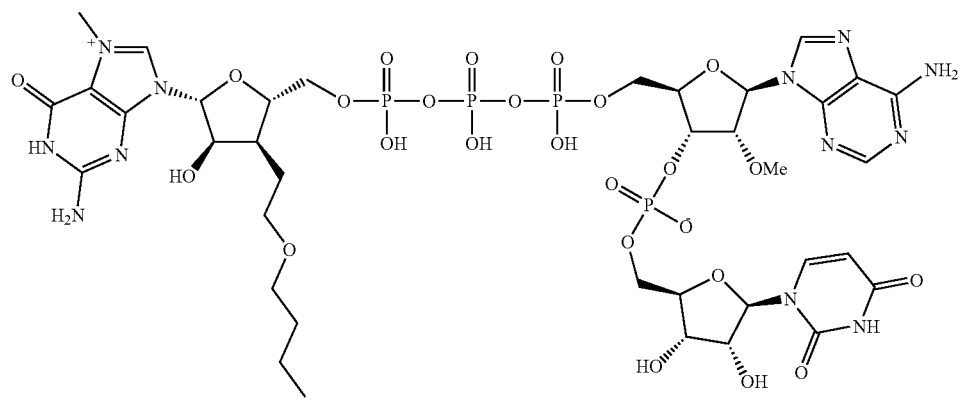
Compound 166
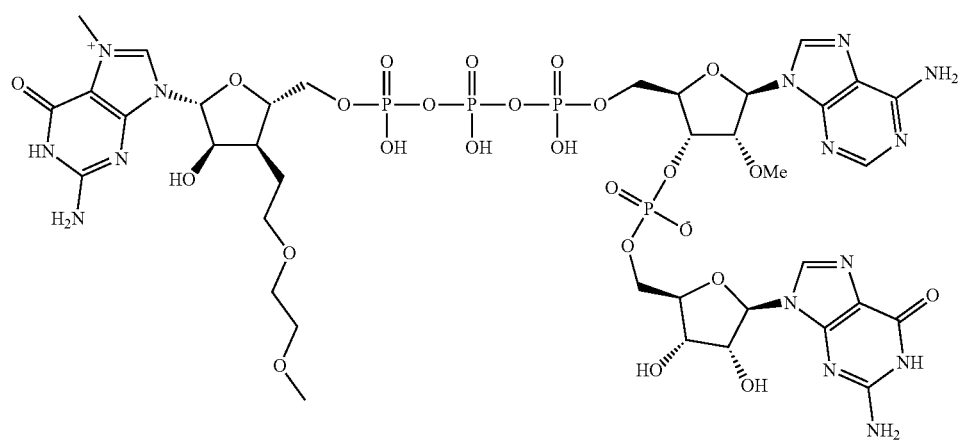
Compound 167
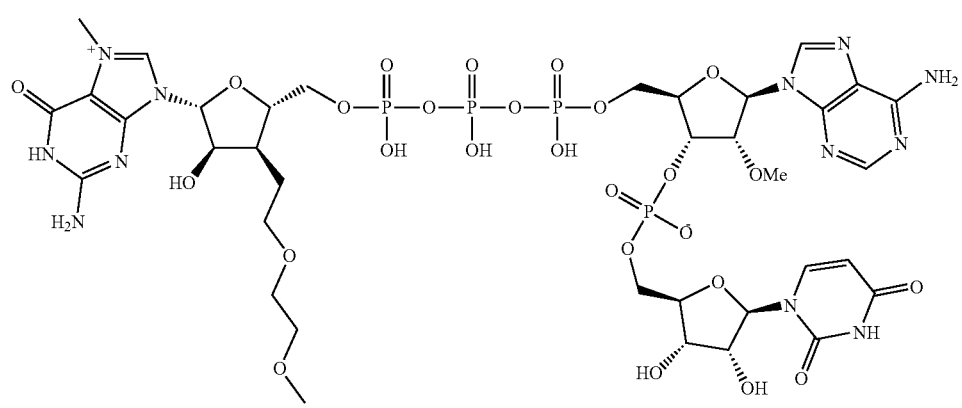
Compound 168

-continued
Compound 169
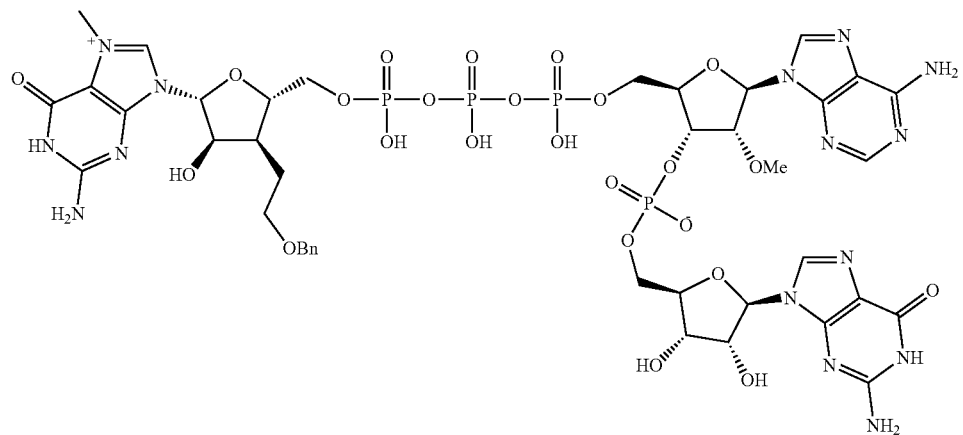
Compound 170
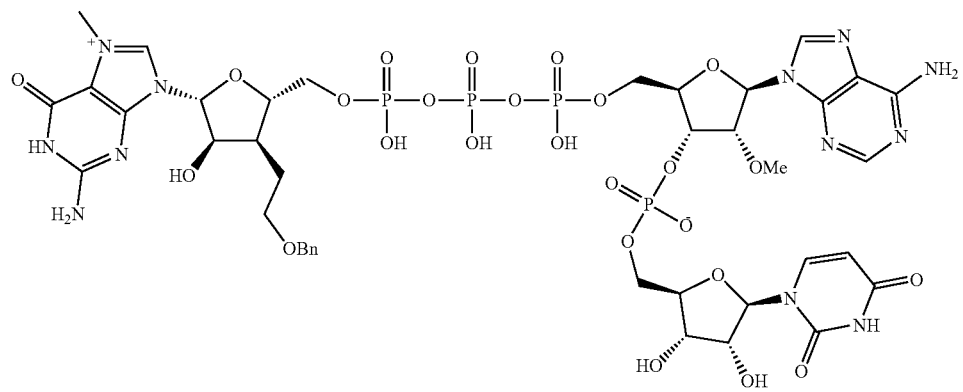
Compound 171
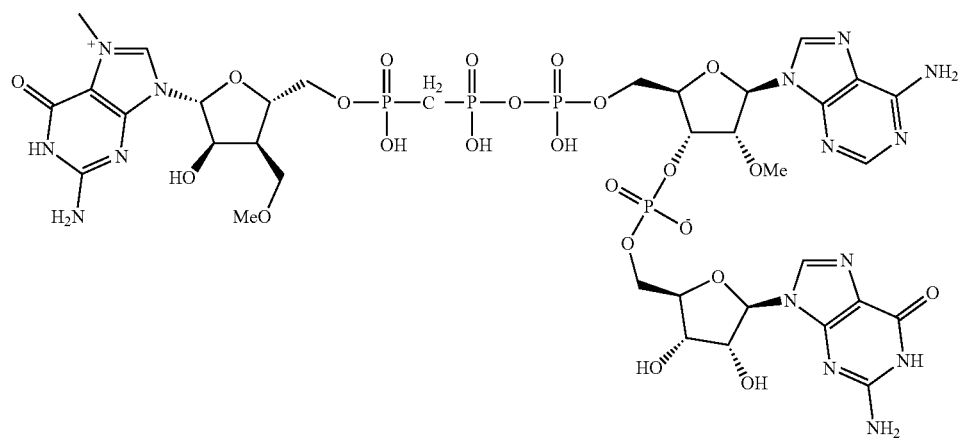
Compound 172
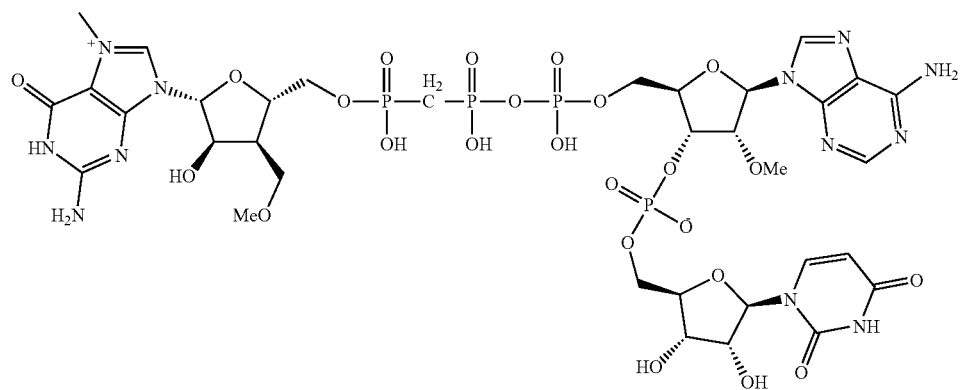

Compound 173
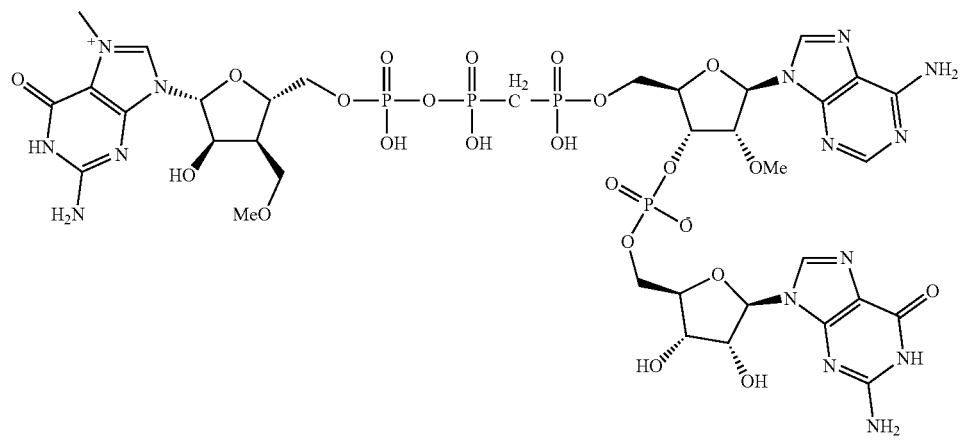
Compound 174
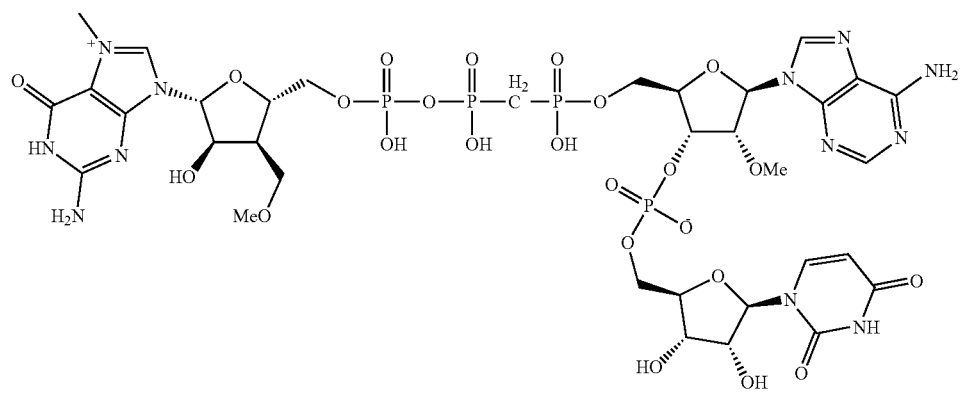
Compound 175
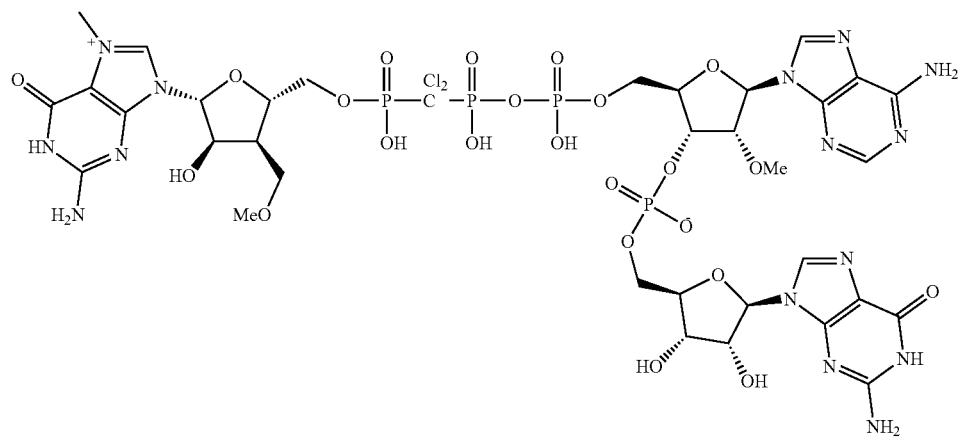
Compound 176
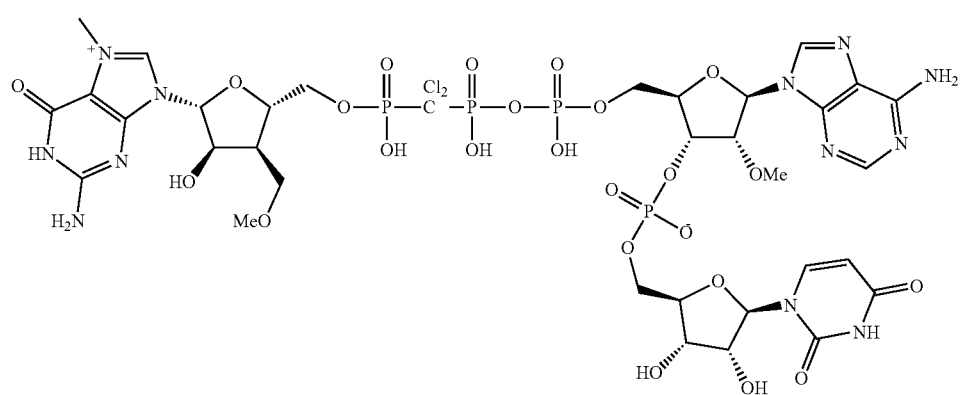

-continued
Compound 177
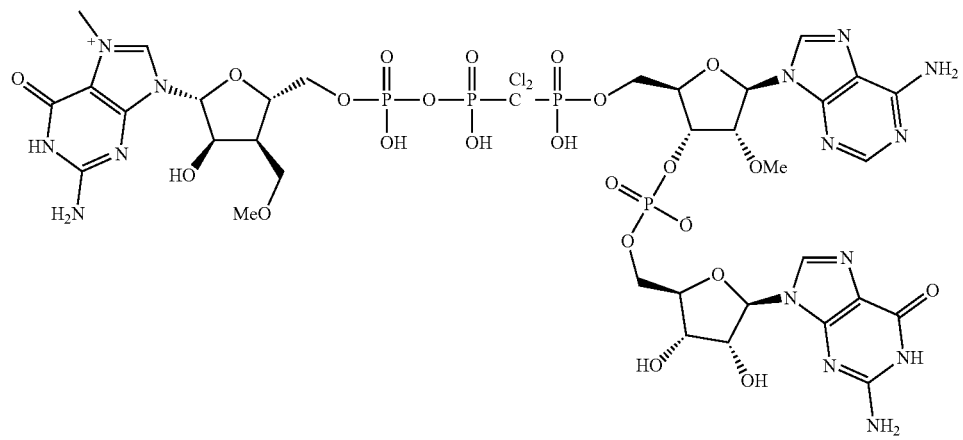
Compound 178
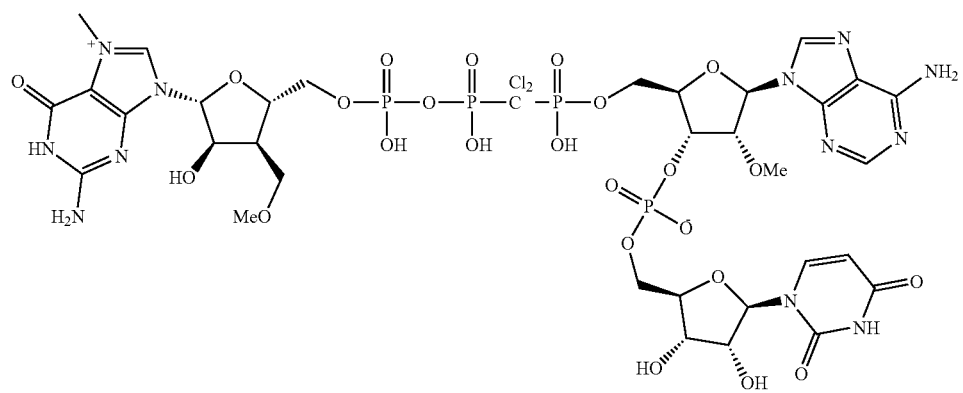
Compound 179
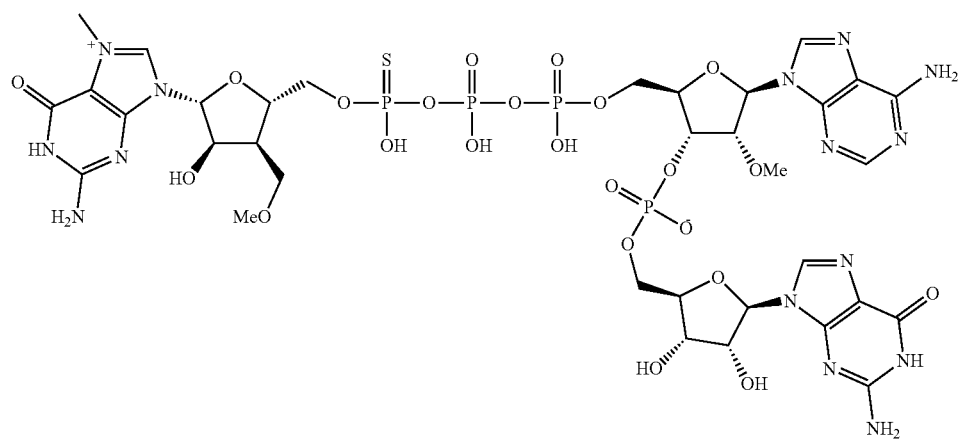
Compound 180
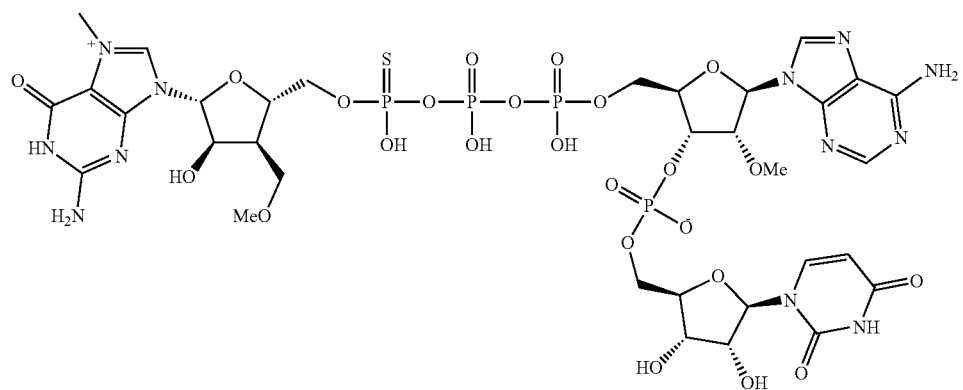

-continued
Compound 181
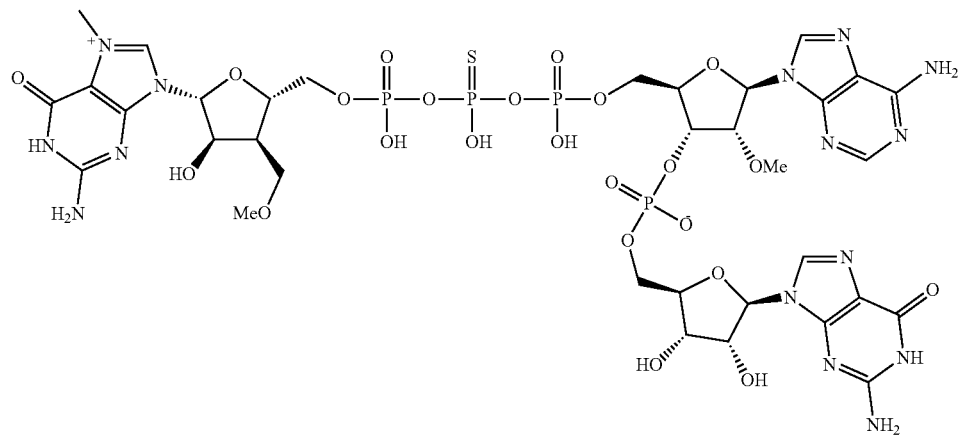
Compound 182
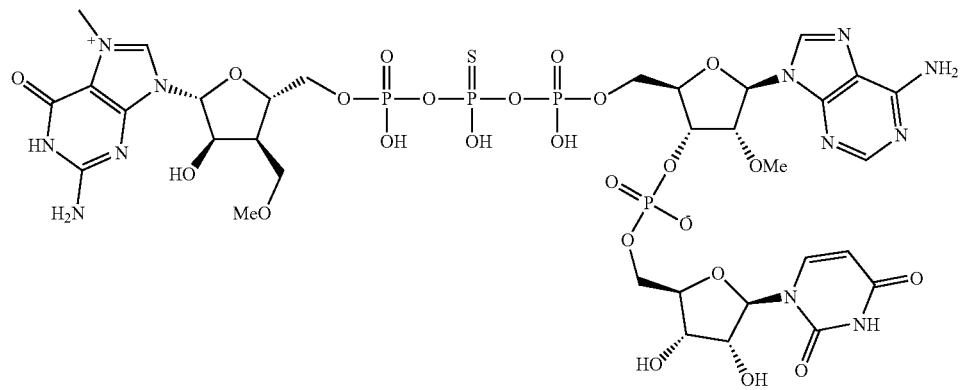
Compound 183
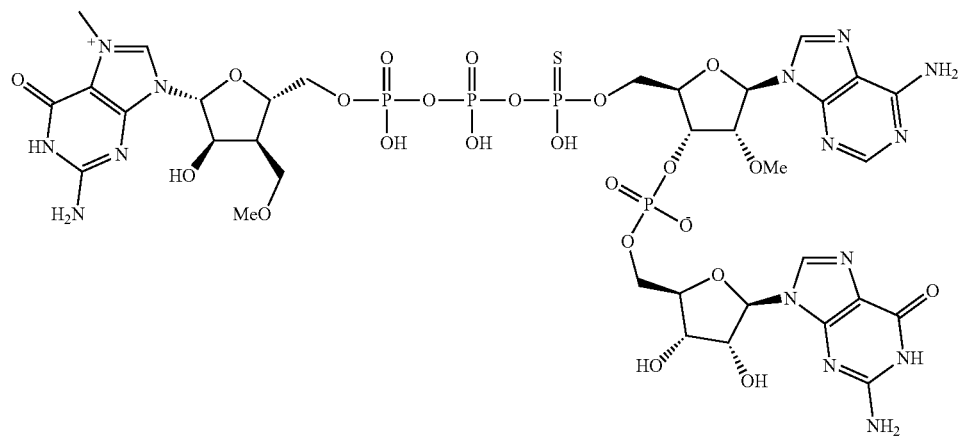
Compound 184
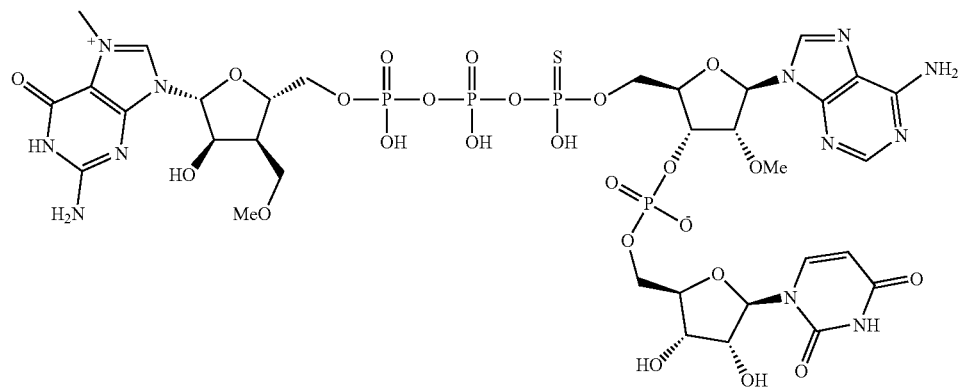

Compound 185
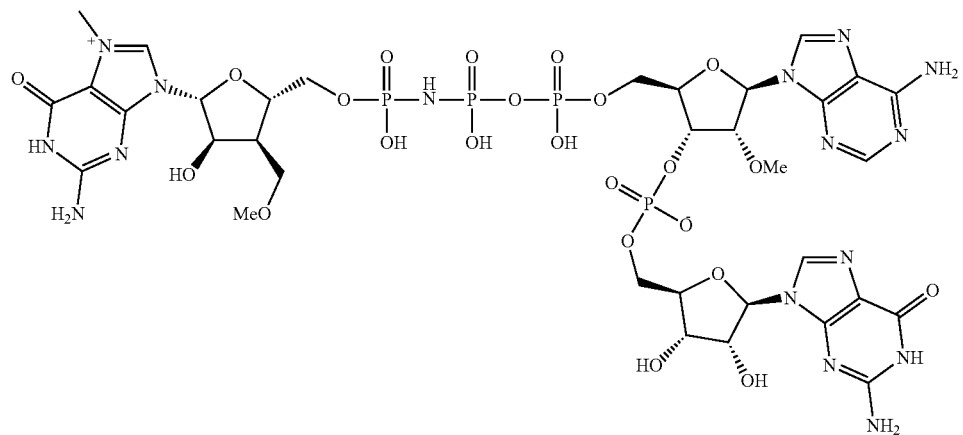
Compound 186
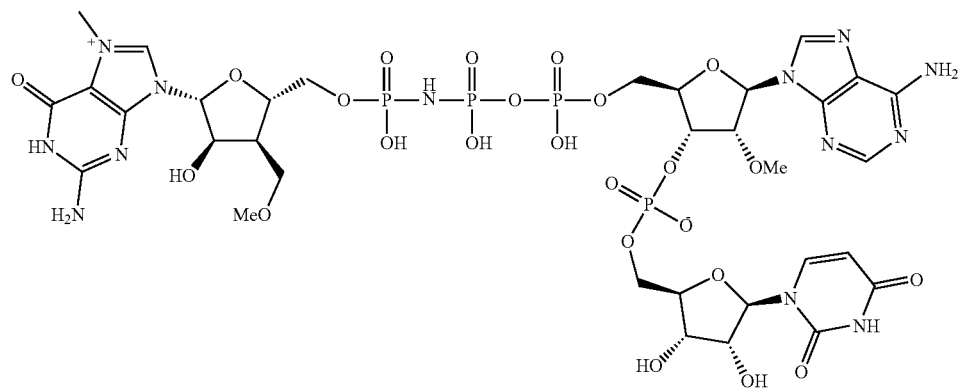
Compound 187
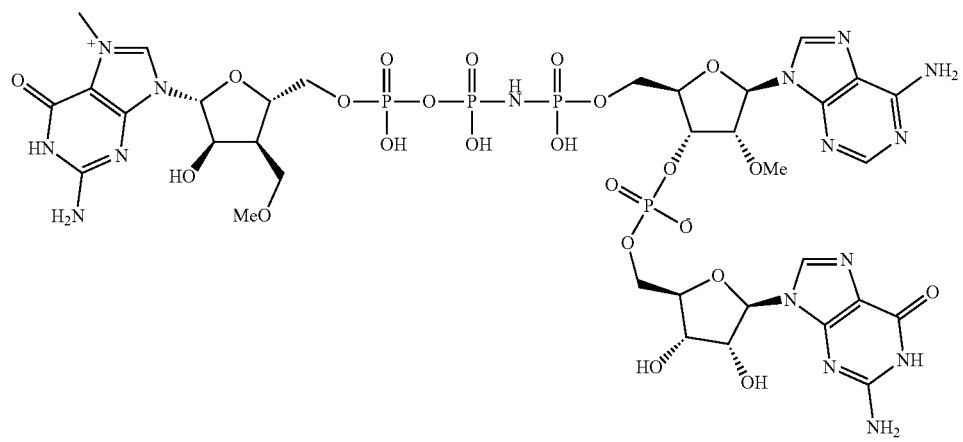
Compound 188
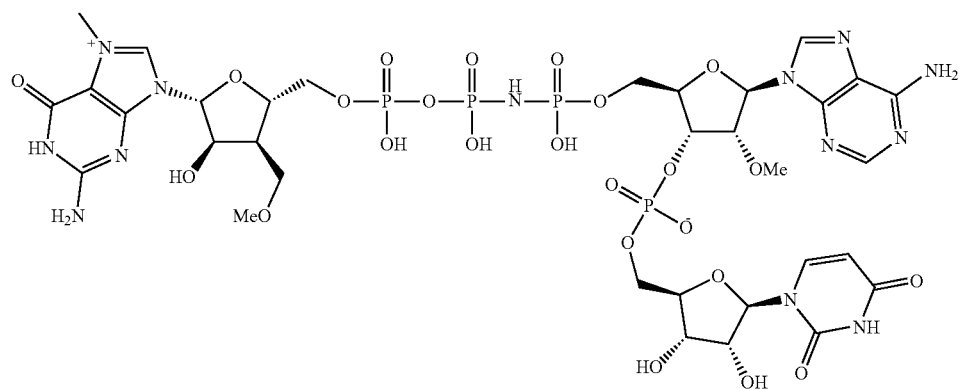

Compound 189
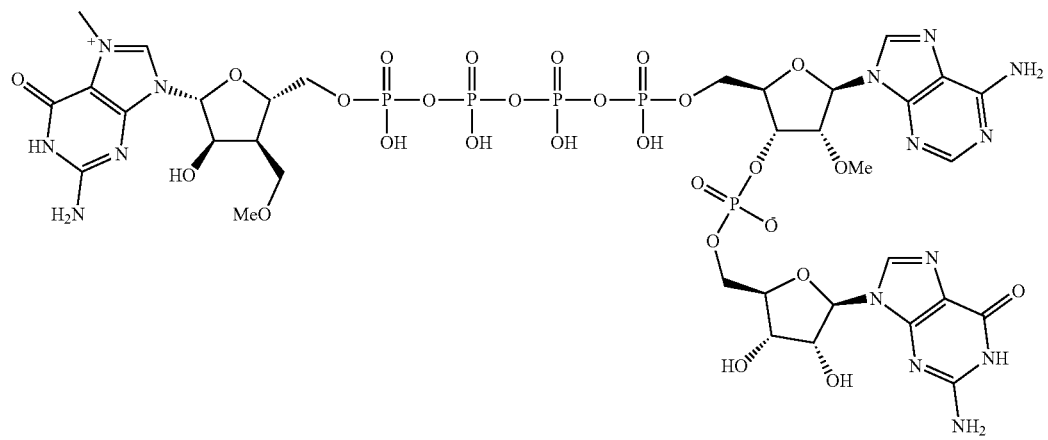
Compound 190
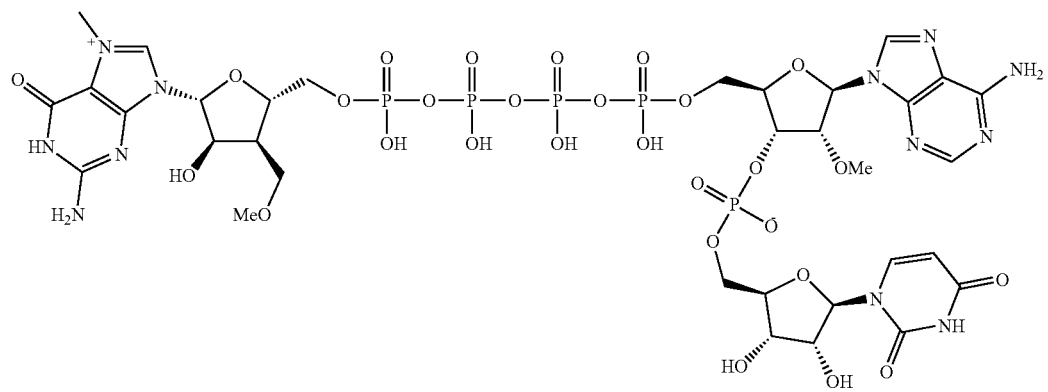
Compound 191
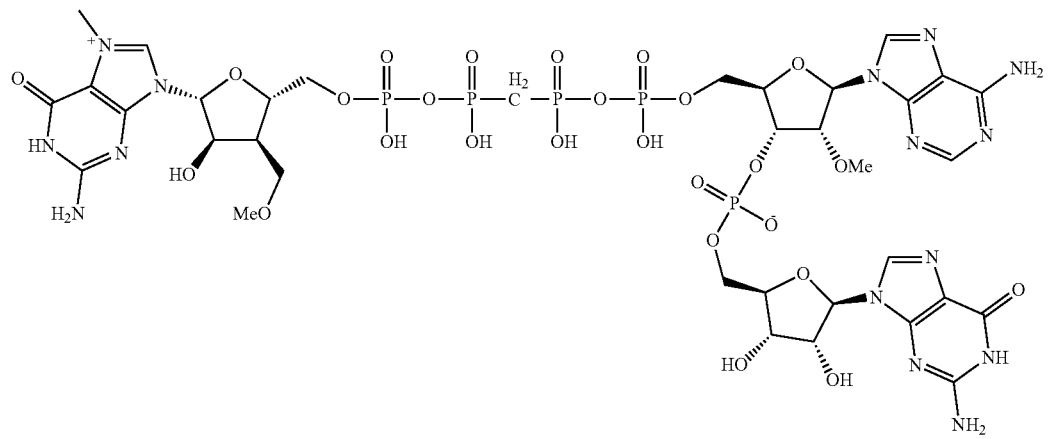
Compound 192
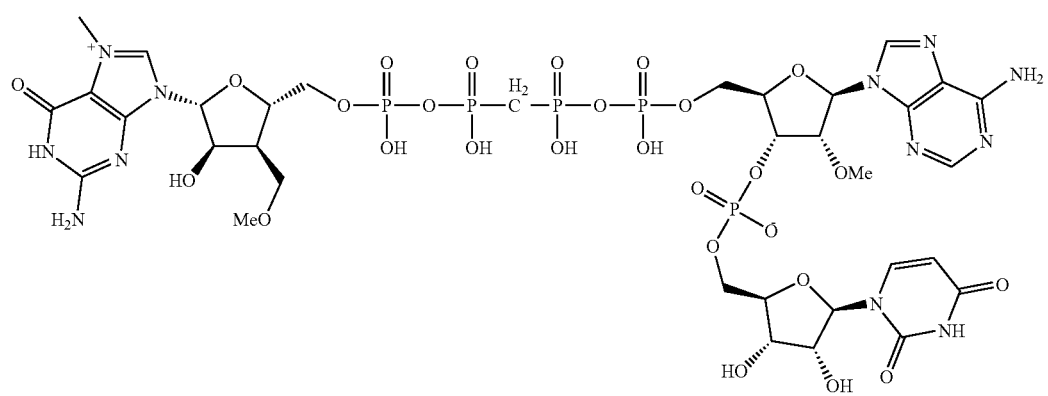

Compound 193
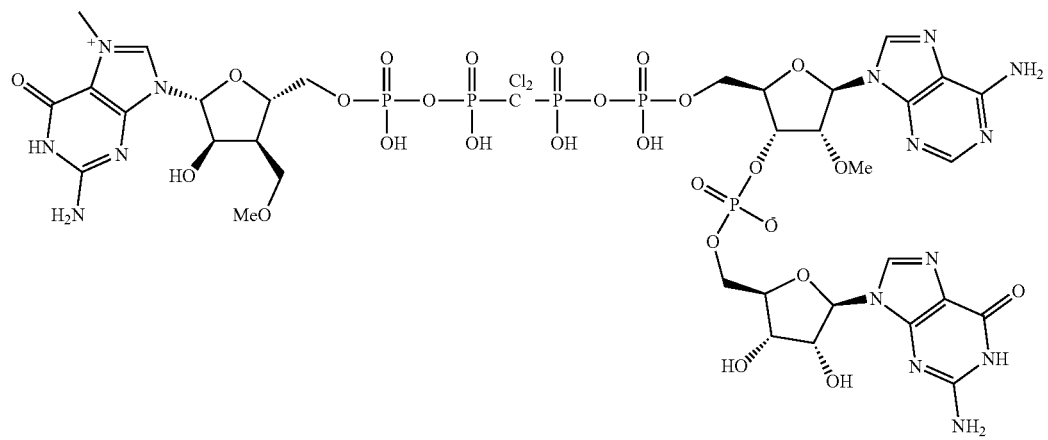
Compound 194
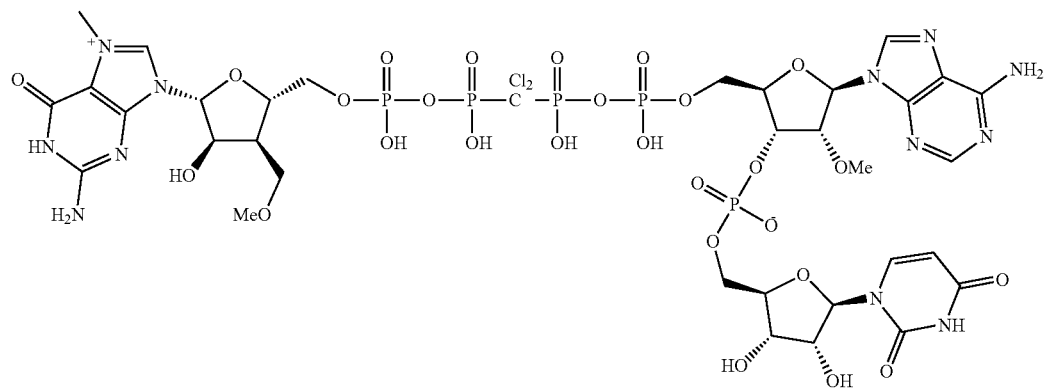
Compound 195
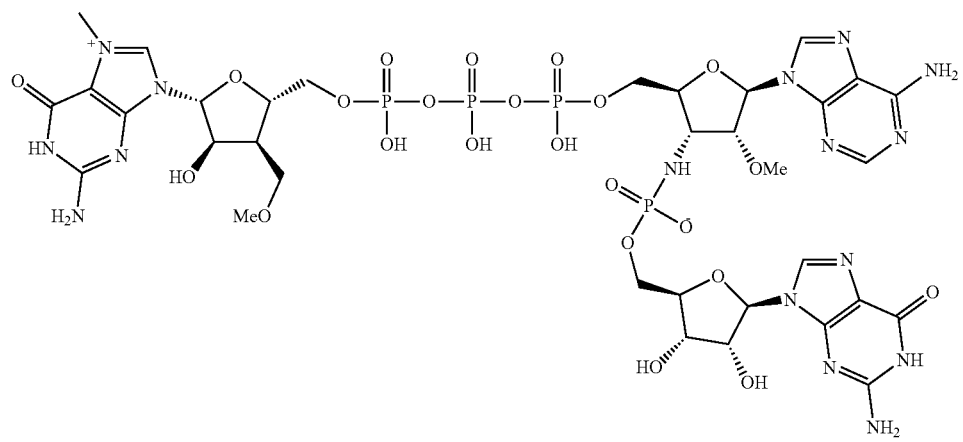
Compound 196
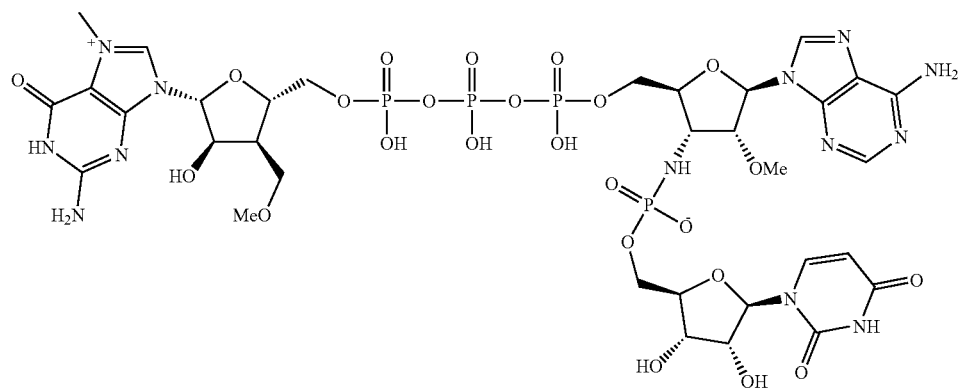

-continued
Compound 197
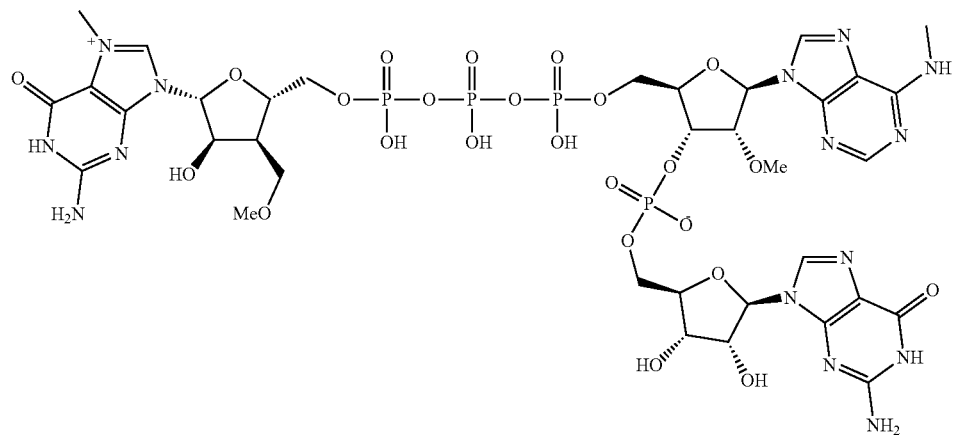
Compound 198
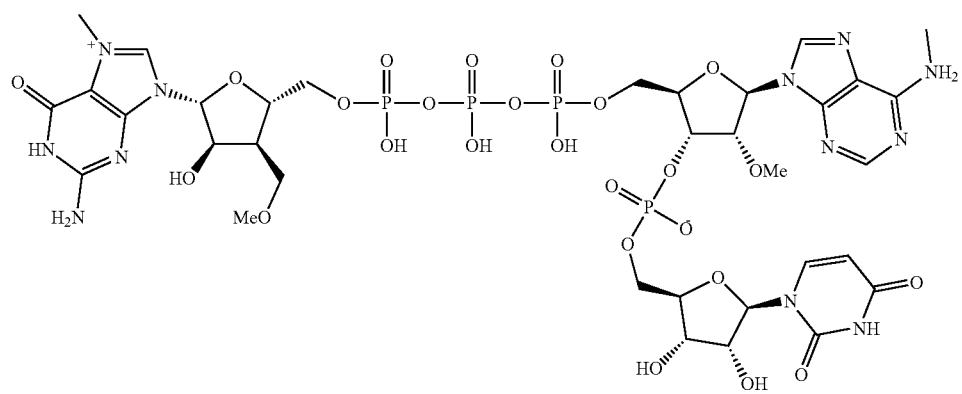
Compound 199
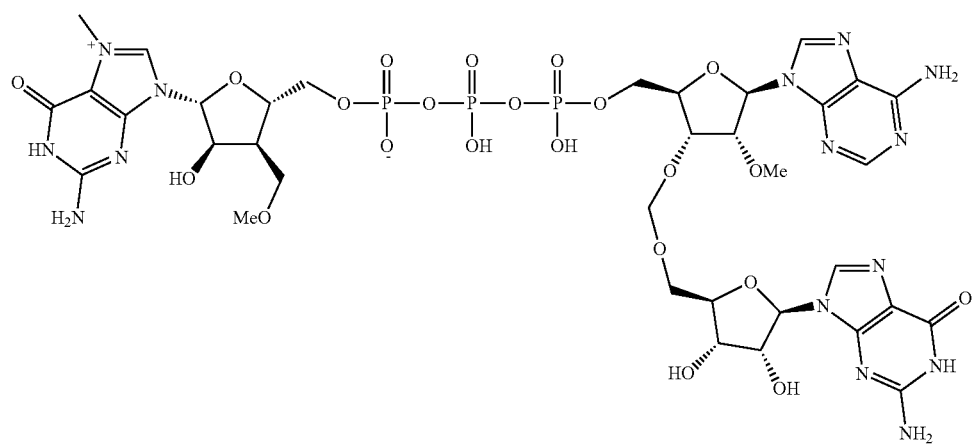

-continued
Compound 200
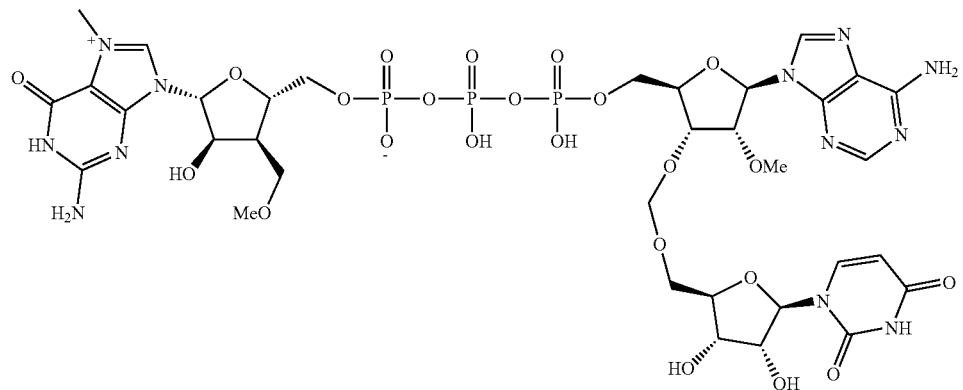
Compound 201
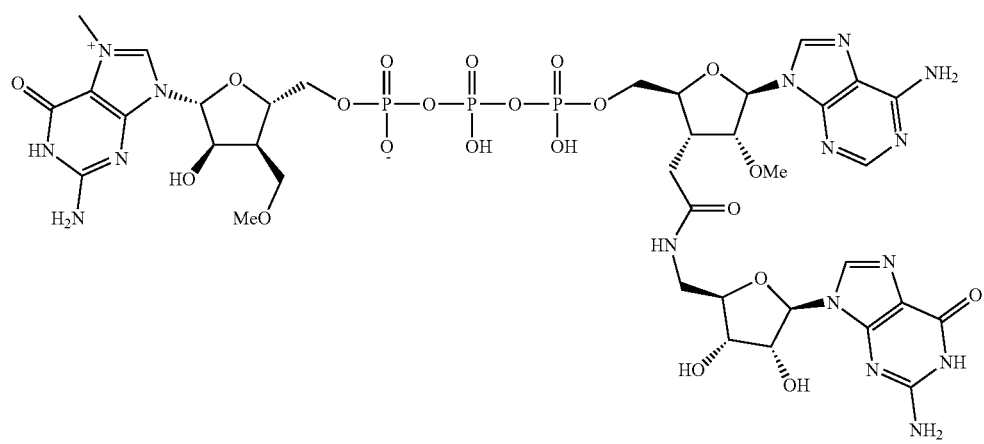
Compound 202
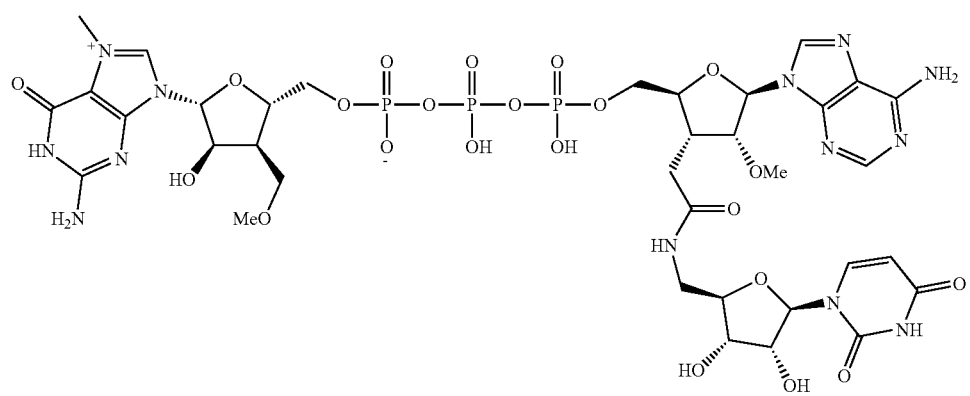
Compound 203
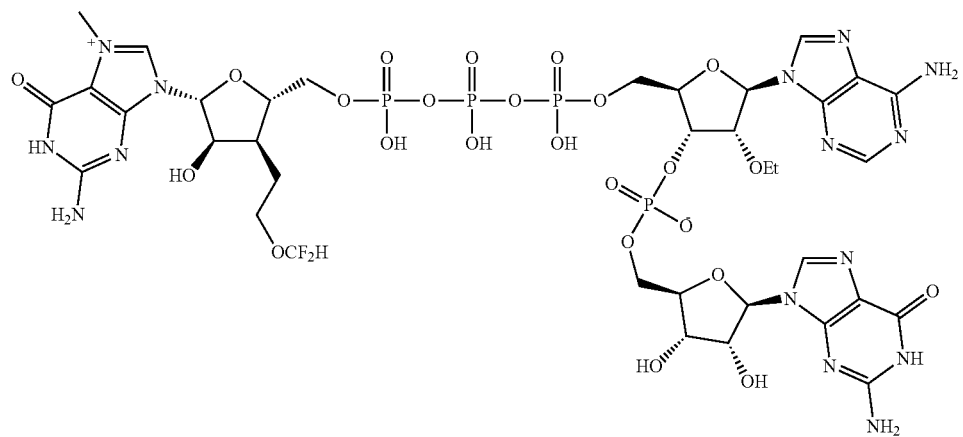

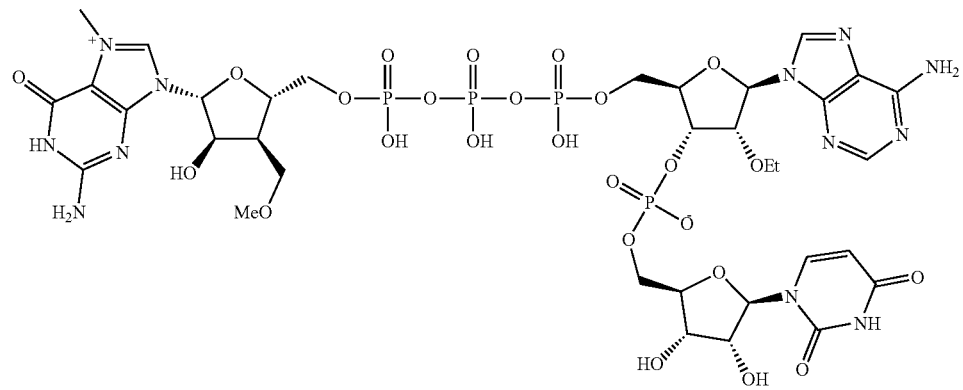
Compound 204
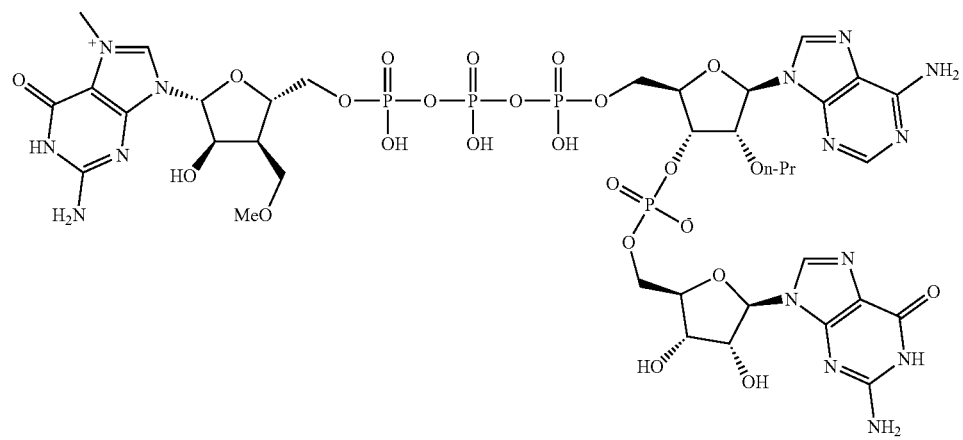
Compound 205
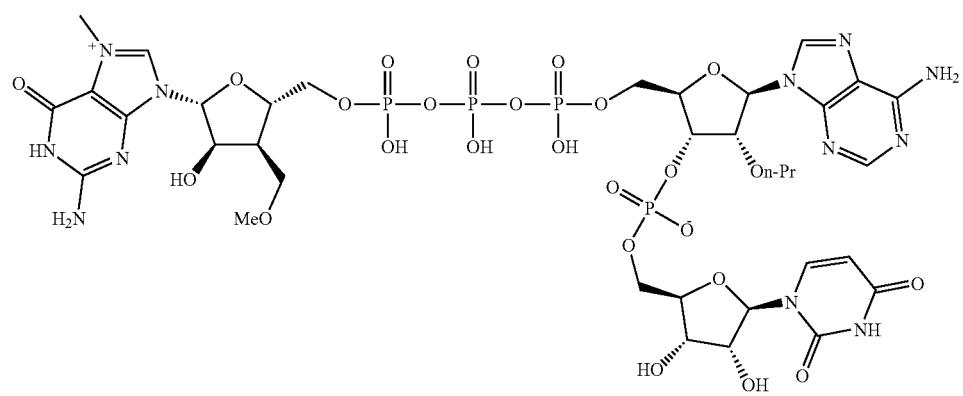
Compound 206
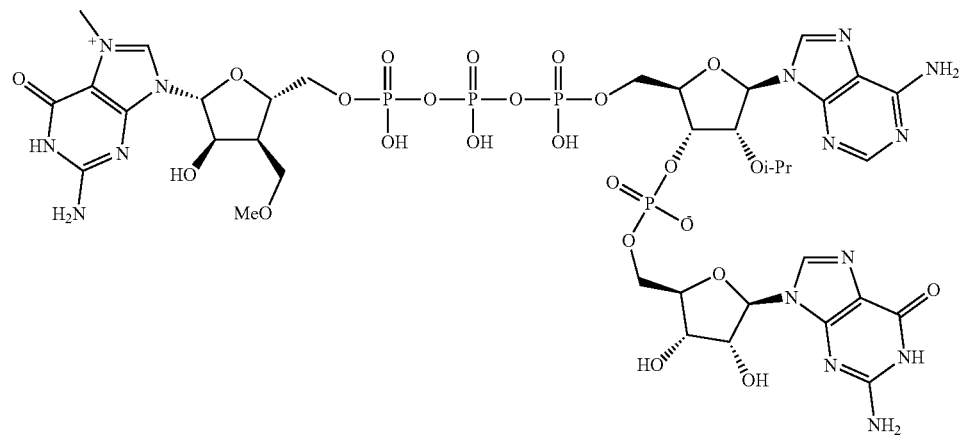
Compound 207

-continued
Compound 208
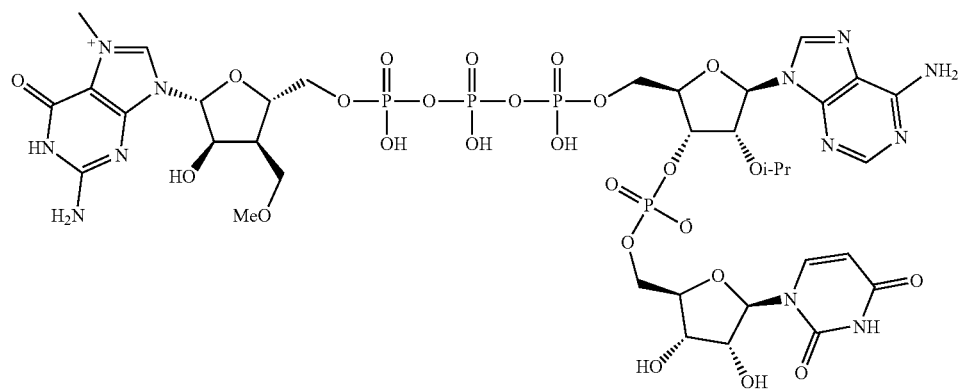
Compound 209
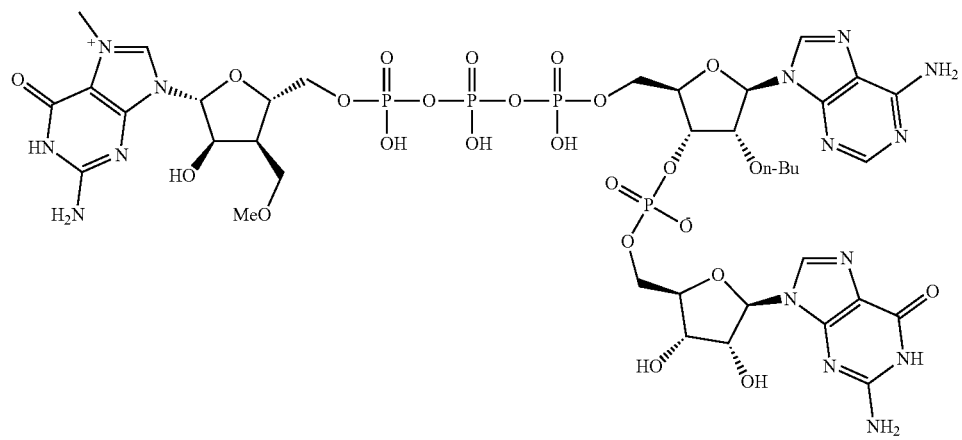
Compound 210
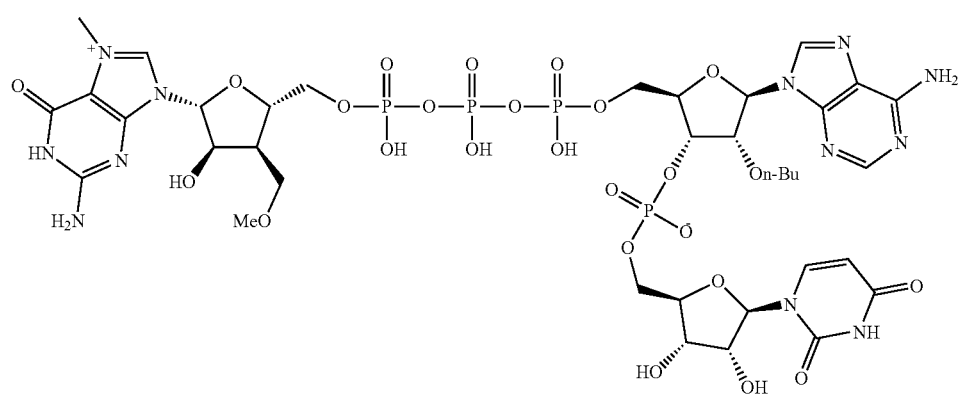

Compound 211
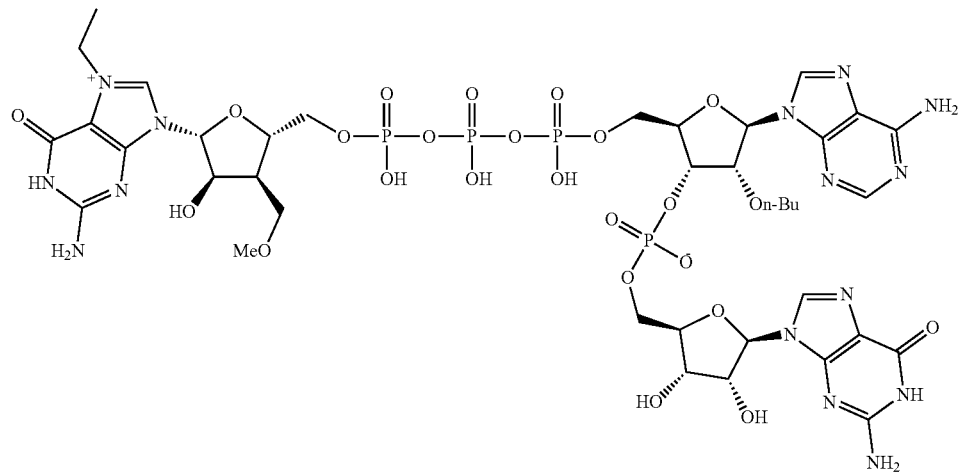
Compound 212
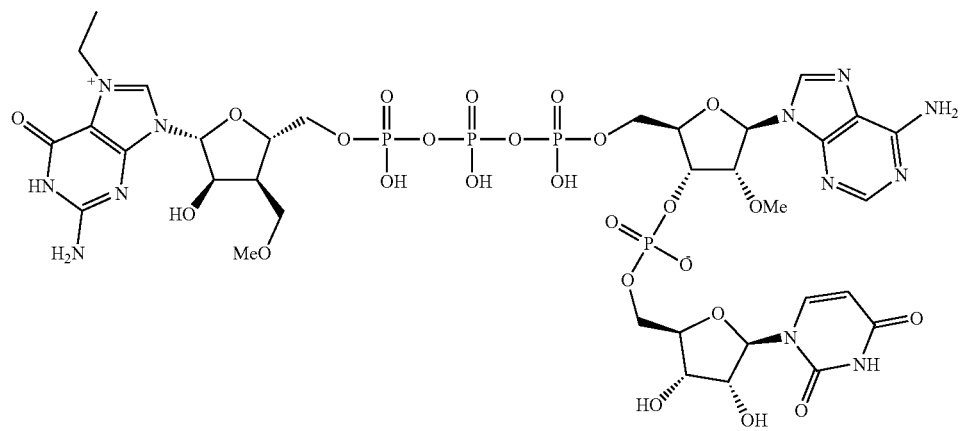
Compound 213
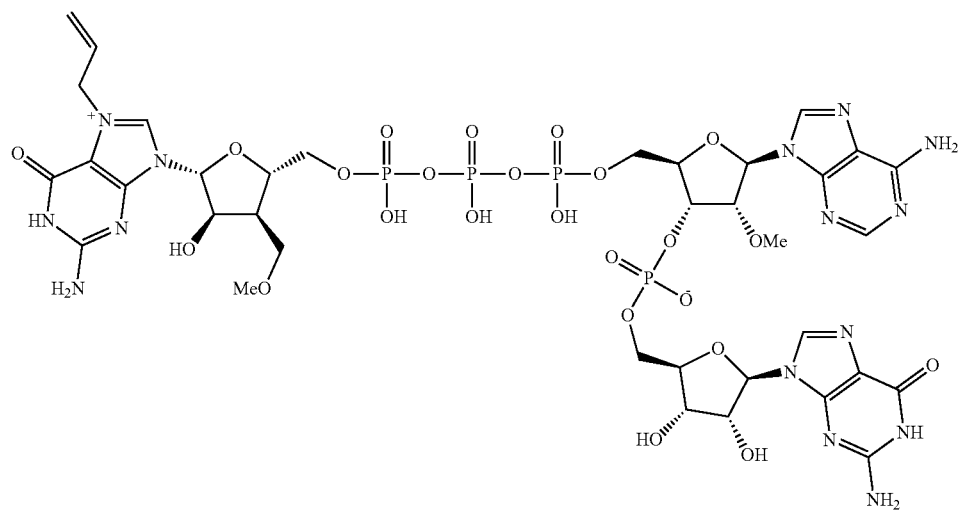

-continued
Compound 214
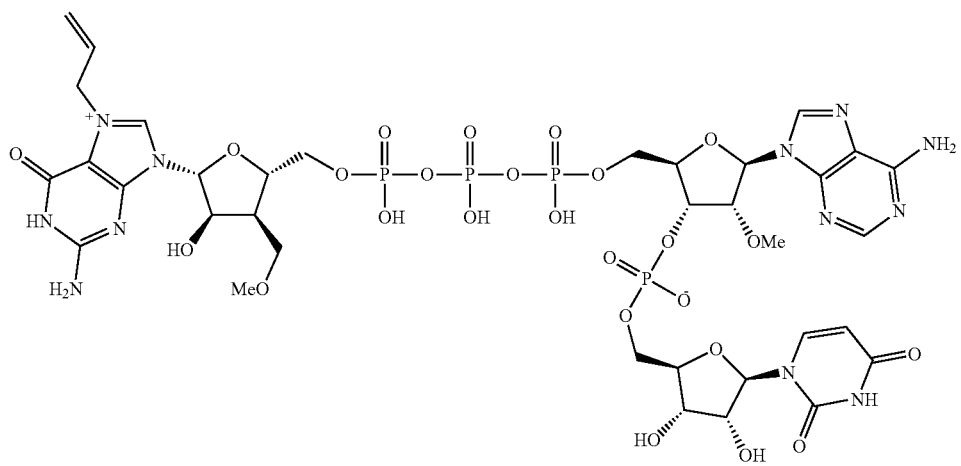
Compound 215
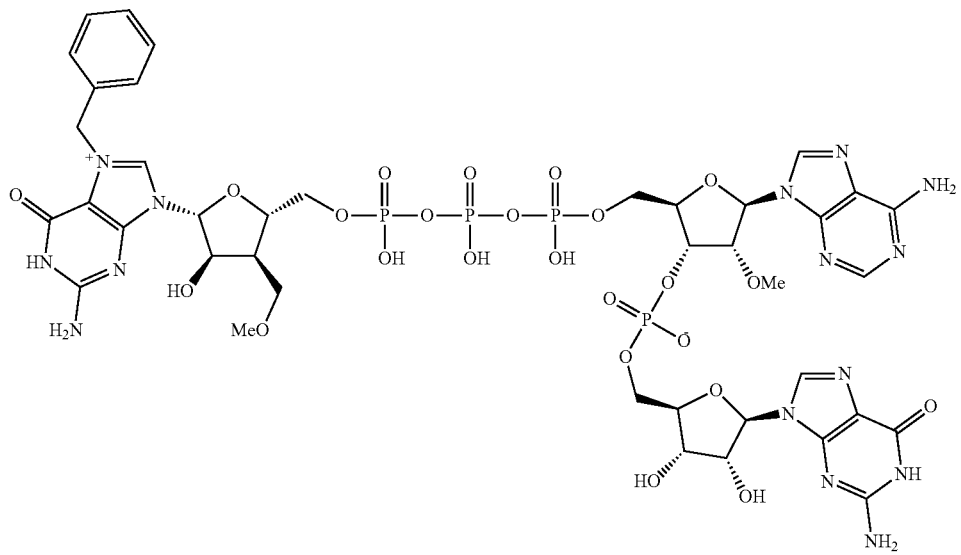
Compound 216
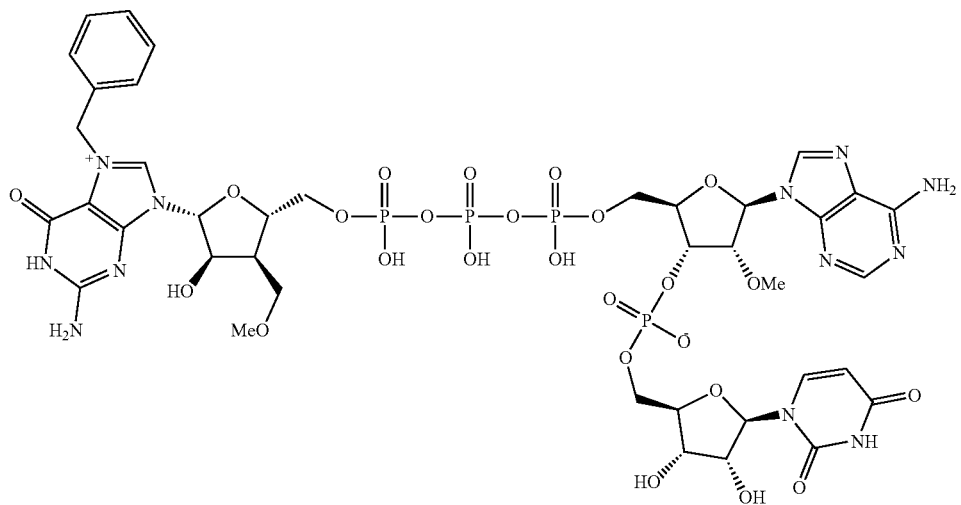

-continued
Compound 217
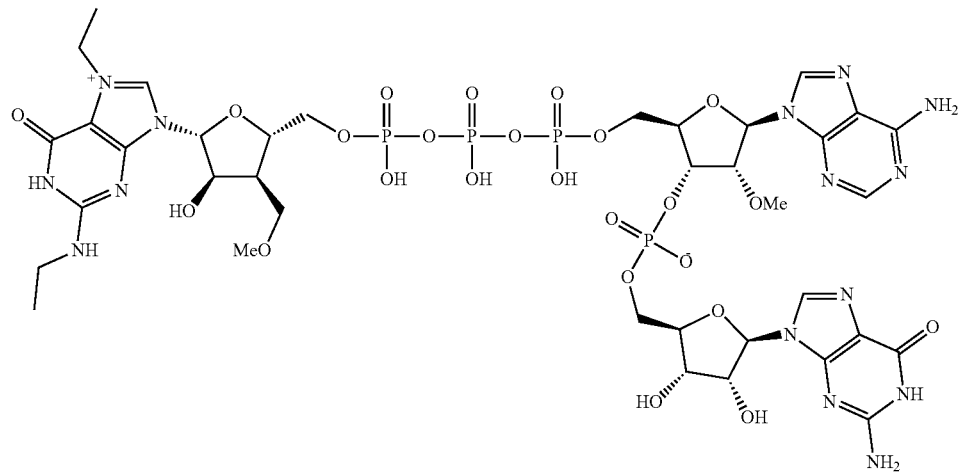
Compound 218
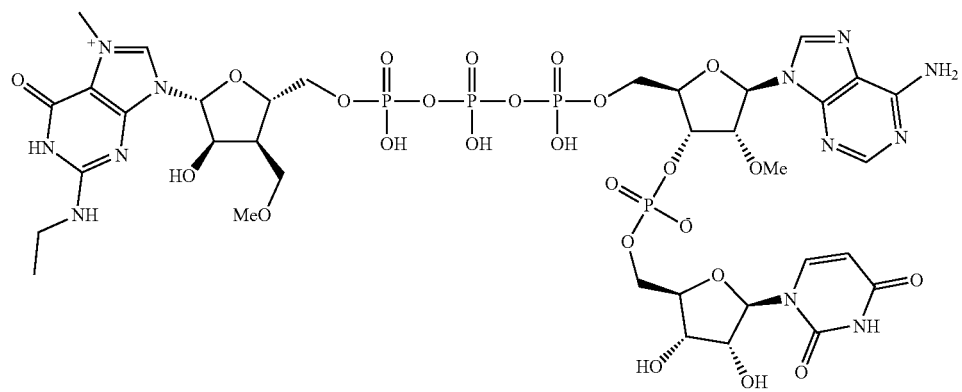
Compound 219
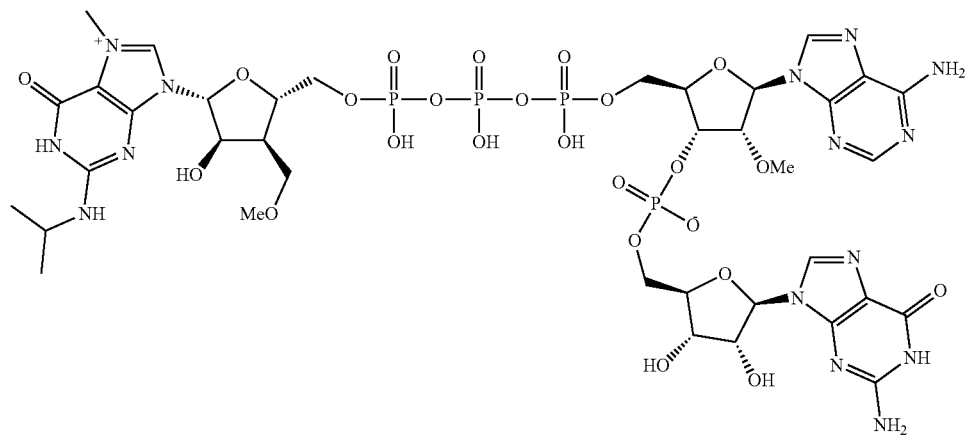

-continued
Compound 220
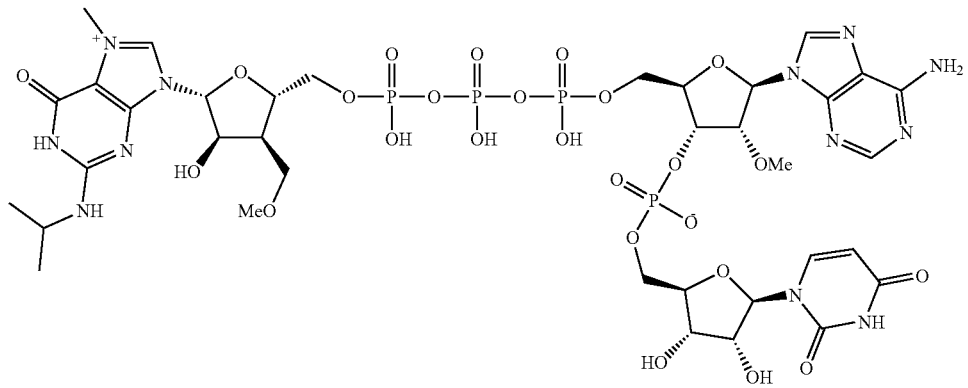
Compound 225
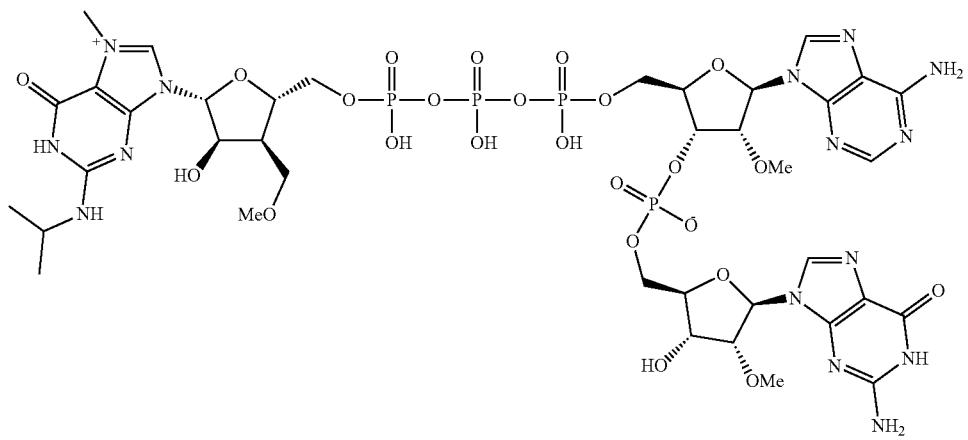
Compound 226
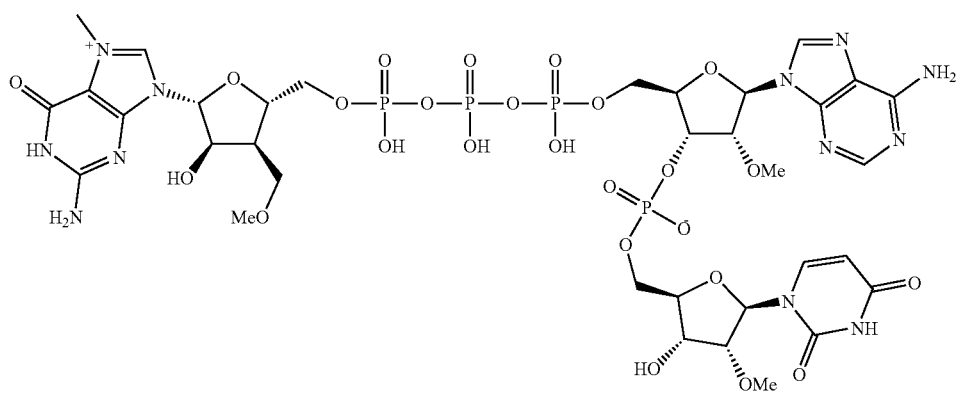
Compound 227
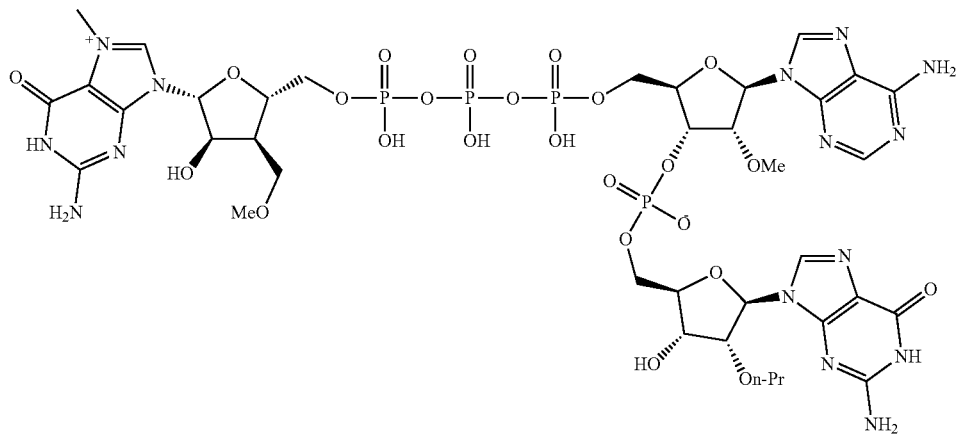

-continued
Compound 228
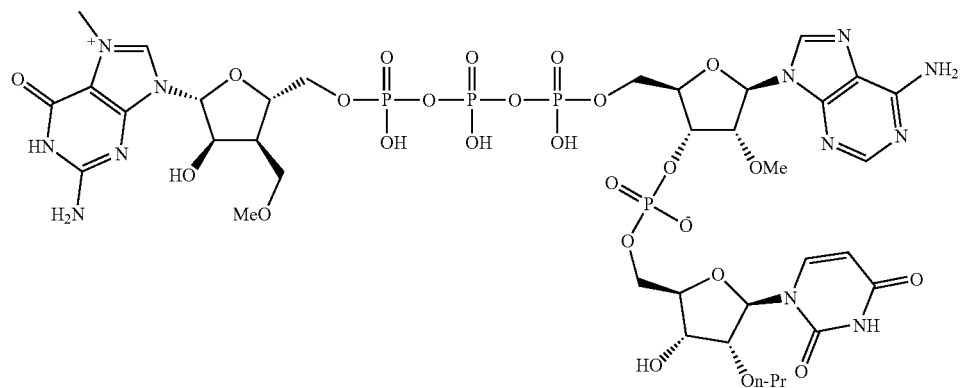
Compound 229
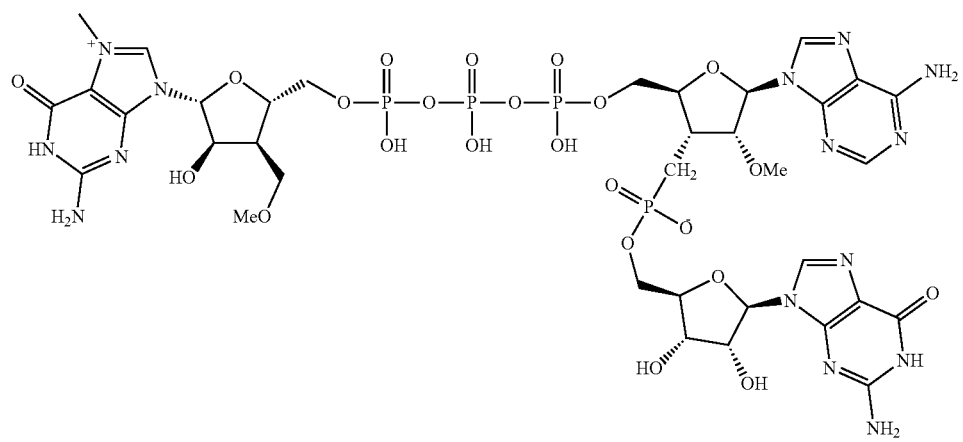
Compound 230
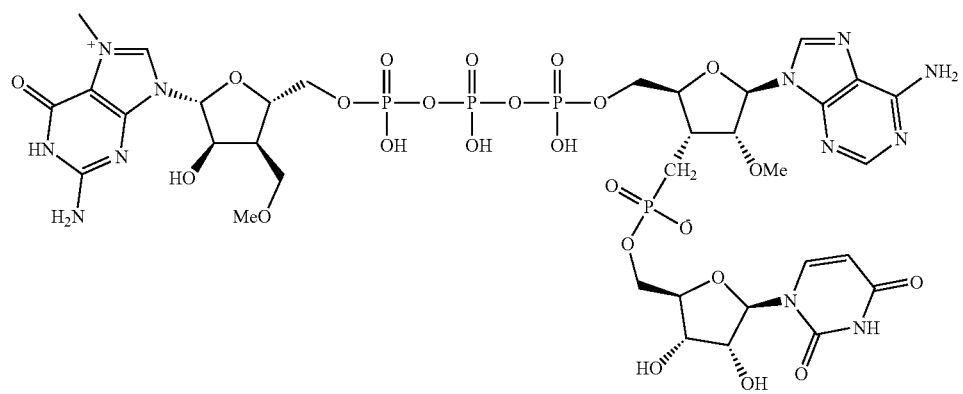
Compound 231
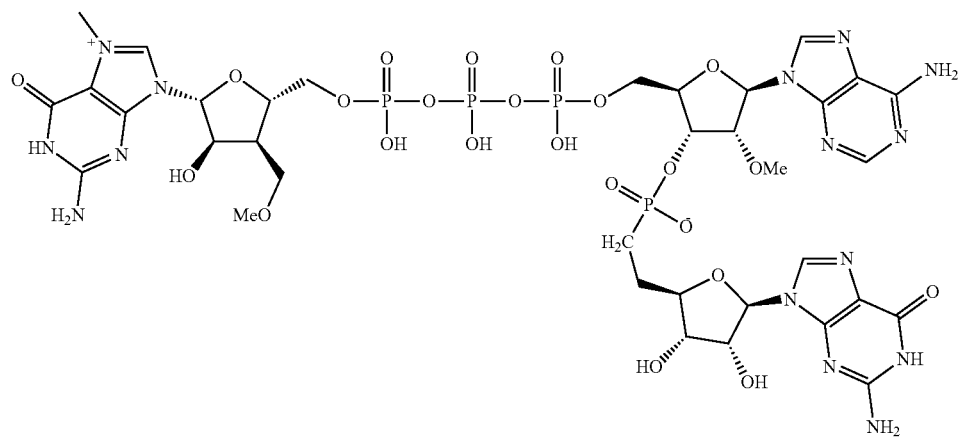

Compound 232
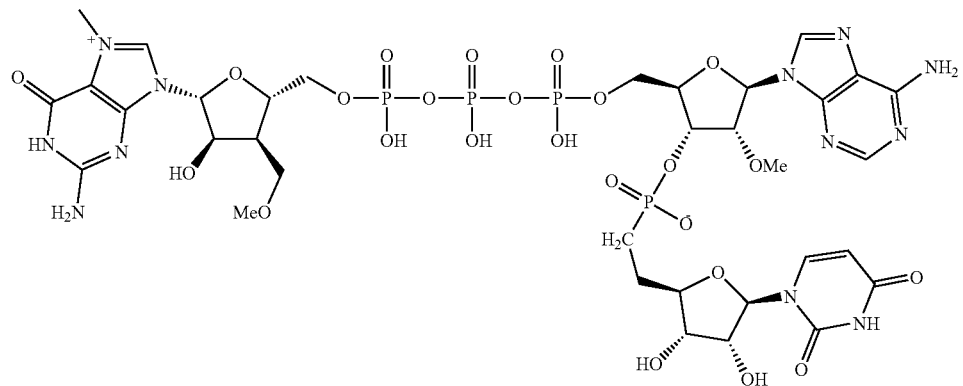
Compound 233
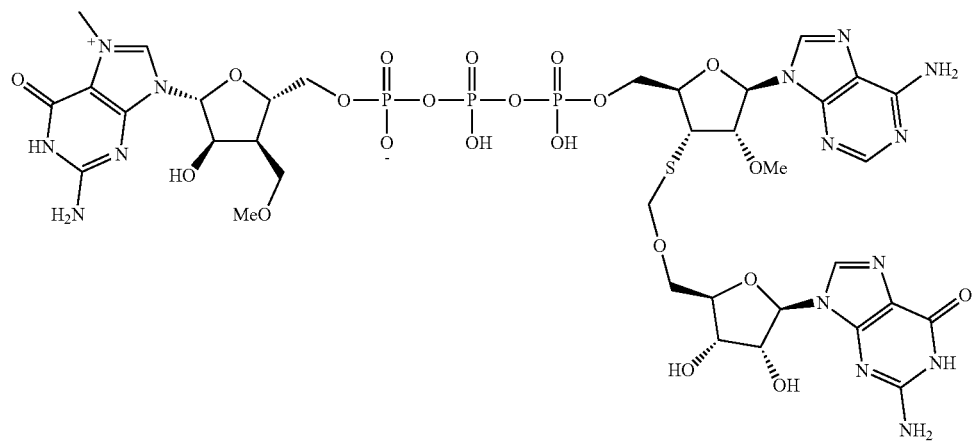
Compound 234
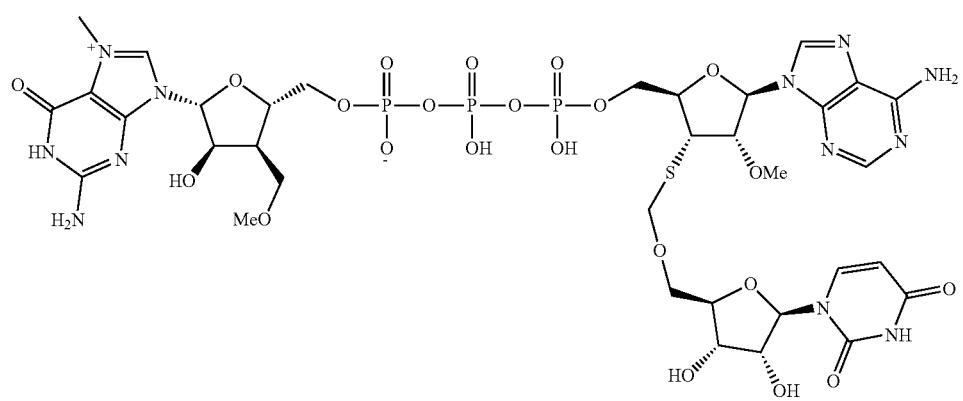
Compound 235
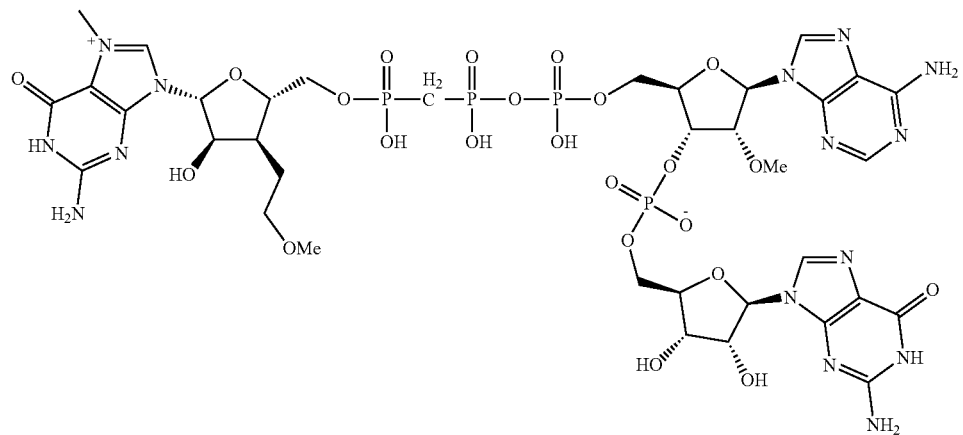

-continued
Compound 236
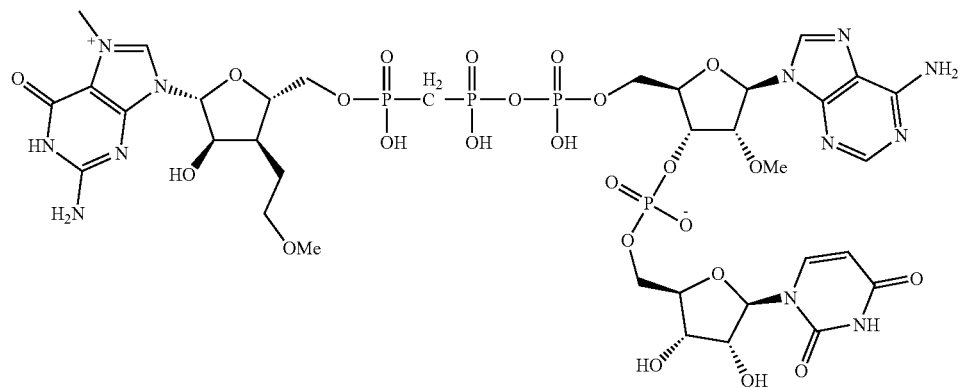
Compound 237
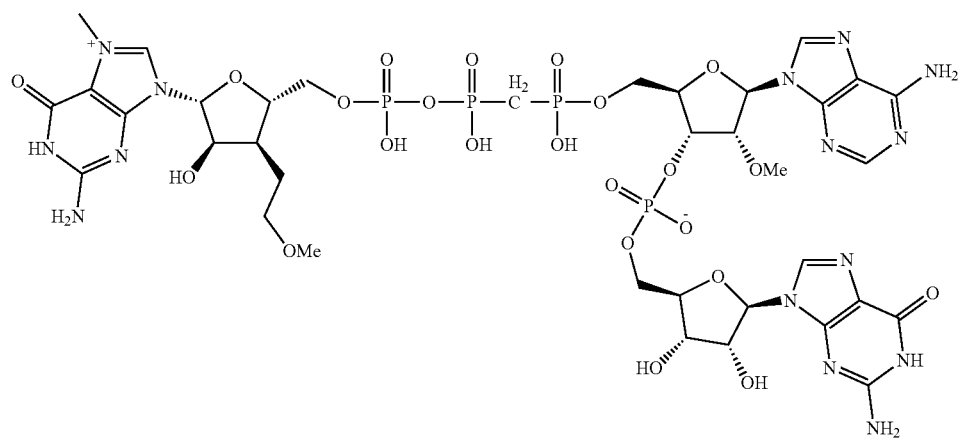
Compound 238
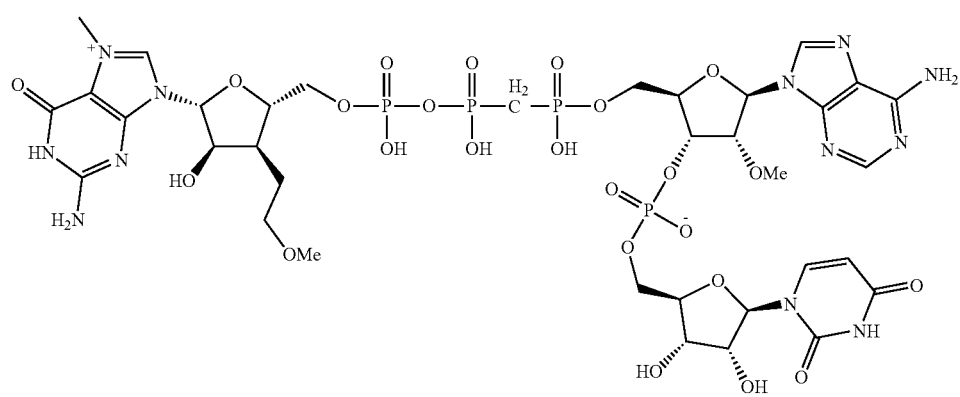
Compound 239
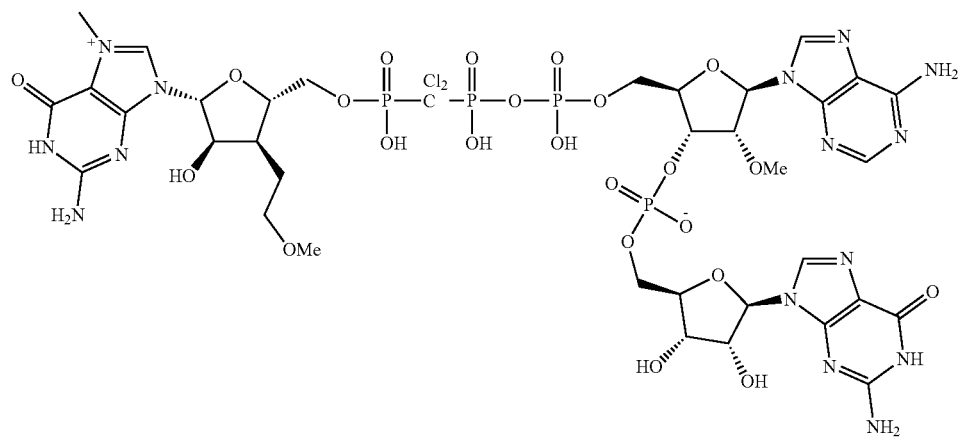

Compound 240
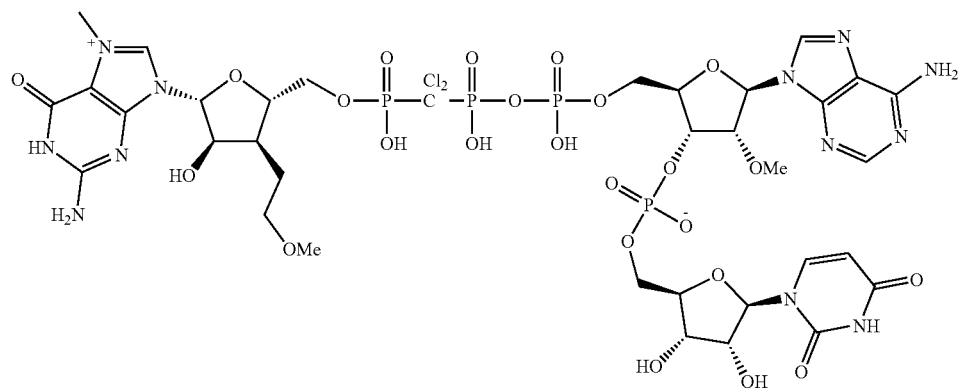
Compound 241
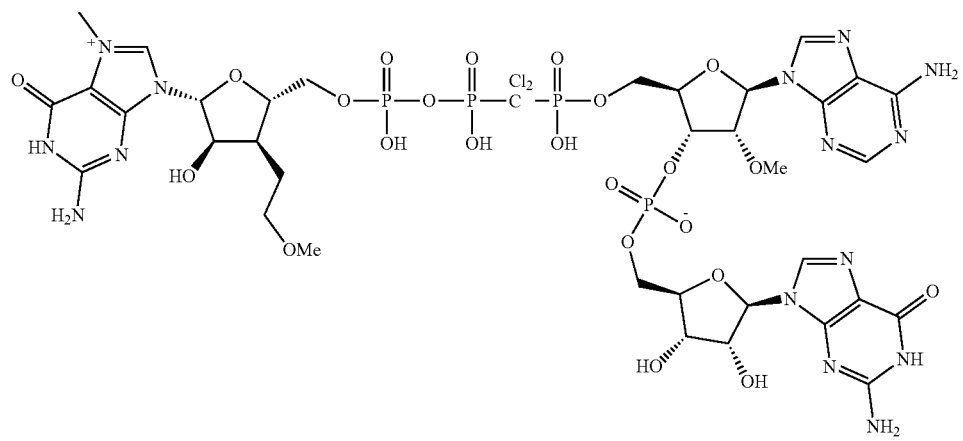
Compound 242
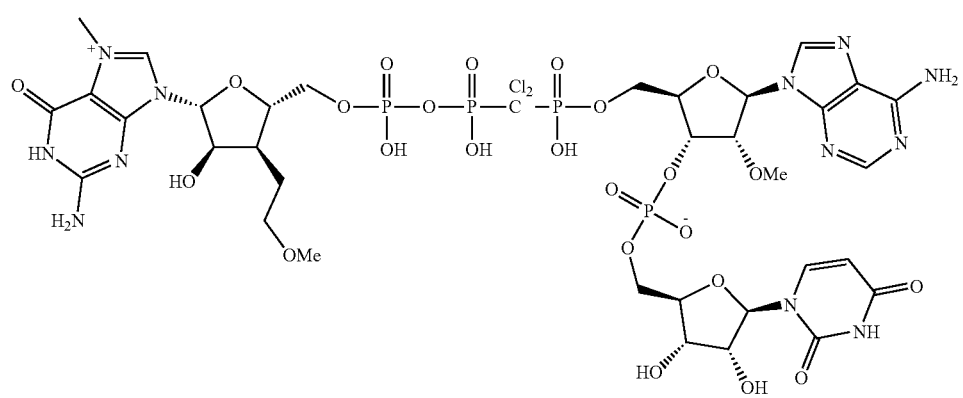
Compound 243
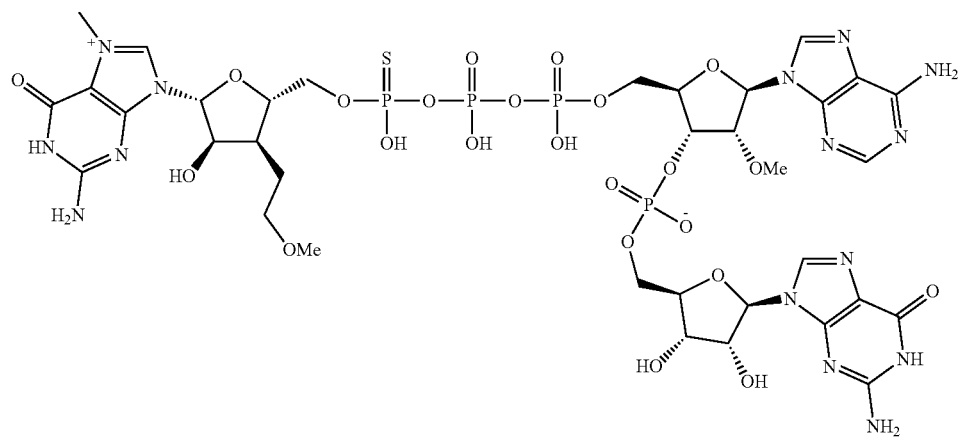

-continued
Compound 244
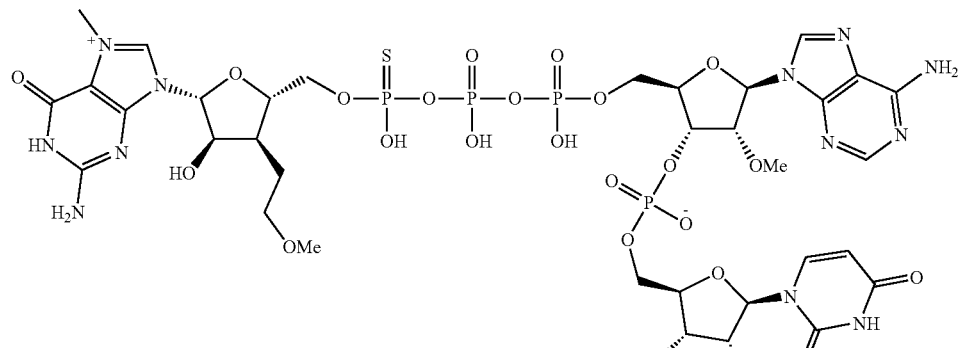
Compound 245
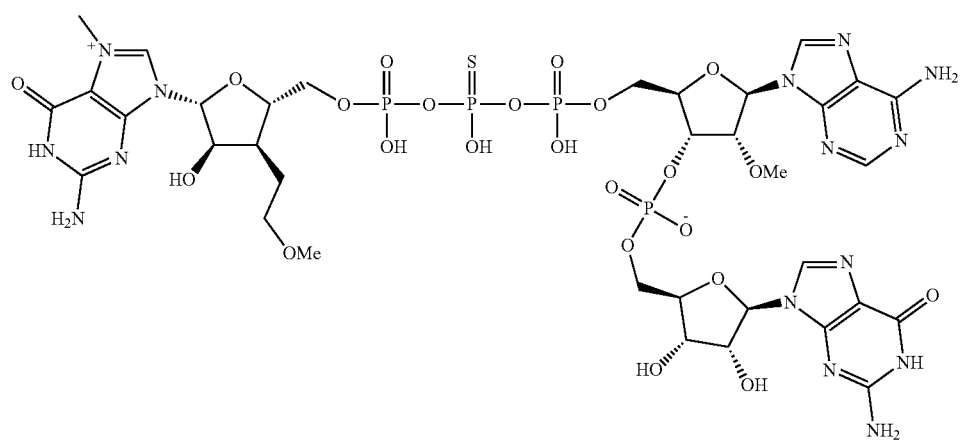
Compound 246
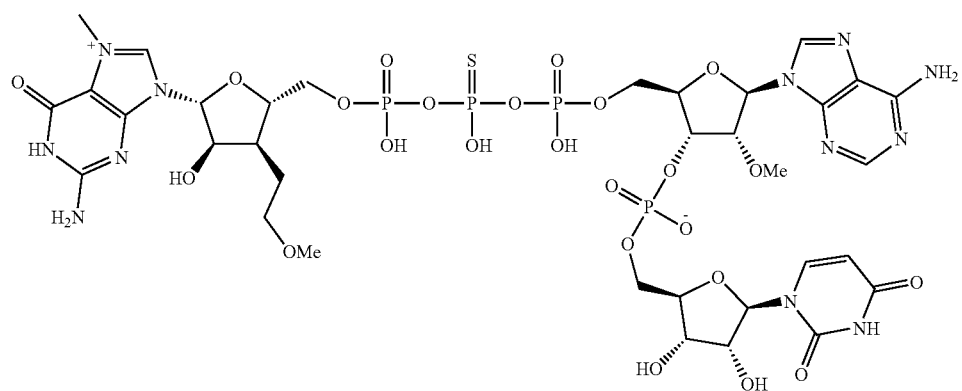
Compound 247
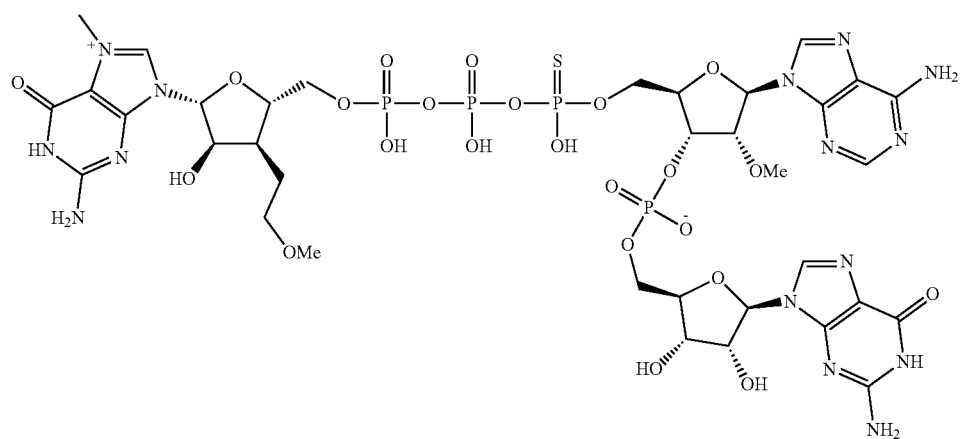

-continued
Compound 248
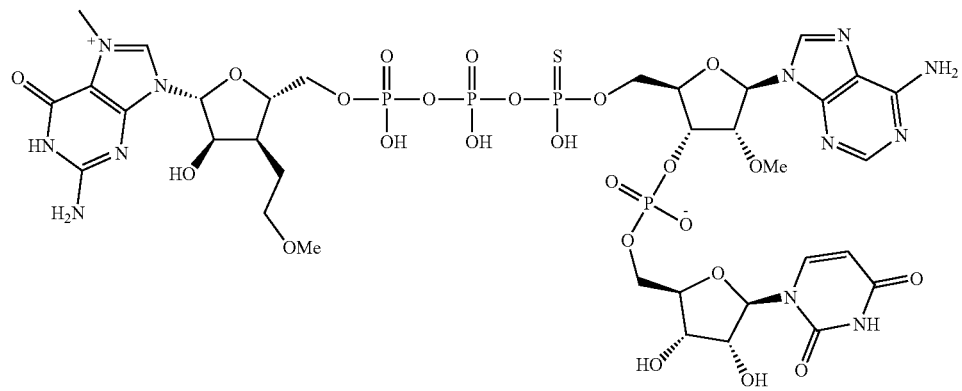
Compound 249
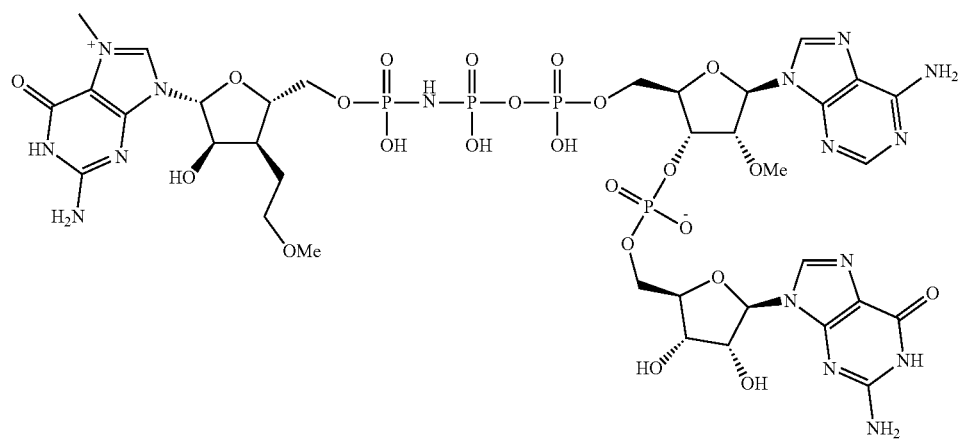
Compound 250
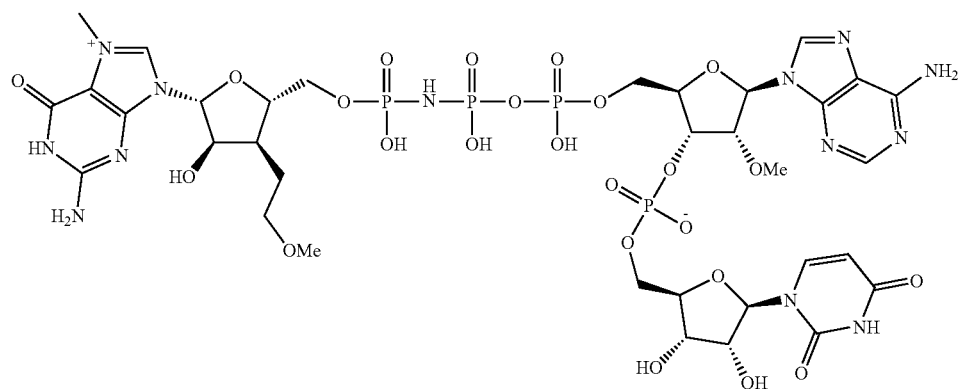
Compound 251
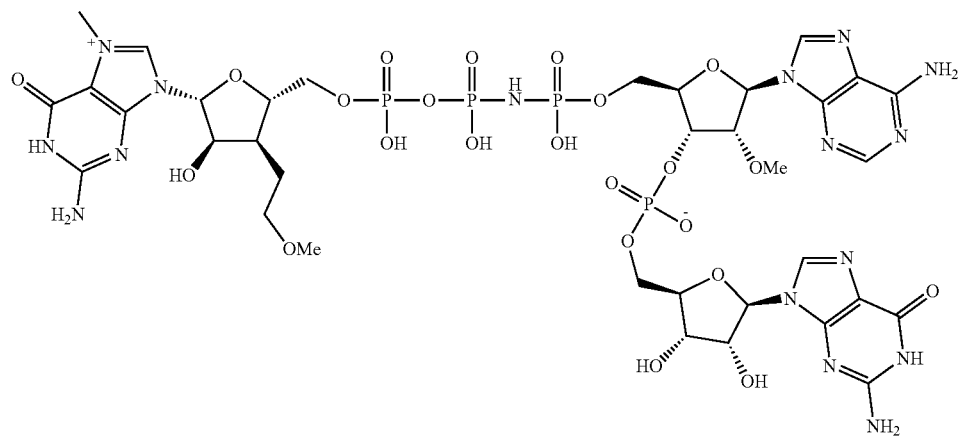

-continued
Compound 252
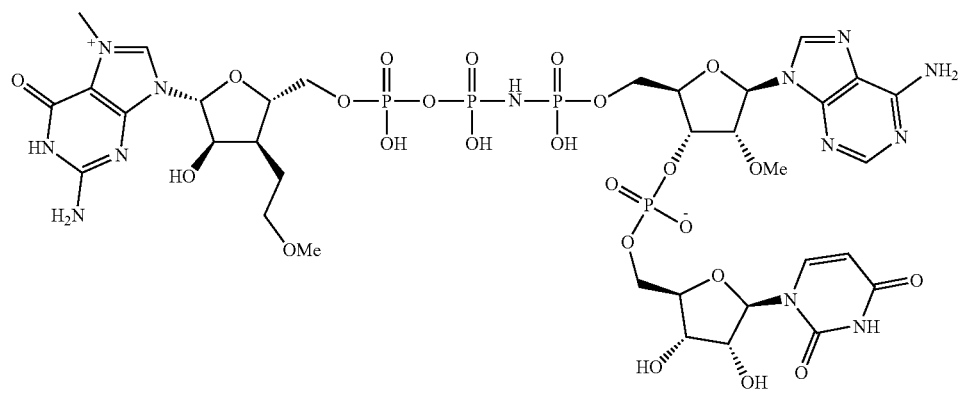
Compound 253
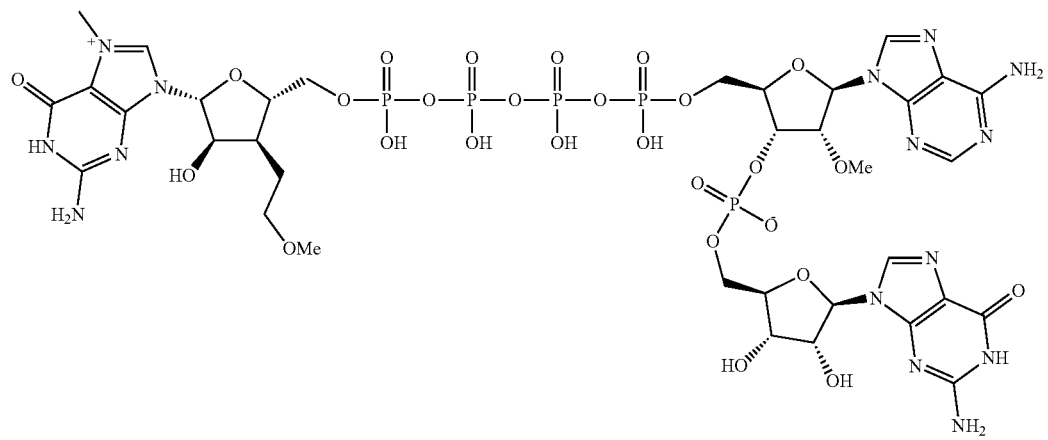
Compound 254
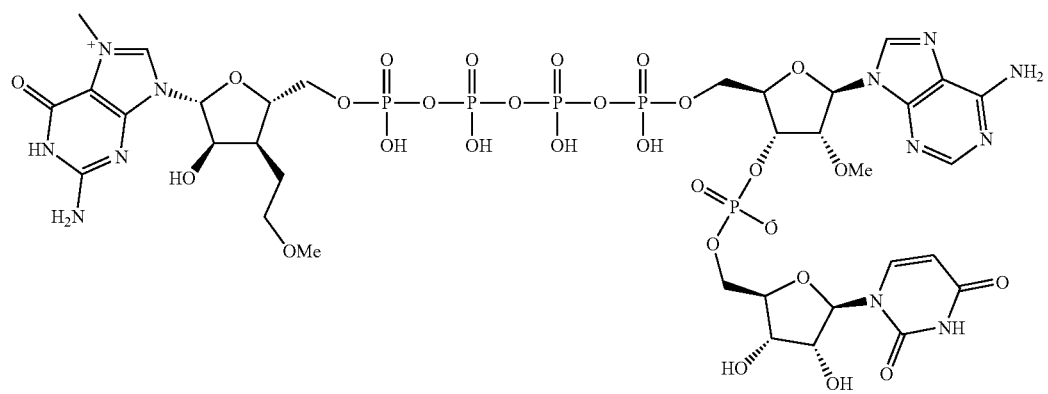
Compound 255
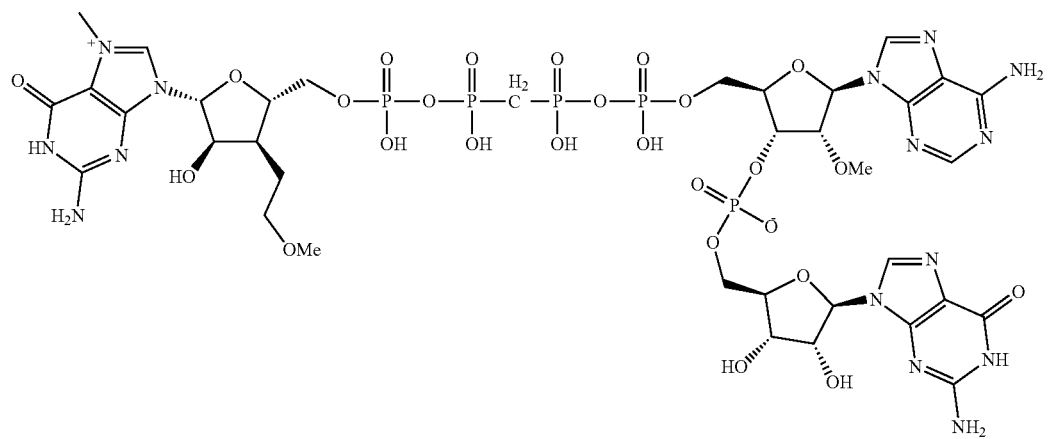

Compound 256
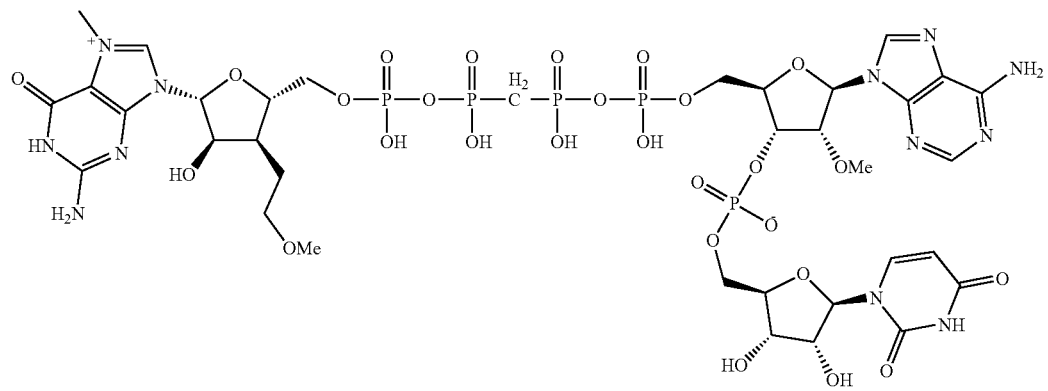
Compound 257
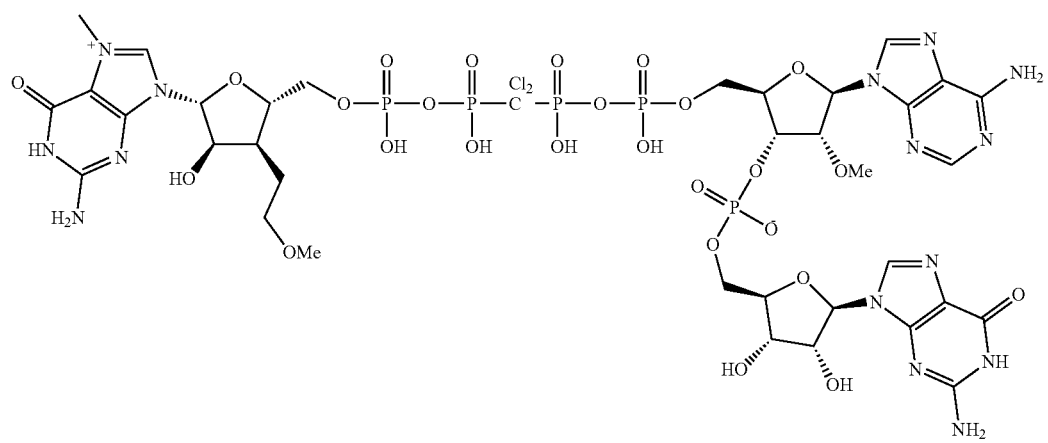
Compound 258
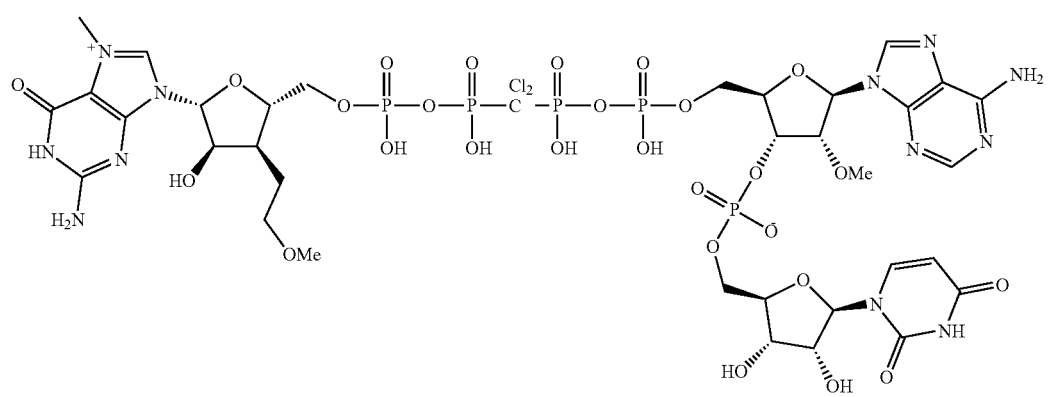
Compound 259
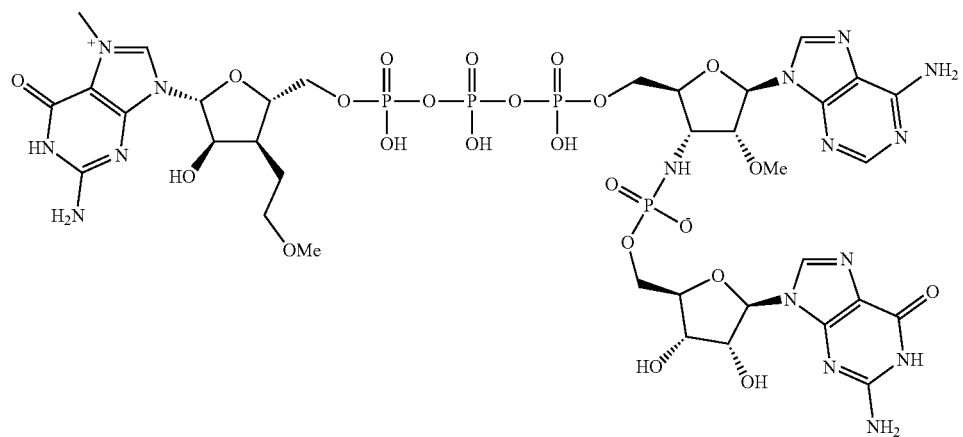

-continued
Compound 260
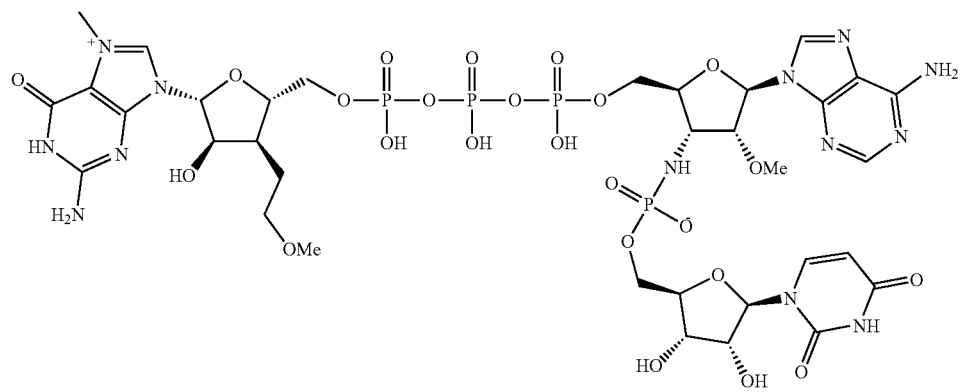
Compound 261
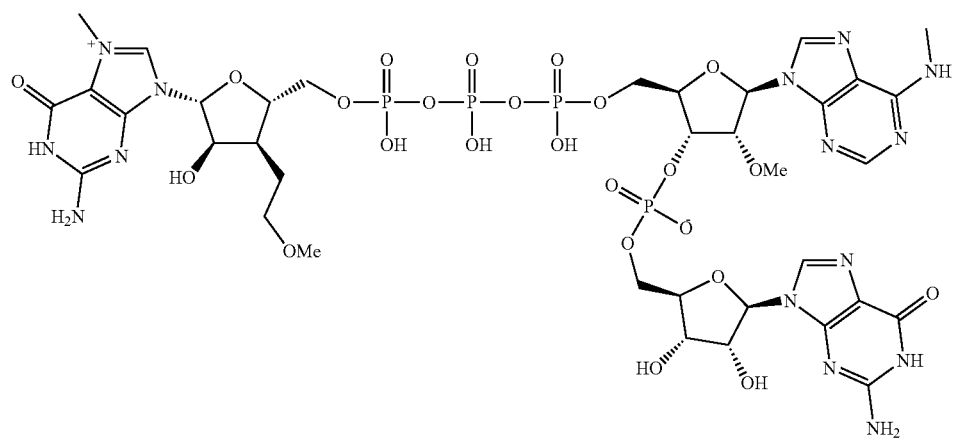
Compound 262
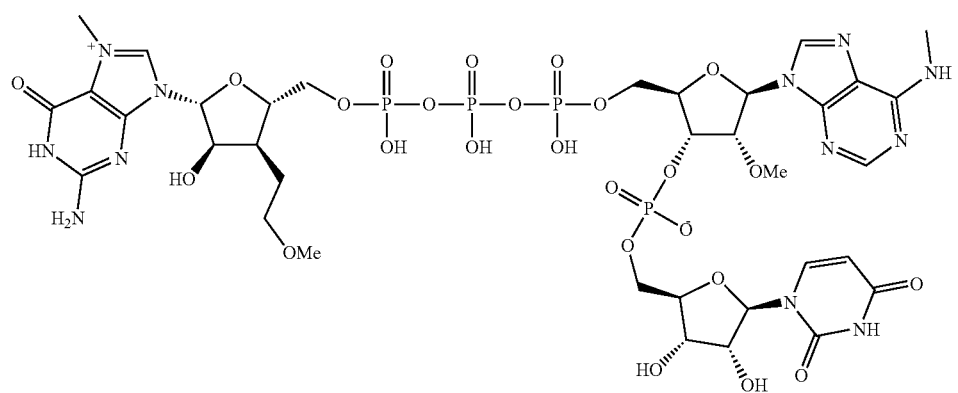
Compound 263
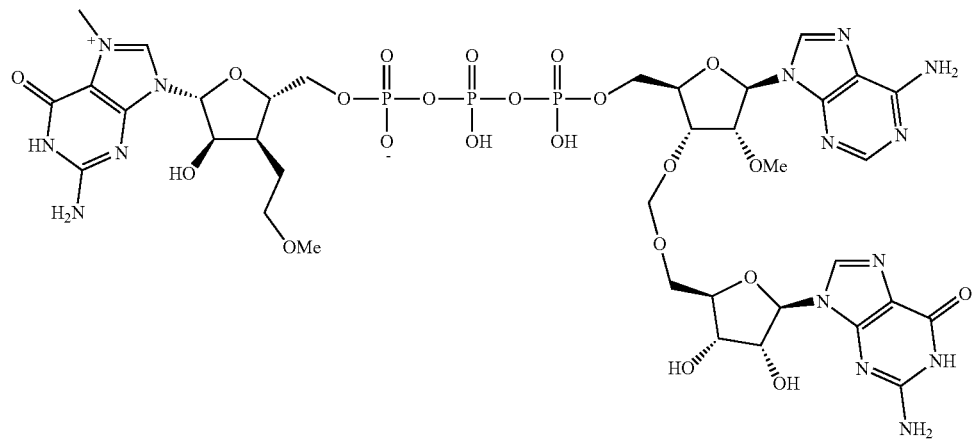

Compound 264
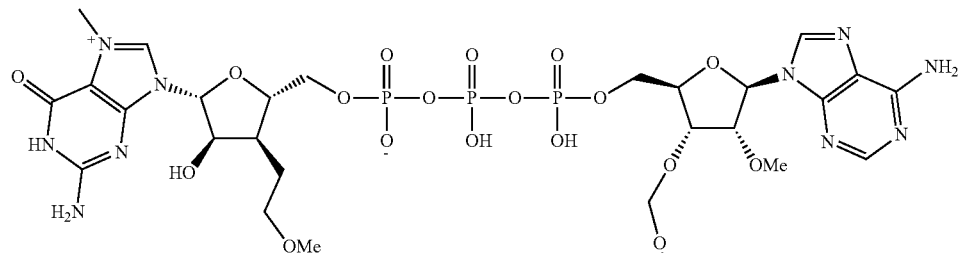
Compound 265
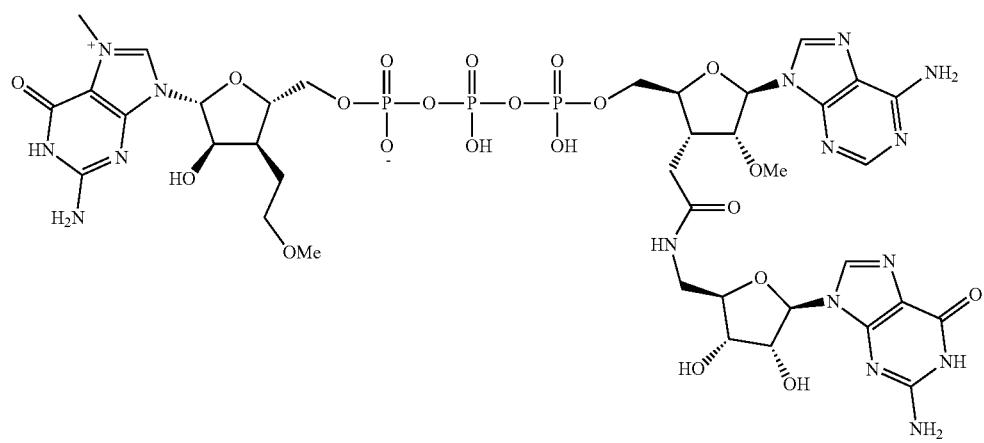
Compound 266
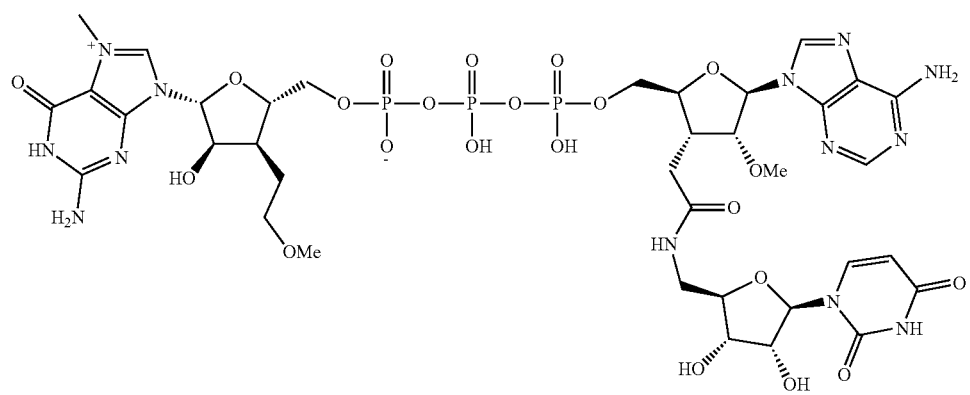
Compound 267
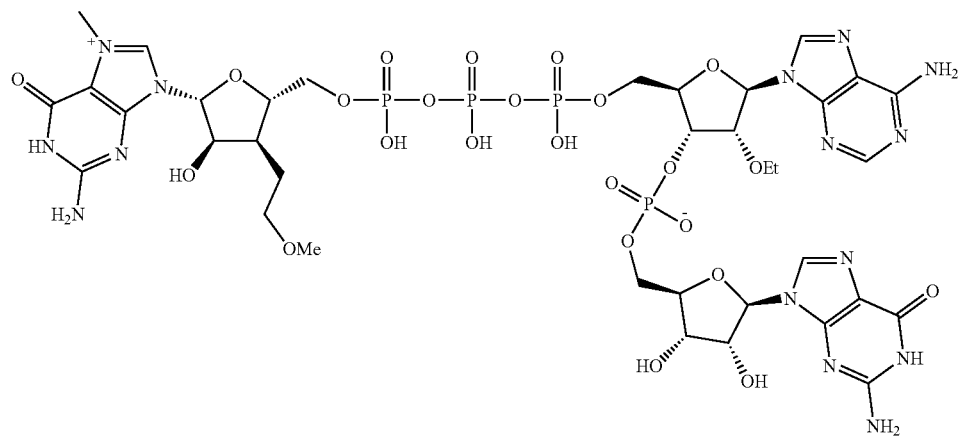

-continued
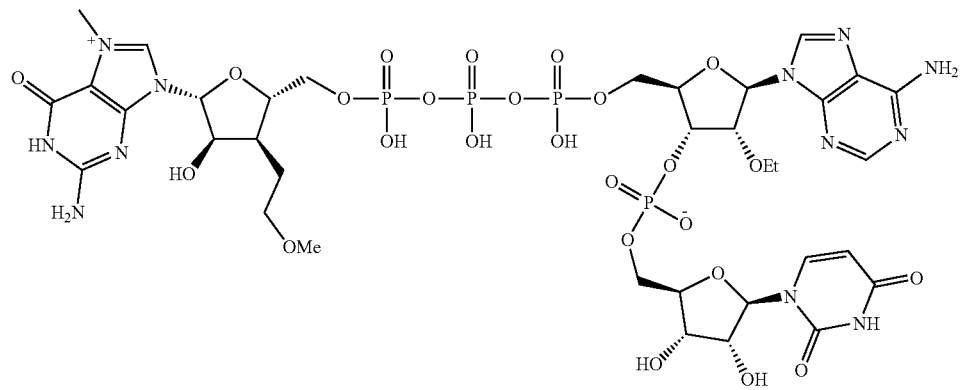
Compound 268
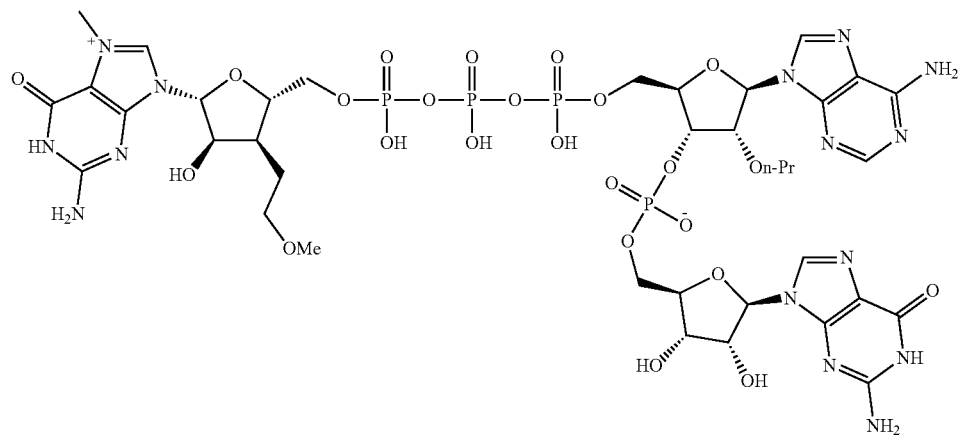
Compound 269
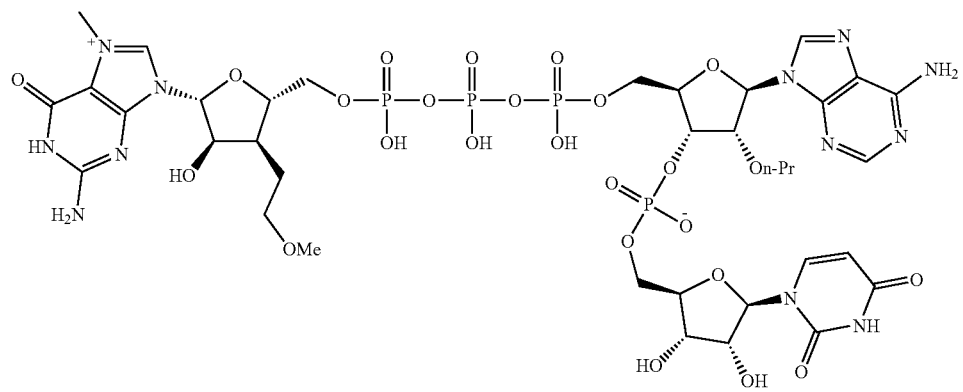
Compound 270
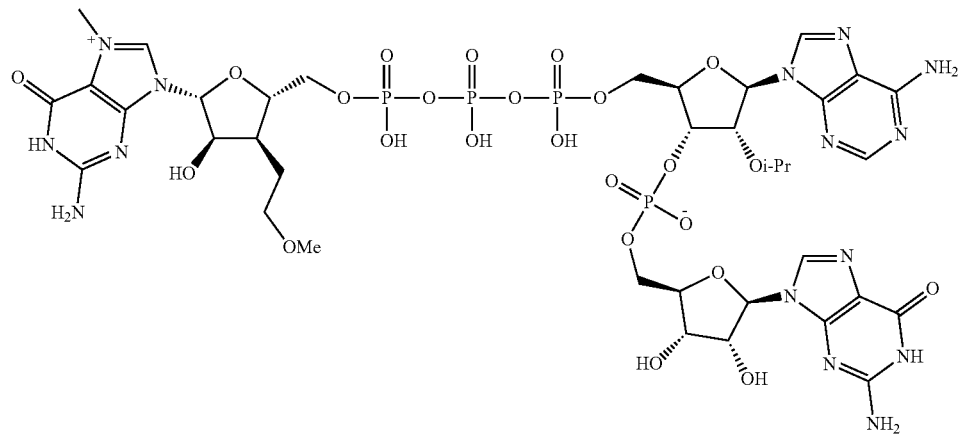
Compound 271

-continued
Compound 272
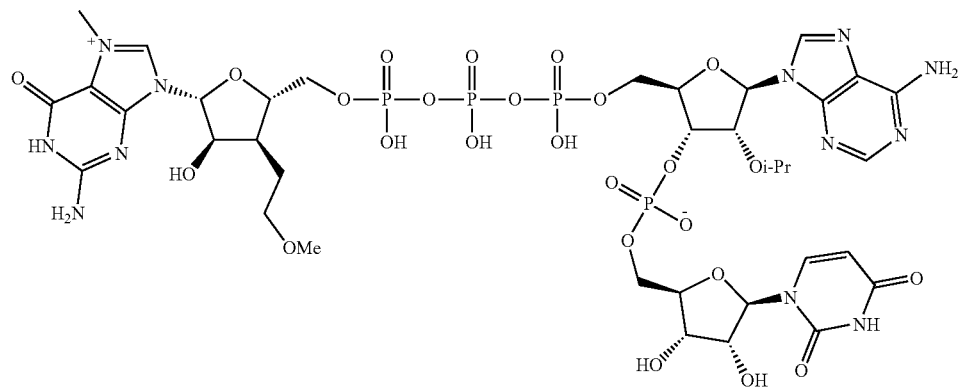
Compound 273
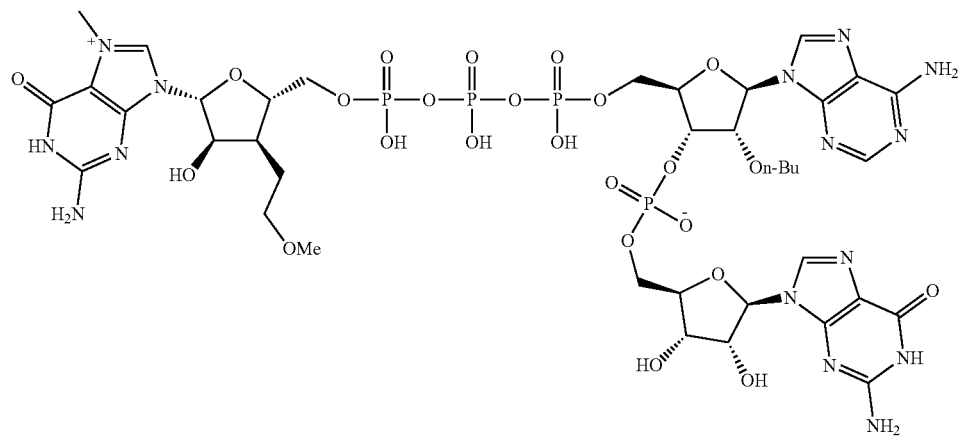
Compound 274
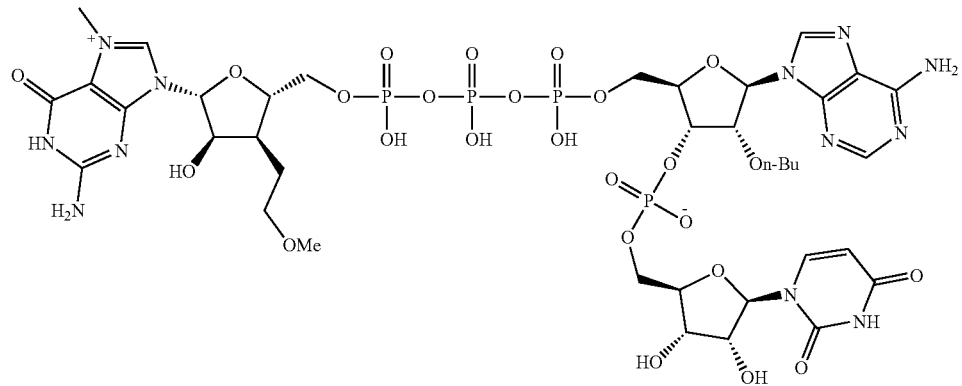

Compound 275
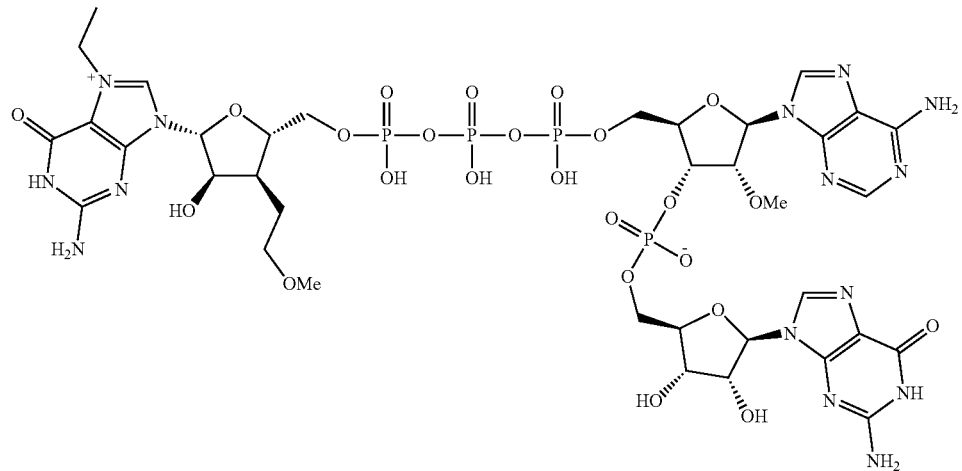
Compound 276
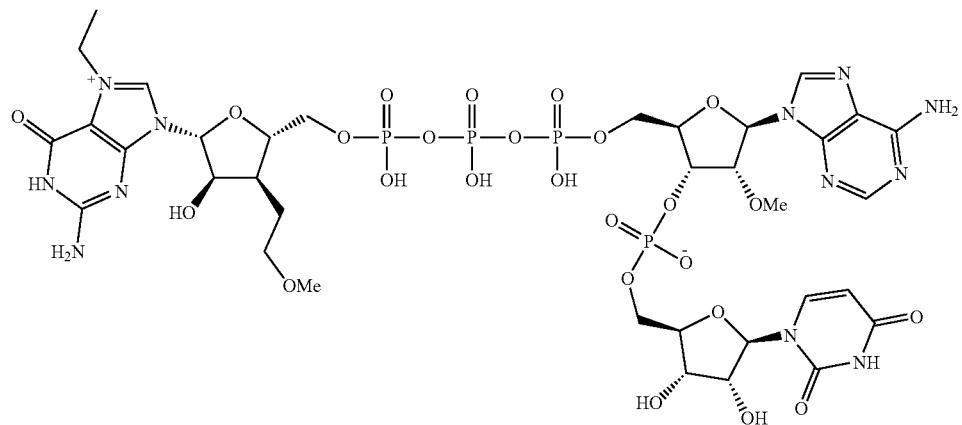
Compound 277
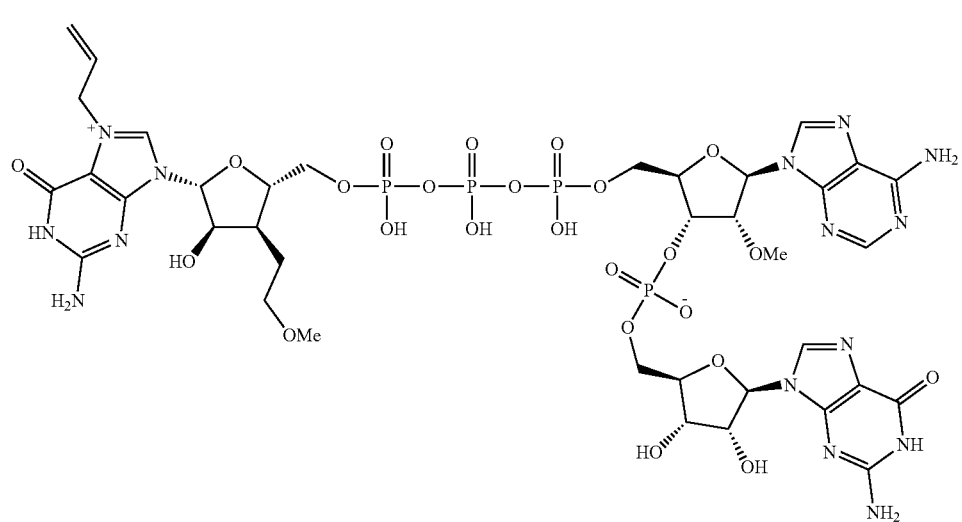

Compound 278
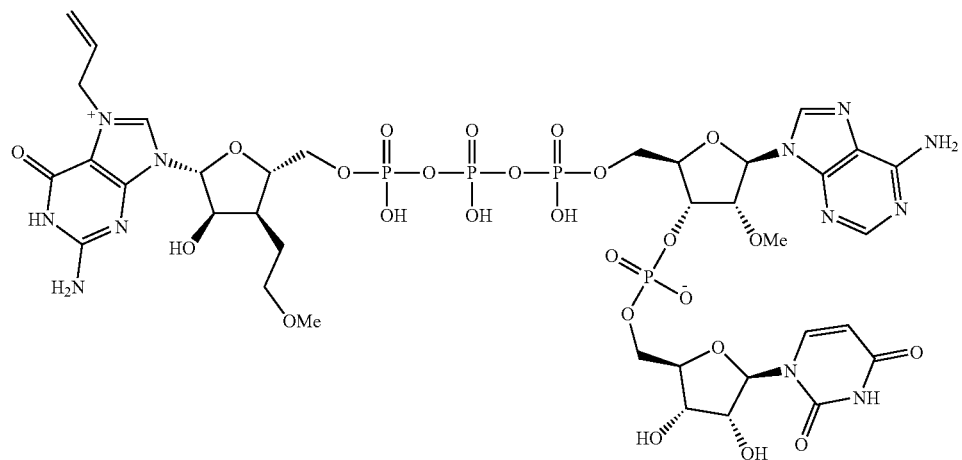
Compound 279
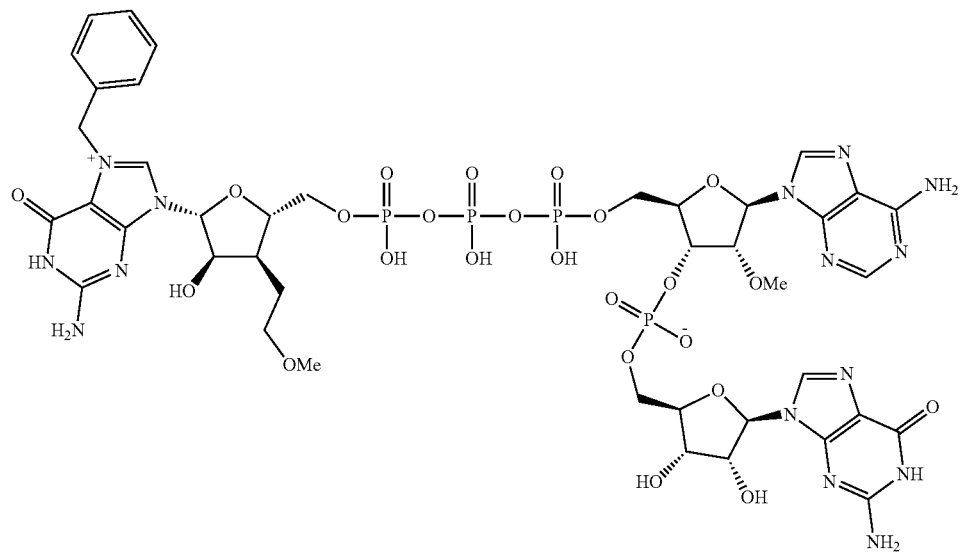
Compound 280
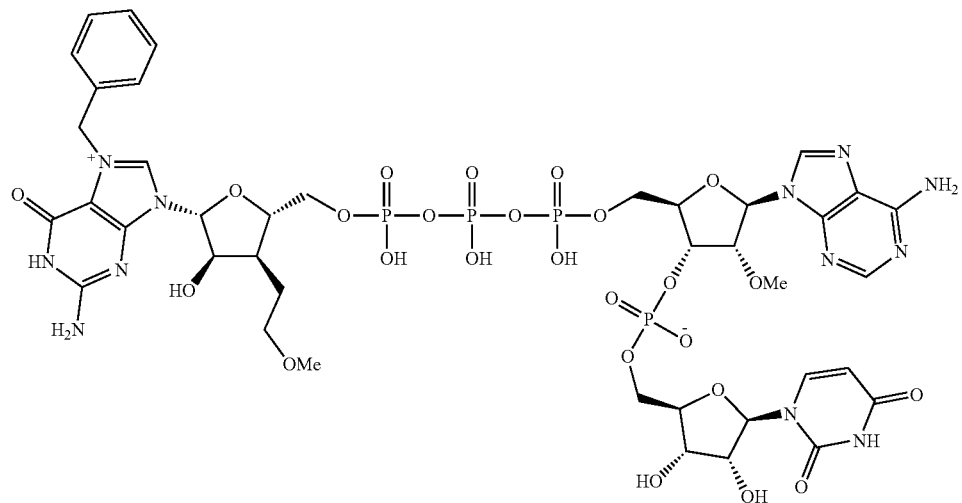

-continued
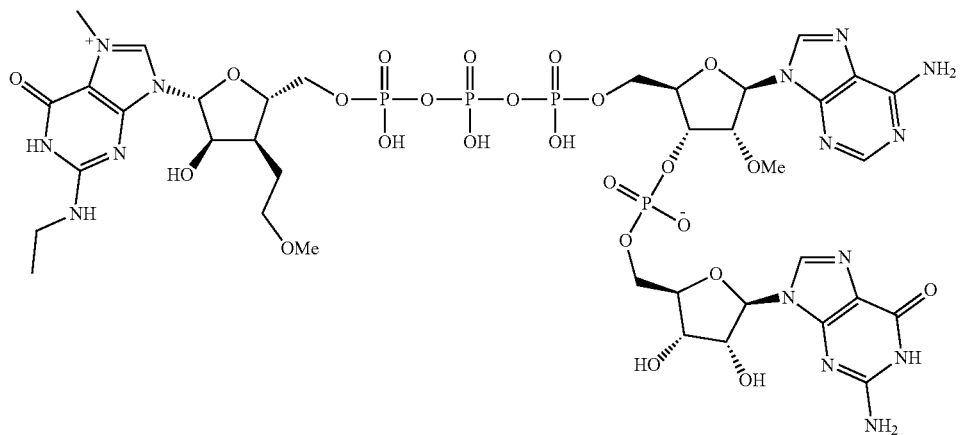
Compound 281
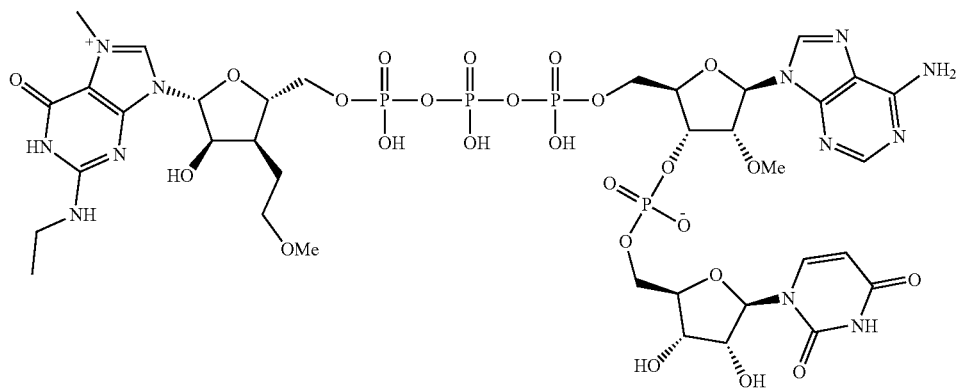
Compound 282
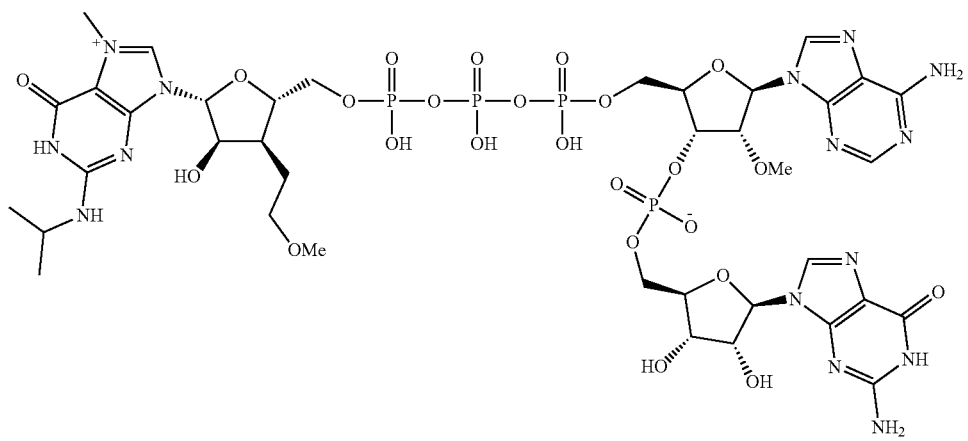
Compound 283
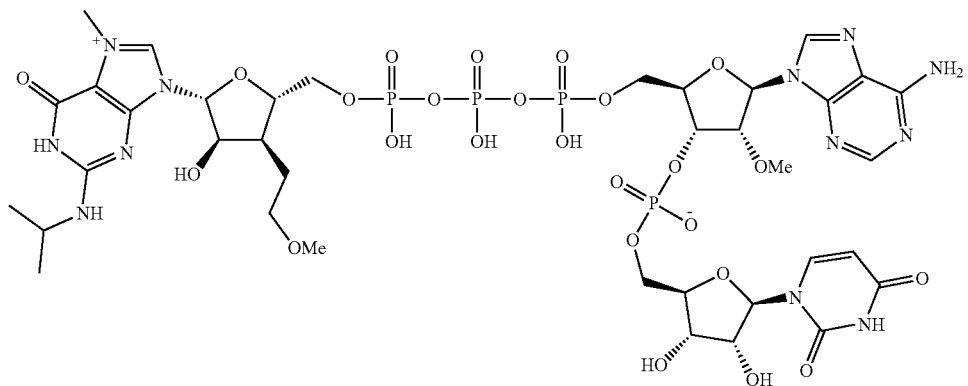
Compound 284

Compound 289
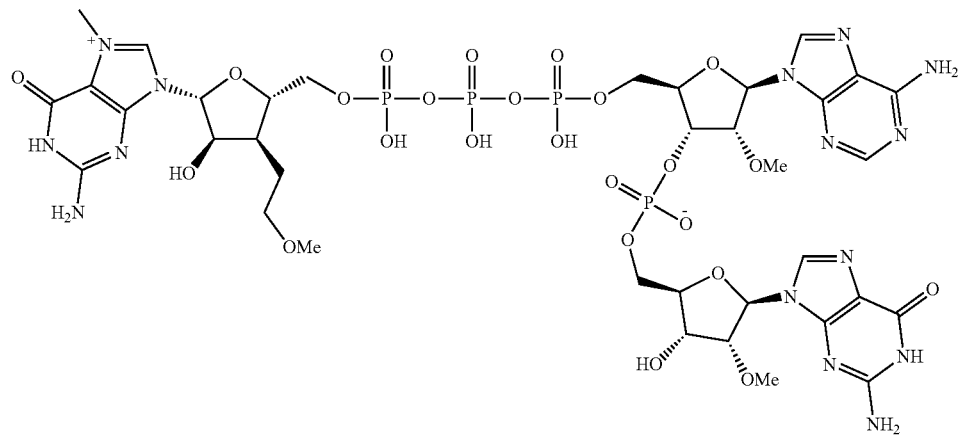
Compound 290
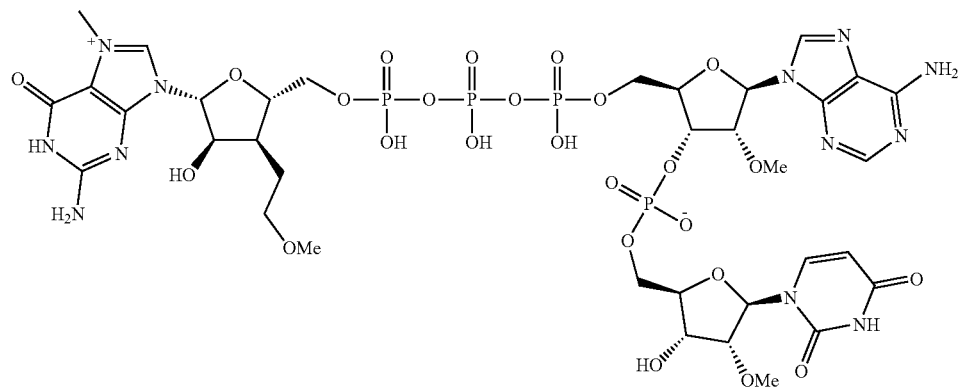
Compound 291
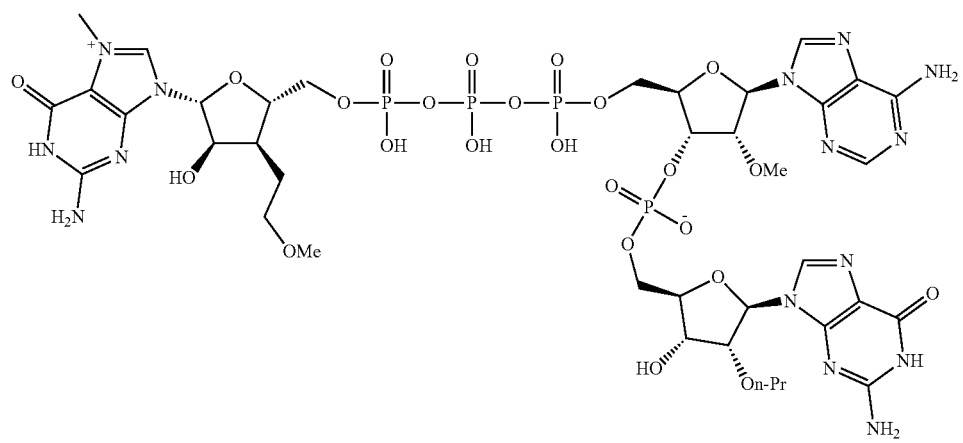
Compound 292
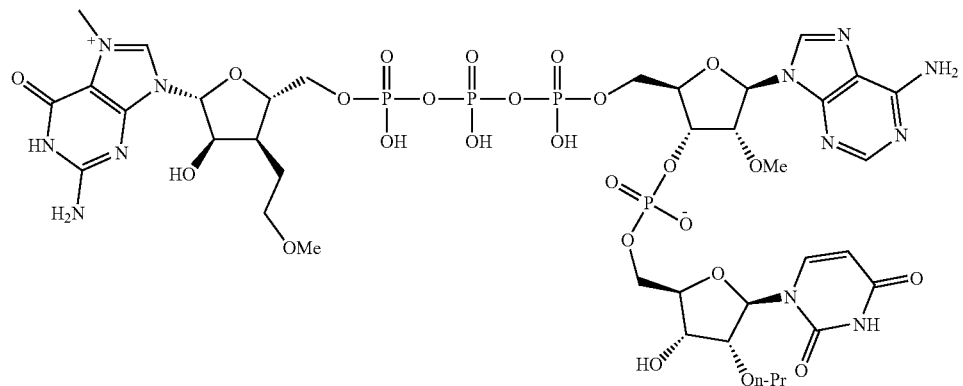

Compound 293
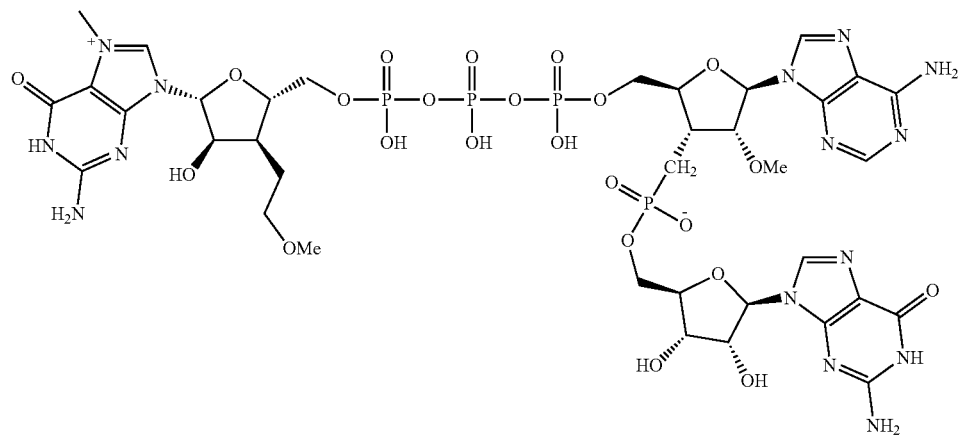
Compound 294
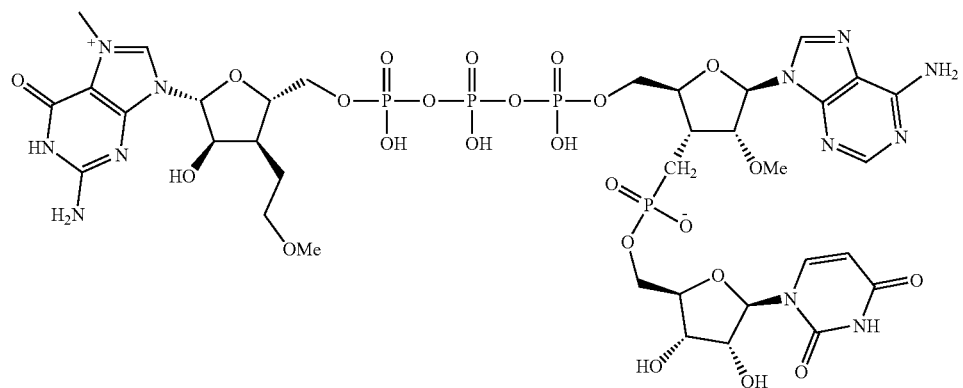
Compound 295
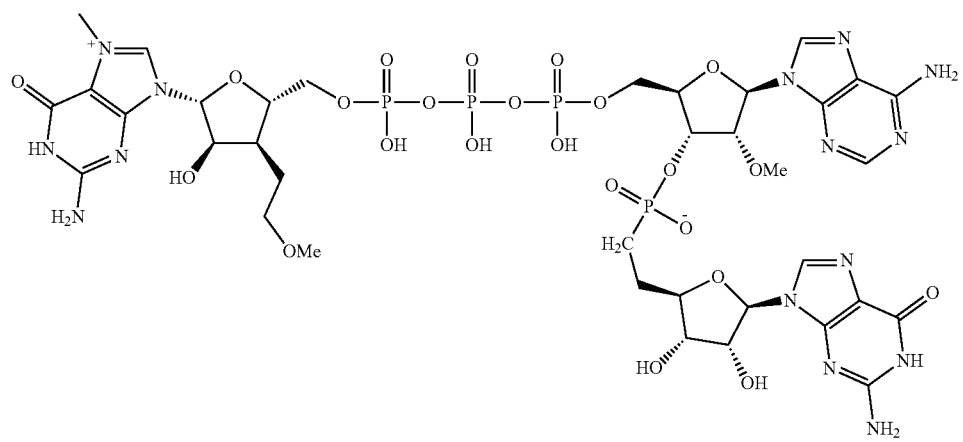
Compound 296
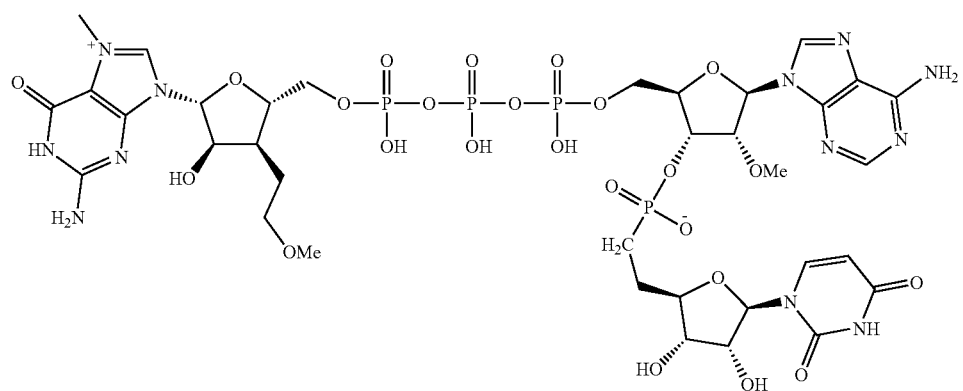

Compound 297
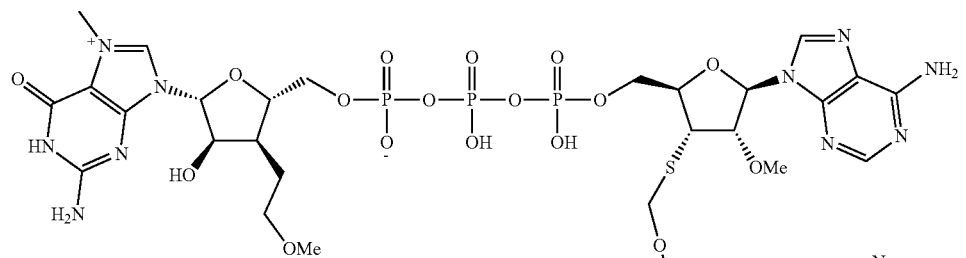
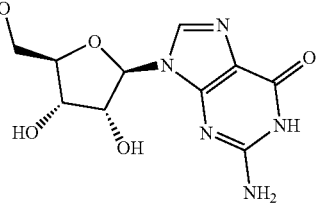
Compound 298
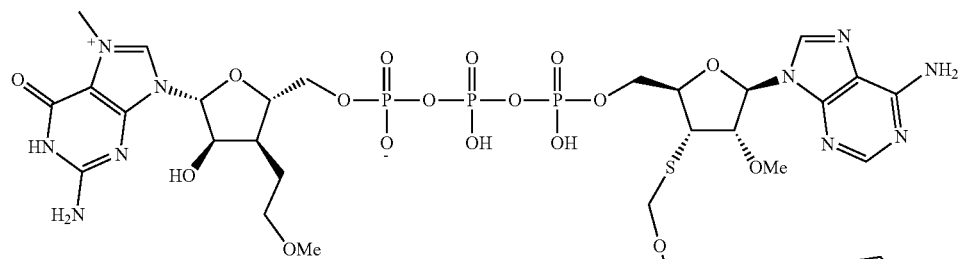
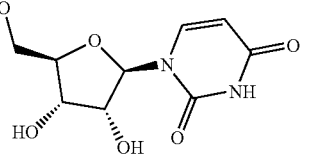
Compound 299
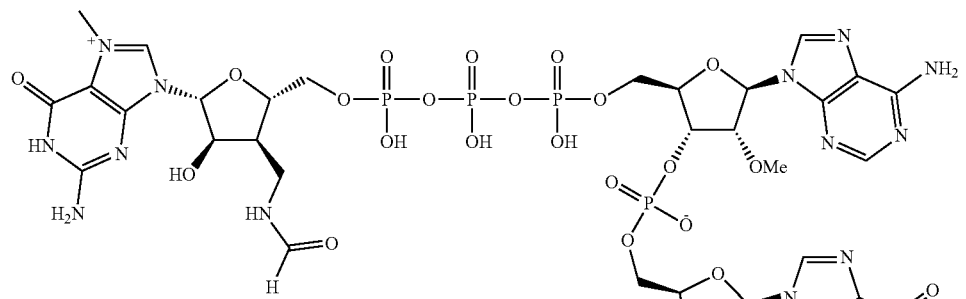
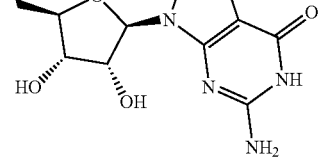
Compound 300
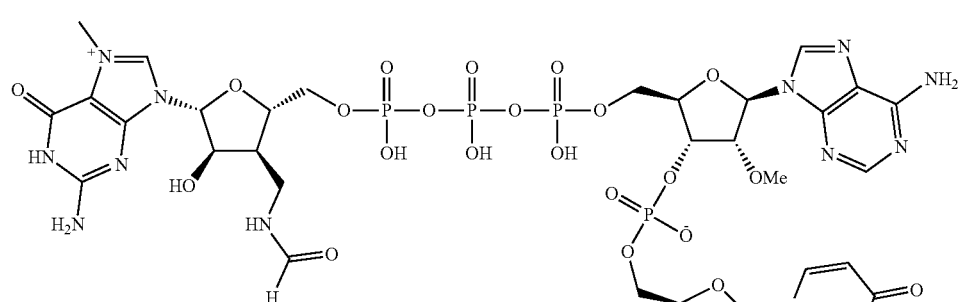
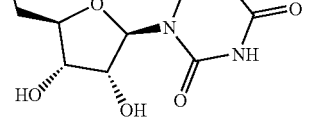

-continued
Compound 301
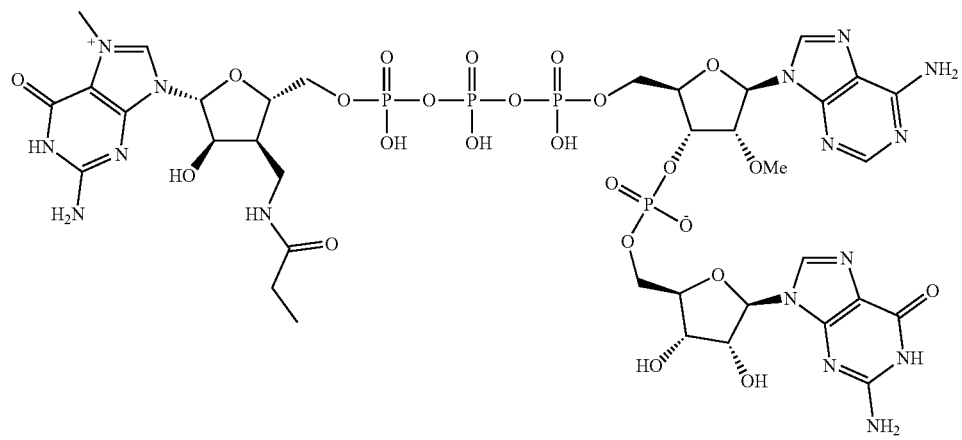
Compound 302
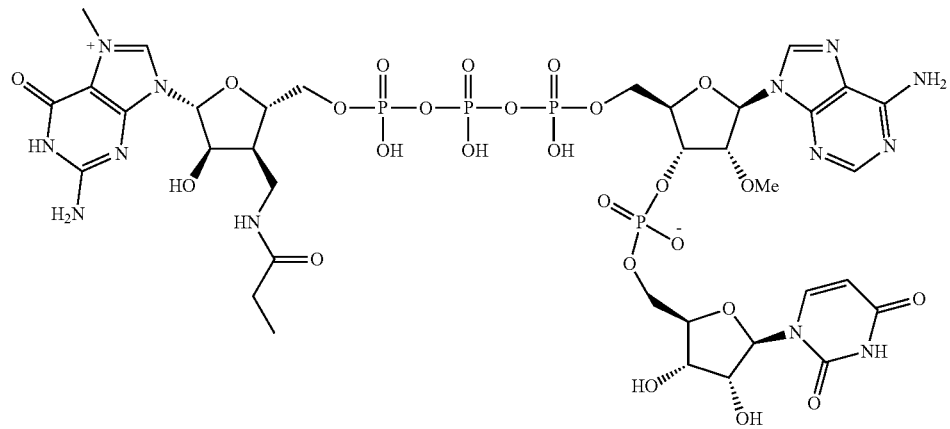
Compound 303
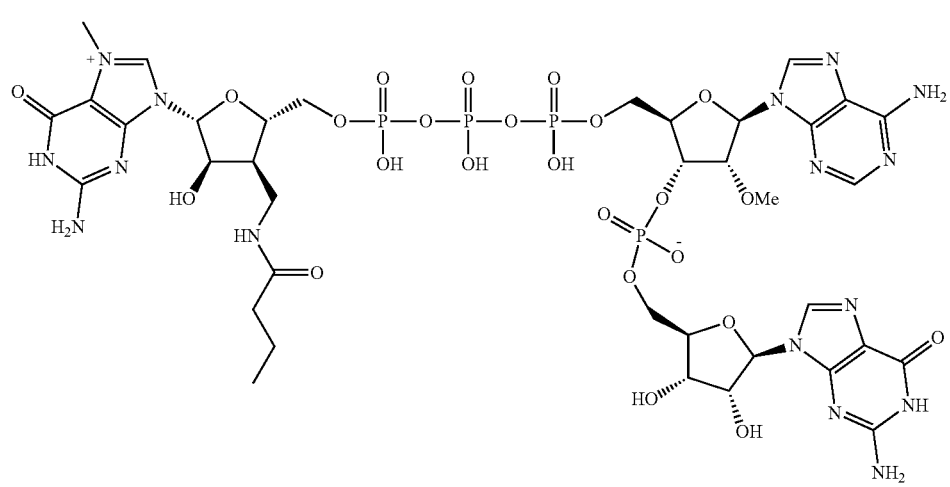

Compound 304
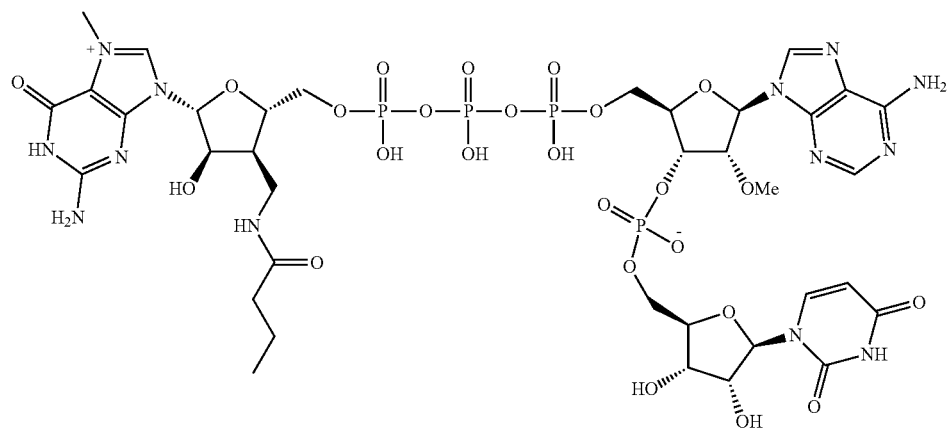
Compound 305
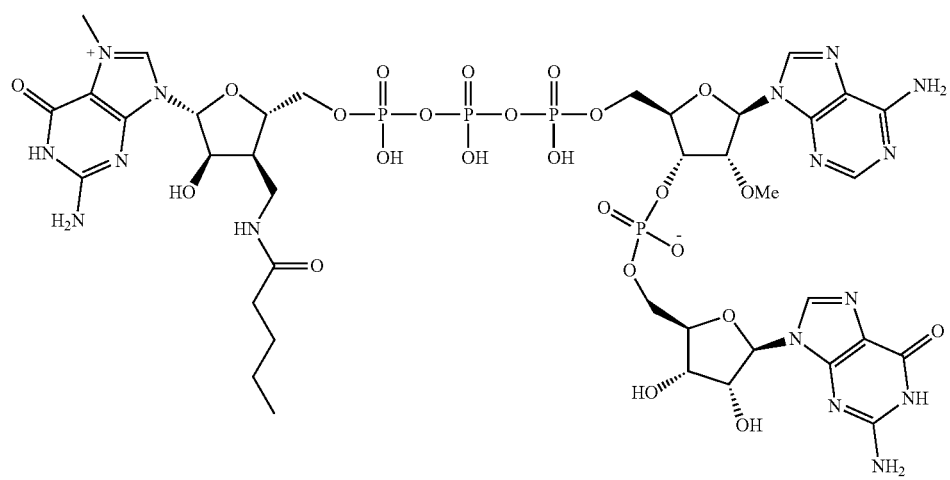
Compound 306
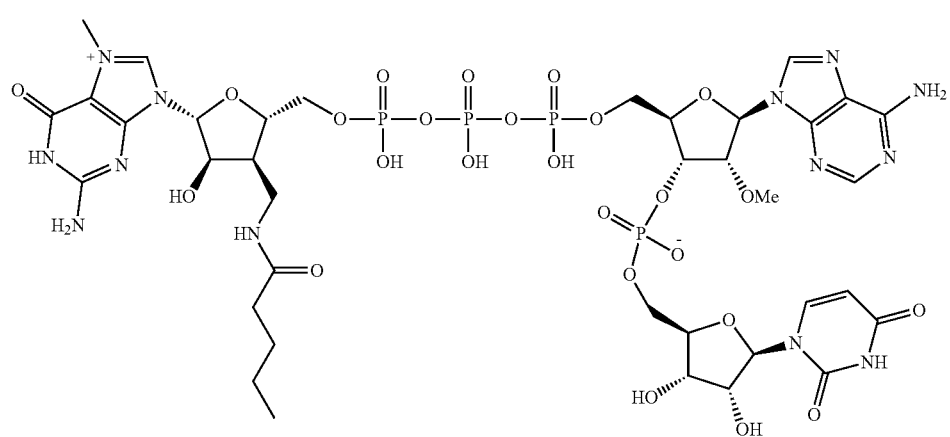

Compound 307
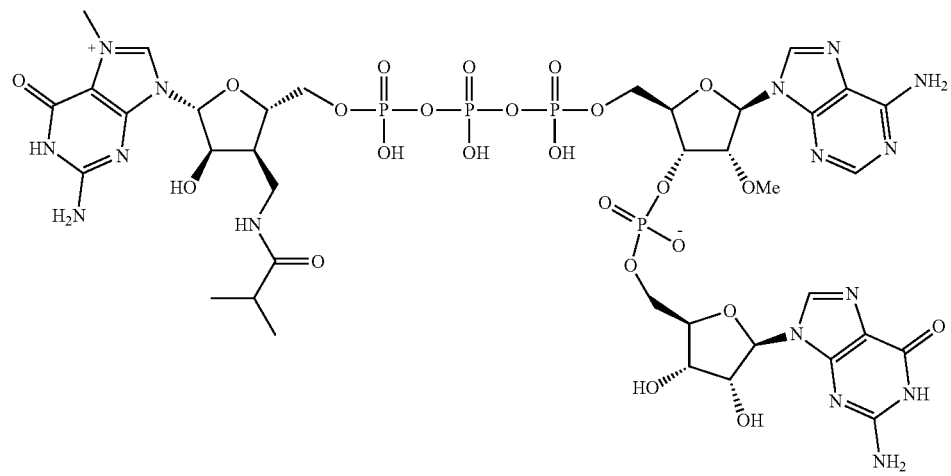
Compound 308
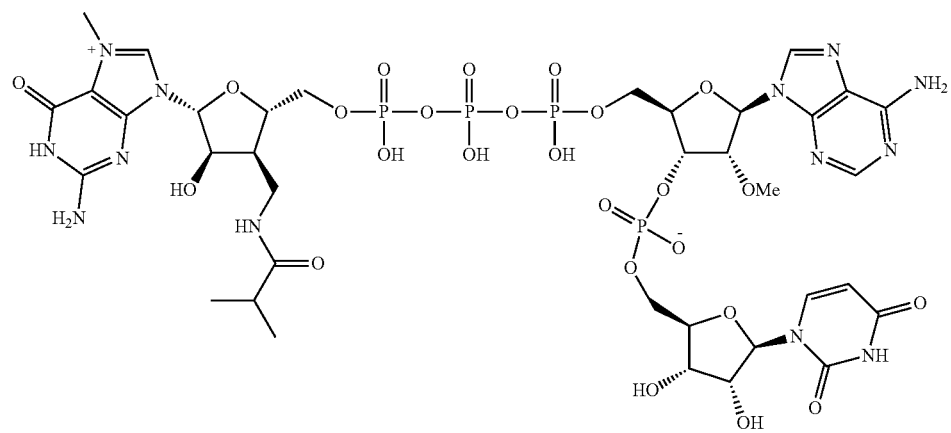
Compound 309
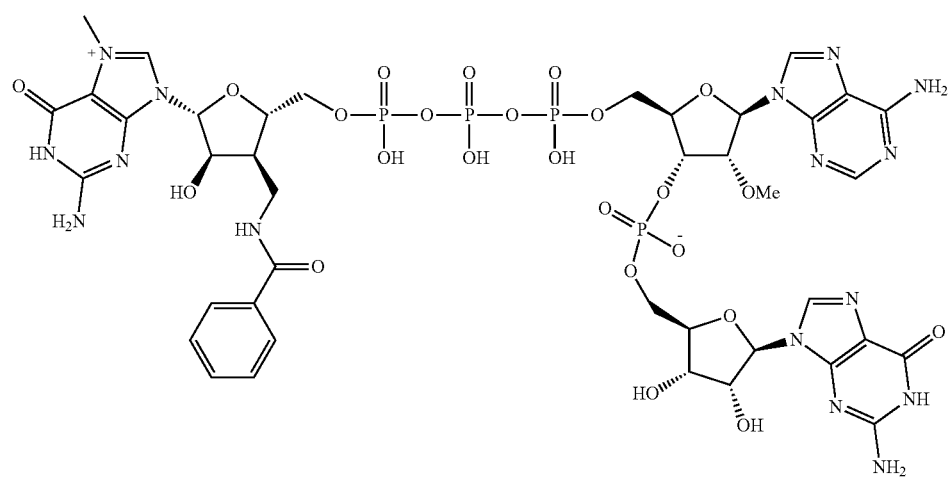

Compound 310
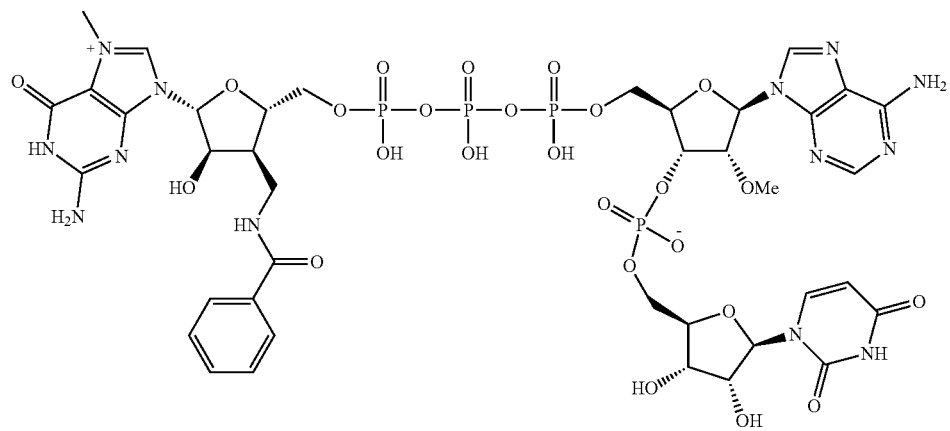
Compound 311
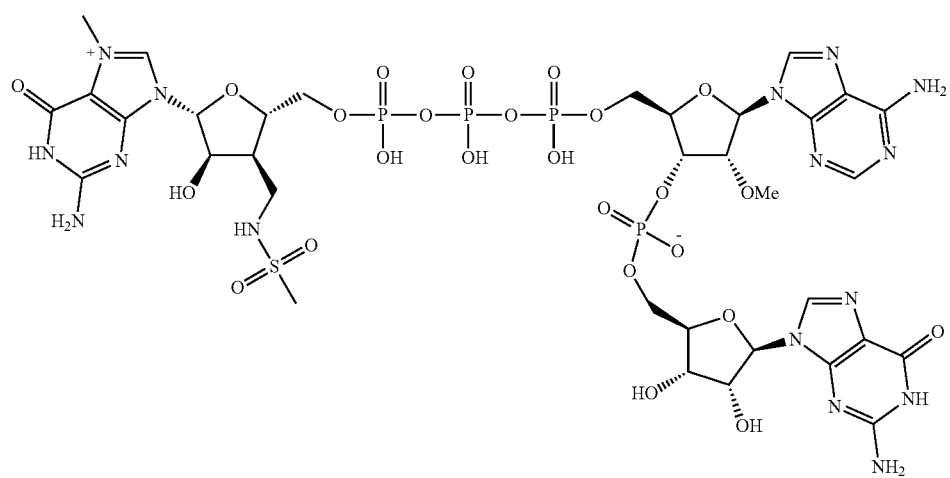
Compound 312
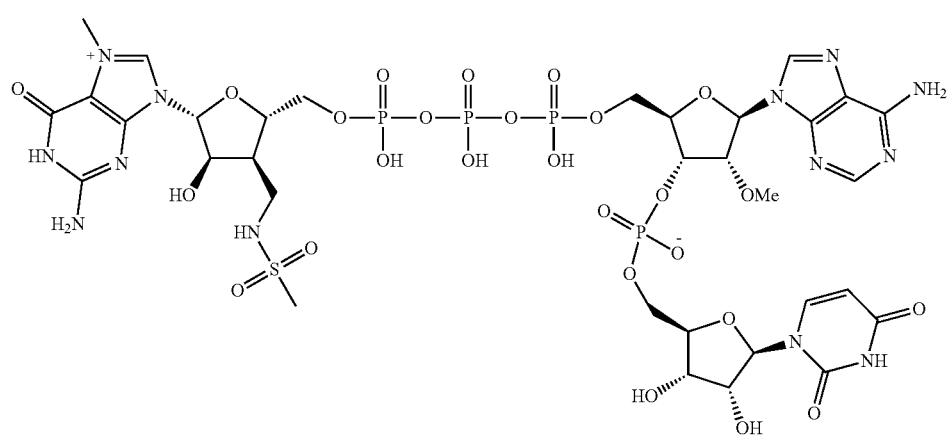

-continued
Compound 313
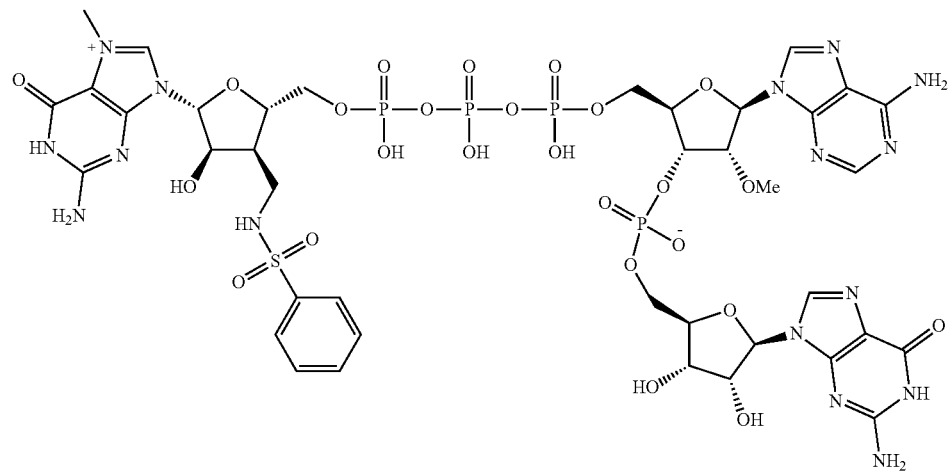
Compound 314
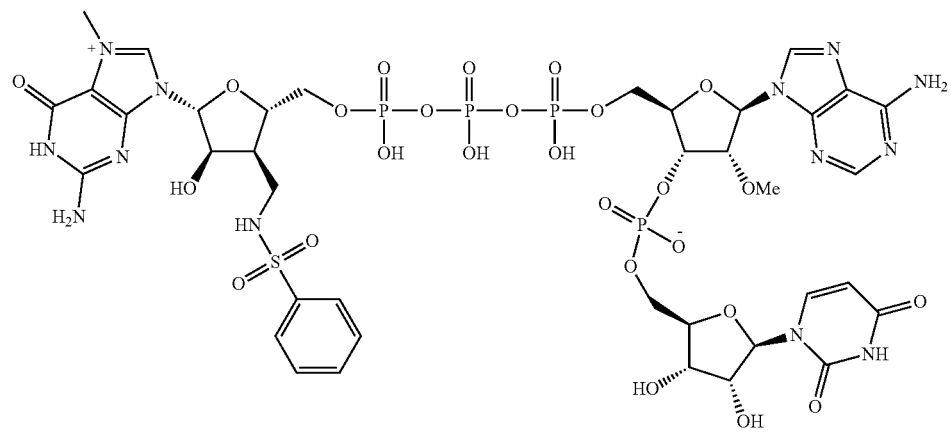
Compound 315
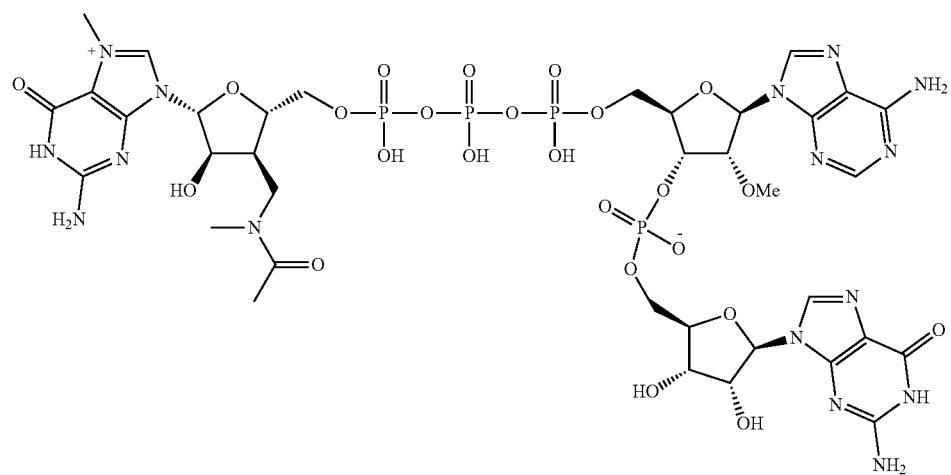

-continued
Compound 316
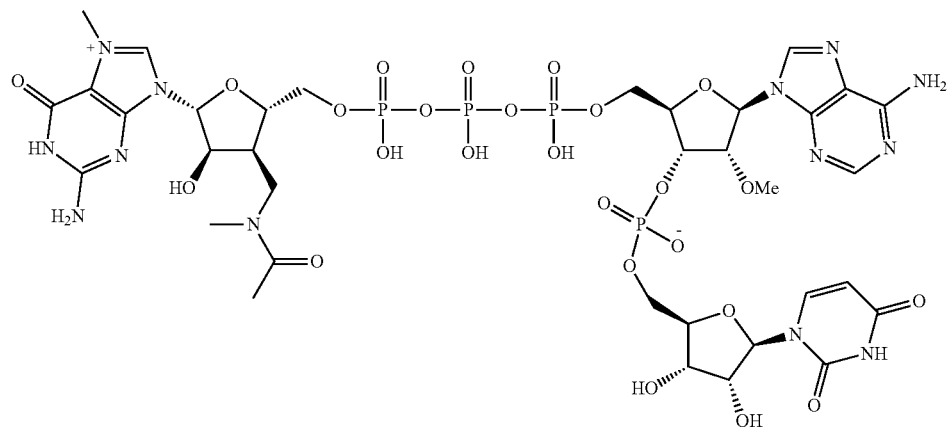
Compound 317
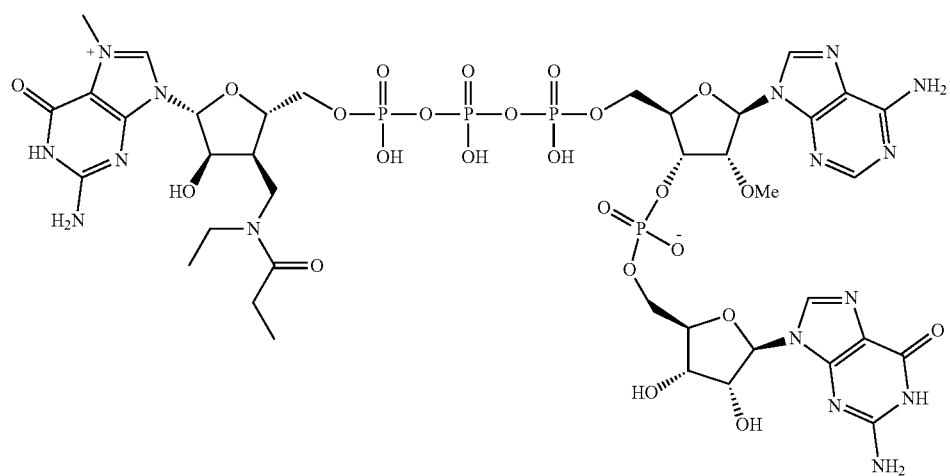
Compound 318
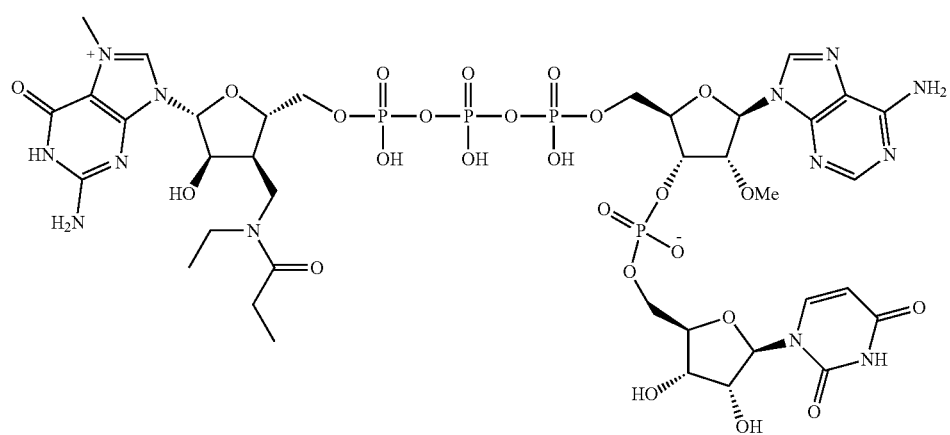

Compound 319
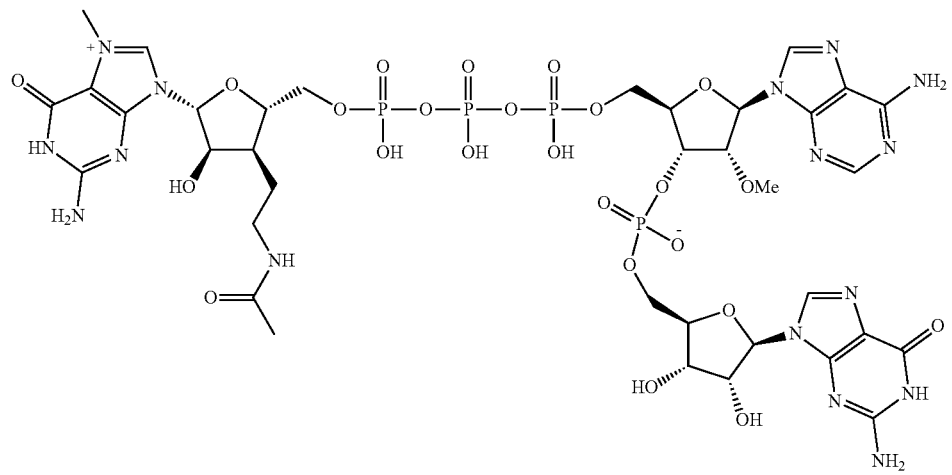
Compound 320
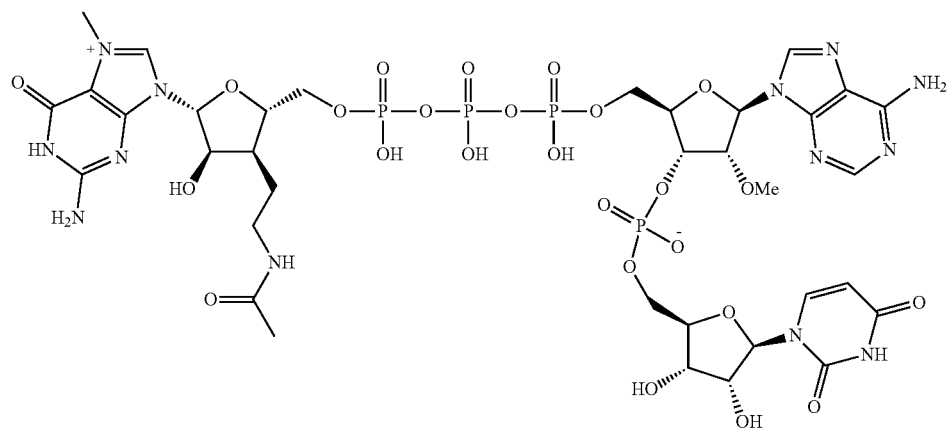
Compound 321
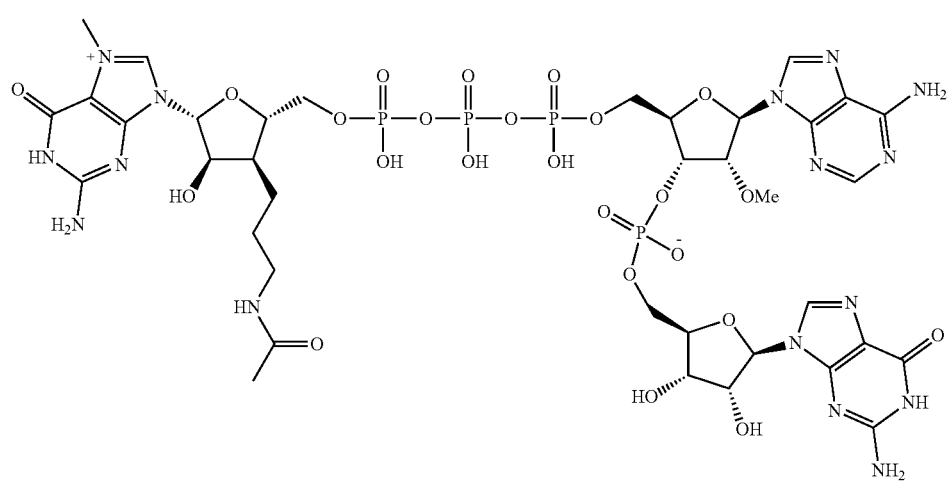

Compound 322
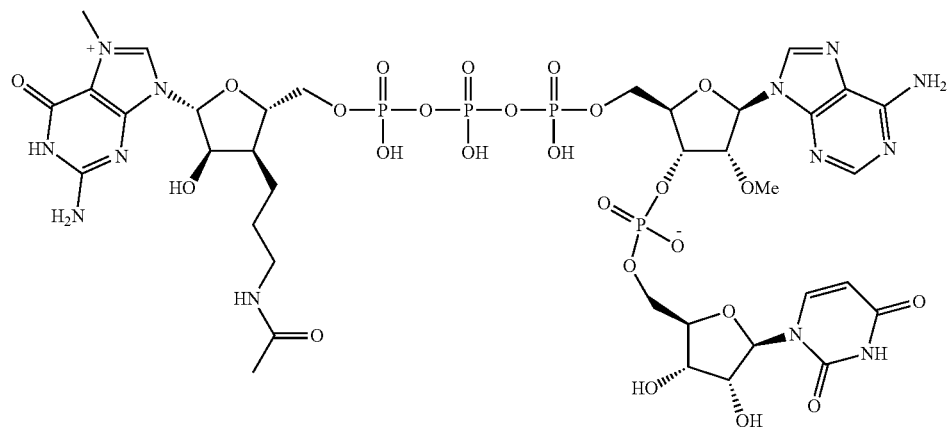
Compound 323
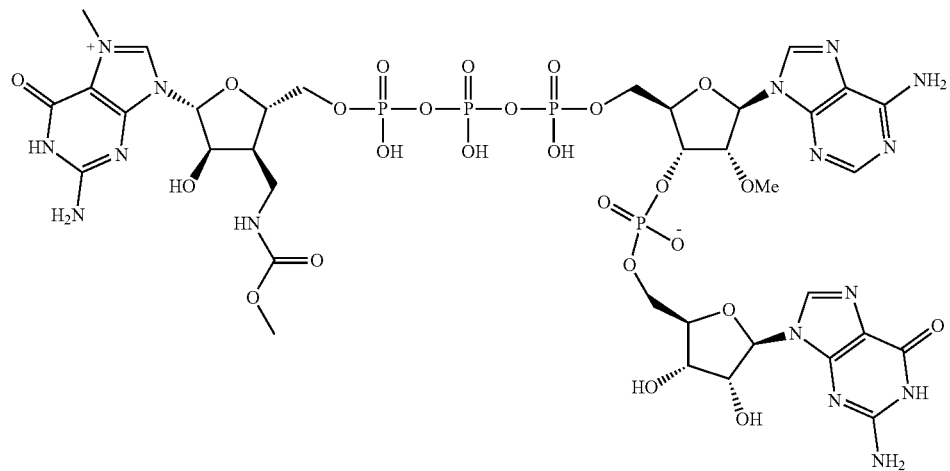
Compound 324
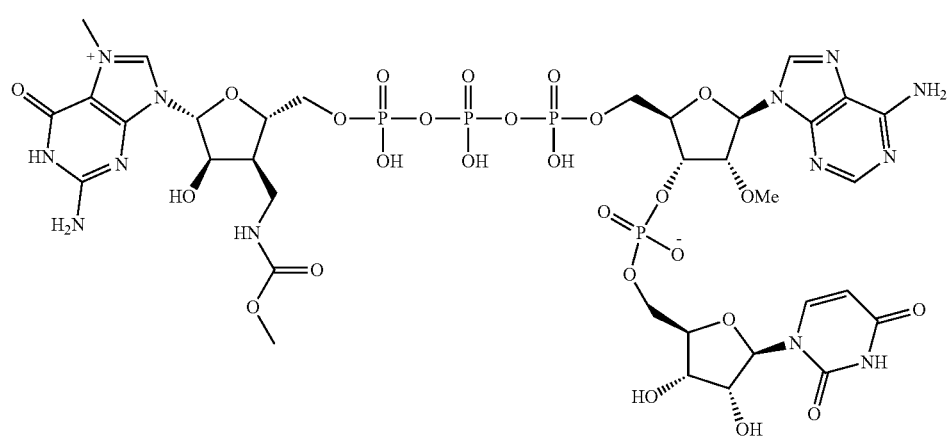

Compound 325
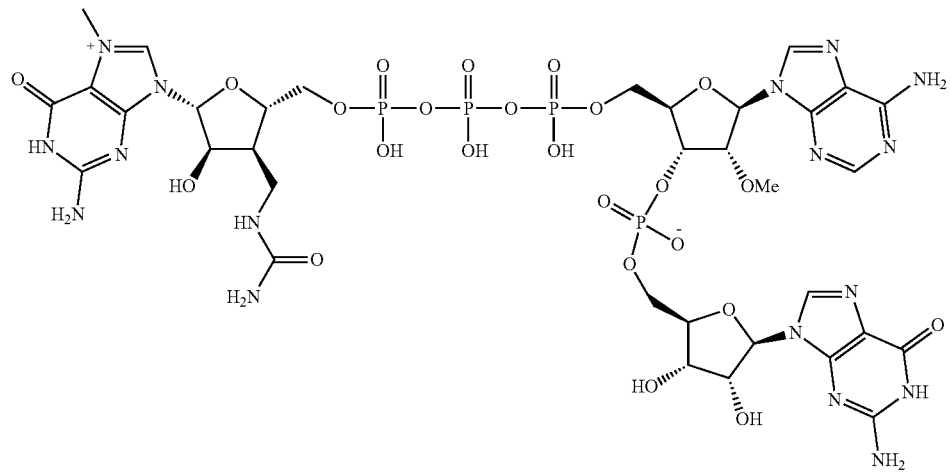
Compound 326
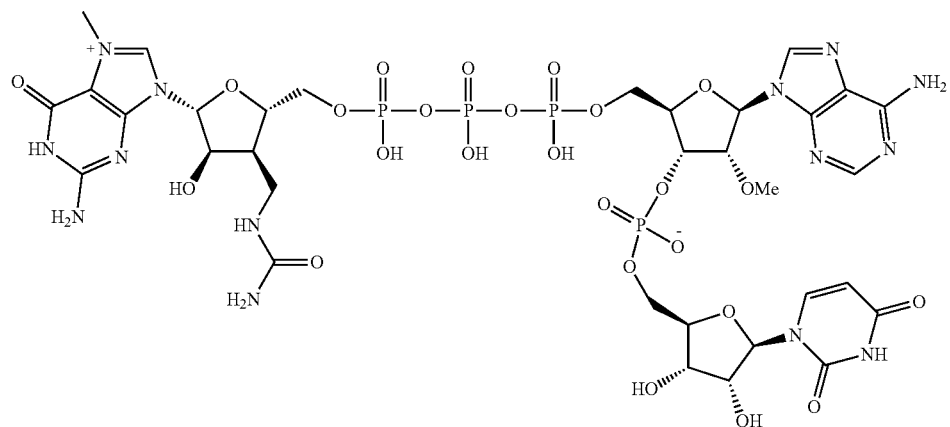
Compound 327
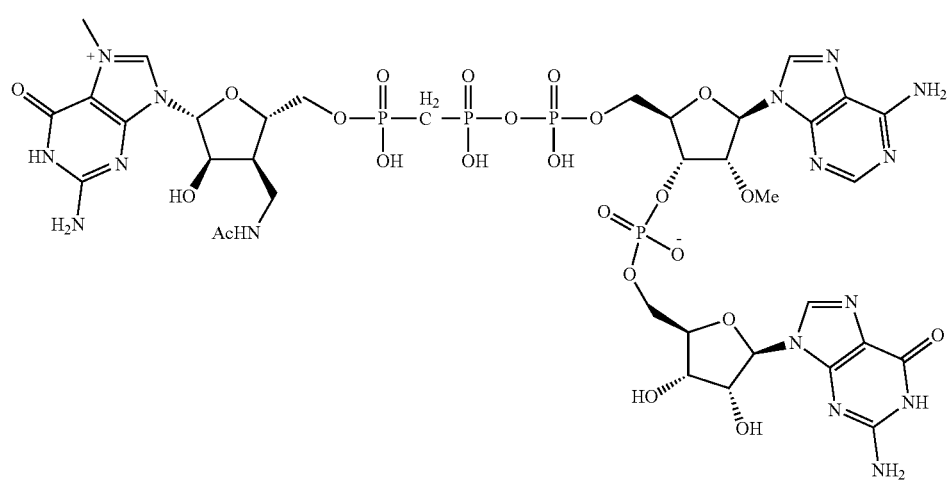

Compound 328
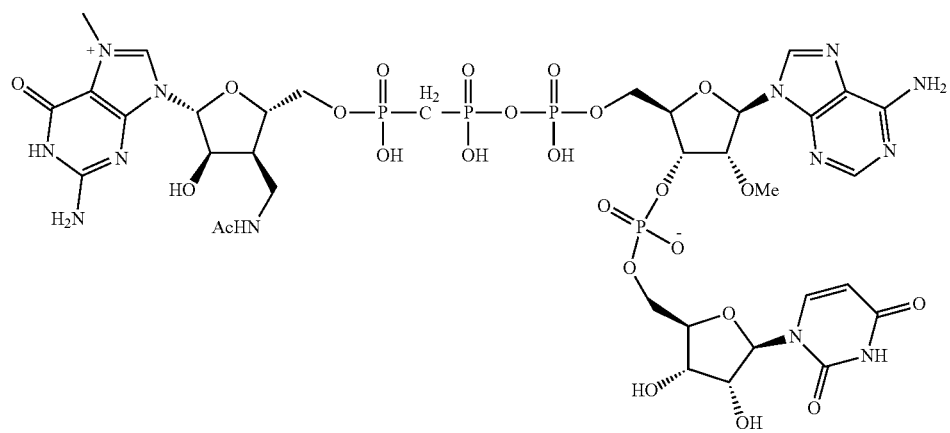
Compound 329
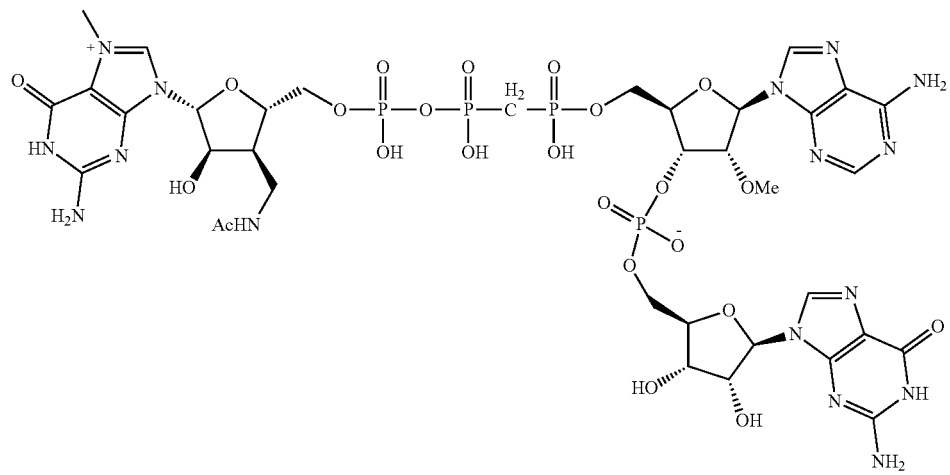
Compound 330
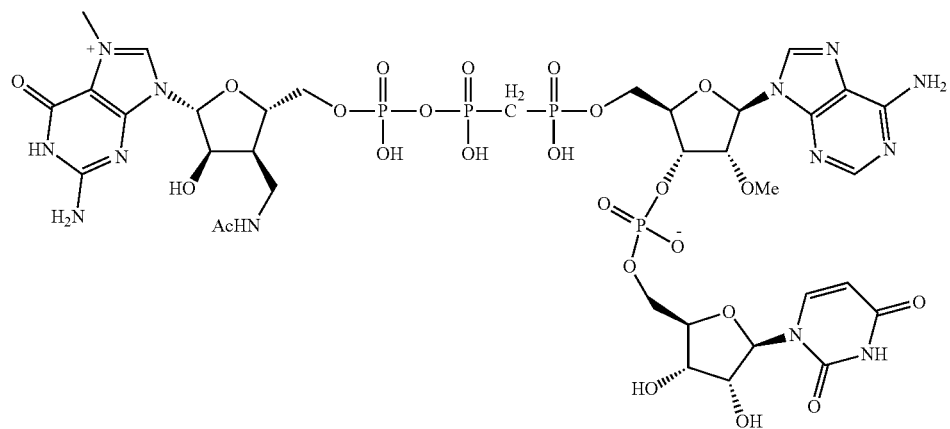

-continued
Compound 331
Compound 332
Compound 333
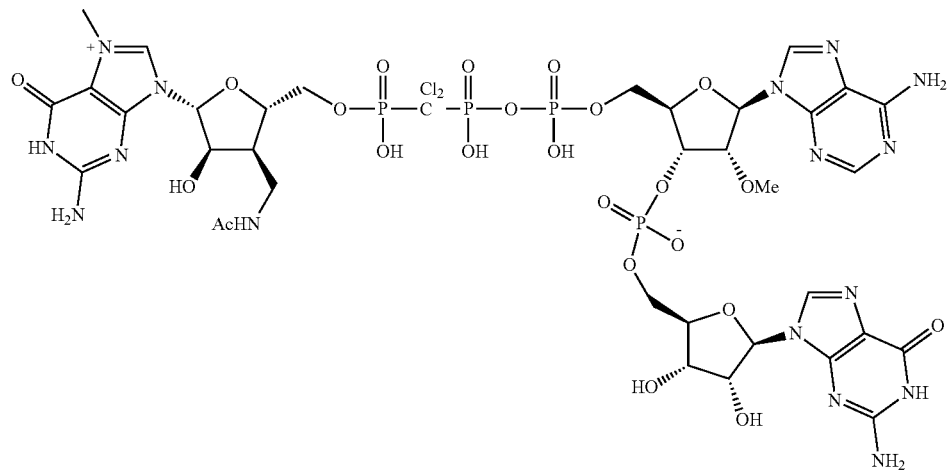

Compound 334
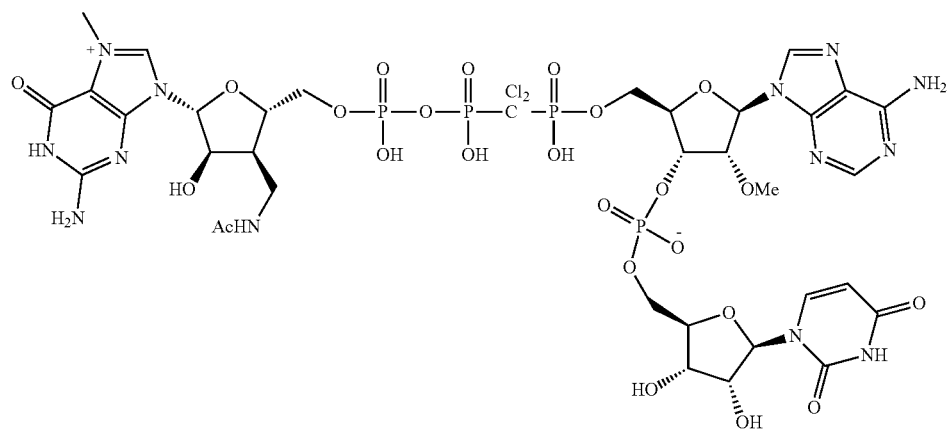
Compound 335
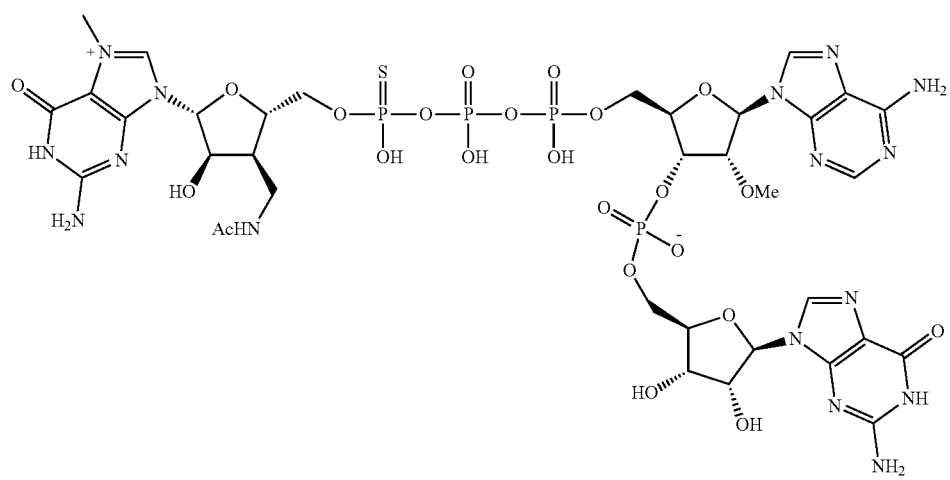
Compound 336
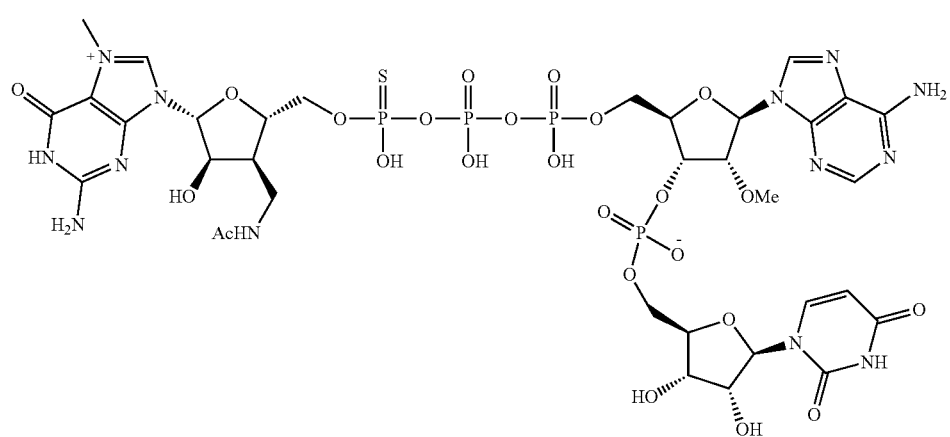

Compound 337
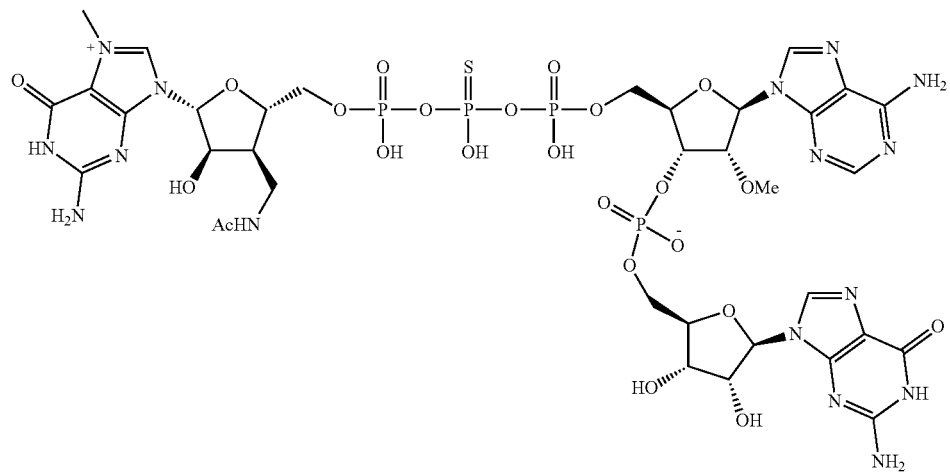
Compound 338
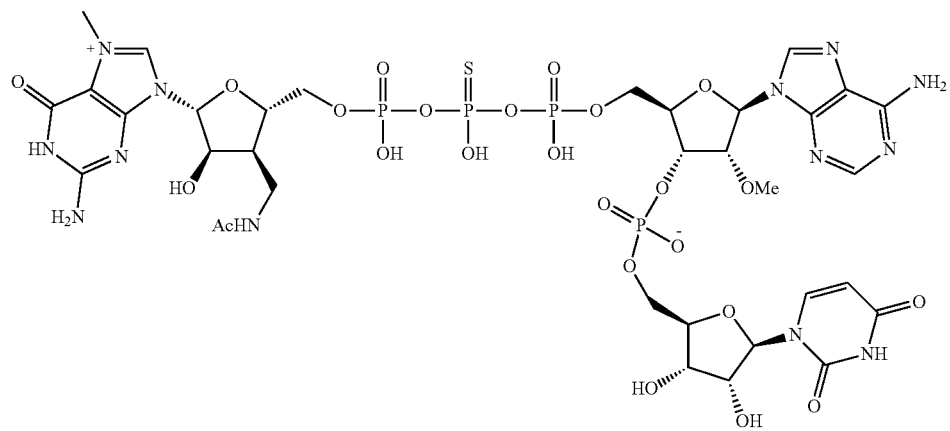
Compound 339
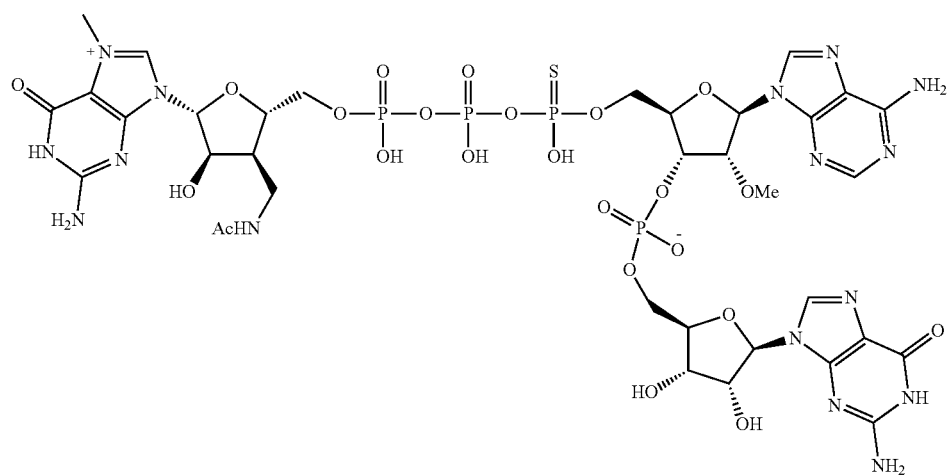

Compound 340
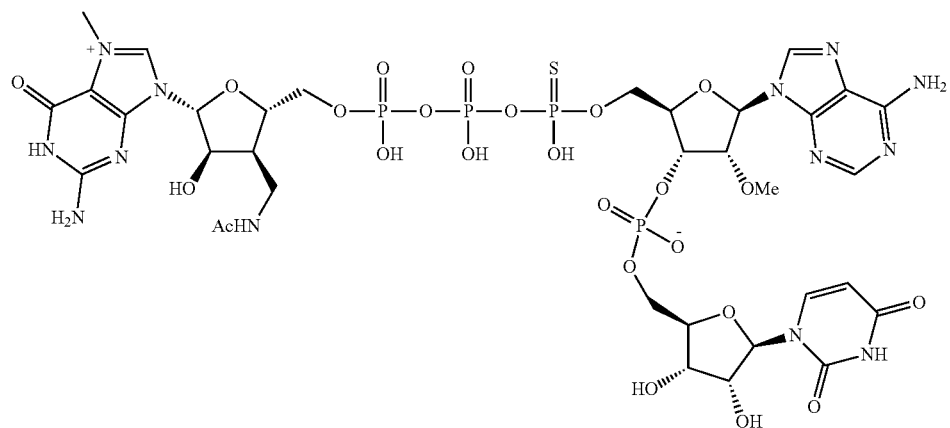
Compound 341
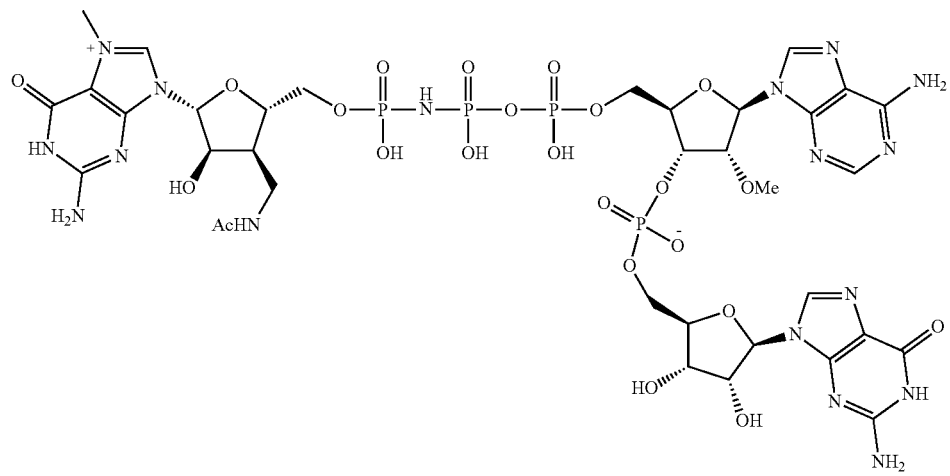
Compound 342
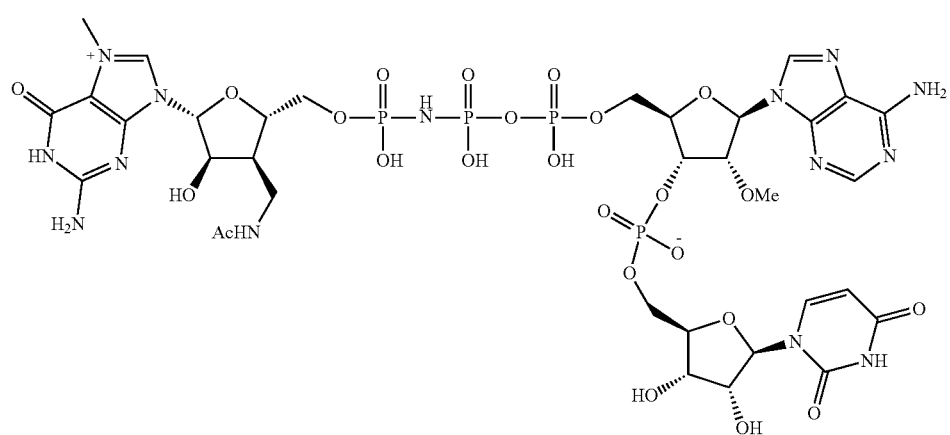

-continued
Compound 343
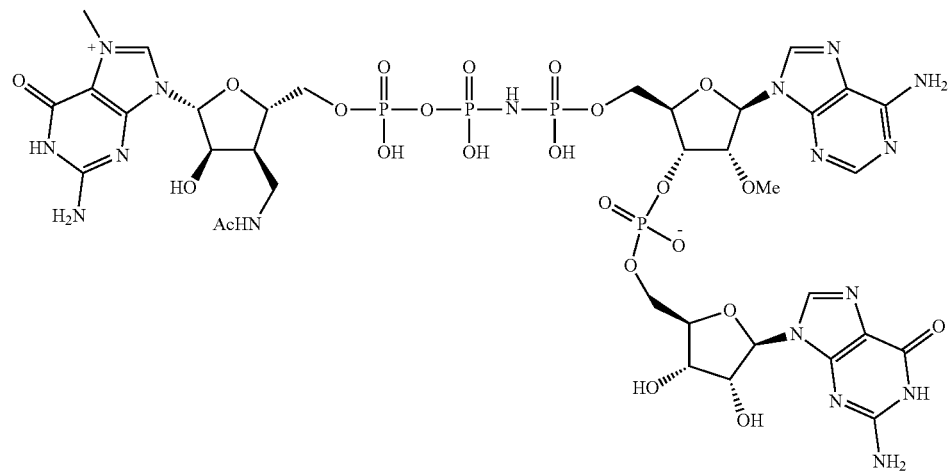
Compound 344
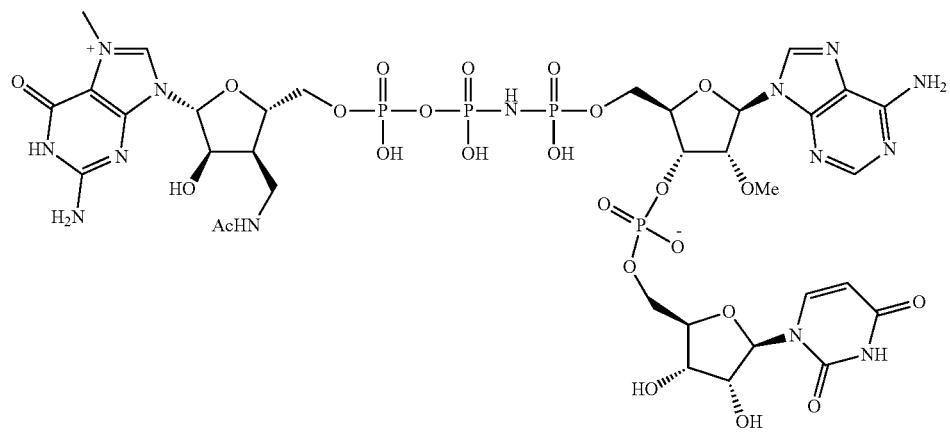
Compound 345
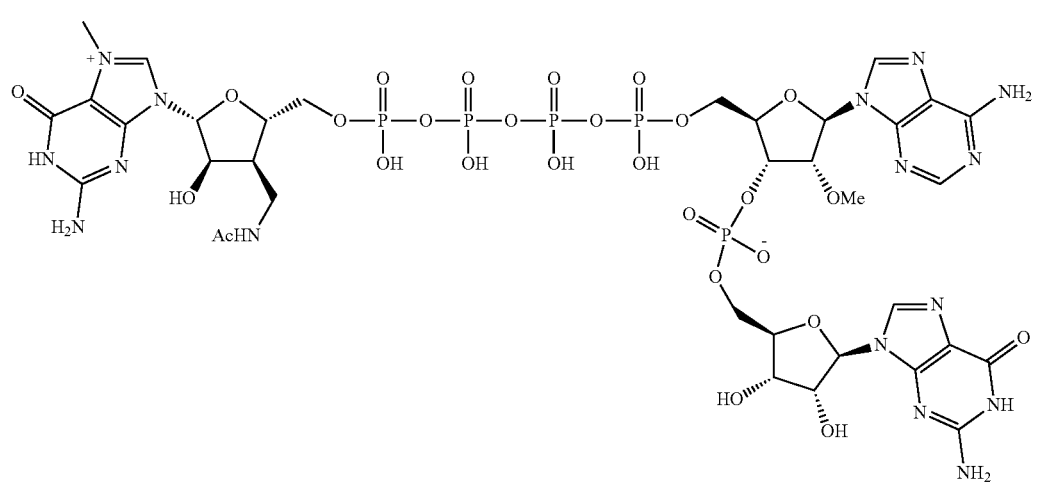

-continued
Compound 346
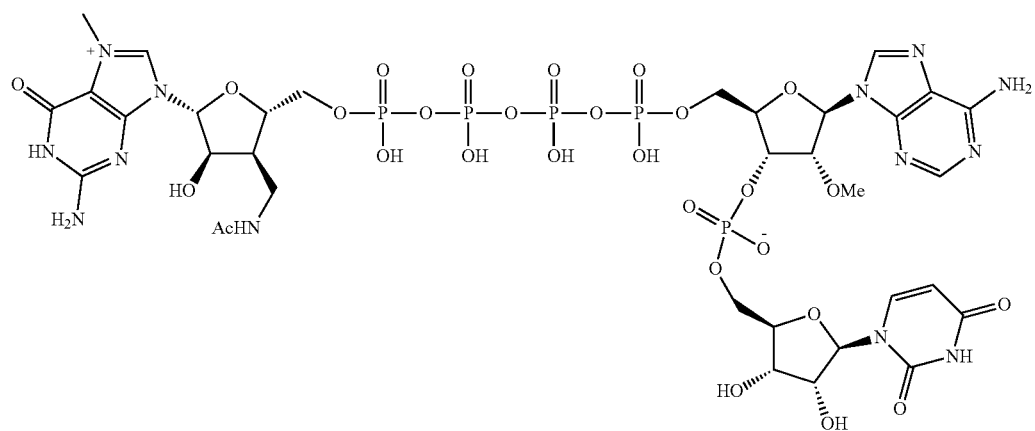
Compound 347
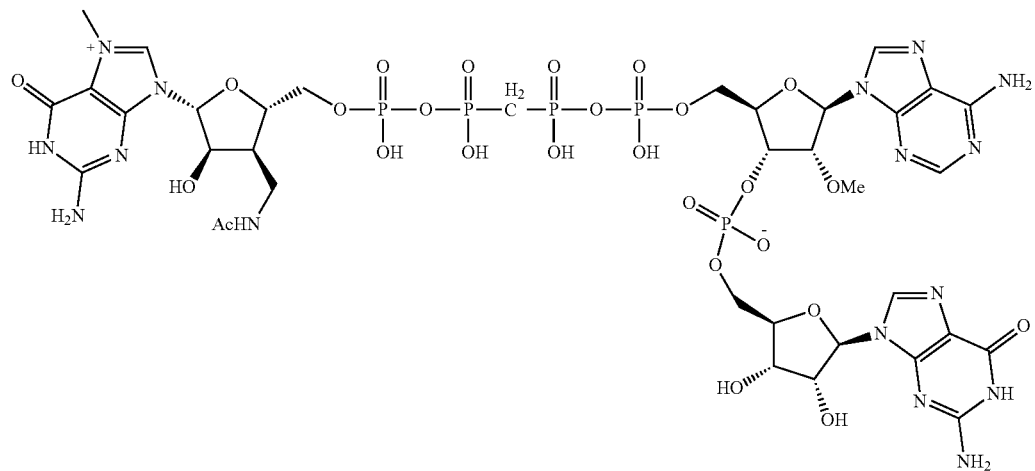
Compound 348
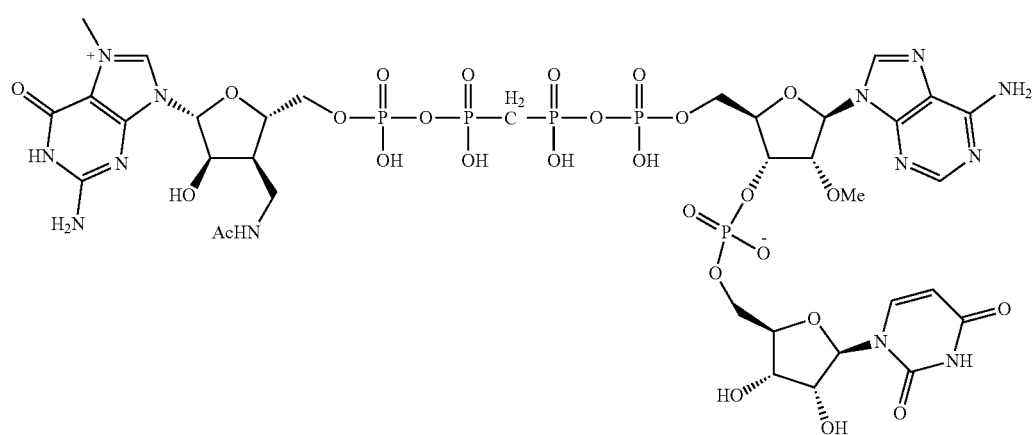

Compound 349
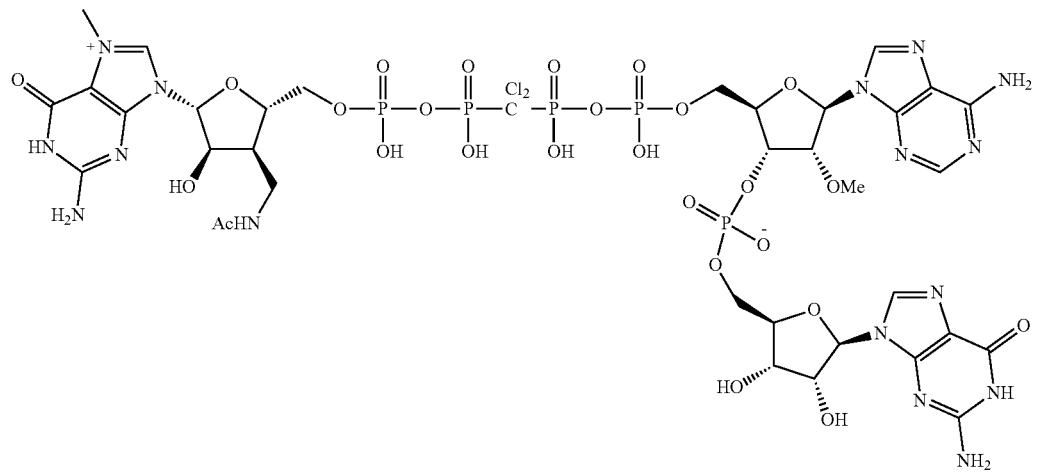
Compound 350
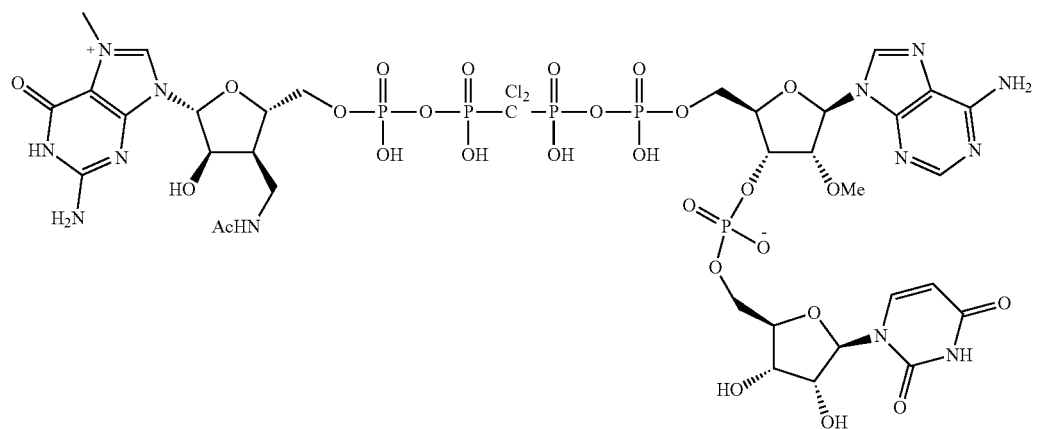
Compound 351
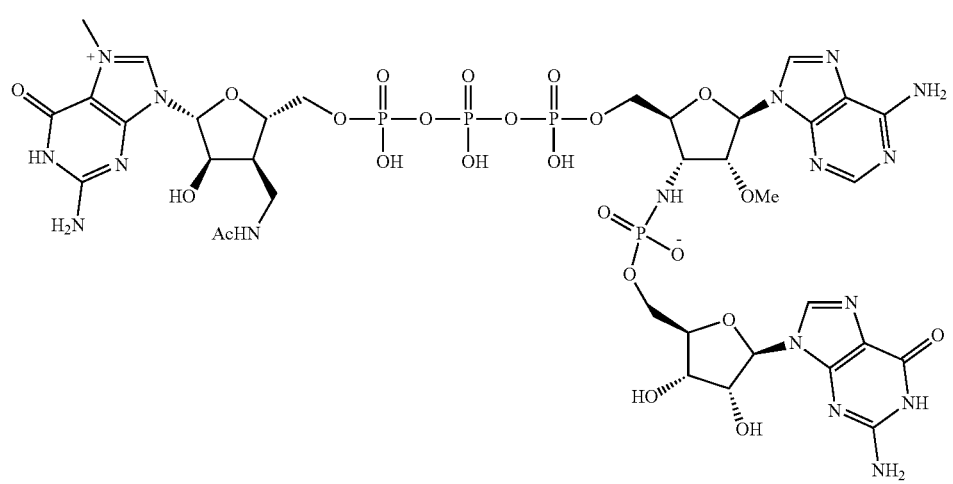

-continued
Compound 352
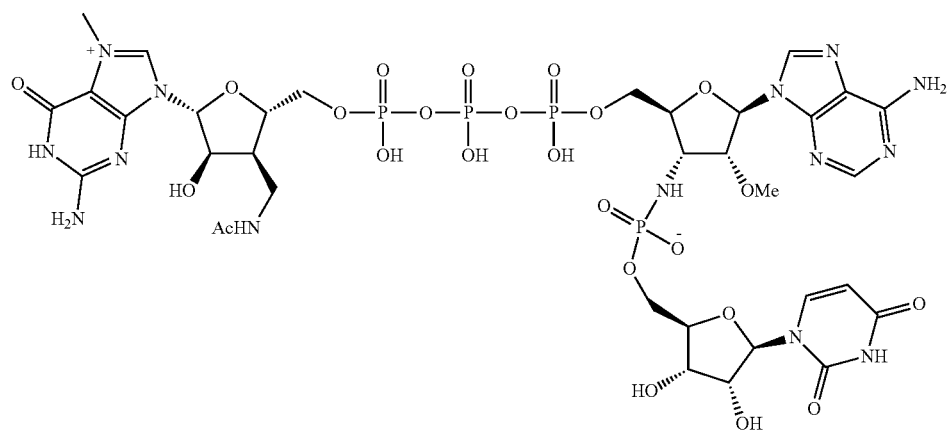
Compound 353
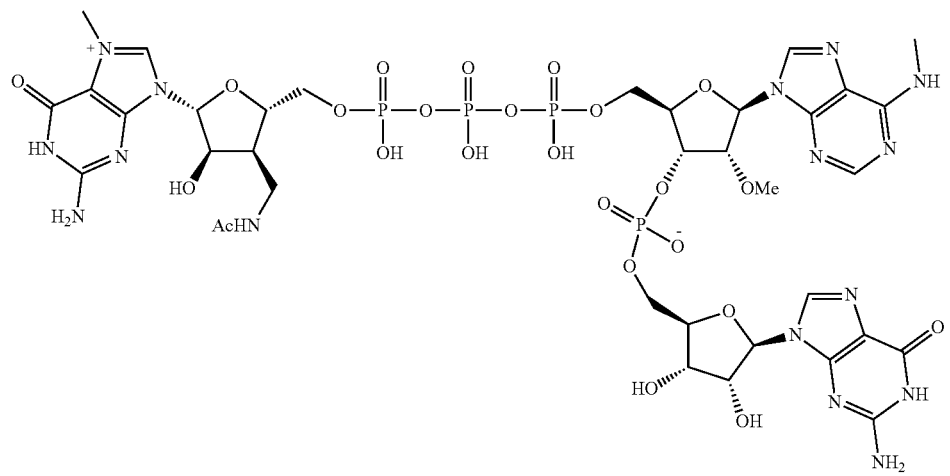
Compound 354
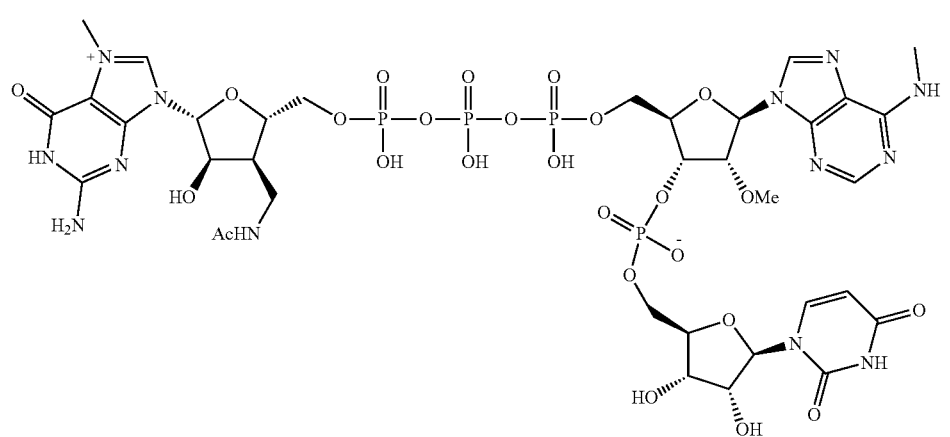

Compound 355
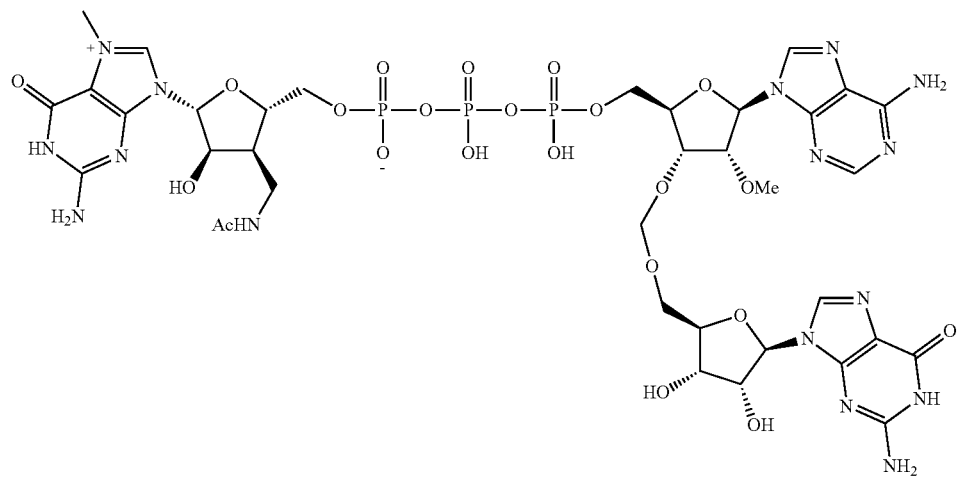
Compound 356
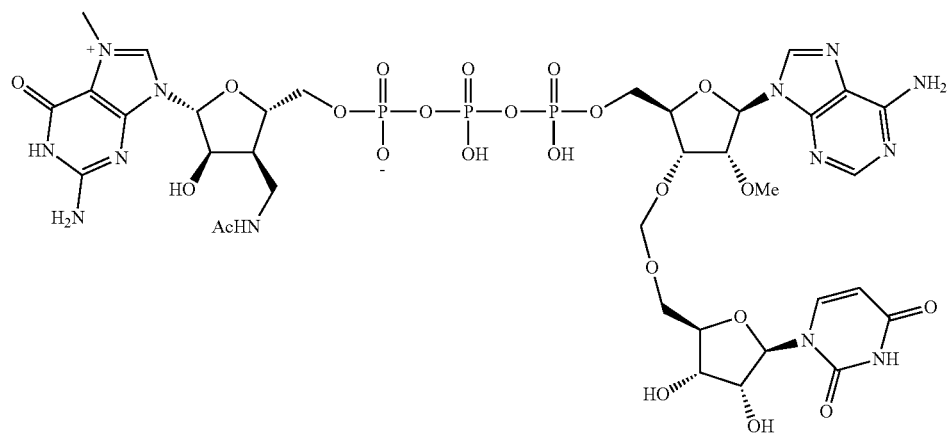
Compound 357
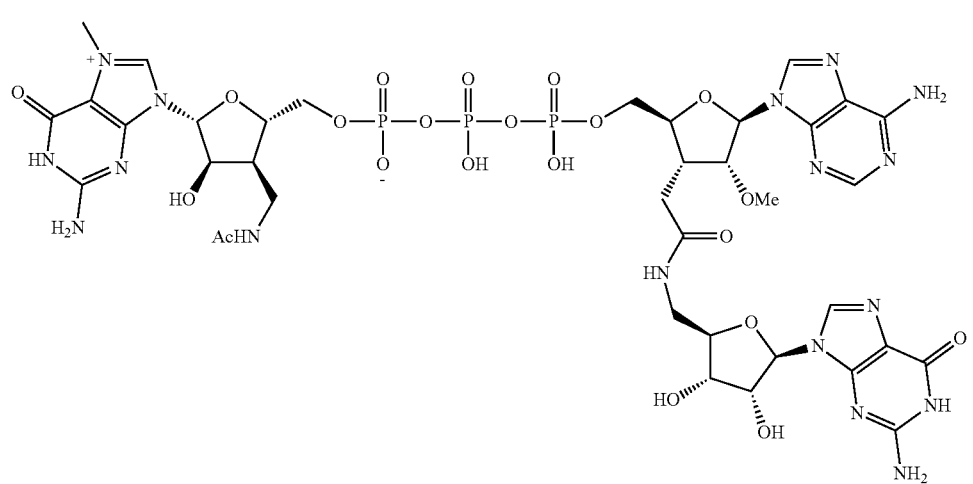

Compound 358
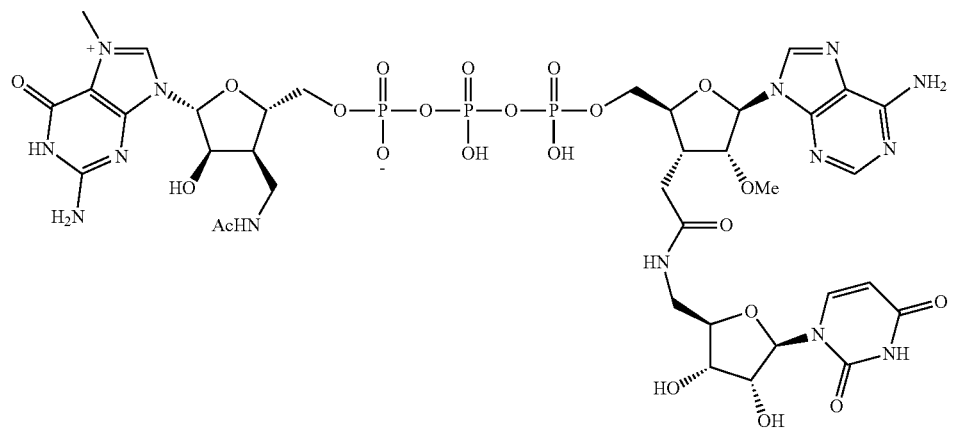
Compound 359
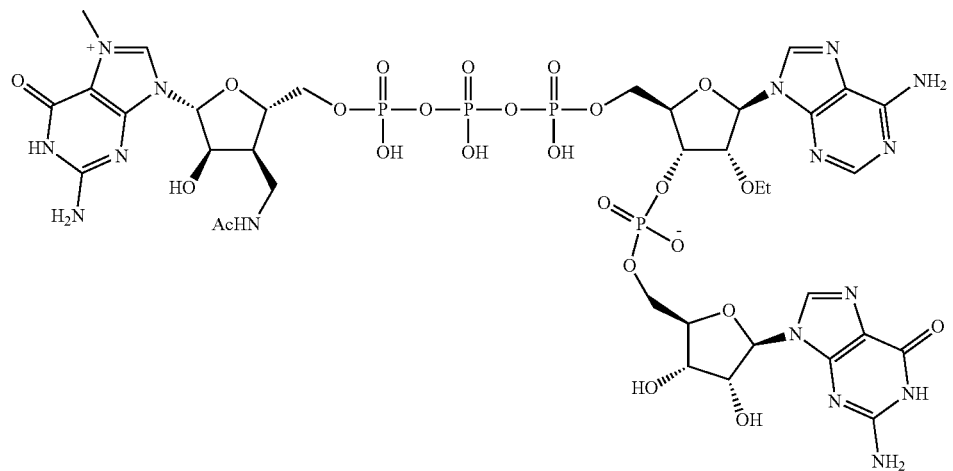
Compound 360
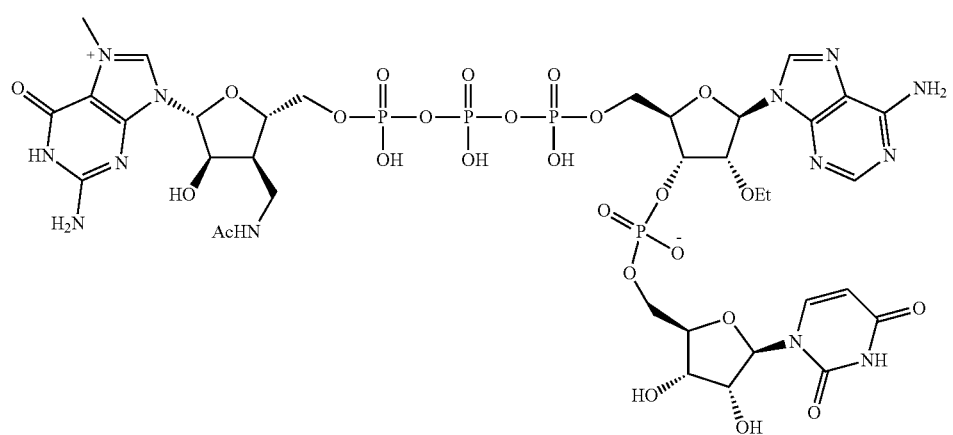

-continued
Compound 361
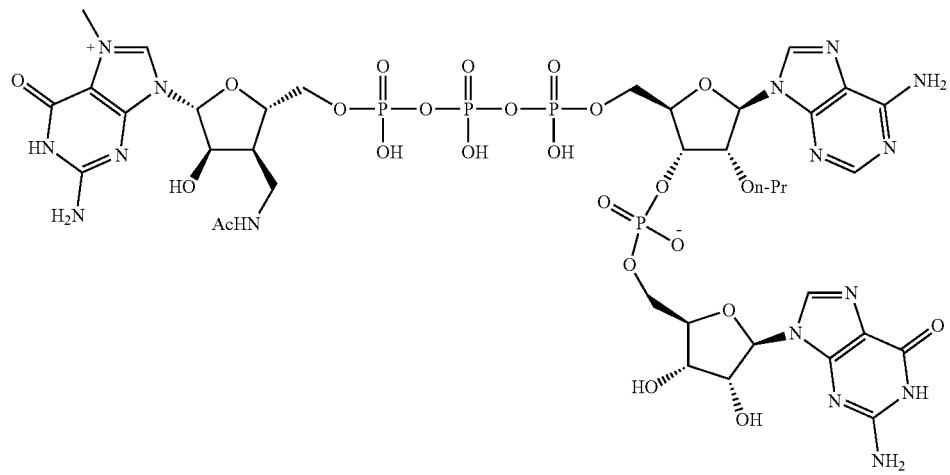
Compound 362
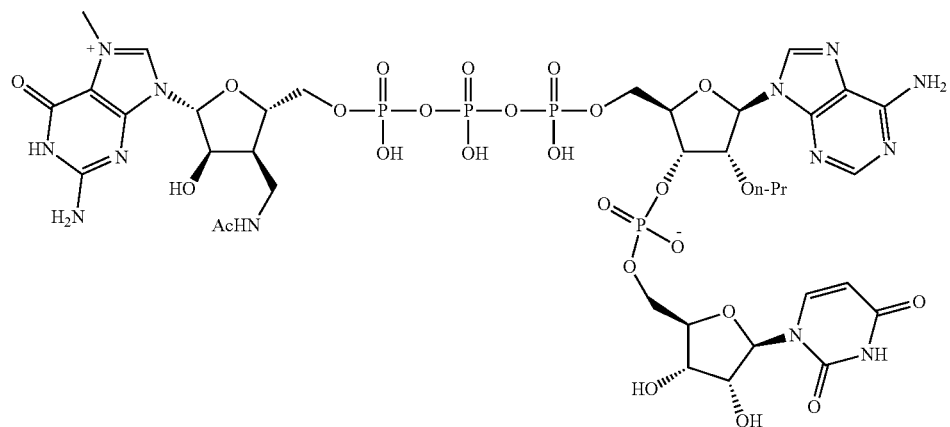
Compound 363
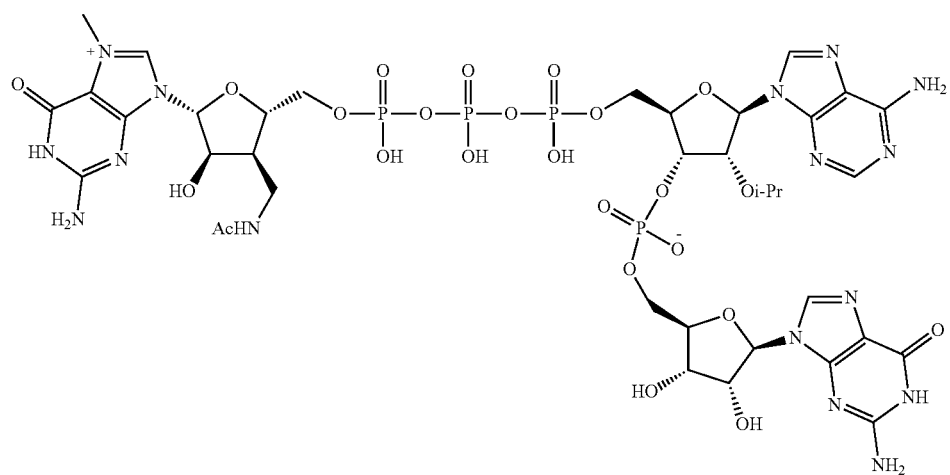

-continued
Compound 364
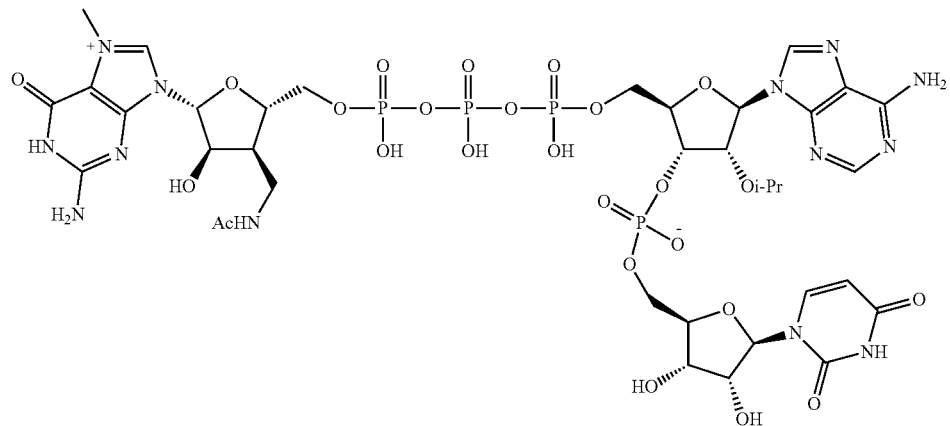
Compound 365
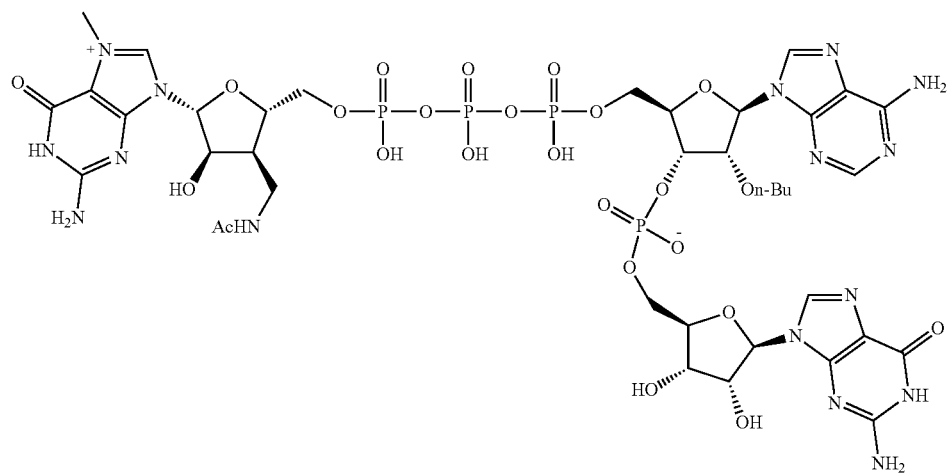
Compound 366
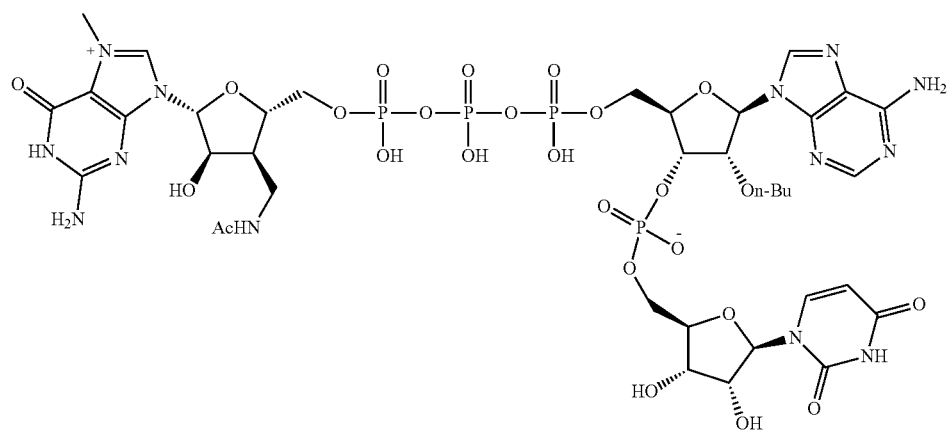

Compound 367
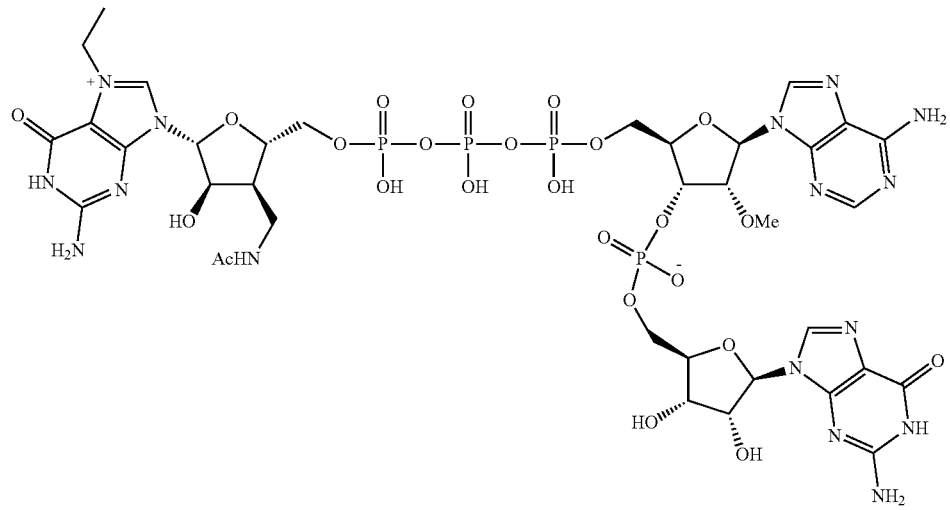
Compound 368
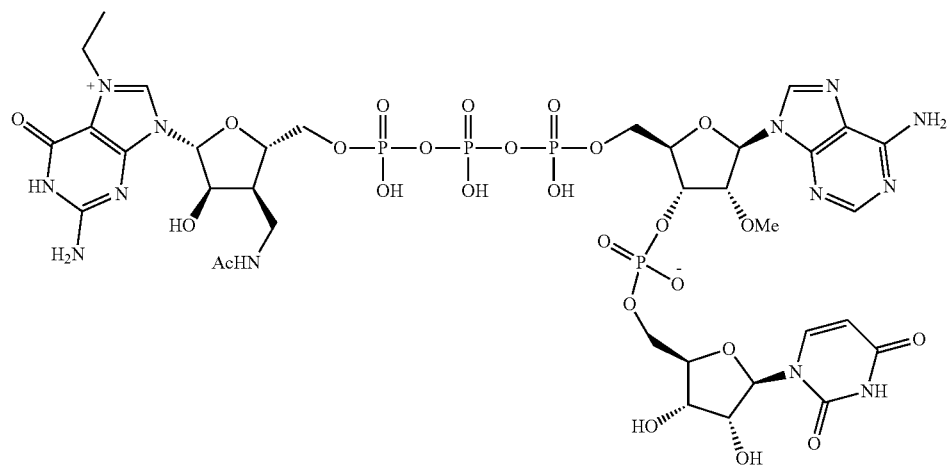
Compound 369
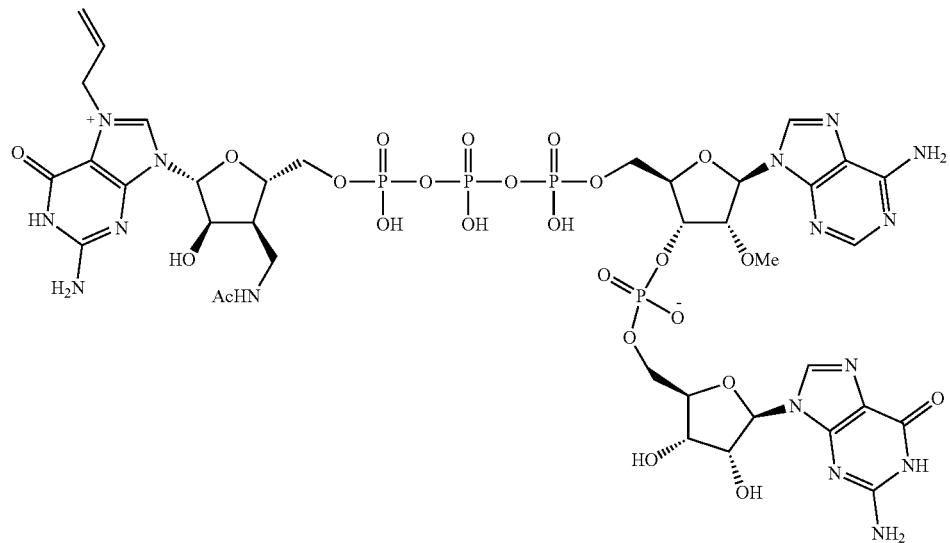

-continued
Compound 370
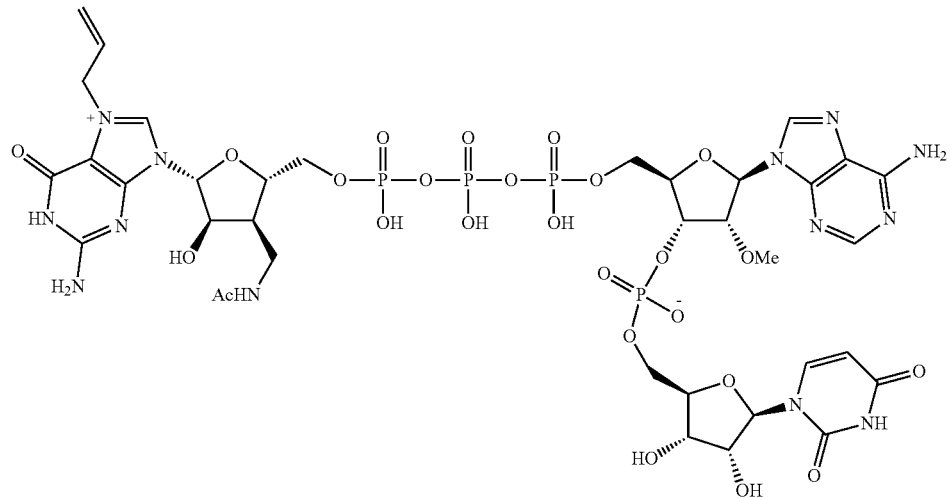
Compound 371
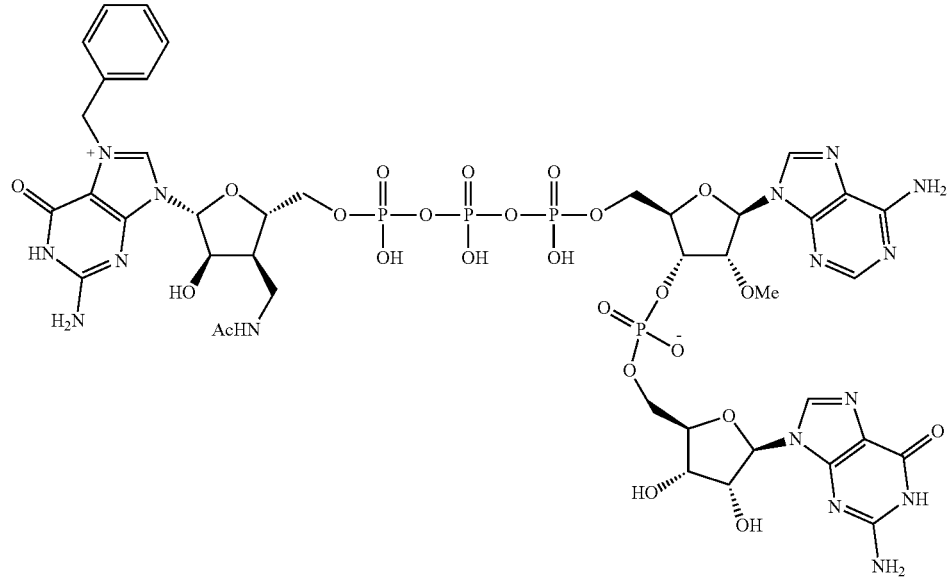
Compound 372
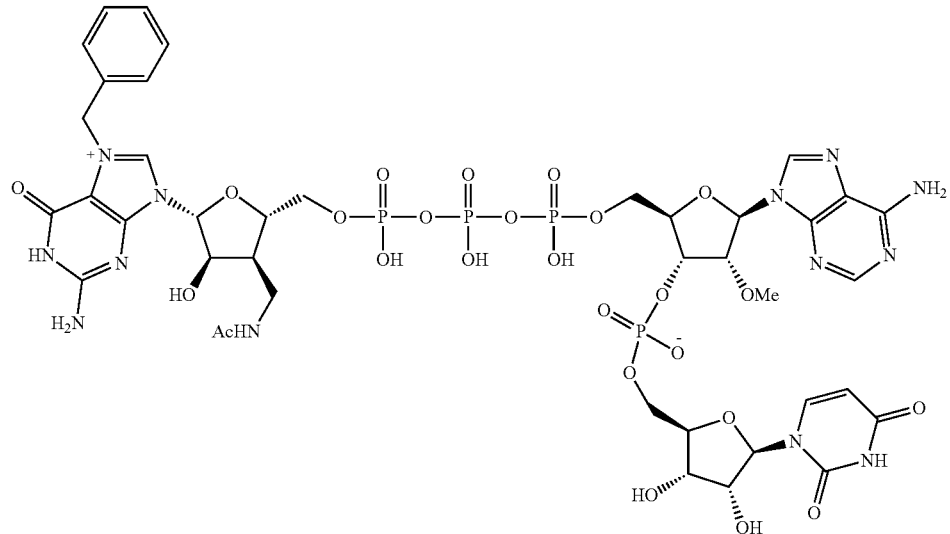

Compound 373
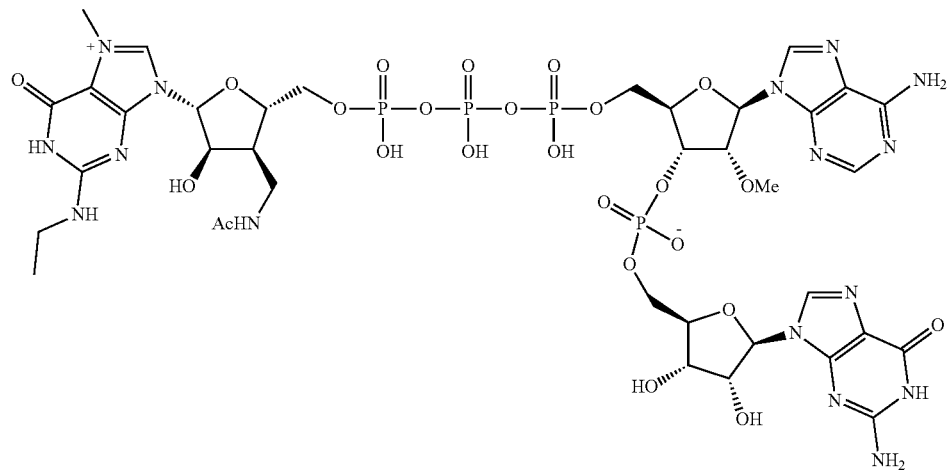
Compound 374
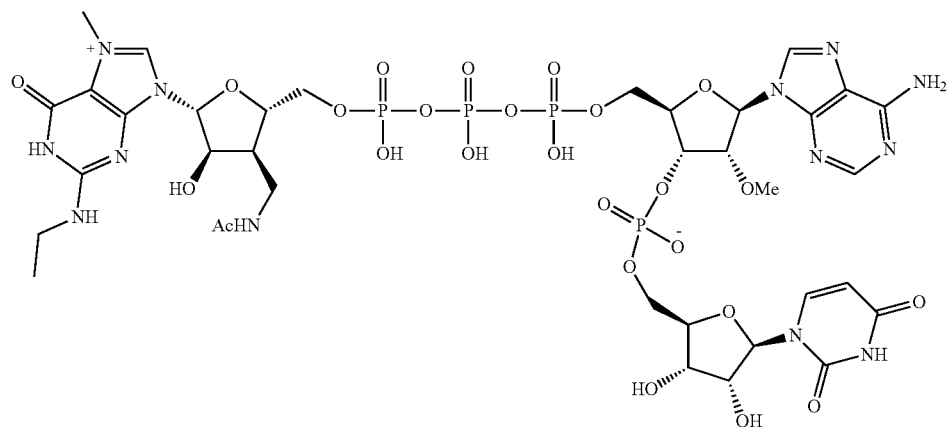
Compound 375
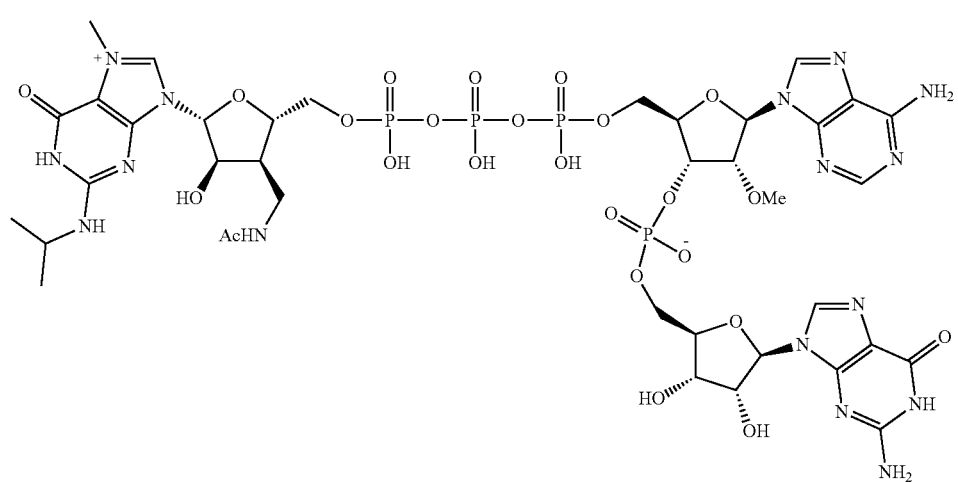

-continued
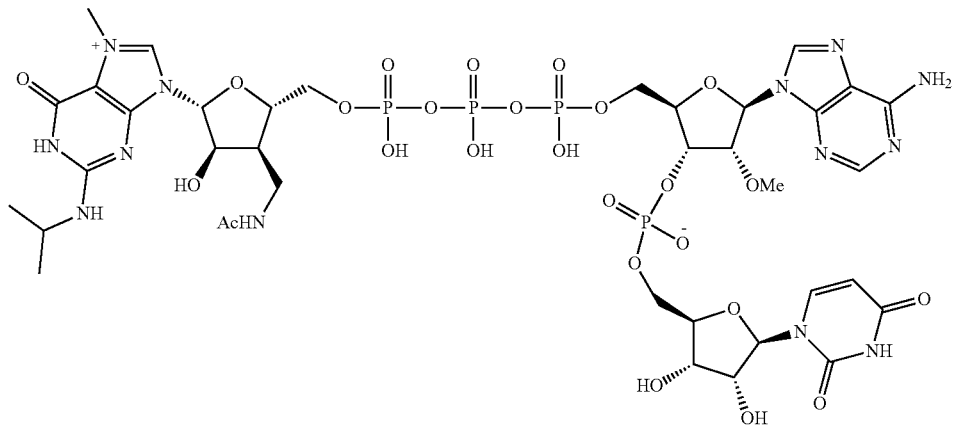
Compound 376
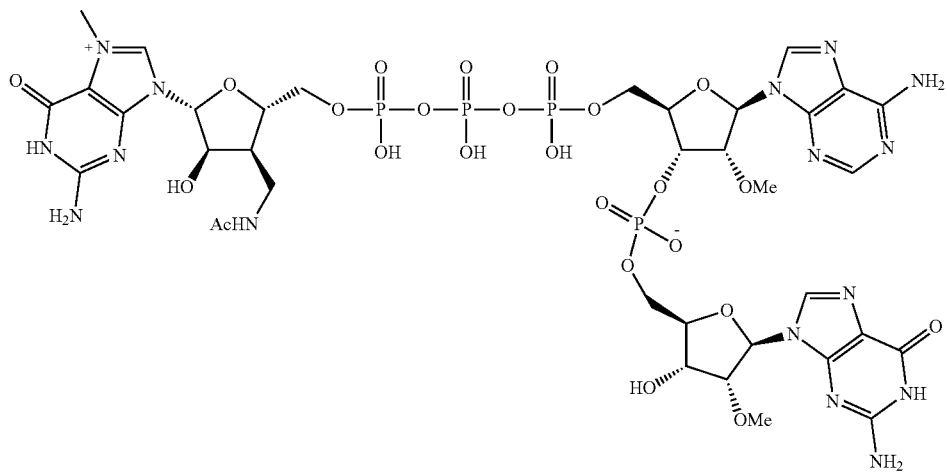
Compound 381
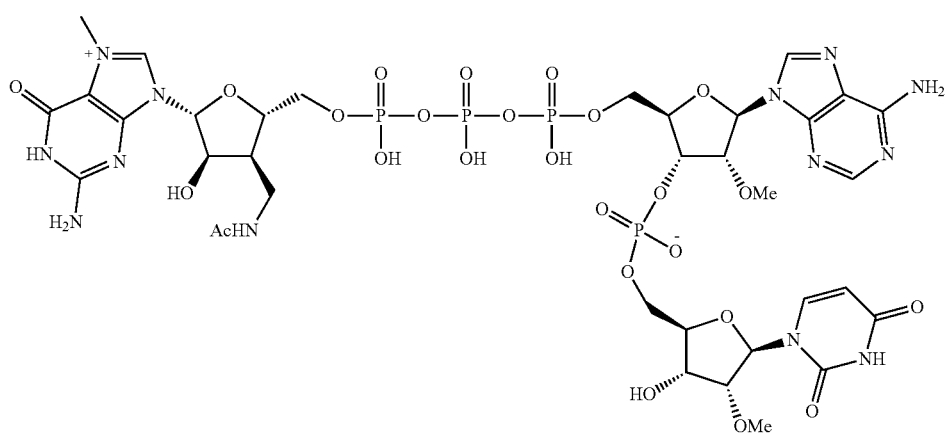
Compound 382

Compound 383
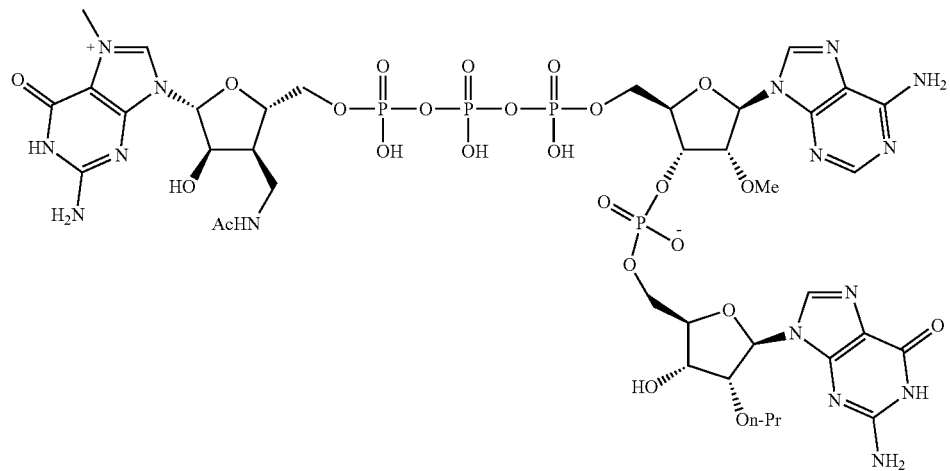
Compound 384
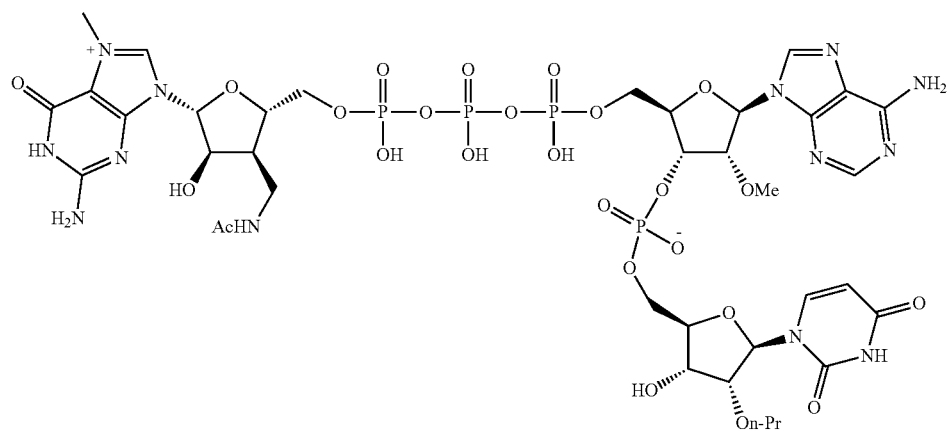
Compound 385
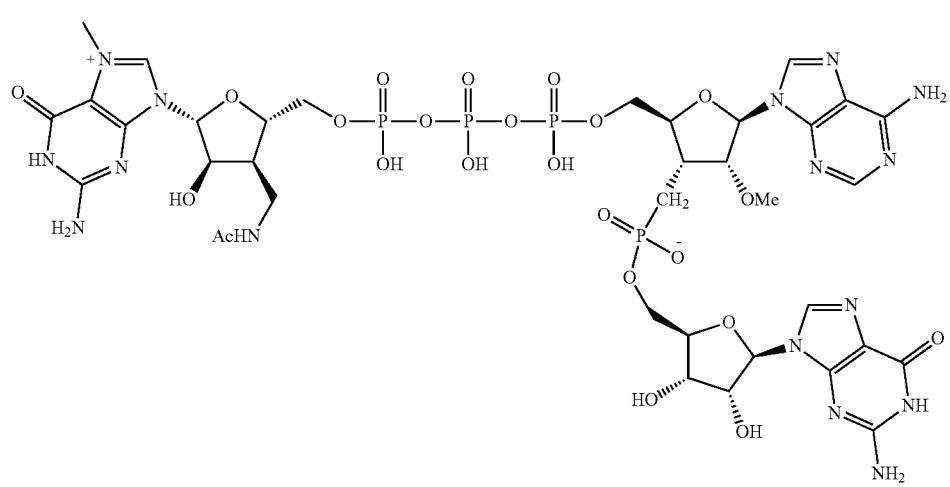

-continued
Compound 386
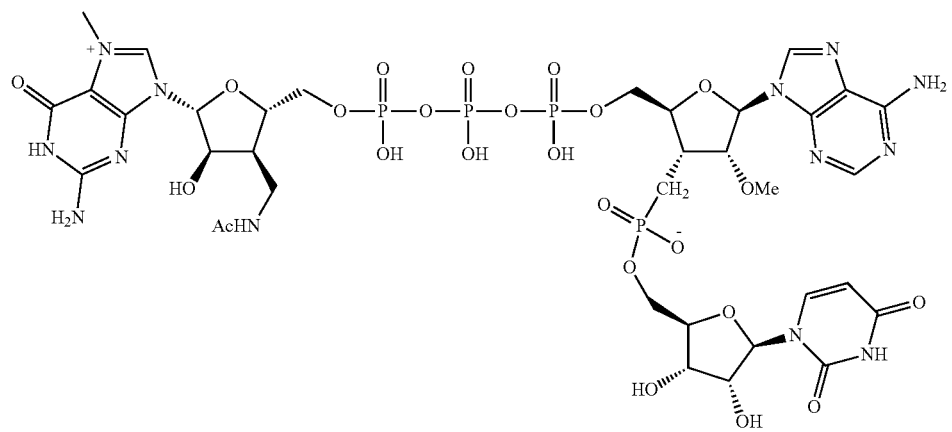
Compound 387
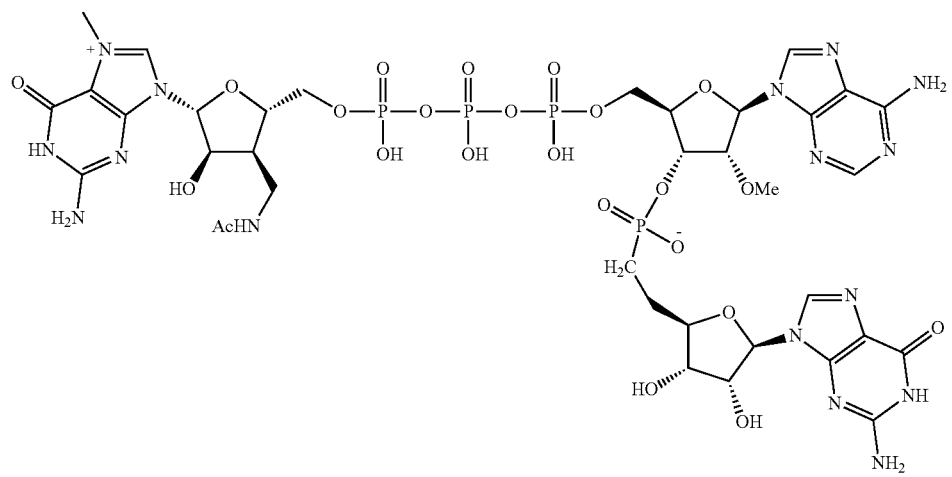
Compound 388
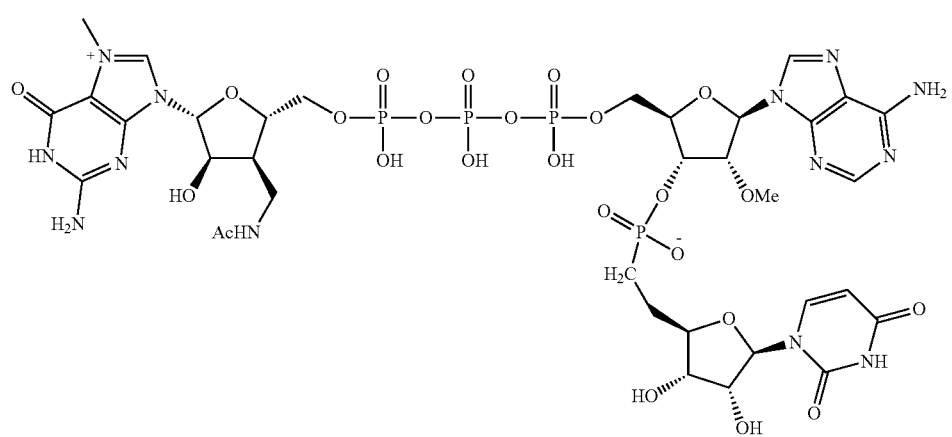

Compound 389
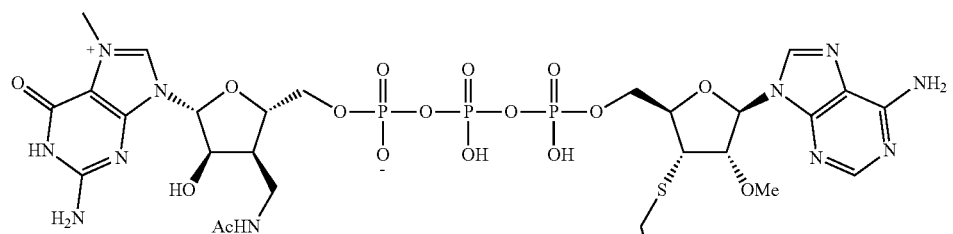
Compound 390
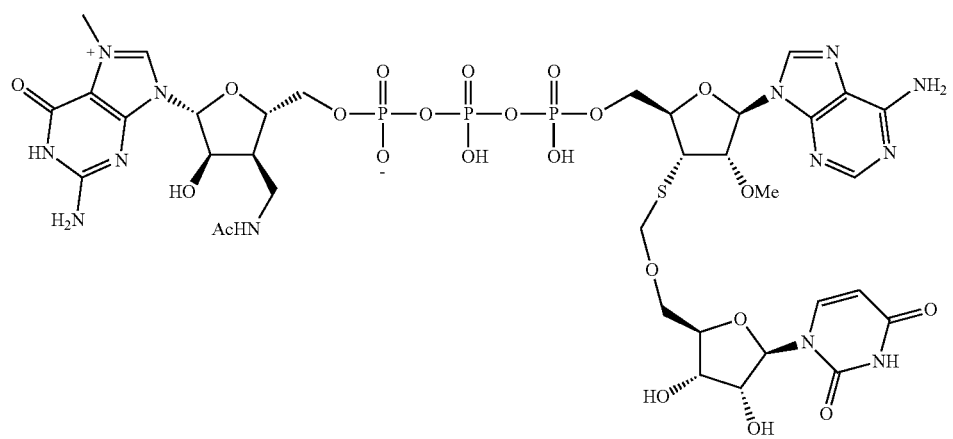
Compound 391
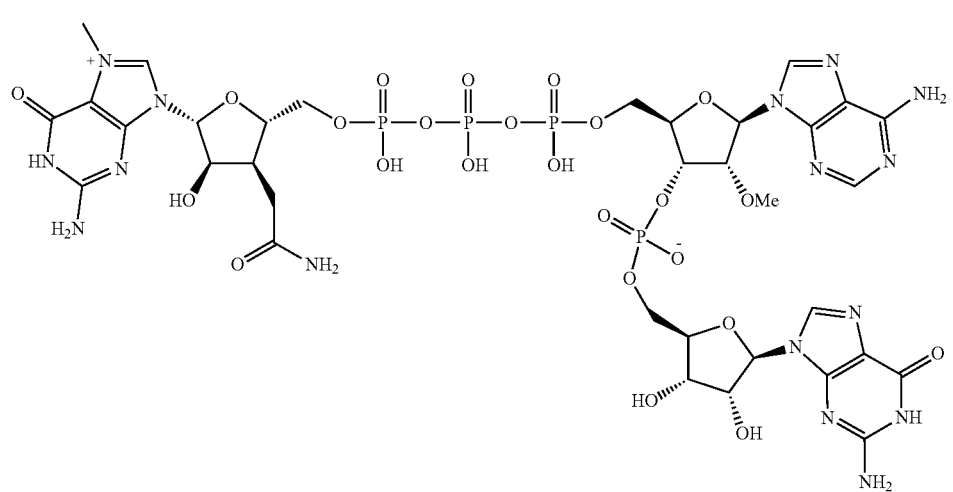

Compound 392
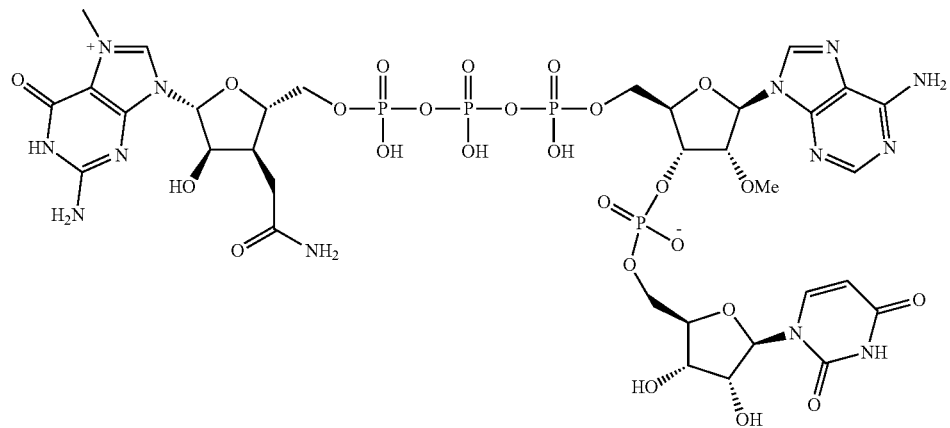
Compound 393
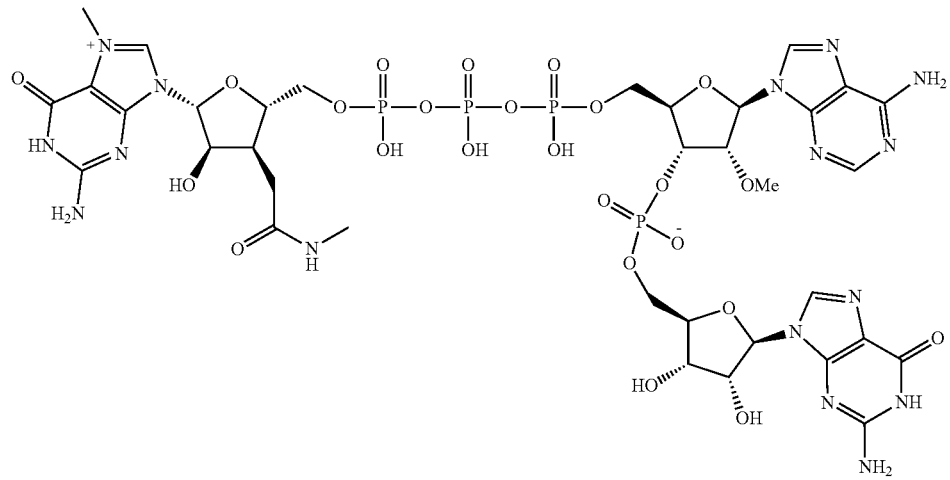
Compound 394
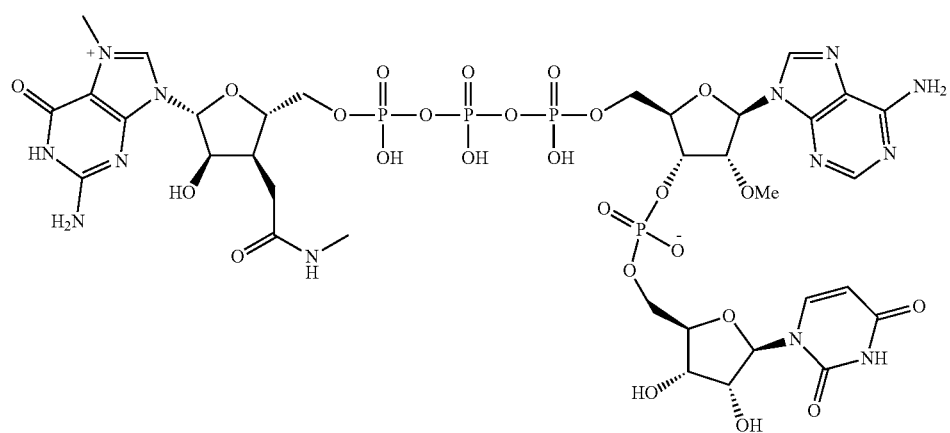

Compound 395
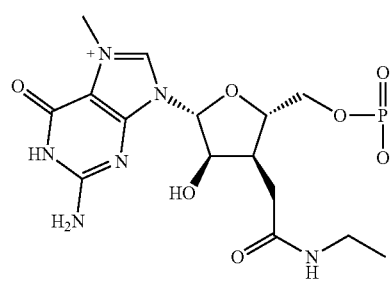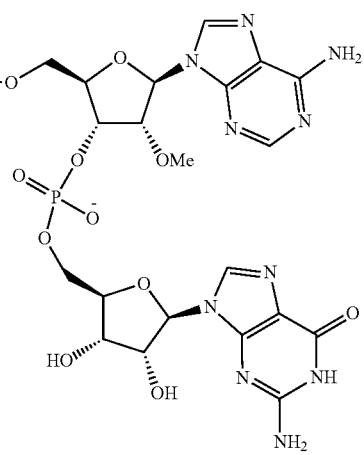
Compound 396
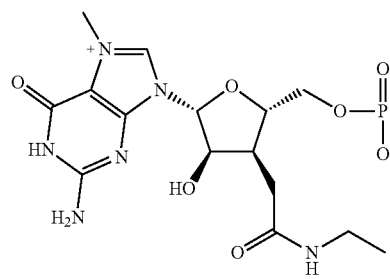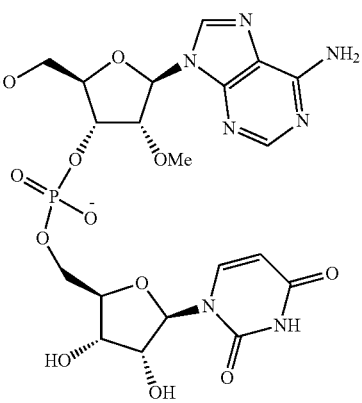
Compound 397
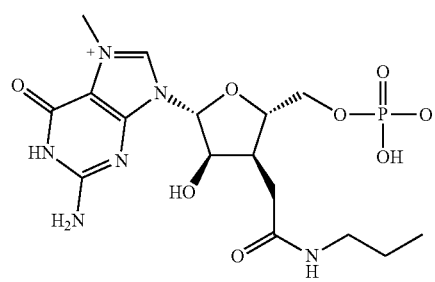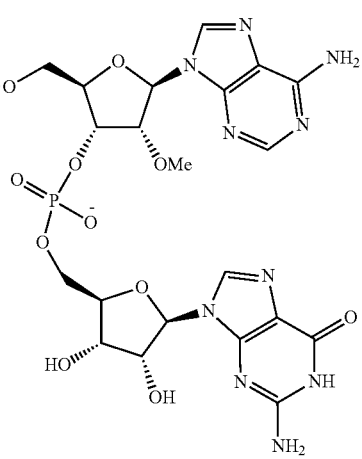

Compound 398
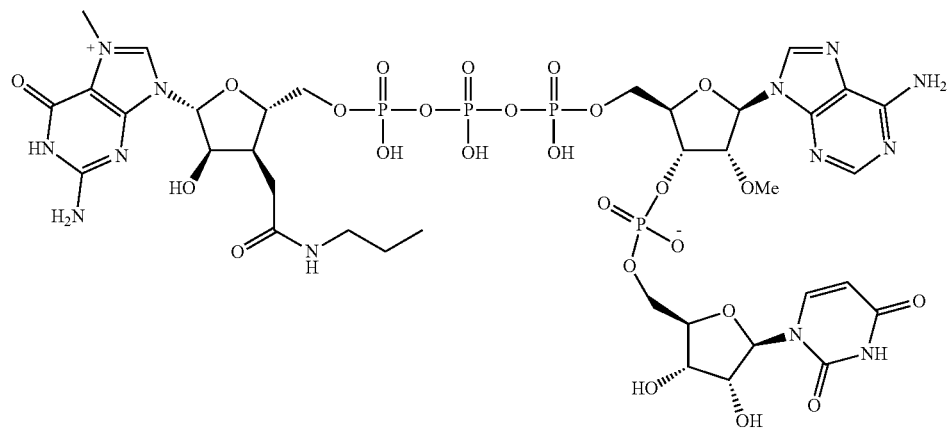
Compound 399
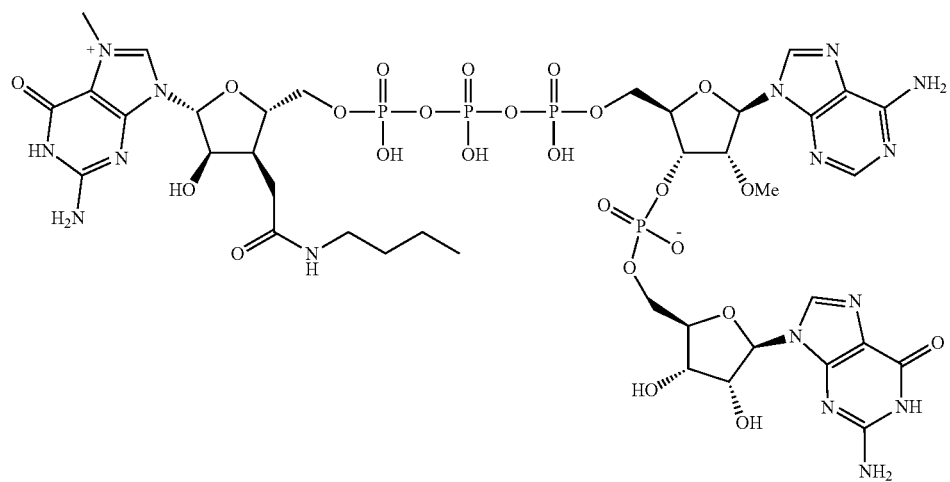
Compound 400
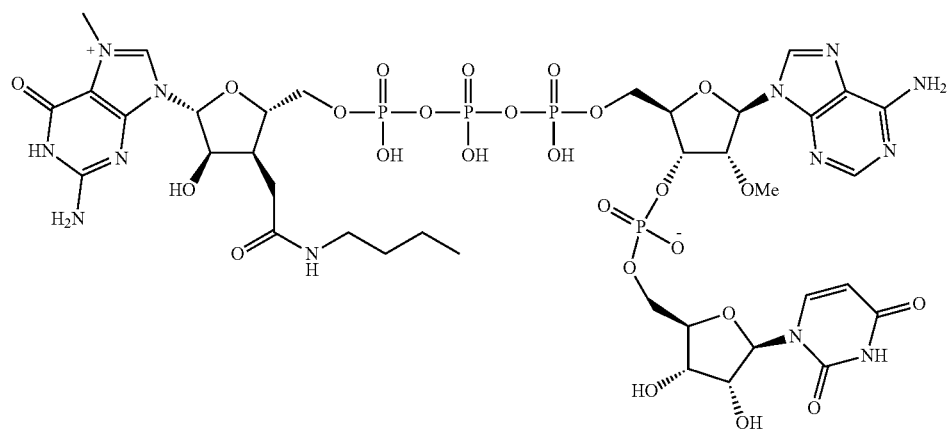

-continued
Compound 401
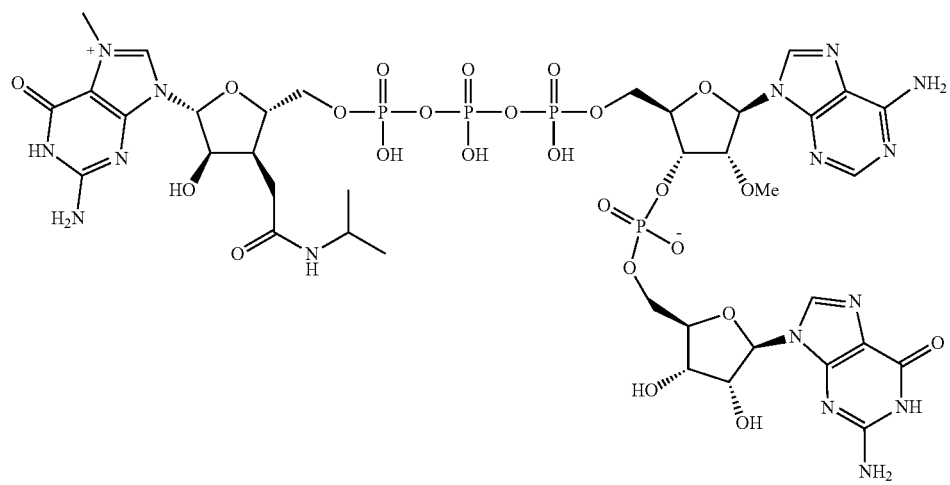
Compound 402
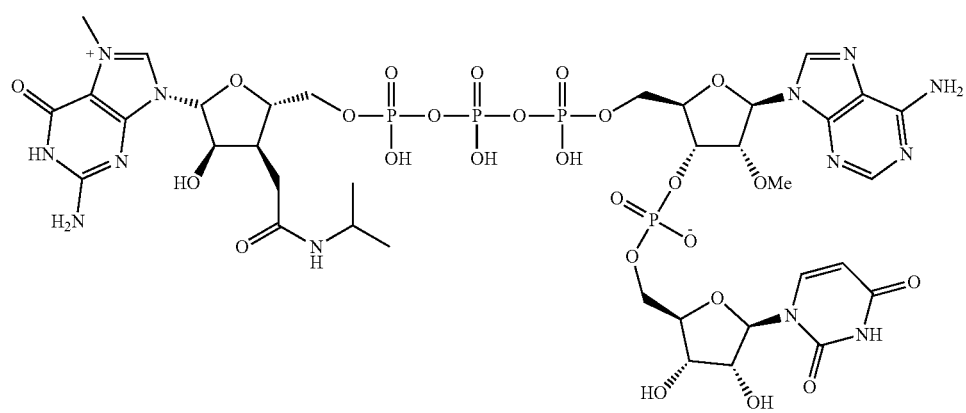
Compound 403
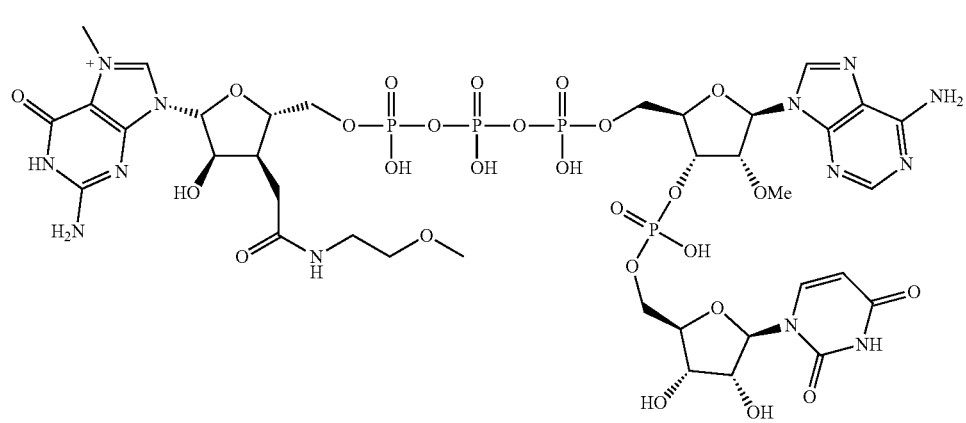

-continued
Compound 404
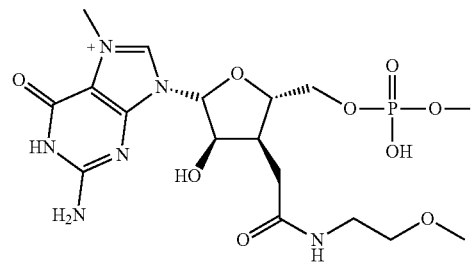
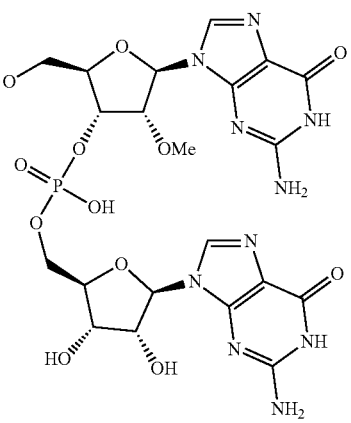
Compound 405
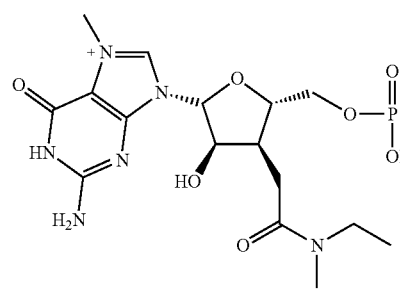
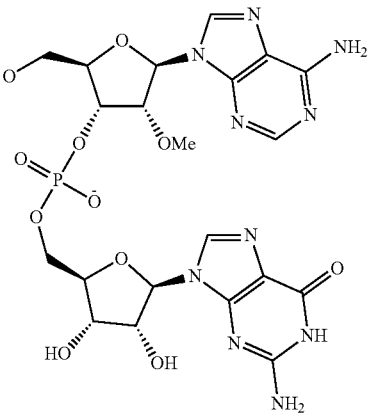
Compound 406
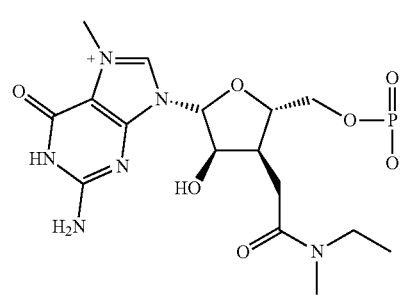
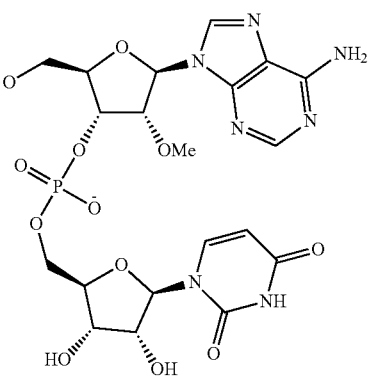

Compound 407
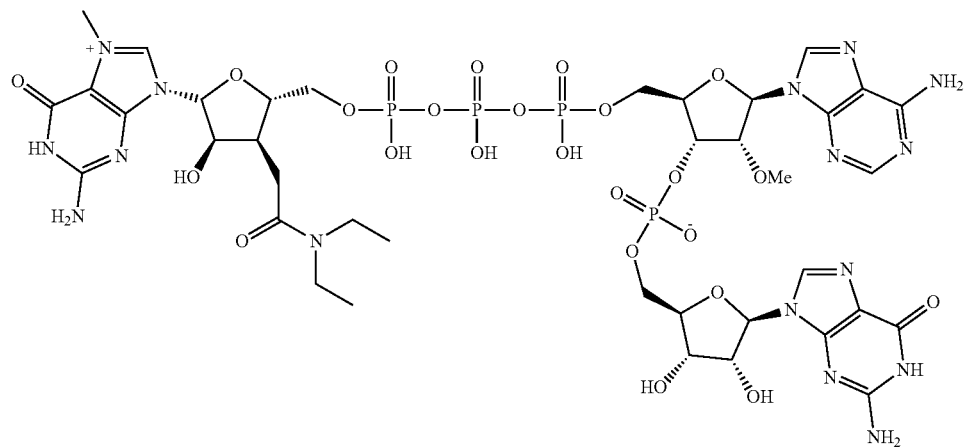
Compound 408
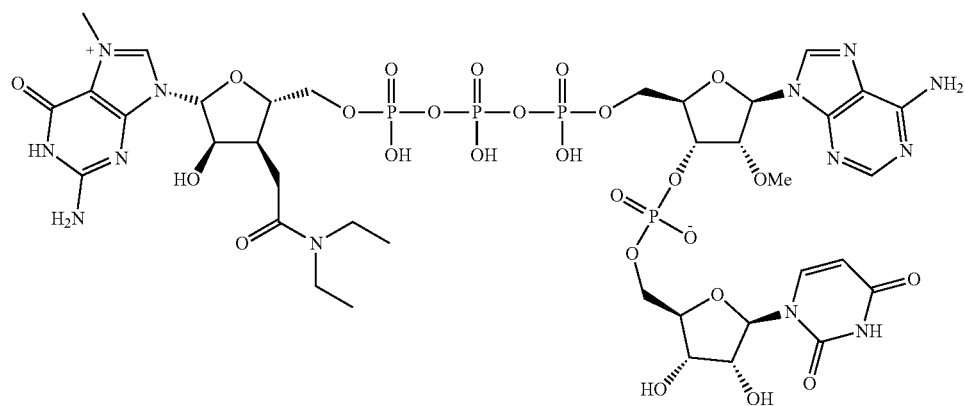
Compound 409
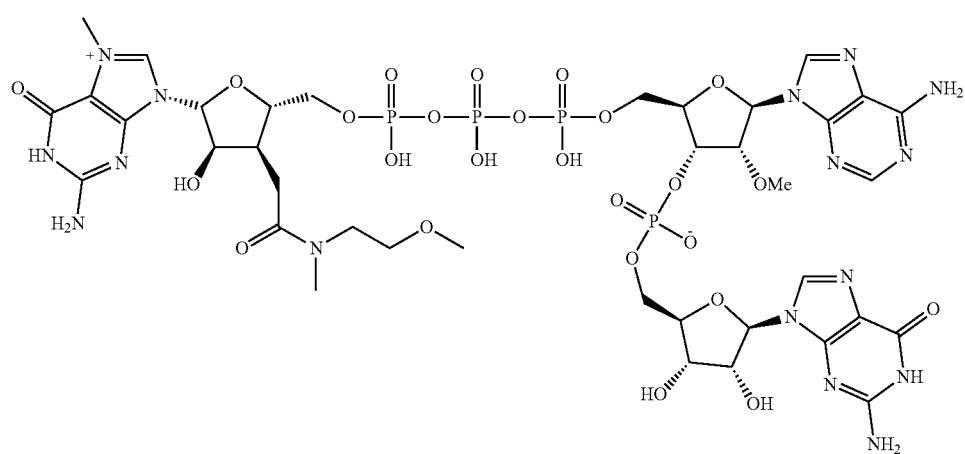

-continued
Compound 410
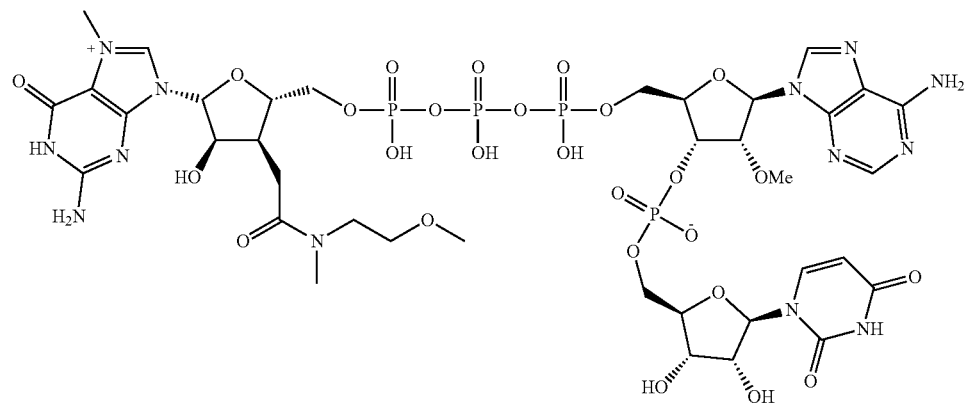
Compound 411
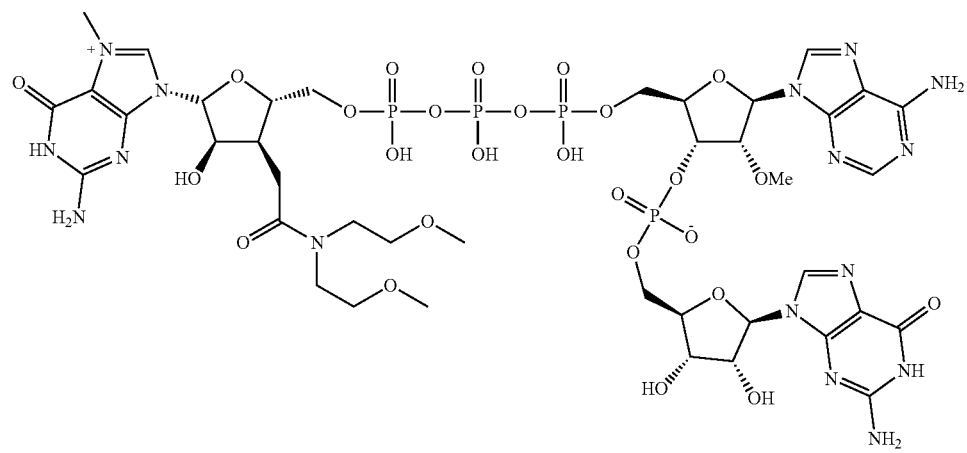
Compound 412
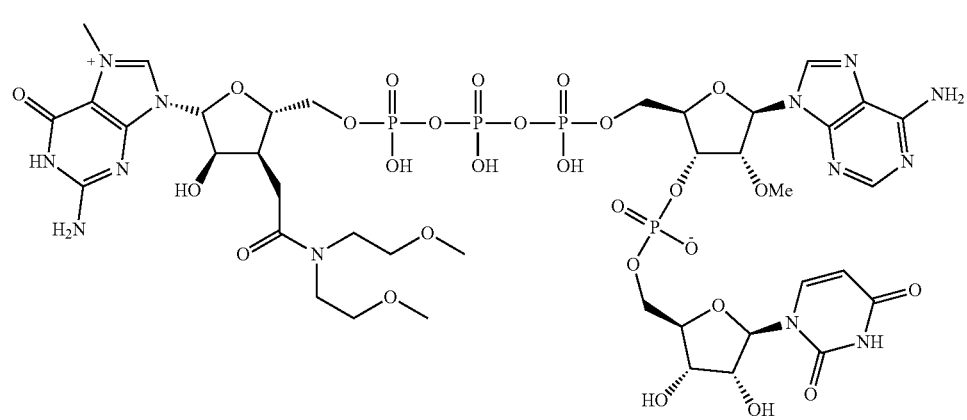

-continued
Compound 413
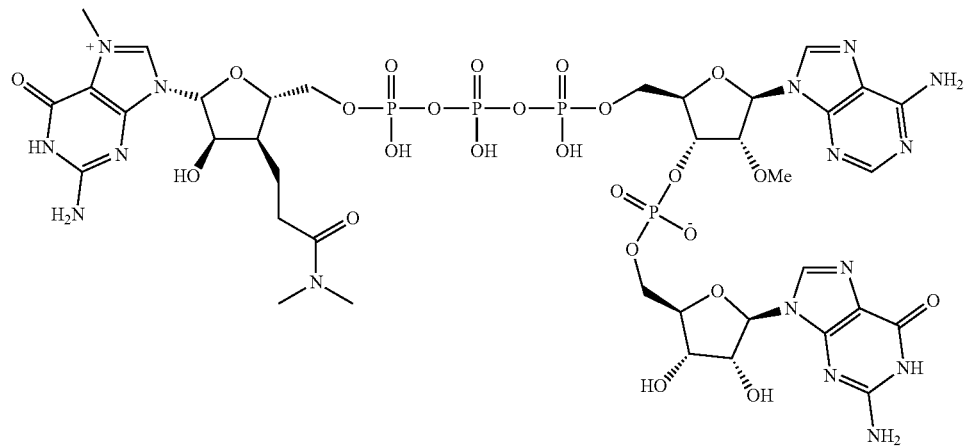
Compound 414
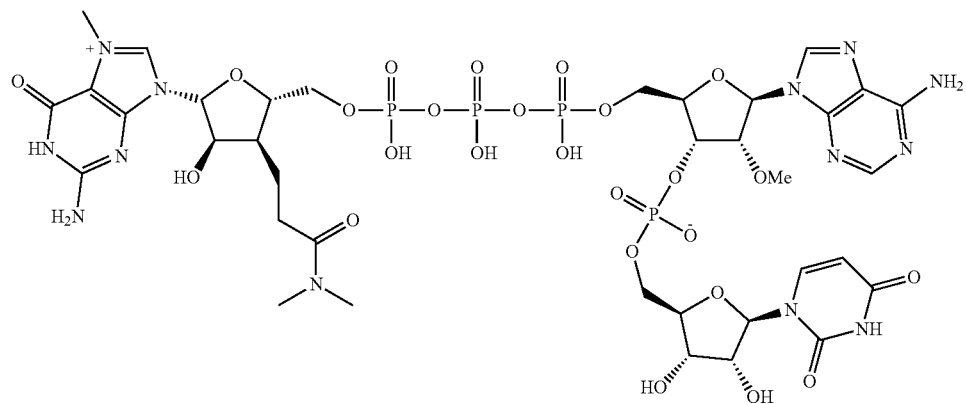
Compound 415
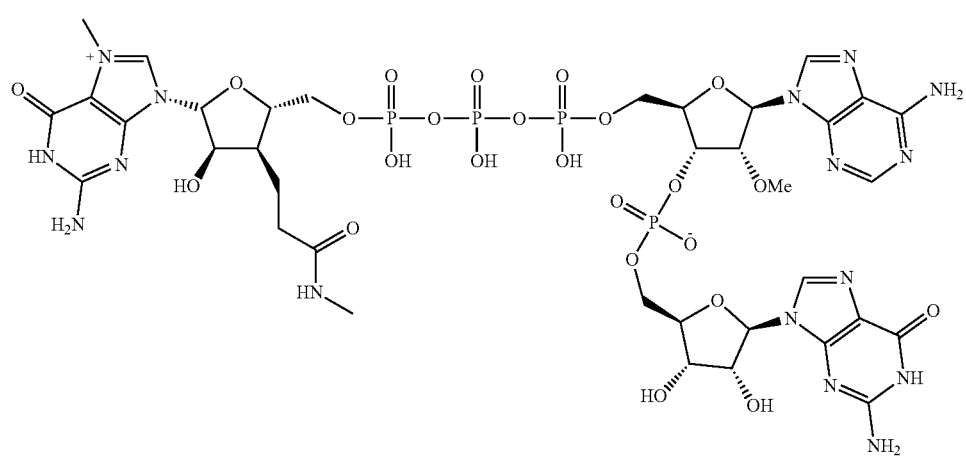

Compound 416
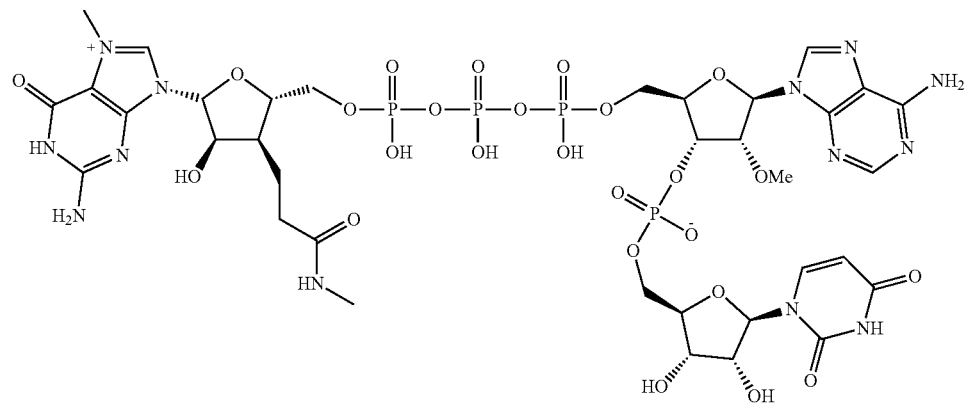
Compound 417
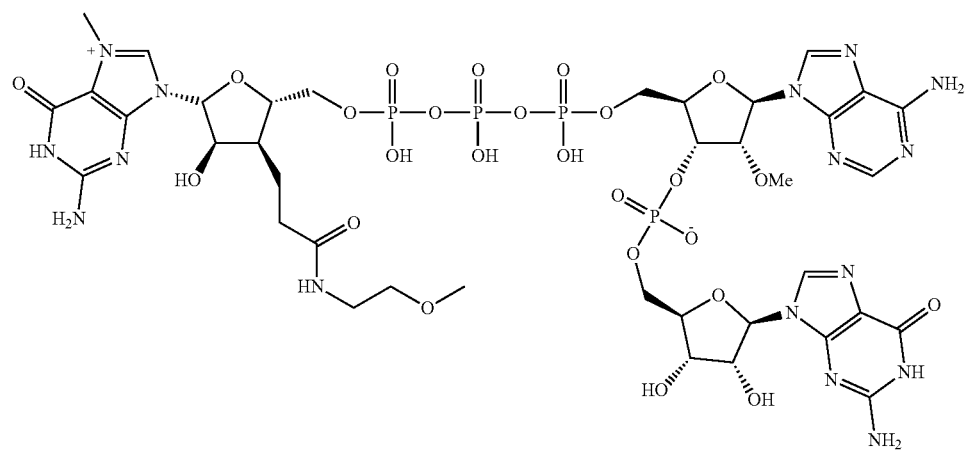
Compound 418
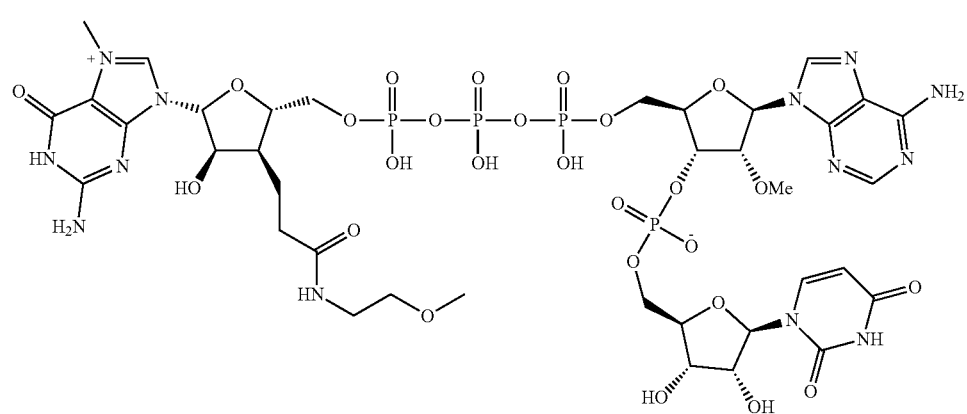

-continued
Compound 419
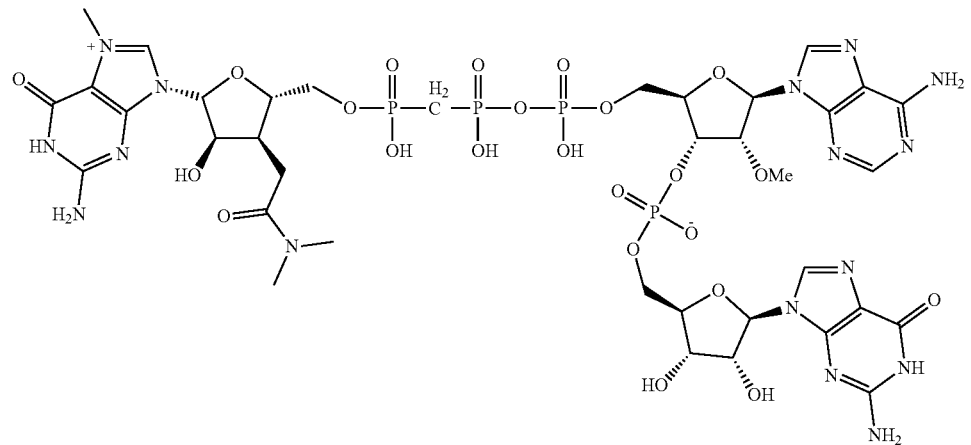
Compound 420
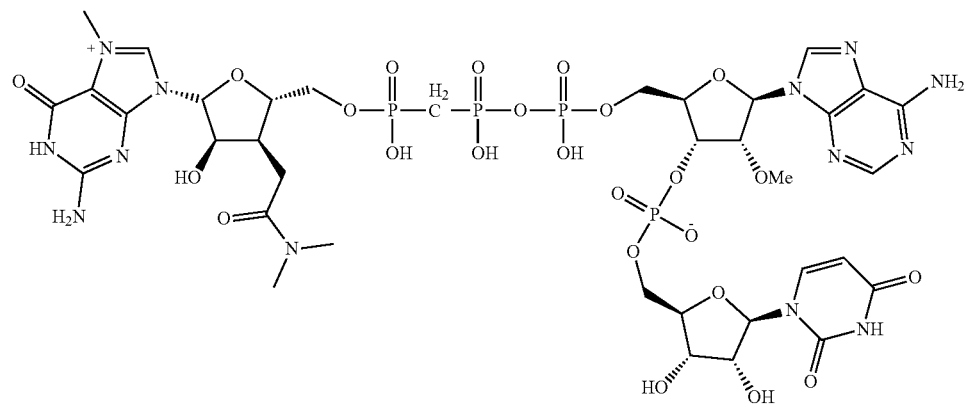
Compound 421
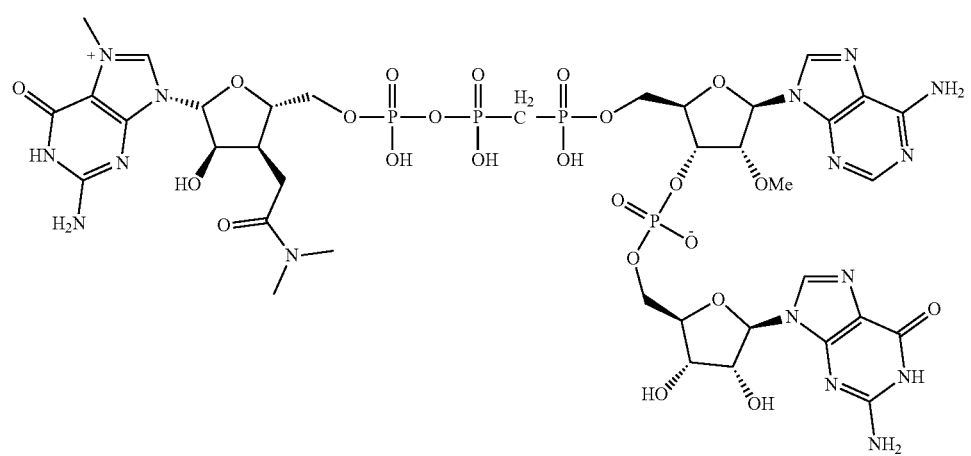

-continued
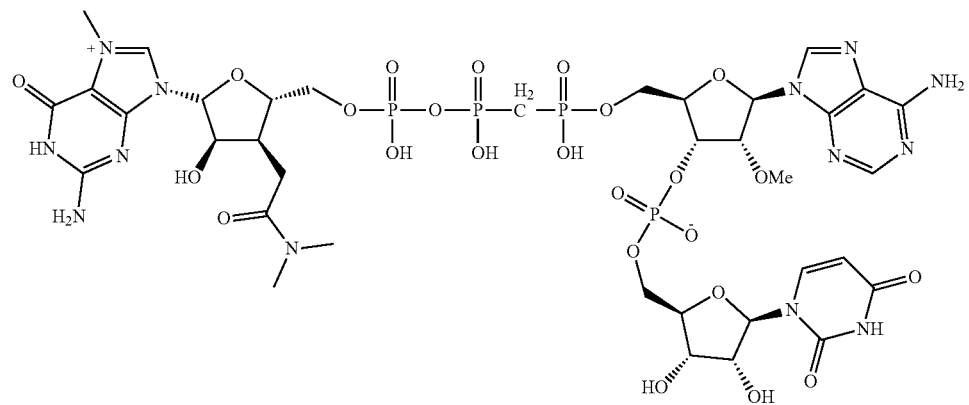
Compound 422
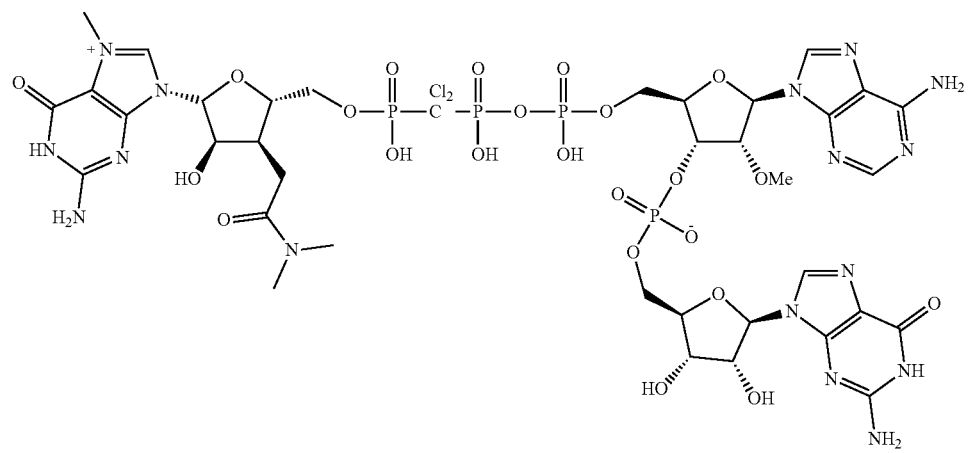
Compound 423
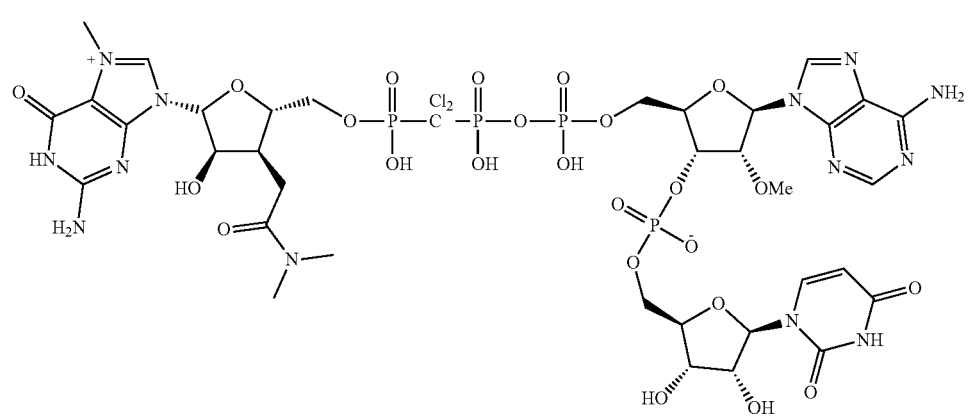
Compound 424

-continued
Compound 425
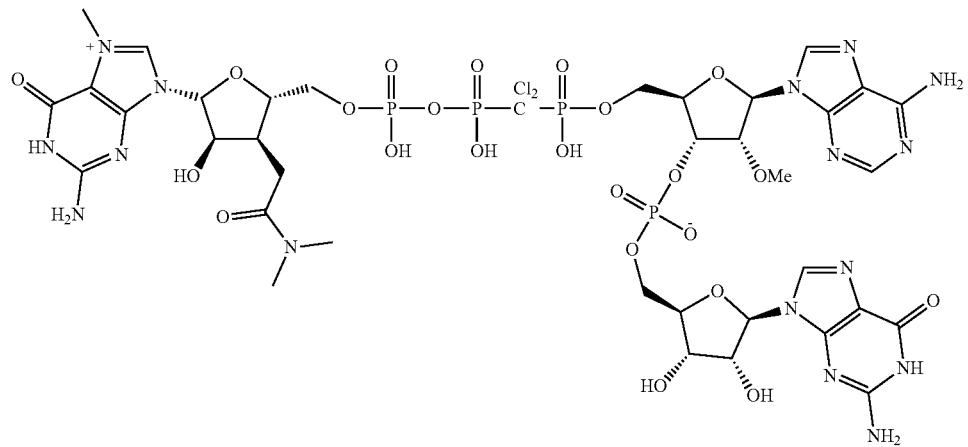
Compound 426
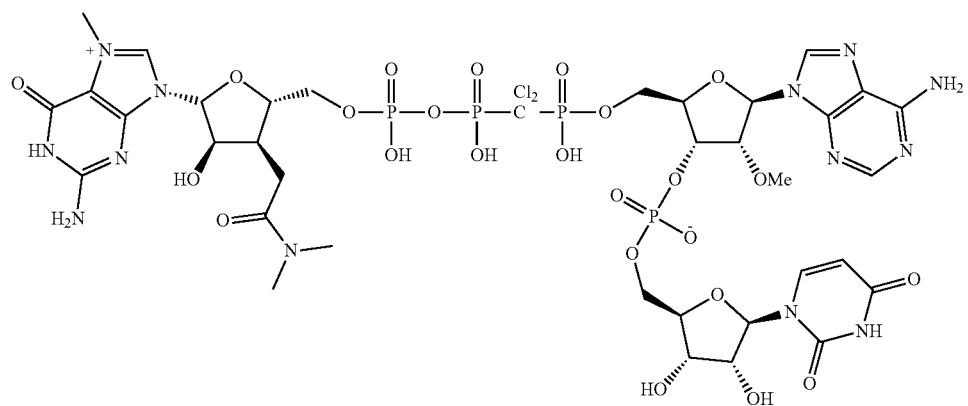
Compound 427
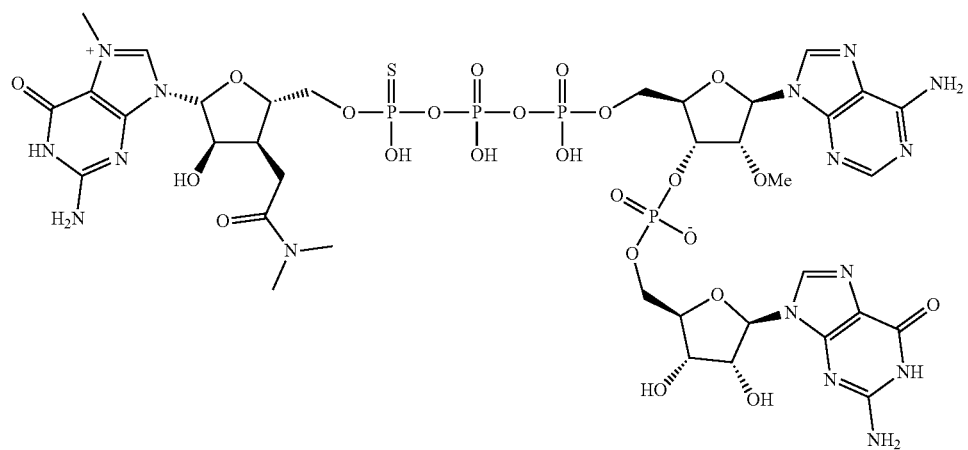

Compound 428
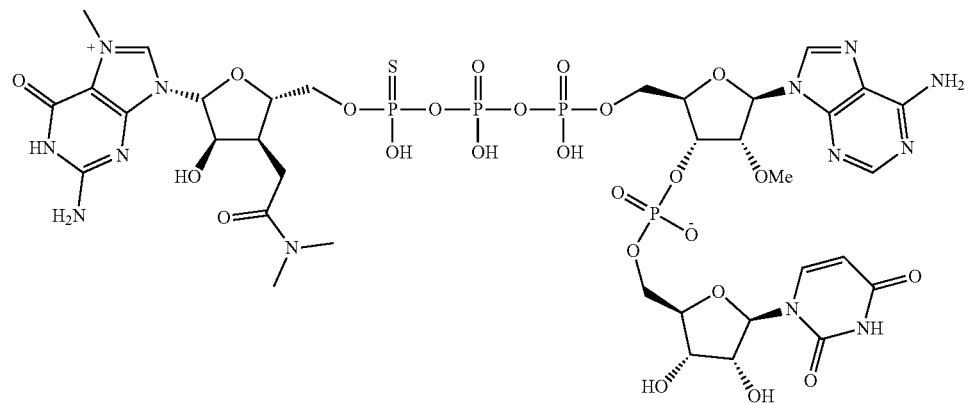
Compound 429
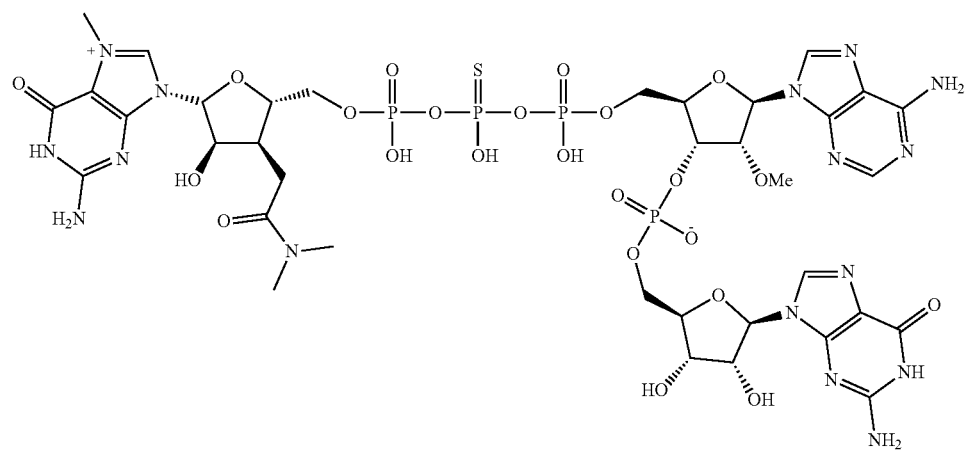
Compound 430
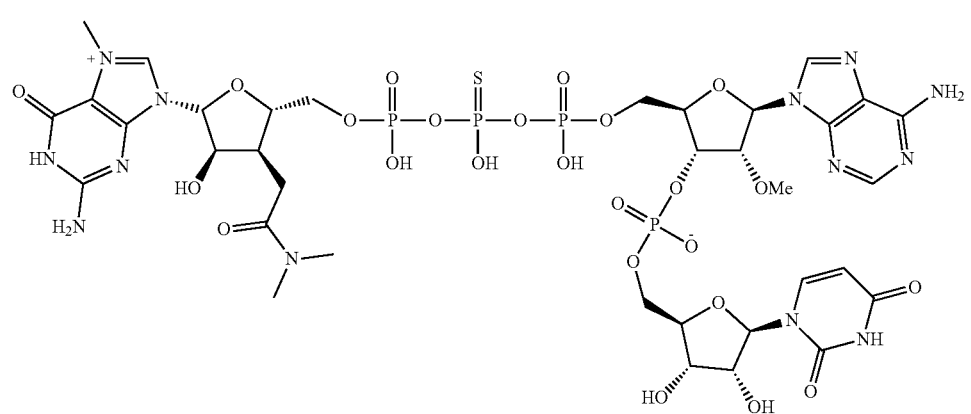

-continued
Compound 431
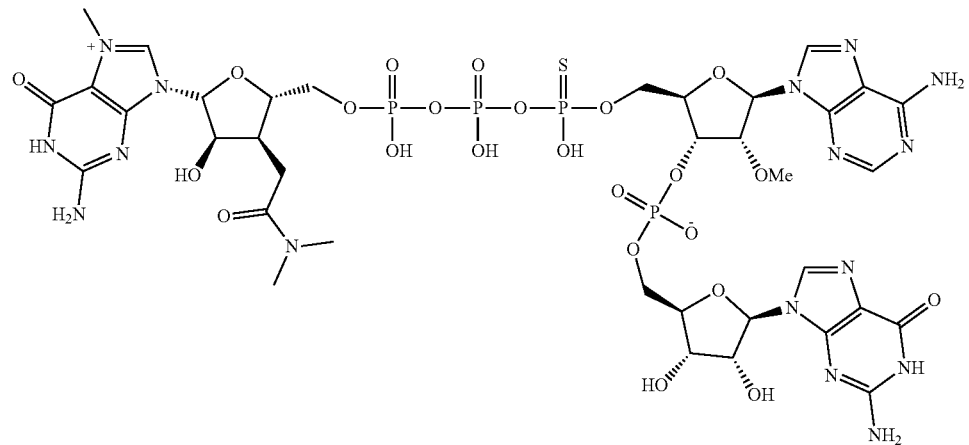
Compound 432
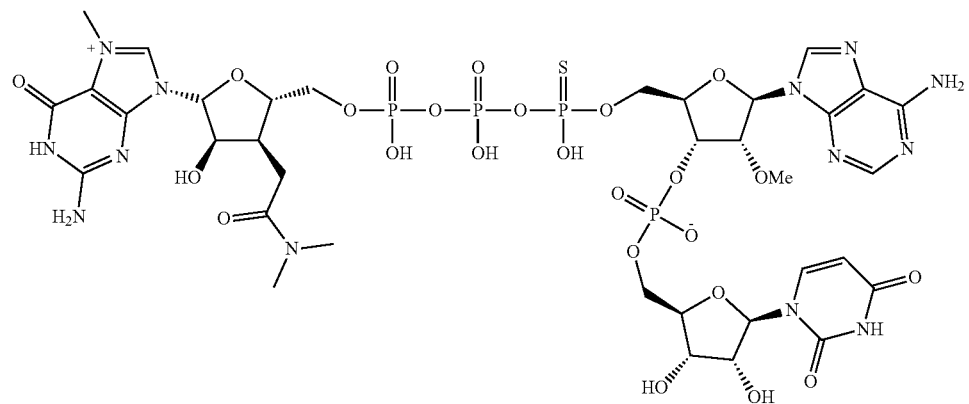
Compound 433
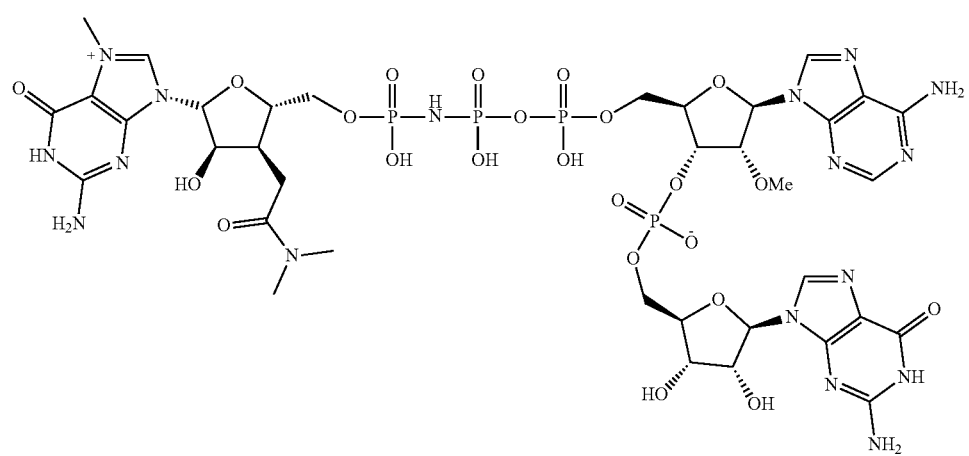

Compound 434
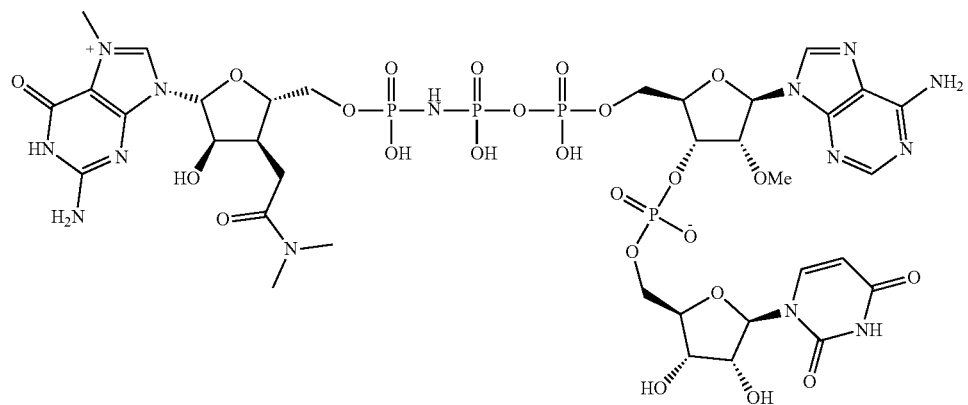
Compound 435
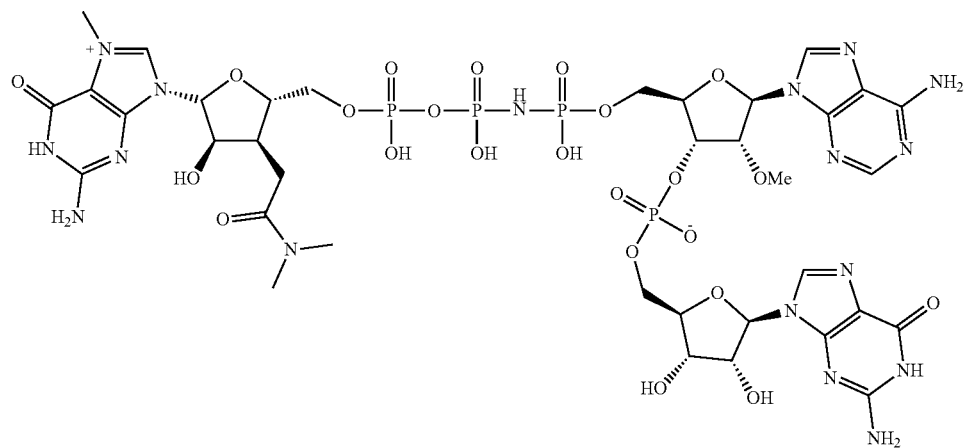
Compound 436
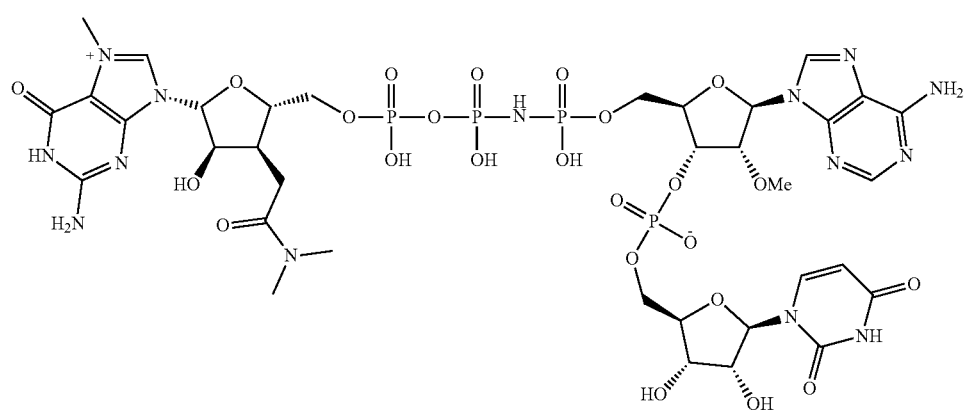

Compound 437
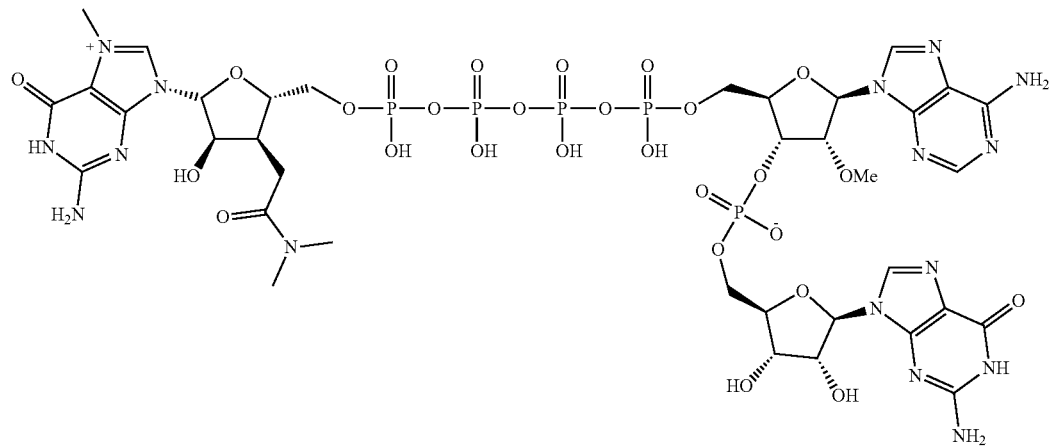
Compound 438
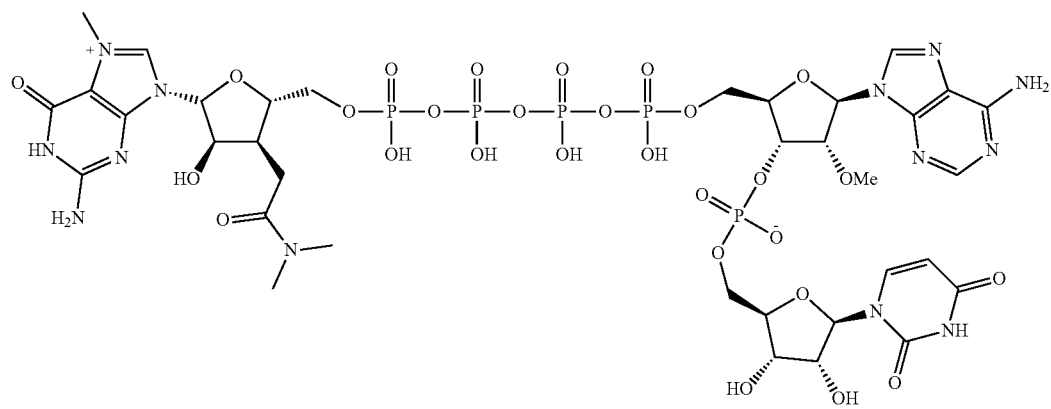
Compound 439
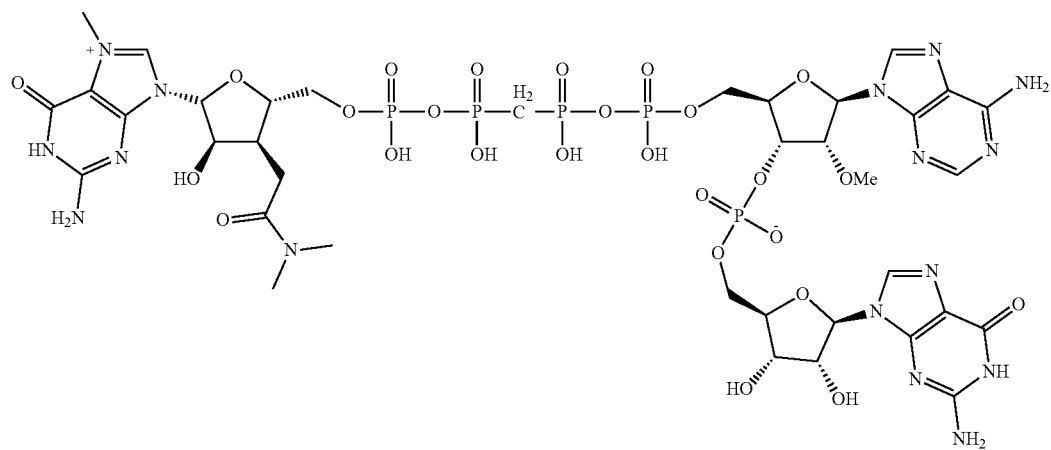

-continued
Compound 440
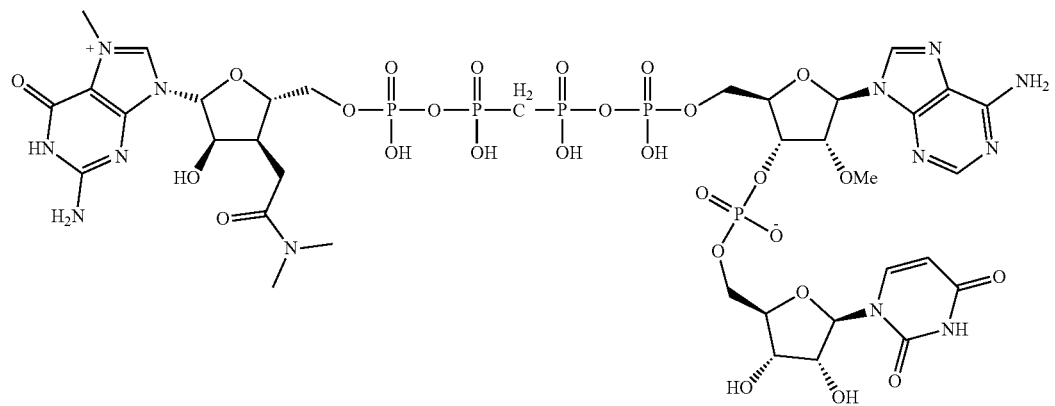
Compound 441
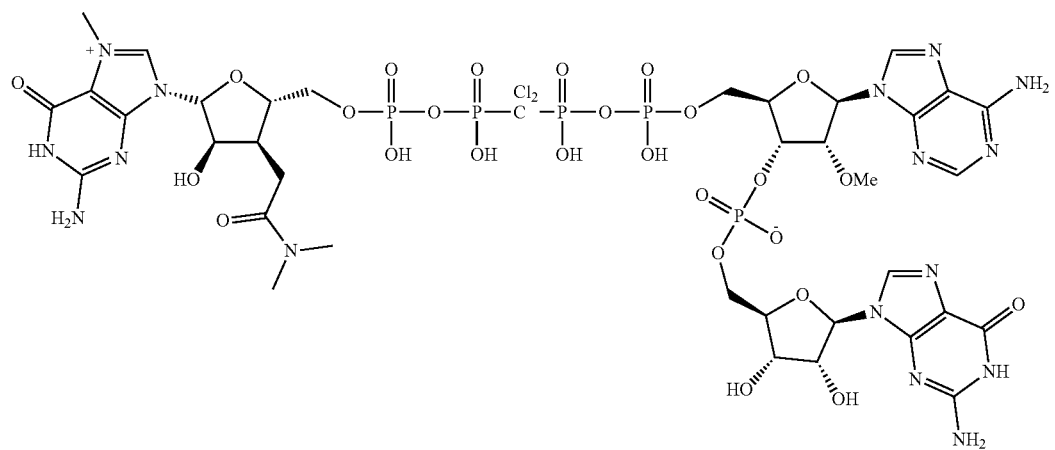
Compound 442
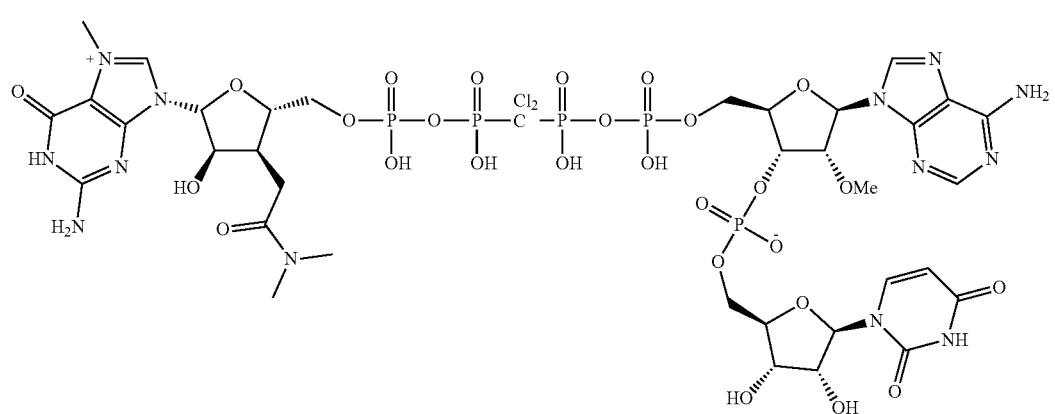

-continued
Compound 443
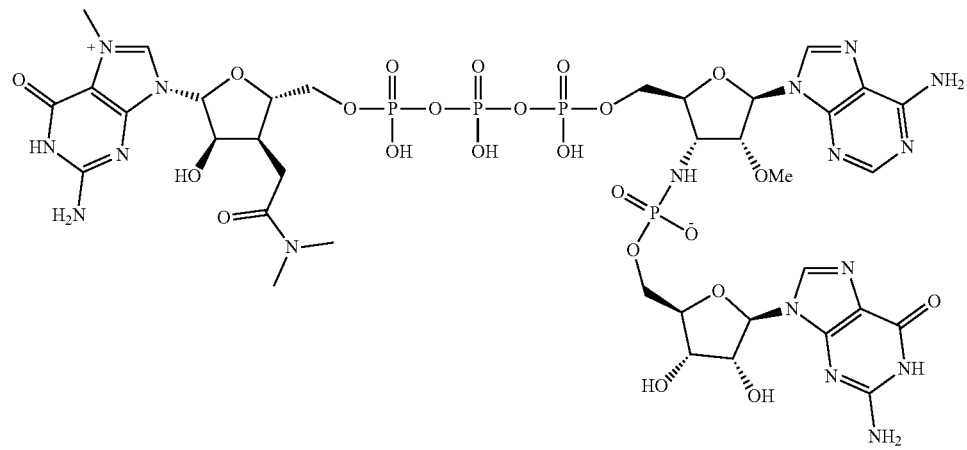
Compound 444
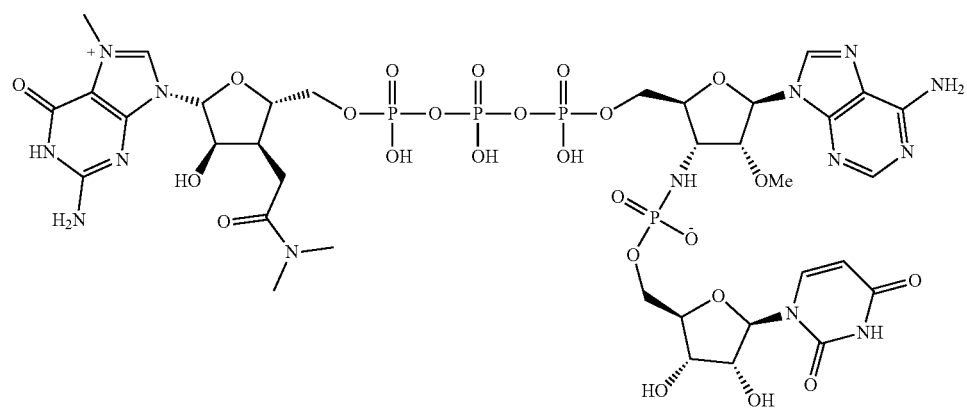
Compound 445
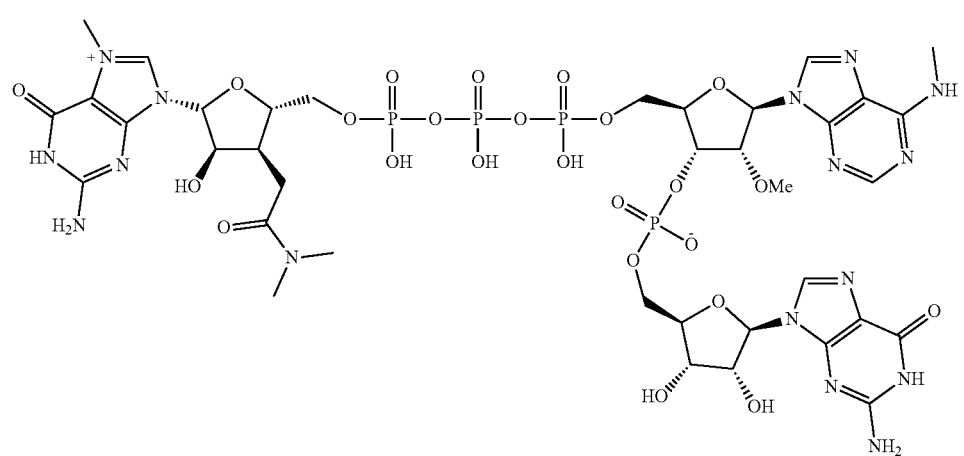

-continued
Compound 446
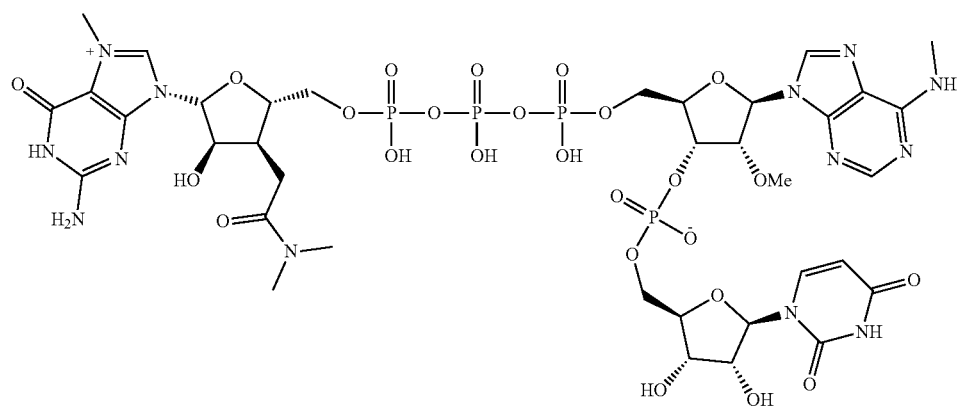
Compound 447
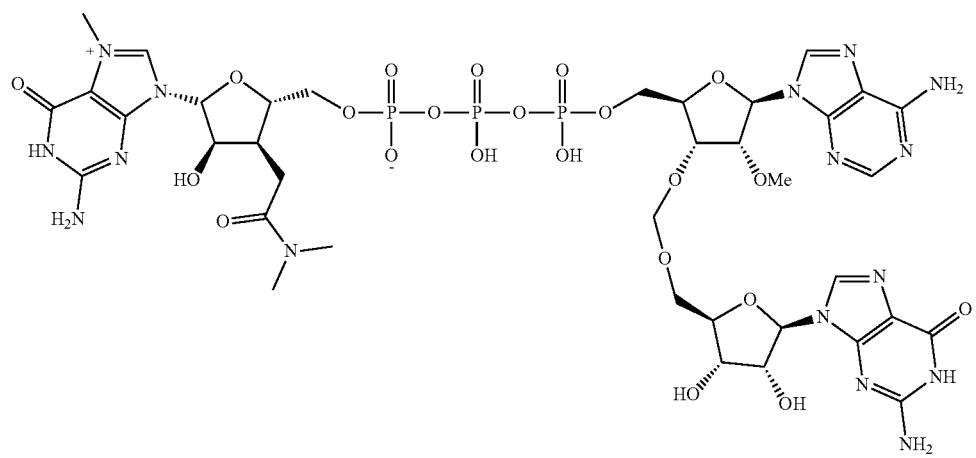
Compound 448
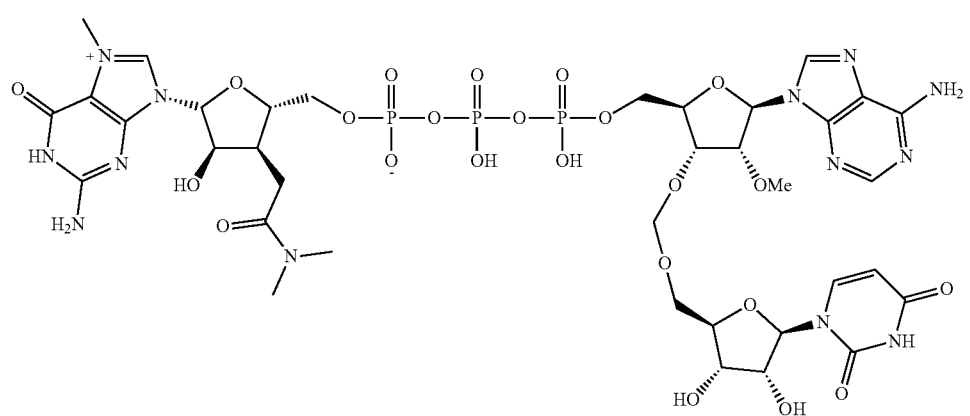

-continued
Compound 449
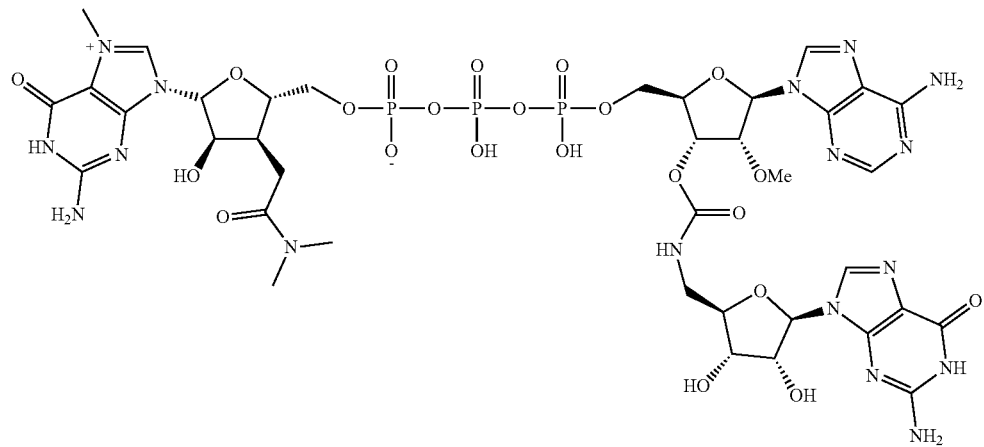
Compound 450
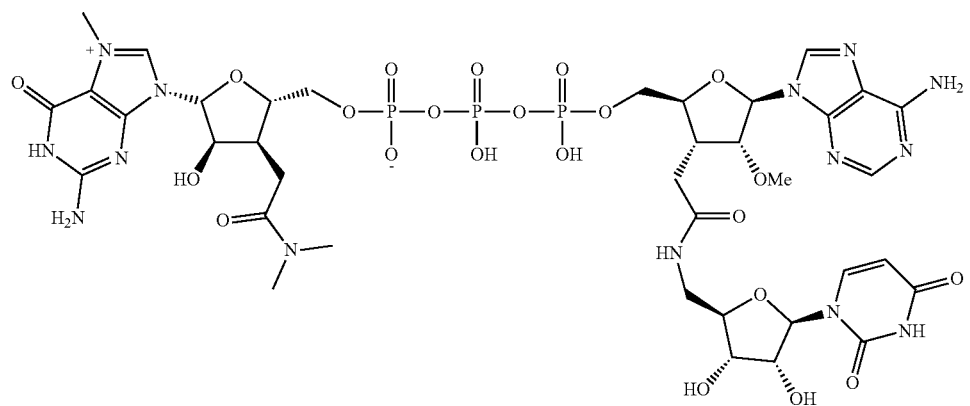
Compound 451
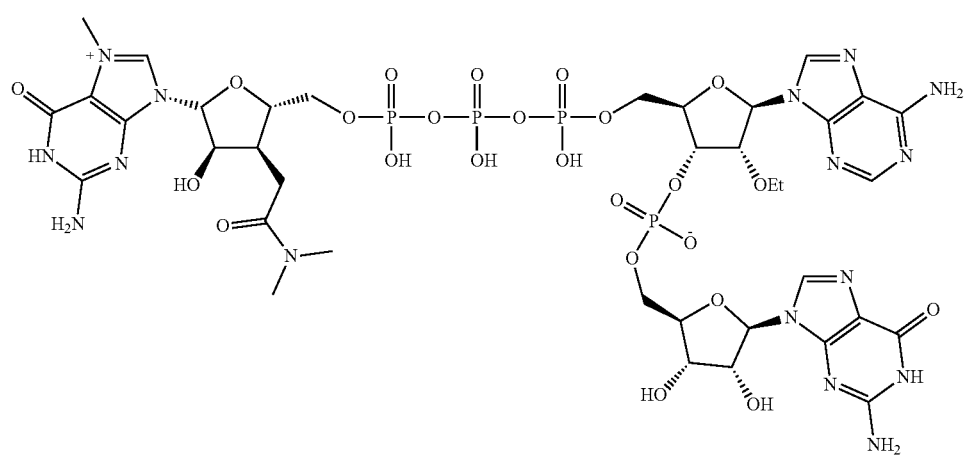

-continued
Compound 452
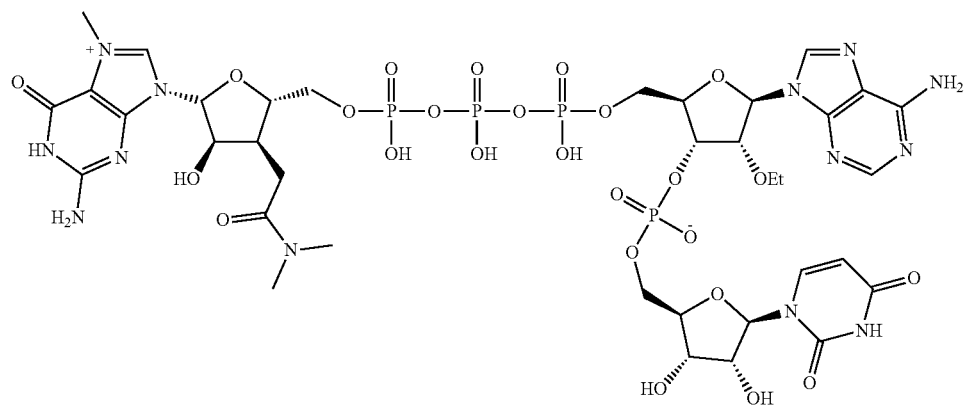
Compound 453
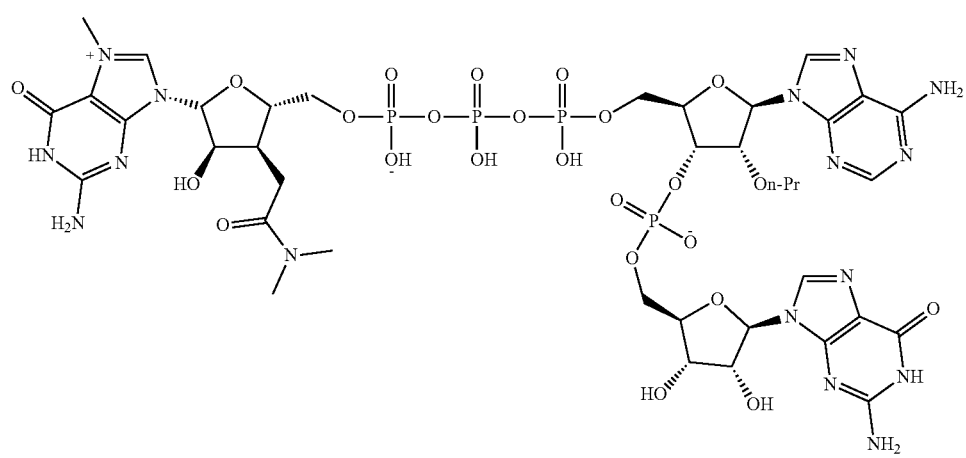
Compound 454
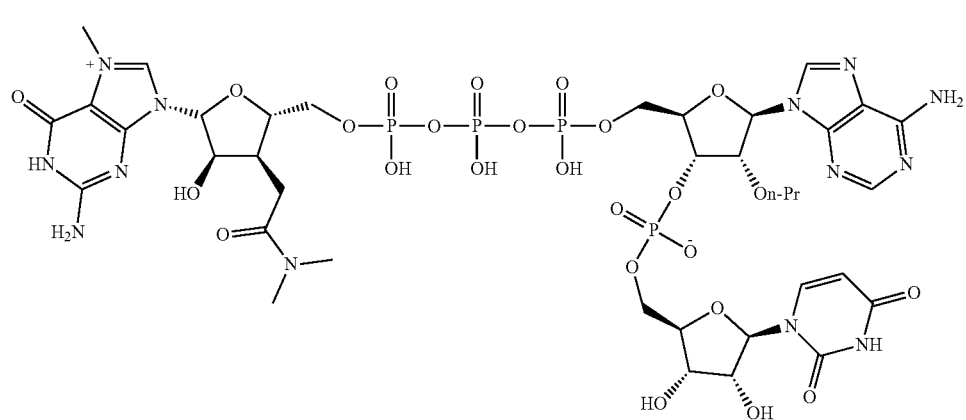

-continued
Compound 455
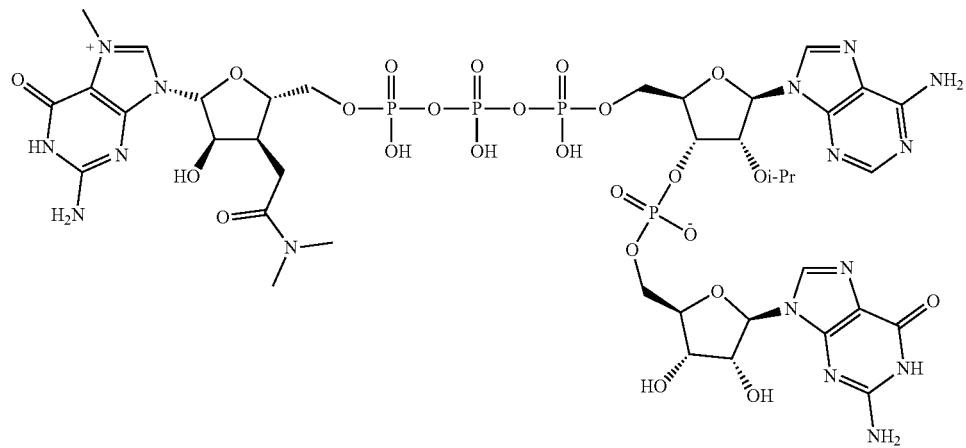
Compound 456
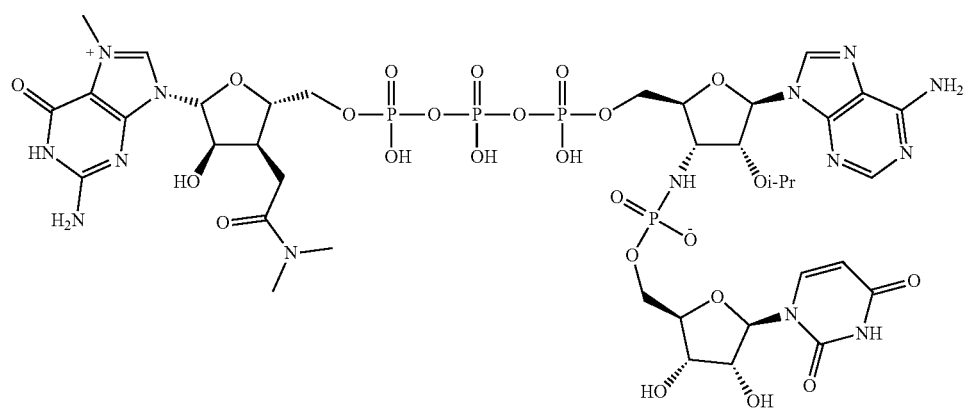
Compound 457
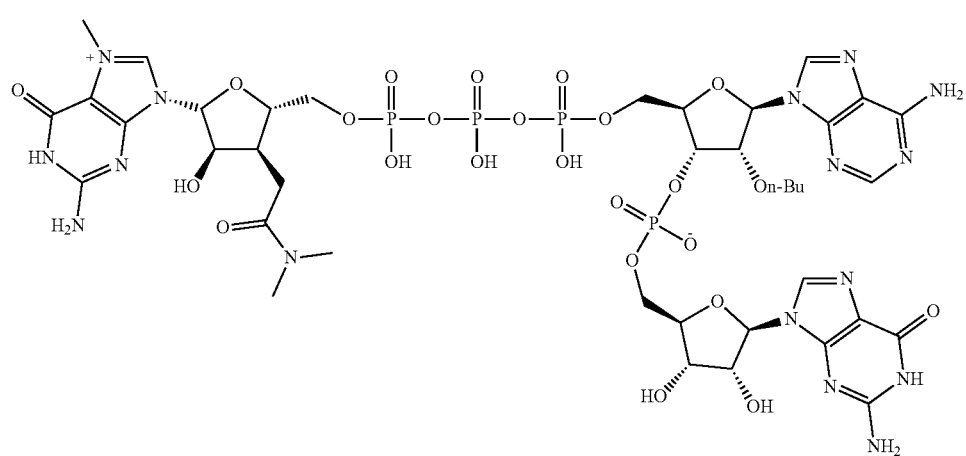

-continued
Compound 458
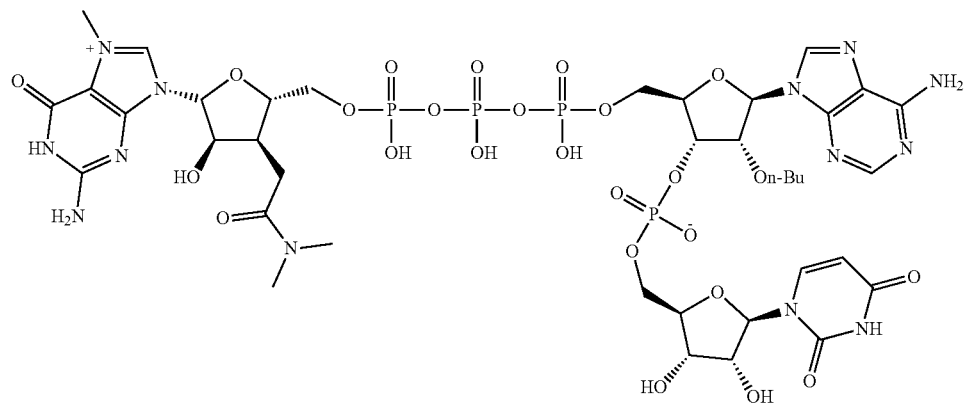
Compound 459
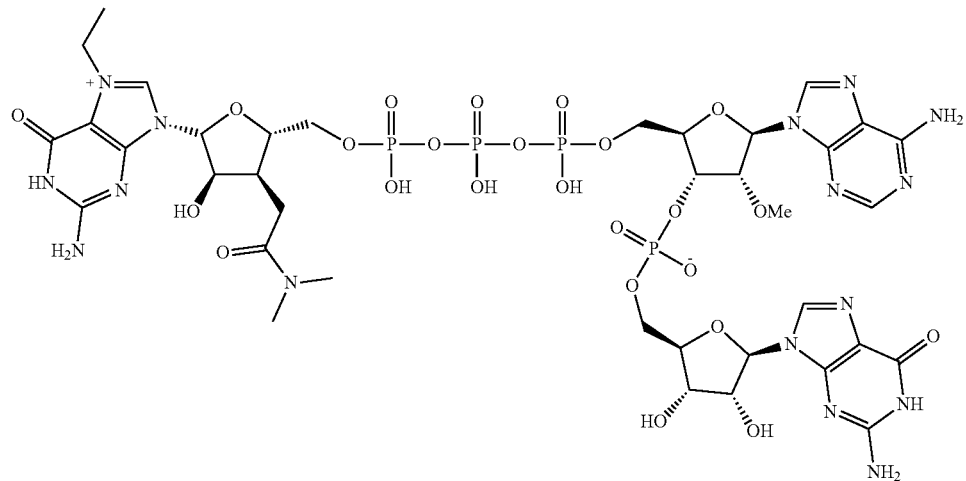
Compound 460
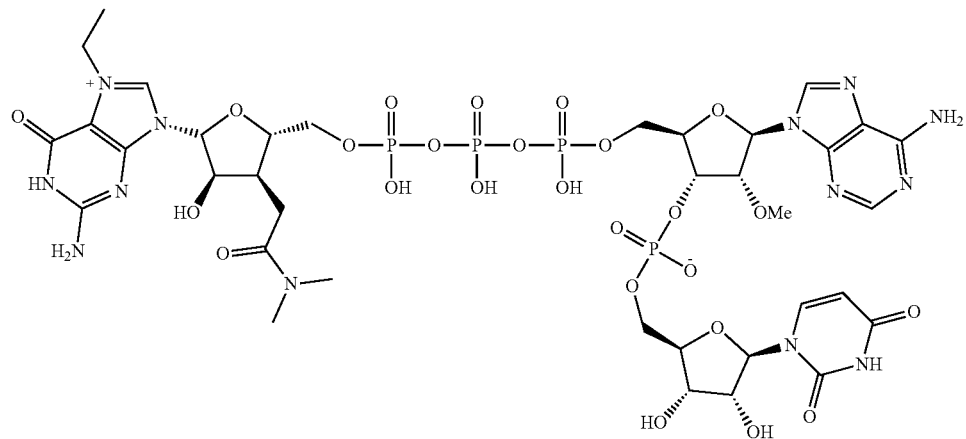

Compound 461
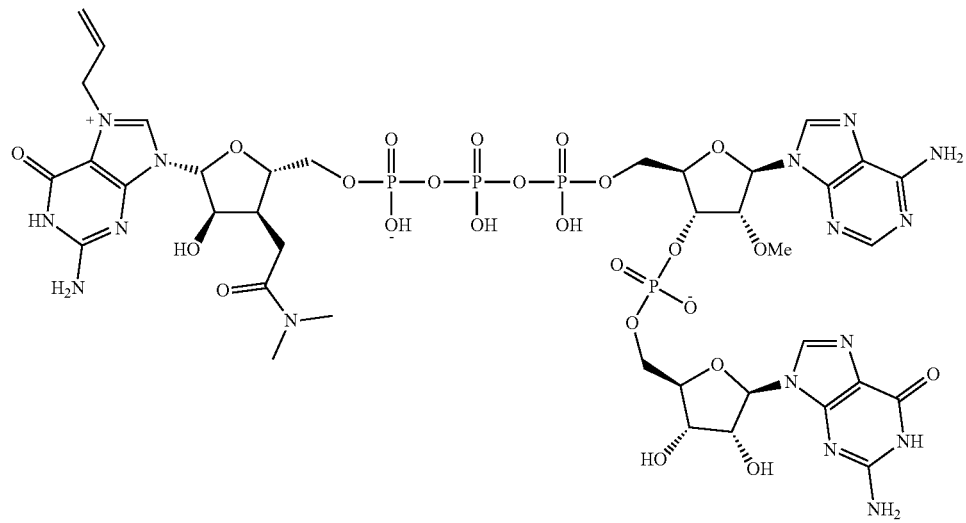
Compound 462
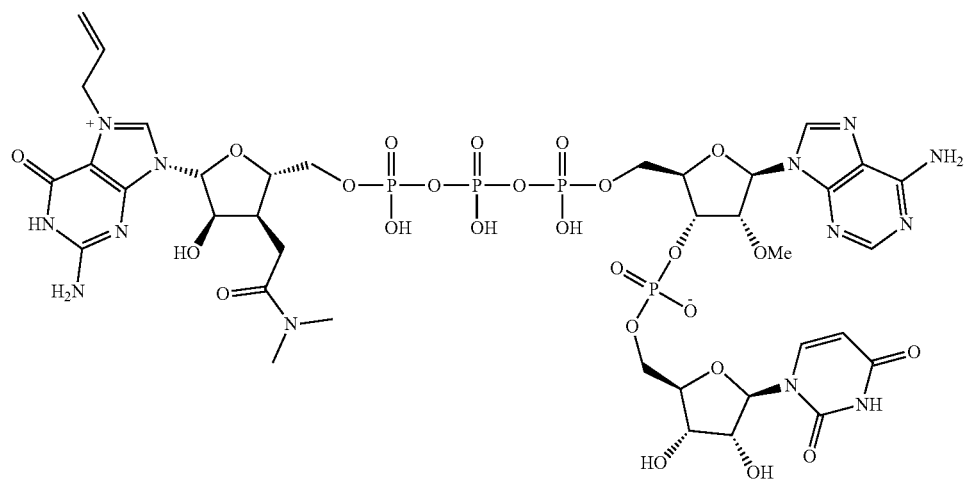
Compound 463
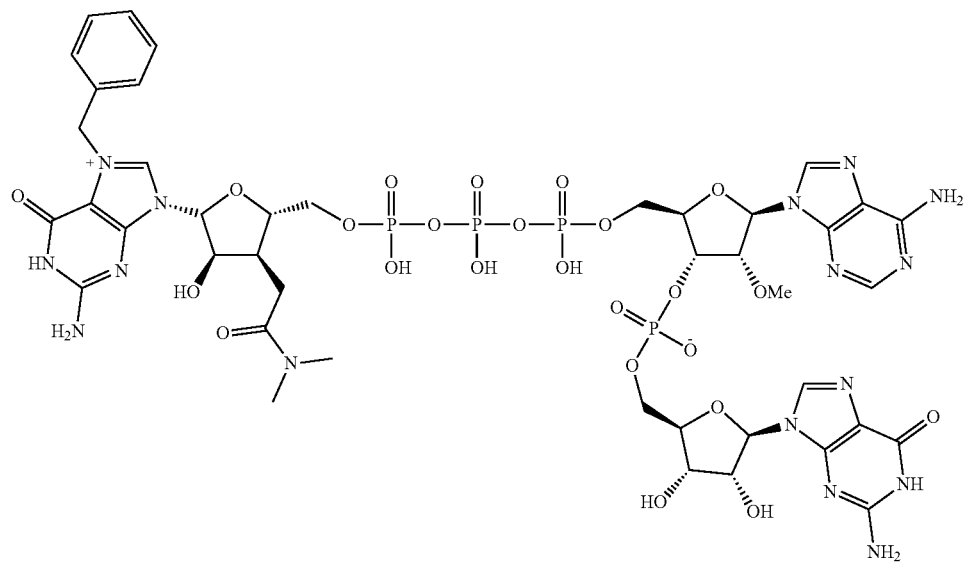

-continued
Compound 464
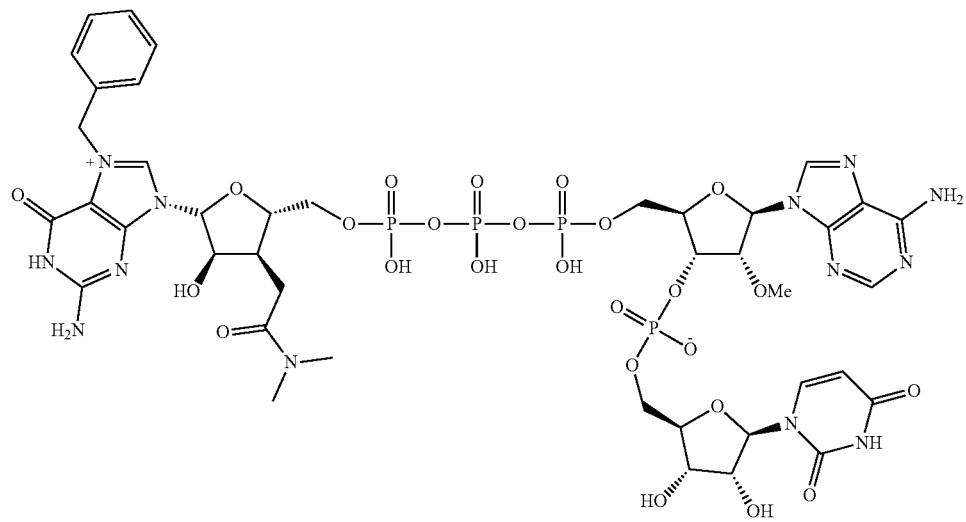
Compound 465
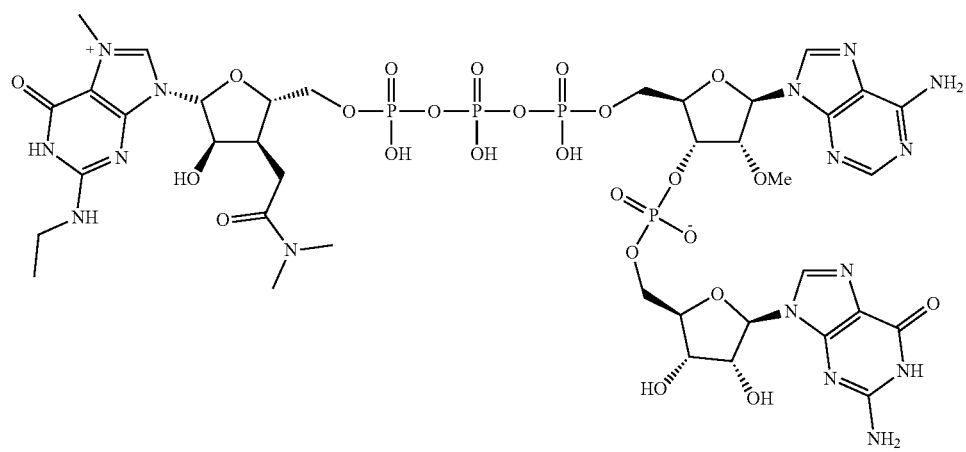
Compound 466
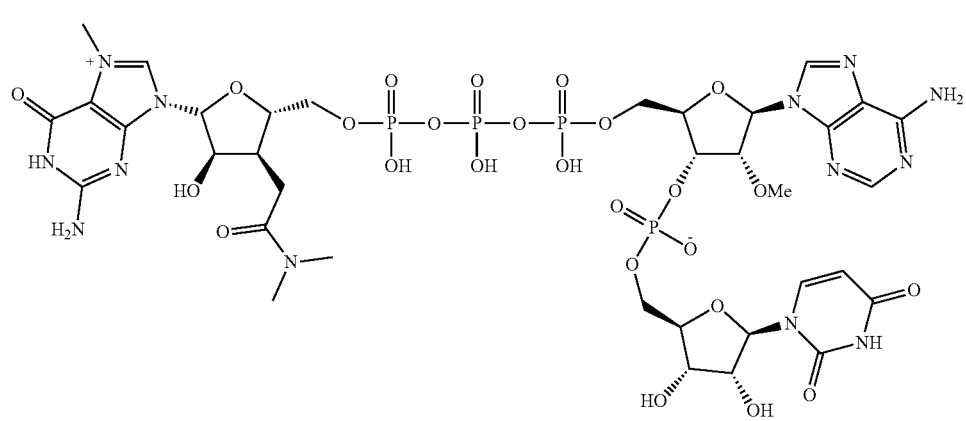

-continued
Compound 467
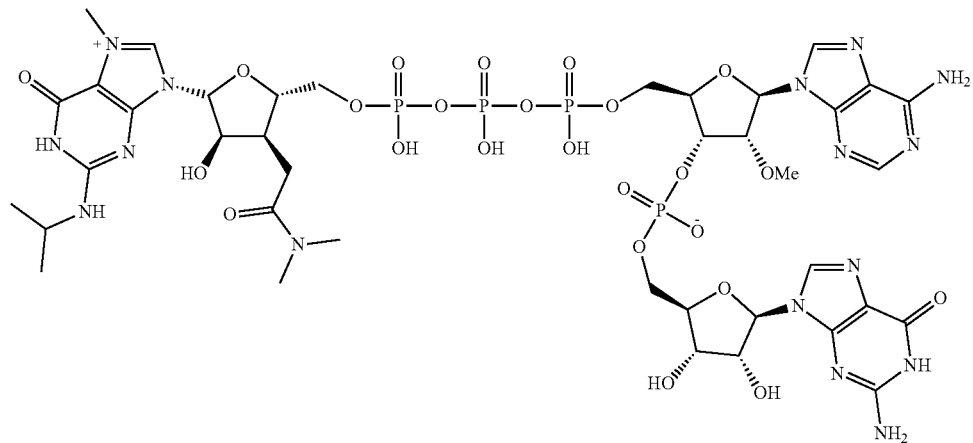
Compound 468
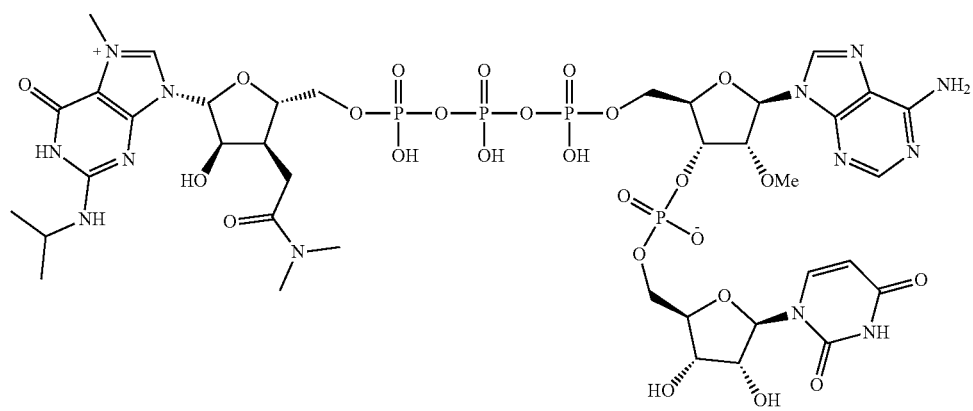
Compound 473
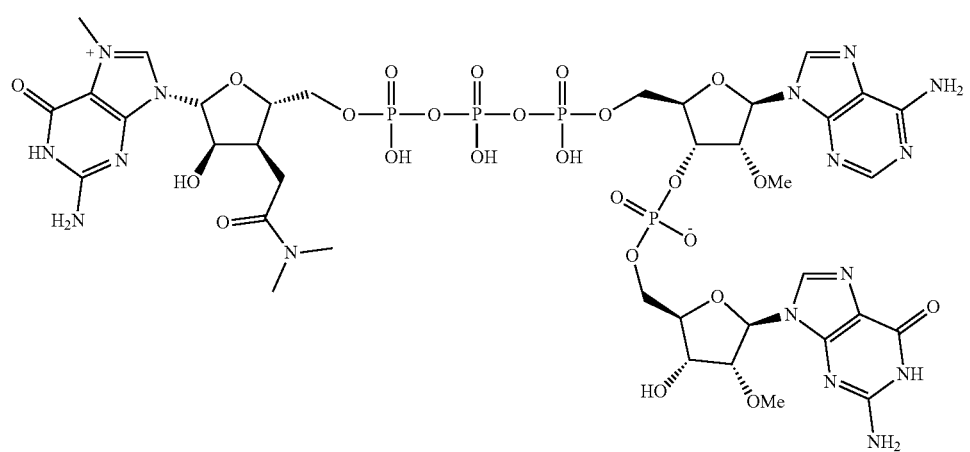

Compound 474
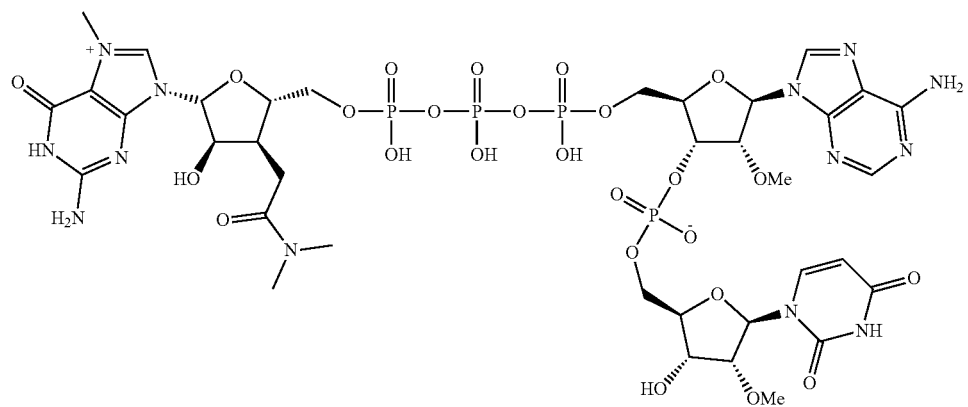
Compound 475
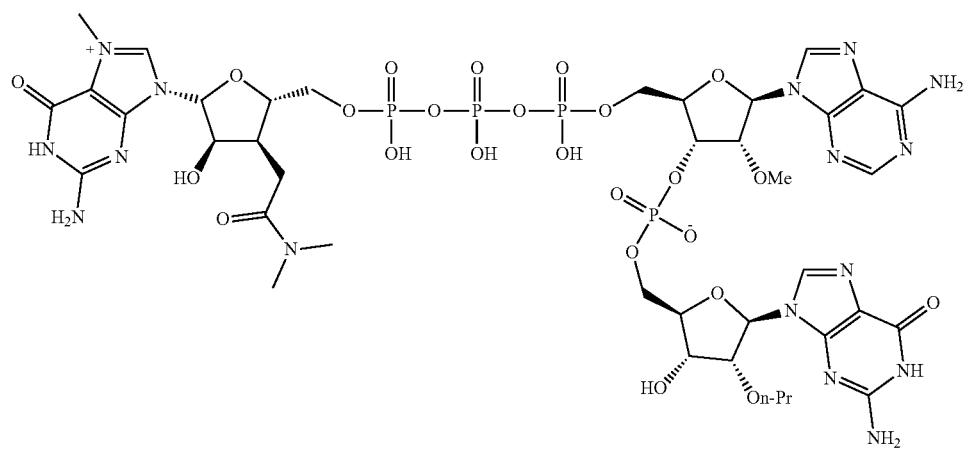
Compound 476
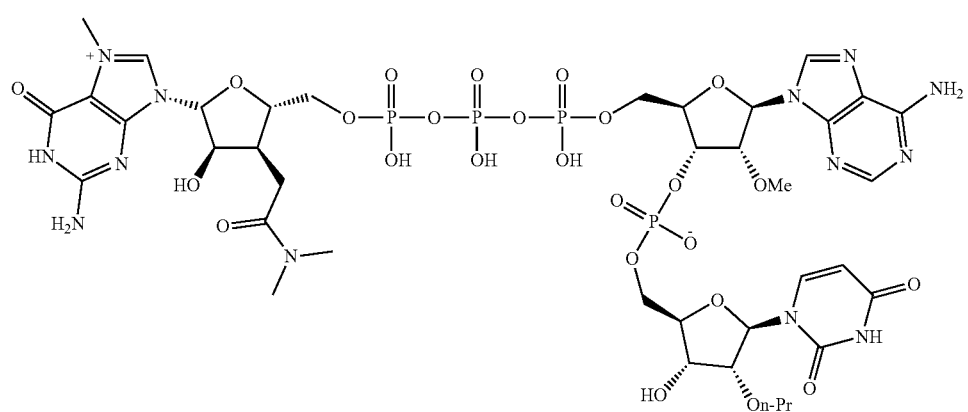

-continued
Compound 477
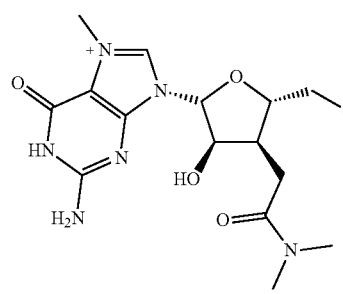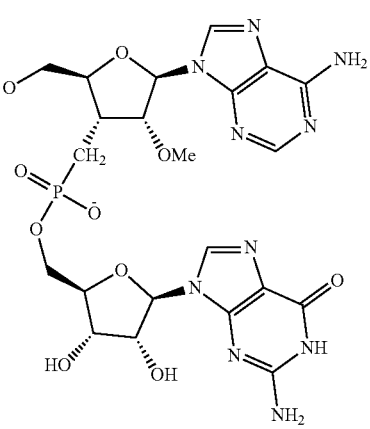
Compound 478
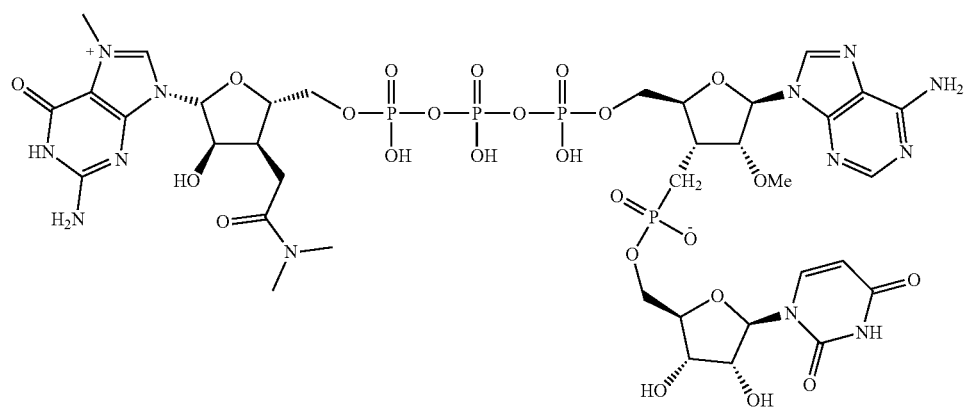
Compound 479
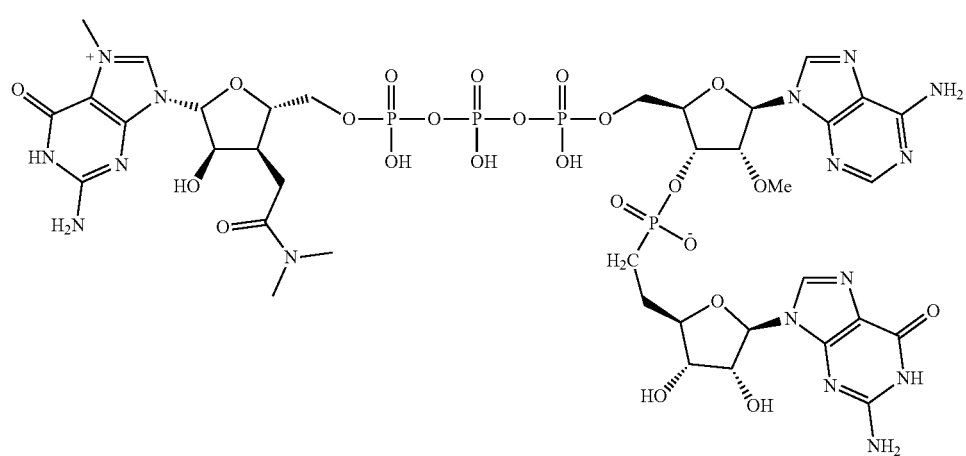

Compound 480
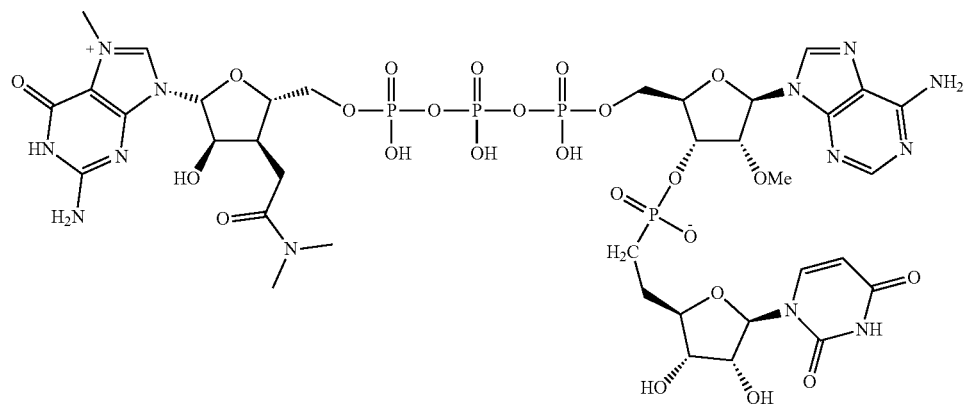
Compound 481
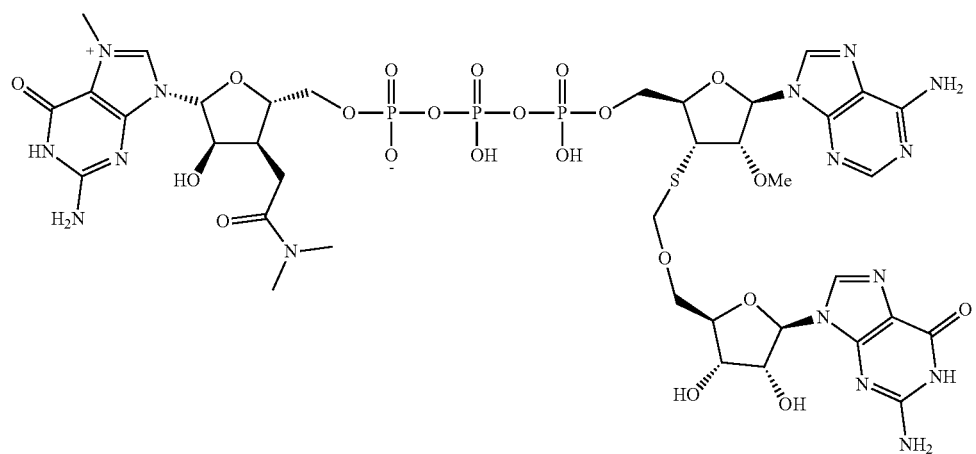
Compound 482
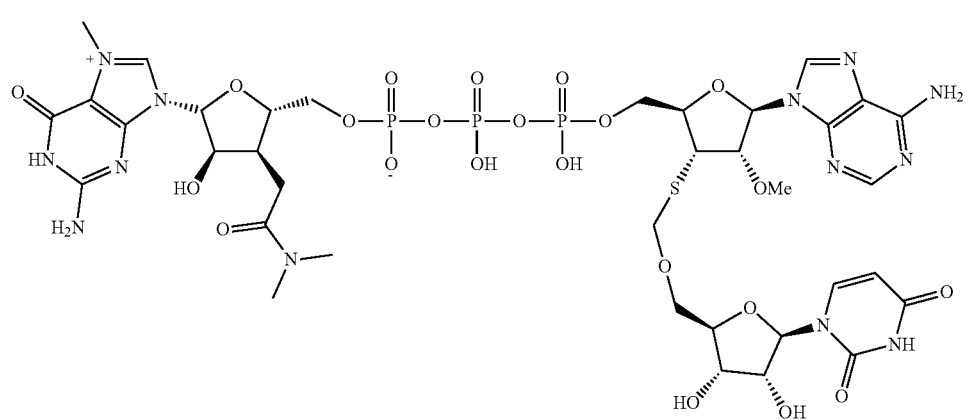

Compound 524
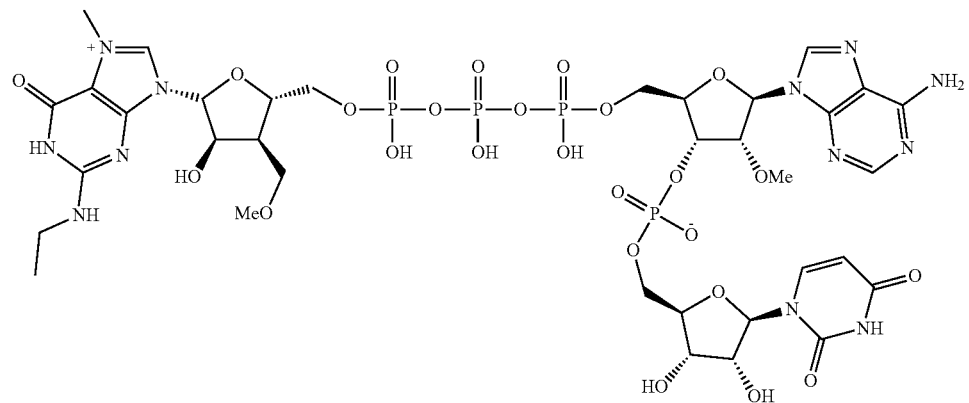
Compound 539
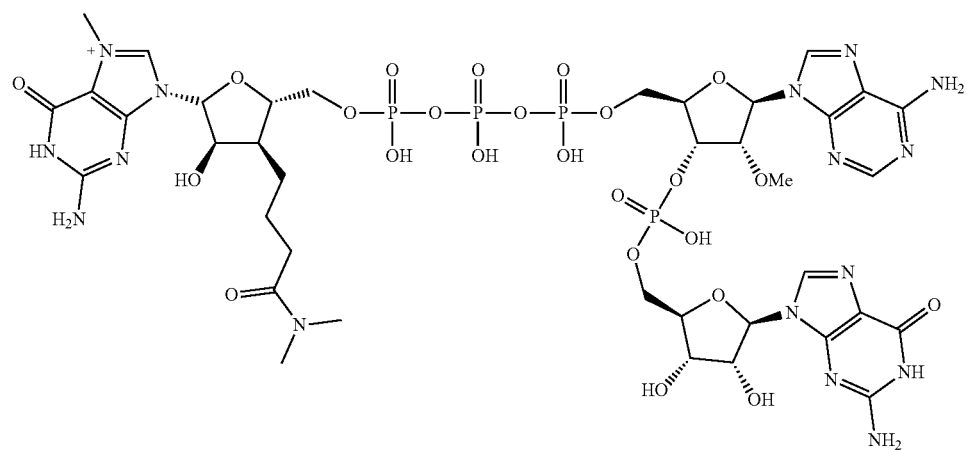
Compound 540
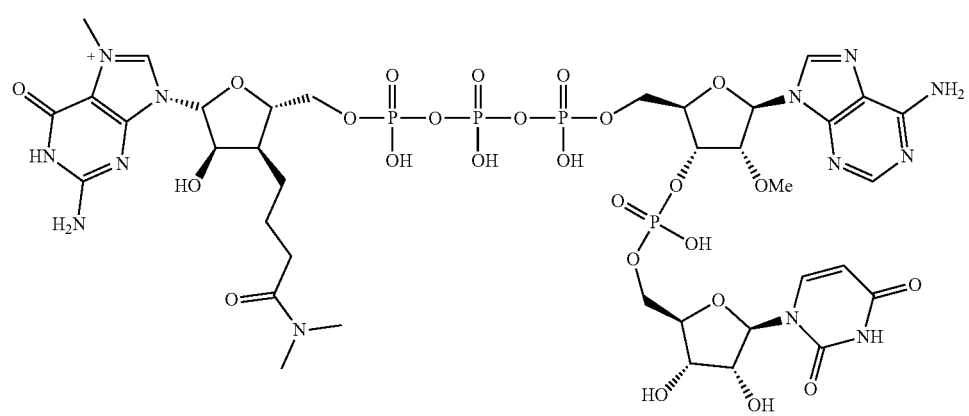

-continued
Compound 541
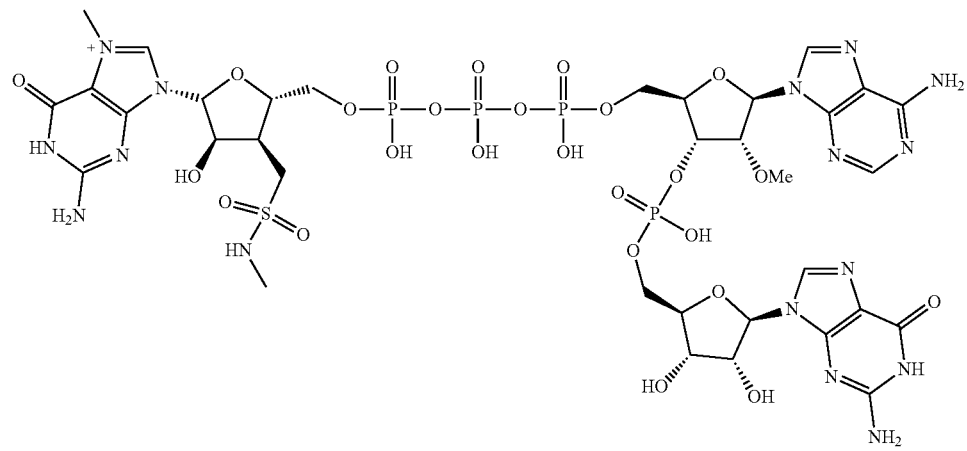
Compound 542
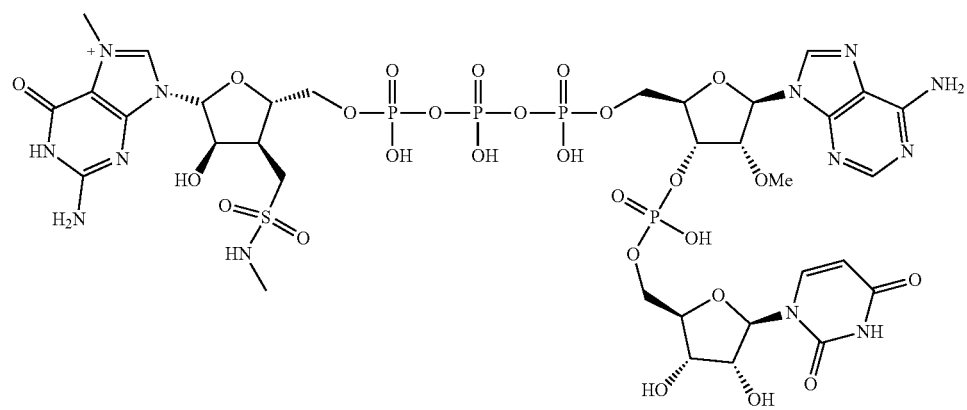
Compound 543
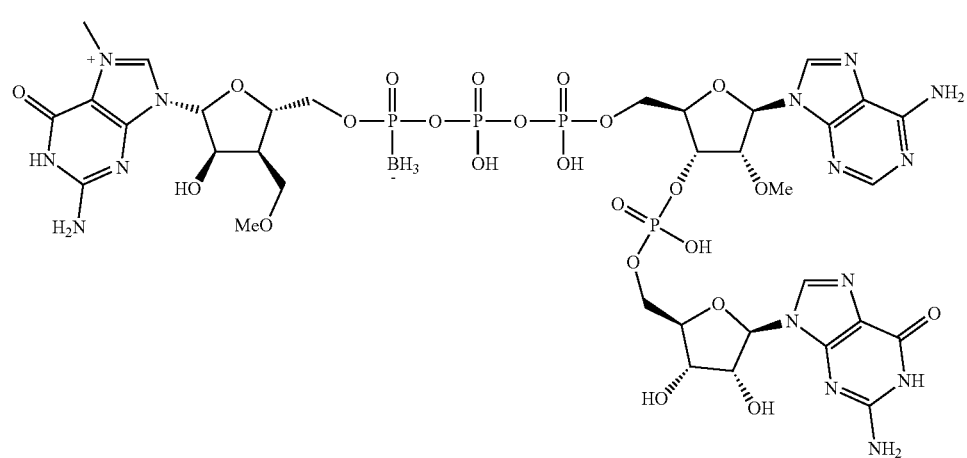

Compound 544
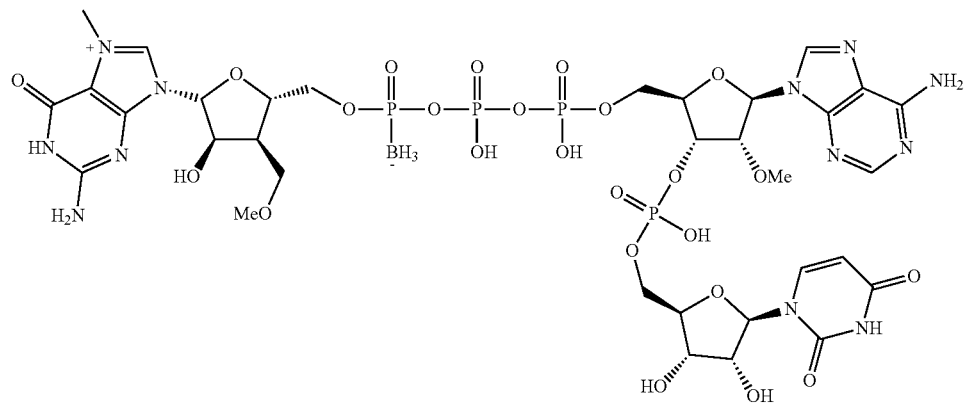
Compound 545
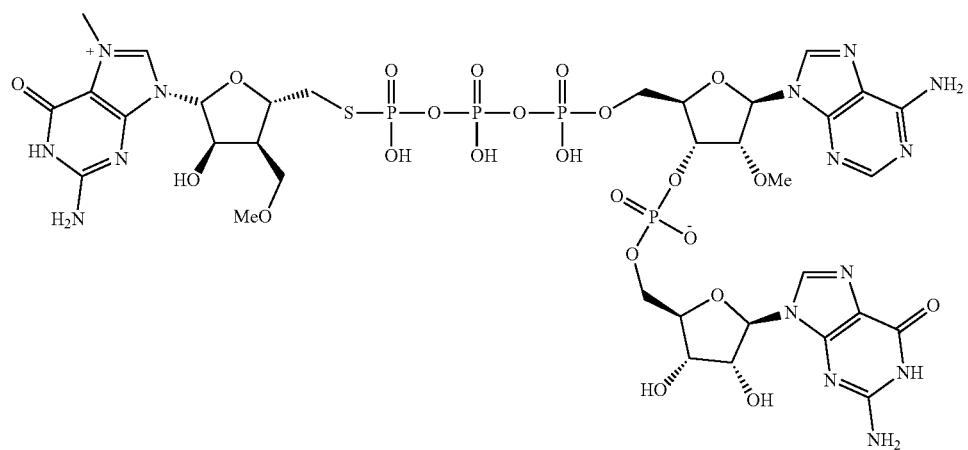
Compound 546
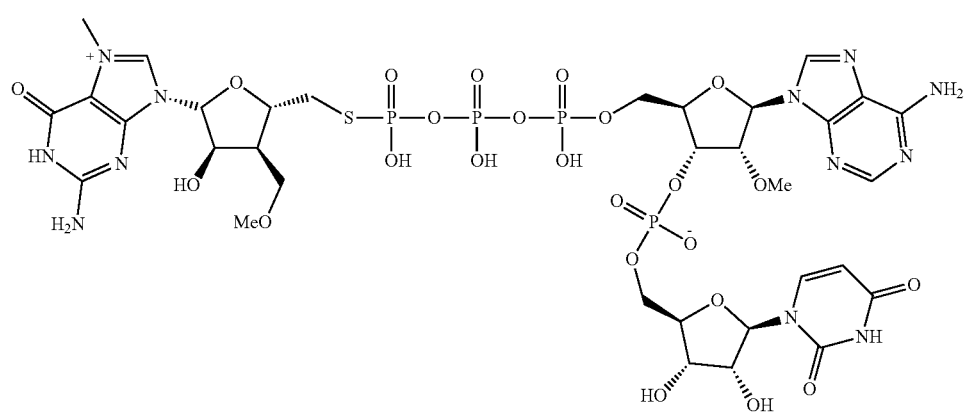

-continued
Compound 547
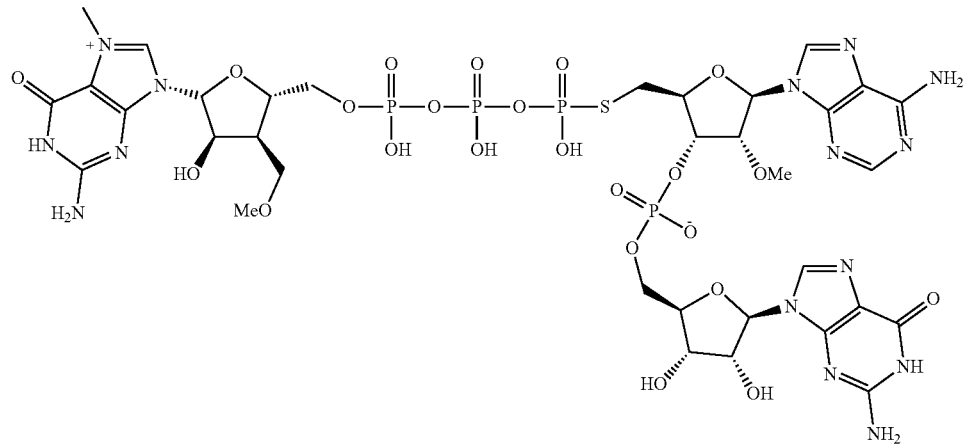
Compound 548
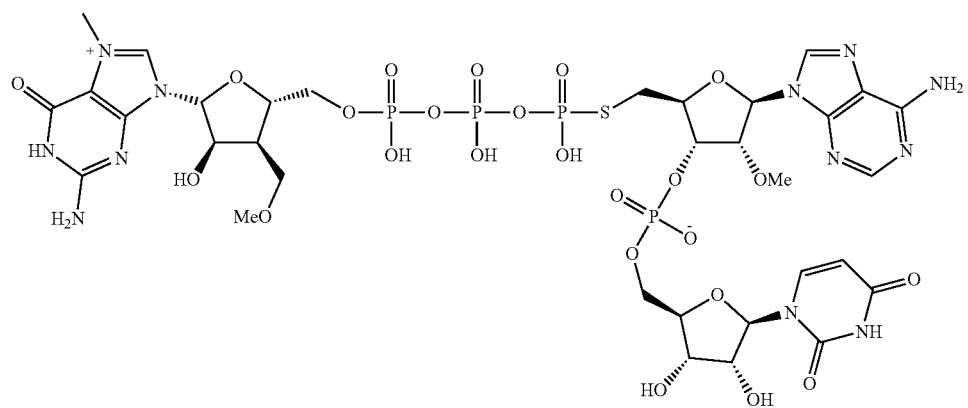
Compound 549
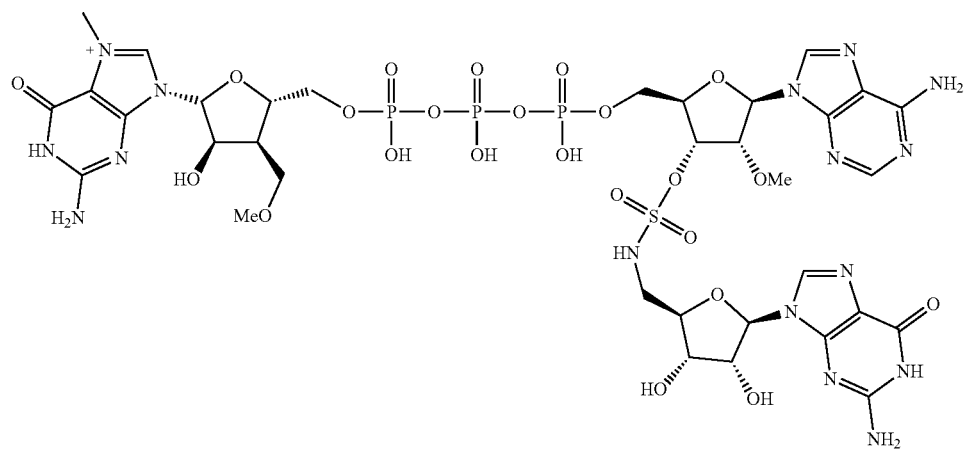

Compound 550
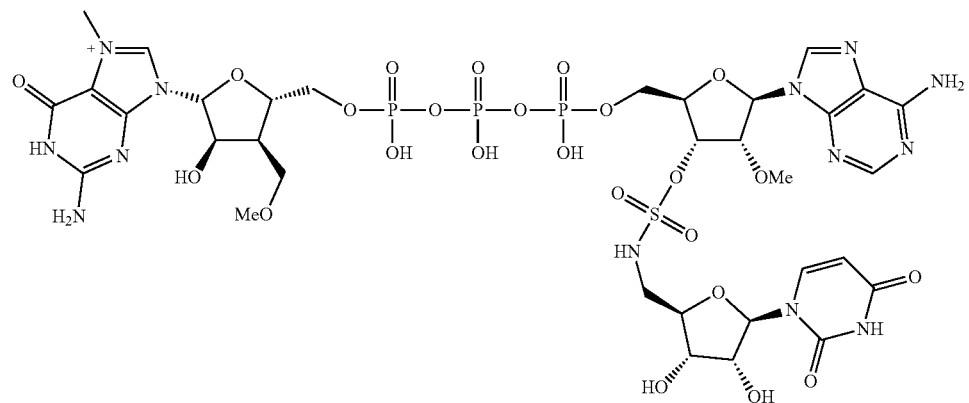
Compound 551
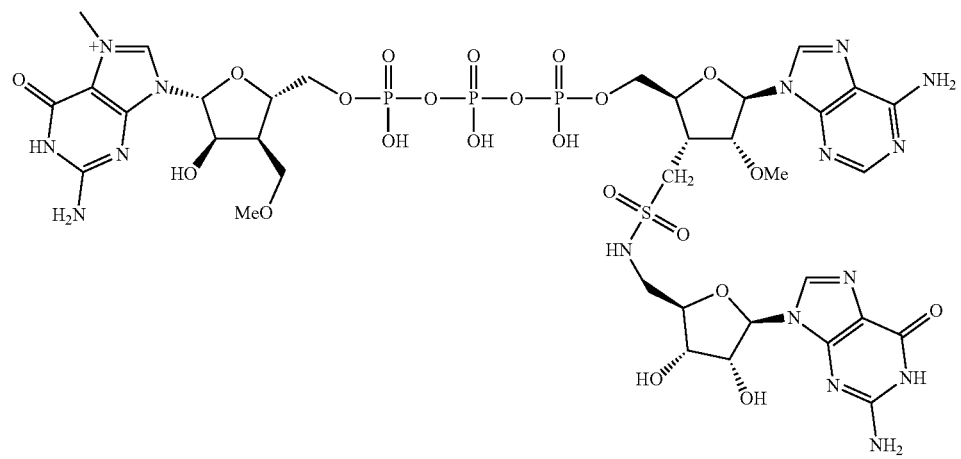
Compound 552
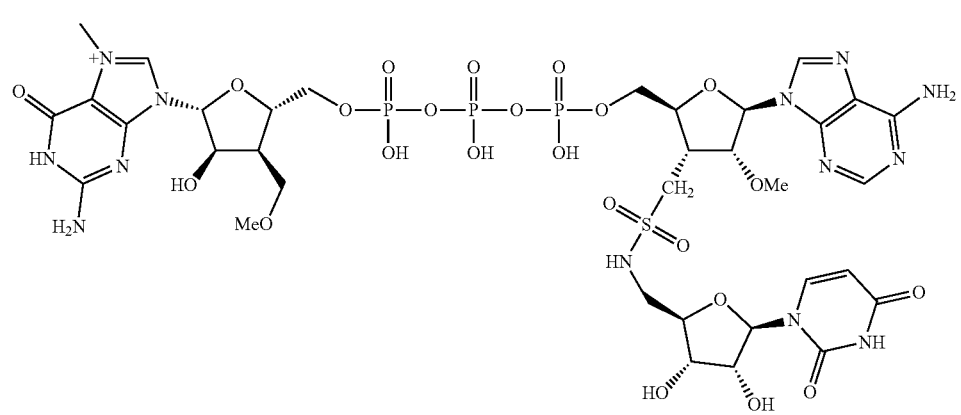

-continued
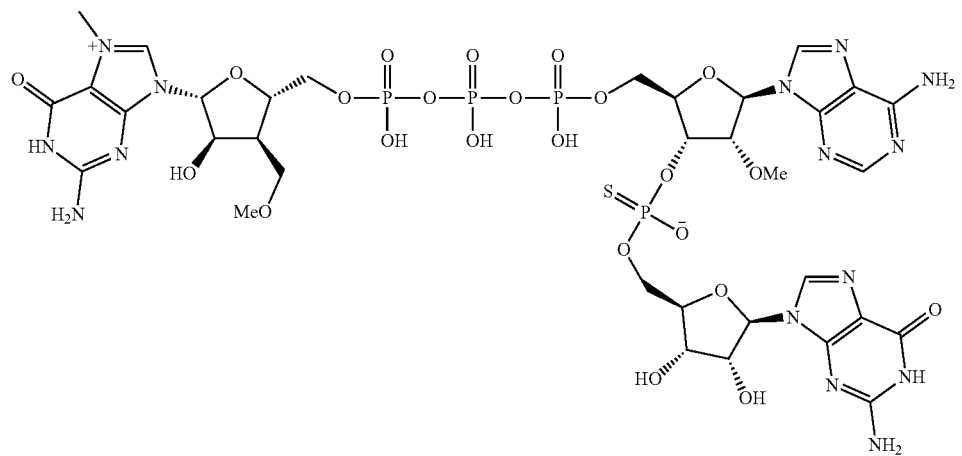
Compound 553
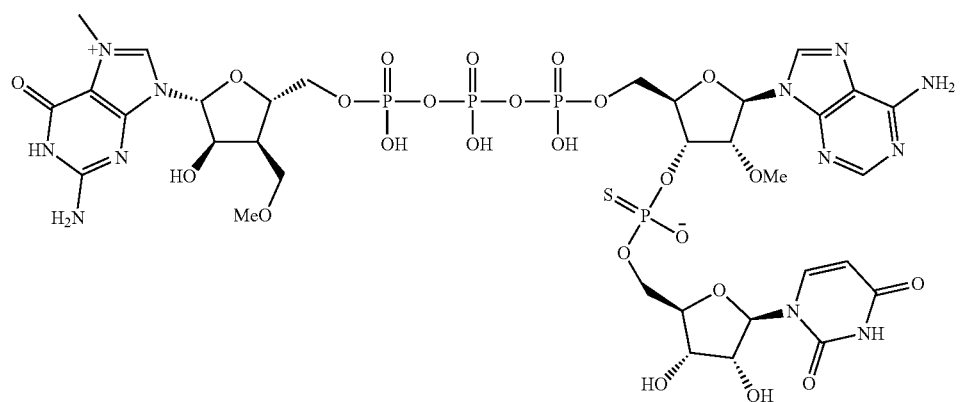
Compound 554
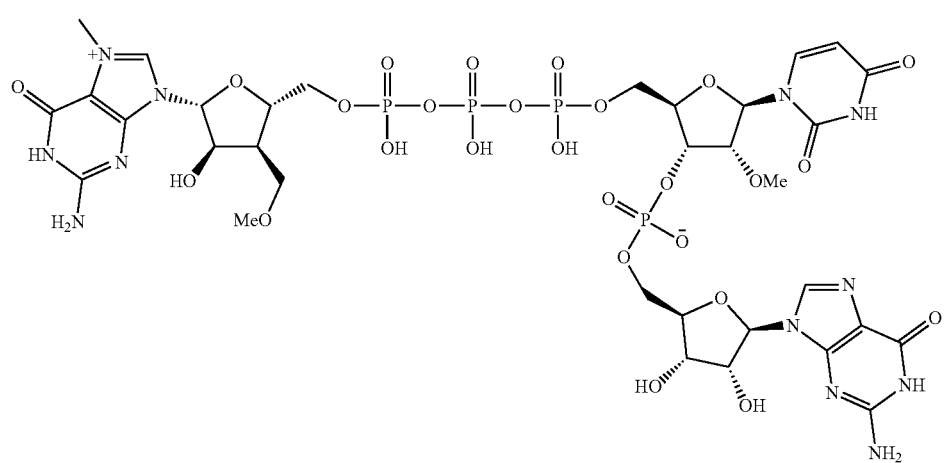
Compound 555

-continued
Compound 556
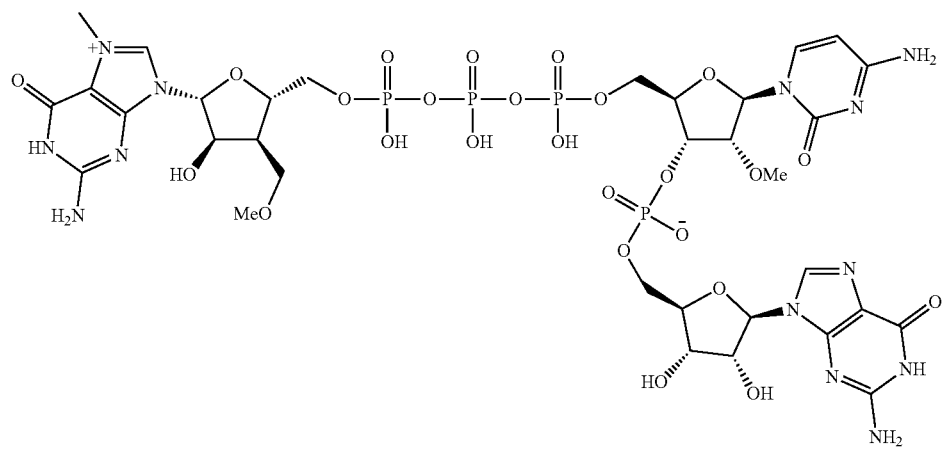
Compound 557
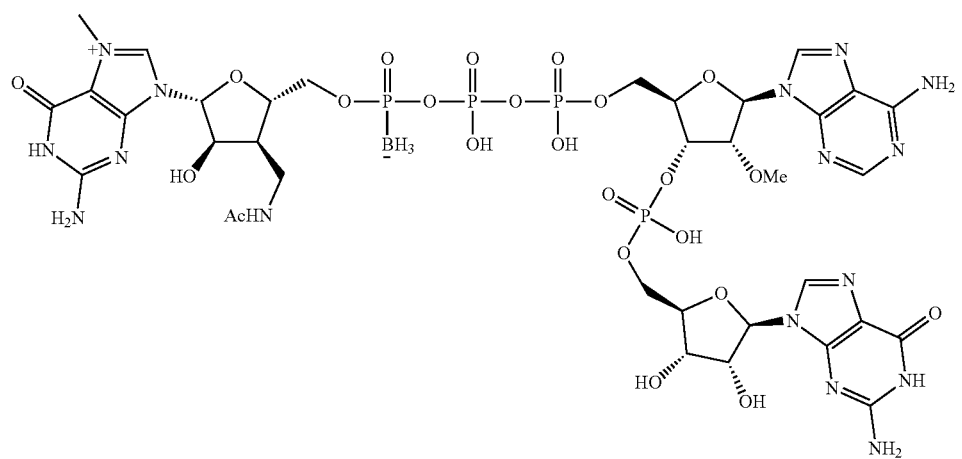
Compound 558
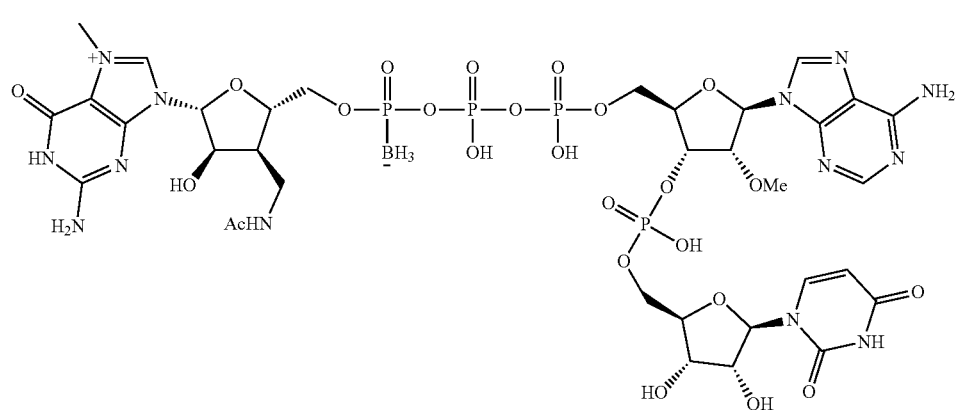

-continued
Compound 559
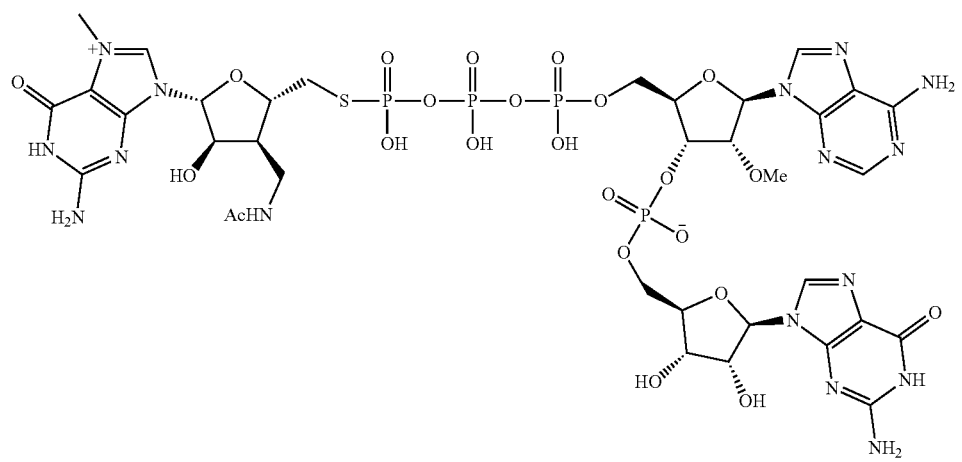
Compound 560
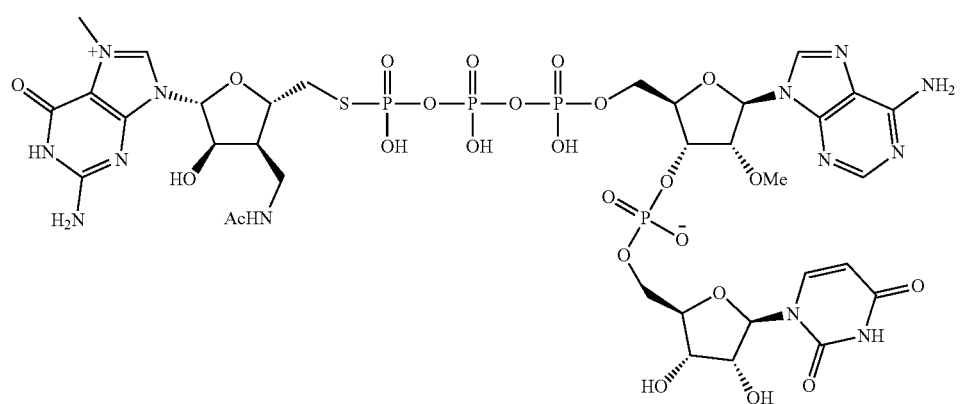
Compound 561
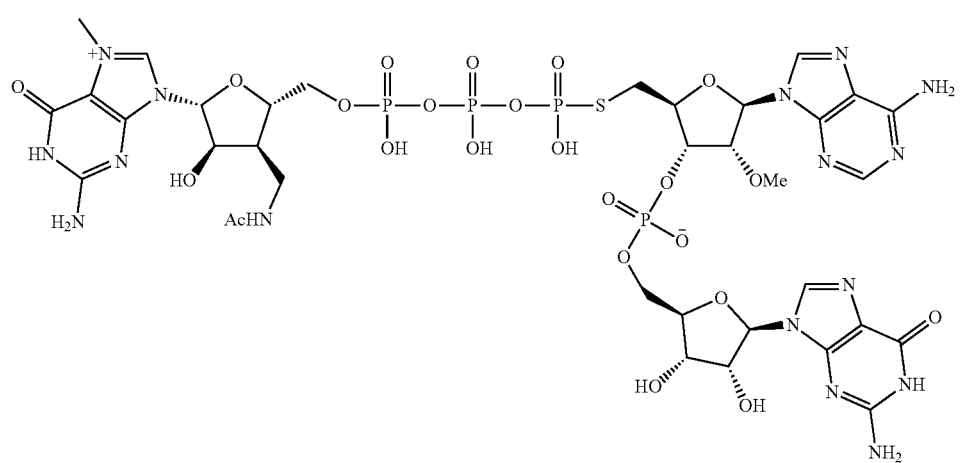

-continued
Compound 562
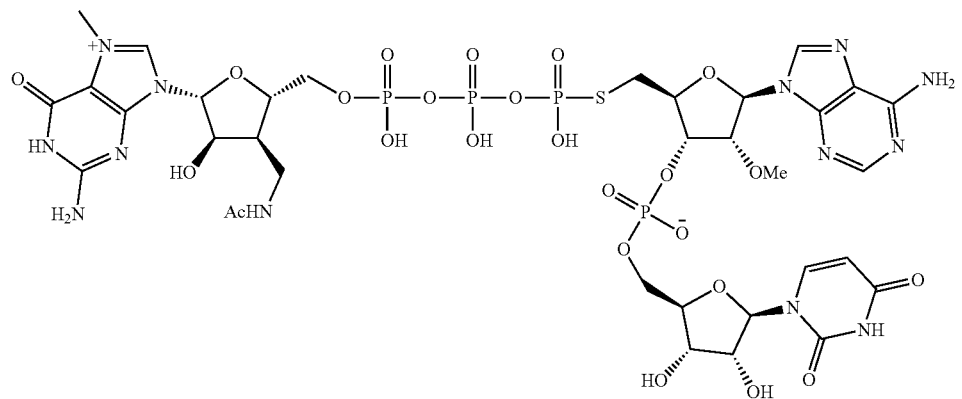
Compound 563
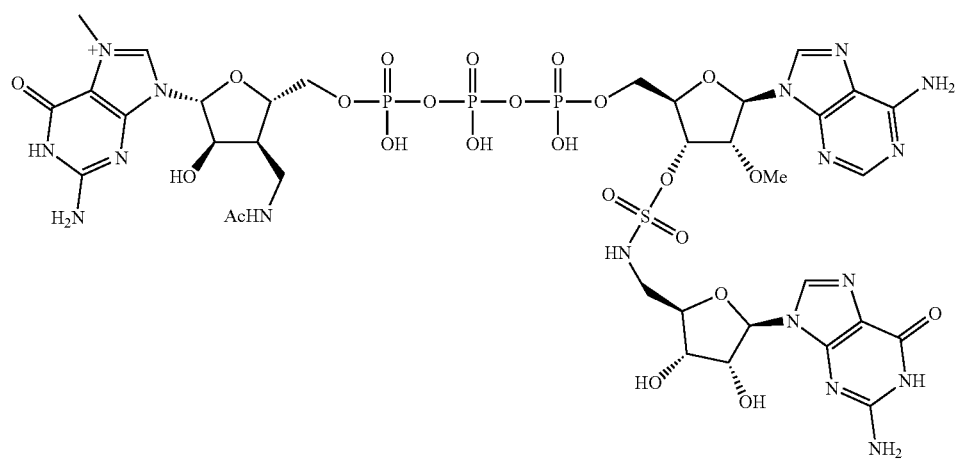
Compound 564
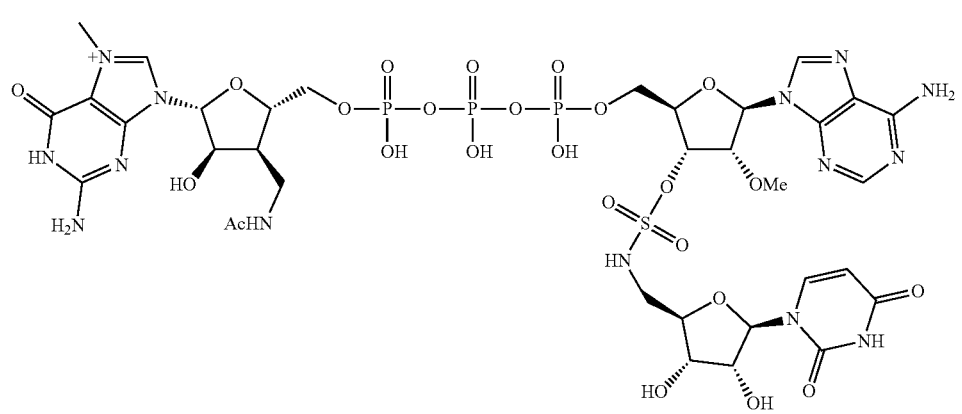

Compound 565
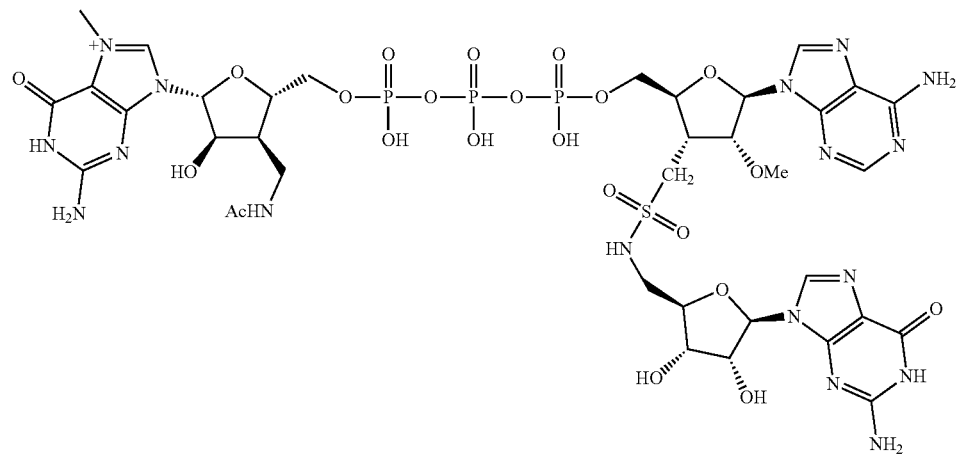
Compound 566
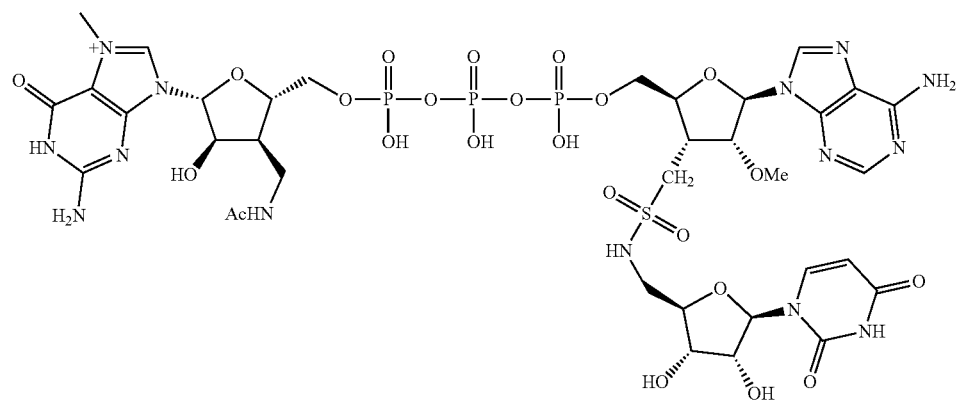
Compound 567
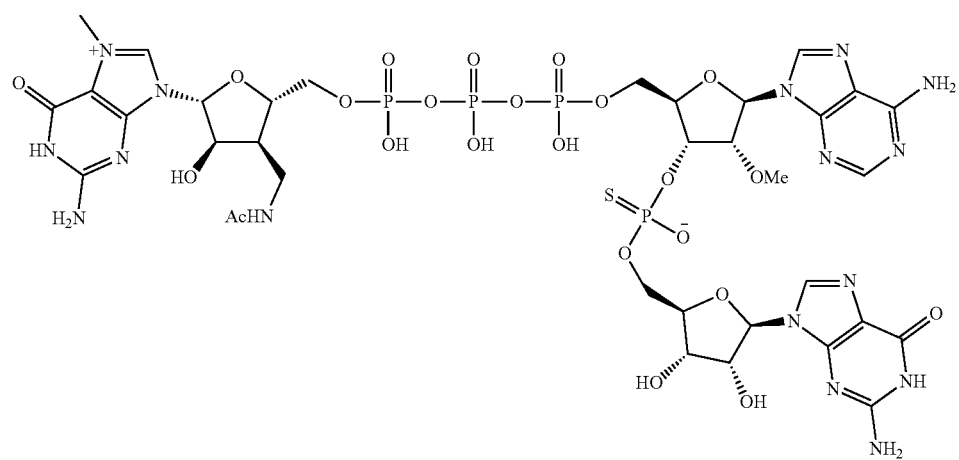

Compound 568
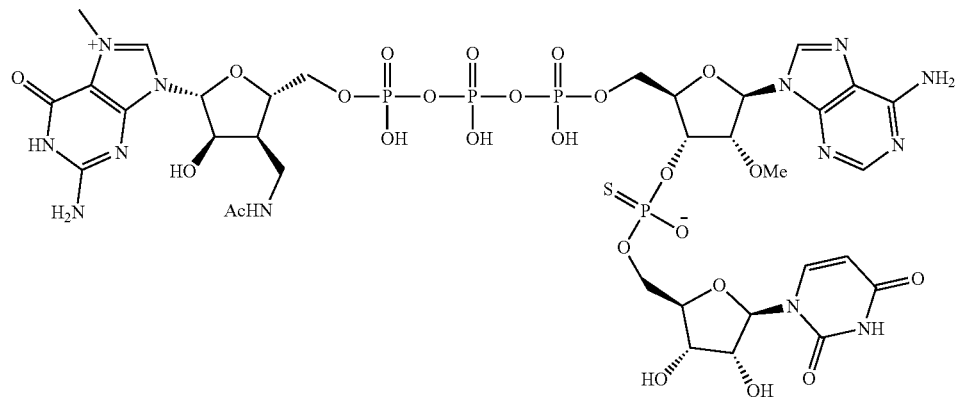
Compound 569
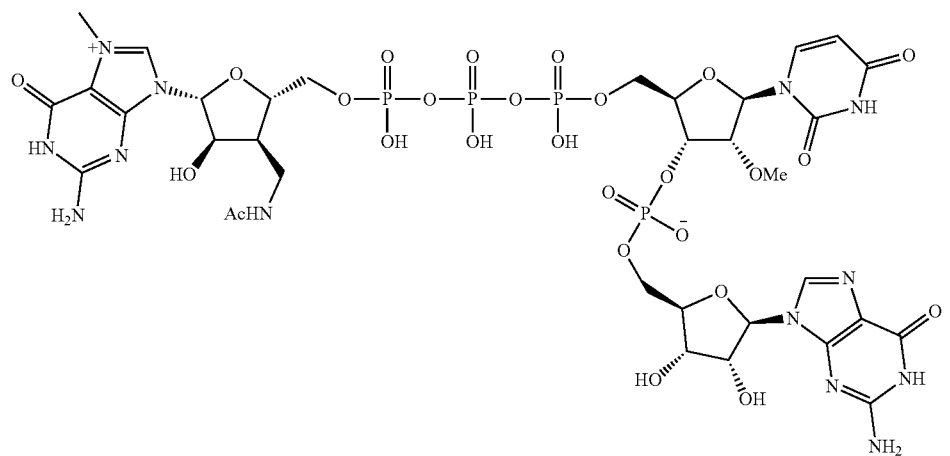
Compound 570
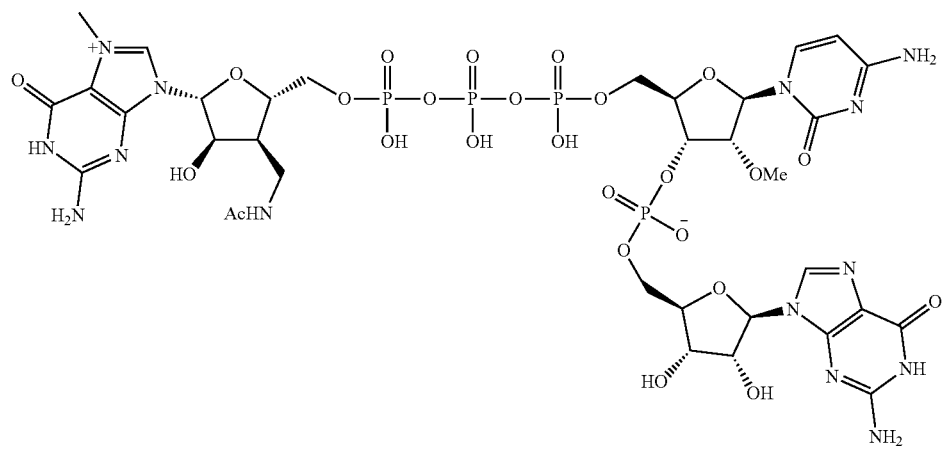

Compound 571
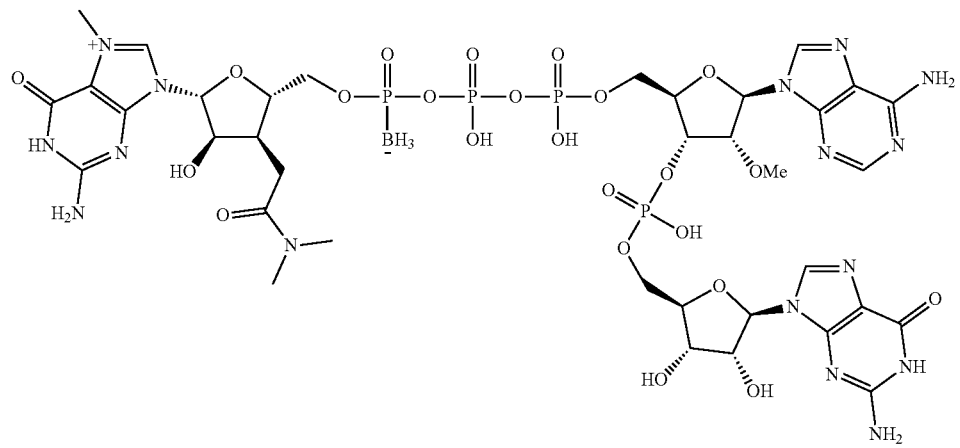
Compound 572
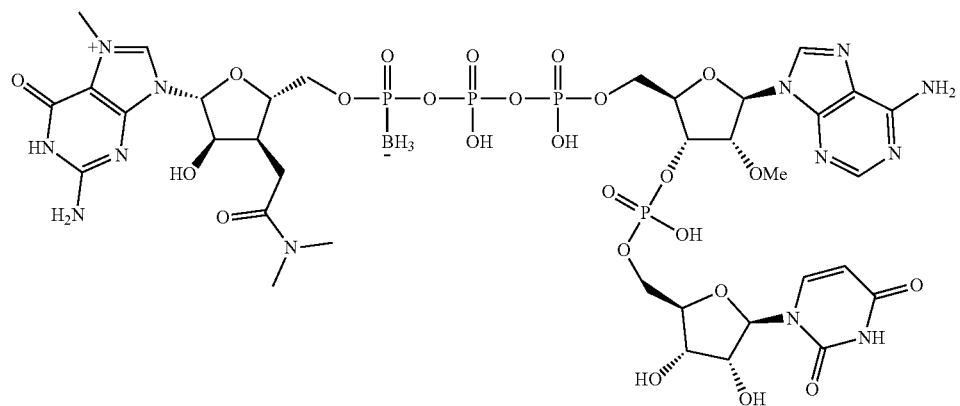
Compound 573
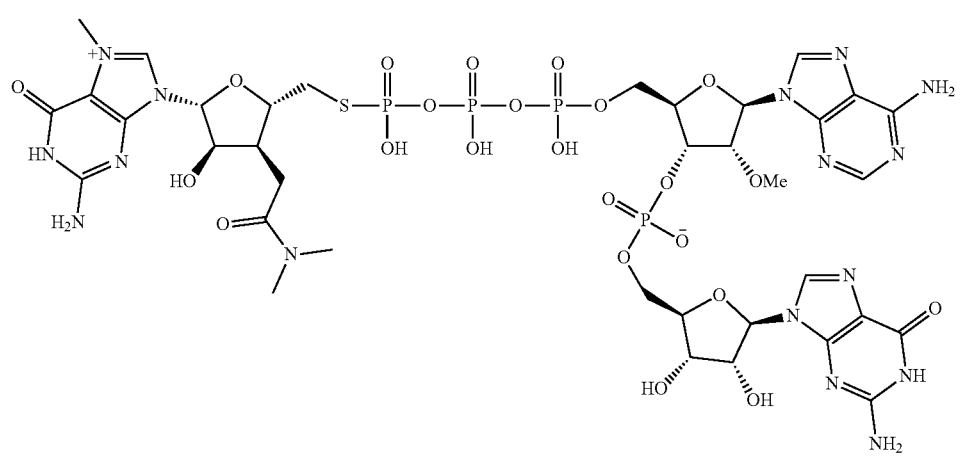

Compound 574
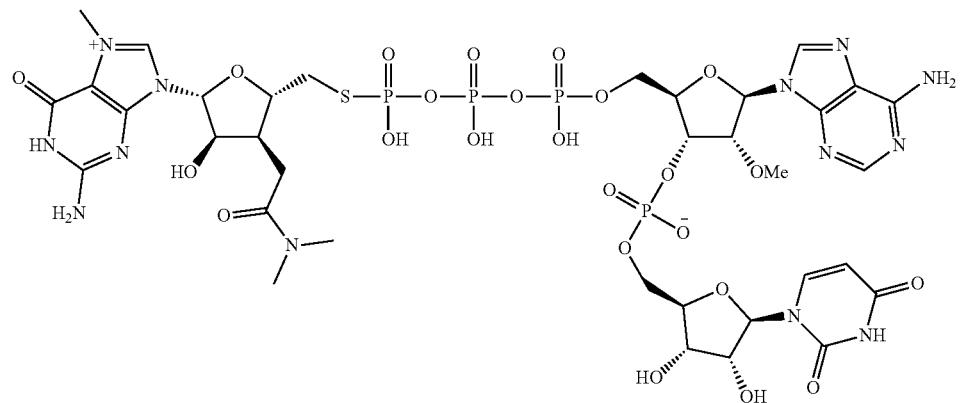
Compound 575
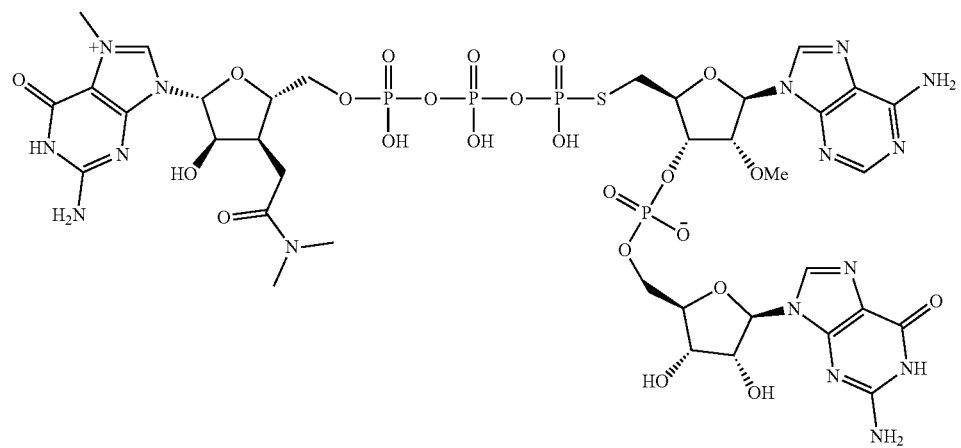
Compound 576
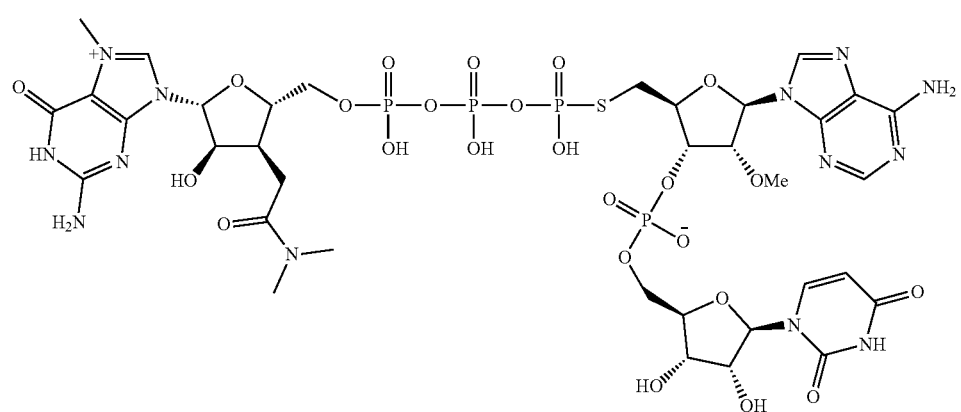

Compound 577
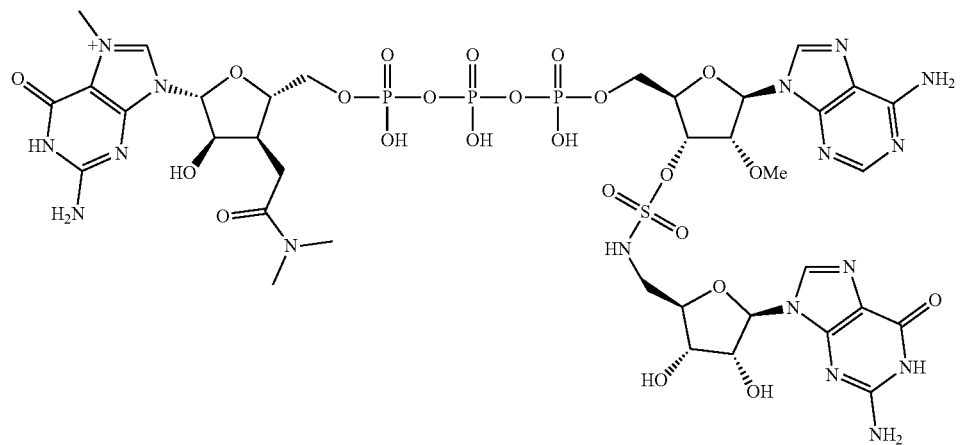
Compound 578
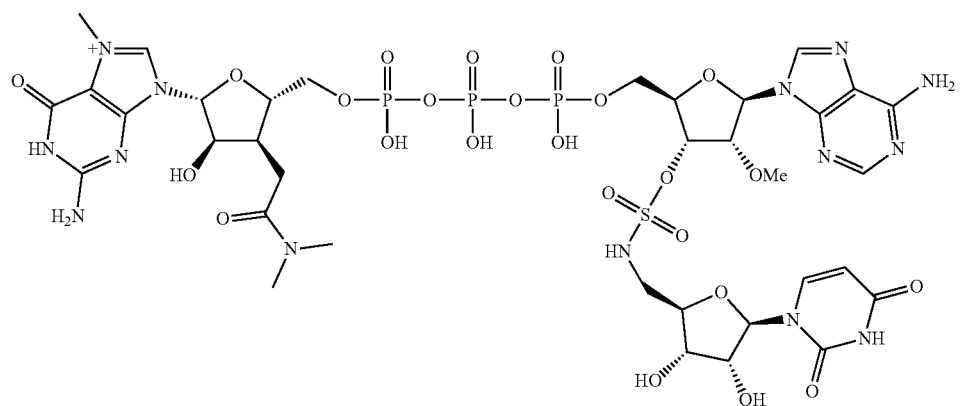
Compound 579
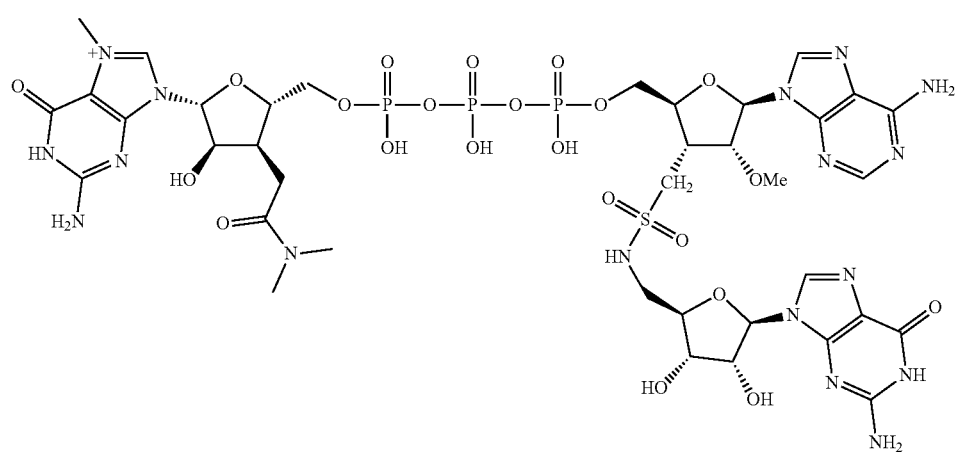

-continued
Compound 580
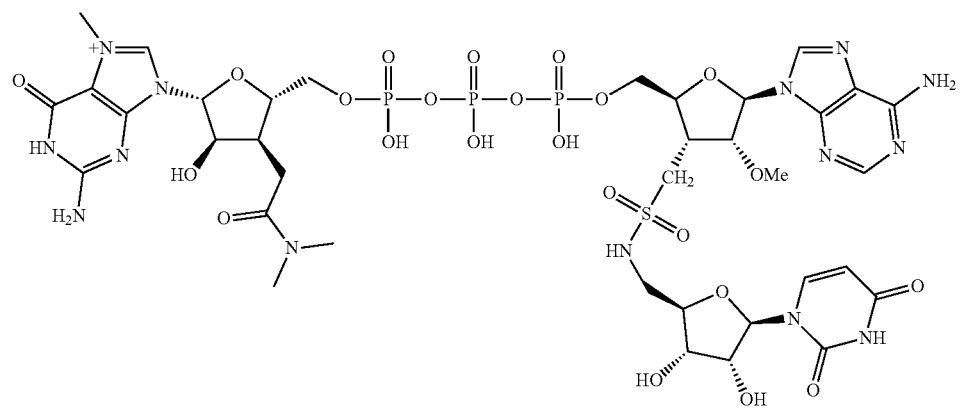
Compound 581
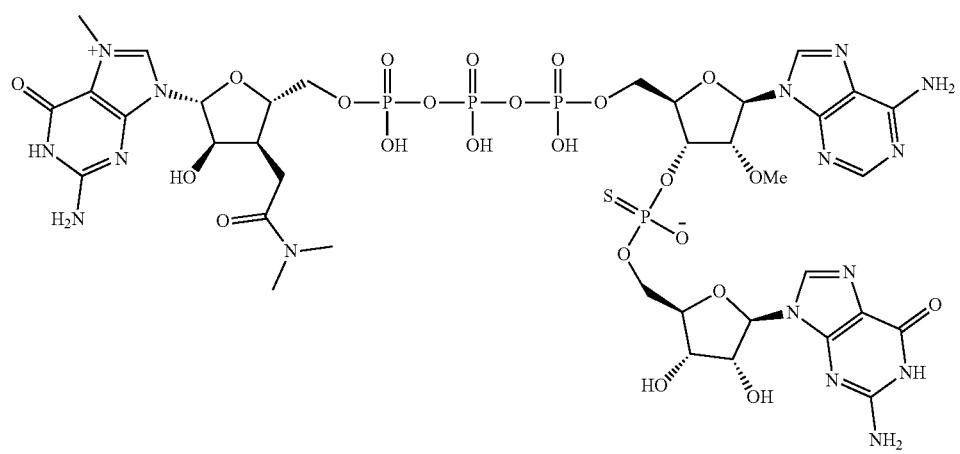
Compound 582
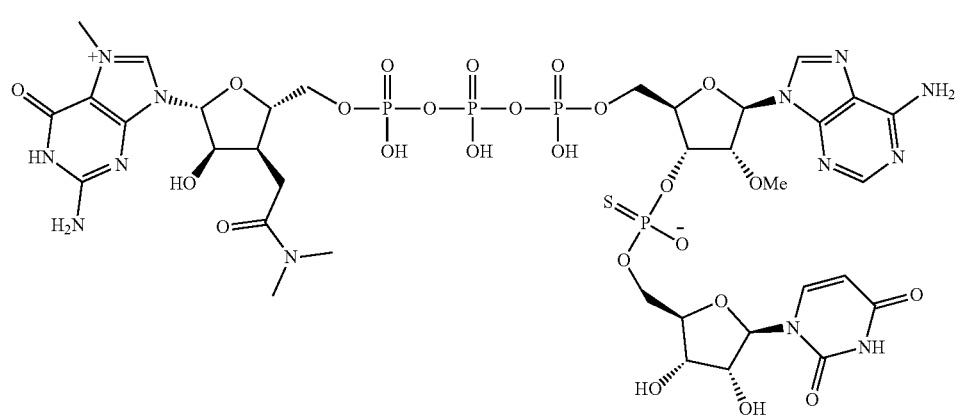

-continued
Compound 583
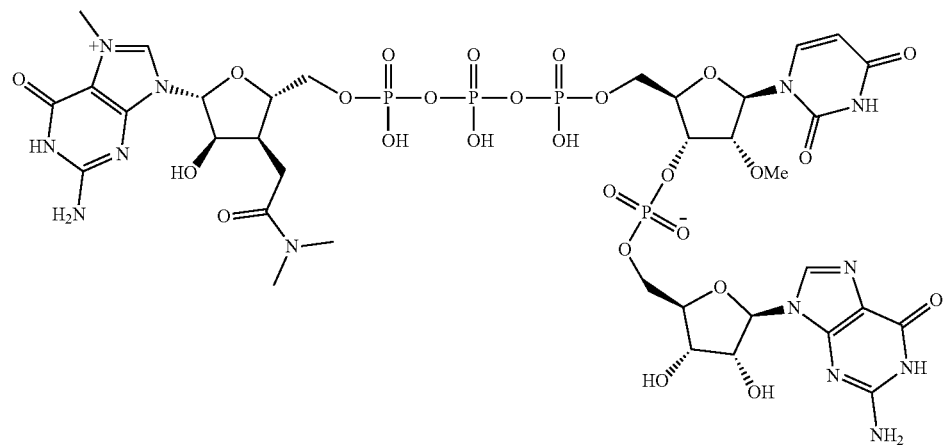
Compound 584
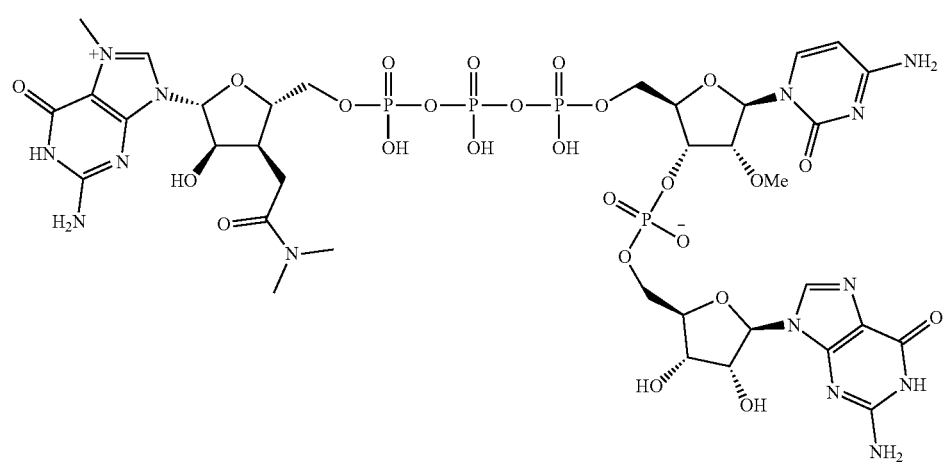
Compound 599
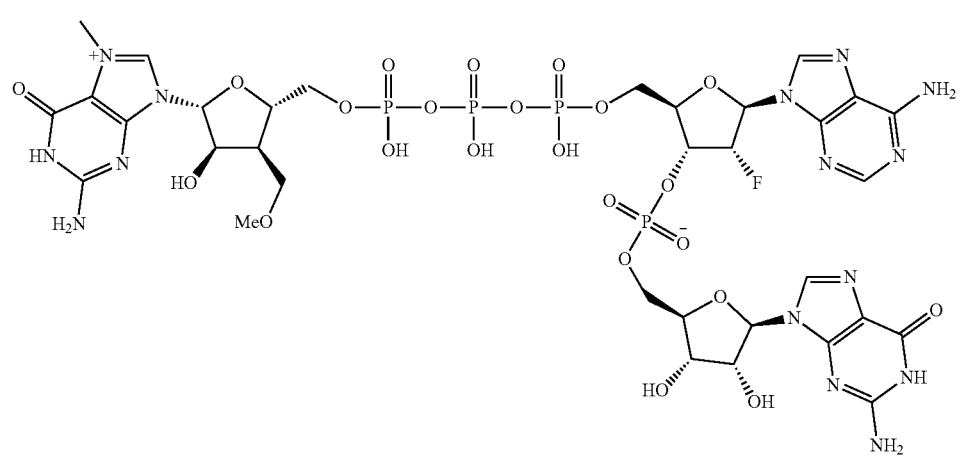

Compound 600
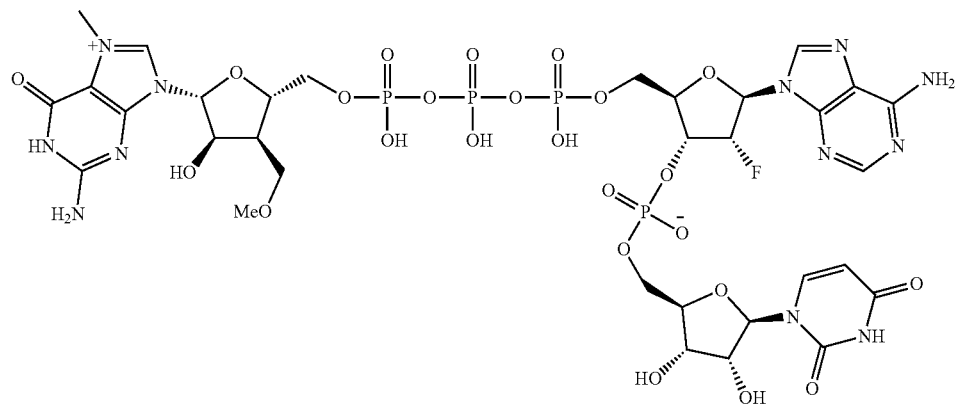
Compound 601
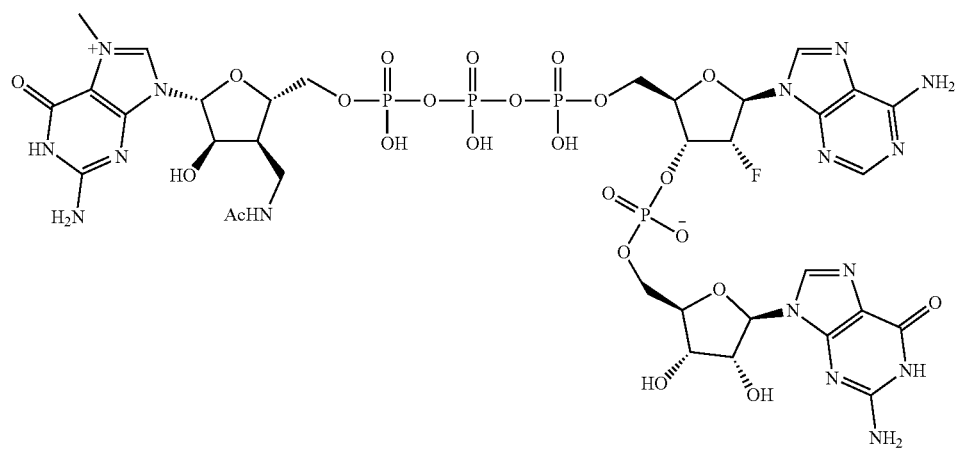
Compound 602
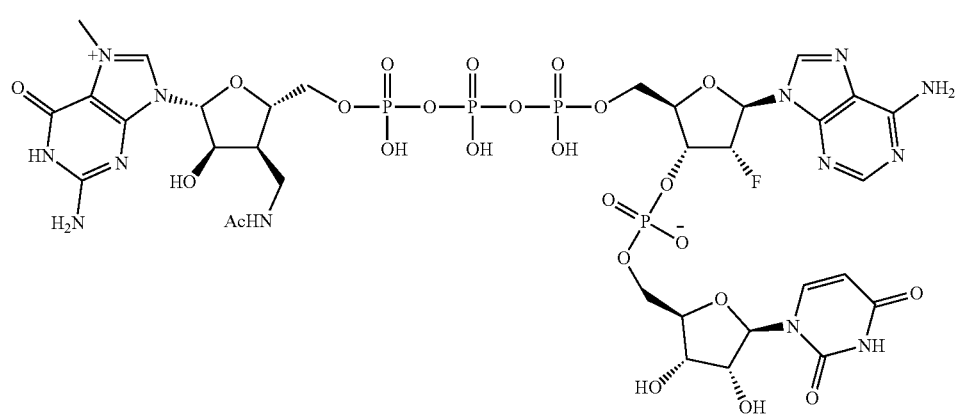

-continued
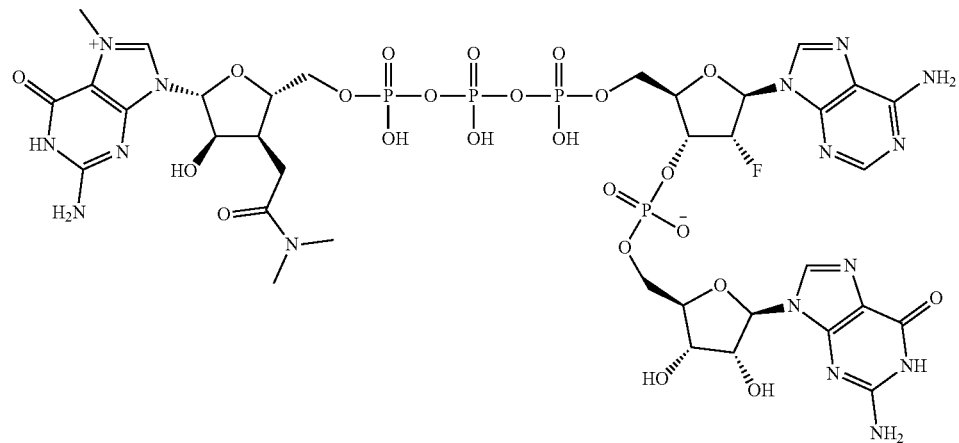
Compound 603
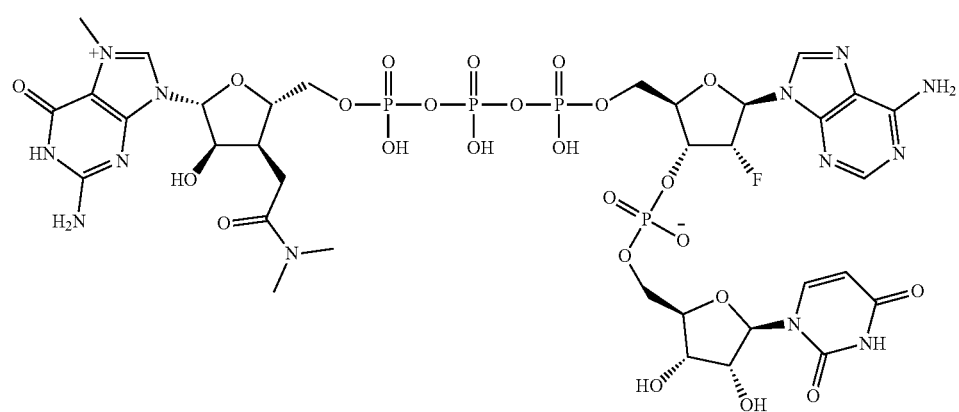
Compound 604
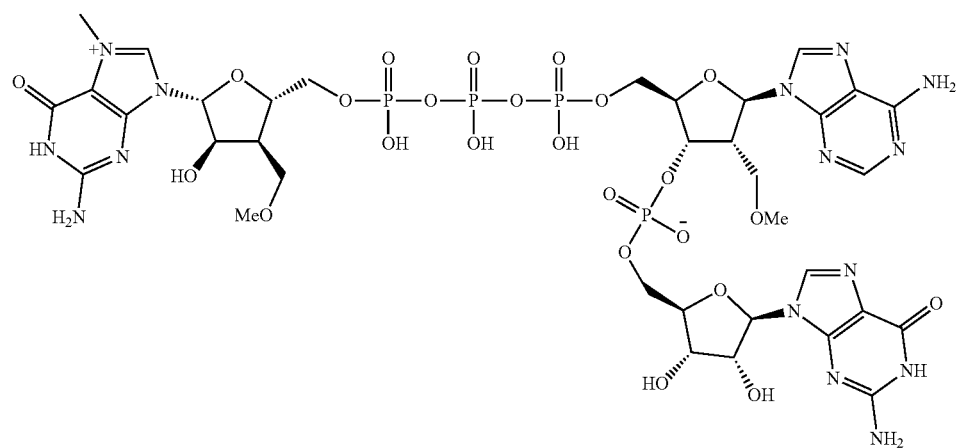
Compound 627

-continued
Compound 628
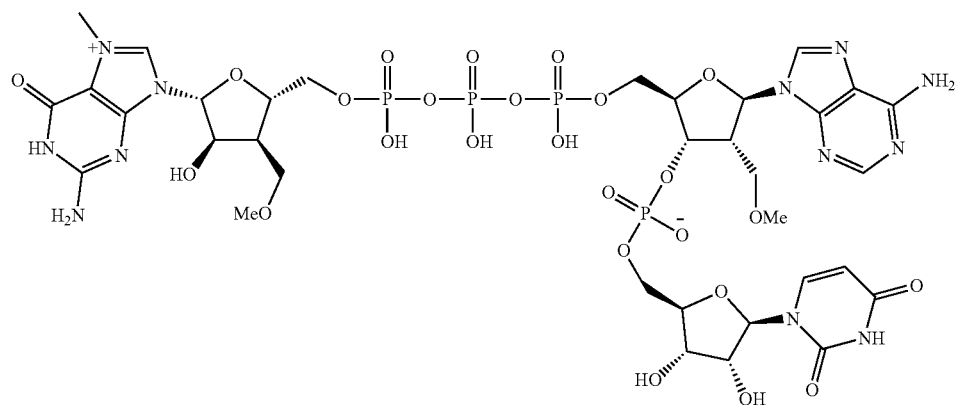
Compound 629
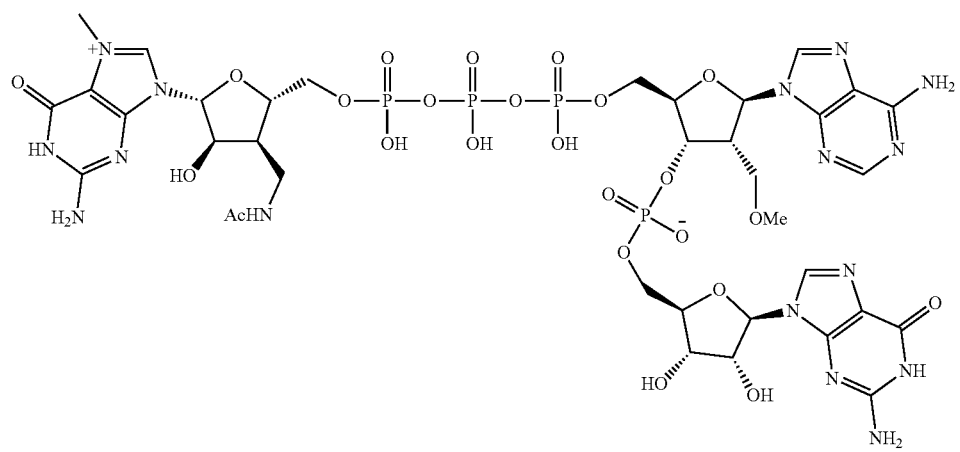
Compound 630
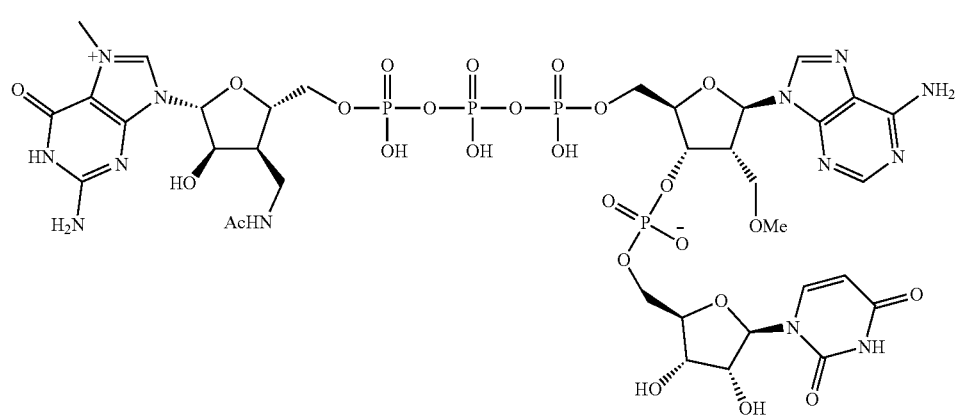

Compound 631
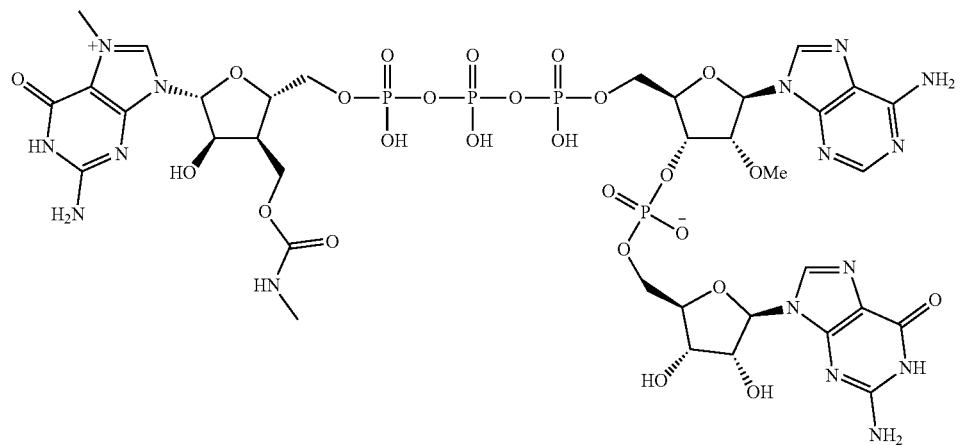
Compound 632
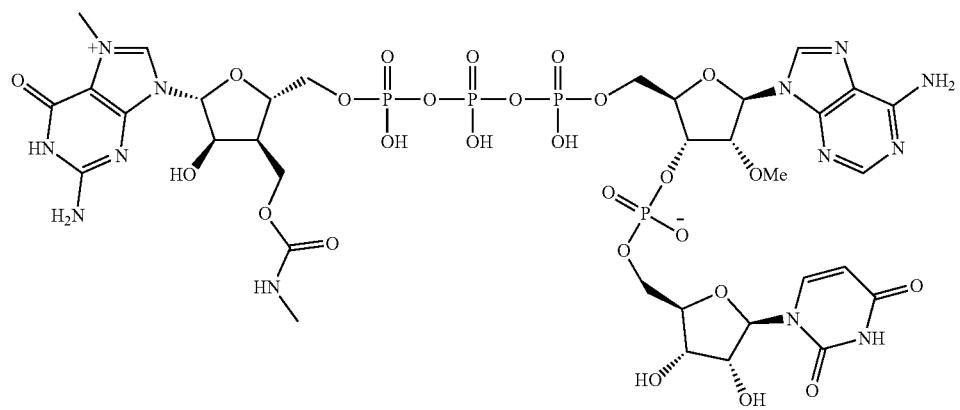
Compound 633
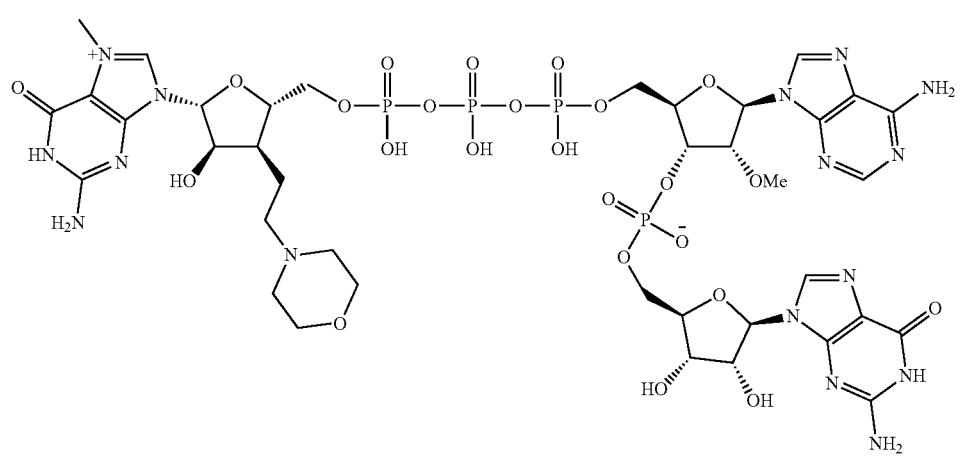

-continued
Compound 634
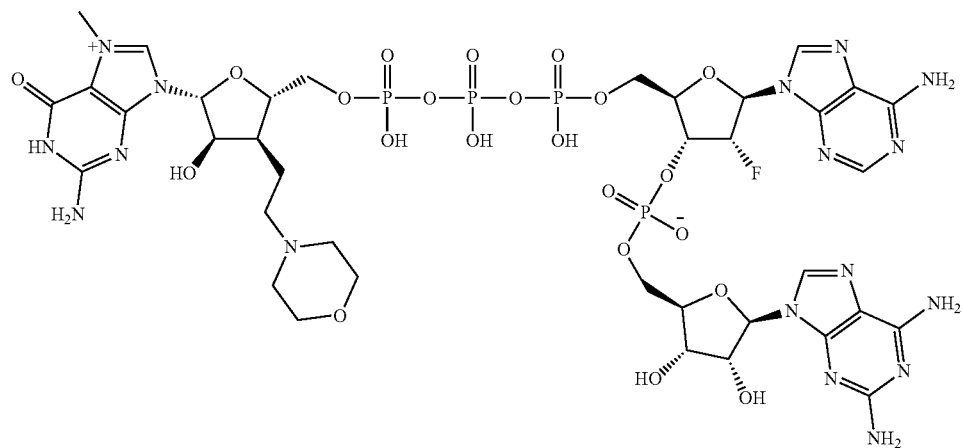
Compound 635
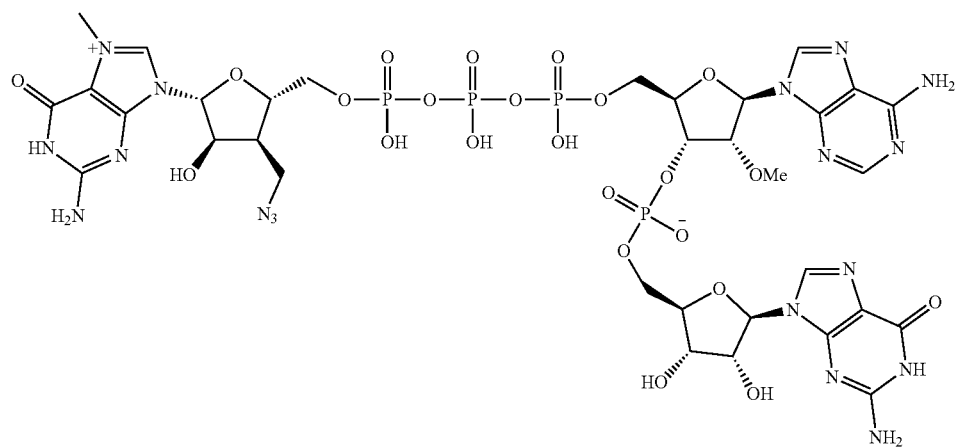
Compound 636
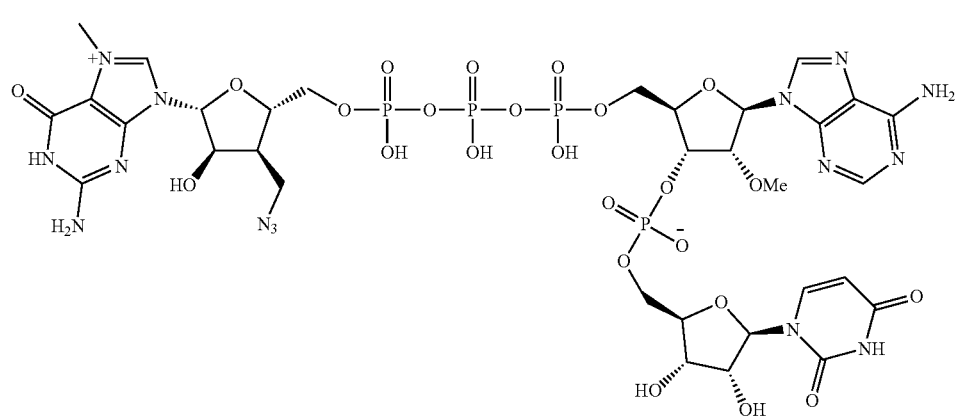

Compound 637
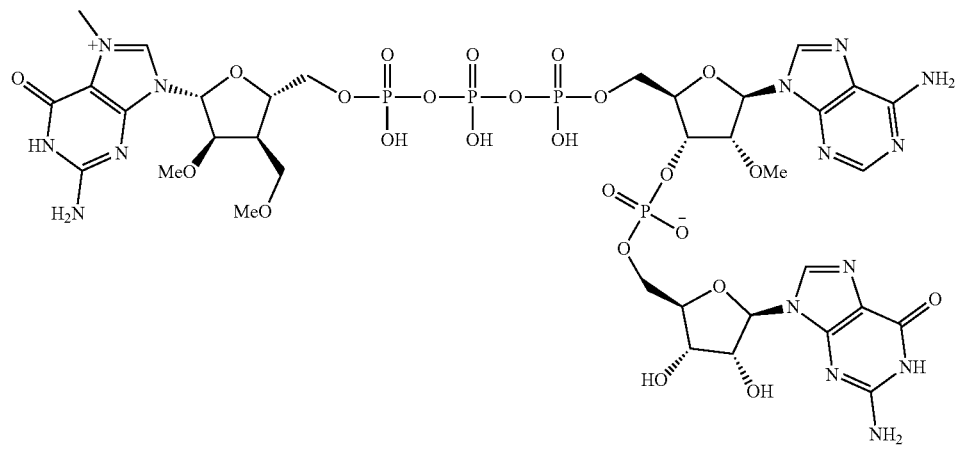
Compound 638
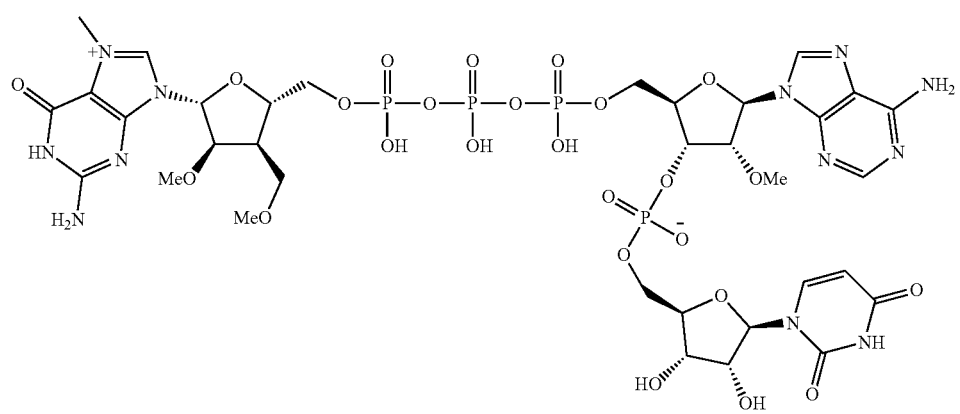
Compound 639
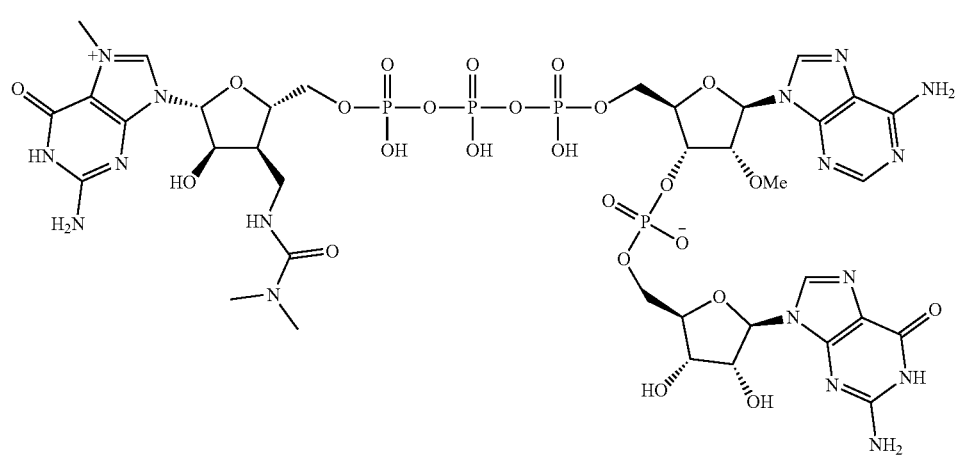

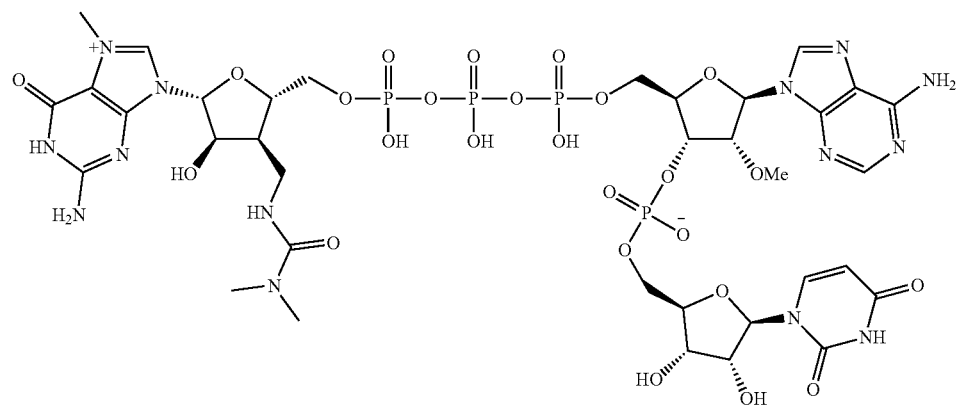
Compound 640
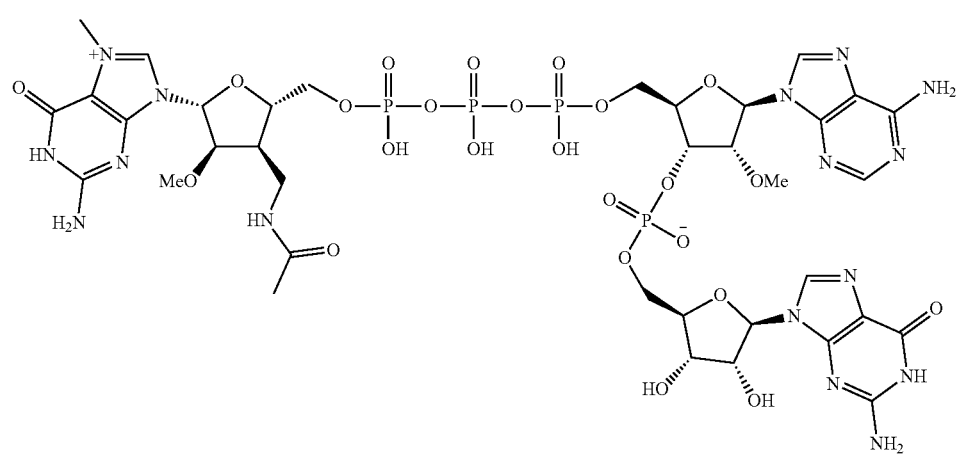
Compound 641
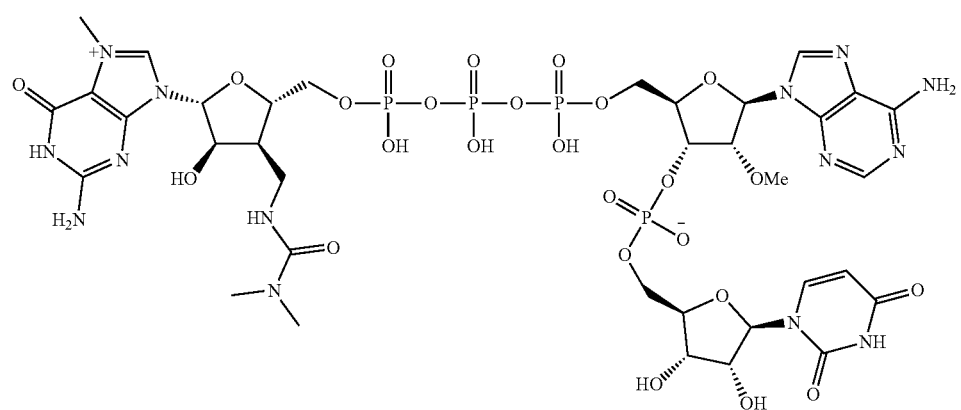
Compound 642

-continued
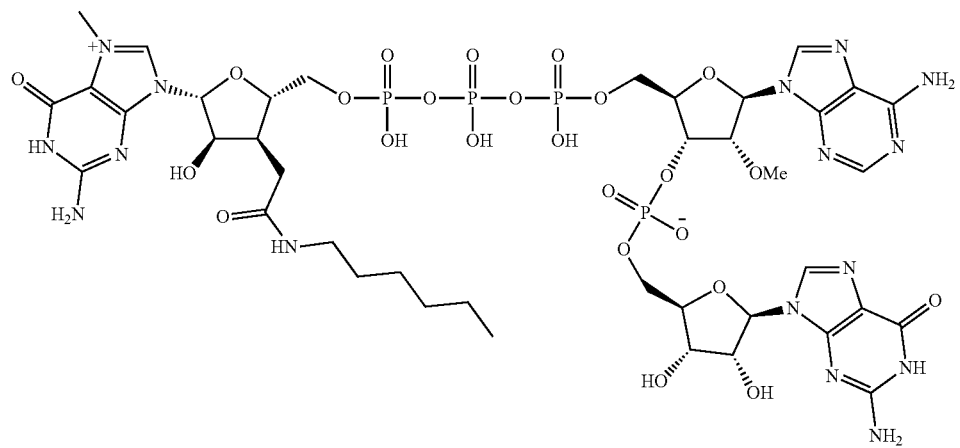
Compound 643
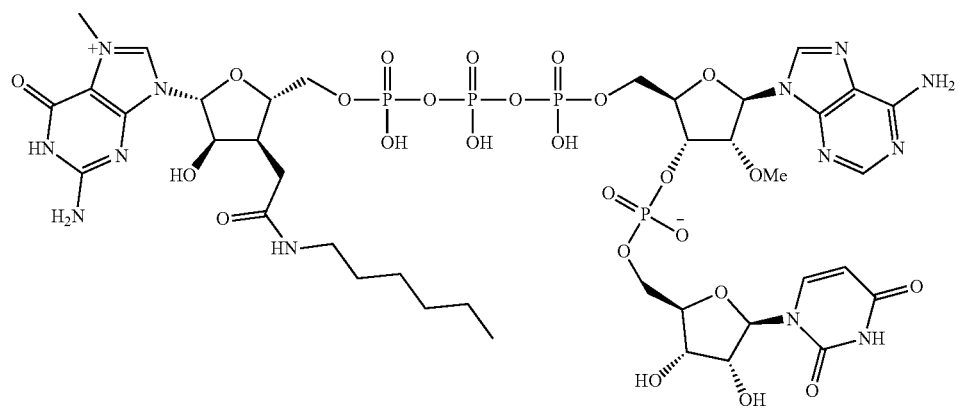
Compound 644
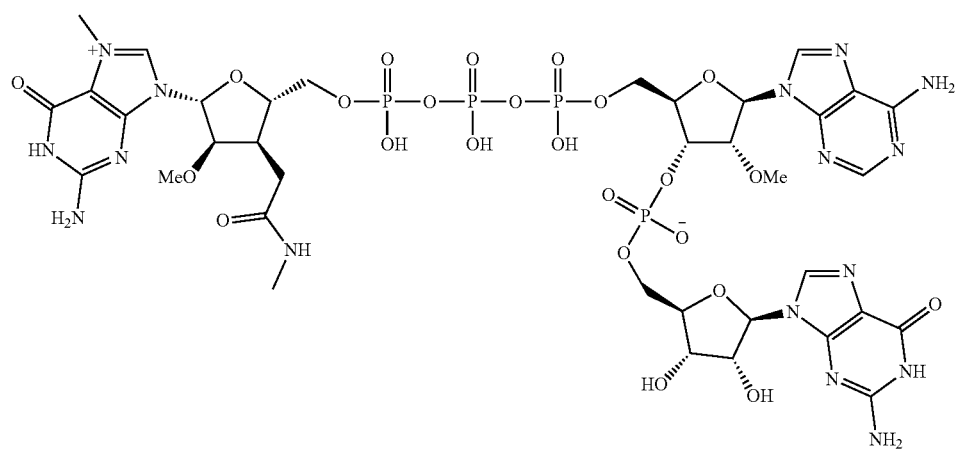
Compound 645

Compound 646
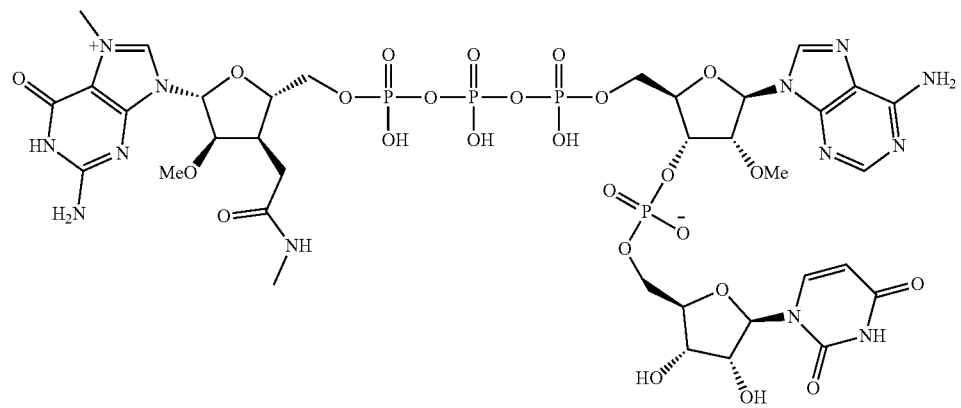
Compound 647
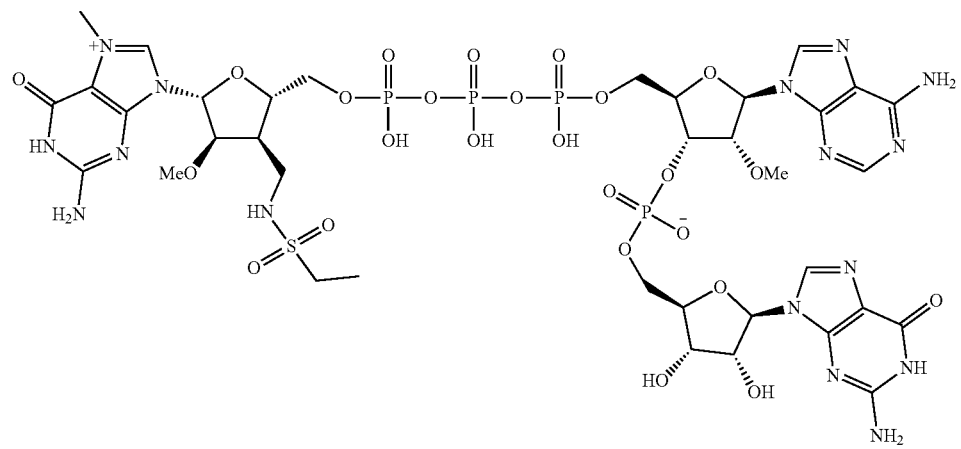
Compound 648
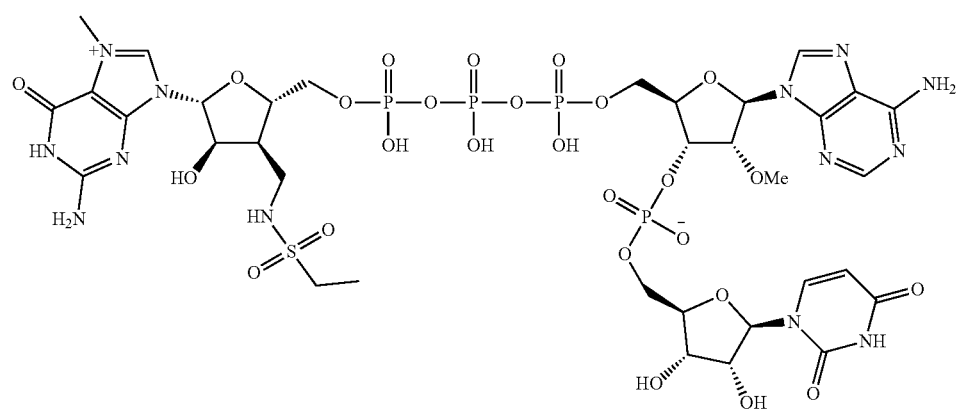

-continued
Compound 649
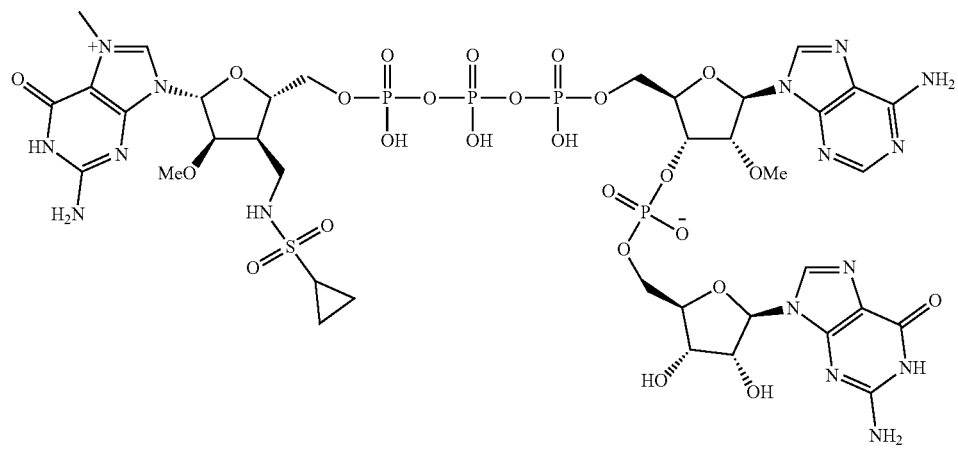
Compound 650
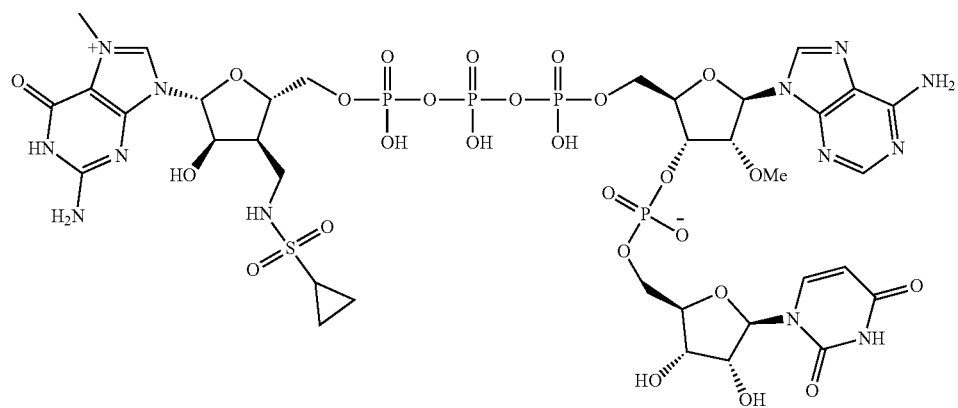
Compound 651
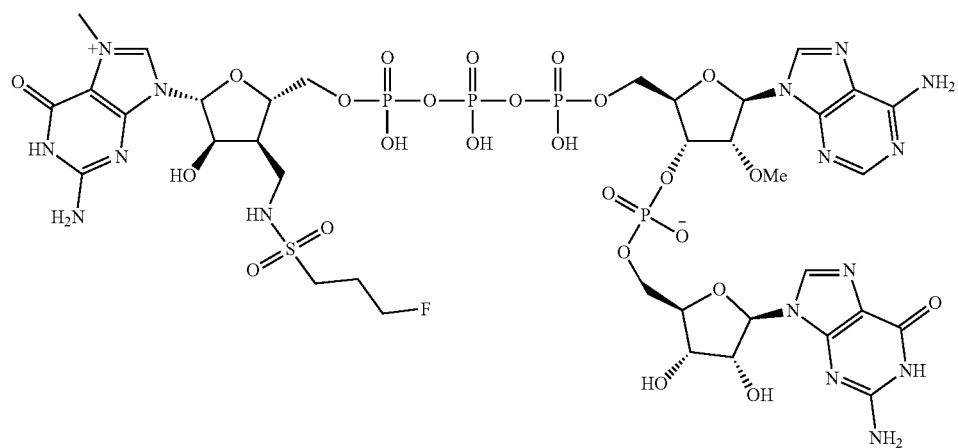

-continued
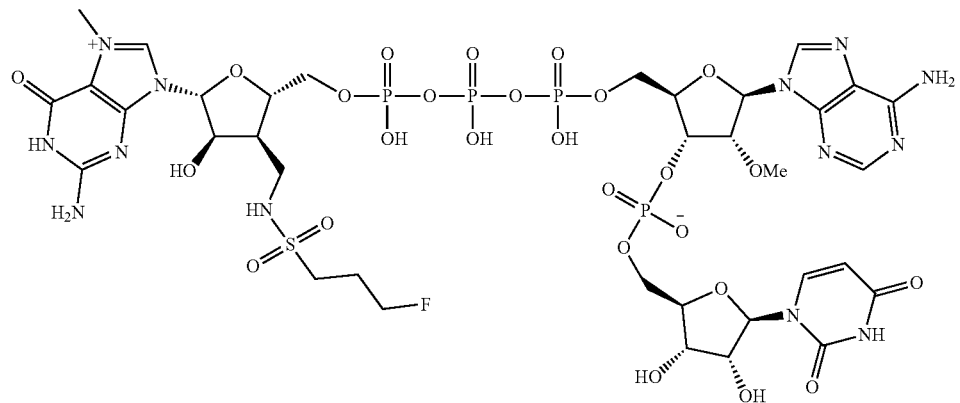
Compound 652
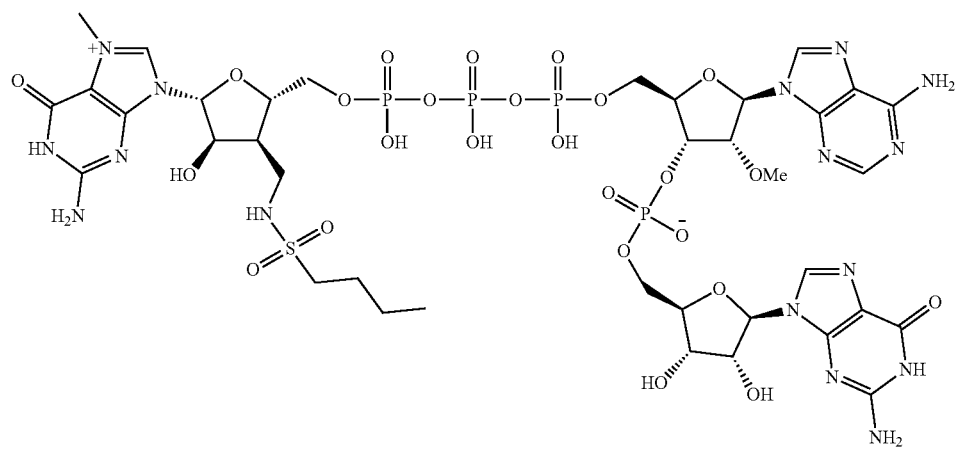
Compound 653
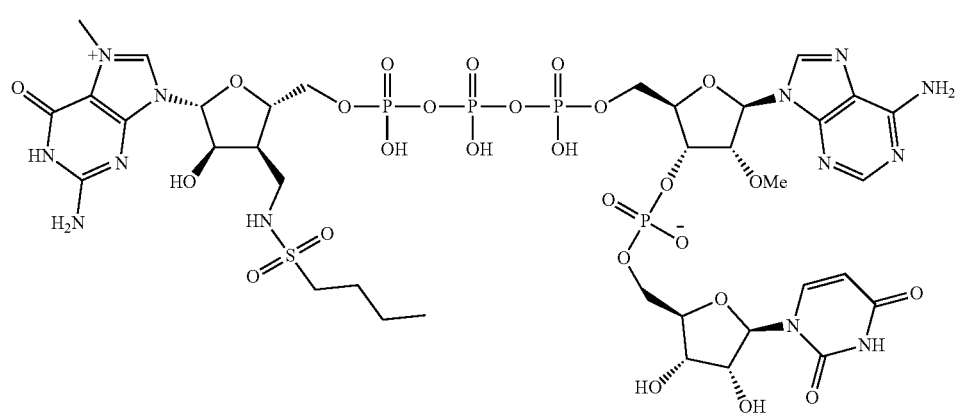
Compound 654

Compound 655
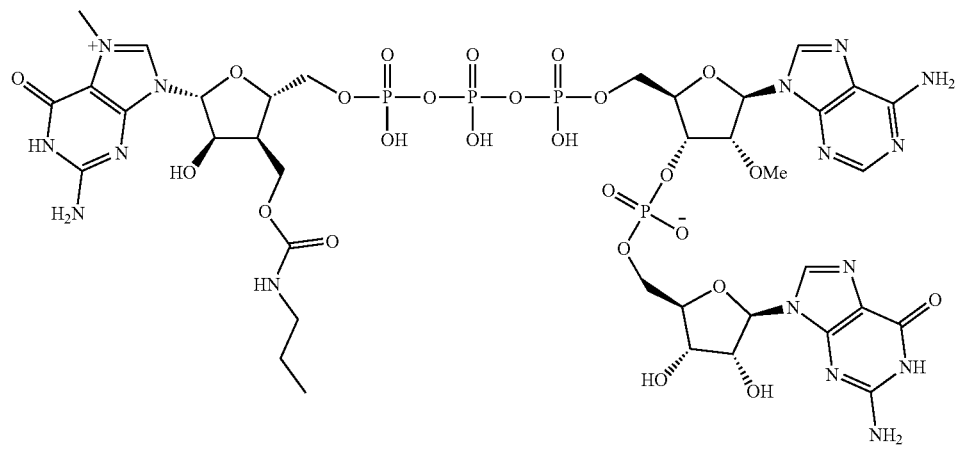
Compound 656
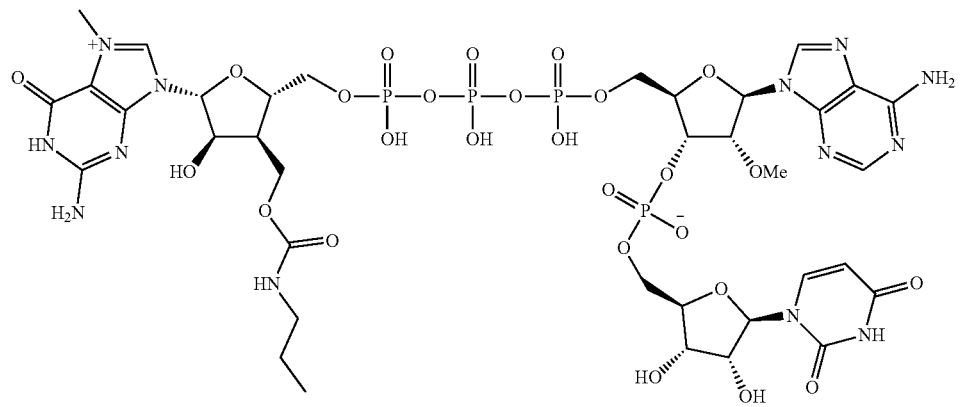
Compound 657
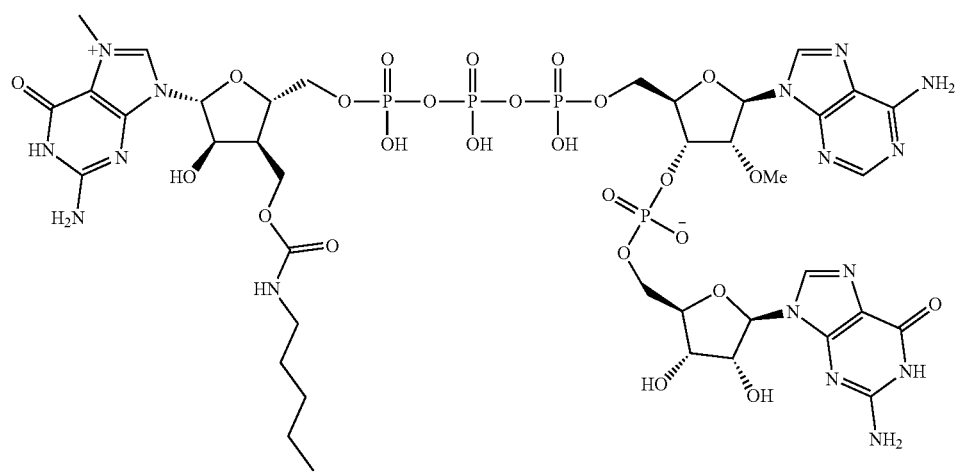

-continued
Compound 658
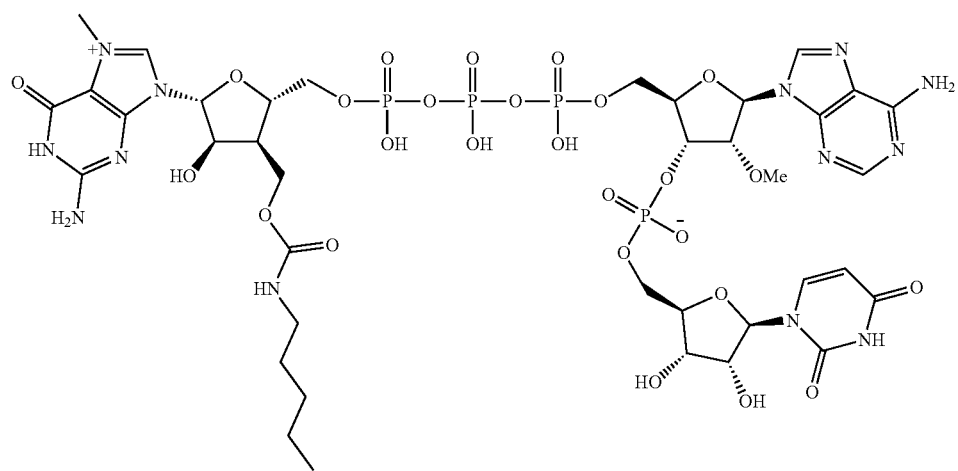
Compound 659
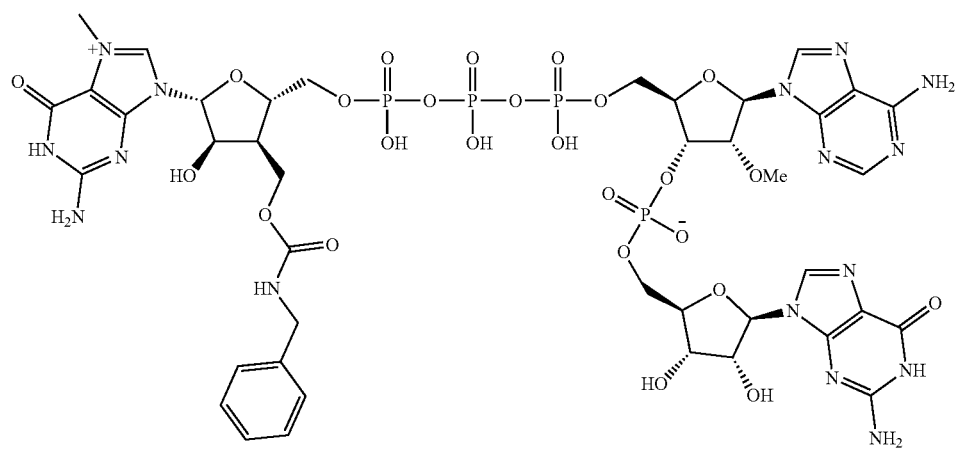
Compound 660
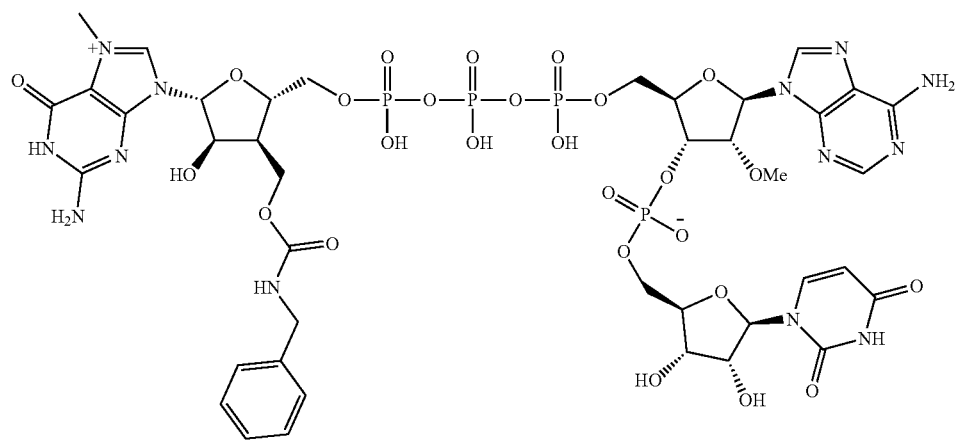

Compound 661
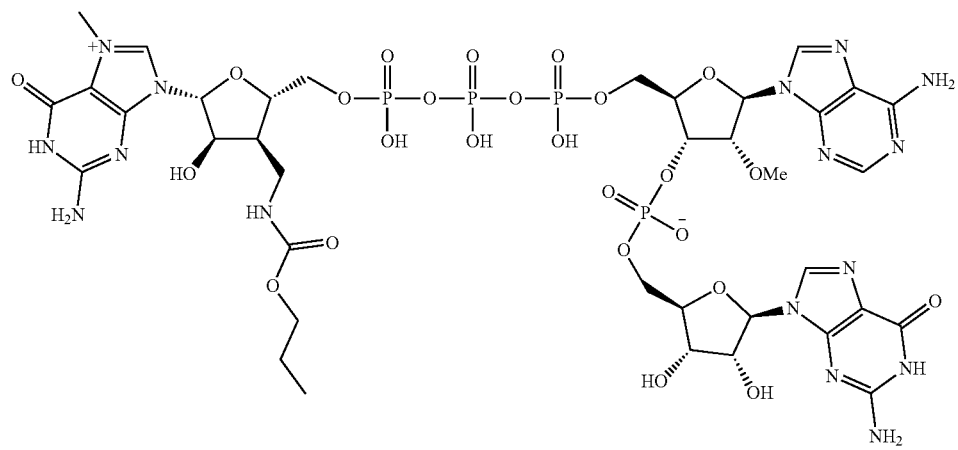
Compound 662
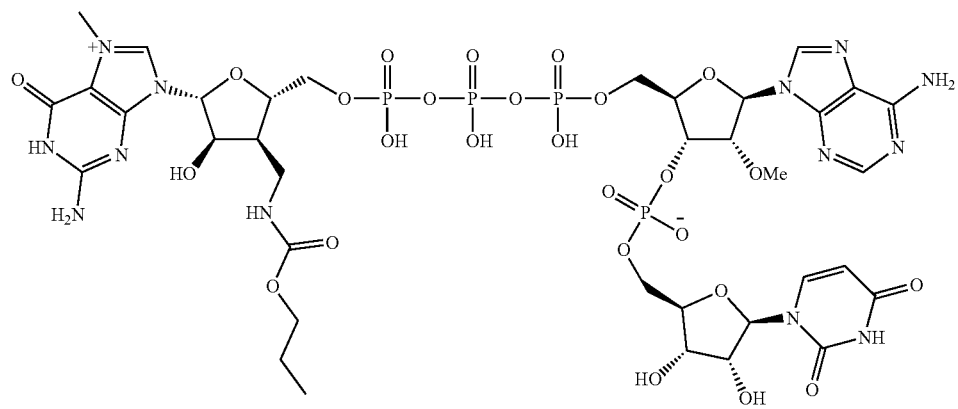
Compound 663
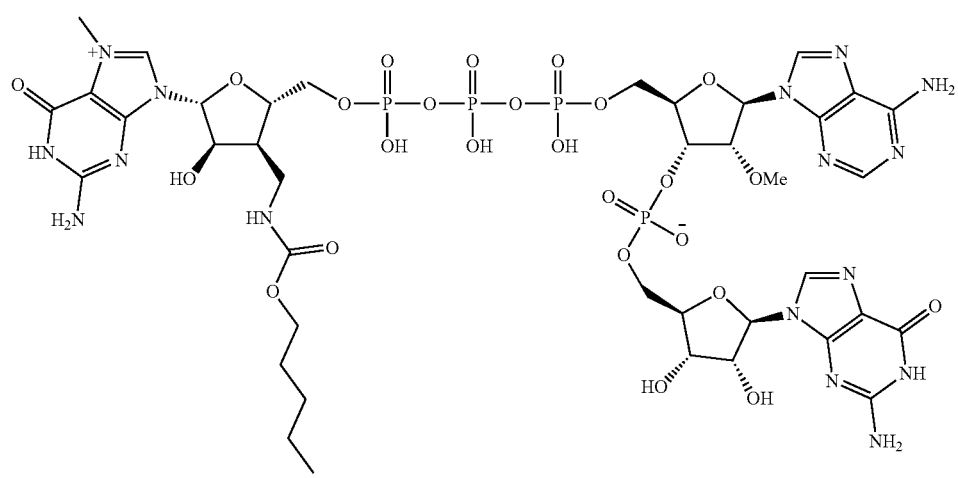

-continued
Compound 664
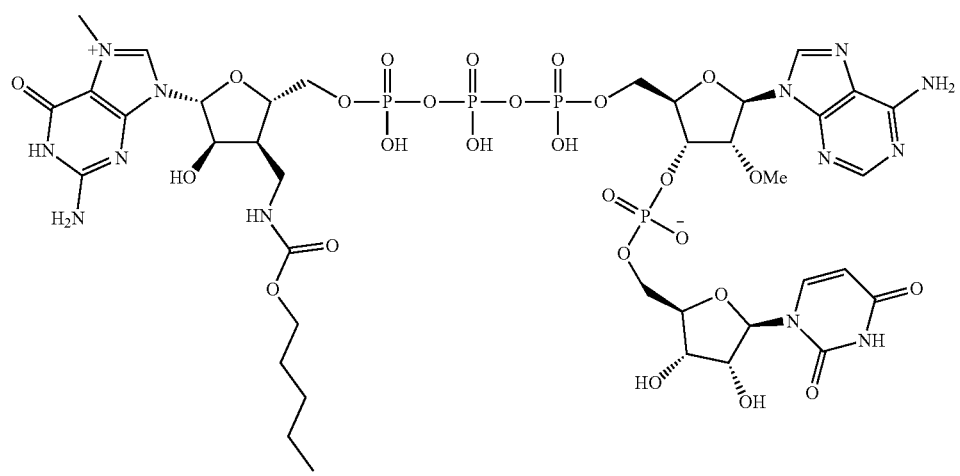
Compound 665
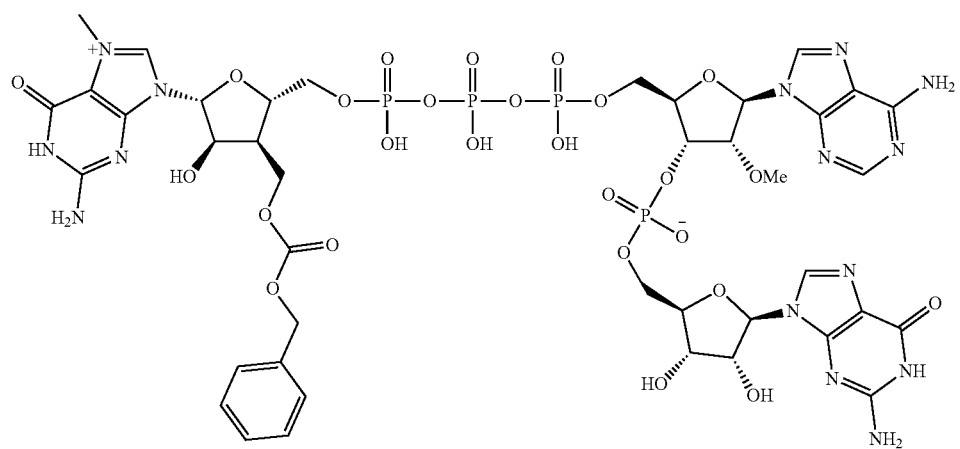
Compound 666
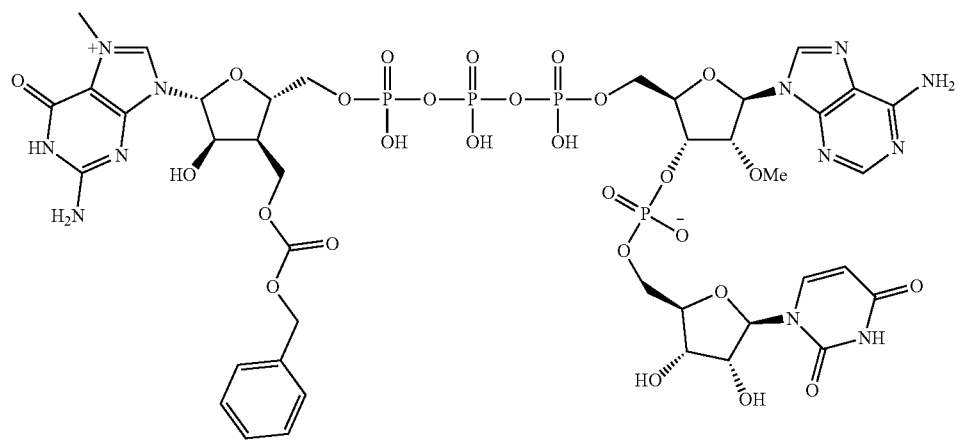

-continued
Compound 667
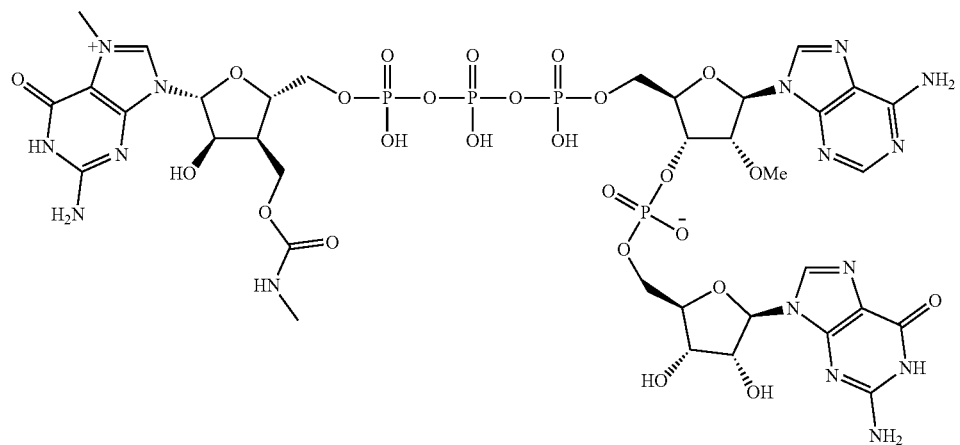
Compound 668
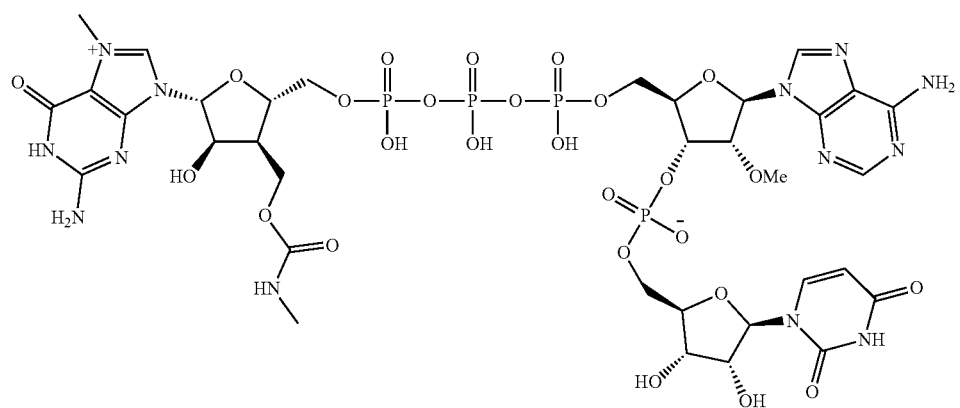
Compound 669
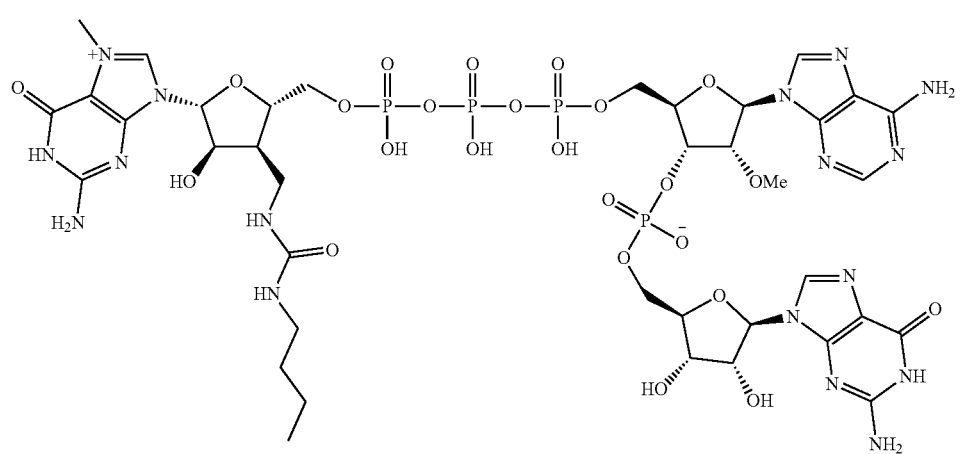

-continued

Compound 670
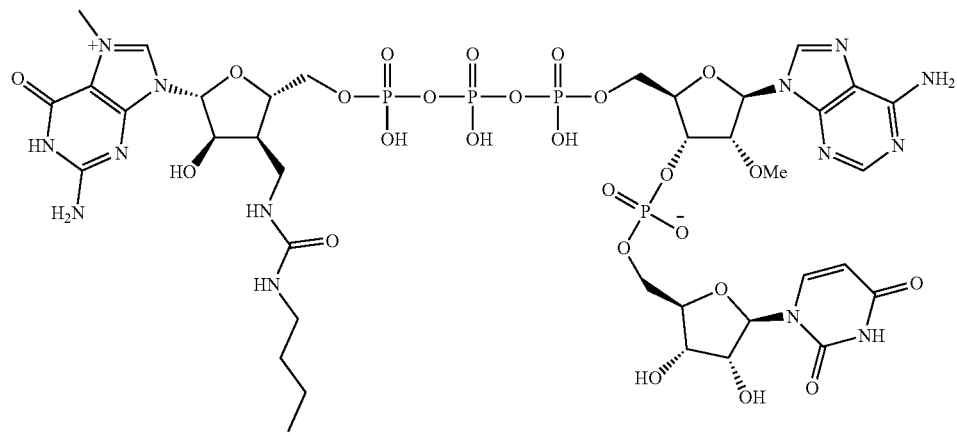

Compound 671
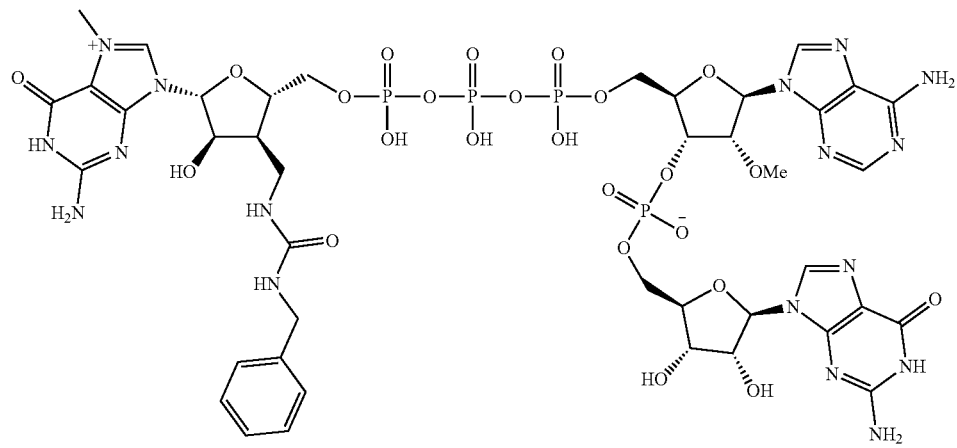

Compound 672
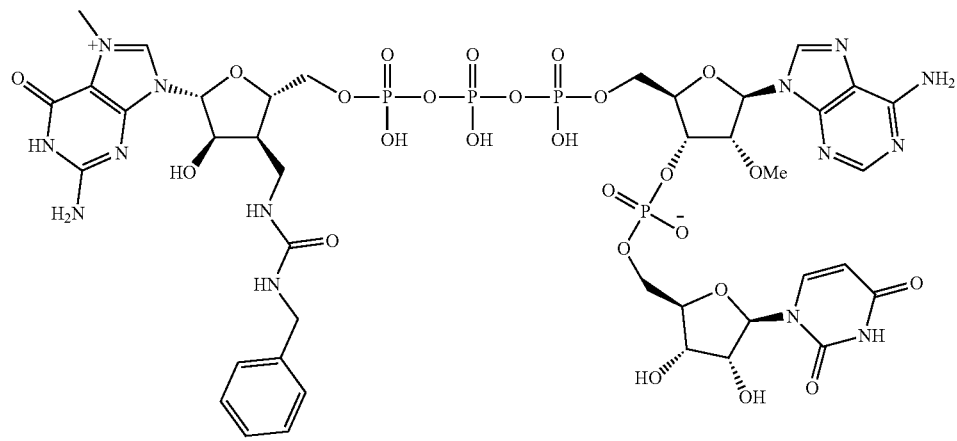

Another aspect relates to use of the above-mentioned compound as a co-transcription reagent for RNA capping in vitro.

Another aspect relates to an RNA molecule, comprising the above-mentioned compound as a cap structure or a cap structure fragment.

Another aspect relates to RNA molecule that can be used as a mRNA vaccine, or can be used as RNA medicament, or can be used in cell therapy of precision medicine.

Another aspect relates to a pharmaceutical composition, comprising the above-mentioned RNA molecule, and a pharmaceutically acceptable carrier.

Another aspect relates to a method of synthesizing the above-mentioned RNA molecule, comprising the steps of:
co-incubating the above-mentioned compound and a polynucleotide template and transcribing the template.

Another aspect relates to a transcription reaction system for RNA capping, comprising a polynucleotide template, the above-mentioned compound, NTPs, and RNA polymerases.

Compared to the conventional art, the present disclosure has the following advantages:

Compounds of the present disclosure for RNA capping can be used as a primer for initiating mRNA capping and present good capping efficiency, and the capped mRNA exhibits a high transcription level and increased expression. The cost will significantly decrease when using compounds as provided herein to capping RNA, thus indicating a broad potential for their application.

BRIEF DESCRIPTION

Some of the examples will be described in detail, with reference to the following FIGURE, wherein like designations denote like members, wherein:

FIG. 1 depicts luminescence units of luciferase expressed by capped mRNA treated with decapping enzyme in Examples.

DETAILED DESCRIPTION

In order to gain a better understanding of the present disclosure, the present disclosure is described more fully below with reference to the relevant FIGURES. Embodiments of the present disclosure are provided in the FIGURES. However, the present disclosure can be implemented in many different forms and is not limited to the embodiments described herein. Rather, these embodiments are provided for the purpose of providing a more thorough and comprehensive understanding of the content disclosed in the present disclosure.

Unless otherwise defined, all technical and scientific terms used herein have the same meaning as commonly understood by one skilled in the conventional art belonging to the technical field of the present disclosure. The terms used herein in the specification of the present disclosure are for the purpose of describing specific embodiments only and are not intended to limit the present disclosure.

Terms:

Pyrimidine base includes but not limited to uracil, thymine, cytosine, 5-methylcystein, 5-fluorouracil, 5-fluorocytosine, et cetera.

Purine derivative includes but not limited to adenine, guanine, 6-N-methyladenine, 6-N,N-dimethyladenine, 2-N-methylguanine, 2-N,N,-dimethylguanine, et cetera.

The term " . . . , in each instance, is a single bond or a double bond" means that such bond structure is a chemical bond, and specifically a single bond, or a double bond. For example, "—$X_4$—, in each instance, is a single bond or a double bond" means that when optional —$X_4$— is a single bond or a double bond, the parent moiety of formula I is a five-membered ring, the groups flanking $X_4$ are directly connected with each other.

The term "form a ring by a chemical bond" refers to "connect two groups together to form a ring structure by carbon-carbon bond, carbon-oxygen bond, carbon-nitrogen bond, carbon-sulfur bond, et cetera", with the corresponding group reduced by 1 to 2 hydrogen atoms if necessary.

"Stereoisomers" refer to compounds that have the same formula but differ in the orientation of their atoms or groups in space. The stereoisomers include enantiomers, diastereomers, conformational isomers (rotational isomers), geometrical isomers (cis/trans isomers), atropisomers, etc.

Any asymmetric atoms (e.g., carbon, etc.) of a compound disclosed herein can exist in racemic or enantiomerically enriched form, such as (R)-configuration, (S)-configuration, or (R, S)-configuration. In some embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)-configuration or (S)-configuration.

In general, the term "substituted" means that one or more hydrogen atoms in a given structure are replaced by a specified substituent. Unless otherwise stated, one substituted group can have a substituent at each substitutable position of the group. When more than one position in the given structural formula can be substituted by one or more substituents selected from a specific group, then the substituents can be substituted at each position with the same or different substitutions.

The term "each of . . . is independently selected from . . . " should be understood in a broad sense. It may mean that specific options expressed with the same symbol in different groups do not affect each other, and it also may mean that specific options expressed with the same symbol in the same group do not affect each other.

In each part of the description of the present disclosure, the substituents of the compounds disclosed in the present disclosure are disclosed according to the type or scope of the group. In particular, the present disclosure includes each independent sub-combination of each member of the type and scope of these groups. For example, the term "$C_{1-6}$ alkyl" specifically refers to independently disclosed methyl, ethyl, $C_3$ alkyl, $C_4$ alkyl, $C_5$ alkyl, and $C_6$ alkyl.

In each part of the description of the present disclosure, the term linking substituent is described. When the structure clearly needs a linking group, the Markush variables listed for the group should be understood as the linking group. For example, if the structure requires a linking group and the Markush group definition for the variable lists "alkyl" or "aryl", it should be understood that the "alkyl" or "aryl" respectively represents a linked alkylene group or arylene group.

The term "alkyl" or "alkyl group" used herein means a saturated linear or branched monovalent hydrocarbon group, wherein the alkyl group may be optionally substituted with one or more substituents described herein. The alkyl group may be optionally substituted with one or more substituents described herein.

Embodiments of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, etc.

The term "alkenyl" means a linear or branched monovalent hydrocarbyl group containing 2 to 30 carbon atoms, wherein there is at least one unsaturation point, that is, a carbon-carbon $sp^2$ double bond, which includes "cis" and "trans" configurations, or "E" and "Z" configurations. Embodiments of alkenyl group include, but are not limited to, ethenyl (—CH=CH$_2$), propenyl (—CH$_2$CH=CH$_2$), etc. The alkenyl group may be optionally substituted with one or more substituents described herein.

The term "alkynyl" means at least one unsaturation point, that is, a carbon-carbon sp triple bond. Embodiments of alkynyl group include, but are not limited to, ethynyl (—C≡CH), propargyl (—CH$_2$C≡CH), 1-propynyl (—C≡C—CH$_3$), etc. The alkynyl group may be optionally substituted with one or more substituents described herein.

The term "cycloalkyl" used herein, unless otherwise specified, refers to a monovalent saturated or partially unsaturated (but not aromatic) monocyclic or polycyclic hydrocarbon. In some embodiments, the cycloalkyl group may be a bridged or unbridged, spiro cyclic or non-spiro cyclic, and/or fused or non-fused bicyclic. In some embodiments, the cycloalkyl group includes 3 to 10 carbon atoms, i.e. $C_3$ to $C_{10}$ cycloalkyl.

In some embodiments, the cycloalkyl group has 3 to 15 ($C_{3-15}$), 3 to 10 ($C_{3-10}$), or 3 to 7 ($C_{3-7}$) carbon atoms. In some embodiments, the cycloalkyl group is monocyclic or bicyclic. In some embodiments, the cycloalkyl group is monocyclic. In some embodiments, the cycloalkyl group is bicyclic. In some embodiments, the cycloalkyl group is tricyclic. In some embodiments, the cycloalkyl group is fully saturated. In some embodiments, the cycloalkyl group is partially saturated. In some embodiments, the cycloalkyl group is cyclopropyl, cyclobutyl, cyclopentyl, cyclohexyl, cycloheptyl, bicyclo[2.1.1]hexyl, bicyclo[2.2.1]heptyl, decahydronaphthyl, or adamantyl. When a cycloalkyl group is substituted, it can be on any ring, that is, on any aromatic or non-aromatic ring contained by the cycloalkyl group, and it is independently substituted with one or more substituents described herein.

The term "haloalkyl" refers to alkyl with at least one of H substituted by a halogen, wherein the halogen is at least one or more selected from a group consisted of F, Cl, Br, or I.

The term "alkylamino" refers to amino with at least one of H substituted by alkyl.

The terms "heterocyclyl" and "heterocycle" are used interchangeably herein, and unless otherwise specified, they refer to a monovalent monocyclic non-aromatic ring system and/or polycyclic ring system containing at least one non-aromatic ring; wherein the non-aromatic monocyclic atoms comprise one or more heteroatoms (in some embodiments, there being 1, 2, 3, or 4 heteroatoms) independently selected from O, S(O)$_{0-2}$ and N, and the remaining ring atoms are all carbon atoms; and wherein the ring atoms in the polycyclic ring system comprise one or more heteroatoms (in some embodiments, there being 1, 2, 3, or 4 heteroatoms) independently selected from O, S(O)$_{0-2}$ and N, and the remaining ring atoms are all carbon atoms. In some embodiments, the heterocyclyl contains 1 or 2 heteroatoms, which are nitrogen atoms. In some embodiments, the heterocyclyl is polycyclic and contains one heteroatom in a non-aromatic ring, or contains one heteroatom in an aromatic ring, or contains two heteroatoms in an aromatic ring, or contains two heteroatoms, one an aromatic ring and the other in a non-aromatic ring. In some embodiments, the heterocyclyl group has 3 to 20, 3 to 15, 3 to 10, 3 to 8, 4 to 7, or 5 to 6 ring atoms. In some embodiments, the heterocyclyl group is a monocyclic, bicyclic, tricyclic, or tetracyclic ring system. In some embodiments, the heterocyclyl group may be a bridged or unbridged, spiro cyclic or non-spiro cyclic, and/or fused or non-fused bicyclic. One or more nitrogen atoms and sulfur atoms can be optionally oxidized, and one or more nitrogen atoms can be optionally quaternized, and one or more carbon atoms can be optionally substituted with

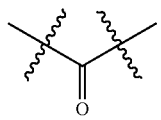

Some rings may be partially or fully saturated, or aromatic, provided that the heterocycle is not fully aromatic. The monocyclic heterocycle and polycyclic heterocycle may be connected to the main structure at any heteroatoms or carbon atoms that result in a steady compound. The polycyclic heterocyclyl can be connected to the main structure through any ring, including any aromatic or non-aromatic ring, regardless of whether the ring contains a heteroatom or not. In some embodiments, the heterocyclyl is a "heterocycloalkyl group", which is 1) a saturated or partially unsaturated (but not aromatic) monovalent monocyclic group containing at least one heterocycloatom as described herein, or 2) saturated or partially unsaturated (but not aromatic) monovalent bicyclyl or tricyclic group, wherein at least one ring contains at least one heteroatom as described herein. When the heterocyclyl and heterocycloalkyl group are substituted, they can be substituted on any ring, that is, on any aromatic or non-aromatic ring contained by the heterocyclyl and heterocycloalkyl group. In some embodiments, such heterocyclyl group includes, but is not limited to, epoxyethanyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, benzodioxanyl, benzodioxolyl, benzofuranone, benzopyranone, benzopyranyl, dihydrobenzofuranyl, benzotetrahydrothienyl, benzothiopyranyl, benzoxazinyl, β-carbolinyl, benzopyranyl, chromonyl, cinnolyl, coumaryl, decahydroquinolinyl, decahydroisoquinolinyl, dihydrobenzisothiazinyl, dihydrobenzisoxazinyl, dihydrofuranyl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithiopyranyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isobenzodihydropyranyl, isocoumarinyl, isodihydroindolyl(isoindolinyl), 1-oxo-isodihydroindolyl, 1,3-dioxo-isodihydroindolyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxohexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidinone, 2-oxopyrrolidinyl, 2,5-dioxopyrrolidinyl, quinuclidinyl, tetrahydroisoquinolinyl, 3,5-dioxo-thiomorpholinyl, thiazolidinyl, 2,4-dioxo-thiazolidinyl, tetrahydroquinolinyl, phenothiazinyl, phenoxazinyl, xanthene and 1,3,5-trithiocyclohexyl. Embodiments of the —CH$_2$— group in the heterocyclyl substituted with —C(=O)— include, but are not limited to, 2-oxopyrrolidinyl, oxo-1,3-thiazolidinyl, 2-piperidone, 3,5-dioxopiperidinyl and pyrimidinedione. Embodiments of sulfur atom oxidized in the heterocyclyl include, but are not limited to, sulfolanyl and a 1,1-dioxothiomorpholinyl. The heterocyclyl may be optionally substituted with one or more substituents described herein.

In one embodiment, the heterocyclyl is a heterocyclyl composed of 3 to 8 atoms and refers to a saturated or partially unsaturated monocyclic ring containing 3 to 8 ring atoms, wherein at least one ring atom is selected from nitrogen, sulfur and oxygen atoms. Unless otherwise specified, the heterocyclyl consisting of 3 to 8 atoms may be a carbon group or a nitrogen group, and the —$CH_2$— group may be optionally substituted with —C(=O)—. The sulfur atom of the ring can optionally be oxidized to S-oxide. The nitrogen atom of the ring can optionally be oxidized to an N-oxide. Embodiments of heterocyclyl consisting of 3 to 8 atoms include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl. Embodiments of —$CH_2$— group in the heterocyclyl substituted with —C(=O)— include, but are not limited to, 2-oxopyrrolidinyl, oxo-1,3-thiazolidinyl, 2-piperidinonyl, 3,5-dioxopiperidinyl and pyrimidinedionyl. Embodiments of sulfur atom in the heterocyclyl oxidized include, but are not limited to, sulfolanyl and 1,1-dioxothiomorpholinyl. The heterocyclyl consisting of 3 to 8 atoms can be optionally substituted with one or more substituents described herein.

In one embodiment, the heterocyclyl is a heterocyclyl consisting of 3 to 6 atoms and refers to a saturated or partially unsaturated monocyclic ring containing 3 to 6 ring atoms, wherein at least one ring atom is selected from nitrogen, sulfur and oxygen atoms. Unless otherwise specified, the heterocyclyl consisting of 3 to 6 atoms may be a carbon group or a nitrogen group, and the —$CH_2$— group may be optionally substituted with —C(=O)—. The sulfur atom of the ring can optionally be oxidized to S-oxide. The nitrogen atom of the ring can optionally be oxidized to an N-oxide. The heterocyclyl consisting of 3 to 6 atoms can be optionally substituted with one or more substituents described herein.

In another embodiment, the heterocyclyl is a heterocyclyl consisting of 5 to 6 atoms and refers to a saturated or partially unsaturated monocyclic ring containing 5 to 6 ring atoms, wherein at least one ring atom is selected from nitrogen, sulfur and oxygen atoms. Unless otherwise specified, the heterocyclyl consisting of 5 to 6 atoms may be a carbon group or a nitrogen group, and the —$CH_2$— group may be optionally substituted with —C(=O)—. The sulfur atom of the ring can optionally be oxidized to S-oxide. The nitrogen atom of the ring can optionally be oxidized to an N-oxide. Embodiments of heterocyclyl consisting of 5 to 6 atoms include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxocyclopentyl, dithiocyclopentyl, 2-oxopyrrolidinyl, oxo-1,3-thiazolidinyl, sulfolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, 2-piperidinonyl, 3,5-dioxopiperidinyl and pyrimidinedionyl, 1,1-dioxylthiomorpholinyl. The heterocyclyl consisting of 5 to 6 atoms may be optionally substituted with one or more substituents described herein.

The term "aryl" used herein, unless otherwise specified, refers to a monovalent $C_6$-$C_{14}$ carbocyclyl system containing at least one aromatic ring, wherein the aromatic ring system is monocyclic, bicyclic, or tricyclic. The aryl group can be connected to the main structure through any of its rings, that is, any aromatic or non-aromatic ring. In some embodiments, the aryl group is phenyl, naphthyl, bicyclo [4.2.0]octyl-1,3,5-trienyl, indanyl, fluorenyl, or tetrahydronaphthyl. When the aryl group is substituted, it can be substituted on any ring, that is, on any aromatic or non-aromatic ring contained by the aryl group. In some or any embodiments, aryl is phenyl, naphthyl, tetrahydronaphthyl, fluorenyl, or indanyl. The aryl group is independently optionally substituted with one or more substituents described herein.

The term "heteroaryl" as used herein, unless otherwise specified, refers to a monovalent monocyclic or polycyclic aromatic group, wherein ring atoms comprise at least one heteroatom (in some embodiments, there being 1, 2, 3, or 4 heteroatoms) independently selected from O, $S(O)_{0-2}$ and N in the ring. The heteroaryl group is connected to the rest of the molecule through any atoms in the ring system in consideration of its valence rules. In some embodiments, each ring of a heteroaryl group may contains 1 or 2 O atoms, 1 or 2 S atoms, and/or 1 to 4 N atoms, or a combination thereof, provided that the total number of heteroatoms in each ring is 4 or less, and each ring contains at least 1 carbon atom. In some embodiments, the heteroaryl group has 5 to 20, 5 to 15, or 5 to 10 ring atoms. When the heteroaryl group is substituted, it can be substituted on any ring. In certain embodiments, monocyclic heteroaryl groups include, but are not limited to, furyl, imidazolyl, isothiazolyl, isoxazolyl, oxadiazolyl, oxazolyl, pyrazinyl, pyrazolyl, pyridazinyl, pyridinyl, pyrimidinyl, pyrrolyl, thiadiazolyl, thiazolyl, thienyl, tetrazolyl, triazinyl and triazolyl. In certain embodiments, bicyclic heteroaryl groups include, but are not limited to, benzofuranyl, benzimidazolyl, benzisoxazolyl, benzopyranyl, benzothiadiazolyl, benzothiazolyl, benzothienyl, benzotriazolyl, benzoxazolyl, furopyridyl, imidazopyridyl, imidazothiazolyl, indazinyl, indolyl, indazolyl, isobenzofuryl, isobenzothienyl, isoindolyl, isoquinolinyl, isothiazolyl, naphthyridinyl, oxazolopyridyl, phthalazinyl, pteridinyl, purinyl, pyridopyridyl, pyrrolepyridyl, quinolinyl, quinoxalinyl, quinazolinyl, thiadiazolopyrimidinyl and thienopyridinyl. In certain embodiments, tricyclic heteroaryl groups include, but are not limited to, acridinyl, benzindolyl, carbazolyl, dibenzofuranyl, perimidinyl, phenanthrolinyl, phenanthridinyl and phenazinyl. In some or any embodiments, the heteroaryl group is phenylene, naphthylene, pyridylidene, pyrimidylidene, pyrazinylidene, pyridazinylidene, thiazolylidene, benzothiazolyl, benzo[d]isothiazolyl, imidazo[1,2-α]pyridyl, quinolyl, 1H-indolyl, pyrrolo [1,2-b]pyridazinyl, benzofuranyl, benzo[b]thienyl, 1H-indolyl, benzo[d]isoxazolyl, quinazolinyl, 1H-pyrrolo[3, 2-c]pyridyl, pyrazol[1,5-α]pyrimidyl, imidazo[1,2-b] pyridazinyl, or pyrazol[1,5-α]pyridyl; each of which is optionally substituted with 1, 2, 3, or 4 groups defined as described herein.

The "solvate" of the present disclosure refers to the association complex formed by one or more solvent molecules and the compounds of the present disclosure. The solvents that form solvates include, but are not limited to, water, isopropanol, ethanol, methanol, dimethyl sulfoxide, ethyl acetate, acetic acid, and aminoethanol. The term "hydrate" refers to an association complex formed by the solvent molecule, which is water.

When the solvent is water, the term "hydrate" can be used. In some embodiments, a compound of the present disclosure can be connected to one water molecule, such as monohydrate; in further embodiments, a compound of the present disclosure can be connected to more than one water molecules, such as dihydrate, and in yet another embodiment, a compound of the present disclosure can be connected to less than one water molecule, such as hemihydrate. It should be noted that the hydrates of the present disclosure retain the biologically effectiveness of the compound in its non-hydrated form.

Unless otherwise specified, the compounds used in the embodiments are available in the market; unless otherwise specified, the methods used in the following embodiments are common methods.

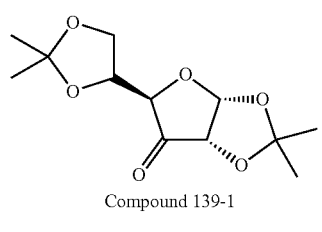

Compound 139-1

PPh₃CH₃Br, nBuLi
────────────────→
THF, -78° C.-r.t.

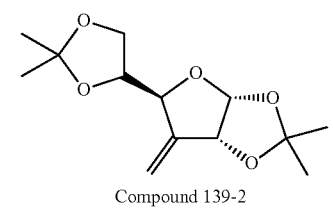

Compound 139-2

1. BH₃-Me₂S, THF, 0° C.
2. H₂O₂, NaOH, H₂O, r.t.
─────────────────→

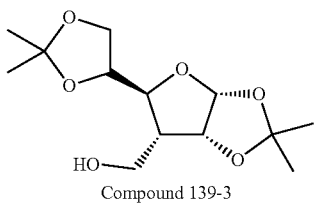

Compound 139-3

NaH, CH₃CH₂I, THF
──────────────→
0° C.-r.t.

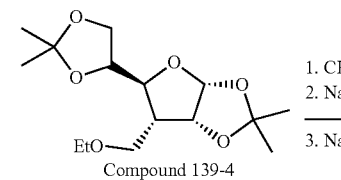

Compound 139-4

1. CH₃COOH/H₂O, 50° C.
2. NaIO₄, MeOH/H₂O, 0° C.-r.t.
3. NaBH₄, MeOH/H₂O, 0° C.-r.t.
─────────────────→

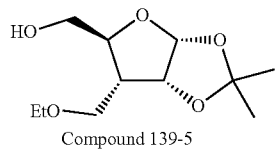

Compound 139-5

BzCl, TEA
─────────→
DCM, 0° C.-r.t.

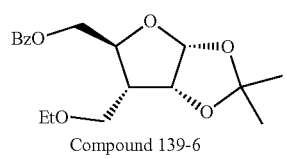

Compound 139-6

H₂SO₄, Ac₂O
─────────→
AcOH, EA, 40° C.

-continued

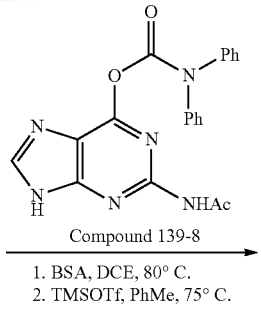

Compound 139-7

Compound 139-8
─────────────→
1. BSA, DCE, 80° C.
2. TMSOTf, PhMe, 75° C.

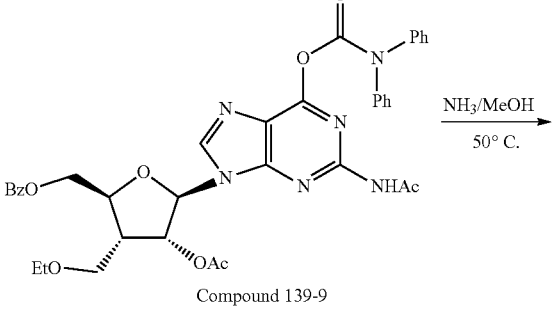

Compound 139-9

NH₃/MeOH
─────────→
50° C.

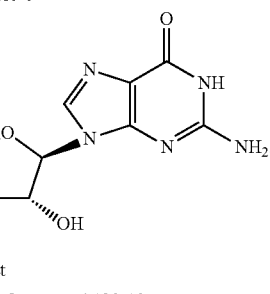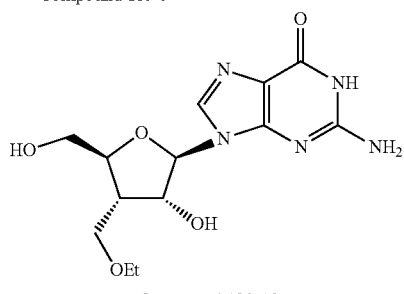

Compound 139-10

Example 1 Synthesis of Compound 139

According to the above synthetic route, methyltriphenylphosphonium bromide (163.2 g, 454.6 mmol) was dissolved in anhydrous tetrahydrofuran (1.5 L) under the nitrogen atmosphere protection, and the mixture was cooled to −78° C. Then, n-butyllithium (206.1 mL, 515.2 mmol, 2.5 M) was added dropwise. After addition, the mixture was stirred for 2 hours at 0° C., and then it was further cooled to −78° C. Compound 139-1 (known compound, 78.8 g, 303.1 mmol, dissolved in 100 mL of anhydrous tetrahydrofuran) was dripped into the reaction liquid. After addition, the temperature was gradually increased to room temperature, and meanwhile the mixture was stirred overnight. The temperature was then cooled to 0° C., and saturated ammonium chloride solution (500 mL) was gradually added and then the reaction was quenched. Subsequently, ethyl acetate (300 mL) was added, and the organic phases were successively washed with waster (200 mL*2) and saturated saline, dried over anhydrous sodium sulfate, concentrated under reduced pressure, and purified by column chromatography on silica gel (petroleum ether/ethyl acetate=20:1), to obtain 82.0 g of Compound 139-2.

The Compound 139-2 (30.0 g, 117 mmol) was dissolved in anhydrous tetrahydrofuran (300 mL) under the nitrogen atmosphere protection at room temperature. Then, the temperature was cooled to 0° C., and borane dimethyl sulfide (23.4 mL, 234 mmol, 10M) was added. After addition, the mixture was stirred for 20 hours at 0° C. Subsequently, sodium hydroxide solution (28 g, 702 mmol, in 305 mL of water) was added, followed by hydrogen peroxide (80 mL, 30% water solution). The mixture was stirred for 2 hours at room temperature. Subsequently, ethyl acetate (200 mL) was added, and the organic phases were successively washed with water (100 mL*2) and saturated saline, dried over anhydrous sodium sulfate, and concentrated under reduced pressure to obtain 20.5 g of Compound 139-3, which was used for the next reaction without further purification.

The Compound 139-3 (17.0 g, 62 mmol) was dissolved in 100 mL of anhydrous THF at room temperature, and the iodoethane (14.5 g, 93 mmol) was added. After the temperature was cooled to −10° C., NaH (4.0 g, 99.2 mmol) was gradually added. After addition, the temperature was gradually increased to room temperature, and the mixture was stirred for 5 hours at room temperature. Then, the temperature was cooled to 0° C., 1 mL of methanol and 150 mL of saturated ammonium chloride solution were added. Subsequently, ethyl acetate (150 mL) was added, and the organic phases were successively washed with water (100 mL*2) and saturated saline, dried over anhydrous sodium sulfate, and concentrated under reduced pressure to obtain 18.0 g of Compound 139-4, which was used for the next reaction without further purification.

The Compound 139-4 (18.0 g, 59.6 mmol) was dissolved in 140 mL of acetic acid at room temperature, followed by 60 mL of water. The mixture was stirred for 1.5 hours at 50° C. Subsequently, solvent was removed under reduced pressure, and 150 mL of methanol and 50 mL of water were added. Anhydrous sodium bicarbonate was used for adjusting pH to basic. Then, the reaction liquid was cooled to 0° C., and sodium periodate (12.84 g, 60 mmol) was stirred to react for 1 hour at room temperature. Subsequently, 50 mL of methanol was added to the mixture, and filtered. The filtrate was cooled to 0° C., and sodium borohydride (2.66 g, 70 mmol) was added. After addition, the mixture was stirred for 0.5 h at room temperature. The temperature was cooled to 0° C., and acetic acid was used for adjusting pH to neutral. Most of methanol was removed under reduced pressure, and 200 mL of water was then added. The reaction liquid was extracted with dichloromethane (100 mL*3), dried over anhydrous sodium sulfate, and concentrated under reduced pressure to obtain 11.8 g of Compound 139-5, which was used for the next reaction without further purification.

Benzoyl chloride (4.30 g, 30 mmol) was gradually added to a solution of Compound 139-5 (11.80 g, 35 mmol) and triethylamine (5.30 g, 53 mmol) in dichloromethane (80 mL) under the nitrogen atmosphere protection in an ice bath. After addition, the mixture was stirred overnight at room temperature. Water (100 mL) was added to the reaction system, and the mixture was extracted with dichloromethane (100 mL*3). Subsequently, the organic phases were combined, concentrated under reduced pressure. The residue was purified by column chromatography on silica gel (petroleum ether/ethyl acetate=20:1), to obtain 14.0 g of Compound 139-6.

Concentrated sulfuric acid (0.45 g, 1.5 mmol) was added to a solution of Compound 139-6 (14.0 g, 41.6 mmol) and acetic acid (5.00 g, 83.2 mmol) in ethyl acetate (80 mL) at room temperature. After the temperature was increased to 40° C., acetic anhydride (6.36 g, 62.4 mmol), which was diluted with ethyl acetate (10 mL), was dropwise added into the reaction system. After addition, the mixture was stirred for 3 hours at a constant temperature. Then, the temperature was cooled to 0° C., and triethylamine (0.35 g, 3.52 mmol) was added and stirred for 5 min, followed by gradually addition of saturated sodium bicarbonate solution (50 mL). The aqueous phase was extracted with ethyl acetate (50 mL), and the organic phases were combined and successively washed with saturated bicarbonate solution (50 mL) and saturated sodium chloride solution (50 mL), dried over anhydrous sodium sulfate, and concentrated under reduced pressure to obtain 14.20 g of Compound 139-7.

N,O-bis(trimethylsilyl)acetamide (BSA, 15.23 g, 83.2 mmol) was added to a suspension of Compound 139-8 (known compound, 14.50 g, 37.4 mmol) in 1,2-dichloroethane (125 mL) under nitrogen atmosphere protection at room temperature, and the mixture was stirred for 2 hours after the temperature was increased to 80° C. The reaction liquid was concentrated under reduced pressure, and methylbenzene (70 mL) was added. The Compound 139-7 (14.20 g, 37.4 mmol) dissolved in methylbenzene (55 mL) was added to the reaction system, followed by addition of trimethylsilyl trifluoromethanesulfonate (TMSOTf, 8.30 g, 37.4 mmol). The temperature was heated to 70° C. and the mixture was stirred for 2 hours. Then, the temperature was cooled to room temperature, and water (100 mL) was added into the reaction system. The aqueous phase was extracted with ethyl acetate (200 mL), and the organic phases were combined, washed with water (100 mL), dried over anhydrous sodium sulfate, and concentrated under reduced pressure. The residue was purified by column chromatography on silica gel (dichloromethane/ethyl acetate=1:10), to obtain 15.0 g of Compound 139-9.

A solution of ammonia in methanol (100 mL) was added to Compound 139-9 (15.0 g, 21.1 mmol) at room temperature, followed by addition of 20 mL of water. The temperature was increased to 50° C., and the mixture was stirred overnight in a closed atmosphere. The reaction liquid was concentrated under reduced pressure, and the residue was heated to reflux with methanol (100 mL) and water (50 mL), stirred vigorously, and purified to obtain 3.60 g of Compound 139-10.

The characteristic data of Compound 139-10 was: MS (m/z): 325.14 [M+1]$^+$. $^1$H NMR (500 MHz, DMSO) δ 10.62 (s, 1H), 8.00 (s, 1H), 6.46 (s, 2H), 5.71 (d, J=2.1 Hz, 1H), 5.69 (d, J=5.4 Hz, 1H), 5.02 (t, J=5.3 Hz, 1H), 4.38 (td, J=5.4, 2.1 Hz, 1H), 3.98 (dt, J=8.4, 3.2 Hz, 1H), 3.75-3.70 (m, 1H), 3.63 (dd, J=9.4, 6.8 Hz, 1H), 3.55-3.50 (m, 1H), 3.48-3.40 (m, 3H), 2.56-2.52 (m, 1H), 1.11 (t, J=7.0 Hz, 3H).

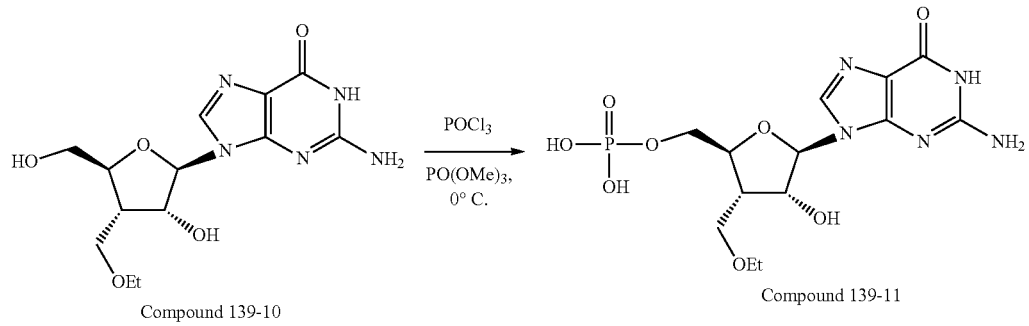
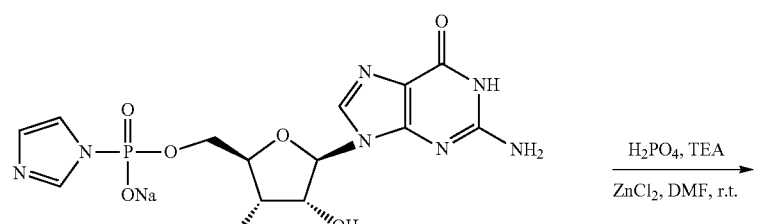
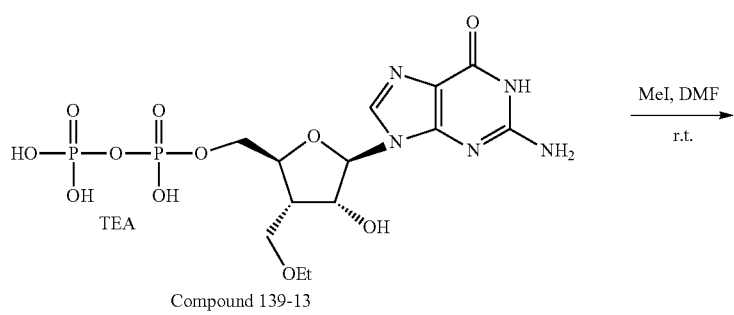
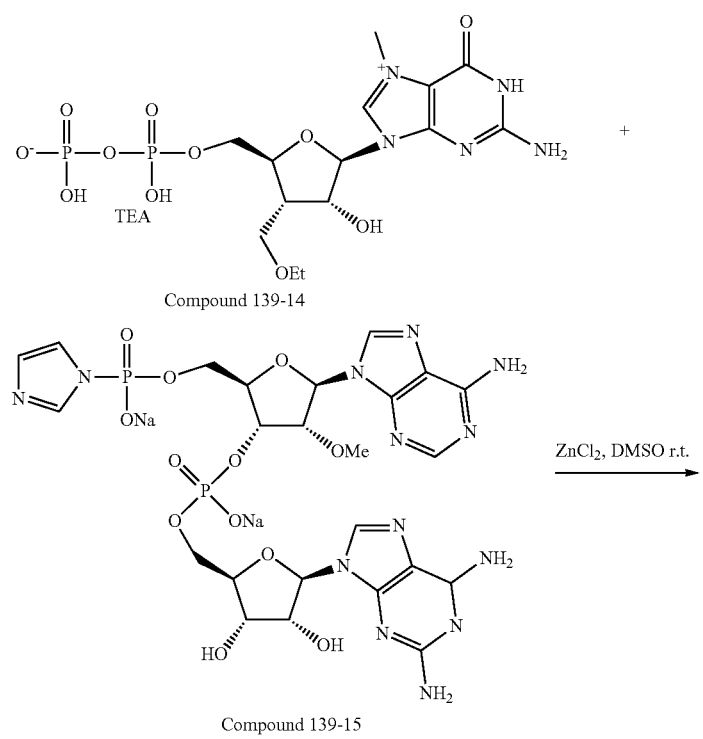

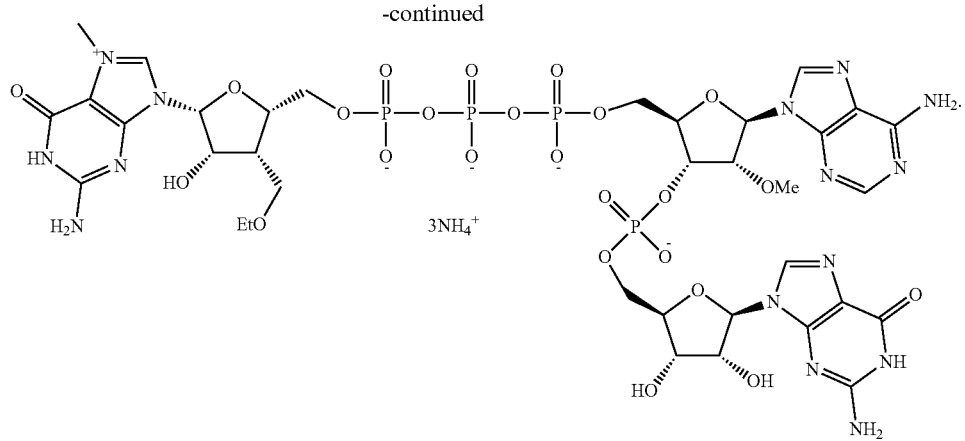

Compound 130

According to the above synthetic route, the Compound 139-10 (1 g, 3.08 mmol) and trimethyl phosphate (10 mL) were added to a reaction flask, and the temperature was cooled to 0° C. under the argon atmosphere protection, then phosphorus oxychloride (0.43 mL, 4.62 mmol) was dropwise added. The mixture was stirred for 4 hours at 0° C. After the reaction was completed, water (4 mL) was added at 0° C., and then the liquid was placed at room temperature and stirred for 0.5 hour. Subsequently, the liquid was washed with dichloromethane (12 mL). The upper aqueous layer was collected, and the organic layer was back-extracted once with water (2 mL). The aqueous layers were combined, concentrated to about 2 mL, then passed through C18 reverse column (gradient elution: acetonitrile: water), and the absorption peak of the desirable compound was collected. Then, the solution passed through ion exchange column (gradient elution:1M TEAB: water) and the peak of the desirable compound was collected. The collected liquid was concentrated under reduced pressure and freeze-dried to obtain 2.30 g of overweight Compound 139-11 (triethylamine salt).

The Compound 139-11 (2.3 g, calculated as 3.08 mmol), imidazole (1.9 g, 27.94 mmol). 2,2'-disulfide bipyridine (2.5 g, 11.36 mmol), N,N-dimethylformamide (20 mL), triethylamine (0.76 mL, 5.47 mmol) were added to a reaction flask. Under stirring, triphenyl phosphine (2.9 g, 11.07 mmol) was added. The mixture was stirred for 2 hours and under nitrogen atmosphere protection at room temperature. After the reaction was completed, the reaction system was poured into a mixture solution of sodium iodide (4.4 g, 29.33 mmol) and acetone (50 mL) under stirring, and the mixture was stirred for 10 min at room temperature. Subsequently, it was filtered, and the filter cake was washed with acetone and collected, and dried under reduced pressure at room temperature to obtain 1.2 g of Compound 139-12.

85% phosphoric acid (0.88 g, 7.63 mmol), triethylamine (1.06 mL, 7.63 mmol), N,N-dimethylformamide (12 mL) were added to a reaction flask and stirred for 5 min at room temperature, followed by addition of Compound 139-12 (1.2 g, 2.64 mmol), anhydrous zinc chloride (0.36 g, 2.64 mmol). The mixture was stirred overnight under the argon atmosphere protection at room temperature. After the reaction was completed, methyl tert-butyl ether (MTBE, 25 mL) was added to the reaction system, stirred, and washed ultrasonically. The supernatant was poured out, and methyl tert-butyl ether (25 mL) was further added to wash bottom pulp again. Subsequently, the supernatant was poured out again, and the pulp was dried under reduced pressure. Water (4 mL) was added to dissolve the pulp. After dissolution, the solution passed through ion exchange column, and a peak of the desirable product was collected. The collected liquid was concentrated under reduced pressure, and freeze-dried, to obtain 1.23 g of Compound 139-13 (triethylamine salt).

The Compound 139-13 (0.33 g, 0.68 mmol), N,N-dimethylformamide (3 mL) were added to a reaction flask, and iodomethane (0.42 mL, 6.74 mmol) was added under stirring. The mixture was stirred overnight at room temperature. After the reaction was completed, methyl tert-butyl ether (10 mL) was added to the reaction system, stirred and then stand. The supernatant was poured out, and the bottom pulp was dried, followed by addition of water (10 mL) to dissolve the pulp until it became a clean solution. Then, the solution passed through ion exchange column and a peak of the desirable product was collected. The collected liquid was concentrated under reduced pressure and freeze-dried, to obtain 107 mg of Compound 139-14 (trimethylamine salt).

The Compound 139-14 (107 mg, 0.21 mmol), Compound 139-15 (known compound, 162 mg, 0.21 mmol), and dimethyl sulfoxide (3 mL) were added to a reaction flask. Zinc chloride (145 mg, 2.1 mmol) was added under the argon atmosphere protection, and the mixture was stirred for 1 day at room temperature. After the reaction was completed, MTBE was added and stirred. The liquid was stood and then the supernatant was poured out. The precipitate was dissolved in water, passed through ion exchange column, eluted with a gradient elution of 1M aqueous ammonium bicarbonate. An absorption peak of the desirable product was collected and concentrated under reduced pressure. The residue was repeatably freeze-dried, to obtain 68 mg of Compound 139 (ammonium salt).

The characteristic data of the Compound 139 was: MS (m/z): 1186.25 [M−1]−. 1H NMR (400 MHz, $D_2O$) δ 9.11 (s, 1H), 8.47 (s, 1H), 8.20 (s, 1H), 7.99 (s, 1H), 6.08 (d, J=5.4 Hz, 1H), 5.85-5.82 (m, 2H), 4.99-4.95 (m, 1H), 4.68 (d, J=4.6 Hz, 1H), 4.55-4.45 (m, 4H), 4.37-4.23 (m, 7H), 4.13-4.10 (m, 1H), 4.03 (s, 3H), 3.74-3.70 (m, 1H), 3.62-3.53 (m, 3H), 3.48 (s, 3H), 2.65-2.58 (m, 1H), 1.16 (t, J=7.0 Hz, 3H); $^{31}P$ NMR (162 MHz, $D_2O$) δ-0.88 (s, 1H), −11.59 (m, 2P), −22.80 (m, 1P).

Example 2 Synthesis of Compound 3
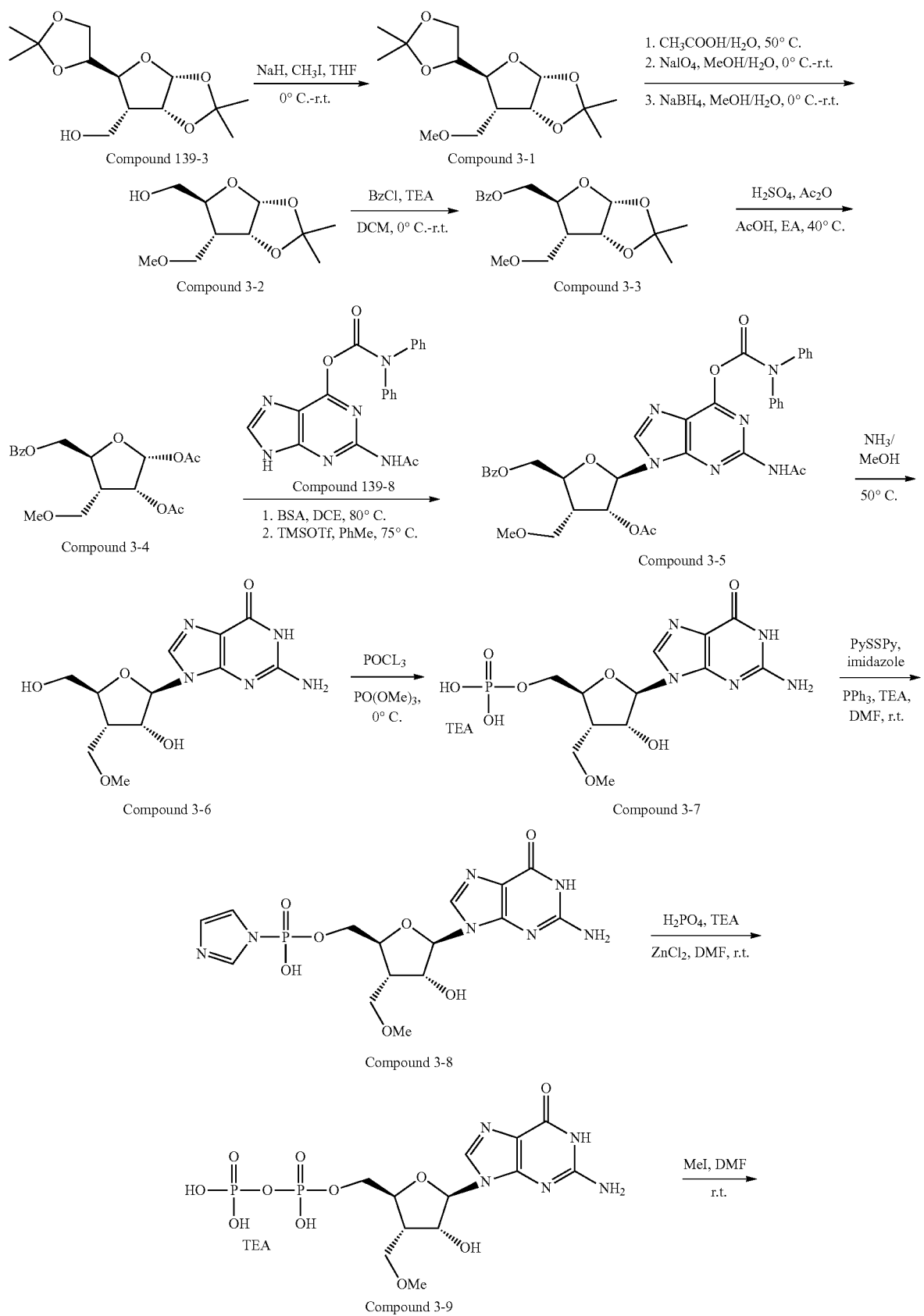

-continued

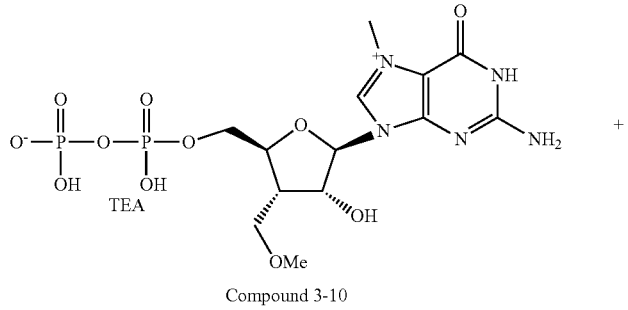

Compound 3-10

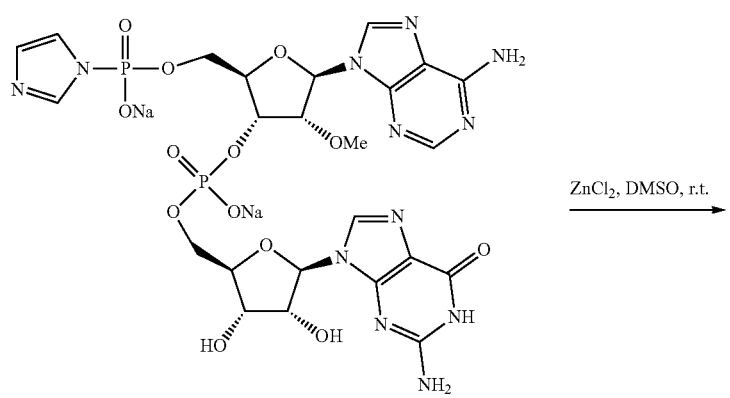

Compound 139-15

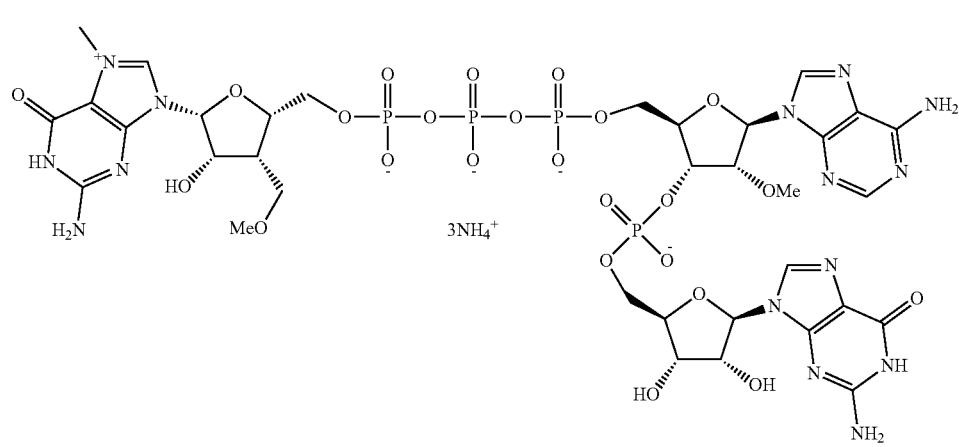

Compound 3

According to the above reaction route, Compound 3-6 was prepared from Compound 139-3 using the procedure for preparation of Compound 139-10, except substituting iodoethane with iodomethane.

The characteristic data of Compound 3-6 was: ¹H NMR (500 MHz, DMSO) δ 10.60 (s, 1H), 7.99 (s, 1H), 6.45 (br, 2H), 5.70 (s, 1H), 5.70-5.67 (d, J=6.0 Hz, 1H), 5.03-4.99 (t, J=5.6 Hz, 1H), 4.41-4.37 (m, 1H), 4.00-3.96 (m, 1H), 3.74-3.68 (m, 1H), 3.60-3.55 (m, 1H), 3.54-3.48 (m, 1H), 3.44-3.39 (m, 1H), 3.26 (s, 3H), 2.58-2.52 (m, 1H).

According to the above reaction route, Compounds 3 (ammonium salt) was prepared from Compound 3-6 using the procedure for preparation of Compound 139.

The characteristic data of the Compound 3 was: MS (m/z): 1172.26[M−1]⁻. ¹H NMR (500 MHz, D₂O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.43 (s, 3H), 3.32 (s, 3H), 2.61-2.52 (m, 1H); ³¹P NMR (202 MHz, D₂O) δ-0.93 (s, 1H), −11.65 (m, 2P), −22.90 (m, 1P).

Example 3 Synthesis of Compound 135
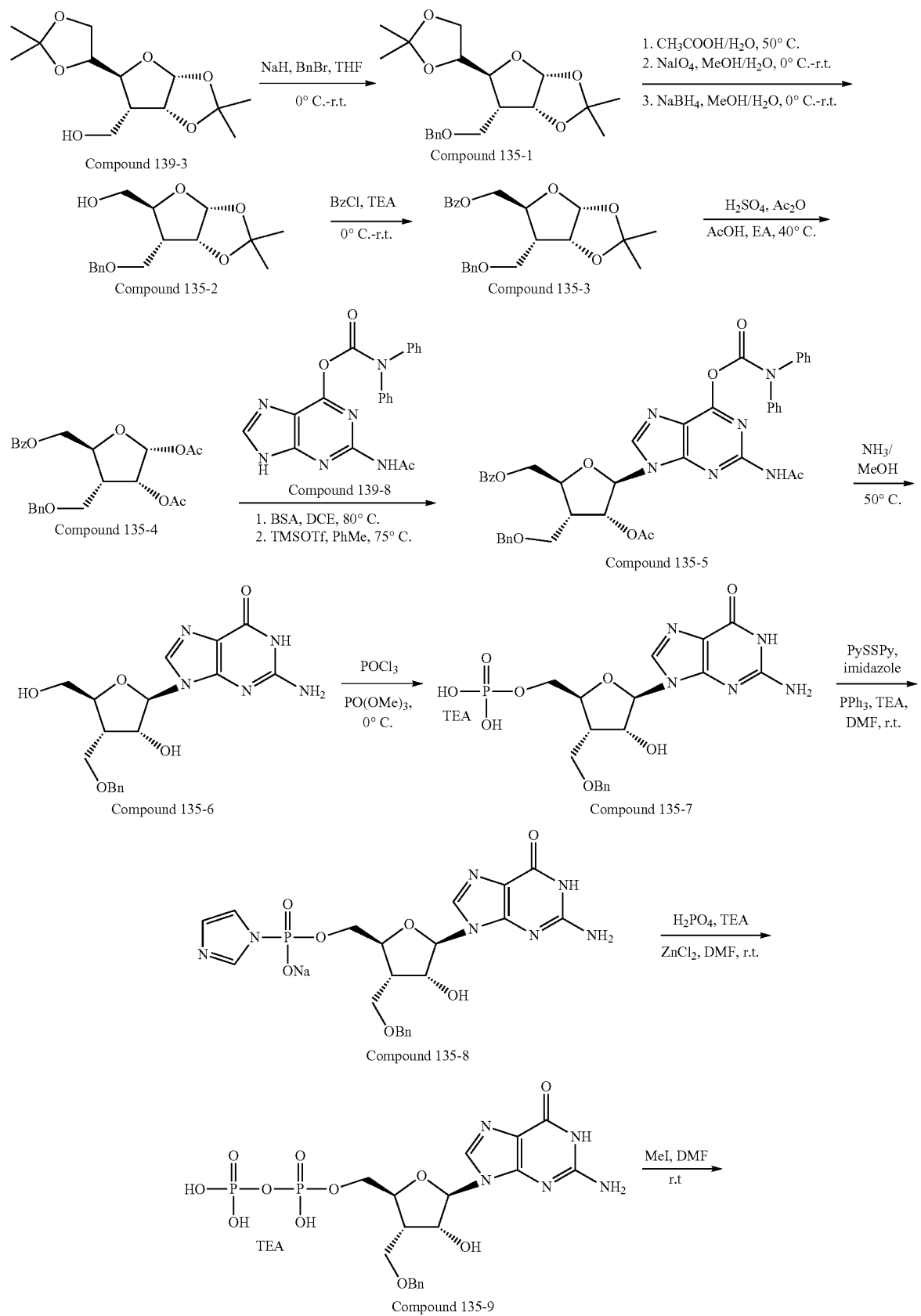

-continued

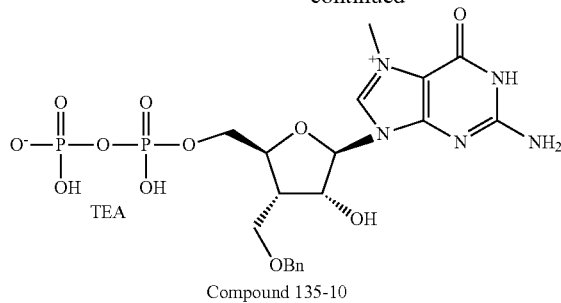

Compound 135-10

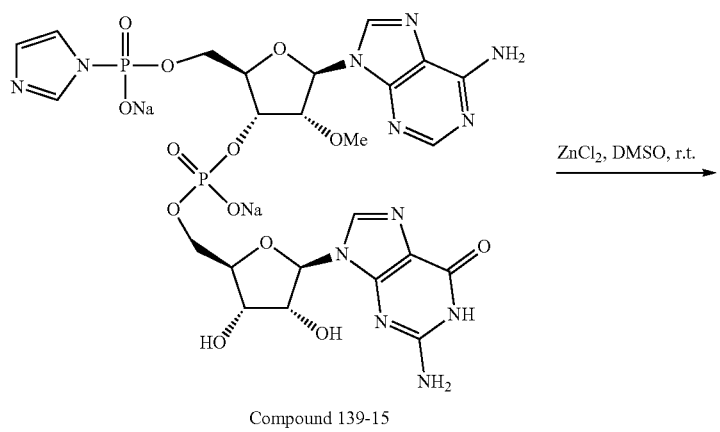

Compound 139-15

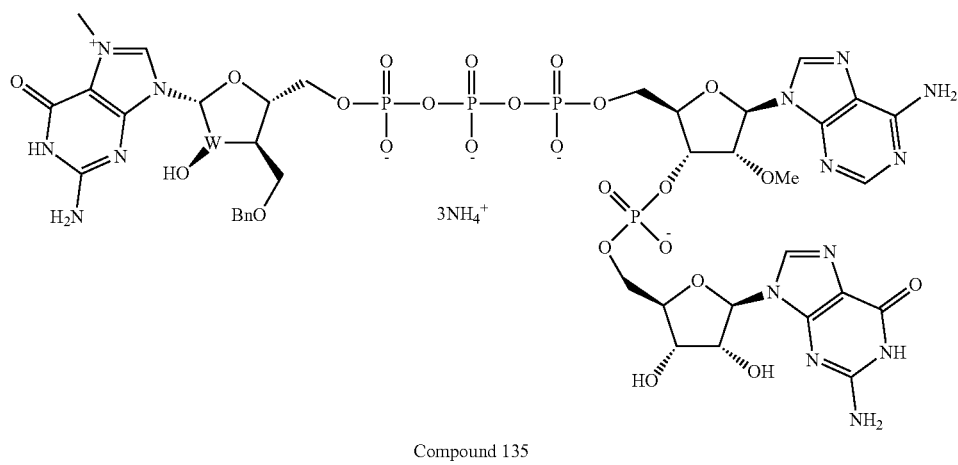

Compound 135

According to the above reaction route, Compounds 135-6 was synthesized from Compound 139-3 using the procedure for preparation of Compound 139-10, except substituting iodoethane with bromotoluene.

The characteristic data of Compound 135-6 was: $^1$H NMR (500 MHz, DMSO) δ 10.60 (s, 1H), 8.01 (s, 1H), 7.37-7.33 (m, 4H), 7.31-7.26 (m, 1H), 6.45 (s, 2H), 5.71 (d, J=5.6 Hz, 2H), 5.02 (t, J=5.4 Hz, 1H), 4.51 (q, J=12.2 Hz, 2H), 4.44-4.40 (m, 1H), 4.06-3.99 (m, 1H), 3.79-3.69 (m, 2H), 3.58-3.51 (m, 2H), 2.66-2.58 (m, 1H).

According to the above reaction route, Compounds 135 (ammonium salt) was synthesized from Compound 135-6 using the procedure for preparation of Compound 139

The characteristic data of the Compound 135 was: MS (m/z) 1248.36[M−1]⁻. $^1$H NMR (500 MHz, D$_2$O) δ 8.34 (s, 1H), 8.06 (s, 1H), 7.92 (s, 1H), 7.26-7.24 (m, 2H), 7.22-7.19 (m, 2H), 7.13 (t, J=7.1 Hz, 1H), 5.98 (d, J=5.7 Hz, 1H), 5.79 (d, J=5.8 Hz, 1H), 5.69 (s, 1H), 4.93-4.90 (m, 1H), 4.74 (d, J=5.5 Hz, 1H), 4.55-4.52 (m, 1H), 4.50 (s, 1H), 4.47 (t, J=4.0 Hz, 1H), 4.43-4.37 (m, 4H), 4.32 (s, 1H), 4.29-4.24 (m, 2H), 4.21-4.18 (m, 3H), 4.04-4.01 (m, 1H), 3.99 (s, 3H), 3.77-3.74 (m, 1H), 3.63-3.60 (m, 1H), 3.41 (s, 3H), 2.46-2.40 (m, 1H); $^{31}$P NMR (202 MHz, D$_2$O) δ-0.93 (s, 1H), −11.55 (d, J=17.4 Hz, 1P), −11.83 (d, J=19.0 Hz, 1P), −22.85 (t, J=17.6 Hz, 1P).

Example 4 Synthesis of Compound 141
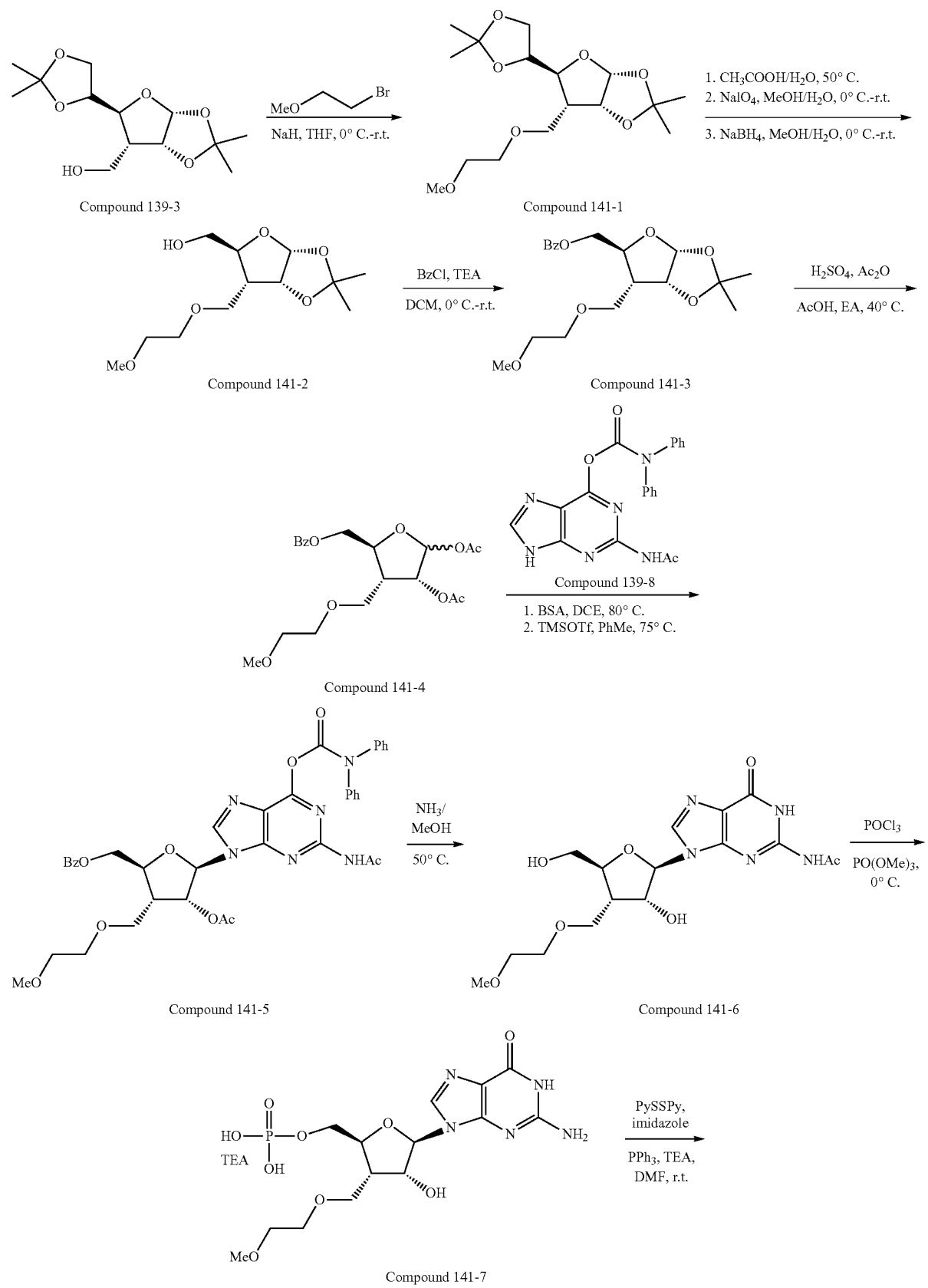

-continued
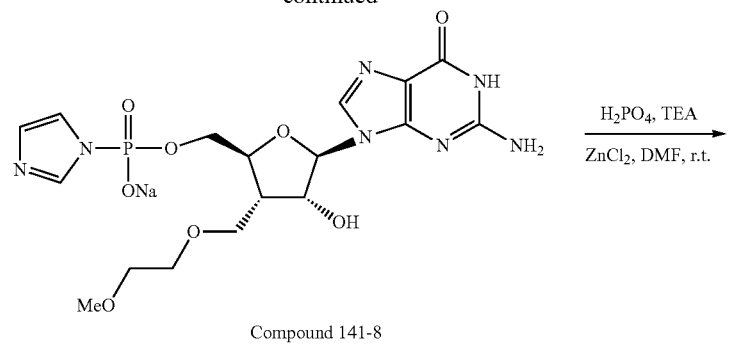
Compound 141-8
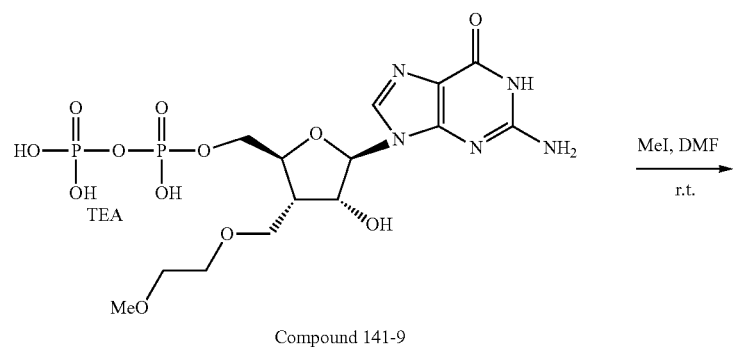
Compound 141-9
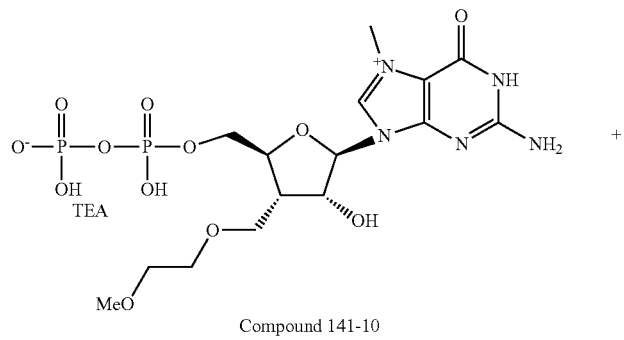
Compound 141-10
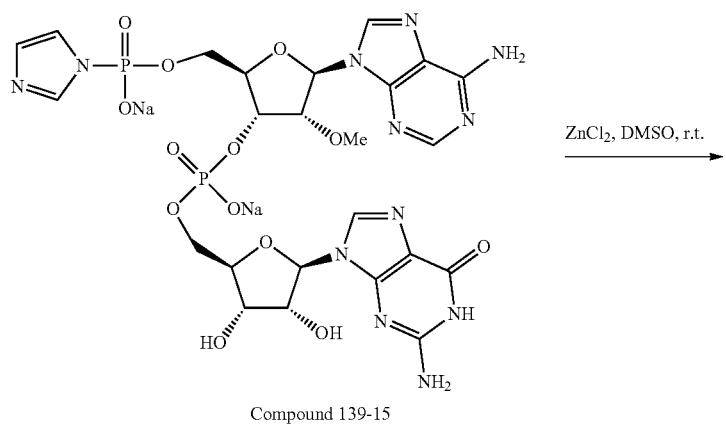
Compound 139-15

-continued

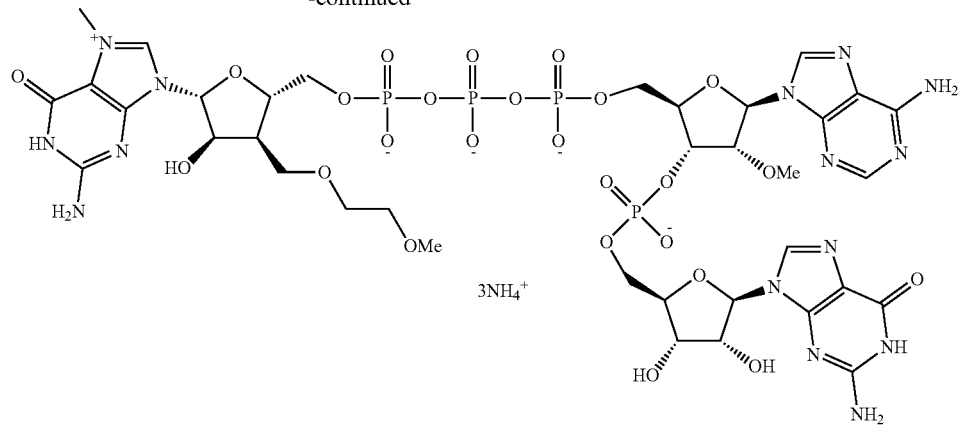

Compound 141

According to the above reaction route, Compounds 141-6 was prepared from Compound 139-3 using the procedure for preparation of Compound 139-10, except substituting iodoethane with 2-methoxy-1-bromoethane.

The characteristic data of Compound 141-6 was: $^1$H NMR (500 MHz, DMSO) δ: $^1$H NMR (500 MHz, DMSO) δ 10.62 (s, 1H), 8.00 (s, 1H), 6.46 (s, 2H), 5.71 (d, J=2.0 Hz, 1H), 5.68 (d, J=5.4 Hz, 1H), 5.01 (t, J=5.4 Hz, 1H), 4.38 (td, J=5.5, 2.1 Hz, 1H), 3.98 (dt, J=8.5, 3.2 Hz, 1H), 3.75-3.70 (m, 1H), 3.68 (dd, J=9.6, 6.8 Hz, 1H), 3.57-3.42 (m, 6H), 3.24 (s, 3H), 2.58-2.52 (m, 1H).

According to the above reaction route, Compounds 141 (ammonium salt) was prepared from Compound 141-6 using the procedure for preparation of Compound 139.

The characteristic data of the Compound 141 was: 1216.02[M−1]$^-$. $^1$H NMR (500 MHz, D$_2$O) δ 9.05 (s, 1H), 8.40 (s, 1H), 8.14 (s, 1H), 7.95 (s, 1H), 6.02 (d, J=5.7 Hz, 1H), 5.83-5.81 (m, 2H), 4.94-4.92 (m, 1H), 4.68 (d, J=4.9 Hz, 1H), 4.52-4.44 (m, 3H), 4.42 (t, J=4.9 Hz, 1H), 4.34 (s, 1H), 4.29-4.23 (m, 3H), 4.20-4.19 (m, 2H), 4.08-4.06 (m, 1H), 4.01 (s, 3H), 3.71-3.68 (m, 1H), 3.63-3.56 (m, 5H), 3.43 (s, 3H), 3.33 (s, 3H), 2.62-2.57 (m, 1H); $^{31}$P NMR (202 MHz, D$_2$O) δ-0.91 (s, 1H), −11.62 (m, 2P), −22.88 (m, 1P).

Example 5 Synthesis of Compound 143

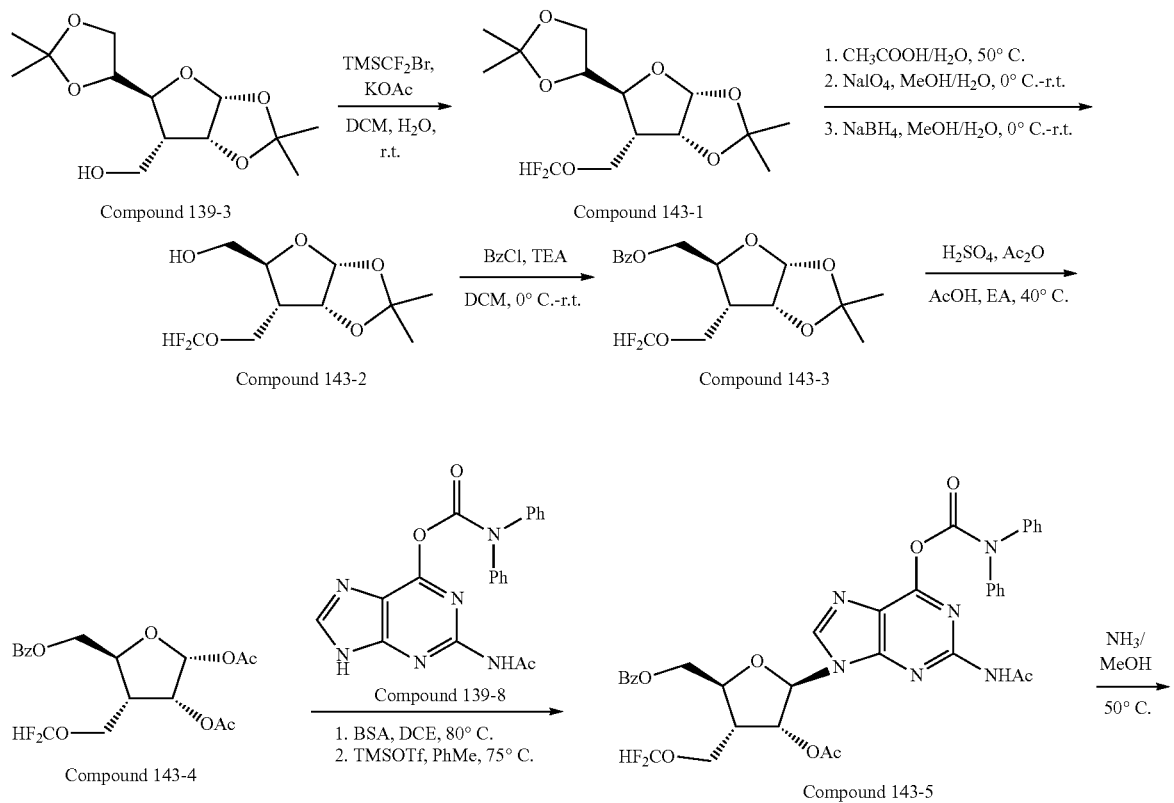

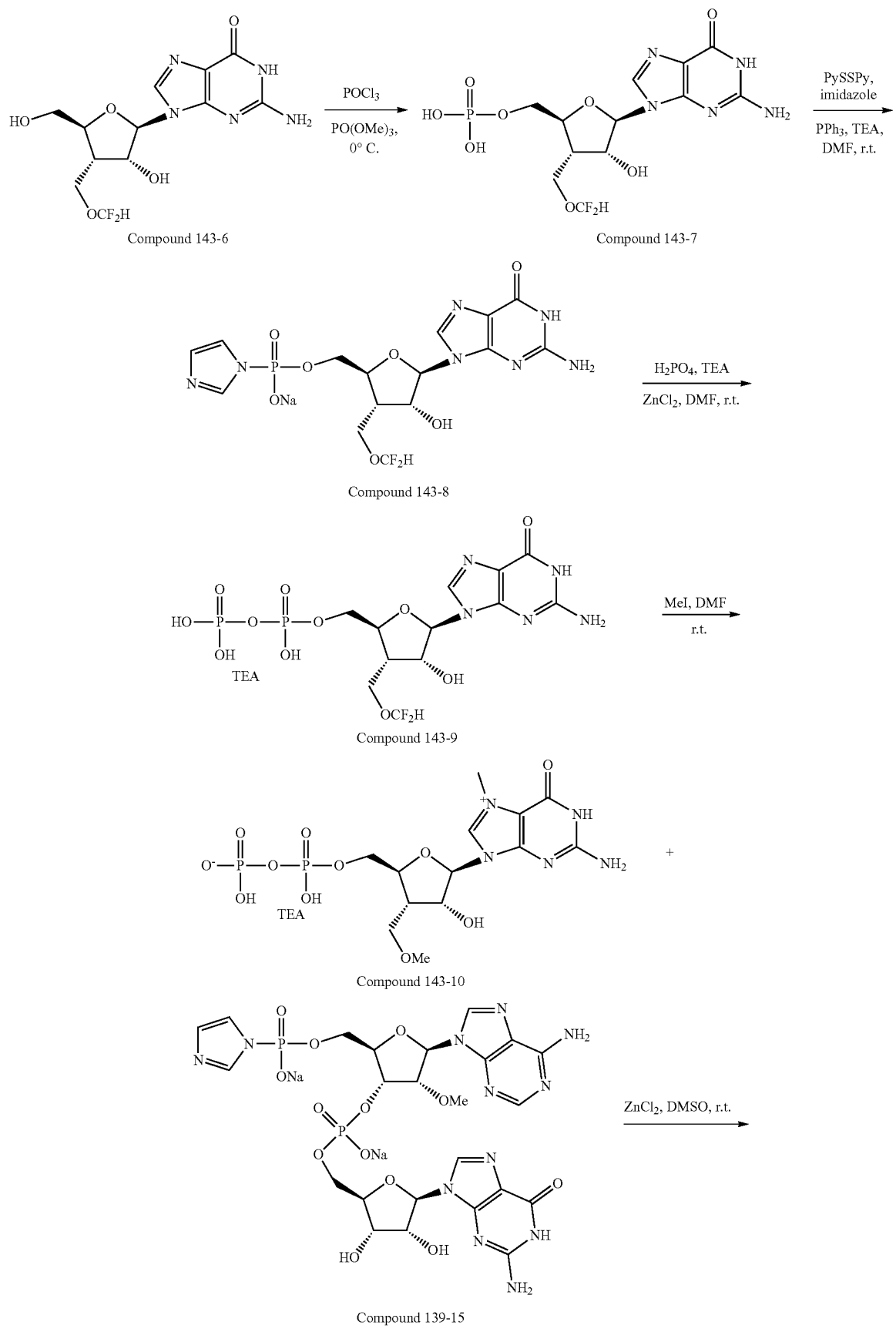
-continued
Compound 143-6 → Compound 143-7 (POCl₃, PO(OMe)₃, 0° C.)
Compound 143-7 → (PySSPy, imidazole, PPh₃, TEA, DMF, r.t.)
Compound 143-8 → (H₂PO₄, TEA, ZnCl₂, DMF, r.t.)
Compound 143-9 → (MeI, DMF, r.t.)
Compound 143-10 +
Compound 139-15 (ZnCl₂, DMSO, r.t.)

-continued

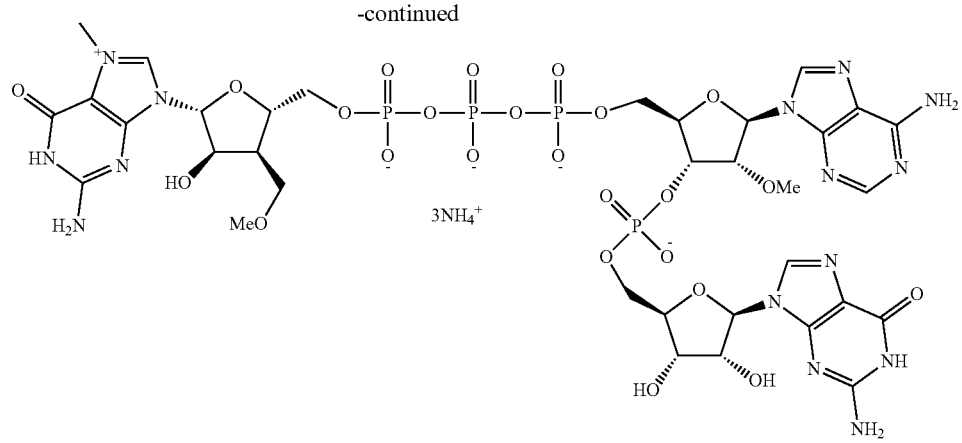

Compound 143

According to the above reaction route, Compound 139-3 (9.0 g, 33 mmol) was dissolved in DCM (80 mL) at room temperature, followed by successively addition of water (80 mL), potassium acetate (12.8 g, 132 mmol), and TMSCF$_2$Br (9.4 g, 46 mmol). After addition, the mixture was stirred for 3 days at room temperature. Dichloromethane (200 mL) was added. Subsequently, the organic phase was successively washed with water (200 mL*2), saturated saline, dried over anhydrous sodium sulfate, and concentrated under reduced pressure. The residue was purified by column chromatography on silica gel (petroleum ether/ethyl acetate=20/1), to obtain 4.4 g of Compound 143-1.

Compound 143-6 was synthesized using the procedure for preparation of Compound 139-10, except substituting Compound 139-4 with Compound 143-1.

The characteristic data of Compound 143-6 was: $^1$H NMR (500 MHz, DMSO) δ 10.62 (s, 1H), 7.99 (s, 1H), 6.69 (t, $J_{H-F}$=70.0 Hz, 1H), 6.46 (s, 2H), 5.92 (d, J=5.4 Hz, 1H), 5.73 (d, J=2.4 Hz, 1H), 5.08 (t, J=5.4 Hz, 1H), 4.46 (td, J=5.6, 2.5 Hz, 1H), 4.09 (dd, J=9.8, 7.0 Hz, 1H), 4.04-3.99 (m, 1H), 3.94 (dd, J=9.8, 6.6 Hz, 1H), 3.74-3.69 (m, 1H), 3.58-3.50 (m, 1H), 2.71-2.64 (m, 1H).

According to the above reaction route, Compounds 143 (ammonium salt) was synthesized from Compound 143-6 using the procedure for preparation of Compound 139.

The characteristic data of the Compound 143 was: MS (m/z): 1208.06[M−1]$^−$. $^1$H NMR (500 MHz, D$_2$O) δ 9.09 (s, 1H), 8.45 (s, 1H), 8.18 (s, 1H), 7.96 (s, 1H), 6.42 (t, $J_{H-F}$=75.0 Hz, 1H), 6.04 (d, J=5.4 Hz, 1H), 5.82-5.81 (m, 2H), 4.95-4.92 (m, 1H), 4.72 (d, J=5.4 Hz, 1H), 4.51-4.48 (m, 4H), 4.38 (d, J=9.5 Hz, 1H), 4.34-4.31 (m, 2H), 4.26-4.23 (m, 1H), 4.20-4.16 (m, 2H), 4.13-4.10 (m, 2H), 4.07-4.04 (m, 1H), 4.01 (s, 3H), 3.45 (s, 3H), 2.75-2.69 (m, 1H); $^1$P NMR (202 MHz, D$_2$O) δ-0.92 (s, 1H), −11.61 (m, 2P), −22.89 (t, J=17.6 Hz, 1P).

Example 6 Synthesis of Compound 137

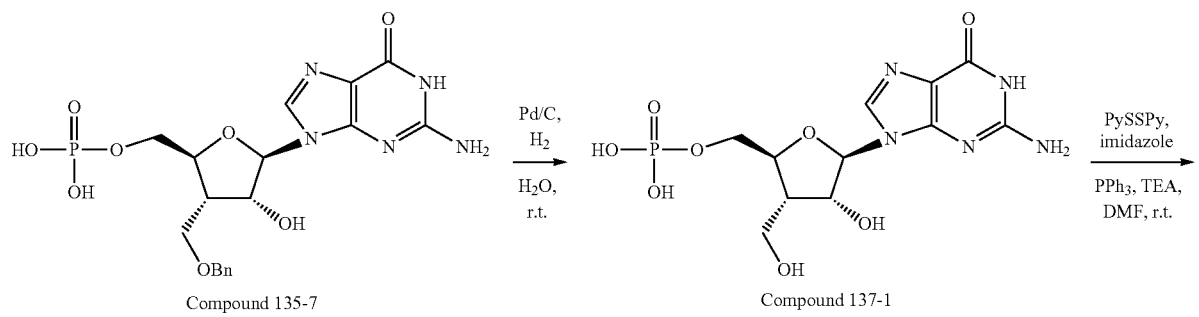

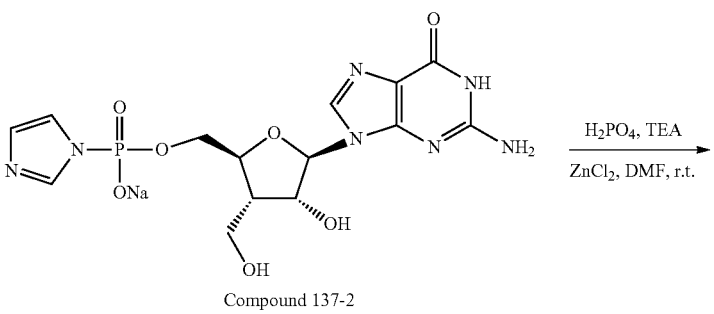

-continued

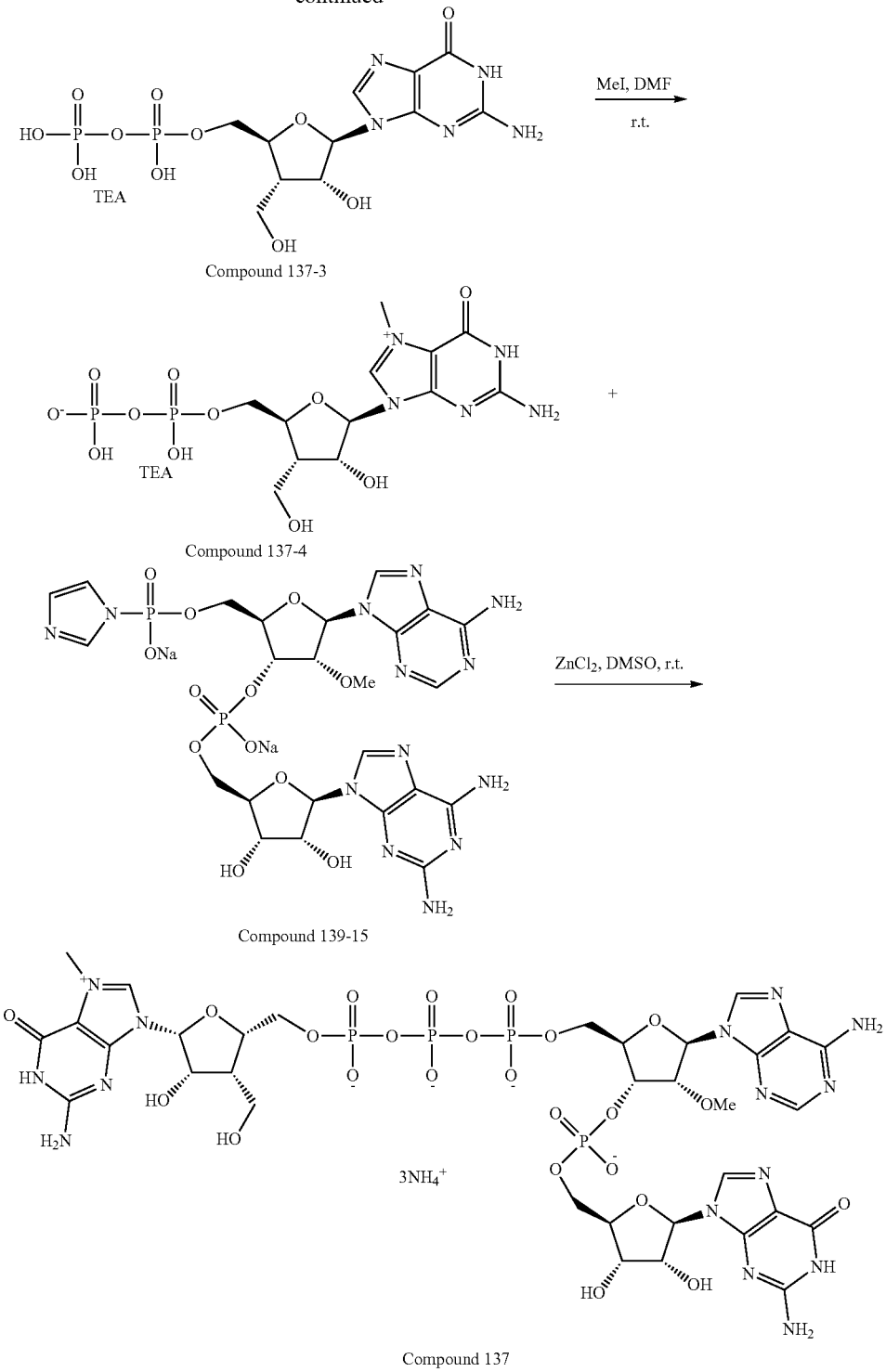

Compound 137-3

Compound 137-4

Compound 139-15

Compound 137

According to the above reaction route, Pd/C (5%, 1 g) was added to Compound 135-7 aqueous solution (2.58 mmol) under hydrogen atmosphere and the mixture was stirred overnight. After the reaction was completed, the reaction liquid was purified by ion exchange column to obtain 1.10 g of Compound 137-1 (triethylamine salt).

An ammonium salt, Compound 137, was synthesized from Compound 137-1 using the procedure for preparation of Compound 139.

The characteristic data of Compound 137 was: MS (m/z): 1158.08[M−1]$^-$. $^1$H NMR (500 MHz, D$_2$O) δ 9.11 (s, 1H), 8.52 (s, 1H), 8.24 (s, 1H), 7.98 (s, 1H), 6.08 (d, J=4.6 Hz, 1H), 5.86-5.78 (m, 2H), 4.94-4.92 (m, 1H), 4.71 (s, 1H), 4.51-4.43 (m, 4H), 4.34 (br, 3H), 4.25-4.15 (m, 4H), 4.00 (s, 3H), 3.87-3.83 (m, 1H), 3.77-3.75 (m, 1H), 3.47 (s, 3H), 3.22-3.17 (m, 2H), 2.61 (br, 1H); $^{31}$P NMR (202 MHz, D$_2$O) δ -0.92 (s, 1H), -11.54 (m, 2P), -22.81 (m, 1P).
Example 7 Synthesis of Compound 635
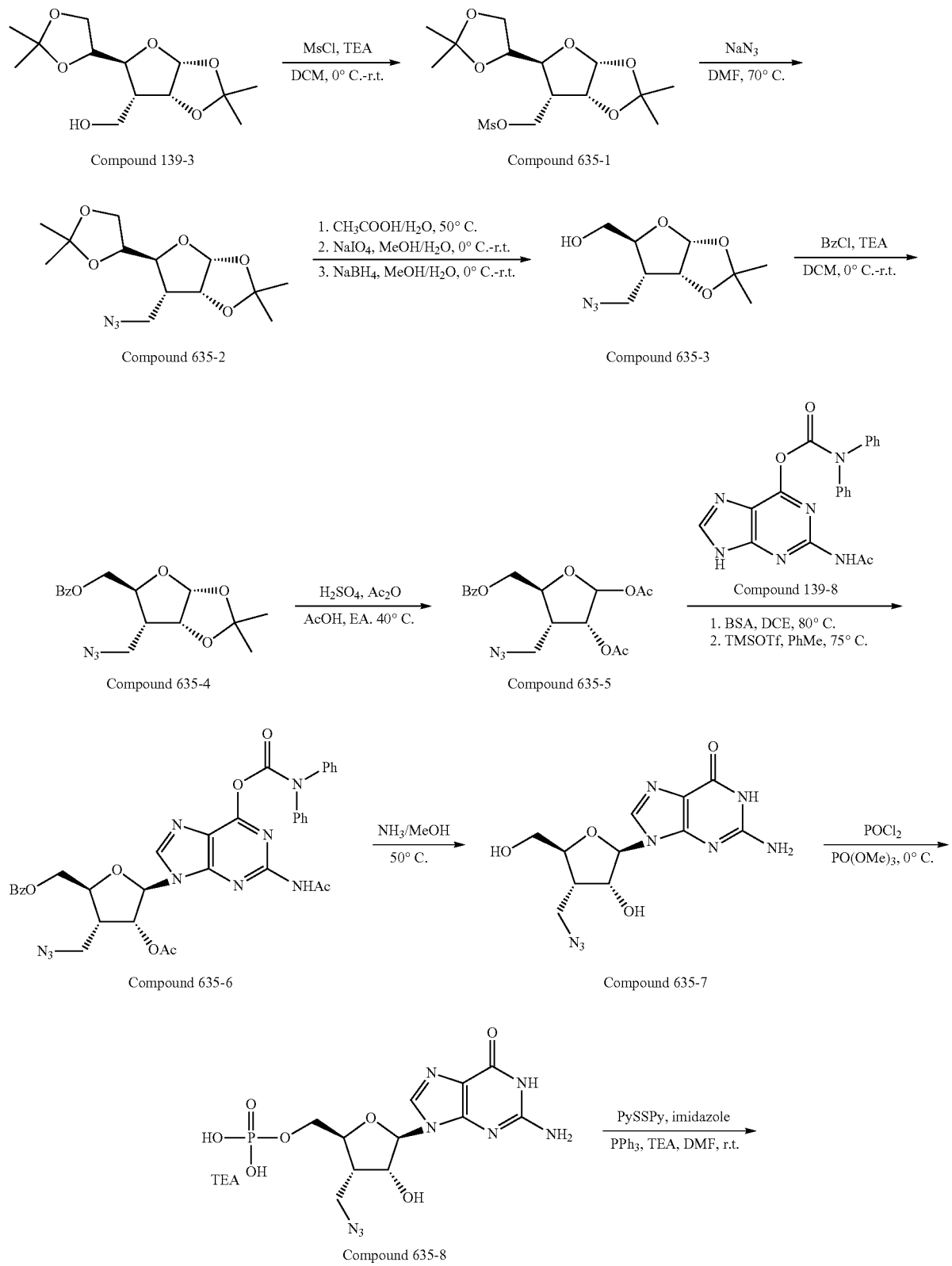

-continued
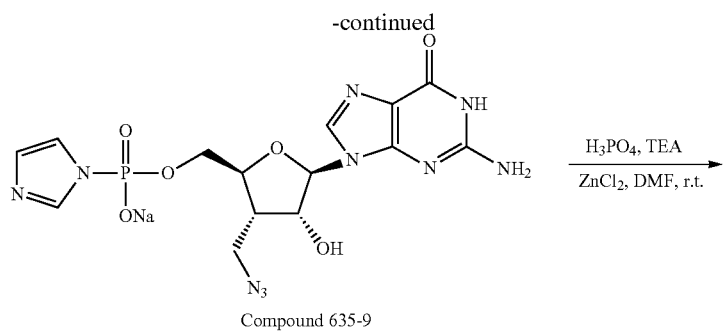
Compound 635-9
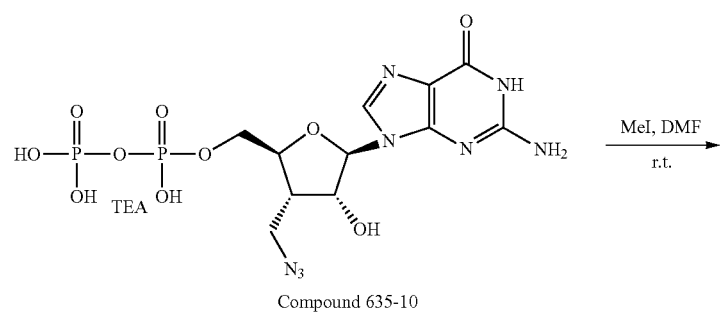
Compound 635-10
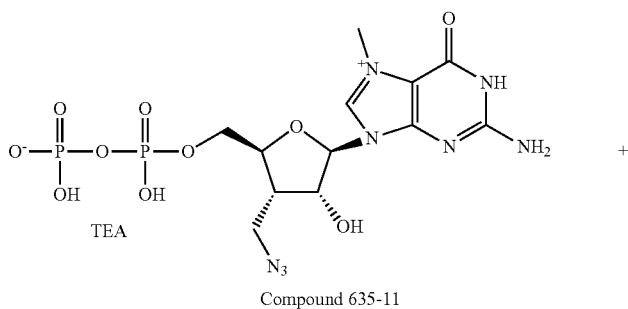
Compound 635-11
+
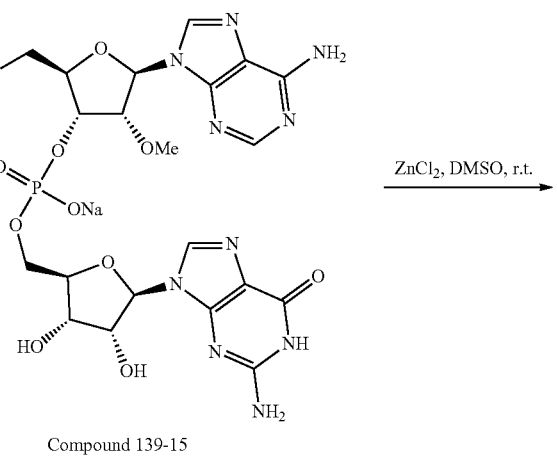
Compound 139-15

-continued

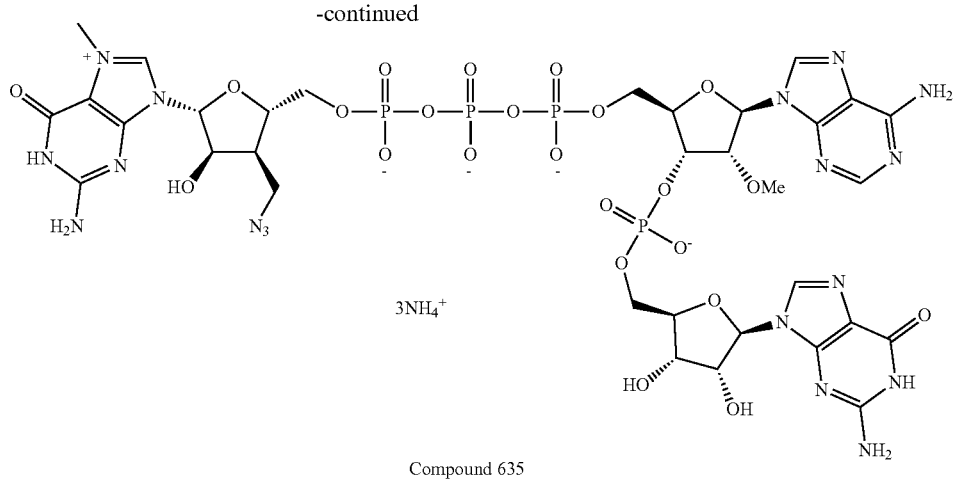

Compound 635

According to the above reaction route, Compound 139-3 (12.0 g, 47 mmol) was dissolved in anhydrous DCM (120 mL) at room temperature, followed by addition of triethylamine (9.5 g, 93.7 mmol). After the temperature was cooled to 0° C., methylsulfonyl chloride (8.05 g, 70.3 mmol) was gradually added. After addition, the temperature was gradually increased to room temperature, and the mixture was stirred overnight at room temperature. Then, the temperature was cooled to 0° C. again, and 150 mL of saturated sodium bicarbonate solution was dropwise added to the mixture. The mixture was separated, wherein the organic phase was successively washed with water (100 mL*2) and saturated saline, dried over anhydrous sodium sulfate, and concentrated under reduced pressure, to obtain 13.2 g of Compound 635-1, which was directly used for the next reaction without purification.

The Compound 635-1 (15.0 g, 42.6 mmol) was dissolved in 75 mL of DMF at room temperature, followed by addition of sodium azide (11.1 g, 170.5 mmol). The mixture was stirred overnight at 70° C., and then it was cooled to room temperature. Water (500 mL) was added to the reaction liquid, and the liquid was extracted with ethyl acetate (150 mL*3), dried over anhydrous sodium sulfate, concentrated under reduced pressure. The residue was purified by column chromatography on silica gel (petroleum ether/ethyl acetate=20/1), to obtain 9.0 g of Compound 653-2.

Compound 635-7 was prepared using the procedure for preparation of Compound 139-10, except substituting Compound 139-4 with Compound 635-2.

The characteristic data of the Compound 635-7 was: $^1$H NMR (500 MHz, DMSO) δ 10.63 (s, 1H), 8.00 (s, 1H), 6.47 (s, 2H), 5.96 (d, J=5.4 Hz, 1H), 5.73 (d, J=2.2 Hz, 1H), 5.08 (t, J=5.4 Hz, 1H), 4.44 (td, J=5.6, 2.3 Hz, 1H), 3.95 (dt, J=8.3, 3.3 Hz, 1H), 3.74-3.67 (m, 1H), 3.64 (dd, J=12.3, 8.1 Hz, 1H), 3.58-3.51 (m, 1H), 3.45 (dd, J=12.3, 5.7 Hz, 1H), 2.63-2.56 (m, 1H).

Compound 635 (ammonium salt) was prepared from Compound 635-7 using the procedure for preparation of Compound 139.

The characteristic data of Compound 635 was: MS (m/z): 1183.05[M−1]$^−$. $^1$H NMR (500 MHz, D$_2$O) δ 9.09 (s, 1H), 8.50 (s, 1H), 8.23 (s, 1H), 7.97 (s, 1H), 6.08 (d, J=5.0 Hz, 1H), 5.80-5.79 (m, 2H), 4.95-4.92 (m, 1H), 4.67 (d, J=4.8 Hz, 1H), 4.52 (s, 1H), 4.49-4.46 (m, 2H), 4.43 (t, J=4.7 Hz, 1H), 4.34-4.31 (m, 3H), 4.26-4.23 (m, 1H), 4.21-4.16 (m, 2H), 4.15-4.13 (m, 1H), 4.00 (s, 3H), 3.64-3.60 (m, 1H), 3.55-3.52 (m, 1H), 3.47 (s, 3H), 2.64-2.58 (m, 1H); $^{31}$P NMR (202 MHz, D$_2$O) δ-0.93 (s, 1H), −11.62 (m, 2P), −22.81 (t, J=18.0 Hz, 1P).

Example 8 Synthesis of Compound 6

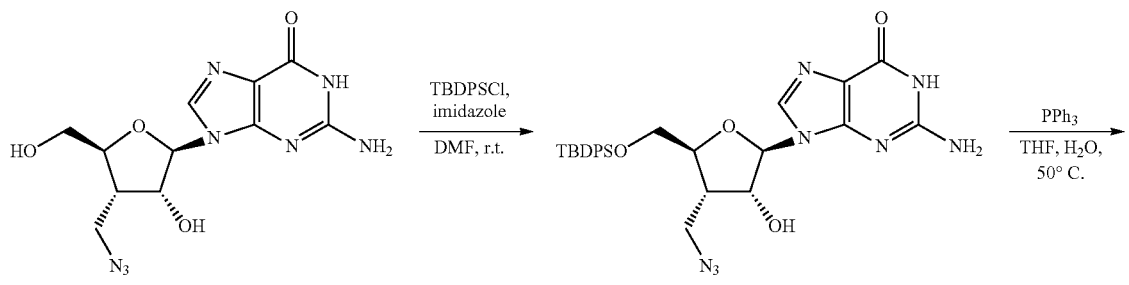

Compound 635-7          Compound 6-1

-continued
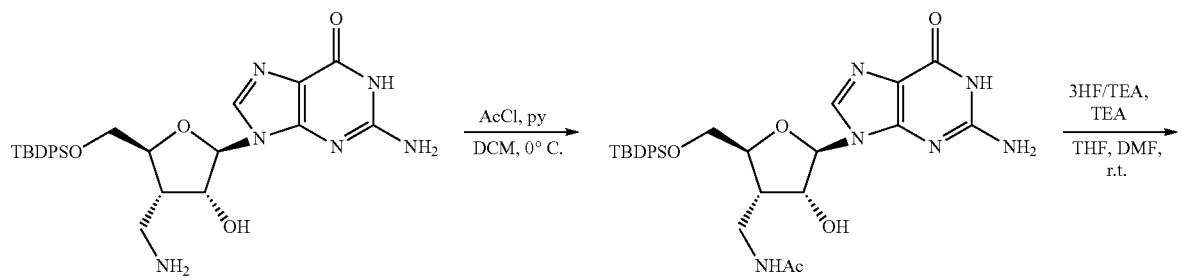
Compound 6-2 → Compound 6-3
Reagents: AcCl, py, DCM, 0° C.
Then: 3HF/TEA, TEA, THF, DMF, r.t.
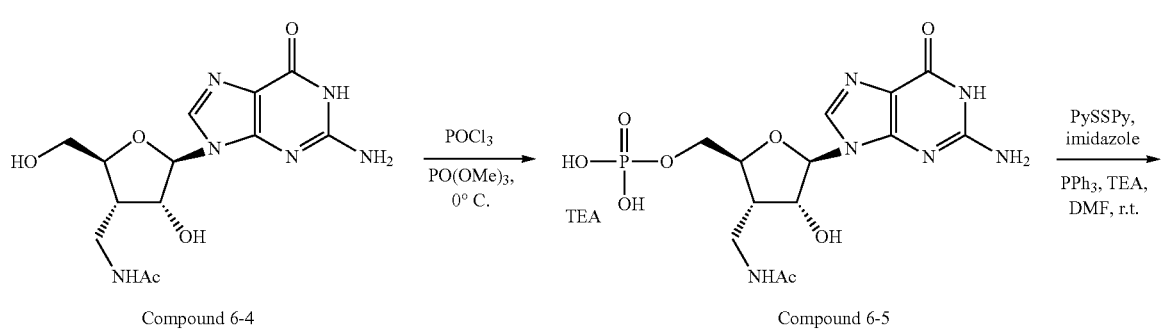
Compound 6-4 → Compound 6-5
Reagents: POCl₃, PO(OMe)₃, 0° C.
Then: PySSPy, imidazole, PPh₃, TEA, DMF, r.t.
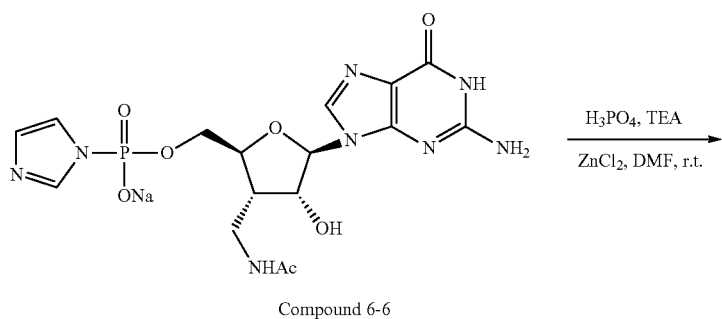
Compound 6-6
Reagents: H₃PO₄, TEA, ZnCl₂, DMF, r.t.
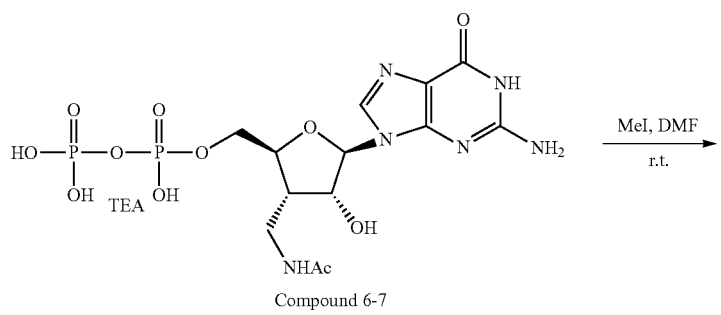
Compound 6-7
Reagents: MeI, DMF, r.t.
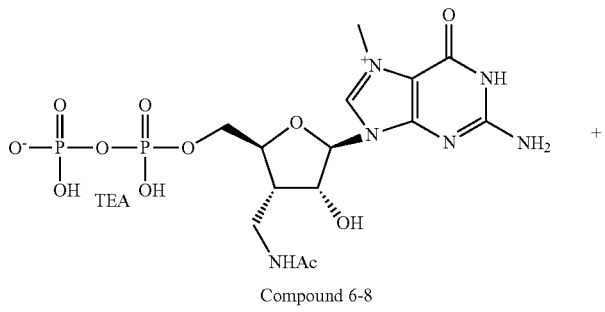
Compound 6-8    +

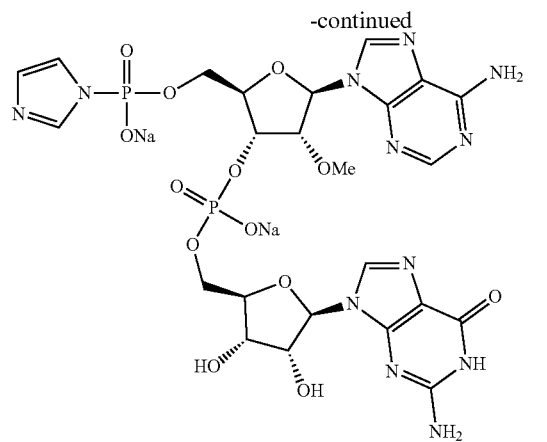

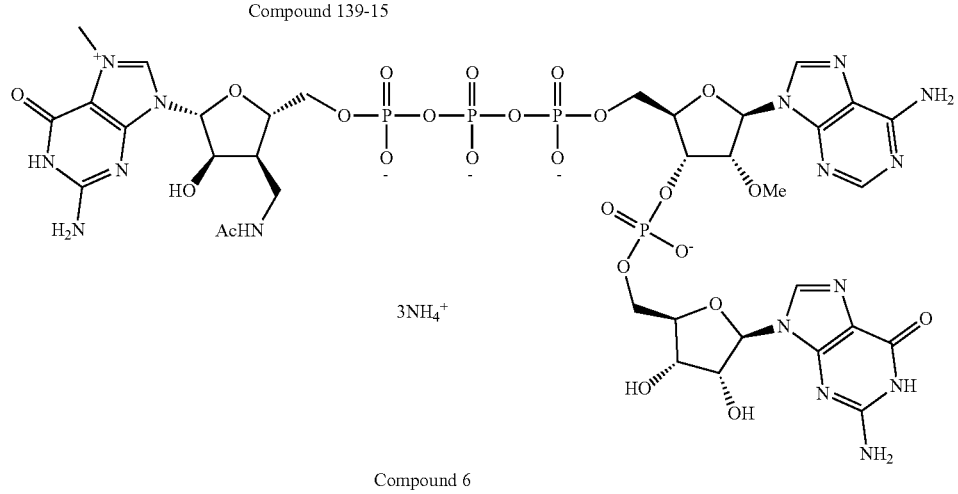

Compound 6

According to the above reaction route, Compound 635-7 (5.0 g, 15.53 mmol) was dissolved in DMF (50 mL), followed by addition of imidazole (3.17 g, 46.58 mmol) and TBDPSCl (5.12 g, 18.63 mmol). The mixture was stirred overnight at room temperature. After the reaction was completed, the reaction liquid was concentrated under reduced pressure to dryness. Ethyl acetate was added for dissolution. The liquid was successively washed with dilute hydrochloric acid, saturated sodium bicarbonate, and saturated saline, dried over anhydrous sodium sulfate, filtered, concentrated under reduced pressure to dryness, and purified by column chromatography to obtain 7.4 g of Compound 6-1.

The Compound 6-1 (5 g, 8.93 mmol) was added to a 250 mL round flask, and THF (90 mL) was added to dissolve it. Then, $H_2O$ (9 mL) and $PPh_3$ (2.81 g, 10.7 mmol) were added to the mixture. The mixture was heated and reacted overnight at 50° C. LCMS detection showed that the starting materials were converted completely. The solvent was removed by rotary evaporation, and 100 mL of MeOH was added to stir vigorously. After filtration, 3.99 g of Compound 6-2 was obtained.

The Compound 6-2 (2.0 g, 3.57 mmol) was dissolved in dichloromethane (10 mL) and pyridine (10 mL), and acetylchloride (0.3 mL, 4.28 mmol) was slowly added. The mixture was reacted for 2 hours, and the reaction was quenched by addition of methanol (5 mL). Subsequently, the reaction liquid was concentrated under reduced pressure to dryness, and the residue was purified by column chromatography to obtain 2.1 g of Compound 6-3.

The Compound 6-3 (2.1 g, 3.67 mmol) was added to DCM (20 mL), followed by successively addition of TEA (1 mL, 7.34 mmol) and TEA-3HF (2.36 g, 14.68 mmol). The mixture was stirred for 2 days at room temperature. HPLC detection showed that the starting materials were reacted completely. The solvent was removed by rotary evaporation, and DCM (20 mL) was added and stirred vigorously. After filtration, a white solid product was obtained, and MeOH (20 mL) was further added and the mixture was heated and stirred vigorously. After filtration, a white solid compound was obtained. Finally, 10 mL of $H_2O$ (0.1% TFA) was used for recrystallization, to obtain 250 mg of Compound 6-4.

The characteristic data of the Compound 6-4 was: $^1$H NMR (500 MHz, $D_2O$) δ 9.07 (s, 1H), 5.99 (s, 1H), 4.64 (d, J=4.5 Hz, 1H), 4.21 (d, J=10.6 Hz, 1H), 3.96 (d, J=13.1 Hz, 1H), 3.69 (dd, J=13.2, 3.4 Hz, 1H), 3.40 (dd, J=14.2, 8.7 Hz, 1H), 3.27 (dd, J=14.1, 5.8 Hz, 1H), 2.56-2.40 (m, 1H), 1.89 (s, 3H).

According to the above reaction route, Compound 6 (ammonium salt) was prepared from Compound 6-4 using the procedure for preparation of Compound 139.

The characteristic data of the Compound 6 was: MS (m/z): 1199.05[M−1]$^−$. $^1$H NMR (500 MHz, $D_2O$) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, $J_1$=14.0 Hz, $J_2$=8.1 Hz, 1H), 3.47 (s, 3H), 3.29 (m, dd, $J_1$=14.0 Hz, $J_2$=6.1 Hz, 1H), 2.64-2.59 (m, 1H), 2.00 (s, 3H); $^{31}$P NMR (202 MHz, $D_2O$) δ-0.95 (s, 1H), −11.49 (d, J=10.9 Hz, 1P), −11.58 (d, J=12.0 Hz, 1P), −22.82 (t, J=18.2 Hz, 1P).

Example 9 Synthesis of Compound 5
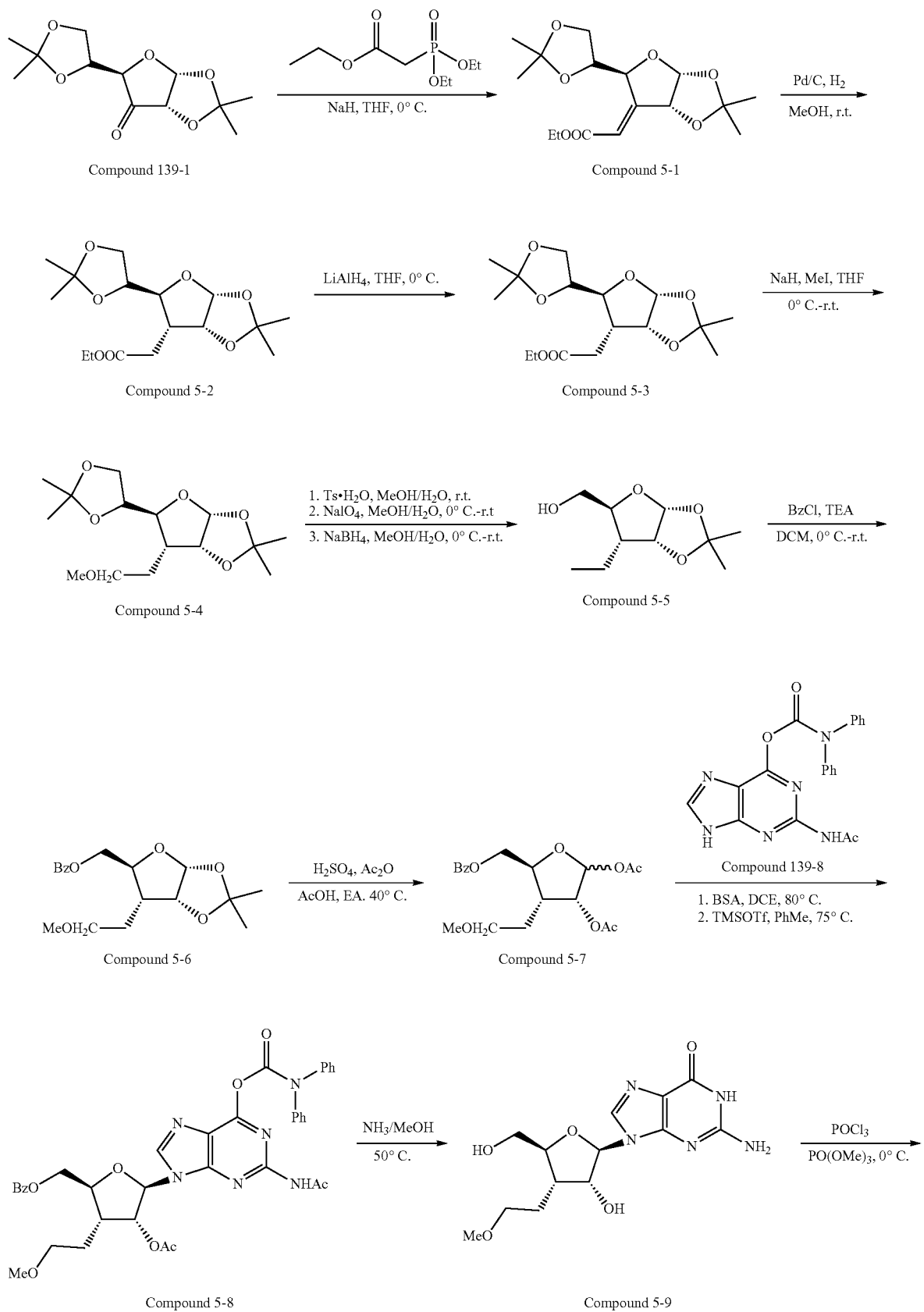

-continued
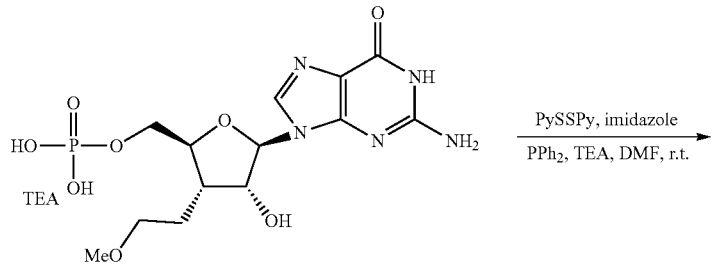
Compound 5-10
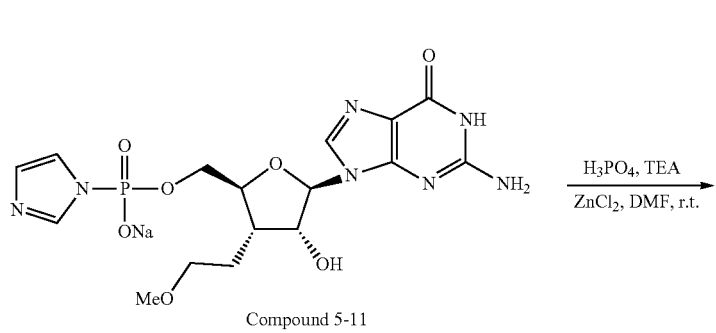
Compound 5-11
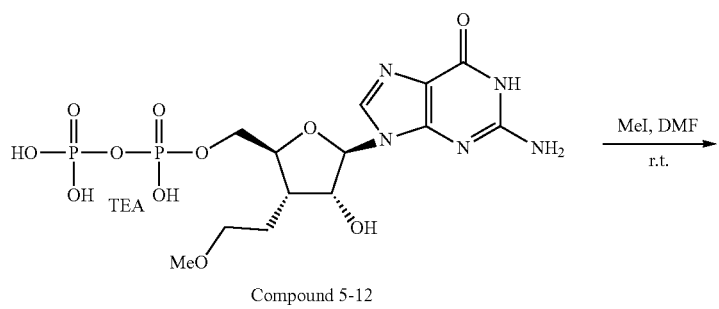
Compound 5-12
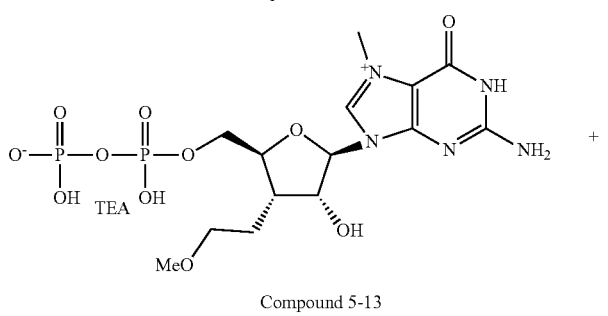
Compound 5-13
+
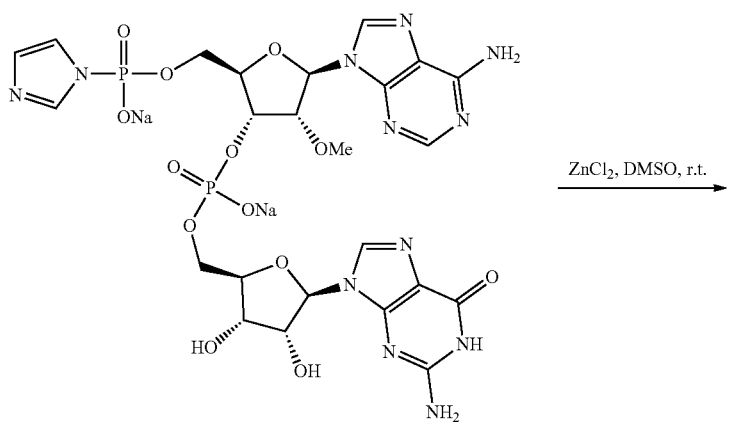
Compound 139-15

-continued

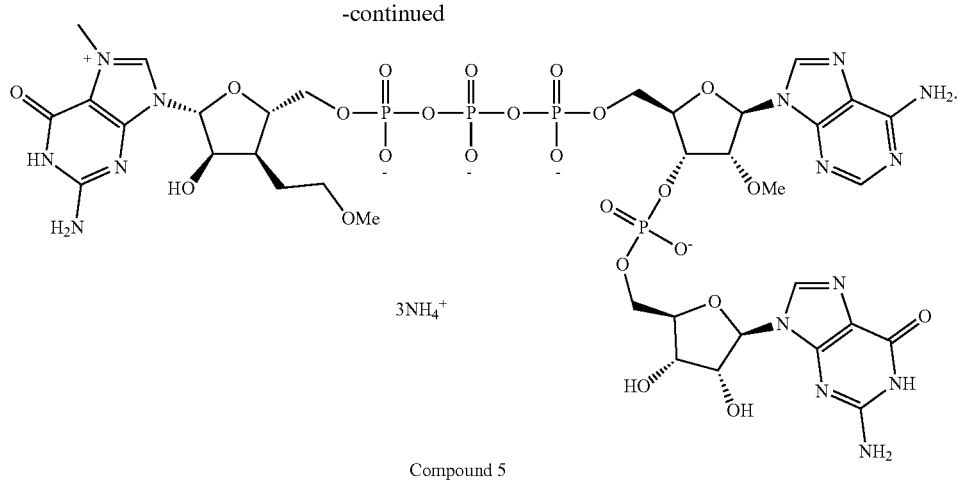

Compound 5

According to the reaction route, NaH (2.40 g, 60 mmol) was gradually added to tetrahydrofuran solution (100 mL) under the nitrogen atmosphere protection at 0° C. Triethyl phosphonoacetate (12.32 g, 55 mmol) was dropwise added to the reaction system, and the system was stirred for 15 min at 0° C. Then, Compound 139-1 (12.9 g, 50 mmol, 40 ml, dissolved in tetrahydrofuran solution) was dropwise added to the reaction system and was stirred for 1 hour. Subsequently, saturated ammonium chloride solution (100 mL) was dropwise added and then the reaction was quenched. After that, ethyl acetate (100 mL) was added, and the organic phase was successively washed with water (100 mL*2) and saturated saline, dried over anhydrous sodium sulfate, and concentrated under reduced pressure. The residue was purified by column chromatography on silica gel (petroleum ether/ethyl acetate=15/1) to obtain 11.50 g of Compound 5-1.

10% of Pb/C (1.00 g) was added to a solution of Compound 5-1 (10.80 g, 33 mmol) in methanol (100 mL) at room temperature. The mixture was stirred overnight under hydrogen atmosphere. Then, the reaction liquid was filtered by vacuum and concentrated under reduced pressure. The residue was dissolved in tetrahydrofuran (40 mL). LiAlH$_4$ was dissolved in tetrahydrofuran (50 mL) and after the temperature was decreased to 0° C., the above residue solution was dropwise added. After addition, the temperature was increased to room temperature, and the solution was stirred for 2 hours at room temperature. Subsequently, the reaction liquid was cooled to 0° C. and the reaction was quenched after addition of 3 mL of ethyl acetate. Subsequently, 2 mL of water and 10.00 g of anhydrous sodium sulfate were added and stirred for 5 min. Siliceous earth was added to filter the solution, and the filtrate was concentrated under reduced pressure, to obtain 8.70 g of Compound 5-3.

Compound 5-9 was prepared from Compound 5-3 using the procedure for preparation of Compound 139-10, except substituting Compound 139-3 with Compound 5-3 and substituting iodoethane with iodomethane.

The characteristic data of Compound 5-9 was: $^1$H NMR (500 MHz, DMSO) δ 10.60 (s, 1H), 8.01 (s, 1H), 6.46 (s, 2H), 5.73 (s, 1H), 5.61 (d, J=5.6 Hz, 1H), 5.03 (t, J=5.3 Hz, 1H), 4.20 (t, J=5.2 Hz, 1H), 3.90-3.85 (m, 1H), 3.77-3.71 (m, 1H), 3.58-3.50 (m, 1H), 3.42-3.35 (m, 2H), 3.21 (s, 3H), 2.34-2.27 (m, 1H), 1.82-1.69 (m, 1H), 1.59-1.50 (m, 1H).

Compound 5 (ammonium salt) was prepared from Compound 5-9 using the procedure for preparation of Compound 139.

The characteristic data of the Compound 5 was: MS (m/z): 1185.95[M−1]$^-$. $^1$H NMR (500 MHz, D$_2$O) δ 8.35 (s, 1H), 8.05 (s, 1H), 7.94 (s, 1H), 6.00 (d, J=5.3 Hz, 1H), 5.80 (d, J=5.2 Hz, 1H), 5.75 (s, 1H), 4.92 (m, 1H), 4.70 (t, J=5.1 Hz, 1H), 4.49-4.47 (m, 4H), 4.41 (m, 1H), 4.33-4.29 (m, 2H), 4.26-4.23 (m, 1H), 4.20-4.18 (m, 3H), 4.12-4.10 (m, 1H), 3.99 (s, 3H), 3.45 (m, 5H), 3.26 (s, 3H), 2.29-2.23 (m, 1H), 1.77-1.65 (m, 2H); $^{31}$P NMR (202 MHz, D$_2$O) δ-0.96 (s, 1H), −11.56 (m, 2P), −22.68 (m, 1P).

Example 10 Synthesis of Compound 153

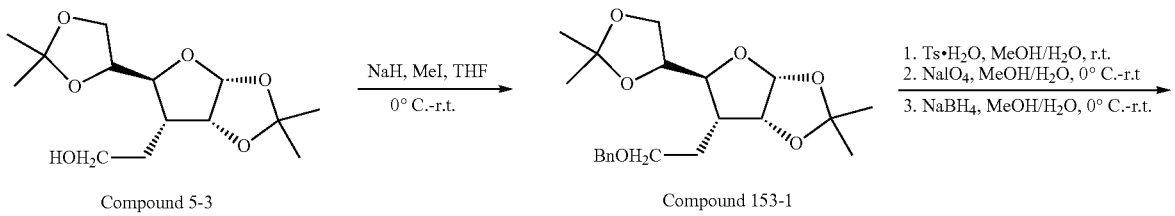

-continued
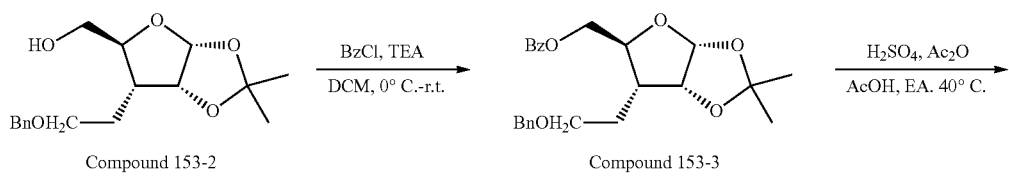
Compound 153-2 → Compound 153-3
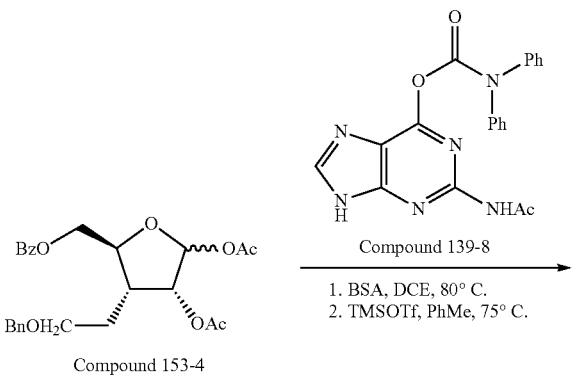
Compound 153-4
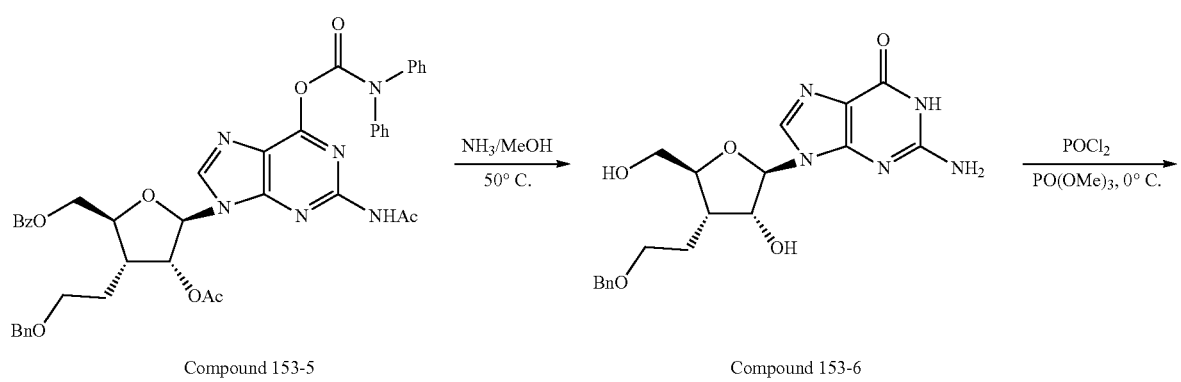
Compound 153-5    Compound 153-6
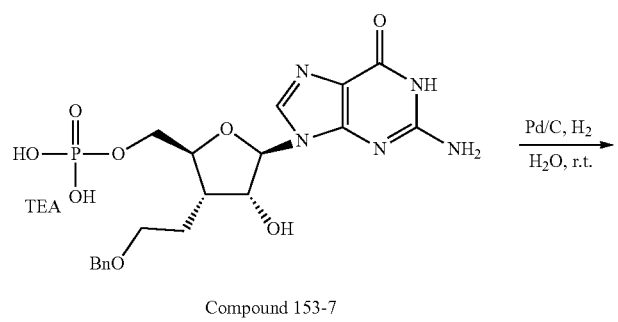
Compound 153-7
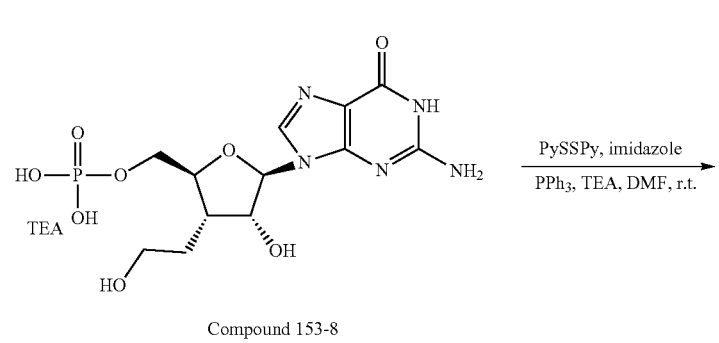
Compound 153-8

-continued
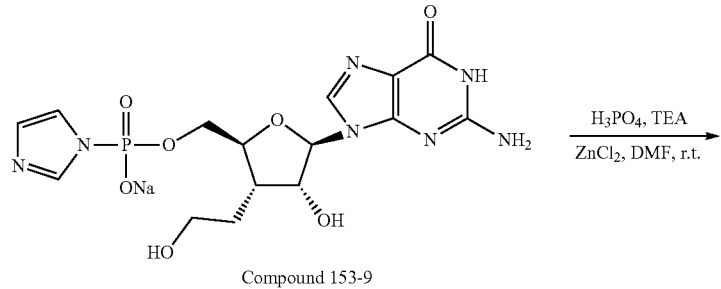
Compound 153-9
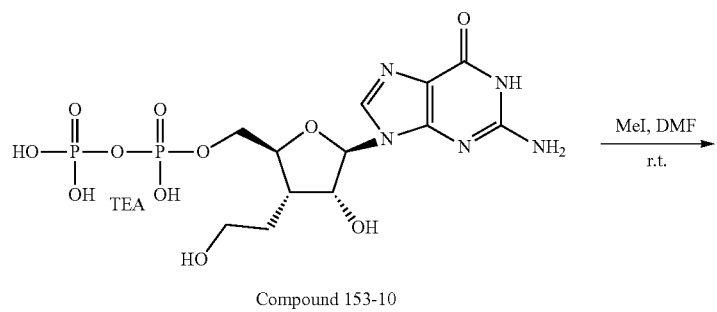
Compound 153-10
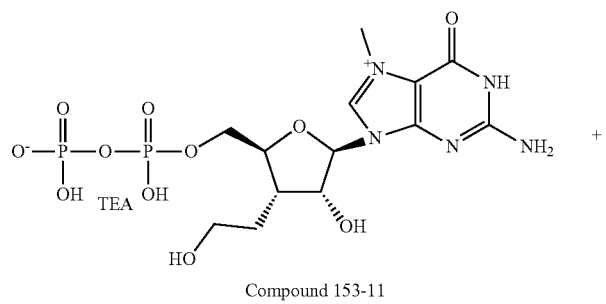
Compound 153-11    +
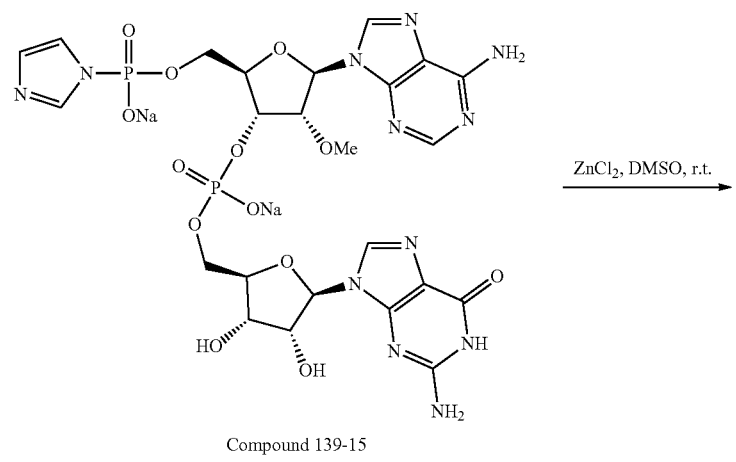
Compound 139-15

-continued

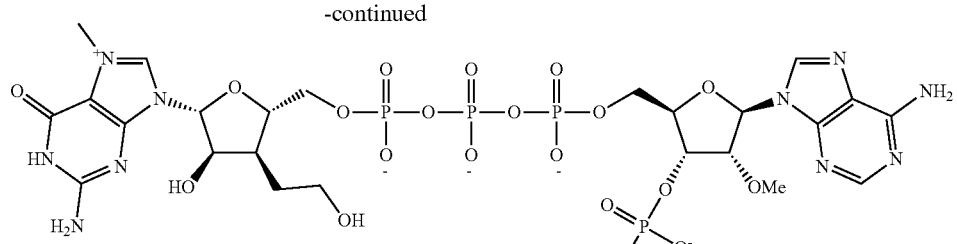
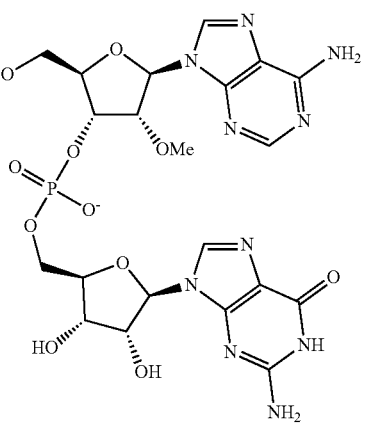

Compound 153

Compound 153-6 was prepared from Compound 5-3 using the procedure for preparation of Compound 139-10, except substituting Compound 139-3 with Compound 5-3 and substituting iodoethane with bromotoluene.

The characteristic data of Compound 153-6 was: $^1$H NMR (500 MHz, DMSO) δ 10.61 (s, 1H), 8.03 (s, 1H), 7.31-7.20 (m, 5H), 6.46 (s, 2H), 5.73 (s, 1H), 5.60 (d, J=5.5 Hz, 1H), 5.06 (t, J=5.0 Hz, 1H), 4.44 (dd, J=35.4, 12.2 Hz, 2H), 4.15 (t, J=4.8 Hz, 1H), 3.89 (d, J=9.7 Hz, 1H), 3.79-3.71 (m, 1H), 3.61-3.41 (m, 3H), 2.40-2.36 (m, 1H), 1.86-1.73 (m, 1H), 1.61 (dd, J=12.8, 5.3 Hz, 1H).

According to the reaction route, Compound 153 (ammonium salt) was prepared from Compound 153-6 using the procedure for preparation of Compounds 139 and 137

The characteristic data of the Compound 153 was: MS (m/z): 1172.04[M−1]$^−$. $^1$H NMR (500 MHz, D$_2$O) δ 8.96 (s, 1H), 8.39 (s, 1H), 8.12 (s, 1H), 8.00 (s, 1H), 6.01 (d, J=5.8 Hz, 1H), 5.83 (d, J=5.6 Hz, 1H), 5.81 (s, 1H), 4.94-4.91 (m, 1H), 4.54 (d, J=4.4 Hz, 1H), 4.50-4.46 (m, 3H), 4.41 (t, J=5.2 Hz, 1H), 4.34 (br, 1H), 4.26-4.23 (m, 3H), 4.21-4.19 (m, 2H), 4.15-4.11 (m, 1H), 3.99 (s, 3H), 3.67-3.63 (m, 1H), 3.59-3.54 (m, 1H), 3.42 (s, 3H), 2.37-2.32 (m, 1H), 1.78-1.71 (m, 1H), 1.69-1.62 (m, 1H); $^{31}$P NMR (202 MHz, D$_2$O) δ-0.94 (s, 1H), −11.52 (m, 2P), −22.56 (m, 1P).

Example 11 Synthesis of Compound 4

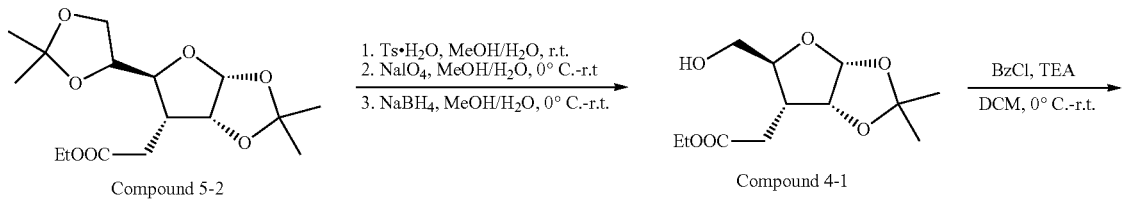

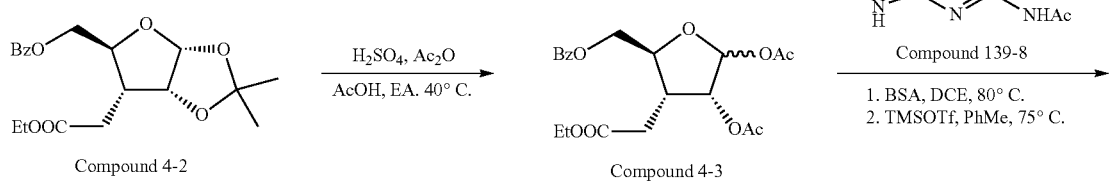

-continued
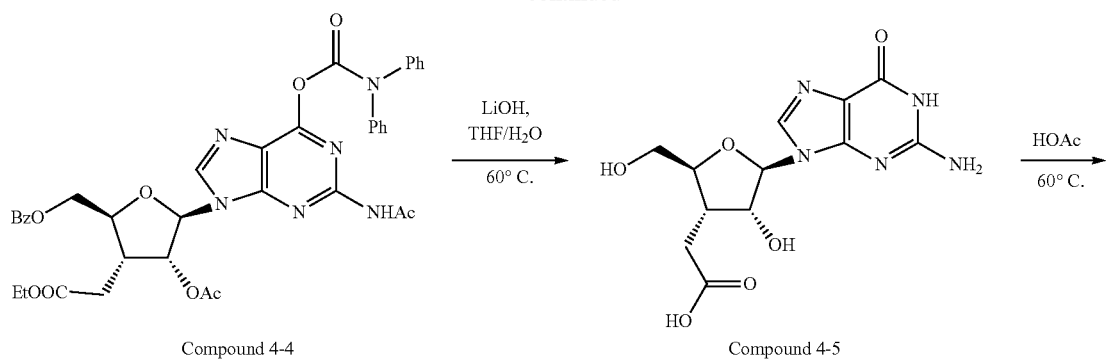
Compound 4-4 → Compound 4-5
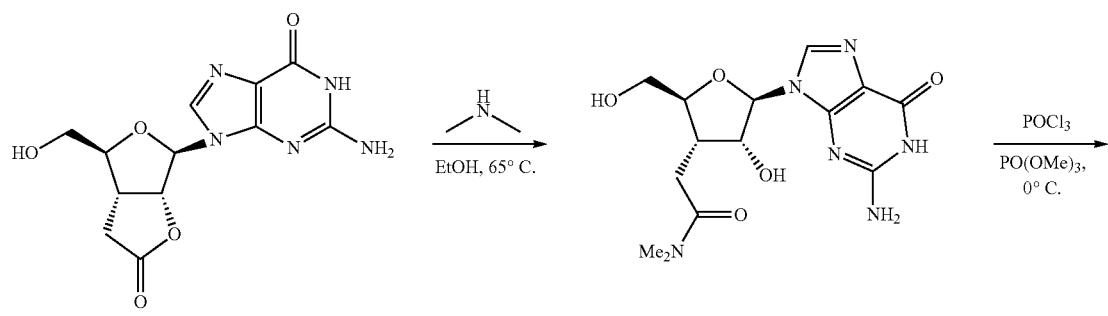
Compound 4-6 → Compound 4-7
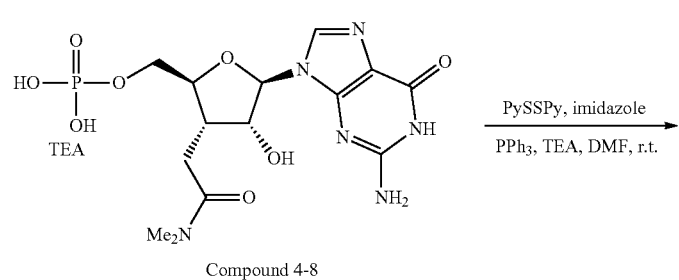
Compound 4-8
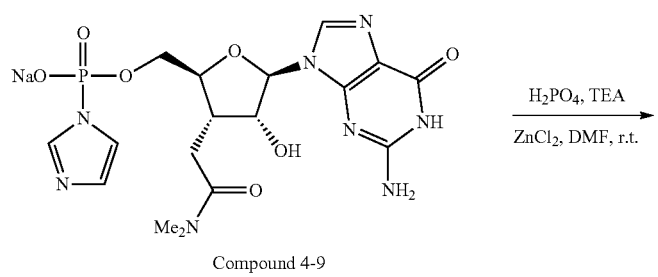
Compound 4-9
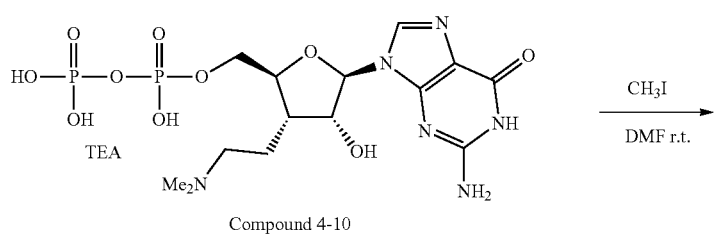
Compound 4-10

-continued

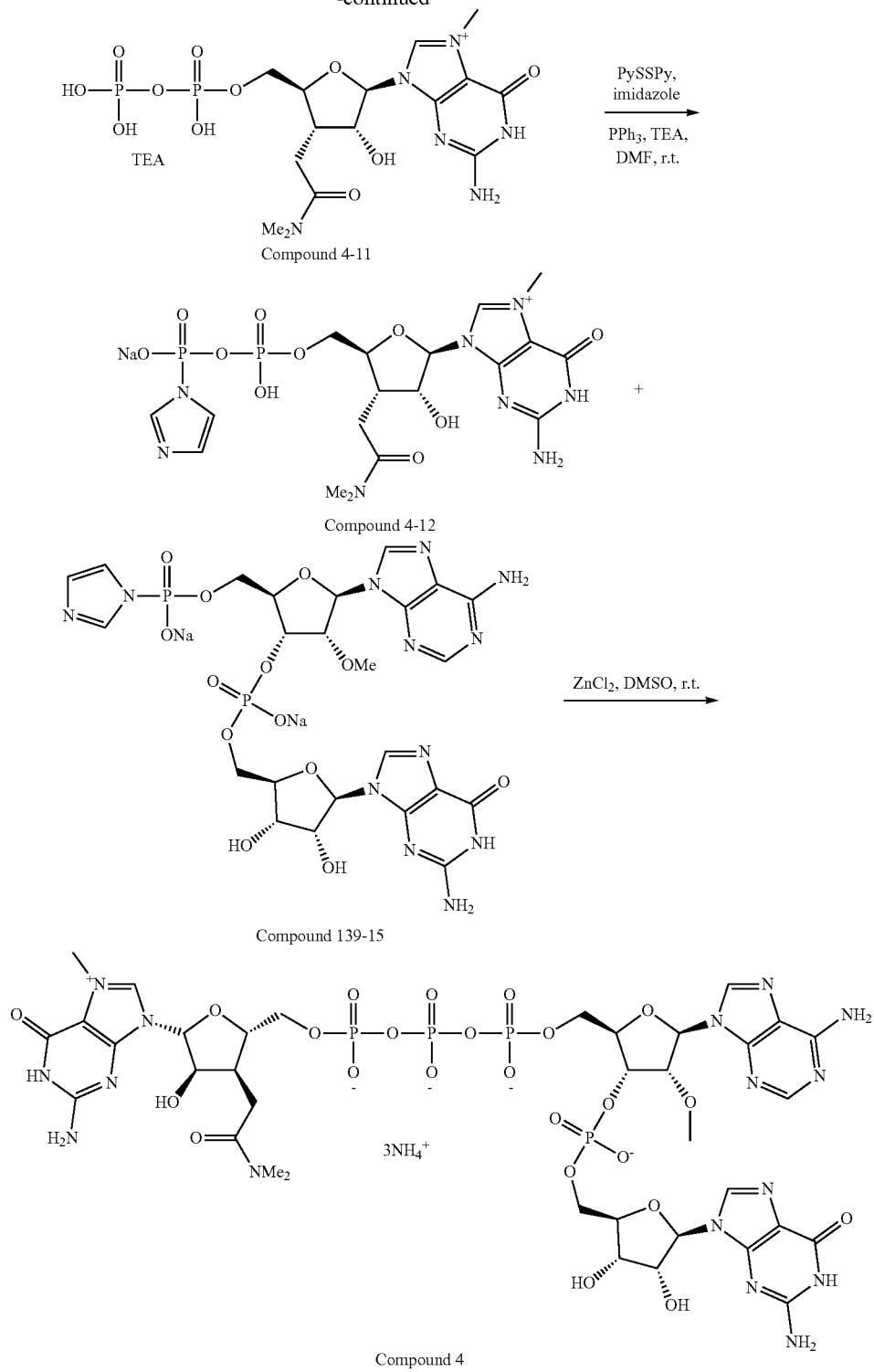

Compound 4-11

Compound 4-12

Compound 139-15

Compound 4

According to the reaction route, Compound 4-4 was prepared from Compound 5-2 using the procedure for preparation of Compound 139-9, except substituting Compound 139-4 with Compound 5-2.

Compound 4-4 (7.22 g, 10 mmol) was dissolved in tetrahydrofuran (50 mL) at room temperature, followed by adding water (50 mL) and lithium hydroxide (2.52 g, 60 mmol). After the temperature was increased to 60° C., the mixture was stirred for 20 hours. Subsequently, the temperature was cooled to room temperature, 50 mL of ethyl acetate was added. The aqueous phase was concentrated under reduced pressure to obtain 6 g of Compound 4-5.

The Compound 4-5 (6 g, 10 mmol, saliferous) was dissolved in acetic acid (50 mL) at room temperature. The temperature was then increased to 60° C., and the mixture was stirred for 20 hours. Subsequently, the temperature was cooled to room temperature, and the liquid was concentrated under reduced pressure to obtain 8 g of Compound 4-6.

The Compound 4-6 (8 g, 10 mmol, saliferous) was dissolved in a solution of dimethylamine in ethanol solution (100 mL) at room temperature. After the temperature was then increased to 65° C., the mixture was stirred for 20 hours. Subsequently, the temperature was cooled to room temperature, and the reaction liquid was concentrated under reduced pressure. The concentrated reaction liquid was firstly passed through C18-column chromatography for desalting, and then separated through medium pressure liquid chromatography, to obtain 0.5 g of Compound 4-7.

The characteristic data of Compound 4-7 was: $^1$H NMR (500 MHz, DMSO) δ 10.67 (s, 1H), 8.01 (s, 1H), 6.50 (s, 2H), 5.72 (s, 1H), 5.67 (s, 1H), 5.02 (s, 1H), 4.33 (s, 1H), 3.90 (d, J=9.3 Hz, 1H), 3.74 (d, J=12.3 Hz, 1H), 3.58 (d, J=12.2 Hz, 1H), 2.98 (s, 3H), 2.82 (s, 3H), 2.69-2.57 (m, 2H), 2.35 (dd, J=15.8, 3.4 Hz, 1H).

According to the reaction route, Compound 4 (ammonium salt) was prepared from Compound 4-7 using the procedure for preparation of Compound 139.

The characteristic data of the Compound 4 was: MS (m/z): 1213.09[M−1]$^-$. $^1$H NMR (500 MHz, D$_2$O) δ 9.10 (s, 1H), 8.46 (s, 1H), 8.19 (s, 1H), 7.98 (s, 1H), 6.07 (d, J=5.5 Hz, 1H), 5.84 (d, J=5.8 Hz, 1H), 5.82 (s, 1H), 4.98-4.95 (m, 1H), 4.79 (m, 1H), 4.65 (d, J=4.1 Hz, 1H), 4.54-4.51 (m, 3H), 4.46 (t, J=5.0 Hz, 1H), 4.37-4.33 (m, 2H), 4.29-4.26 (m, 2H), 4.23-4.20 (m, 2H), 4.14-4.12 (m, 1H), 4.03 (s, 3H), 3.47 (s, 3H), 3.06 (s, 3H), 2.89 (s, 3H), 2.74-2.61 (m, 2H), 2.57-2.54 (m, 1H); $^{31}$P NMR (202 MHz, D$_2$O) δ-0.88 (s, 1H), −11.52-11.70 (m, 2P), −22.82 (t, J=17.9 Hz, 1P).

Example 12 Synthesis of Compound 393

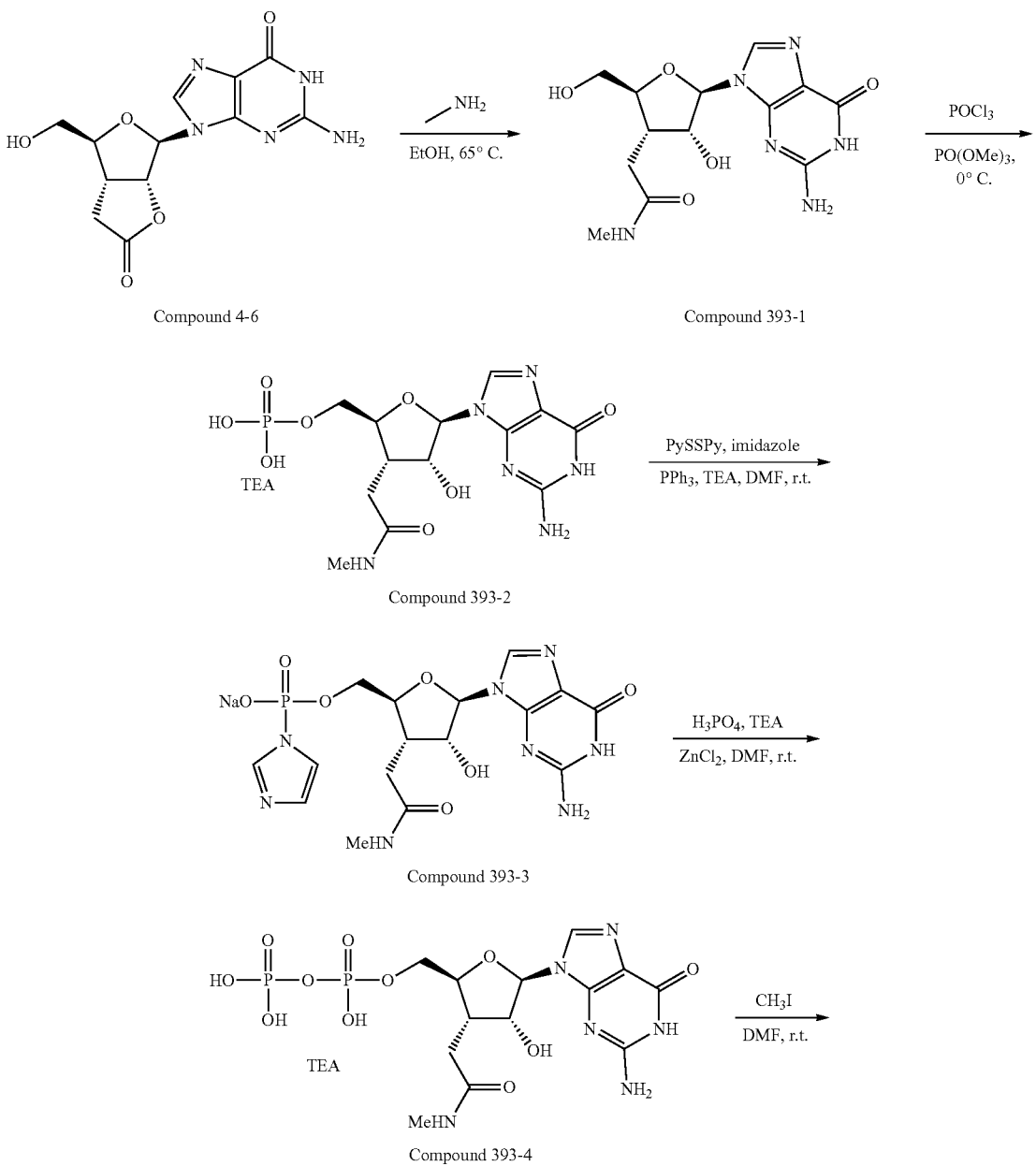

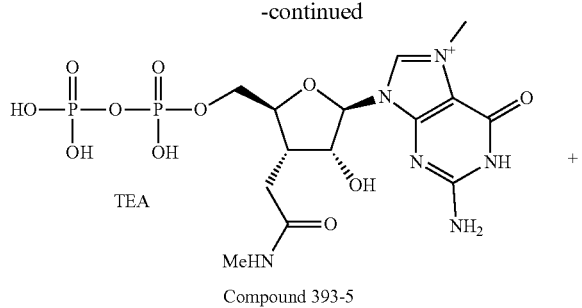

Compound 393-5

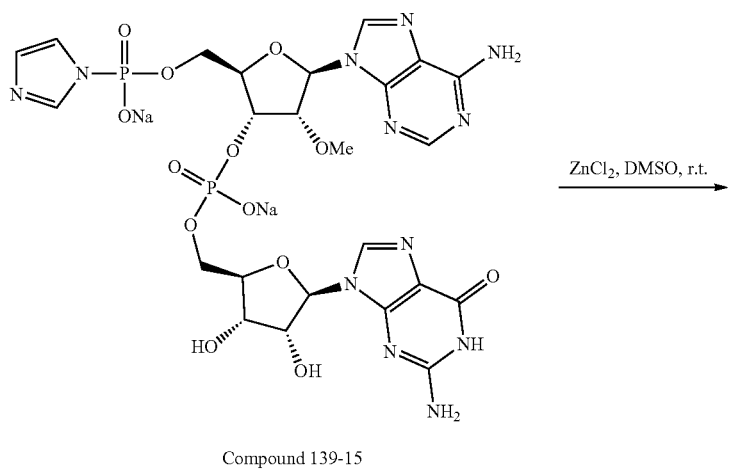

Compound 139-15

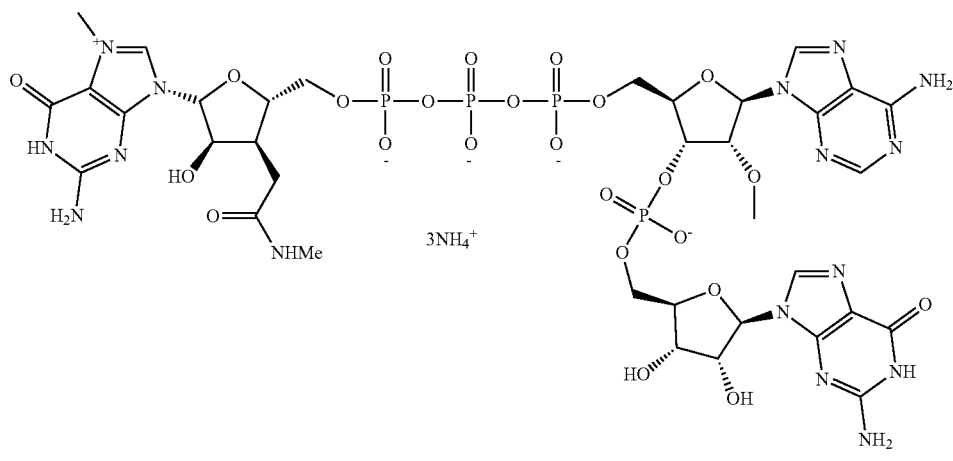

Compound 393

According to the reaction route, Compound 393-1 was prepared using the procedure for preparation of Compound 4-7, except substituting dimethylamine with methylamine and using dimethyl sulfoxide and water as solvents.

The characteristic data of Compound 393-1 was: $^1$H NMR (400 MHz, DMSO) δ 10.59 (s, 1H), 8.01 (s, 1H), 7.84 (d, J=4.4 Hz, 1H), 6.46 (s, 2H), 5.74 (d, J=5.4 Hz, 1H), 5.71 (d, J=1.4 Hz, 1H), 5.02 (t, J=5.3 Hz, 1H), 4.33 (t, J=4.6 Hz, 1H), 3.88 (d, J=9.1 Hz, 1H), 3.75-3.65 (m, 1H), 3.55-3.48 (m, 1H), 2.67-2.61 (m, 1H), 2.58 (d, J=4.5 Hz, 3H), 2.43 (dd, J=15.2, 8.4 Hz, 1H), 2.19 (dd, J=15.2, 5.9 Hz, 1H).

According to the reaction route, Compound 393 (ammonium salt) was prepared from Compound 393-1 using the procedure for preparation of Compound 139.

The characteristic data of the Compound 393 was: MS (m/z): 1199.03[M−1]⁻. $^1$H NMR (500 MHz, D$_2$O) δ 9.05 (s, 1H), 8.44 (s, 1H), 8.17 (s, 1H), 7.96 (s, 1H), 6.04 (d, J=5.5 Hz, 1H), 5.82-5.81 (m, 2H), 4.93 (br, 1H), 4.56 (d, J=4.5 Hz, 1H), 4.51-4.46 (m, 3H), 4.43 (t, J=5.0 Hz, 1H), 4.34-4.30 (m, 2H), 4.26-4.24 (m, 2H), 4.19 (s, 2H), 4.10-4.08 (m, 1H), 4.01 (s, 3H), 3.43 (s, 3H), 2.66 (s, 3H), 2.63-2.62 (m, 1H), 2.48-2.41 (m, 2H); $^{31}$P NMR (202 MHz, D$_2$O) δ-0.91 (s, 1H), −11.61 (m, 2P), −22.88 (m, 1P).

Example 13 Synthesis of Compound 58
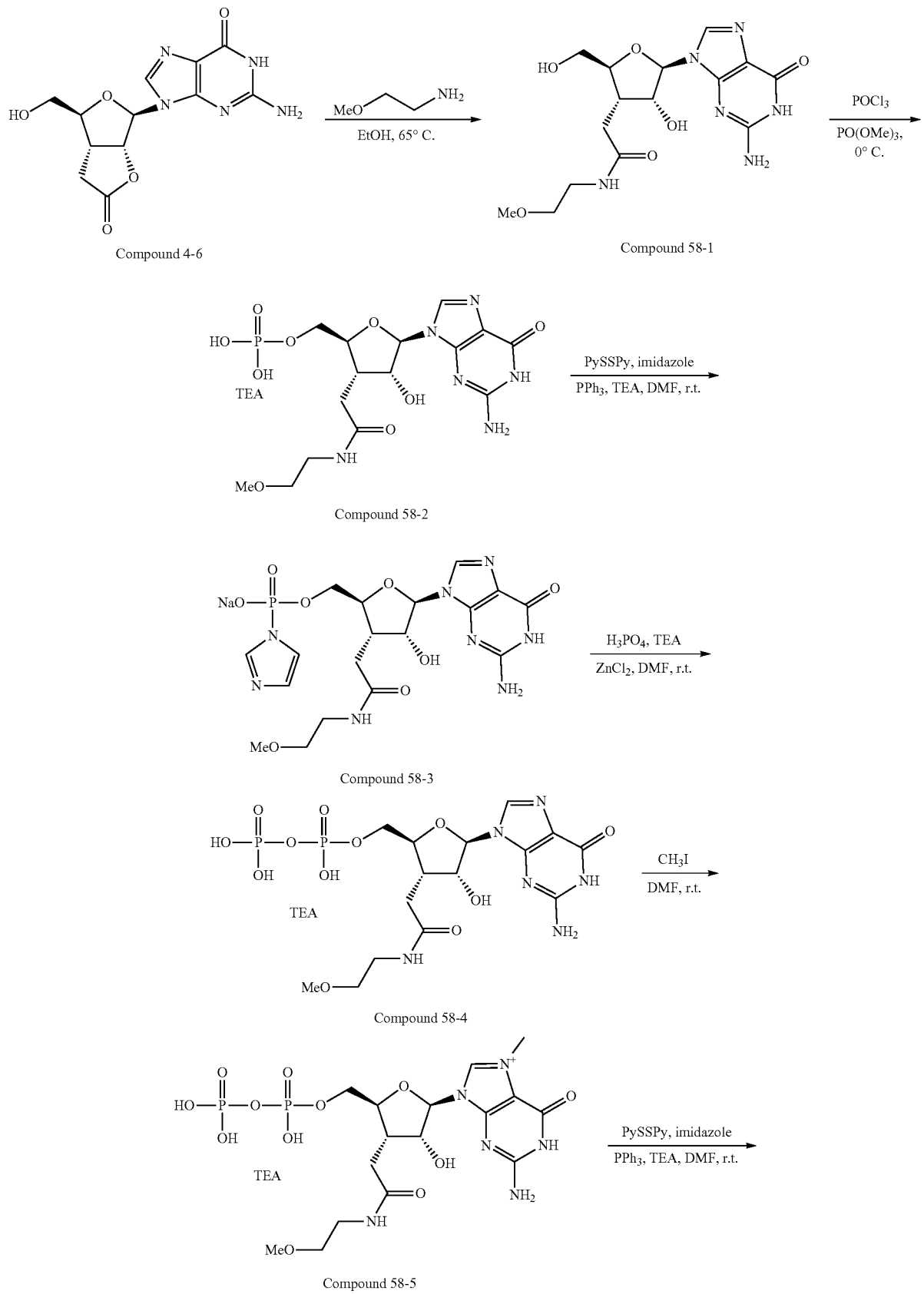

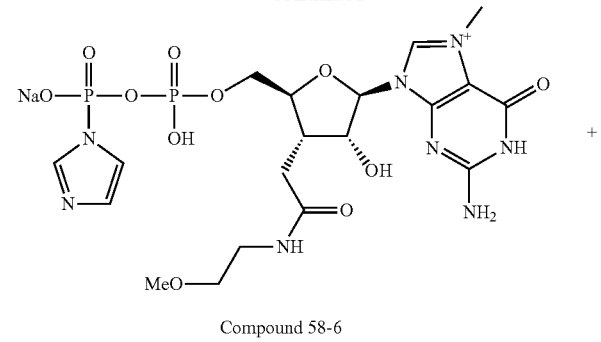

Compound 58-6

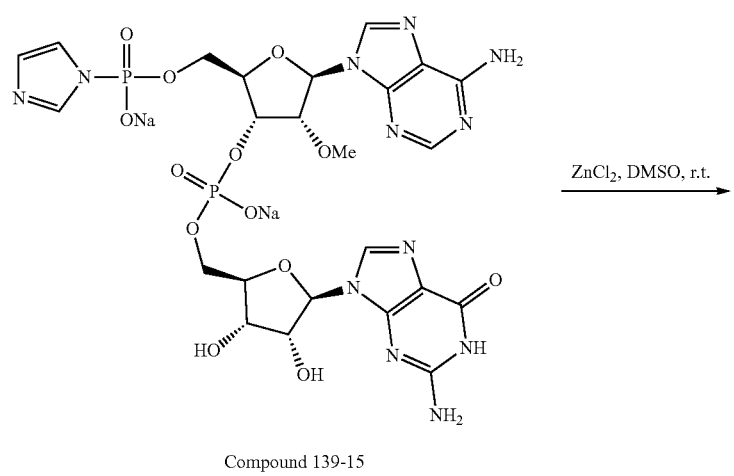

Compound 139-15

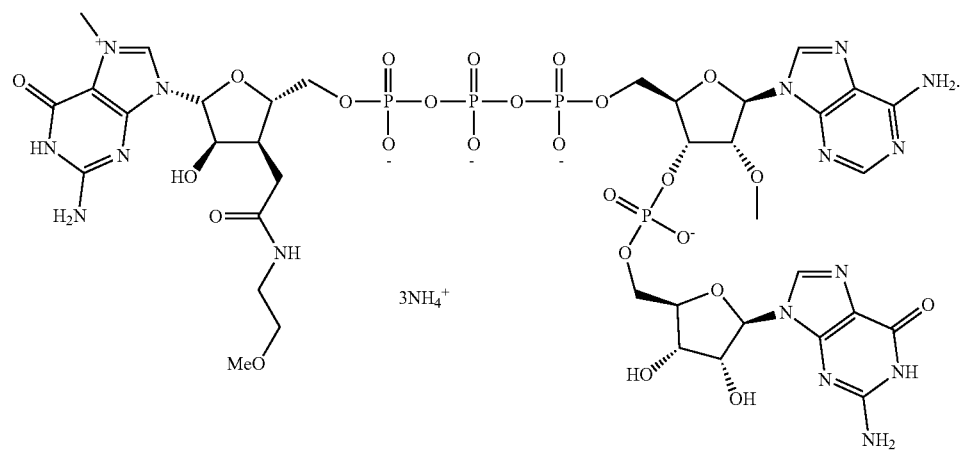

Compound 58

According to the reaction route, Compound 58-1 was prepared using the procedure for preparation of Compound 4-7, except substituting dimethylamine with 2-methoxyethylamine and using dimethyl sulfoxide as a solvent.

The characteristic data of Compound 58-1 was: $^1$H NMR (500 MHz, DMSO) δ 10.62 (s, 1H), 8.00 (s, 1H), 6.45 (s, 2H), 5.72 (d, J=5.3 Hz, 1H), 5.69 (d, J=1.5 Hz, 1H), 5.02 (t, J=5.3 Hz, 1H), 4.32 (t, J=4.4 Hz, 1H), 3.86 (d, J=9.0 Hz, 1H), 3.73-3.65 (m, 1H), 3.53-3.48 (m, 1H), 3.33 (t, J=5.7 Hz, 2H), 3.23 (s, 3H), 3.19-3.16 (m, 2H), 2.65-2.57 (m, 1H), 2.43 (dd, J=15.2, 8.3 Hz, 1H), 2.20 (dd, J=15.2, 6.0 Hz, 1H).

According to the reaction route, Compound 58 (ammonium salt) was prepared from Compound 58-1 using the procedure for preparation of Compound 139.

The characteristic data of the Compound 58 was: MS (m/z): 1243.03[M−1]$^-$. $^1$H NMR (500 MHz, D$_2$O) δ 9.06 (s, 1H), 8.45 (s, 1H), 8.17 (s, 1H), 7.95 (s, 1H), 6.06 (d, J=5.3 Hz, 1H), 5.80 (d, J=5.8 Hz, 1H), 5.78 (s, 1H), 4.96-4.92 (m, 1H), 4.56 (d, J=4.4 Hz, 1H), 4.52-4.48 (m, 3H), 4.43 (t, J=4.9 Hz, 1H), 4.34-4.31 (m, 2H), 4.27-4.25 (m, 2H), 4.20-4.17 (m, 2H), 4.12-4.09 (m, 1H), 4.00 (s, 3H), 3.49 (t, J=5.3 Hz, 2H), 3.37-3.27 (m, 5H), 2.64-2.60 (m, 1H), 2.51-2.43 (m, 2H); $^{31}$P NMR (202 MHz, D$_2$O) δ-0.93 (s, 1H), −11.66 (m, 2P), −22.82 (t, J=18.0 Hz, 1P).

Example 14 Synthesis of Compound 643
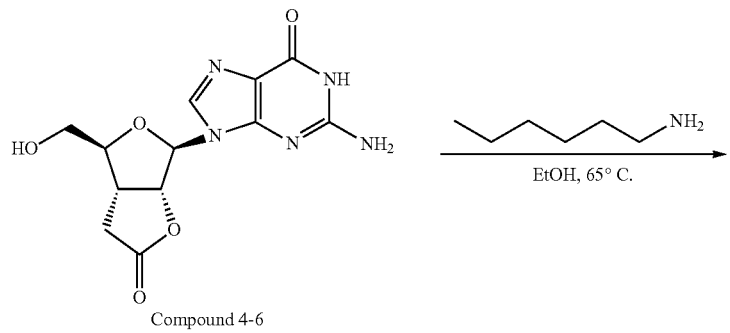
Compound 4-6
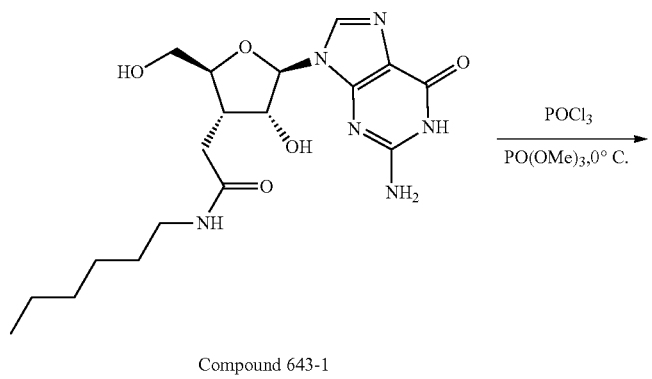
Compound 643-1
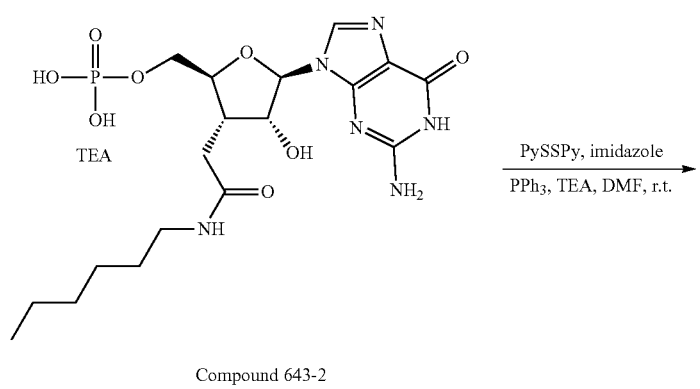
Compound 643-2
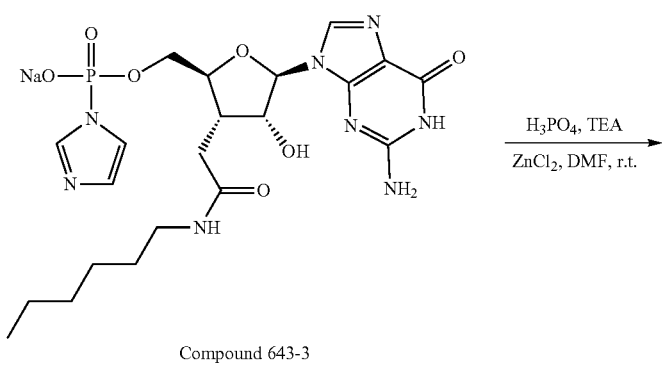
Compound 643-3

-continued
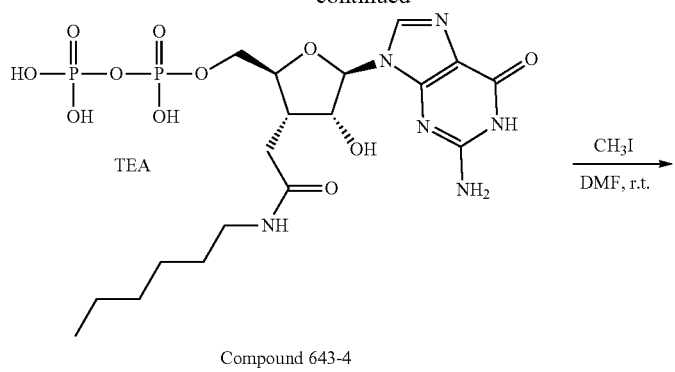
Compound 643-4
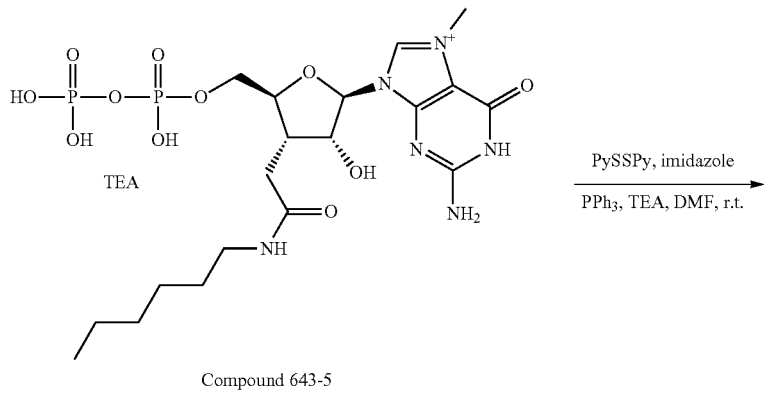
Compound 643-5
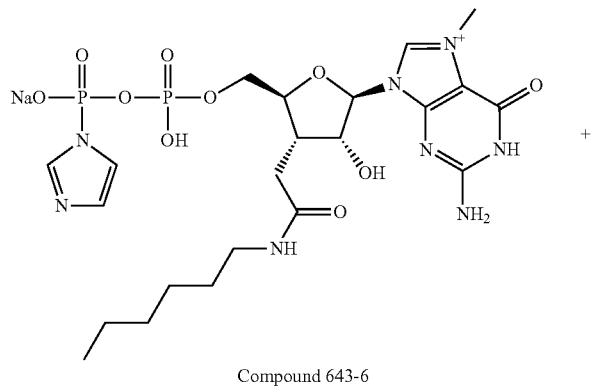
Compound 643-6
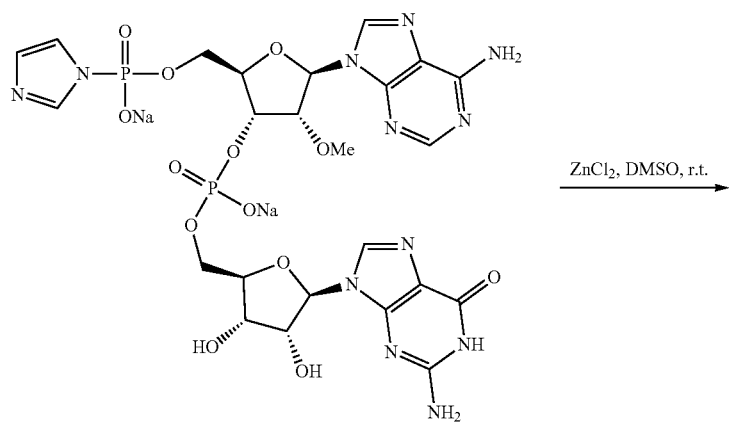
Compound 139-15

-continued

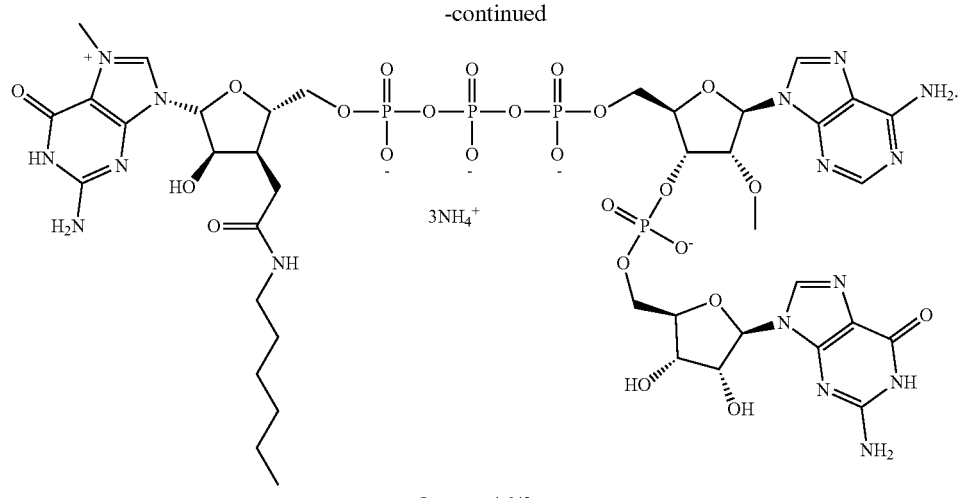

Compound 643

According to the reaction route, Compound 643-1 was prepared using the procedure for preparation of Compound 4-7, except substituting dimethylamine with hexylamine and using dimethyl sulfoxide as a solvent.

The characteristic data of Compound 643-1 was: $^1$H NMR (500 MHz, DMSO) δ 10.60 (s, 1H), 8.00 (s, 1H), 7.88 (s, 1H), 6.44 (s, 2H), 5.73 (d, J=5.3 Hz, 1H), 5.69 (d, J=1.7 Hz, 1H), 5.02 (t, J=5.4 Hz, 1H), 4.31 (t, J=4.4 Hz, 1H), 3.89-3.85 (m, 1H), 3.72-3.67 (m, 1H), 3.55-3.46 (m, 1H), 3.11-2.93 (m, 2H), 2.65-2.58 (m, 1H), 2.41 (dd, J=15.2, 8.3 Hz, 1H), 2.18 (dd, J=15.2, 8.3 Hz, 1H), 1.40-1.35 (m, 2H), 1.27-1.20 (m, 6H), 0.85 (t, J=6.8 Hz, 3H).

According to the reaction route, Compound 643 (ammonium salt) was prepared from Compound 643-1 using the procedure for preparation of Compound 139.

The characteristic data of the Compound 643 was: MS (m/z): 1269.08[M−1]$^−$. $^1$H NMR (500 MHz, D$_2$O) δ 9.17 (s, 1H), 8.61 (s, 1H), 8.33 (s, 1H), 8.07 (s, 1H), 6.13 (s, 1H), 5.81 (m, 2H), 4.95 (br, 1H), 4.57-4.44 (m, 5H), 4.35 (m, 2H), 4.27 (m, 2H), 4.20-4.16 (m, 3H), 4.02 (s, 3H), 3.47 (s, 3H), 3.08 (m, 2H), 2.67 (s, 1H), 2.47 (m, 2H), 1.38 (m, 2H), 1.13 (m, 6H), 0.75 (m, 3H); $^{31}$P NMR (202 MHz, D$_2$O) δ-0.90 (s, 1H), −11.61 (m, 2P), −22.74 (m, 1P).

Example 15 Synthesis of Compound 633

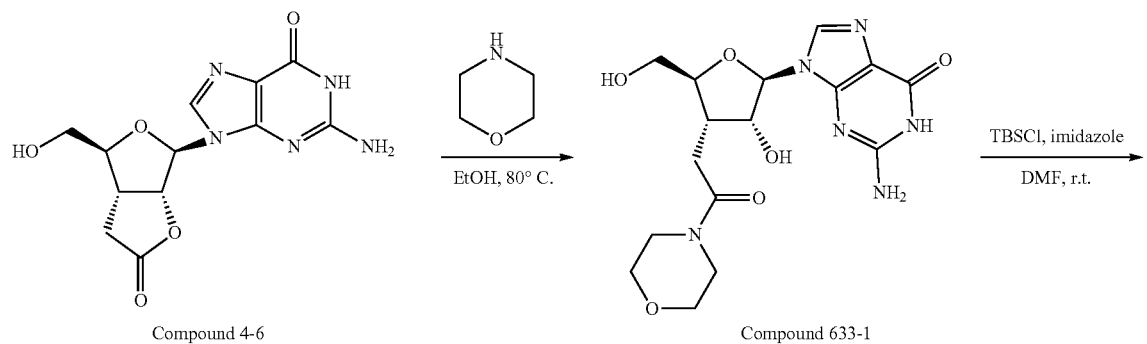

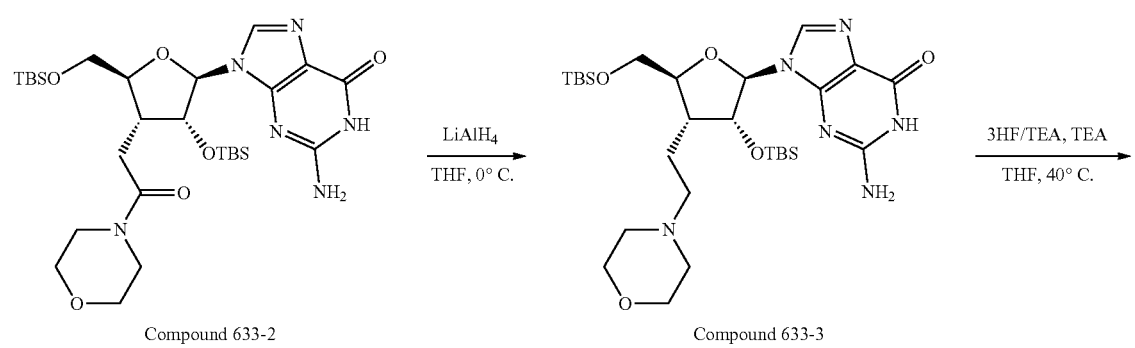

389 -continued 390
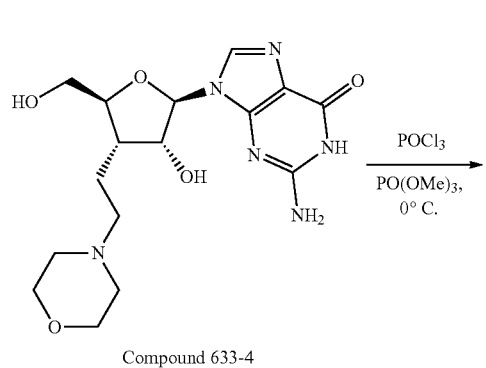
Compound 633-4
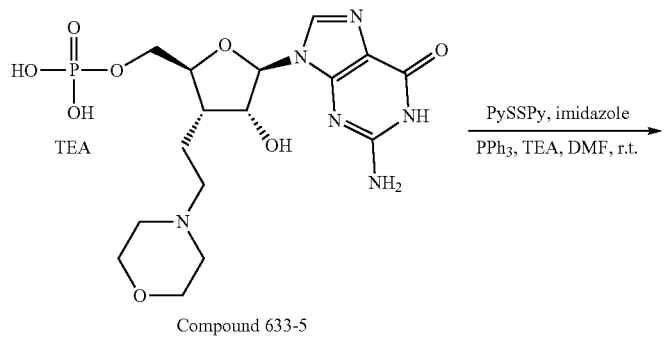
Compound 633-5
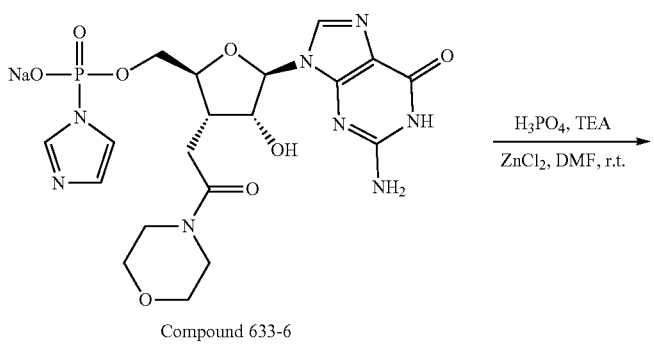
Compound 633-6
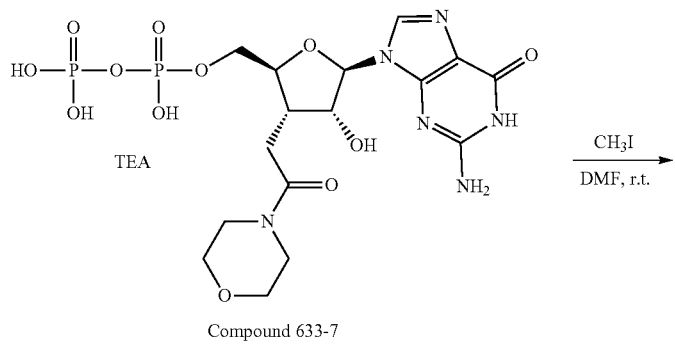
Compound 633-7
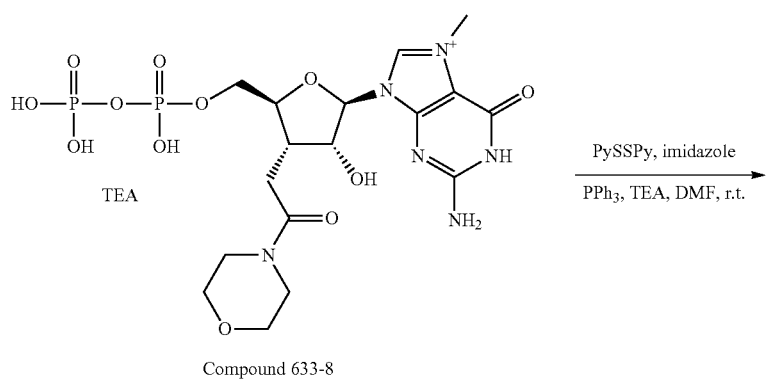
Compound 633-8

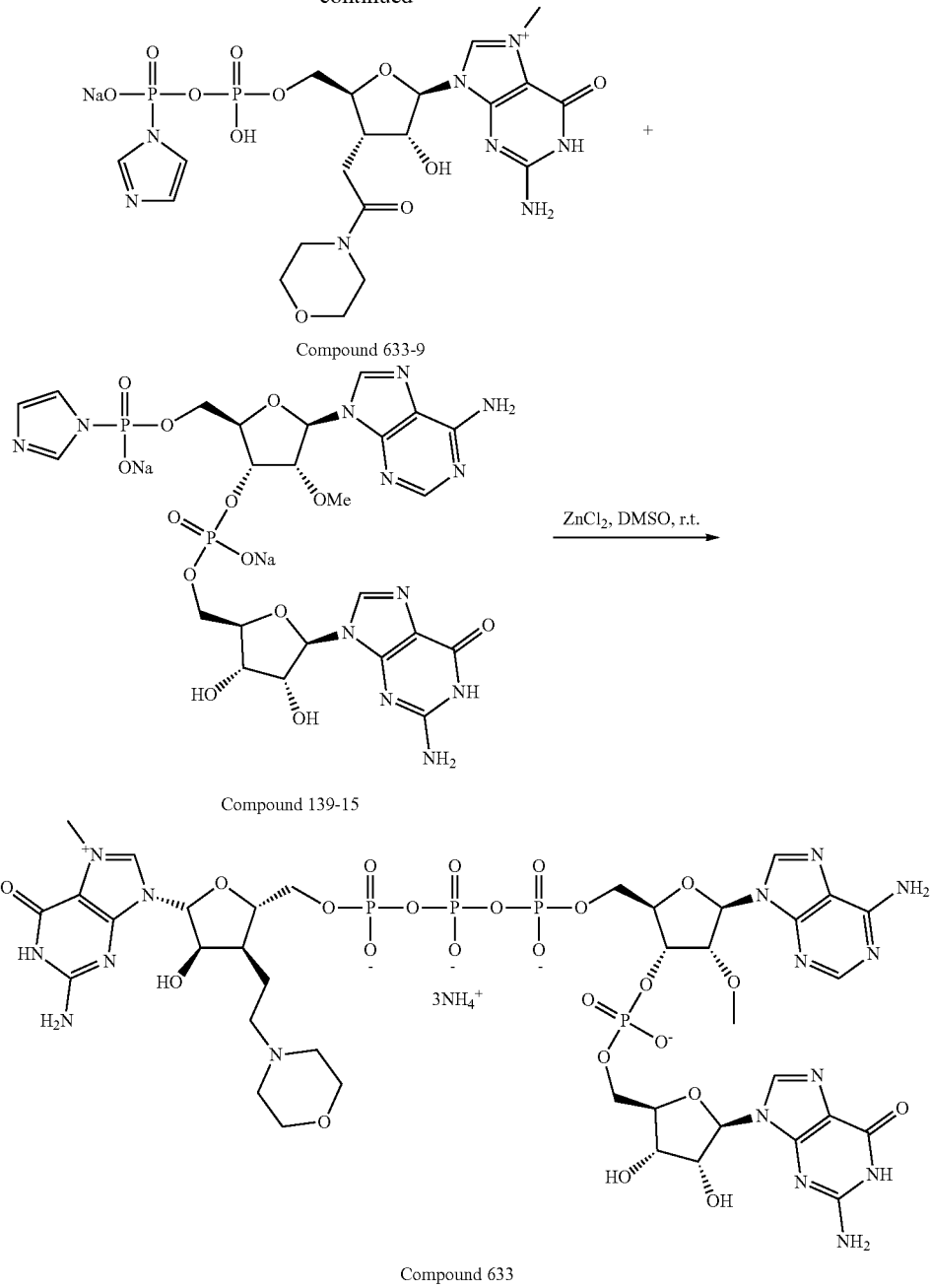

Compound 633

According to the reaction route, Compound 633-1 was prepared from Compound 4-6 using the procedure for preparation of Compound 4-7, except substituting dimethylamine with morpholine.

TBSCl (2.50 g, 18.97 mmol) was added to the solution of Compound 633-1 (1.87 g, 4.74 mmol), imidazole (1.61 g, 23.70 mmol) in anhydrous N,N-dimethylformamide (20.0 mL), and the mixture was stirred overnight. The reaction liquid was poured into ice water (100 mL), stirred for 10 min, and filtered by vacuum. The filter cake was washed with water (20 mL*2), and then collected. After the filter cake was purified by column chromatography on silica gel (ethyl acetate/methanol=10/1), 1.88 g of Compound 633-2 was obtained.

Lithium aluminum hydride (0.21 g, 5.55 mmol) was added in batches to a suspension of Compound 633-2 (1.728 g, 2.77 mmol) in anhydrous tetrahydrofuran (55.0 mL) under the nitrogen atmosphere protection at 0° C. After addition, the mixture was stirred overnight. Water (2.0 mL) was dropwise added to the reaction system in an ice bath and stirred for 10 min, followed by addition of anhydrous sodium sulfate (4.0 g). Then, the mixture was stirred for 10 min, filtered by vacuum. The filter cake was washed with tetrahydrofuran (20 mL*3), and the filtrate was collected to concentrate under reduced pressure. The residue was purified by column chromatography on silica gel (dichloromethane/methanol=8/1) to obtain 1.52 g of Compound 633-3.

Triethylamine (2.1 mL, 14.76 mmol) and triethylamine trihydrofluoride (2.4 mL, 14.76 mmol) were successively added to a solution of Compound 633-3 (1.50 g, 2.46 mmol) in tetrahydrofuran (15.0 mL) at room temperature. After the temperature was increased to 40° C., the mixture was stirred overnight. Subsequently, the reaction liquid was concentrated under reduced pressure to obtain residue, which were purified by C18 column chromatography (acetonitrile/water), to obtain 0.64 g of Compound 633-4.

The characteristic data of Compound 633-4 was: $^1$H NMR (500 MHz, DMSO) δ 10.58 (s, 1H), 8.00 (s, 1H), 6.44 (s, 2H), 5.79 (s, 1H), 5.74 (s, 1H), 5.07-4.95 (m, 1H), 4.24 (d, J=4.7 Hz, 1H), 3.90-3.85 (m, 1H), 3.74 (d, J=12.0 Hz, 1H), 3.60-3.50 (m, 5H), 2.49-2.33 (m, 5H), 2.35-2.27 (m, 2H), 1.75-1.66 (m, 1H), 1.56-1.47 (m, 1H).

According to the reaction route, Compound 633 (ammonium salt) was prepared from Compound 633-4 using the procedure for preparation of Compound 139.

The characteristic data of the Compound 633 was: MS (m/z): 1241.06[M−1]$^-$. $^1$H-NMR (500 MHz, D$_2$O) δ: 8.42 (s, 1H), 8.16 (s, 1H), 7.97 (s, 1H), 6.06 (d, J=6.0 Hz, 1H), 5.91 (s, 1H), 5.85 (d, J=5.7 Hz, 1H), 4.94 (s, 1H), 4.87 (t, J=5.5 Hz, 1H), 4.66 (d, J=4.4 Hz, 1H), 4.54 (t, J=4.3 Hz, 2H), 4.50-4.46 (m, 2H), 4.37 (s, 1H), 4.32-4.30 (m, 2H), 4.26-4.22 (s, 4H), 4.04 (s, 3H), 3.92 (br, 3H), 3.41 (s, 3H), 3.35-3.18 (m, 5H), 2.58-2.52 (m, 1H), 2.09-2.00 (m, 1H), 1.99-1.92 (m, 1H), 1.31 (t, J=7.2 Hz, 2H). $^{31}$P-NMR (202 MHz, D$_2$O) δ: −0.85 (s,1P), −11.36 (m, 2P), −22.74 (m,1P).

Example 16 Synthesis of Compound 309

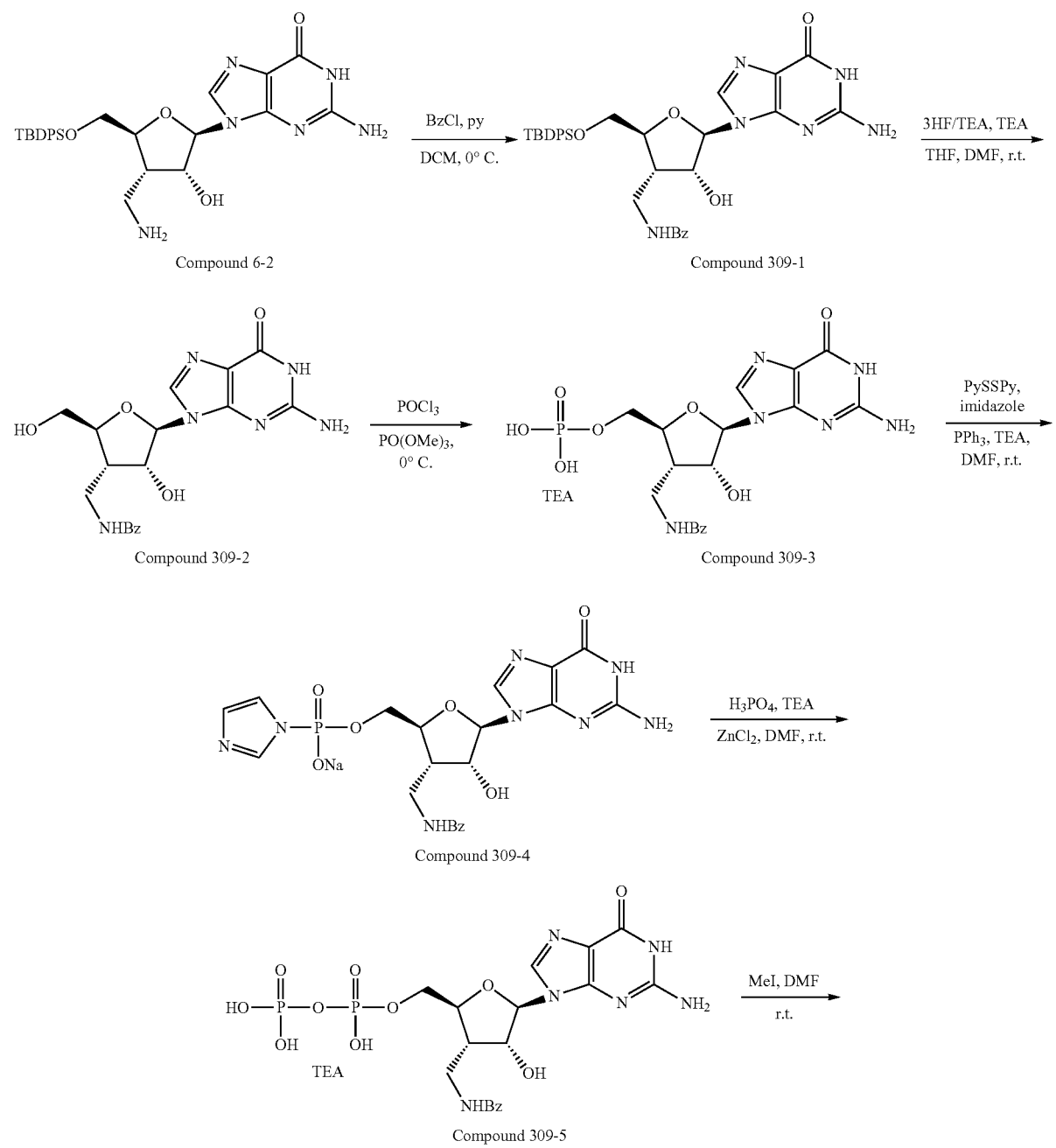

-continued

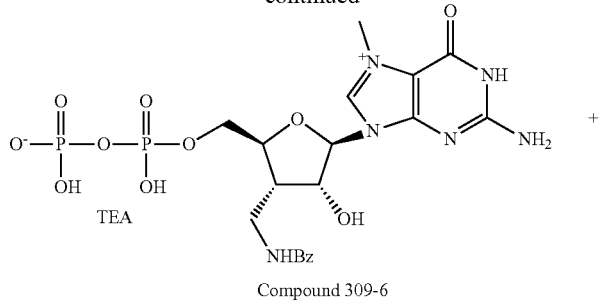

Compound 309-6

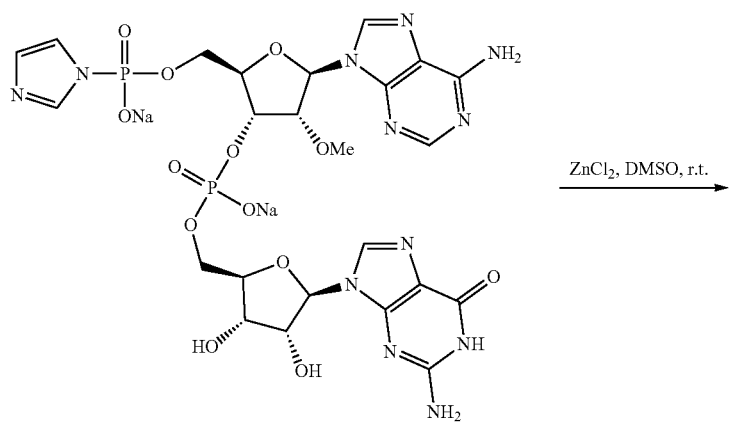

Compound 139-15

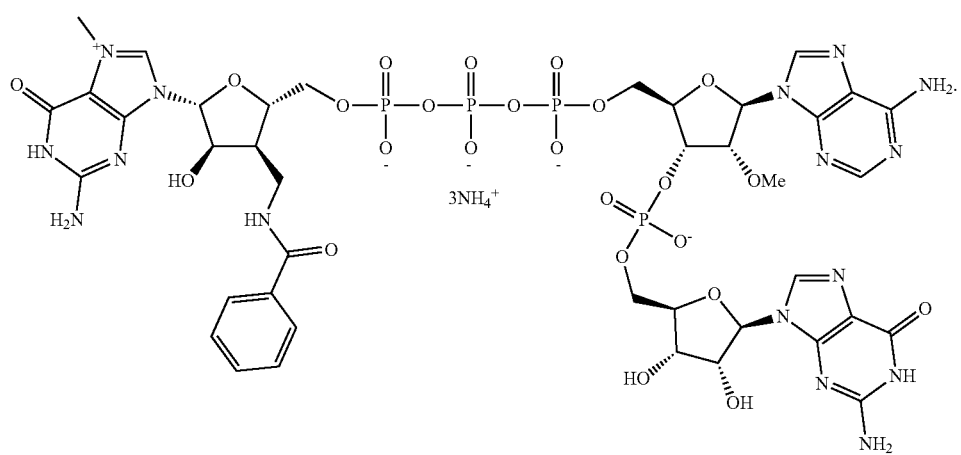

Compound 309

According to the reaction route, Compound 309-2 was prepared from Compound 6-2 using the procedure for preparation of Compound 6-4, except substituting acetyl chloride with benzoyl chloride.

The characteristic data of Compound 309-2 was: $^1$H NMR (400 MHz, DMSO) δ 10.55 (s, 1H), 8.49 (t, J=5.2 Hz, 1H), 8.04 (s, 1H), 7.84 (d, J=7.2 Hz, 2H), 7.54 (t, J=7.3 Hz, 1H), 7.48 (t, J=7.4 Hz, 2H), 6.47 (s, 2H), 5.78 (d, J=3.7 Hz, 2H), 5.13 (t, J=5.1 Hz, 1H), 4.41 (t, J=4.3 Hz, 1H), 4.06-4.00 (m, 0.1H), 3.81-3.73 (m, 1H), 3.65-3.55 (m, 2H), 3.42-3.37 (m, 1H), 2.72-2.62 (m, 1H).

According to the reaction route, Compound 309 (ammonium salt) was prepared from Compound 309-2 using the procedure for preparation of Compound 139.

The characteristic data of the Compound 309 was: MS (m/z): 1261.05[M−1]$^−$. $^1$H NMR (500 MHz, D$_2$O) δ 9.06 (s, 1H), 8.33 (s, 1H), 8.04 (s, 1H), 7.91 (s, 1H), 7.60 (d, J=7.6 Hz, 2H), 7.33 (t, J=7.4 Hz, 1H), 7.25 (t, J=7.6 Hz, 2H), 5.96 (d, J=5.6 Hz, 1H), 5.91 (s, 1H), 5.76 (d, J=5.6 Hz, 1H), 4.90-4.86 (m, 1H), 4.68 (d, J=4.2 Hz, 1H), 4.51-4.47 (m, 3H), 4.39-4.35 (m, 2H), 4.31 (s, 1H), 4.23-4.18 (m, 5H), 3.99 (s, 3H), 3.80-3.75 (m, 1H), 3.44-3.41 (m, 1H), 3.35 (s, 3H), 2.82-2.76 (m, 1H); $^{31}$P NMR (202 MHz, D$_2$O) δ-0.91 (s, 1H), −11.42 (m, 2P), −22.71 (m, 1P).

Example 17 Synthesis of Compound 311
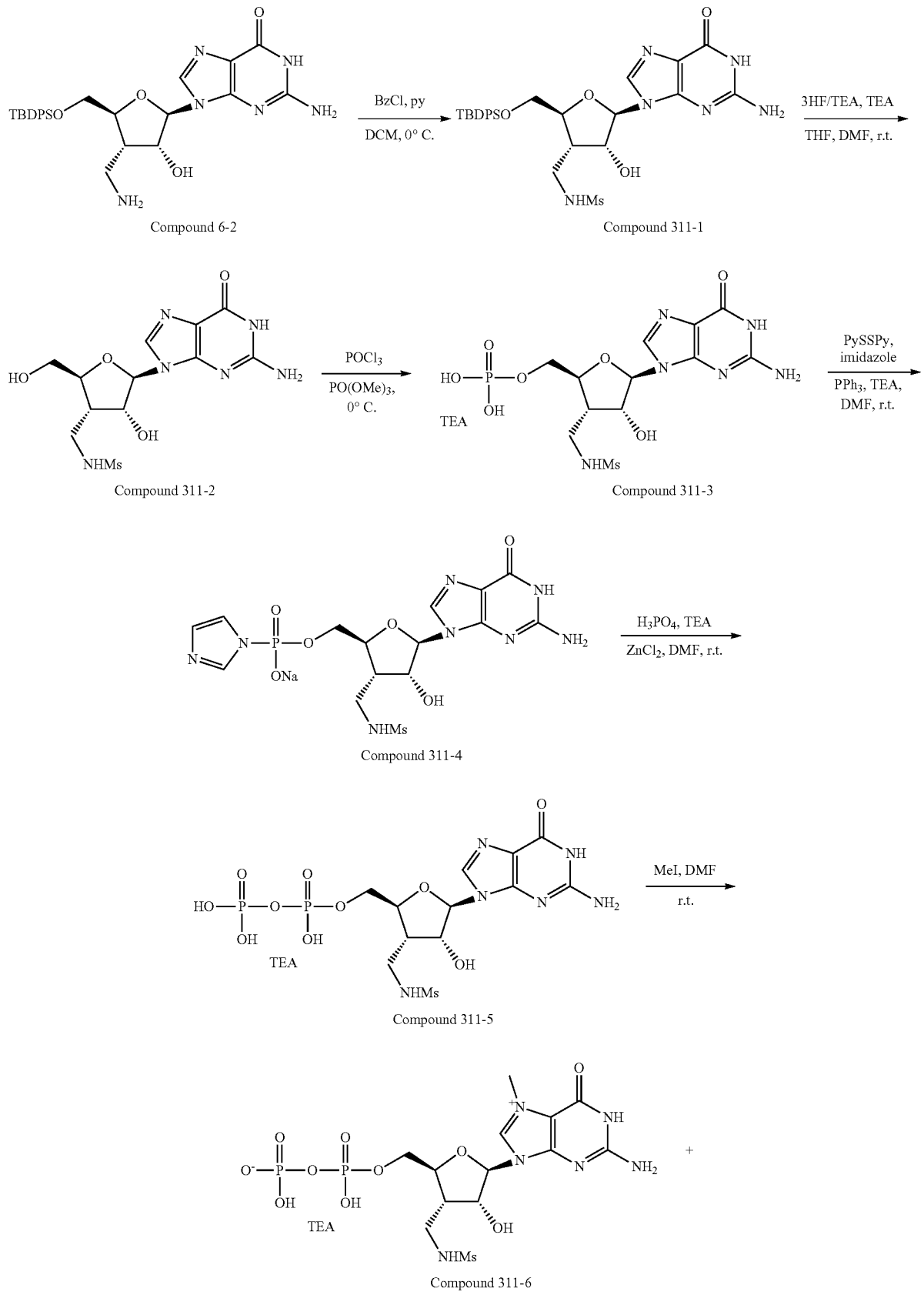

-continued

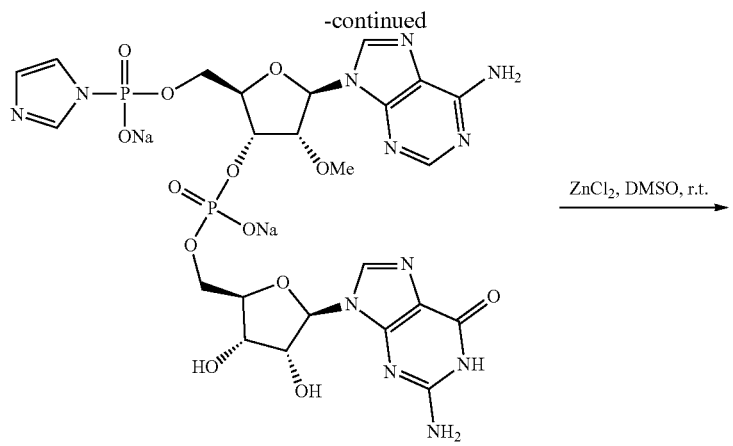

Compound 139-15

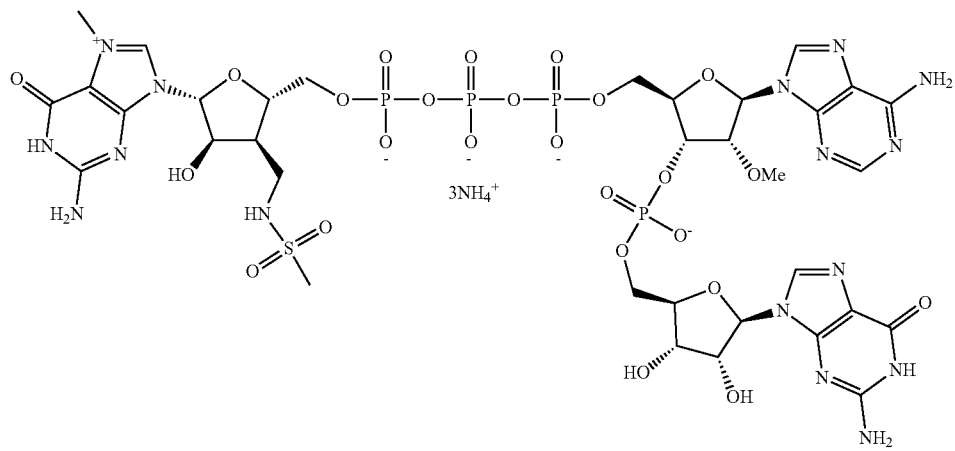

Compound 311

According to the reaction route, Compound 311-2 was prepared from Compound 6-2 using the procedure for preparation of Compound 6-4, except substituting acetyl chloride with methylsulfonyl chloride.

The characteristic data of Compound 311-2 was: $^1$H NMR (500 MHz, DMSO) δ 10.61 (s, 1H), 7.96 (s, 1H), 6.87 (t, J=5.6 Hz, 1H), 6.45 (s, 2H), 5.75 (d, J=5.4 Hz, 1H), 5.71 (d, J=2.0 Hz, 1H), 5.07 (t, J=5.3 Hz, 1H), 4.46-4.44 (m, 1H), 3.97-3.94 (m, 1H), 3.73-3.69 (m, 1H), 3.57-3.52 (m, 1H), 3.28-3.22 (m, 1H), 3.06-3.01 (m, 1H), 2.92 (s, 3H), 2.54-2.50 (m, 1H).

According to the reaction route, Compound 311 (ammonium salt) was prepared from Compound 311-2 using the procedure for preparation of Compound 139.

The characteristic data of the Compound 311 was: MS (m/z): 1235.05 [M−1]$^-$. H NMR (500 MHz, D$_2$O) δ 9.06 (s, 1H), 8.36 (s, 1H), 8.14 (s, 1H), 7.99 (s, 1H), 6.04 (d, J=5.6 Hz, 1H), 5.83 (s, 1H), 5.76 (d, J=5.6 Hz, 1H), 4.90-4.86 (m, 1H), 4.68 (d, J=4.3 Hz, 1H), 4.50-4.45 (m, 3H), 4.39-4.35 (m, 2H), 4.31 (s, 1H), 4.23-4.15 (m, 5H), 3.99 (s, 3H), 3.69-3.65 (m, 1H), 3.37-3.33 (m, 4H), 3.35 (s, 3H), 2.90 (s, 3H), 2.52-2.49 (m, 1H); $^{31}$P NMR (202 MHz, D$_2$O) δ-0.91 (s, 1H), −11.48 (m, 2P), −22.92 (m, 1P).

Example 18 Synthesis of Compound 299
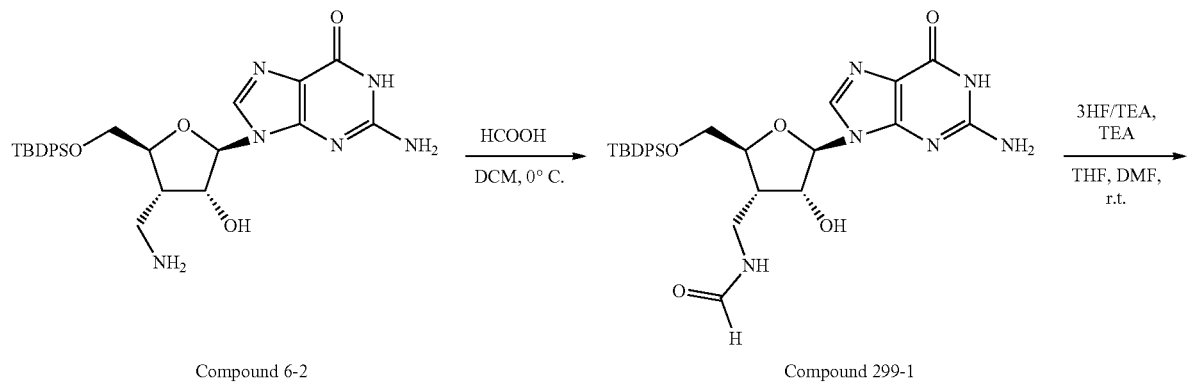
Compound 6-2 → Compound 299-1
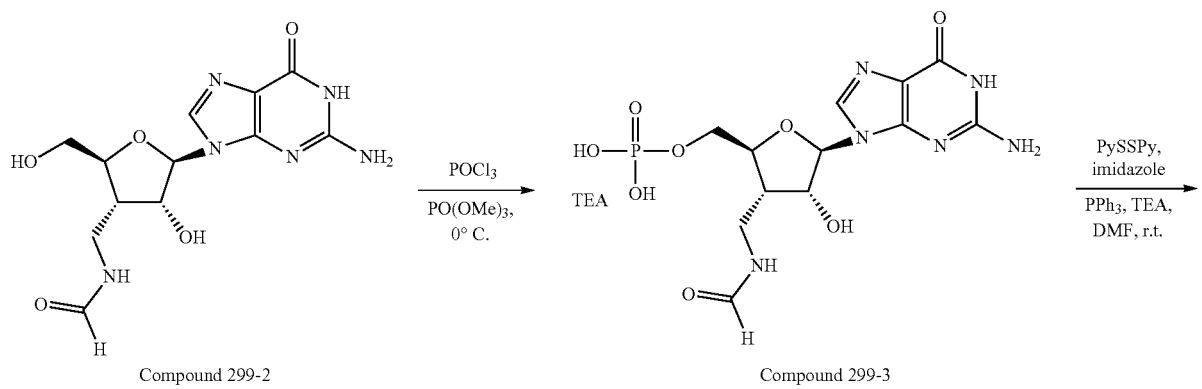
Compound 299-2 → Compound 299-3
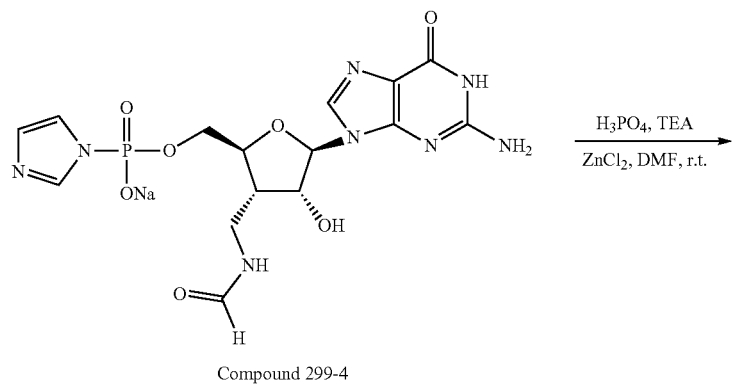
Compound 299-4
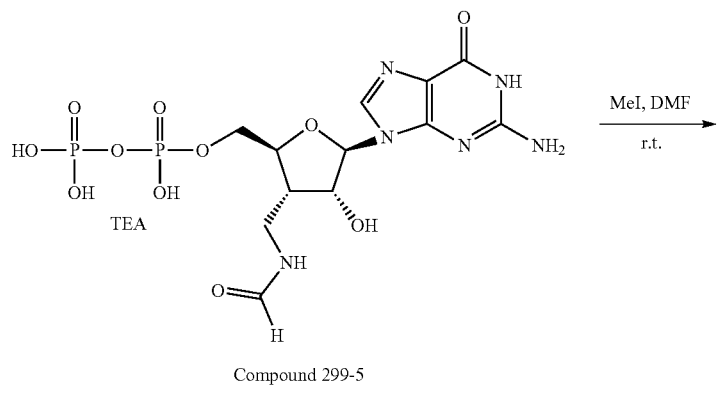
Compound 299-5

-continued

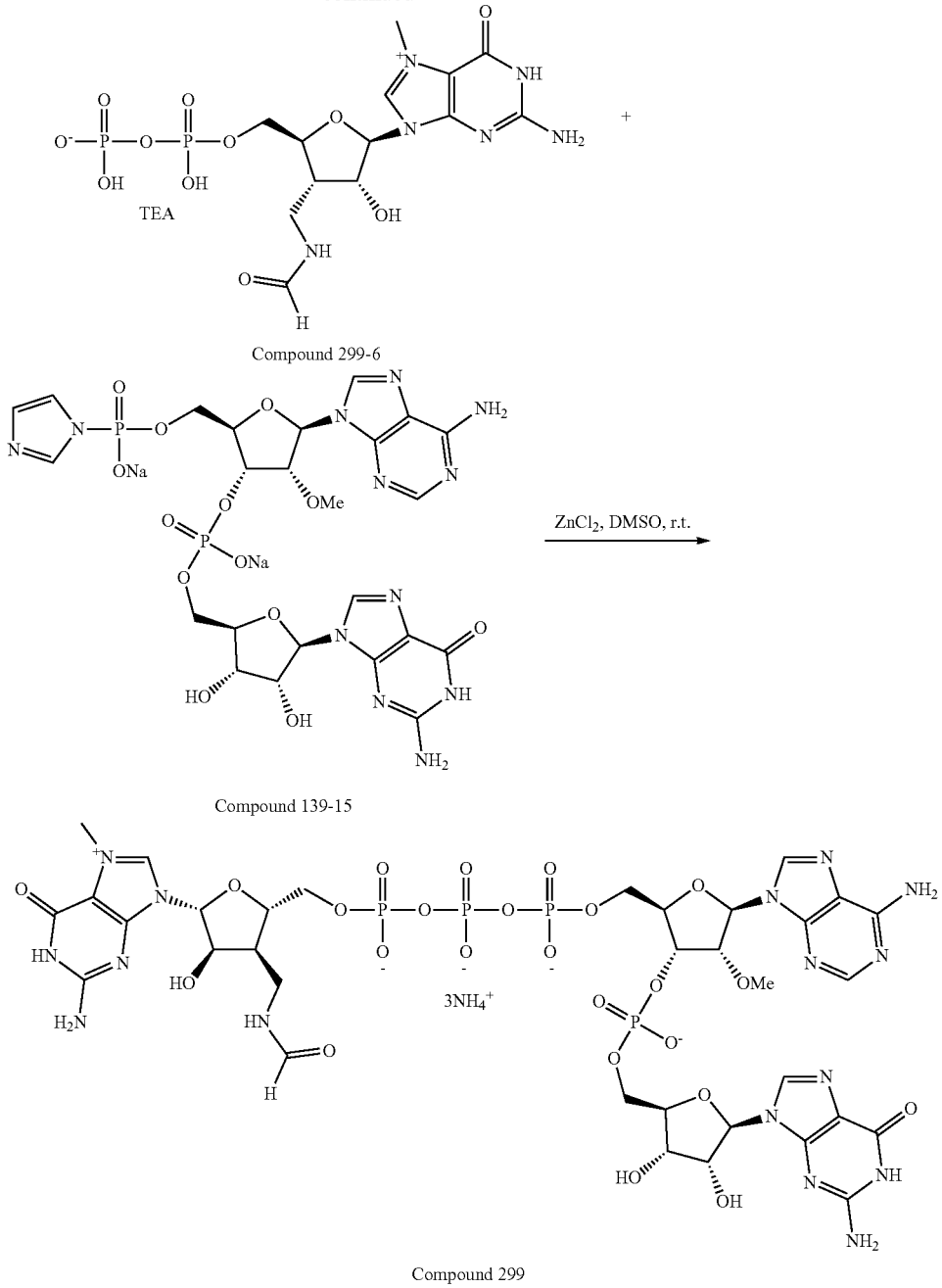

Compound 299-6

Compound 139-15

Compound 299

According to the above reaction route, formic acid (127 µL, 3.37 mmol) and EDCI (0.81 g, 4.21 mmol) were successively added to a solution of Compound 6-2 (1.50 g, 2.81 mmol), HOBT (0.46 g, 3.37 mmol), and triethylamine (0.78 mL, 5.61 mmol) in anhydrous N,N-dimethylformamide (42 mL) under the nitrogen atmosphere protection at room temperature, and the mixture was stirred overnight. Then, the reaction liquid was poured into ice water (160 mL), stirred for 10 min, and filtered by vacuum. The filter cake was washed with water (20 mL), collected, and purified by column chromatography on silica gel (dichloromethane/methanol=8/1) to obtain 0.86 g of Compound 299-1.

Triethylamine trihydrofluoride (0.5 mL, 3.06 mmol) and triethylamine (0.4 mL, 3.06 mmol) were successively added to a solution of Compound 299-1 (0.86 g, 1.53 mmol) in anhydrous tetrahydrofuran (20 mL) at room temperature. After the temperature was increased to 40° C., the mixture was stirred overnight. The reaction liquid was then concentrated under reduced pressure to obtain residue, which were vigorously stirred with acetonitrile (20 mL) to obtain 0.39 g of Compound 299-2.

The characteristic data of Compound 299-2 was: $^1$H NMR (500 MHz, DMSO) δ 9.46 (s, 1H), 8.11-8.04 (m, 1H), 8.02 (s, 1H), 8.00 (s, 1H), 6.49 (s, 2H), 5.77-5.70 (m, 2H), 5.12-5.05 (m, 1H), 4.38-4.33 (m, 1H), 3.96-3.90 (m, 1H), 3.75-3.69 (m, 1H), 3.58-3.50 (m, 1H), 3.32-3.30 (m, 1H), 3.24-3.17 (m, 1H), 2.50-2.44 (m, 1H).

According to the reaction route, Compound 299 (ammonium salt) was prepared from Compound 299-2 using the procedure for preparation of Compound 139.
The characteristic data of the Compound 299 was: MS (m/z): 1185.4 [M−1]⁻. ¹H NMR (500 MHz, D₂O) δ 8.39 (s, 1H), 8.13 (s, 1H), 8.06 (s, 1H), 8.03 (s, 1H), 6.01 (d, J=5.6 Hz, 1H), 5.85-5.83 (m, 2H), 4.92-4.89 (m, 1H), 4.73-4.71 (m, 1H), 4.59 (d, J=3.9 Hz, 1H), 4.50-4.44 (m, 3H), 4.40-4.38 (m, 1H), 4.36-4.33 (m, 2H), 4.24-4.14 (m, 5H), 3.99 (s, 3H), 3.59-3.55 (m, 1H), 3.42 (s, 3H), 3.35-3.31 (m, 1H), 2.61-2.55 (m, 1H); ³¹P NMR (202 MHz, D₂O) δ-1.03 (s, 1H), −11.29 (m, 2P), −22.04 (m, 1P).
Example 19 Synthesis of Compound 219
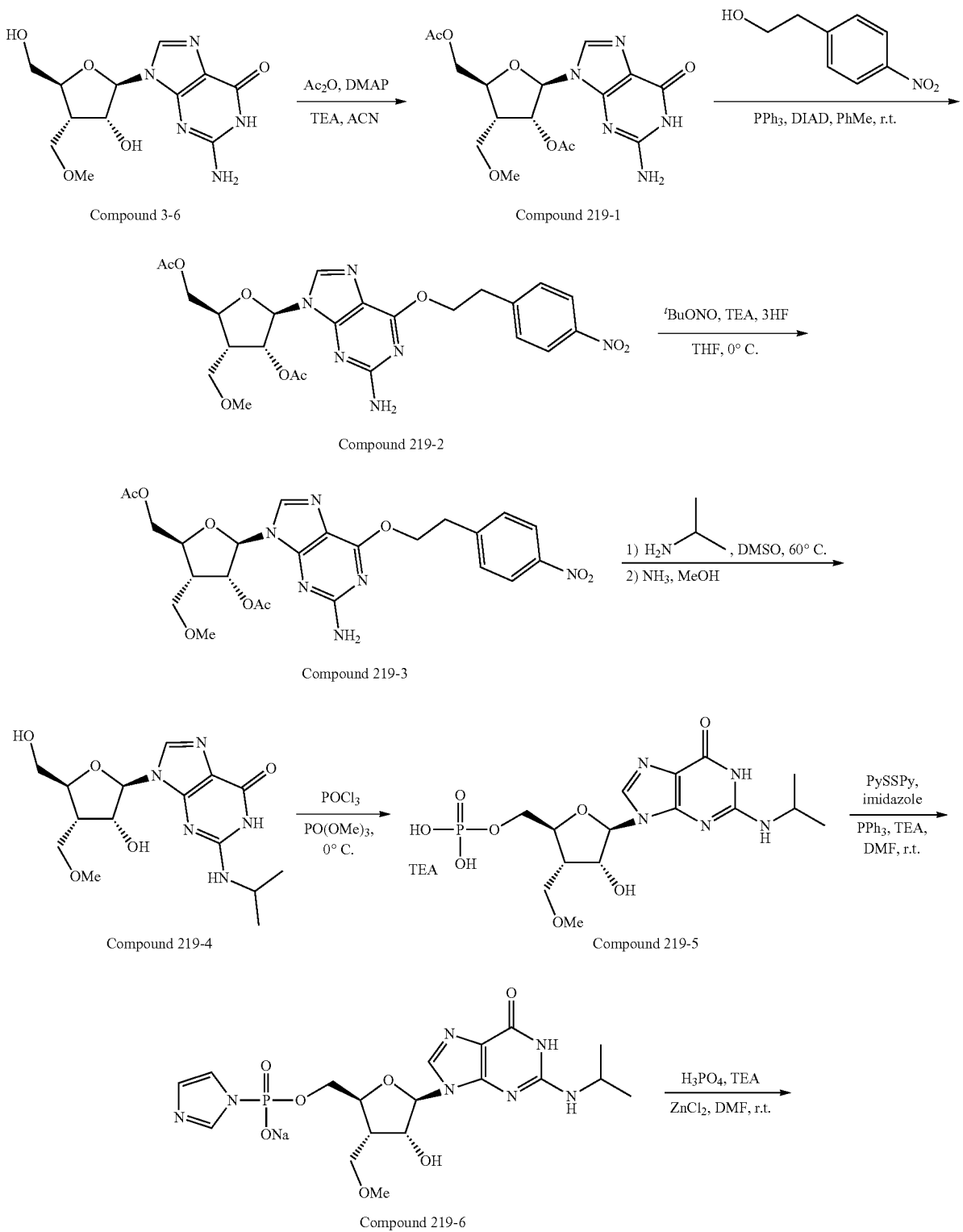

-continued
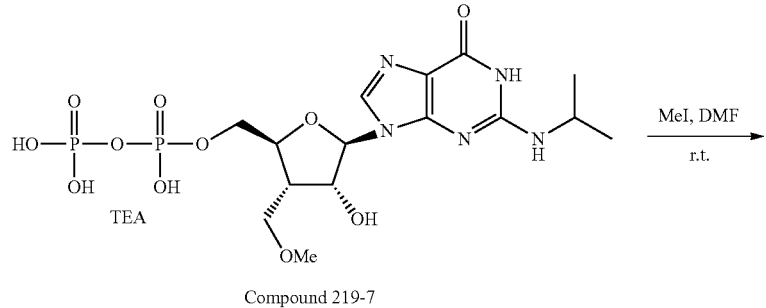
Compound 219-7
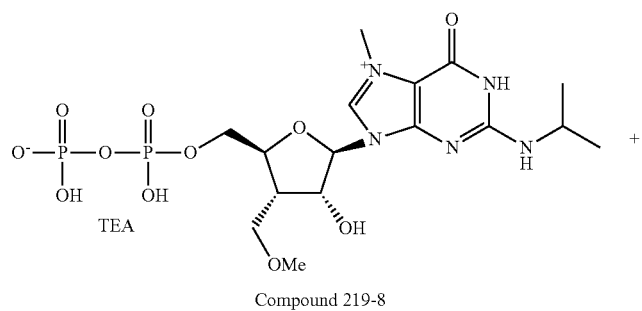
Compound 219-8
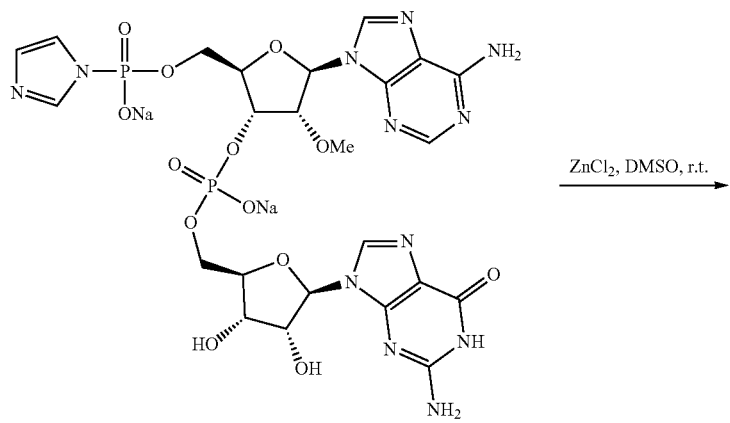
Compound 139-15
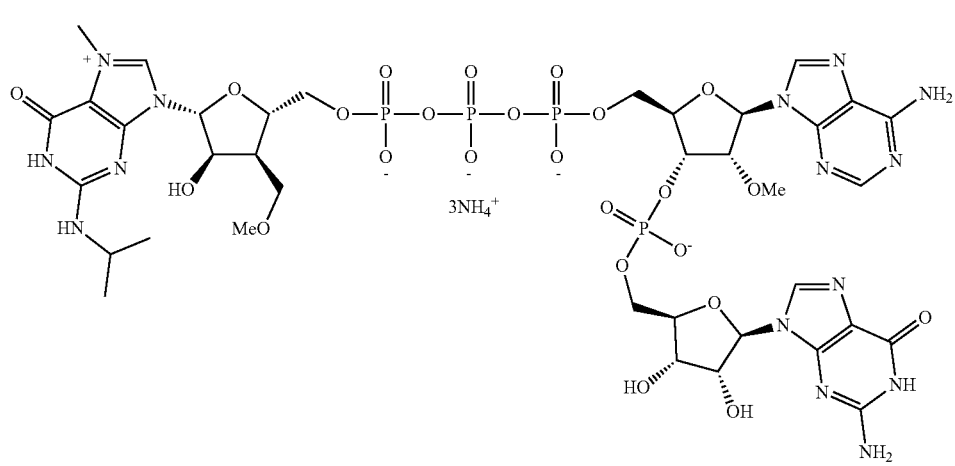
Compound 219

According to the above reaction route, acetic anhydride (3.3 mL, 35.33 mmol) was dripped into a suspension of Compound 3-6 (5.00 g, 16.06 mmol), DMAP (0.20 g, 1.61 mmol), and triethylamine (18 mL, 128.48 mmol) in anhydrous acetonitrile (65 mL) in an ice bath under the nitrogen atmosphere protection. After addition, the temperature was naturally increased to room temperature and the mixture was stirred overnight. Then the reaction liquid was concentrated under reduced pressure to obtain residue, which were vigorously stirred with methanol (50 mL) to obtain 5.50 g of Compound 219-1.

P-nitrobenzene ethanol (3.42 g, 20.49 mmol) and triphenylphosphine (7.16 g, 27.32 mmol) were successively added to a suspension of Compound 219 (5.40 g, 13.66 mmol) in methylbenzene (140 mL) under the nitrogen atmosphere protection at room temperature, and the mixture was stirred for 30 min. Then, DLAD (5.4 mL, 27.32 mmol) was gradually dripped into the reaction system. After addition, the mixture was stirred for 22 hours. The reaction liquid was then concentrated under reduced pressure to obtain residue, which were purified by column chromatography on silica gel (ethyl acetate) to obtain 4.00 g of Compound 219-2.

Triethylamine trihydrofluoride salt (36 mL) was added to a solution of Compound 219-2 (3.90 g, 7.16 mmol) in anhydrous tetrahydrofuran (30 mL) under the nitrogen atmosphere protection in an ice bath, and the mixture was stirred for 5 min. Then, tert-butyl nitrite (2.1 mL, 17.90 mmol) was gradually dripped into the reaction system. After addition, the mixture was stirred for 2 hours under a constant temperature. Saturated sodium bicarbonate aqueous solution was dropwise added to the system for regulating pH to neutralization. Subsequently, water (100 mL) was added, and the liquid was extracted with ethyl acetate (40 mL), dried over anhydrous sodium sulfate, concentrated under reduced pressure to obtain residue, which were purified by column chromatography on silica gel (petroleum ether/ethyl acetate=⅓) to obtain 2.25 g of Compound 219-3.

Isopropylamine (1.7 mL, 19.55 mmol) was added to a solution of Compound 219-3 (2.14 g, 3.91 mmol) in anhydrous dimethyl sulfoxide (15 mL) at room temperature. The temperature was increased to 65° C. in a sealed atmosphere, and the mixture was stirred overnight. After the temperature was cooled to room temperature, a solution of ammonia in methanol (30 mL) was added, and the mixture was reacted for 5 hours at room temperature in a sealed atmosphere. The reaction liquid was concentrated under reduced pressure to obtain residue, which was purified by column chromatography on silica gel (dichloromethane/methanol=7/1) to obtain 1.26 g of Compound 219-4.

The characteristic data of Compound 219-4 was: $^1$H NMR (500 MHz, DMSO) δ 10.22 (s, 1H), 7.94 (s, 1H), 6.25 (d, J=7.4 Hz, 1H), 5.72 (d, J=2.0 Hz, 1H), 5.68 (d, J=5.2 Hz, 1H), 4.90 (t, J=5.5 Hz, 1H), 4.53-4.49 (m, 1H), 4.05-3.95 (m, 2H), 3.73-3.67 (m, 1H), 3.63-3.58 (m, 1H), 3.53-3.47 (m, 1H), 3.44-3.40 (m, 1H), 3.27 (s, 3H), 2.65-2.59 (m, 1H), 1.18 (d, J=2.6 Hz, 3H), 1.17 (d, J=2.6 Hz, 3H).

According to the reaction route, Compound 219 (ammonium salt) was prepared from Compound 219-4 using the procedure for preparation of Compound 139.

The characteristic data of the Compound 219 was: MS (m/z): 1214.05[M−1]$^-$. $^1$H NMR (500 MHz, D$_2$O) δ 9.12 (s, 1H), 8.55 (s, 1H), 8.29 (s, 1H), 8.04 (s, 1H), 6.06 (d, J=5.1 Hz, 1H), 5.89 (s, 1H), 5.80 (d, J=5.7 Hz, 1H), 4.95-4.92 (m, 1H), 4.84-4.83 (m, 1H), 4.52 (s, 1H), 4.49-4.44 (m, 3H), 4.37-4.34 (m, 3H), 4.26-4.16 (m, 3H), 4.11-4.09 (m, 1H), 4.06-4.05 (m, 1H), 4.03 (s, 3H), 3.71-3.68 (m, 1H), 3.61-3.58 (m, 1H), 3.45 (s, 3H), 3.34 (s, 3H), 2.66-2.60 (m, 1H), 1.25 (d, J=6.6 Hz, 3H), 1.20 (d, J=6.5 Hz, 3H); $^1$P NMR (202 MHz, D$_2$O) δ-0.95 (s, 1H), −11.60 (m, 2P), −22.72 (m, 1P).

Example 20 Synthesis of Compound 110

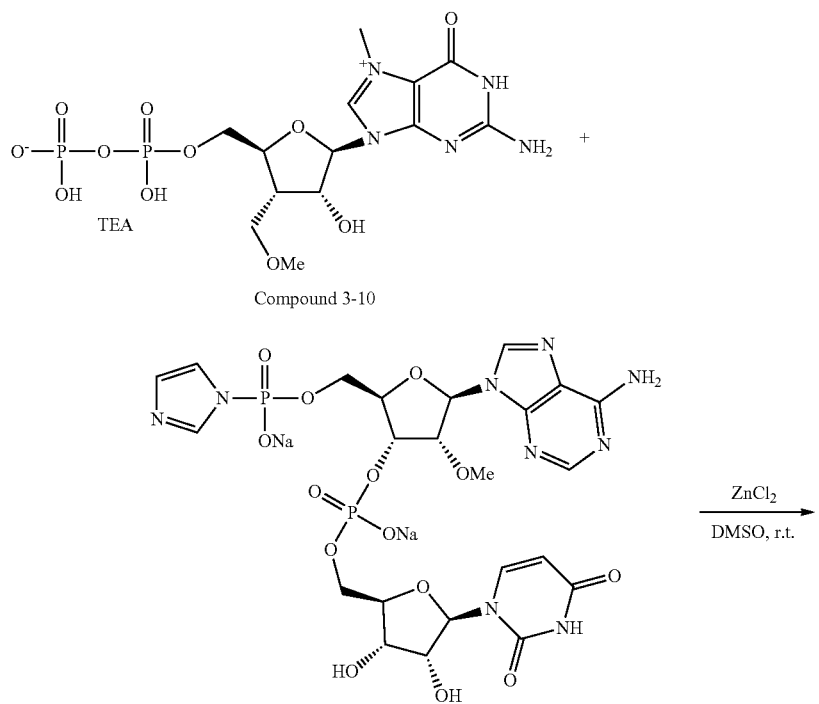

Compound 3-10

Compound 110-1

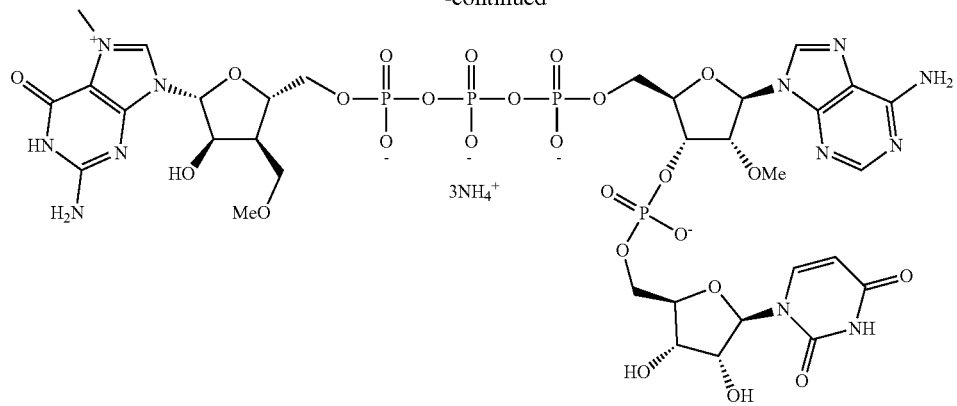

Compound 110

According to the reaction route, Compound 110 (ammonium salt) was prepared from Compound 3-10 using the procedure for preparation of Compound 139, except substituting Compound 139-15 with Compound 110-1.

The characteristic data of the Compound 110 was: MS (m/z): 1133.07[M−1]⁻. $^1$H NMR (500 MHz, D$_2$O) δ 9.07 (s, 1H), 8.50 (s, 1H), 8.23 (s, 1H), 7.86 (d, J=8.1 Hz, 1H), 6.10 (d, J=5.9 Hz, 1H), 5.91 (d, J=4.8 Hz, 1H), 5.80-5.78 (m, 2H), 4.97-4.90 (m, 1H), 4.65 (d, J=4.9 Hz, 1H), 4.57 (s, 1H), 4.49-4.45 (m, 2H), 4.35-4.22 (m, 7H), 4.16-4.14 (m, 1H), 4.09-4.06 (m, 1H), 4.02 (s, 3H), 3.67-3.64 (m, 1H), 3.57-3.54 (m, 1H), 3.49 (s, 3H), 3.34 (s, 3H), 2.62-2.57 (m, 11H); $^{31}$P NMR (202 MHz, D$_2$O) δ-1.07 (s, 1H), −11.65 (m, 2P), −22.92 (m, 1P).

Example 21 Synthesis of Compound 197

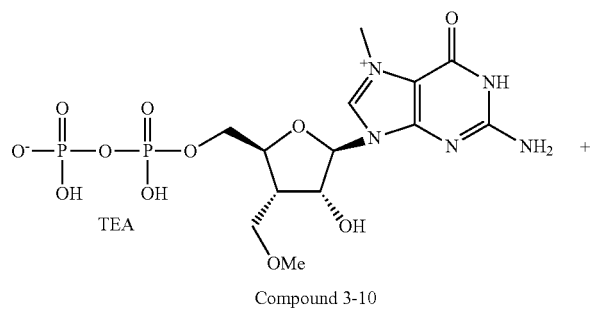

Compound 3-10

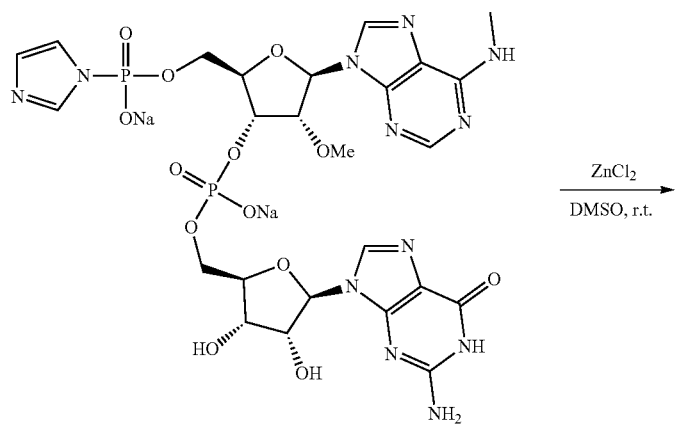

Compound 197-1

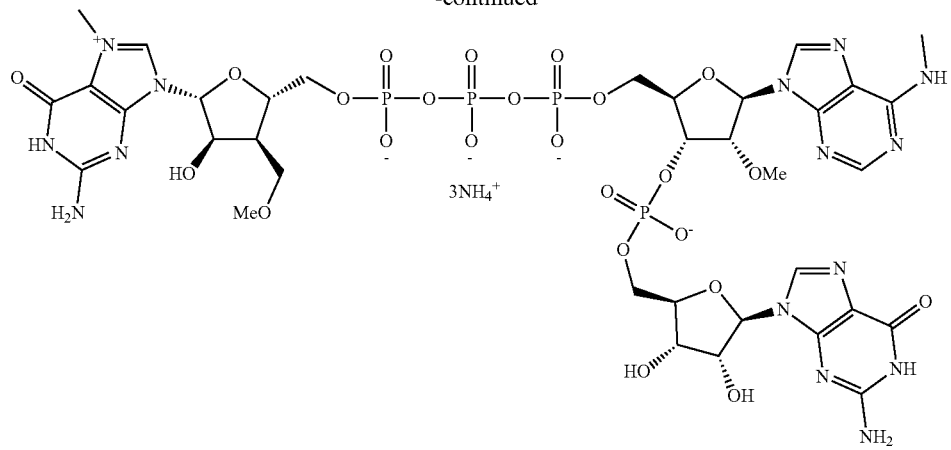

Compound 197

According to the reaction route, Compound 197 (ammonium salt) was prepared from Compound 3-10 using the procedure for preparation of Compound 139, except substituting Compound 139-15 with Compound 197-1.

The characteristic data of the Compound 197 was: MS (m/z): 1186.06[M−1]−. $^1$H NMR (500 MHz, D$_2$O) δ 8.99 (s, 1H), 8.33 (s, 1H), 8.11 (s, 1H), 7.92 (s, 1H), 6.01 (d, J=5.4 Hz, 1H), 5.80 (d, J=5.8 Hz, 1H), 5.79 (s, 1H), 4.94-4.91 (m, 1H), 4.75-4.71 (m, 1H), 4.64 (d, J=4.9 Hz, 1H), 4.51 (m, 11H), 4.48-4.45 (m, 1H), 4.41 (t, J=5.0 Hz, 1H), 4.34-4.23 (m, 4H), 4.20-4.17 (m, 2H), 4.08-4.05 (m, 1H), 3.98 (s, 3H), 3.66-3.63 (m, 1H), 3.56-3.53 (m, 1H), 3.46 (s, 3H), 3.33 (s, 3H), 3.08 (s, 3H), 2.60-2.54 (in, 1H); $^{31}$P NMR (202 MHz, D$_2$O) δ-0.92 (s, 1H), −11.65 (m, 2P), −22.90 (m, 1P).

Example 22 Synthesis of Compound 195

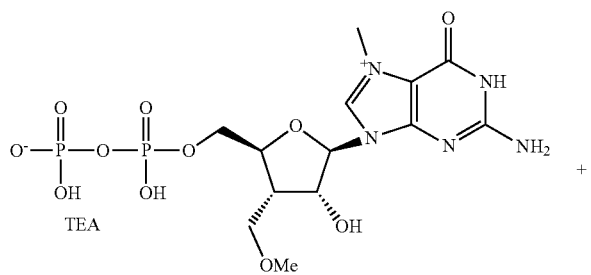

Compound 3-10

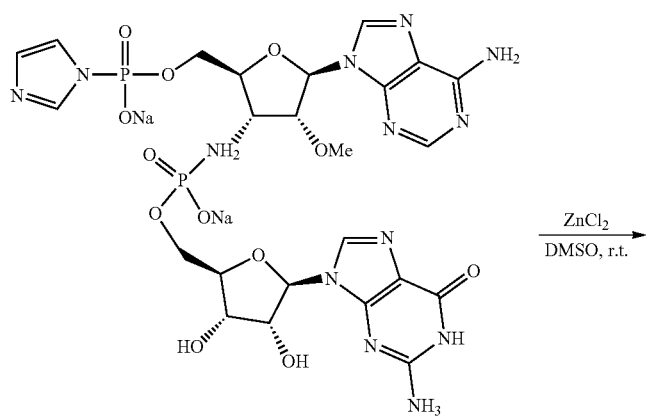

Compound 195-1

-continued

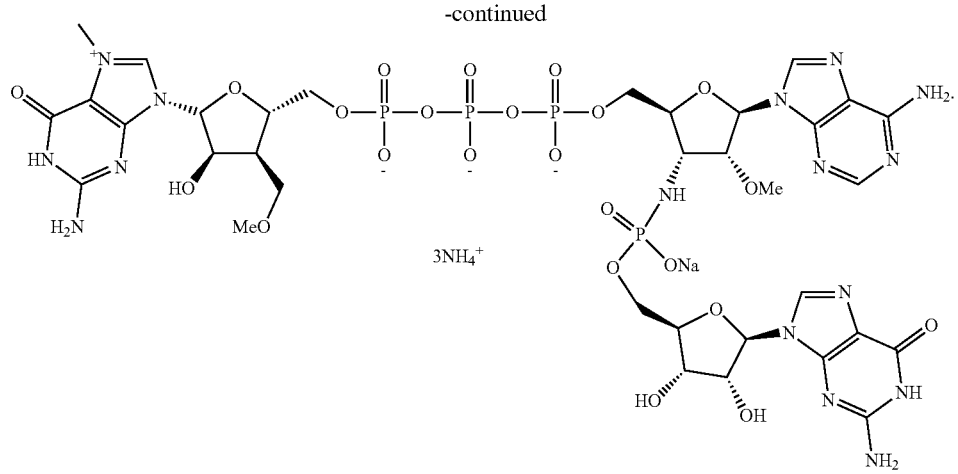

Compound 195

According to the reaction route, Compound 195 (ammonium salt) was prepared from Compound 3-10 using the procedure for preparation of Compound 139, except substituting Compound 139-15 with Compound 195-1.

The characteristic data of the Compound 195 was: MS (m/z): 1171.04[M−1]⁻. $^1$H NMR (500 MHz, D$_2$O) δ 9.15 (s, 1H), 8.52 (s, 1H), 8.25 (s, 1H), 7.94 (s, 1H), 6.14 (s, 1H), 5.72 (s, 1H), 5.64 (d, J=5.3 Hz, 1H), 4.63-4.61 (m, 2H), 4.54-4.49 (m, 2H), 4.39 (t, J=4.8 Hz, 1H), 4.34-4.30 (m, 3H), 4.19-4.17 (m, 1H), 4.14-4.11 (m, 2H), 4.05-4.00 (m, 5H), 3.91-3.86 (m, 1H), 3.70-3.67 (m, 4H), 3.61-3.58 (m, 1H), 3.34 (s, 3H), 2.67-2.61 (m, 1H); $^{31}$P NMR (202 MHz, D$_2$O) δ 6.53 (s, 1H), −11.52 (m, 2P), −22.61 (m, 1P).

Example 23 Synthesis of Compound 171

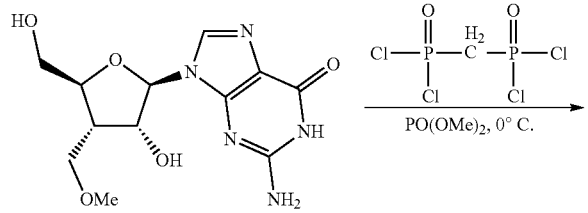

Compound 3-6

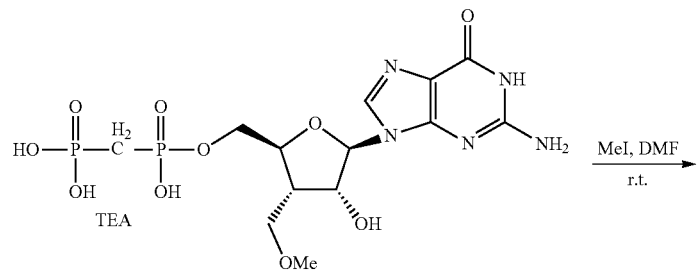

Compound 171-1

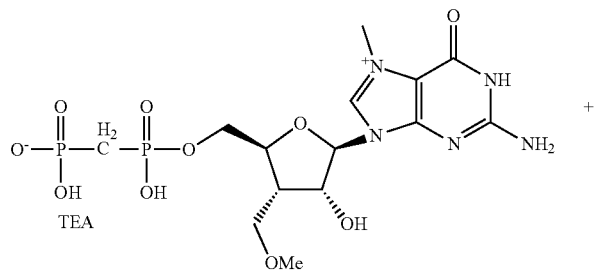

Compound 171-2

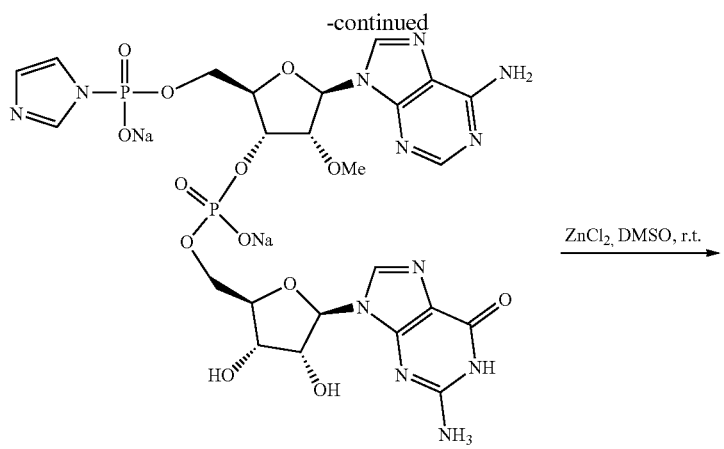

Compound 139-15

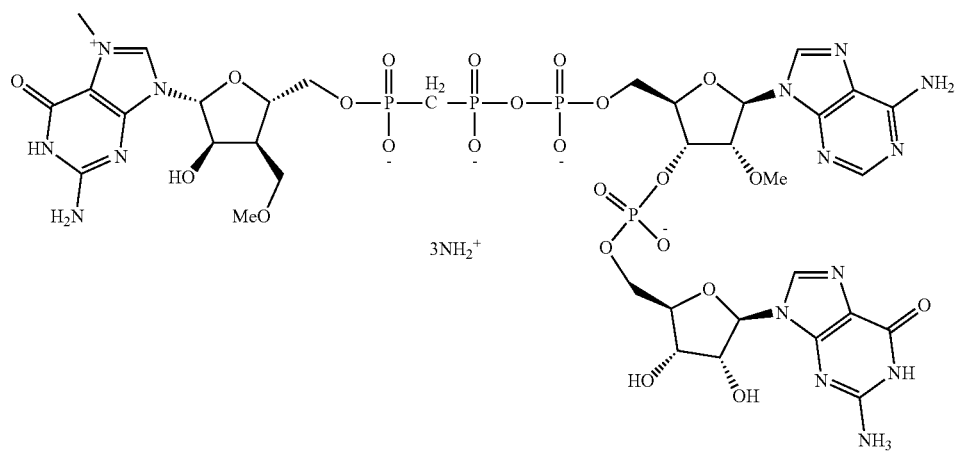

Compound 171

According to the above synthetic route, Compound 3-6 (1 g, 3.2 mmol) was added into a two-neck flask, and trimethyl phosphate (15 mL) was added to the flask. Subsequently, the temperature was cooled to 0° C., and methylene bis(phosphonic dichloride) (1.61 g, 6.43 mmol) was added under the argon atmosphere protection. After addition, the mixture was reacted for 3 hours. HPLC showed that the reaction was completed and the reaction was stopped. Sodium bicarbonate aqueous solution (269 mg in 2 ml water) was added. After addition, the mixture was reacted at room temperature for 5 min. The reaction liquid was concentrated under reduced pressure to remove water, followed by addition of methyl tertiary butyl ether (2*30 mL). The liquid was sonicated for 2 min, and then the supernatant was removed. The residue was separated through C18 column, purified by ion exchange column, and freeze-dried to obtain 1.9 g of Compound 171-1 (triethylamine salt).

Compound 171 (ammonium salt) was prepared using the procedure for preparation of Compound 139, except substituting Compound 139-13 with Compound 171-1.

The characteristic data of the Compound 171 was: LC-MS[M-H]: 1170.11. $^1$H-NMR (500 MHz, D$_2$O) δ: 9.35 (s, 1H), 8.51 (s, 1H), 8.22 (s, 1H), 7.96 (s, 1H), 6.09 (d, J=4.8 Hz, 1H), 5.82 (s, 1H), 5.78 (d, J=5.6 Hz, 1H), 4.93-4.89 (m, 1H), 4.76-4.72 (m, 1H), 4.67 (d, J=5.0 Hz, 1H), 4.50-4.48 (m, 2H), 4.41-4.39 (m, 2H), 4.37-4.35 (m, 1H), 4.33 (m, 2H), 4.23-4.20 (m, 3H), 4.10-4.07 (m, 1H), 3.99 (s, 3H), 3.71-3.67 (m, 1H), 3.62-3.58 (m, 1H), 3.46 (s, 3H), 3.35 (s, 3H), 2.72-2.67 (m, 1H), 2.56-2.38 (m, 2H). $^{31}$P-NMR (202 MHz, D$_2$O) δ: 16.88 (d, J=8.2 Hz,1P), 7.65 (dd, J=25.2, 7.9 Hz,1P), −0.90 (s,1P), −11.28 (d, J=25.9 Hz,1P).

Example 24 Synthesis of Compound 173
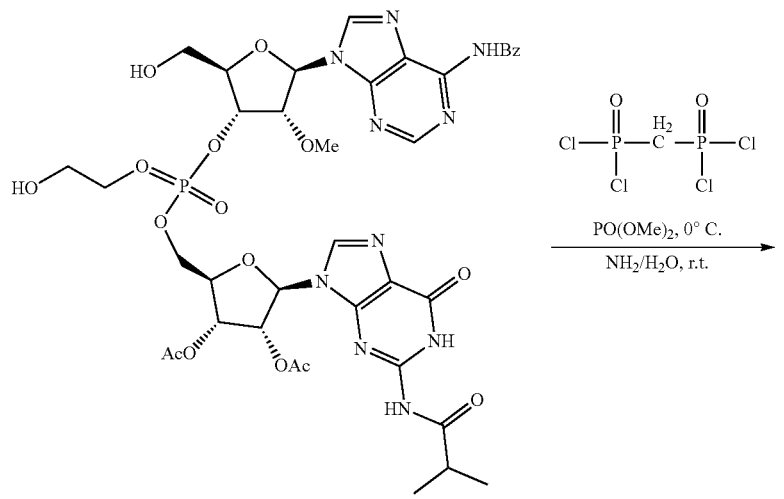
Compound 173-1
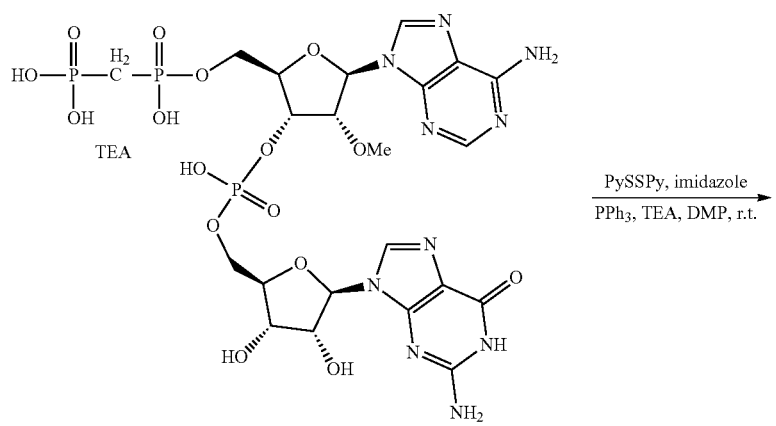
Compound 173-2
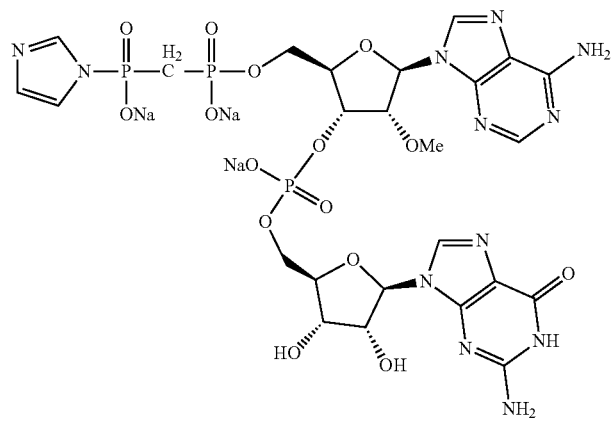
Compound 173-3

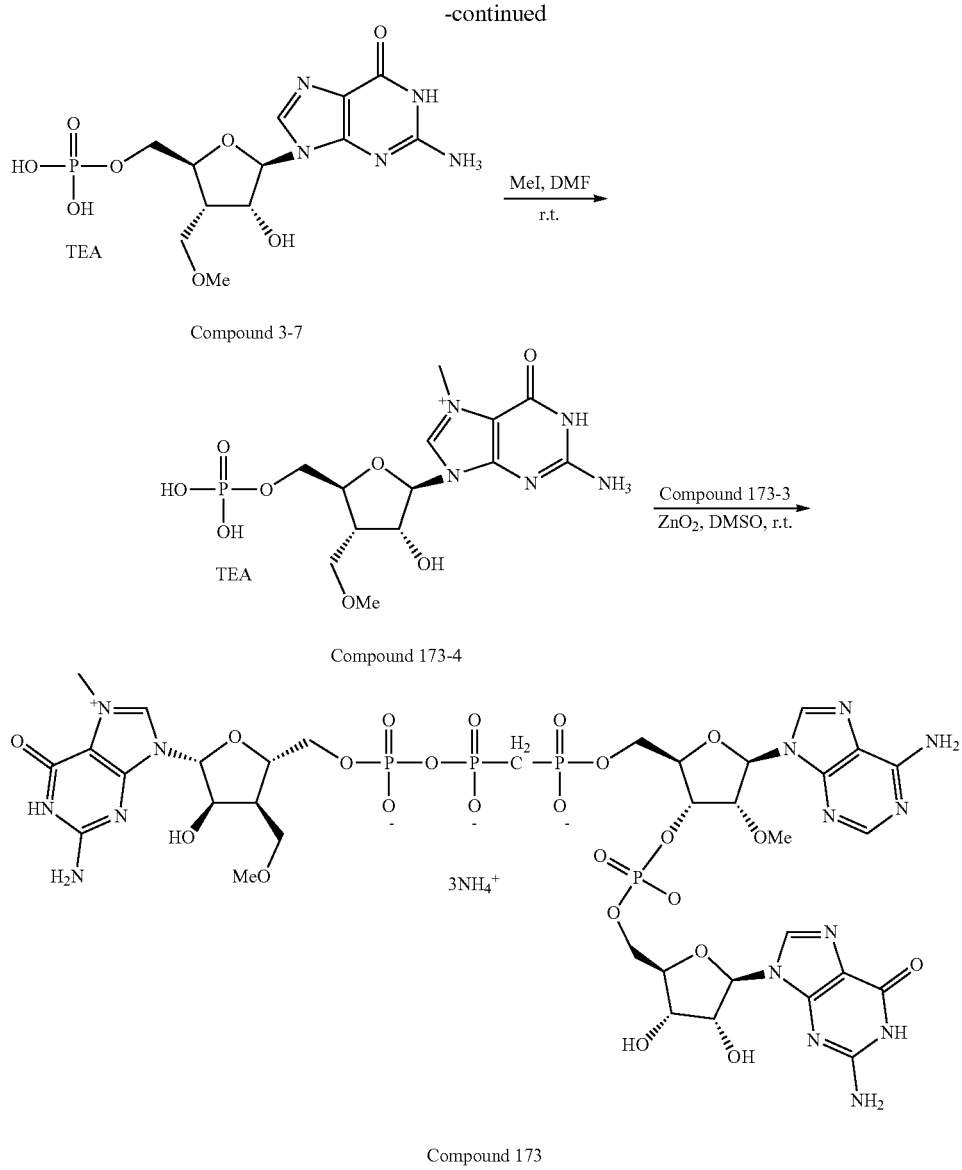

Compound 3-7

Compound 173-4

Compound 173

According to the above synthetic route, Compound 173-1 (0.5 g, 0.533 mmol) was added into a two-neck flask, and trimethyl phosphate (5 mL) was added to the flask. Subsequently, the temperature was cooled to 0° C. and methylene bis(phosphonic dichloride) (266 mg, 1.066 mmol) was added under the argon atmosphere protection. After addition, the mixture was reacted for 3 hours. Subsequently, methylene bis(phosphonic dichloride) (266 mg, 1.066 mmol) was added further and the mixture was reacted overnight at 0° C. LCMS showed that the reaction was completed and the reaction was stopped. The sodium bicarbonate aqueous solution (269 mg in 2 ml water) was added. After addition, the mixture was reacted at room temperature for 5 min. The reaction liquid was concentrated under reduced pressure to remove water, followed by addition of methyl tertiary butyl ether (2*30 mL). The liquid was sonicated for 2 min, and then the supernatant was removed. The residue was separated and purified by C18 column, and freeze-dried to obtain 1.0 g of crude product.

The above crude product (1.0 g) was dissolved in ammonium hydroxide (15 mL) and the mixture was reacted for 4.5 hours after it was heated to 50° C. Subsequently, the heating was stopped, and the mixture was reacted overnight at room temperature. LCMS showed that the reaction was completed and the reaction was stopped. The reaction liquid was concentrated and dried, followed by addition of water (100 mL) for diluting the liquid. The liquid was purified by ion column ($H_2O$: TEAB), and freeze-dried to obtain 354 mg of Compound 173-2 (triethylamine salt).

The Compound 173-2 (triethylamine salt, 354 mg, 0.298 mmol) was dissolved in DMF (3 mL), and then imidazole (101 mg, 1.49 mmol) and 2,2'-dithiobipyridine (131 mg, 0.596 mmol) were added, followed by addition of triethylamine (30 mg, 0.298 mmol) and triphenylphosphine (156 mg. 0.596 mmol) under three argon gas displacement, and the mixture was reacted for 6 hours at room temperature. HPLC showed that the reaction was completed and the reaction was stopped. A solution of sodium iodide (223 mg, 1.49 mmol) in acetone (35 mL) was poured into the reaction liquid, and the mixture was stirred for 5 min, and centrifuged. The supernatant was removed to obtain a solid, and acetone (2*20 mL) were added to it. The mixture was centrifuged twice, and the solid was concentrated under reduced pressure and dried to obtain 243 mg of Compound 173-3.

Compound 3-7 (230 mg, 0.58 mmol) was dissolved in N,N-dimethylformamide (5 mL), and iodomethane (0.42 mL, 6.74 mmol) was added under stirring. The mixture was stirred overnight at room temperature. After the reaction was completed, MTBE (10 mL) was added to the reaction system and stirred. Then, the reaction liquid was stand, and the supernatant was poured out. The bottom pulp was dried and 10 mL of water was used to dissolve it well. After that, the solution passed through ion exchange column and a peak of the desirable product was collected. The collected solution was concentrated under reduced pressure, and freeze-dried to obtain 210 mg of Compound 173-4 (triethylamine salt).

Compound 173-4 (87 mg, 0.215 mmol) was added into a single-neck flask, followed by addition of DMSO (5.4 mL), Compound 173-3 (243 mg, 0.284 mmol), and zinc chloride (387 mg, 1.79 mmol), and the mixture was reacted overnight at room temperature. HPLC showed that the reaction was completed and the reaction was stopped. Water (100 mL) and ethylene diamine tetraacetic acid disodium (930 mg) were added and stirred until the solution was clear. The solution was purified by ion column ($H_2O$: ammonium bicarbonate), then freeze-dried to constant weight, and finally 48.6 mg of Compound 173 (ammonium salt) was obtained.

The characteristic data of the Compound 173 was: LC-MS[M-H]$^-$: 1170.11. $^1$H-NMR (500 MHz, $D_2O$) δ: 9.23 (s, 1H), 8.61 (s, 1H), 8.26 (s, 1H), 8.02 (s, 1H), 6.09 (d, J=4.8 Hz, 1H), 5.81-5.80 (m, 2H), 4.94-4.91 (m, 1H), 4.66 (d, J=4.6 Hz, 1H), 4.51-4.47 (m, 3H), 4.43 (t, J=4.6 Hz, 1H), 4.39 (d, J=10.2 Hz, 1H), 4.34 (m, 1H), 4.30-4.27 (m, 1H), 4.23-4.17 (m, 3H), 4.12-4.10 (m, 1H), 3.99 (s, 3H), 3.73-3.69 (m, 1H), 3.63-3.59 (m, 1H), 3.48 (s, 3H), 3.35 (s, 3H), 2.70-2.65 (m, 1H), 2.47 (t, J=20.4 Hz, 2H). $^{31}$P-NMR (202 MHz, $D_2O$) δ:16.79 (s, 1P), 7.80 (dd, J=25.4, 6.8 Hz,1P), −0.89 (s, 1P), −11.31 (d, J=26.5 Hz, 1P).

Example 25 Synthesis of Compound 189

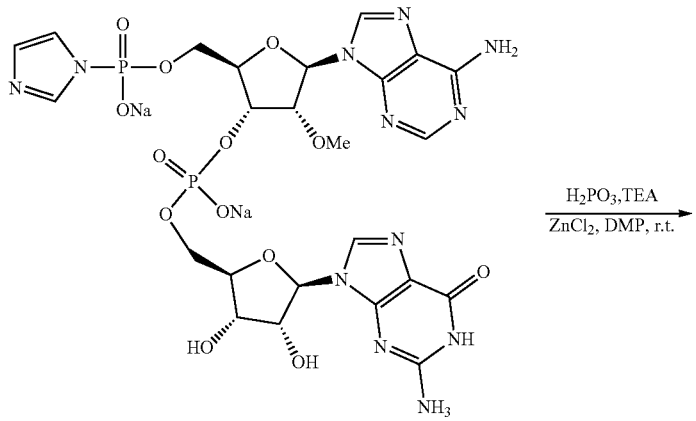

Compound 139-15

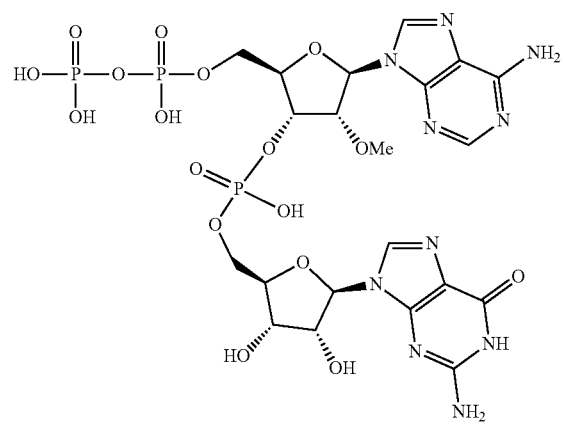

Compound 189-1

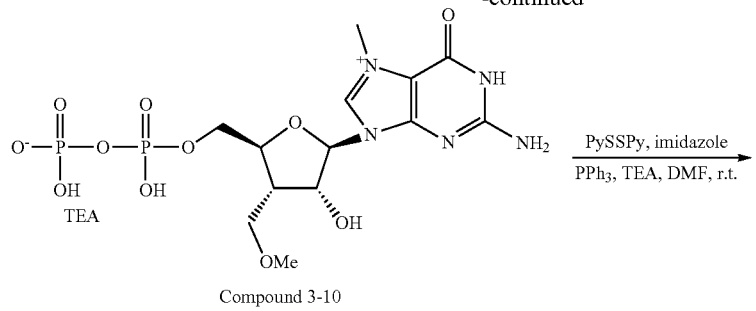

Compound 3-10

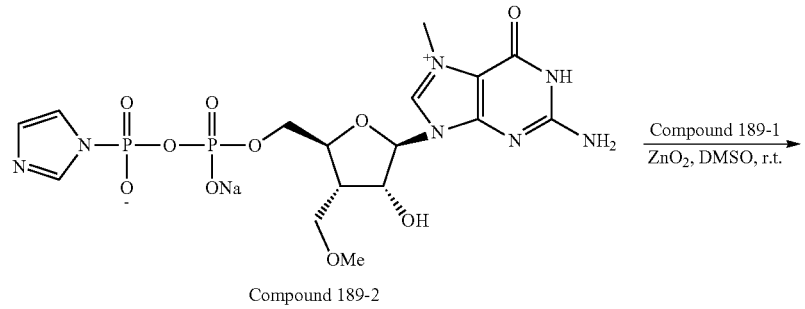

Compound 189-2

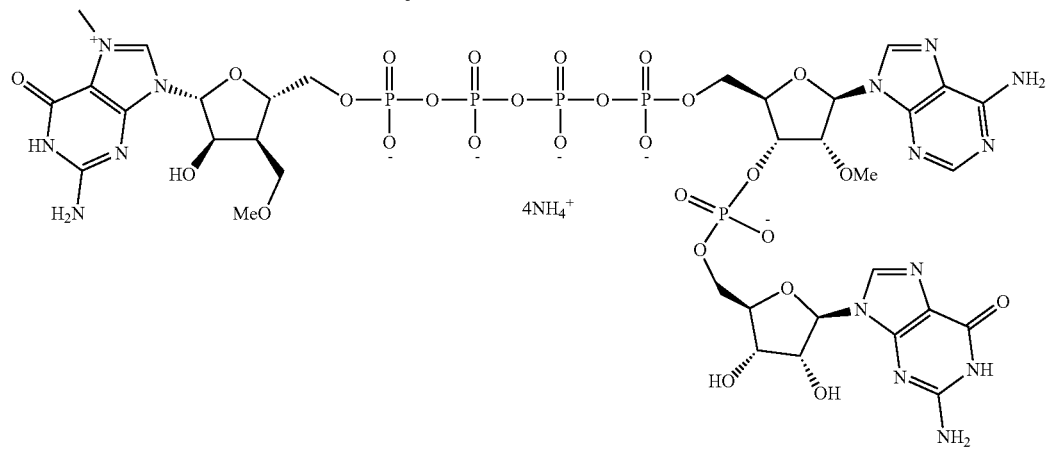

Compound 189

According to the above synthetic route, 85% phosphoric acid (89 mg, 0.77 mmol) and N,N-dimethylformamide (2.5 mL) were added to a reaction flask, and triethylamine (108 μL, 0.77 mmol) was added under stirring. After the mixture was stirred for 5 min at room temperature, Compound 139-15 (200 mg, 0.26 mmol) was added. The mixture was reaction overnight. After the reaction was completed, MTBE (6 mL) was added to the reaction system. Then, the reaction liquid was sonicated and the product was precipitated completely. After the supernatant was poured out, the solid precipitation was dissolved in water (6 mL) until the solution was clear. Subsequently, the solution passed through ion exchange column (gradient elution: 1M TEAB/water) and a peak of the desirable product was collected. The collected solution was concentrated under reduced pressure and freeze-dried to obtain 150 mg of Compound 189-1 (triethylamine salt).

The Compound 3-10 (triethylamine salt, 200 mg, 0.261 mmol), imidazole (88.5 mg, 1.3 mmol), 2,2'-dithiodipyridine (115 mg. 0.52 mmol), N,N-dimethylformamide (2 mL), triethylamine (40 μL, 0.26 mmol) were added to a reaction flask, and triphenylphosphine (137 mg, 0.52 mmol) was added under stirring. The mixture was stirred for 5 hours under the nitrogen atmosphere protection and at room temperature. After the reaction was completed, the reaction system was poured into a mixture solution of sodium perchlorate (160 mg, 1.3 mmol) and acetone (5 mL), and the mixture was stirred for 10 min at room temperature. Then, the mixture was filtered, and the filter cake was washed with acetone. After that, the filter cake was collected, dried under reduced pressure at room temperature, to obtain 168 mg of Compound 189-2.

The Compound 189-1 (triethylamine salt, 140 mg, 0.125 mmol), Compound 189-2 (102 mg, 0.15 mmol), and dimethyl sulfoxide (2 mL) were added to a reaction flask, followed by addition of zinc chloride (255 mg, 1.87 mmol) under the argon atmosphere protection, and the mixture was stirred for 80 hours at room temperature. After the reaction was completed, the reaction system was added into a solution of EDTA-2Na (630 mg, 1.87 mmol) in water (6 mL), and water was further added for diluting the reaction liquid to about 15 mL, and then the solution passed through ion exchange column. The liquid was eluted with 1M ammonium bicarbonate aqueous solution to collect a peak of the desirable product, which was concentrated under reduced pressure. The residue was freeze-dried repeatedly to obtain 22 mg of Compound 189 (ammonium salt).

The characteristic data of the Compound 189 was: LC-MS[M-H]⁻: 1251.87. ¹H-NMR (500 MHz, D₂O) δ: 9.14 (s, 1H), 8.53 (s, 1H), 8.21 (s, 1H), 7.89 (s, 1H), 6.05 (d, J=4.4 Hz, 1H), 5.72 (d, J=5.1 Hz, 1H), 5.69 (s, 1H), 4.90-4.87 (m, 1H), 4.74 (t, J=5.0 Hz, 1H), 4.60 (d, J=4.6 Hz, 1H), 4.48 (br, 2H), 4.44 (t, J=4.6, 1H), 4.37-4.30 (m, 4H), 4.24-4.08 (m, 4H), 3.97 (s, 3H), 3.68-3.64 (m, 1H), 3.58-3.54 (m, 1H), 3.44 (s, 3H), 3.31 (s, 3H), 2.63-2.57 (m, 1H). ³¹P-NMR (202 MHz, D₂O) δ: −0.99 (s,1P), −11.65 (m, 2P), −22.91 (m,2P).

Example 26 Synthesis of Compound 191

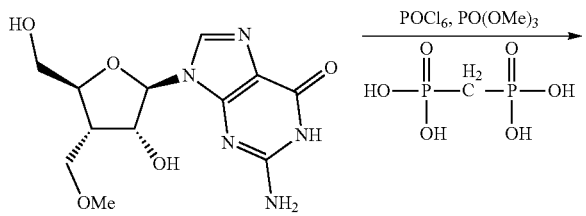

Compound 3-6

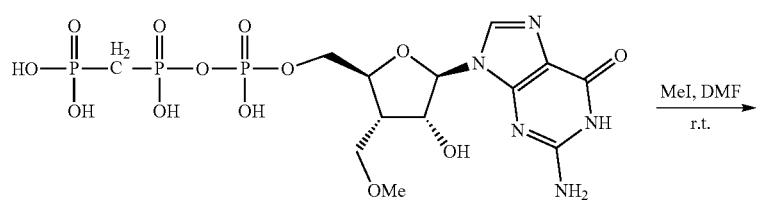

Compound 191-1

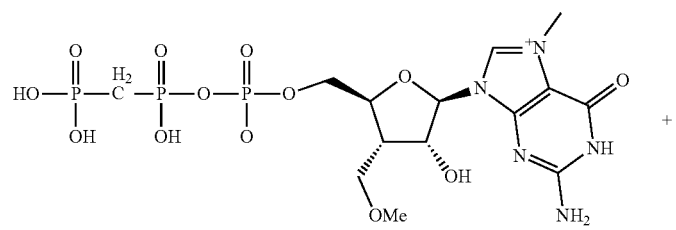

Compound 191-2

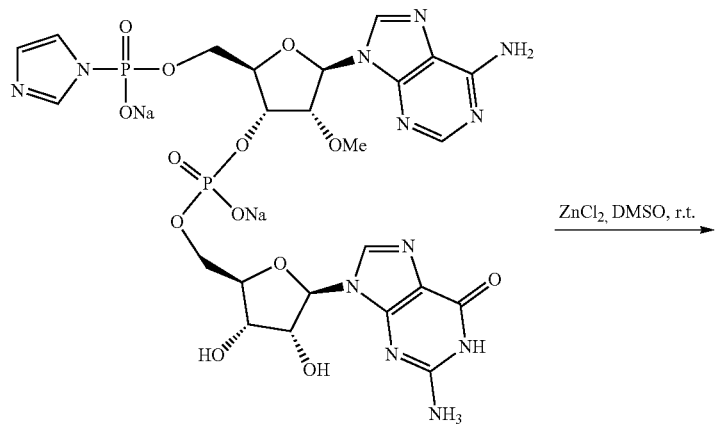

Compound 139-15

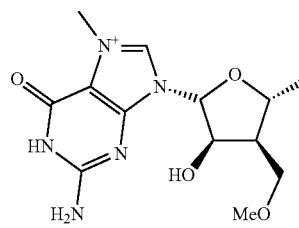
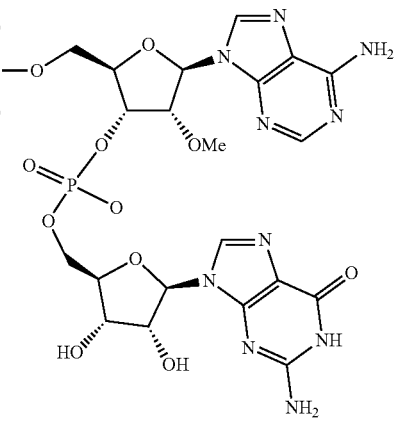

Compound 191

According to the above synthetic route, Compound 3-6 (200 mg, 0.64 mmol) and trimethyl phosphate (4 mL) were added to a reaction flask. The temperature of the reaction system was decreased to about 0° C. under argon displacement protection, phosphorus oxychloride (0.1 mL) was added to the system and the mixture was stirred for 3 hours at 0° C. Phosphorus oxychloride (0.1 mL) was further added and the mixture was continued to react for 3 hours under stirring at 0° C. Subsequently, the temperature of the system was decreased to about −10° C., and a mixture solution of methylene diphosphonic acid (450 mg, 2.56 mmol), acetonitrile (2 mL), and tripropylamine (1.3 mL) was added, followed by further addition of tripropylamine (0.85 mL), and the mixture was stirred for 3.5 hours at −10° C. The reaction system was placed in an ice bath and the reaction was quenched with TEAB (20 mL). After that, the mixture was stirred overnight at room temperature. The reaction system was concentrated under reduced pressure to dryness. MTBE (15 mL) was added to the residue, which were washed ultrasonically. Subsequently, the supernatant was poured out and the bottom pulp was dissolved in water (6 mL). Saturated sodium bicarbonate was used for adjusting pH to 7 to 8. The liquid was concentrated to dryness under reduced pressure and then was dissolved in water (4 mL) until the liquid was clear. Further, the liquid passed through C18 reverse column (gradient eluent: acetonitrile/water) and a peak of desirable product was collected. Finally, the collected liquid was concentrated to 12 mL of solution under reduced pressure, and then passed through ion exchange column (gradient eluent: 1M TEAB/water) to collect a peak of desirable product, which was concentrated under reduced pressure, and freeze-dried to obtain 113 mg of Compound 191-1 (triethylamine salt).

The Compound 191-1 (triethylamine salt, 105 mg, 0.11 mmol), N,N-dimethylformamide (1.5 mL), and iodomethane (55 μL, 0.88 mmol) were added to a reaction flask, and the mixture was stirred for 8 hours under the sealed condition at room temperature. After the reaction was completed, excess iodomethane was removed by vacuum under reduced pressure. Water (6 mL) was added for dissolving the system. Subsequently, the liquid was purified by ion column chromatography (gradient eluent: 1M TEAB/water) to collect a peak of the desirable product, which was concentrated under reduced pressure, and freeze-dried to obtain 69 mg of Compound 191-2 (triethylamine salt).

The Compound 191-2 (triethylamine salt, 65 mg, 0.075 mmol), Compound 139-15 (59 mg, 0.075 mmol), and dimethyl sulfoxide (1.5 mL) were added to a reaction flask, followed by addition of zinc chloride (102 mg, 0.75 mmol) under the argon atmosphere protection, and the mixture was stirred overnight at room temperature. After the reaction was completed, the reaction system was added to a solution of EDTA-2Na (252 mg, 0.75 mmol) in water (6 mL). The reaction liquid passed through ion exchange column, and eluted with 1M ammonium bicarbonate solution to collect a peak of the desirable product, which was concentrated under reduced pressure, and freeze-dried repeatedly to obtain 49 mg of Compound 191 (ammonium salt).

The characteristic data of the Compound 191 was: LC-MS[M-H]$^-$: 1250.15. $^1$H-NMR (500 MHz, D$_2$O) δ: 9.31 (s, 1H), 8.68 (s, 1H), 8.30 (s, 1H), 7.95 (s, 1H), 6.13 (d, J=4.3 Hz, 1H), 5.77 (d, J=5.2 Hz, 1H), 5.68 (s, 1H), 4.91-4.87 (m, 1H), 4.70 (t, J=5.2 Hz, 1H), 4.56 (d, J=4.7 Hz, 1H), 4.52-4.49 (m, 2H), 4.47 (t, J=4.9 Hz, 1H), 4.39-4.27 (m, 2H), 4.33 (br, 2H), 4.28-4.22 (m, 2H), 4.19-4.12 (m, 2H), 3.97 (s, 3H), 3.70 (dd, J=10.1, 7.6 Hz, 1H), 3.60 (dd, J=10.1, 5.8 Hz, 1H), 3.52 (s, 3H), 3.35 (s, 3H), 2.67-2.59 (m, 3H). $^{31}$P-NMR (202 MHz, D$_2$O) δ: 7.98 (d, J=25.5 Hz, 2P), −0.99 (s,1P), −11.28 (m, 2P).

Example 27 Synthesis of Compound 33
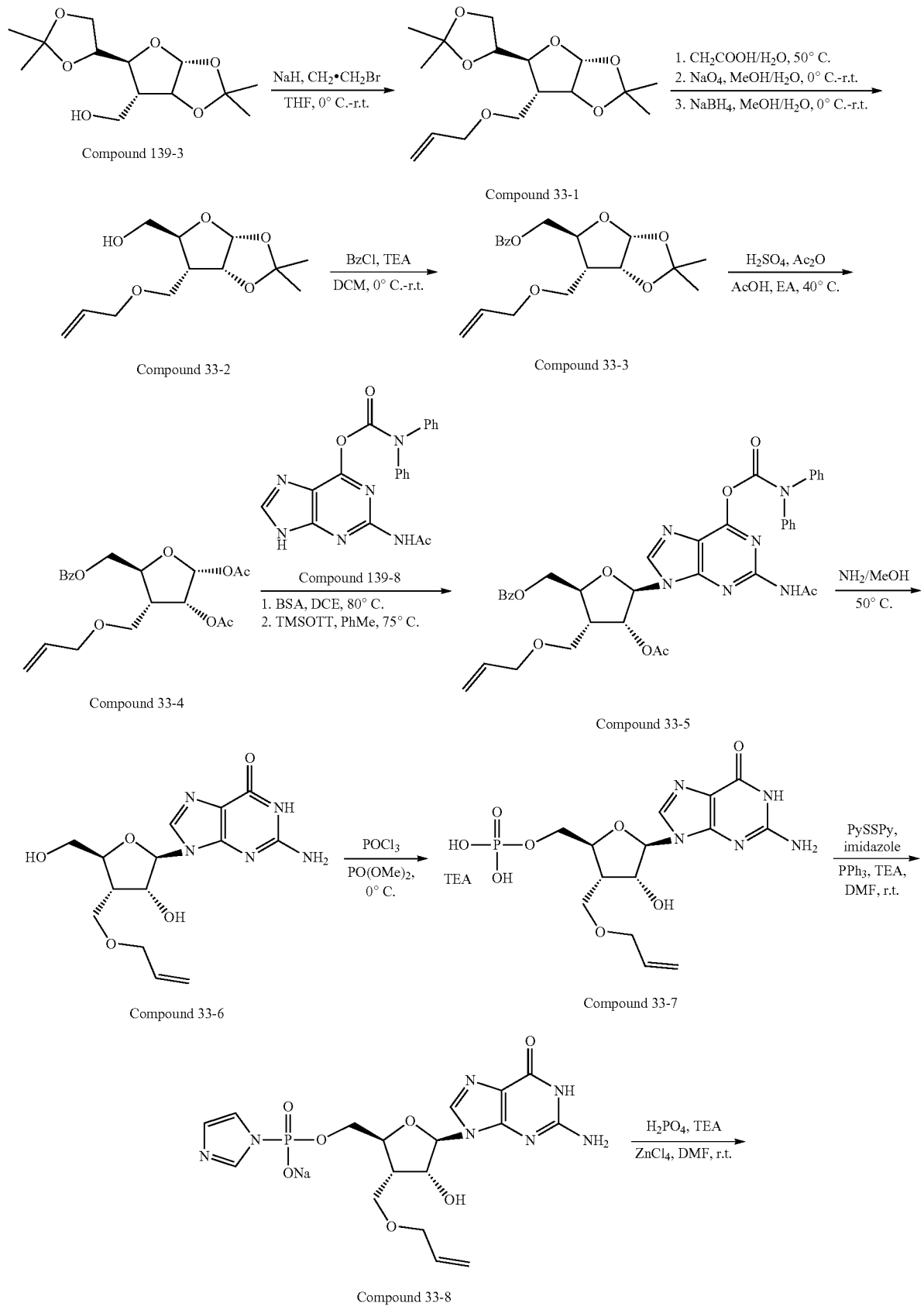

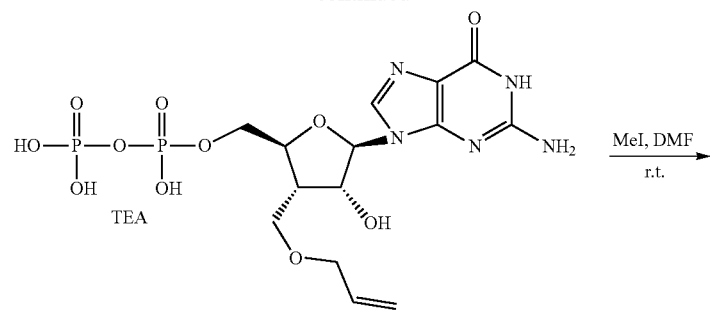
Compound 33-9
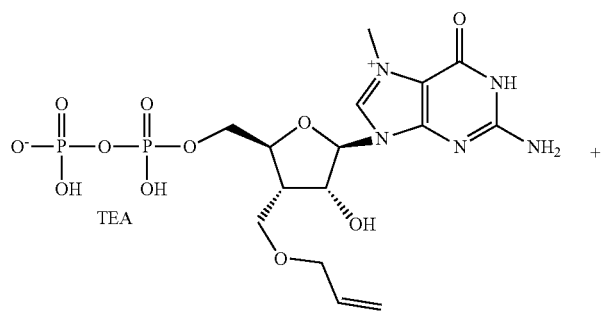
Compound 33-10
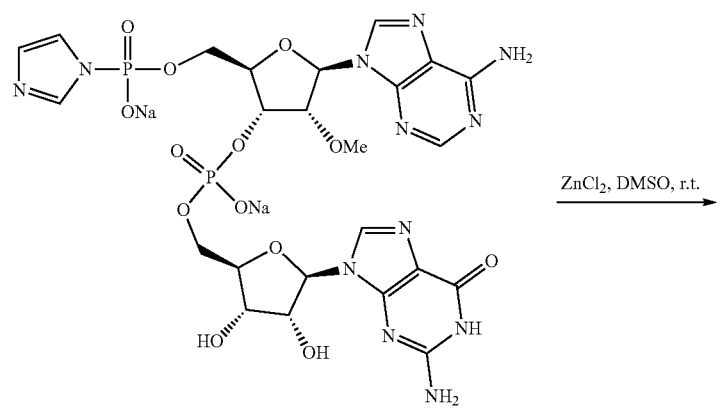
Compound 139-15
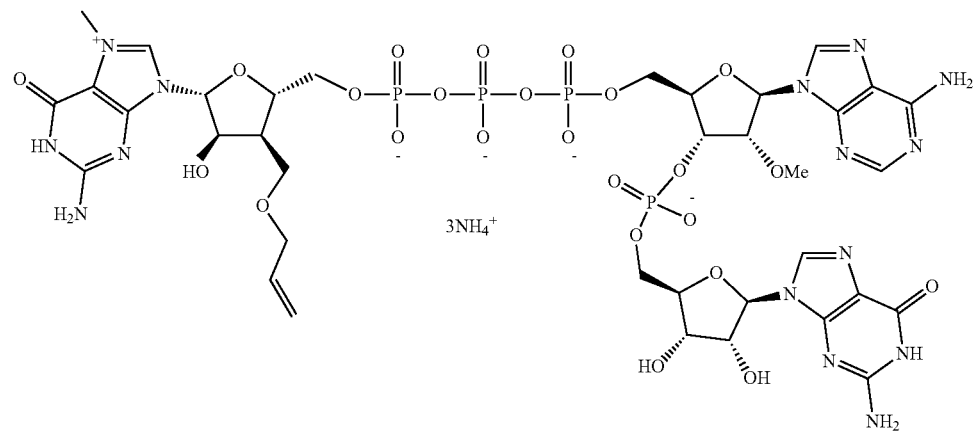
Compound 33

According to the reaction route, Compound 33-6 was prepared from Compound 139-3 using the procedure for preparation of Compound 139-10, except substituting iodoethane with bromopropylene.

The characteristic data of Compound 33-6 was: $^1$H NMR (500 MHz, DMSO) δ 10.62 (s, 1H), 8.00 (s, 1H), 6.46 (s, 2H), 6.07-6.03 (m, 1H), 5.71 (d, J=2.1 Hz, 1H), 5.69 (d, J=5.4 Hz, 1H), 5.45-5.43 (m, 1H), 5.33-5.30 (m, 1H), 5.02 (t, J=5.3 Hz, 1H), 4.38 (td, J=5.4, 2.1 Hz, 1H), 3.98 (dt, J=8.4, 3.2 Hz, 1H), 3.75-3.70 (m, 1H), 3.63 (dd, J=9.4, 6.8 Hz, 1H), 3.55-3.50 (m, 1H), 3.48-3.40 (m, 3H), 2.56-2.52 (m, 1H).

According to the reaction route, Compound 33 (ammonium salt) was prepared from Compound 33-6 using the procedure for preparation of Compound 139.

The characteristic data of the Compound 33 was: MS (m/z): 1198.04[M−1]$^−$. $^1$H NMR (500 MHz, D$_2$O) δ 9.05 (s, 1H), 8.40 (s, 1H), 8.13 (s, 1H), 7.93 (s, 1H), 6.07-6.03 (m, 1H), 6.01 (d, J=5.5 Hz, 1H), 5.80 (d, J=5.9 Hz, 1H), 5.78 (s, 1H), 5.45-5.43 (m, 1H), 5.33-5.30 (m, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 3H), 3.99 (s, 3H), 3.65-3.62 (m, 1H), 3.55-3.52 (m, 1H), 3.43 (s, 3H), 2.61-2.52 (m, 1H); $^{31}$P NMR (202 MHz, D$_2$O) δ-0.93 (s, 1H), −11.65 (m, 2P), −22.90 (m, 1P).

Example 28 Synthesis of Compound 151

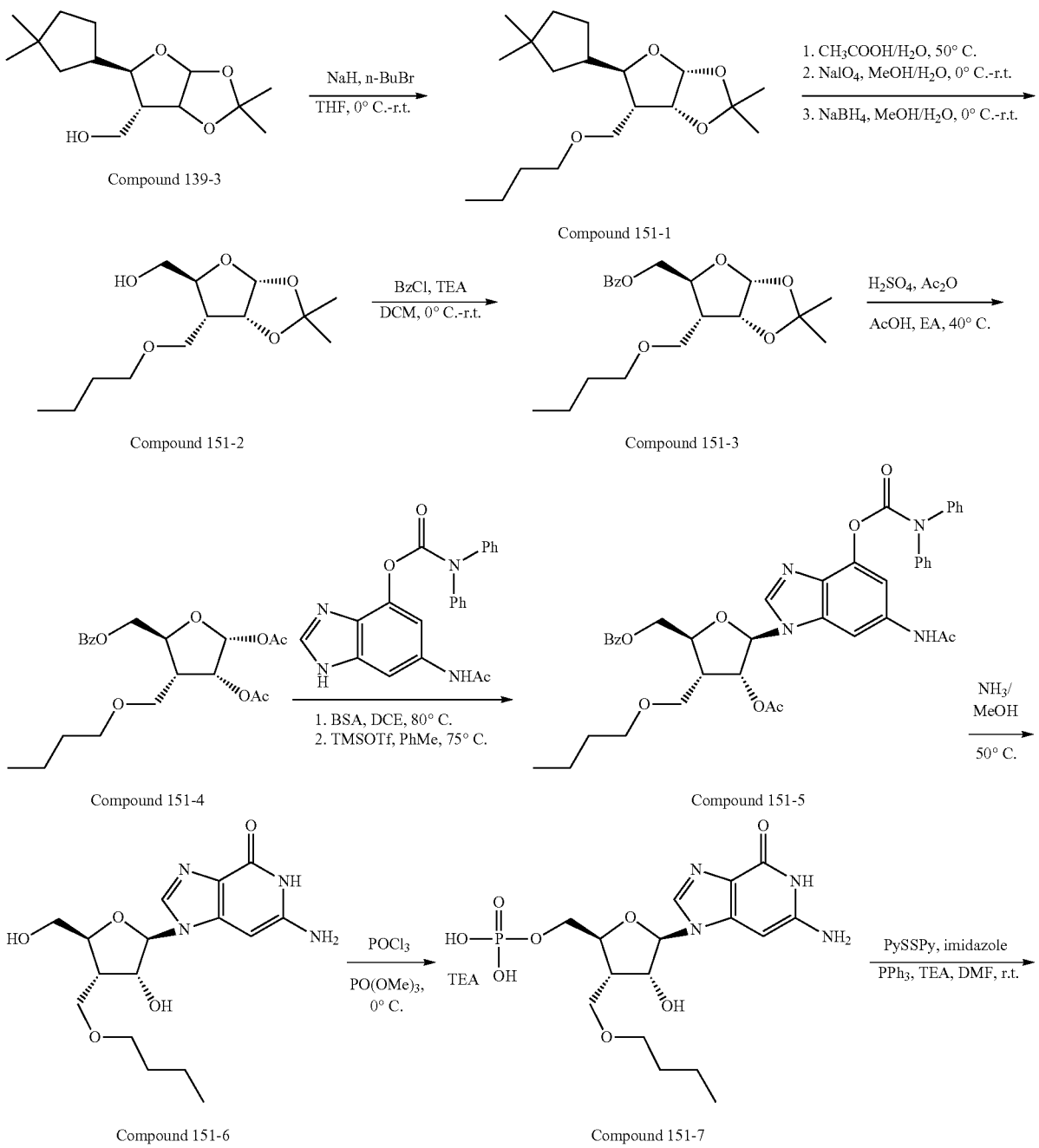

-continued
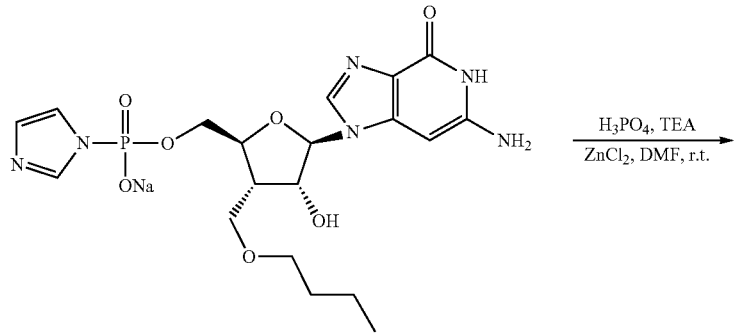
Compound 151-8
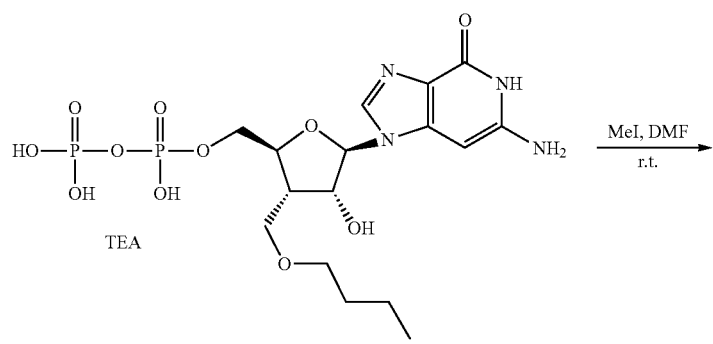
Compound 151-9
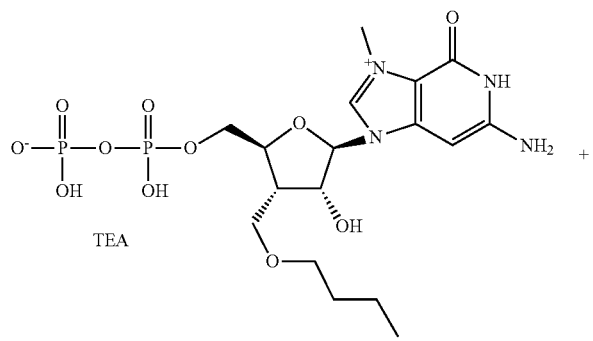
Compound 151-10
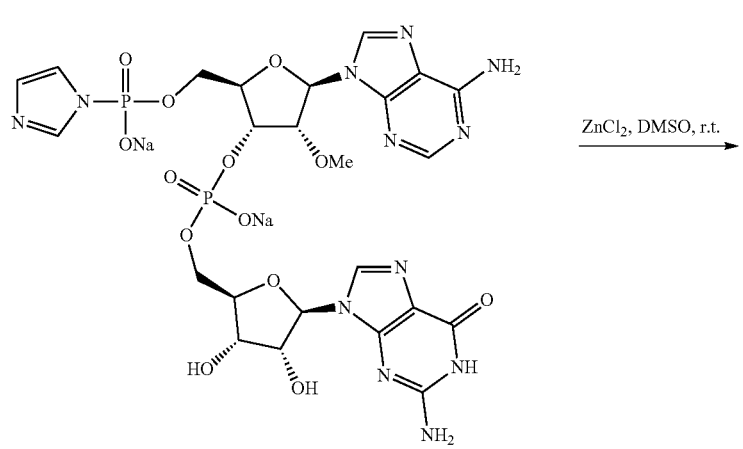
Compound 139-15

-continued

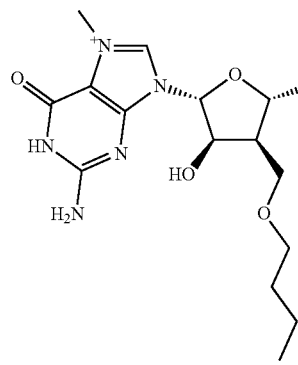 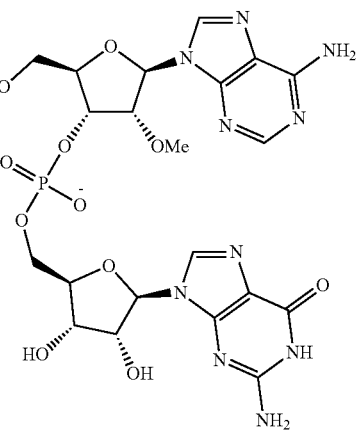

Compound 151

According to the reaction route, Compound 151-6 was prepared from Compound 139-3 using the procedure for preparation of Compound 139-10, except substituting iodoethane with bromobutane.

The characteristic data of Compound 151-6 was: $^1$H NMR (500 MHz, DMSO) δ: 10.60 (s, 1H), 7.99 (s, 1H), 6.45 (br, 2H), 5.70 (s, 1H), 5.70-5.67 (d, J=6.0 Hz, 1H), 5.03-4.99 (t, J=5.6 Hz, 1H), 4.41-4.37 (m, 1H), 4.00-3.96 (m, 1H), 3.74-3.68 (m, 1H), 3.60-3.55 (m, 1H), 3.54-3.48 (m, 1H), 3.44-3.39 (m, 1H), 3.20 (m, 2H), 2.58-2.52 (m, 1H), 1.57-1.50 (m, 2H), 1.48-1.45 (m, 2H), 0.88 (t, J=6.5 Hz, 3H).

According to the reaction route, Compound 151 (ammonium salt) was prepared from Compound 151-6 using the procedure for preparation of Compound 139.

The characteristic data of the Compound 151 was: MS (m/z): 1214.06[M−1]−. $^1$H NMR (500 MHz, D$_2$O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.43 (s, 3H), 3.35 (t, J=6.5 Hz, 2H), 2.61-2.52 (m, 1H), 1.57-1.50 (m, 2H), 1.48-1.45 (m, 2H), 0.88 (t, J=6.5 Hz, 3H); $^{31}$P NMR (202 MHz, D$_2$O) δ -0.93 (s, 1H), −11.65 (m, 2P), −22.90 (m, 1P).

Example 29 Synthesis of Compound 51

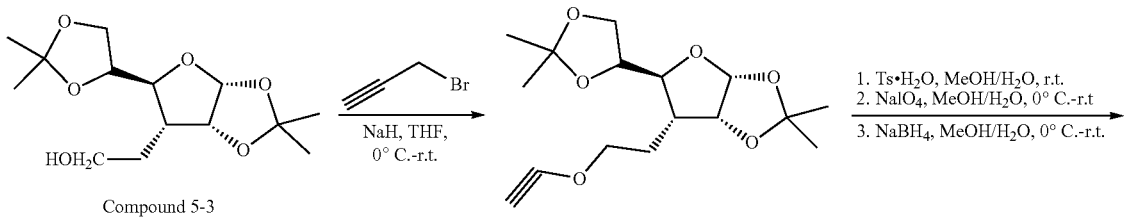

Compound 5-3 → Compound 51-1

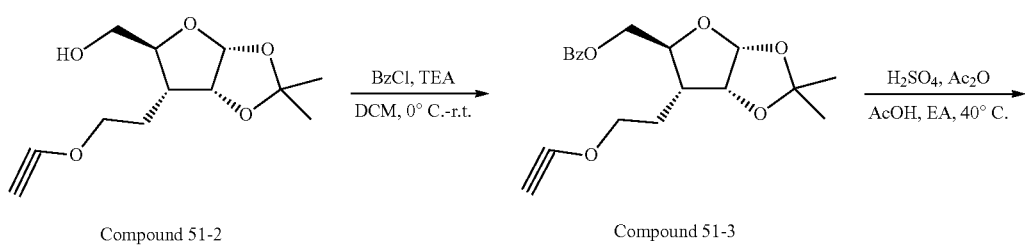

Compound 51-2 → Compound 51-3

-continued
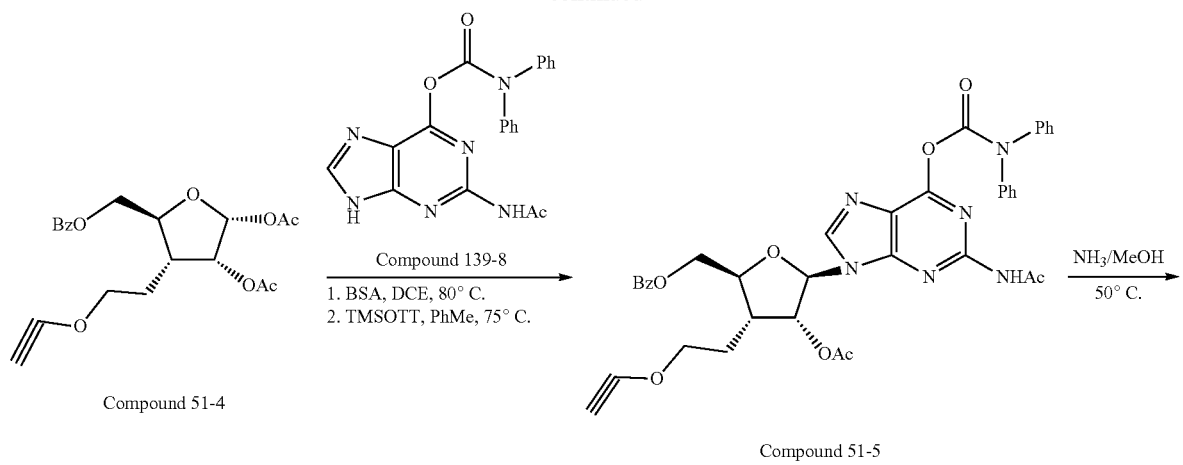
Compound 51-4 → Compound 51-5
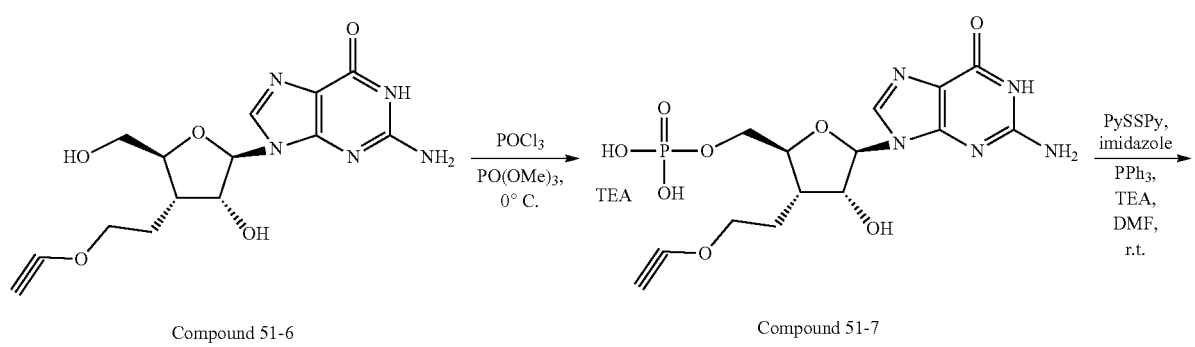
Compound 51-6 → Compound 51-7
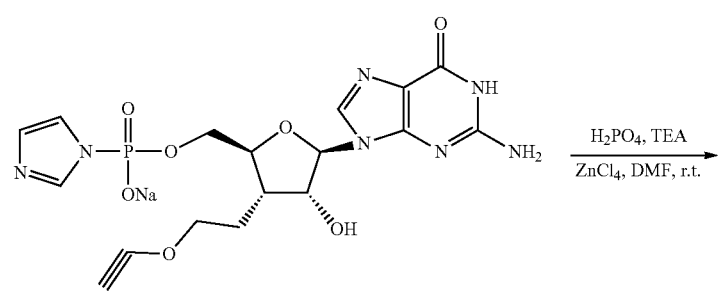
Compound 51-8
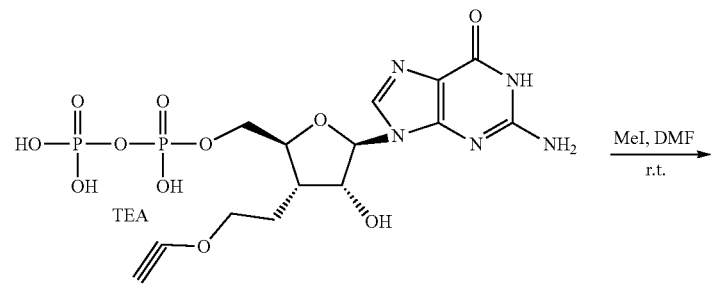
Compound 51-9

-continued

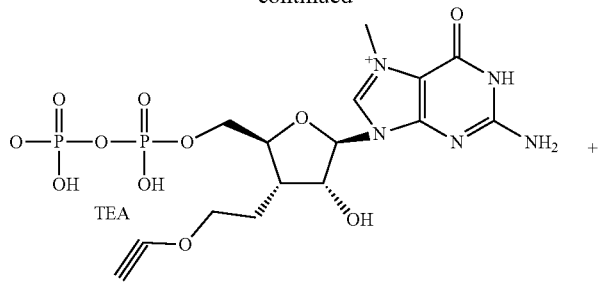

Compound 51-10

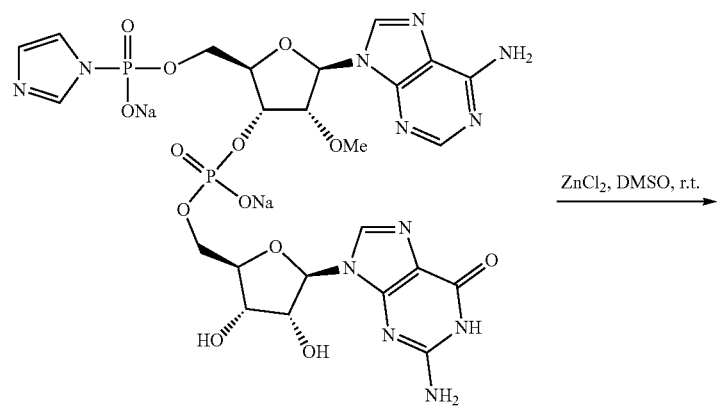

Compound 139-15

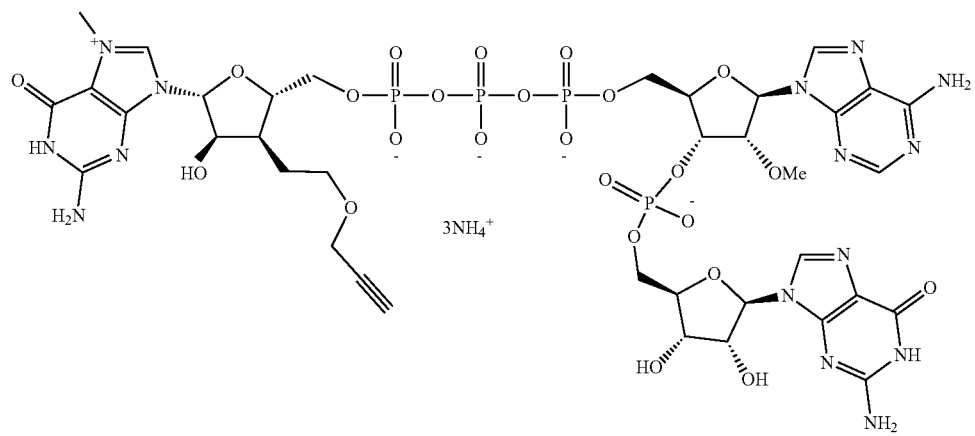

Compound 51

According to the reaction route, Compound 51-6 was prepared from Compound 5-3 using the procedure for preparation of Compound 139-10, except substituting Compound 139-3 with Compound 5-3 and substituting iodoethane with bromopropyne.

The characteristic data of Compound 51-6 was: $^1$H NMR (500 MHz, DMSO) δ 10.60 (s, 1H), 8.01 (s, 1H), 6.46 (s, 2H), 5.73 (s, 1H), 5.61 (d, J=5.6 Hz, 1H), 5.03 (t, J=5.3 Hz, 1H), 4.20 (t, J=5.2 Hz, 1H), 4.15 (s, 2H), 3.90-3.85 (m, 1H), 3.77-3.71 (m, 1H), 3.58-3.50 (m, 1H), 3.42-3.35 (m, 2H), 3.32 (s, 1H), 2.34-2.27 (m, 1H), 1.82-1.69 (m, 1H), 1.59-1.50 (m, 1H).

According to the reaction route, Compound 51 (ammonium salt) was prepared from Compound 51-6 using the procedure for preparation of Compound 139.

The characteristic data of the Compound 51 was: MS (m/z): 1210.04[M−1]$^−$. $^1$H NMR (500 MHz, D$_2$O) δ 9.07 (s, 1H), 8.35 (s, 1H), 8.05 (s, 1H), 7.94 (s, 1H), 6.00 (d, J=5.3 Hz, 1H), 5.80 (d, J=5.2 Hz, 1H), 5.75 (s, 1H), 4.92 (m, 1H), 4.70 (t, J=5.1 Hz, 1H), 4.49-4.47 (m, 4H), 4.41 (m, 11H), 4.33-4.29 (m, 2H), 4.26-4.23 (m, 1H), 4.20-4.18 (m, 3H), 4.12-4.10 (m, 3H), 3.99 (s, 3H), 3.45 (m, 5H), 3.32 (s, 1H), 2.29-2.23 (m, 1H), 1.77-1.65 (m, 2H); $^{31}$P NMR (202 MHz, D$_2$O) δ-0.96 (s, 1H), −11.56 (m, 2P), −22.68 (m, 1P).

Example 30 Synthesis of Compound 163
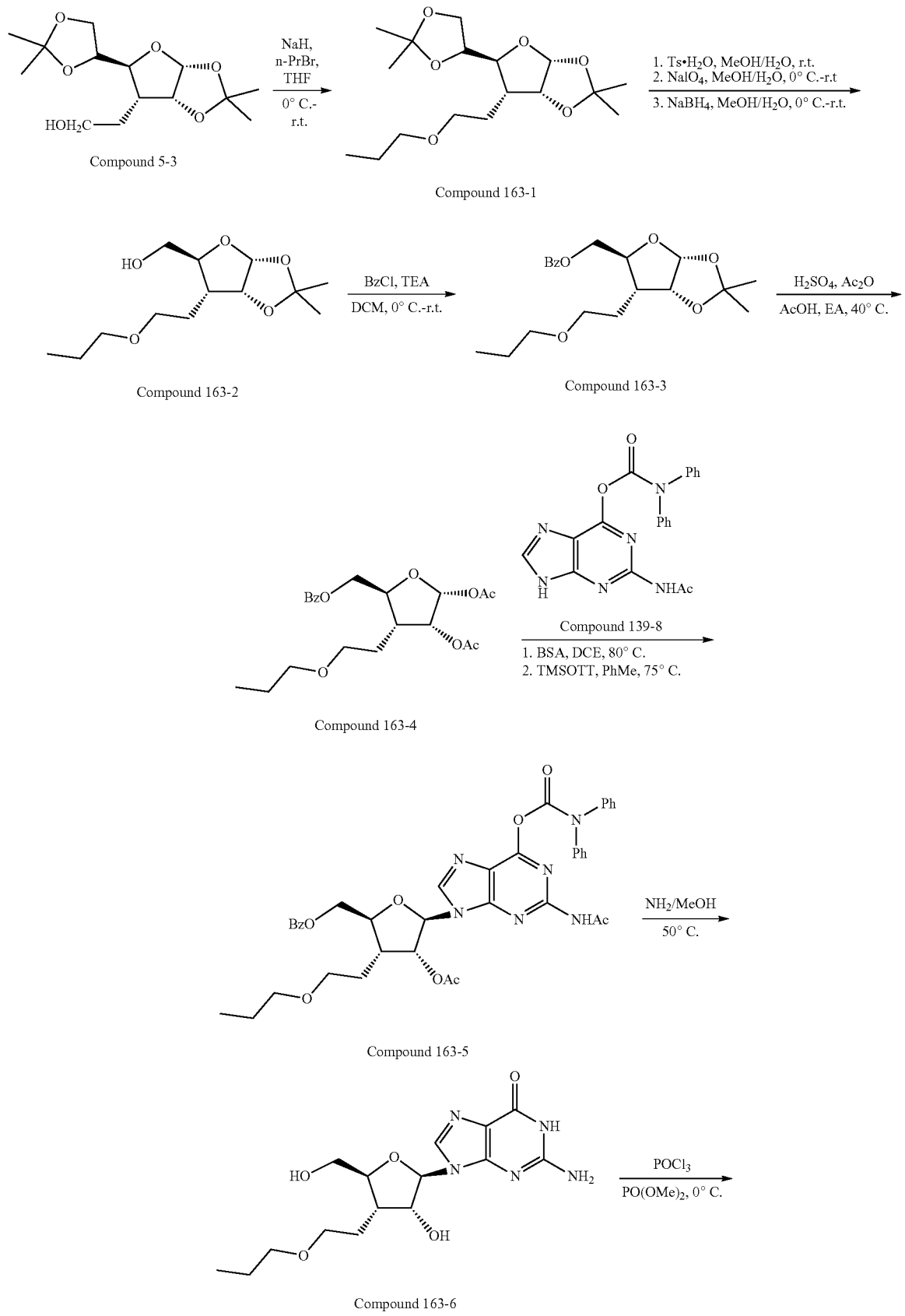

-continued

Compound 163-7
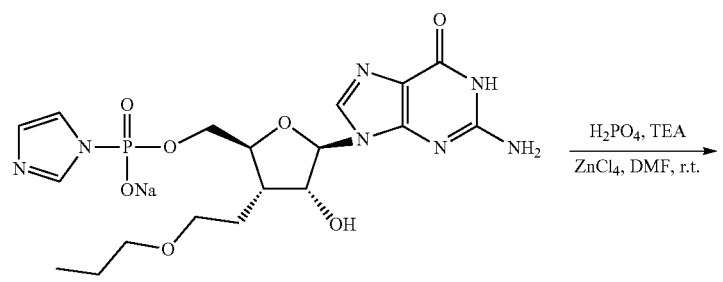
Compound 163-8
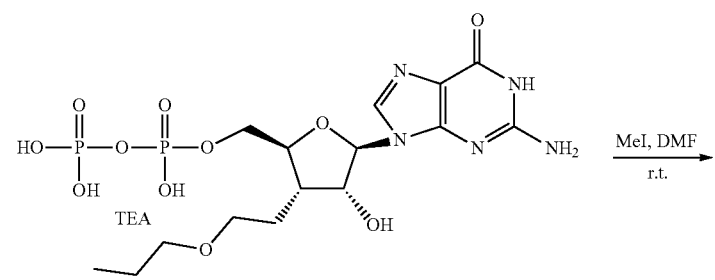
Compound 163-9
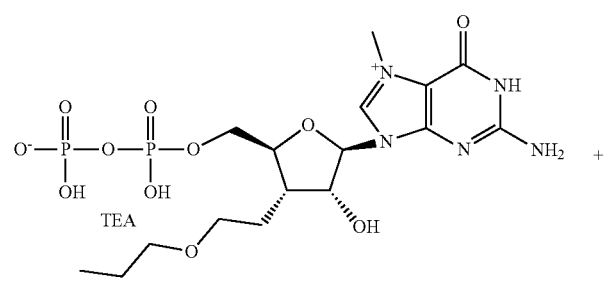
Compound 163-10

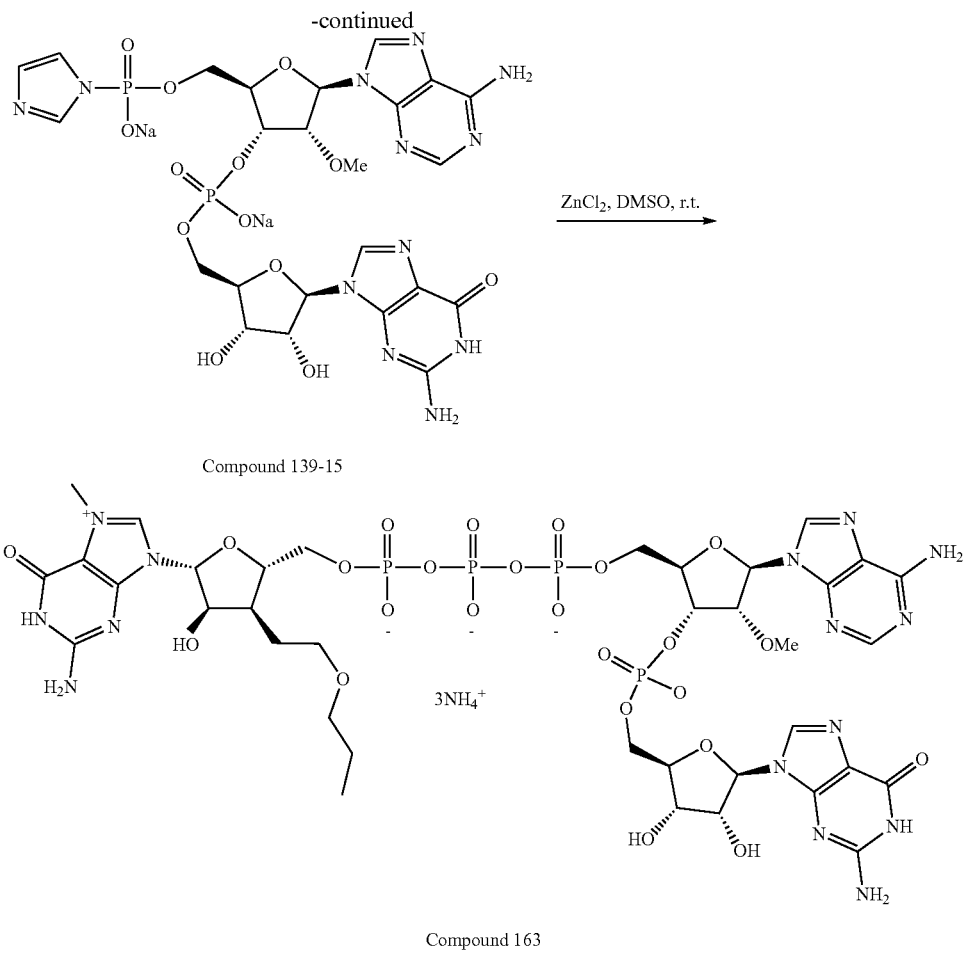

Compound 139-15

Compound 163

According to the reaction route, Compound 163-6 was prepared from Compound 5-3 rather than Compound 139-3 using the procedure for preparation of Compound 139-10, except substituting iodoethane with bromopropane.

The characteristic data of Compound 163-6 was: $^1$H NMR (500 MHz, DMSO) δ 10.60 (s, 1H), 8.01 (s, 1H), 6.46 (s, 2H), 5.73 (s, 1H), 5.61 (d, J=5.6 Hz, 1H), 5.03 (t, J=5.3 Hz, 1H), 4.20 (t, J=5.2 Hz, 1H), 3.90-3.85 (m, 1H), 3.77-3.71 (m, 1H), 3.58-3.50 (m, 1H), 3.42-3.35 (m, 2H), 3.23-3.20 (m, 2H), 2.34-2.27 (m, 1H), 1.82-1.69 (m, 1H), 1.59-1.55 (m, 1H), 1.53-1.50 (m, 2H), 0.88 (t, J=6.5 Hz, 3H).

According to the reaction route, Compound 163 (ammonium salt) was prepared from Compound 163-6 using the procedure for preparation of Compound 139.

The characteristic data of the Compound 163 was: MS (m/z): 1214.04[M−1]$^-$. $^1$H NMR (500 MHz, D$_2$O) δ 9.02 (s, 1H), 8.35 (s, 1H), 8.05. (s, 1H), 7.94 (s, 1H), 6.00 (d, J=5.3 Hz, 1H), 5.80 (d, J=5.2 Hz, 1H), 5.75 (s, 1H), 4.92 (m, 1H), 4.70 (t, J=5.1 Hz, 1H), 4.49-4.47 (m, 4H), 4.41 (m, 1H), 4.33-4.29 (m, 2H), 4.26-4.23 (m, 1H), 4.20-4.18 (m, 3H), 4.12-4.10 (m, 1H), 3.99 (s, 3H), 3.45 (m, 5H), 3.28 (t, J=6.5 Hz, 2H), 2.29-2.23 (m, 1H), 1.77-1.65 (m, 2H), 1.55-1.52 (m, 2H), 0.88 (t, J=6.5 Hz, 3H); $^{31}$P NMR (202 MHz, D$_2$O) δ-0.96 (s, 1H), −11.56 (m, 2P), −22.68 (m, 1P).

Example 31 Synthesis of Compound 631

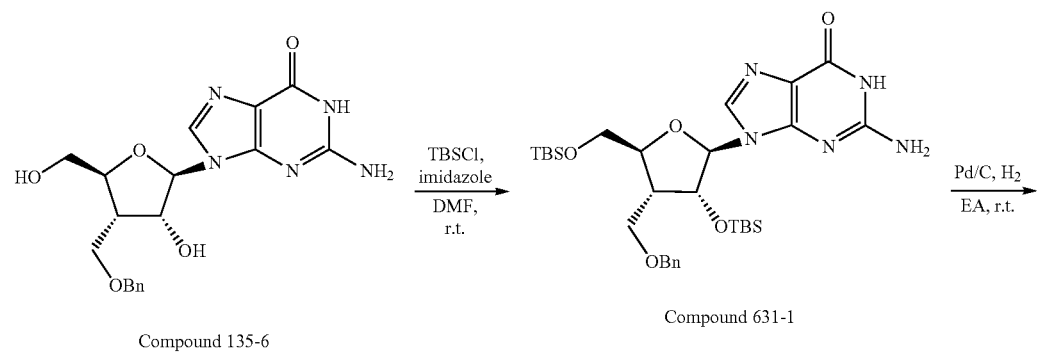

Compound 135-6      Compound 631-1

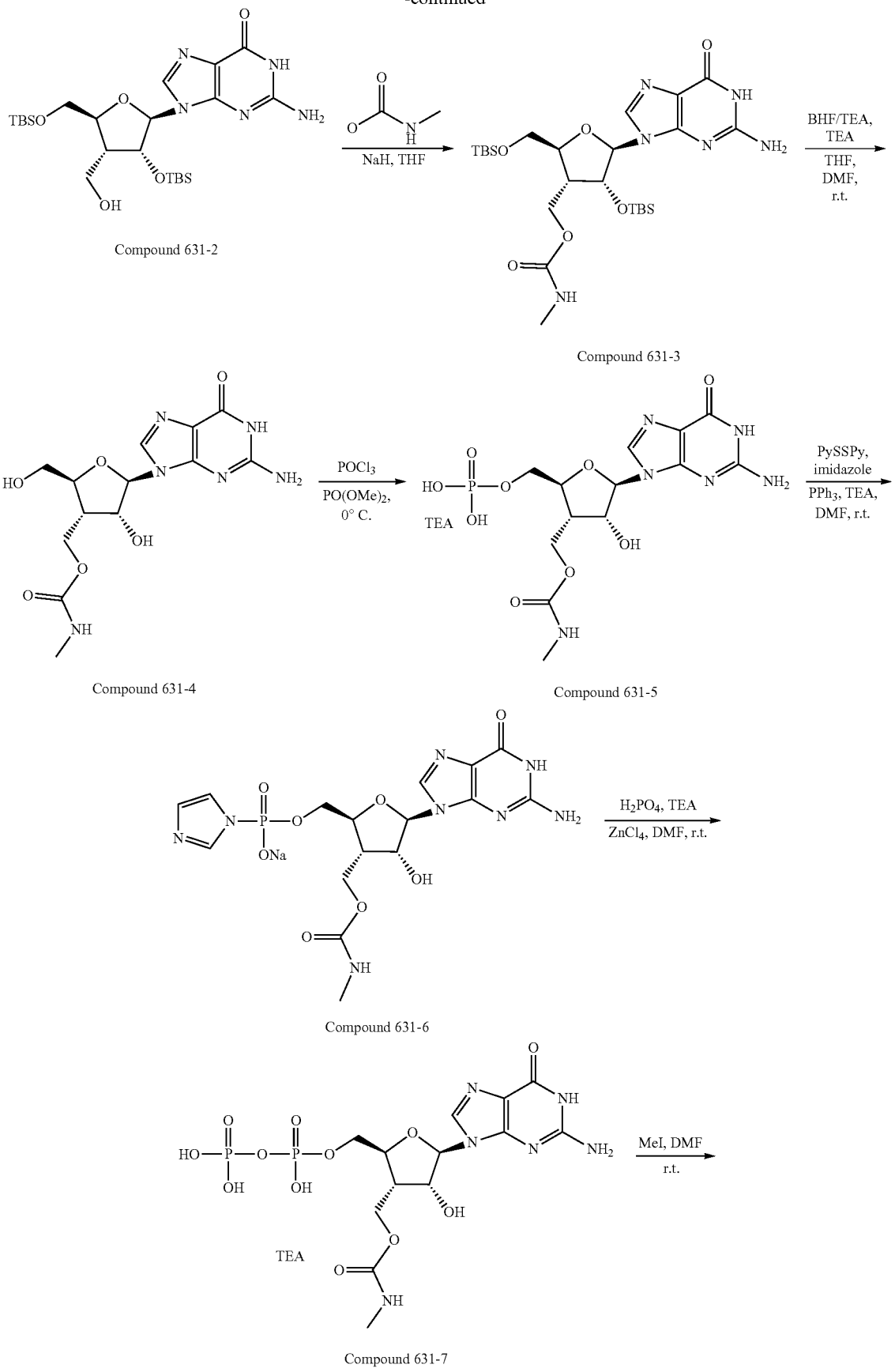
-continued

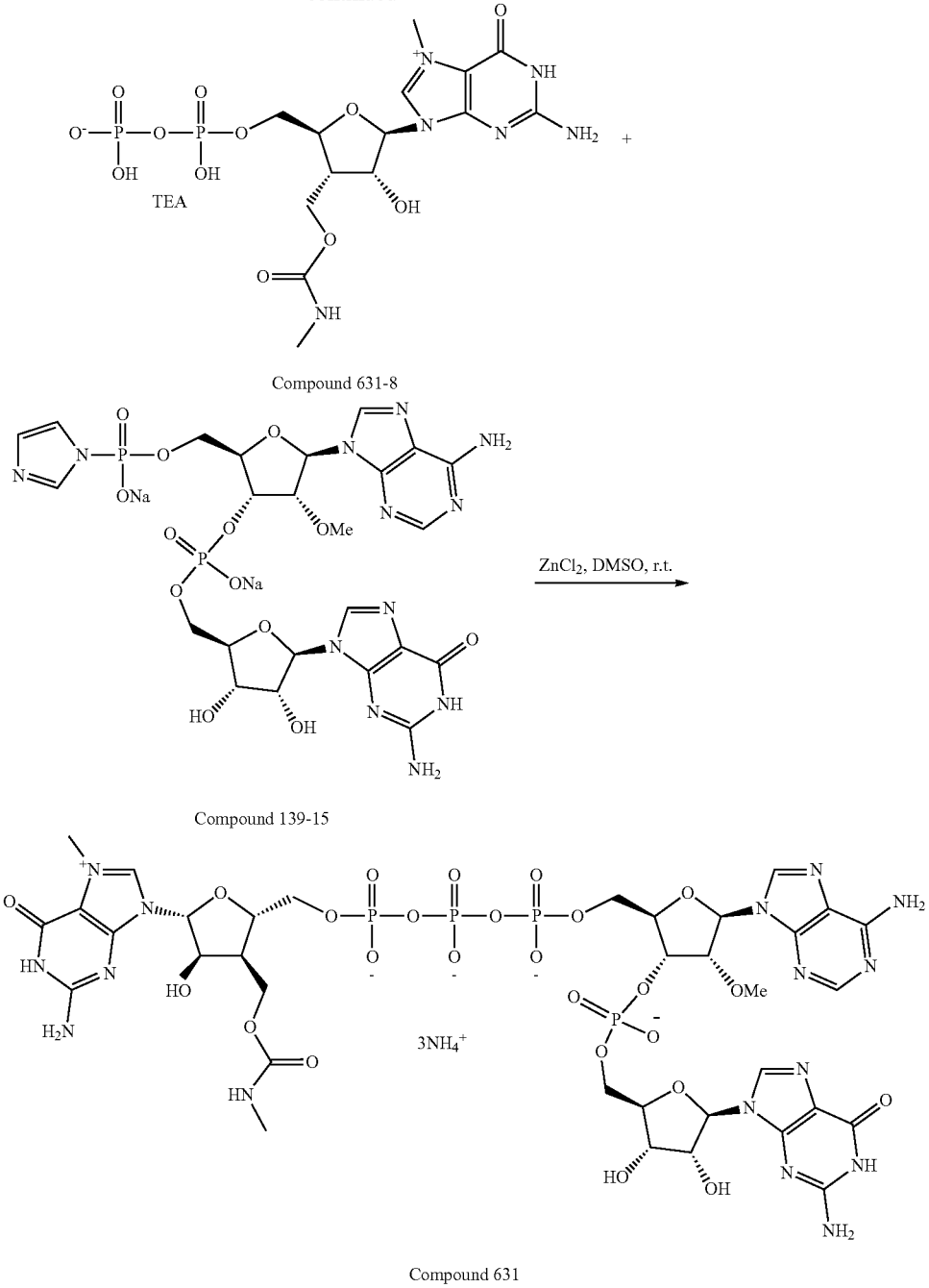

Compound 631

According to the above reaction route, Compound 135-6 (5 g, 12.91 mmol) was dissolved in DMF (50 mL), imidazole (4.39 g, 64.53 mmol) and TBSCl (4.86 g, 32.27 mmol) were further added, and the mixture was stirred overnight at room temperature. After the reaction was completed, the reaction liquid was concentrated under reduced pressure to dryness. Ethyl acetate was added to dissolve the reaction product. Then the product was successively washed with diluent hydrochloric acid, saturated sodium bicarbonate, and saturated saline, dried over anhydrous sodium sulfate, filtered, concentrated under reduced pressure to dryness, and purified by column chromatography to obtain 7.7 g of Compound 631-1.

10% Pd/C (1.00 g) was added to a solution of Compound 631-1 (7.7 g, 12.50 mmol) in ethyl acetate (100 mL), and the mixture was stirred overnight at room temperature under hydrogen atmosphere. Then, the reaction liquid was filtered by vacuum and the filtrate was concentrated under reduced pressure to obtain 6.2 g of Compound 631-2.

According to the reaction route, Compound 631-4 was prepared from Compound 631-2 using the procedure for preparation of Compound 6-4, except substituting acetyl chloride with methylaminoformyl chloride.

The characteristic data of Compound 631-4 was: $^1$H NMR (500 MHz, DMSO) δ: 10.60 (s, 1H), 7.99 (s, 1H), 6.45 (br, 2H), 5.70 (s, 1H), 5.70-5.67 (d, J=6.0 Hz, 1H), 5.03-4.99 (t, J=5.6 Hz, 1H), 4.41-4.37 (m, 1H), 4.00-3.96 (m, 1H), 3.74-3.68 (m, 1H), 3.60-3.55 (m, 1H), 3.54-3.48 (m, 1H), 3.44-3.39 (m, 11H), 2.76 (s, 3H), 2.58-2.52 (m, 1H).

According to the reaction route, Compound 631 (ammonium salt) was prepared from Compound 631-4 using the procedure for preparation of Compound 139.

The characteristic data of the Compound 631 was: MS (m/z): 1215.07[M−1]⁻. ¹H NMR (500 MHz, D₂O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.43 (s, 3H), 2.68 (s, 3H), 2.61-2.52 (m, 1H); ³¹P NMR (202 MHz, D₂O) δ -0.93 (s, 1H), −11.65 (m, 2P), −22.90 (m, 1P).

Example 32 Synthesis of Compound 637

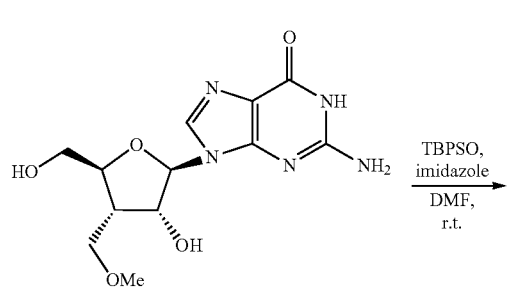

Compound 3-6

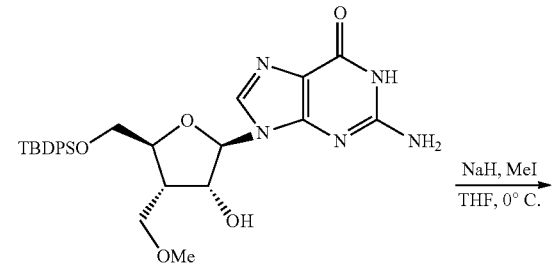

Compound 637-1

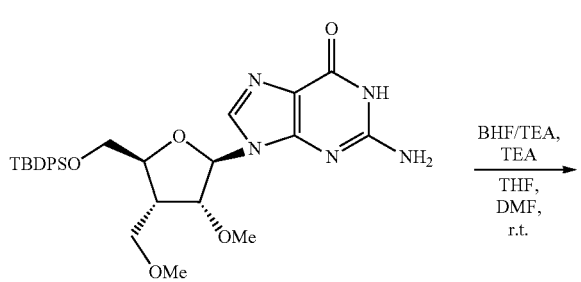

Compound 637-2

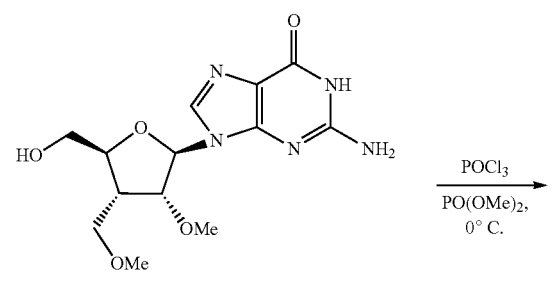

Compound 637-3

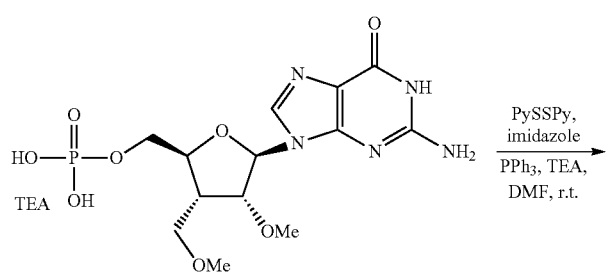

Compound 637-4

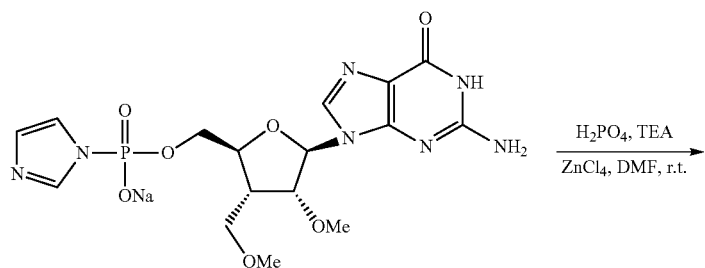

Compound 637-5

-continued

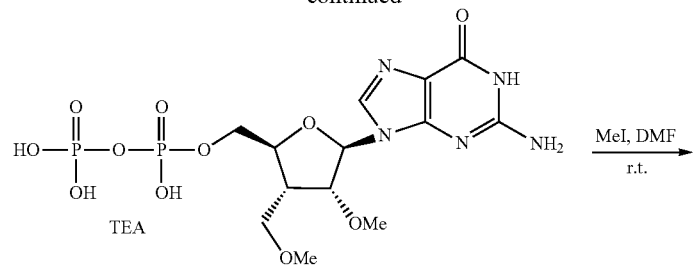

Compound 637-6

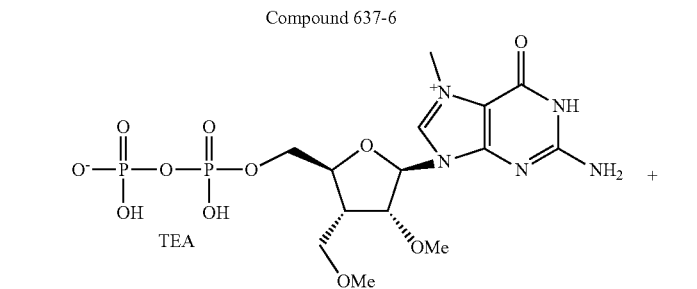

Compound 637-7

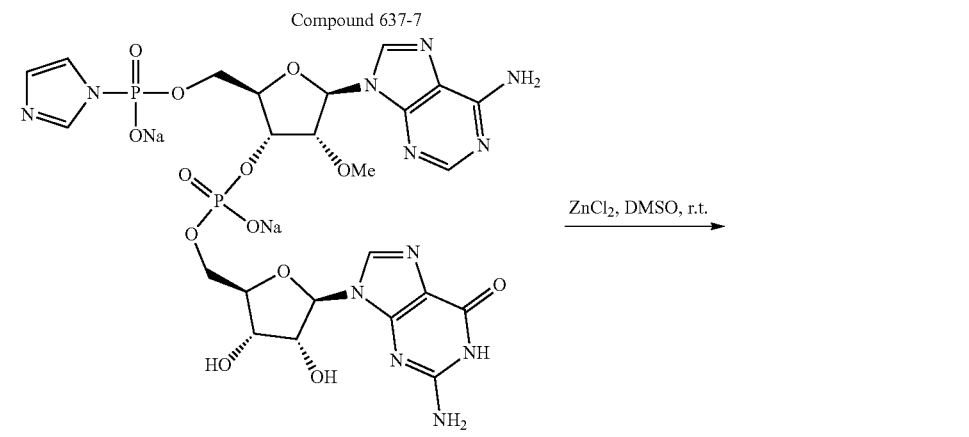

Compound 139-15

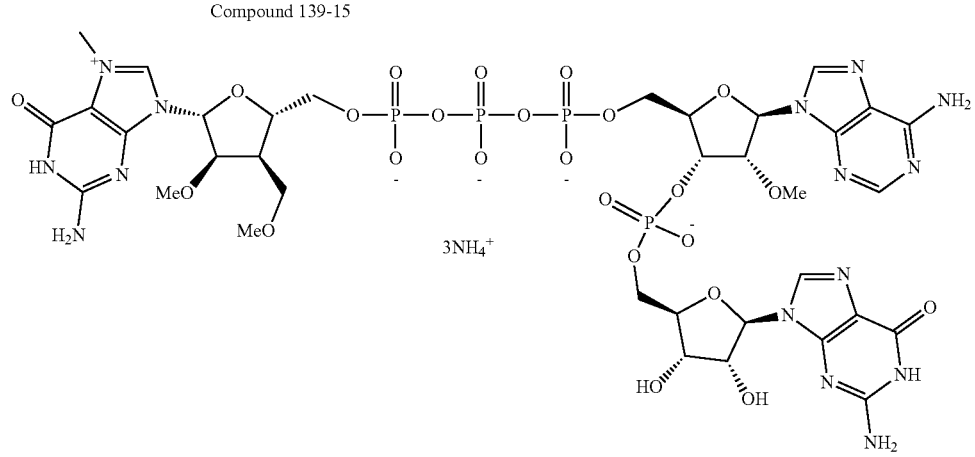

Compound 637

According to the reaction route, Compound 637-1 was prepared from Compound 3-6 using the procedure for preparation of Compound 6-1.

Compound 631-7 (9.8 g, 17.83 mmol) was dissolved in anhydrous THF (100 mL) at room temperature, and after the temperature was cooled to 0° C., NaH (1.07 g, 26.74 mmol) was gradually added. The mixture was stirred for 10 min, followed by addition of iodomethane (2.78 g, 19.61 mmol). After addition, the mixture was stirred for 5 hours at 0° C. Methanol (1 mL) and saturated ammonium chloride solution (150 mL) were then added. After addition ethyl acetate (150 mL), the solution was separated, and the organic phase was successively washed with water (100 mL*2) and saturated saline, dried over anhydrous sodium sulfate. Subsequently, the organic phase was concentrated under reduced pressure and purified by column chromatography, to obtain 2.21 g of Compound 637-2.

The Compound 637-2 (2.21 g, 3.92 mmol) was added to DCM (20 ml), and then TEA (1 mL, 7.34 mmol) and TEA-3HF (2.36 g, 14.68 mmol) were successively added. The mixture was stirred overnight at room temperature. HPLC detection showed that the raw materials were reacted completely. The solvent was removed by rotary evaporation. DCM was added to product, which was vigorously stirred. After filtration, a white solid was heated and vigorously stirred with MeOH (20 mL), and then the product was filtered and recrystallized with 10 mL of H$_2$O (0.1% TFA) to obtain 870 mg of Compound 637-3.

The characteristic data of Compound 637-3 was: $^1$H NMR (500 MHz, DMSO) δ: 10.60 (s, 1H), 7.99 (s, 1H), 6.45 (br, 2H), 5.70 (s, 1H), 5.70-5.67 (d, J=6.0 Hz, 1H), 5.03-4.99 (t, J=5.6 Hz, 1H), 4.41-4.37 (m, 1H), 4.00-3.96 (m, 1H), 3.74-3.68 (m, 1H), 3.60-3.55 (m, 1H), 3.54-3.48 (m, 1H), 3.44-3.39 (m, 1H), 3.26 (s, 3H), 3.20 (s, 3H), 2.58-2.52 (m, 1H).

According to the reaction route, Compound 637 (ammonium salt) was prepared from Compound 637-3 using the procedure for preparation of Compound 139.

The characteristic data of the Compound 637 was: MS (m/z): 1186.04[M−1]$^-$. $^1$H NMR (500 MHz, D$_2$O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 11H), 4.76-4.75 (m, 1$), 4.63 (d, J=4.9 Hz, 11H), 4.50 (m, 1H), 4.48 (t, J=4.5 Hz, 1H), 4.43 (m, 11H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.43 (s, 3H), 3.32 (s, 3H), 3.23 (s, 3H), 2.61-2.52 (m, 1H); $^{31}$P NMR (202 MHz, D$_2$O) δ-0.93 (s, 1H), −11.65 (m, 2P), −22.90 (m, 1P).

Example 33 Synthesis of Compound 215

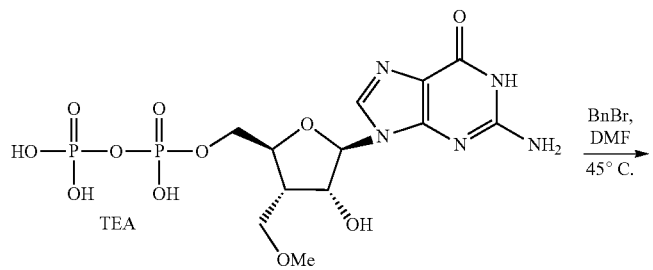

Compound 3-9

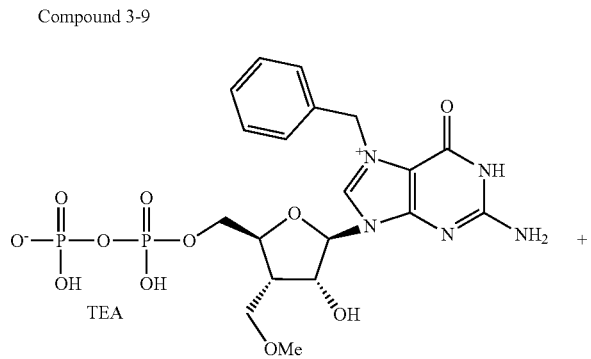

Compound 215-1

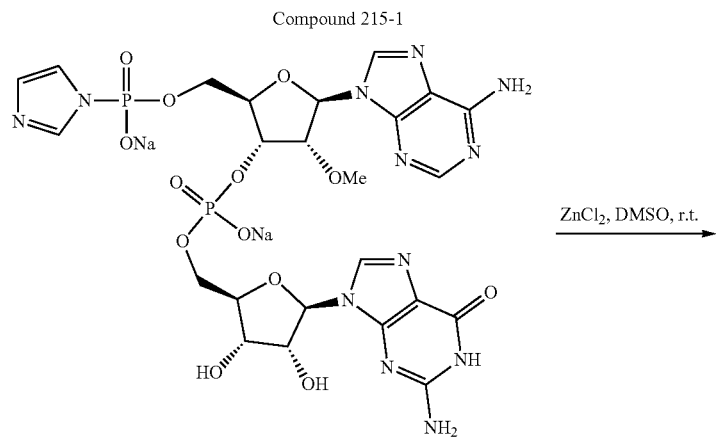

Compound 139-15

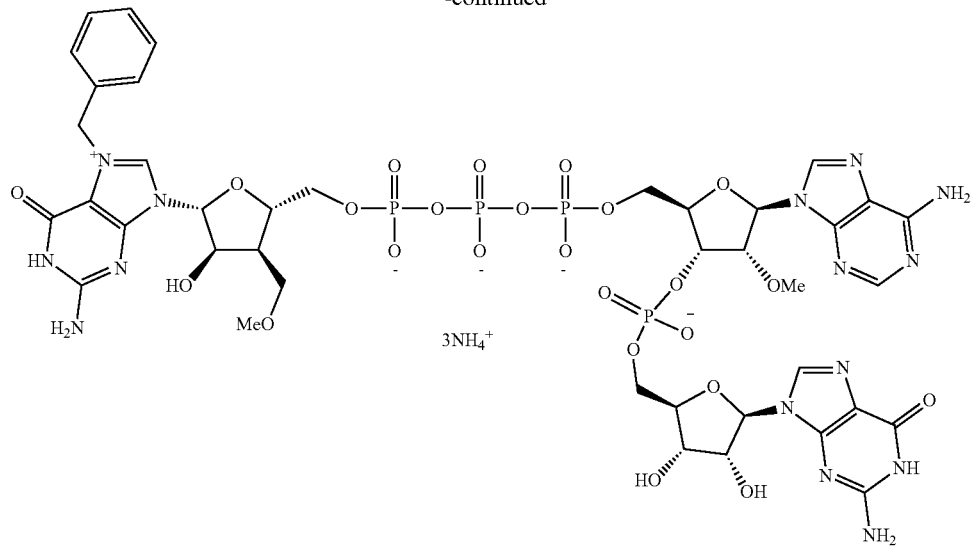

Compound 215

According to the reaction route, Compound 215 (ammonium salt) was prepared from Compound 3-9 using the procedure for preparation Compound 139, except substituting iodomethane with bromotoluene.

The characteristic data of the Compound 215 was: MS (m/z): 1248.07[M−1]⁻. $^1$H NMR (500 MHz, D$_2$O) δ 8.37 (s, 1H), 8.07 (s, 1H), 7.96 (s, 1H), 7.49-7.44 (m, 5H), 5.93-5.97 (m, 3H), 5.74 (d, J=6.2 Hz, 1H), 5.66 (d, J=3.8 Hz, 1H), 4.81 (d, J=23.6 Hz, 2H), 4.48 (d, J=4.2 Hz, 1H), 4.42 (s, 1H), 4.38 (d, J=4.6 Hz, 1H), 4.35 (s, 1H), 4.29-4.21 (m, 3H), 4.20-4.12 (m, 2H), 4.09 (d, J=15.0 Hz, 3H), 4.01 (s, 3H), 3.65-3.62 (m, 1H), 3.55-3.52 (m, 1H), 3.43 (d, J=9.3 Hz, 3H), 3.39 (s, 3H), 2.55-2.50 (m, 1H); $^{31}$P NMR (202 MHz, D$_2$O) δ-0.98 (s, 1P), −11.76−(m, 2P), −23.23 (m, 1P).

Example 34 Synthesis of Compound 181

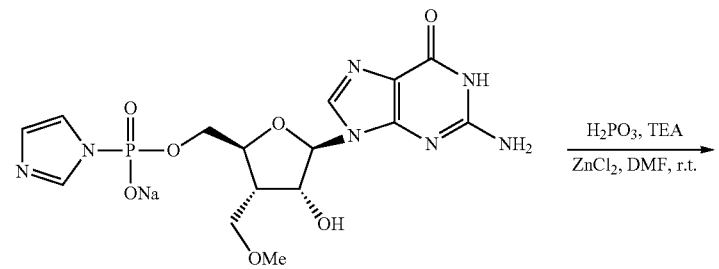

Compound 3-8

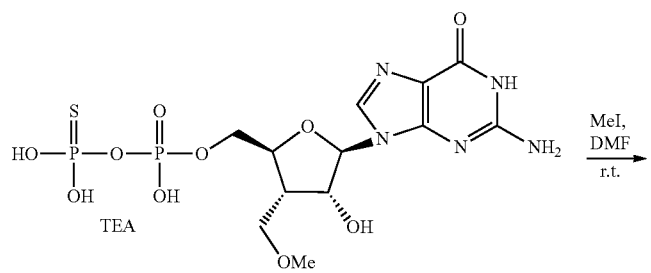

Compound 181-1

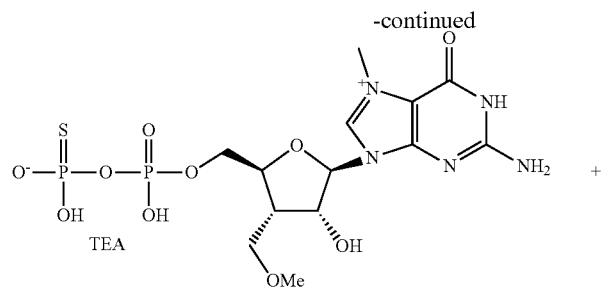

Compound 181-2

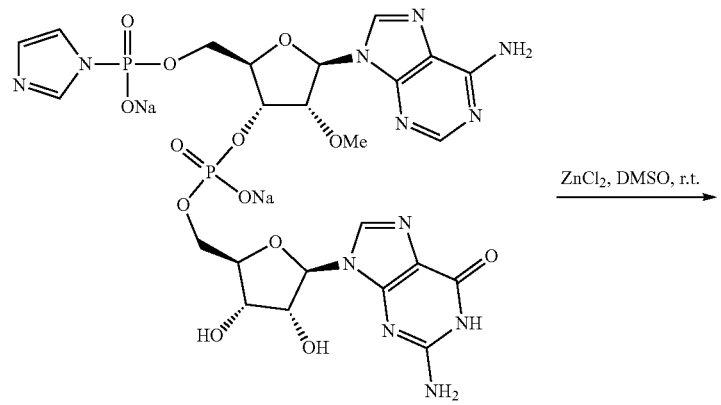

Compound 139-15

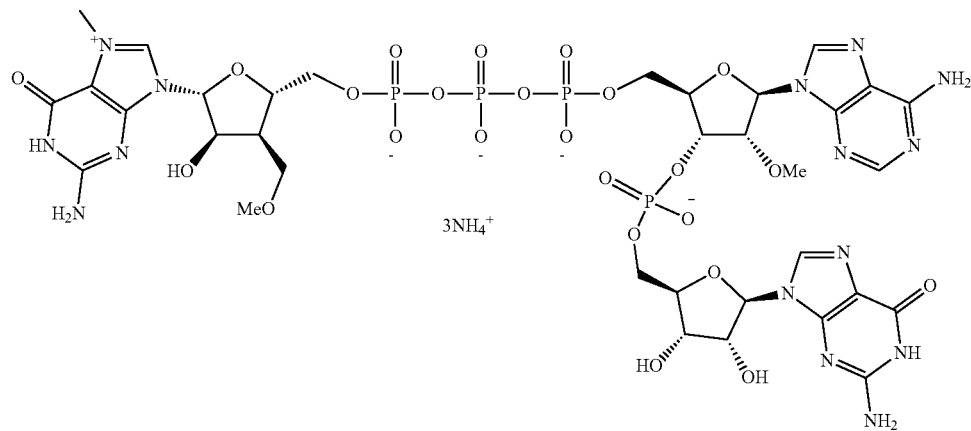

Compound 181

According to the reaction route, Compound 181 (ammonium salt) was prepared from Compound 3-8 using the procedure for preparation of Compound 139, except substituting phosphoric acid with thiophosphoric acid.

The characteristic data of the Compound 181 was: MS (m/z): 1188.08[M−1]⁻. $^1$H NMR (500 MHz, D$_2$O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H, 3.65-3.62 (m, 1H), 3.55-3.52 (m, 1H), 3.43 (s, 3H), 3.32 (s, 3H), 2.61-2.52 (m, 1H); $^{31}$P NMR (202 MHz, D$_2$O) δ 29.38 (m, 1P), −0.94 (s, 1H), −11.58 (m, 2P).

Example 35 Synthesis of Compound 547

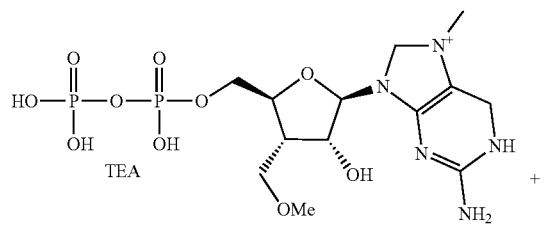

Compound 3-10

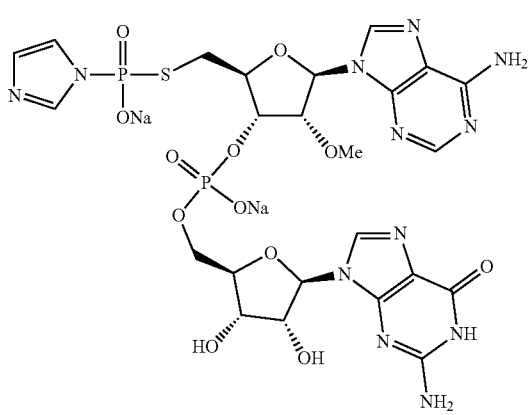

Compound 547-1

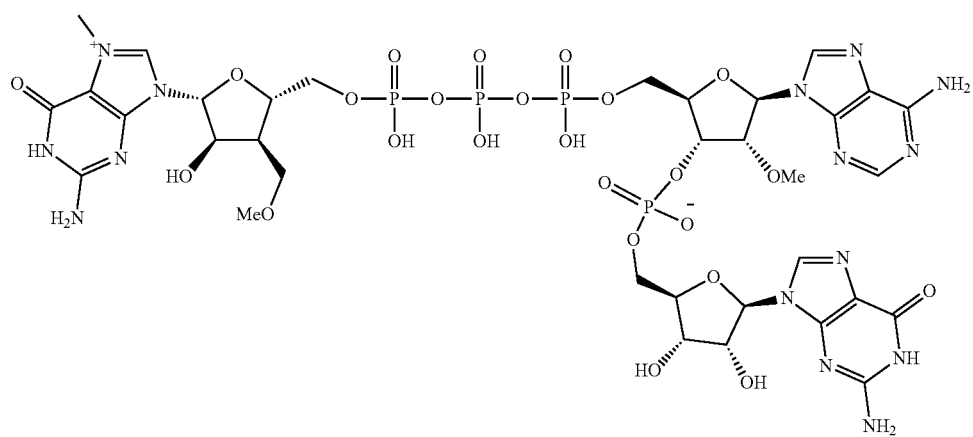

Compound 547

According to the reaction route, Compound 547 (ammonium salt) was prepared from Compound 3-10 and Compound 547-1 using the procedure for preparation of Compound 139.

The characteristic data of the Compound 547 was: MS (m/z): 1188.08[M−1]⁻. $^1$H NMR (500 MHz, D$_2$O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.43 (s, 3H), 3.32 (s, 3H), 2.61-2.52 (m, 1H); $^{31}$P NMR (202 MHz, D$_2$O) δ 7.55 (m, 1P), −0.93 (s, 1H), −11.60 (m, 1P), −23.02 (m, 1P).

Example 36 Synthesis of Compound 199
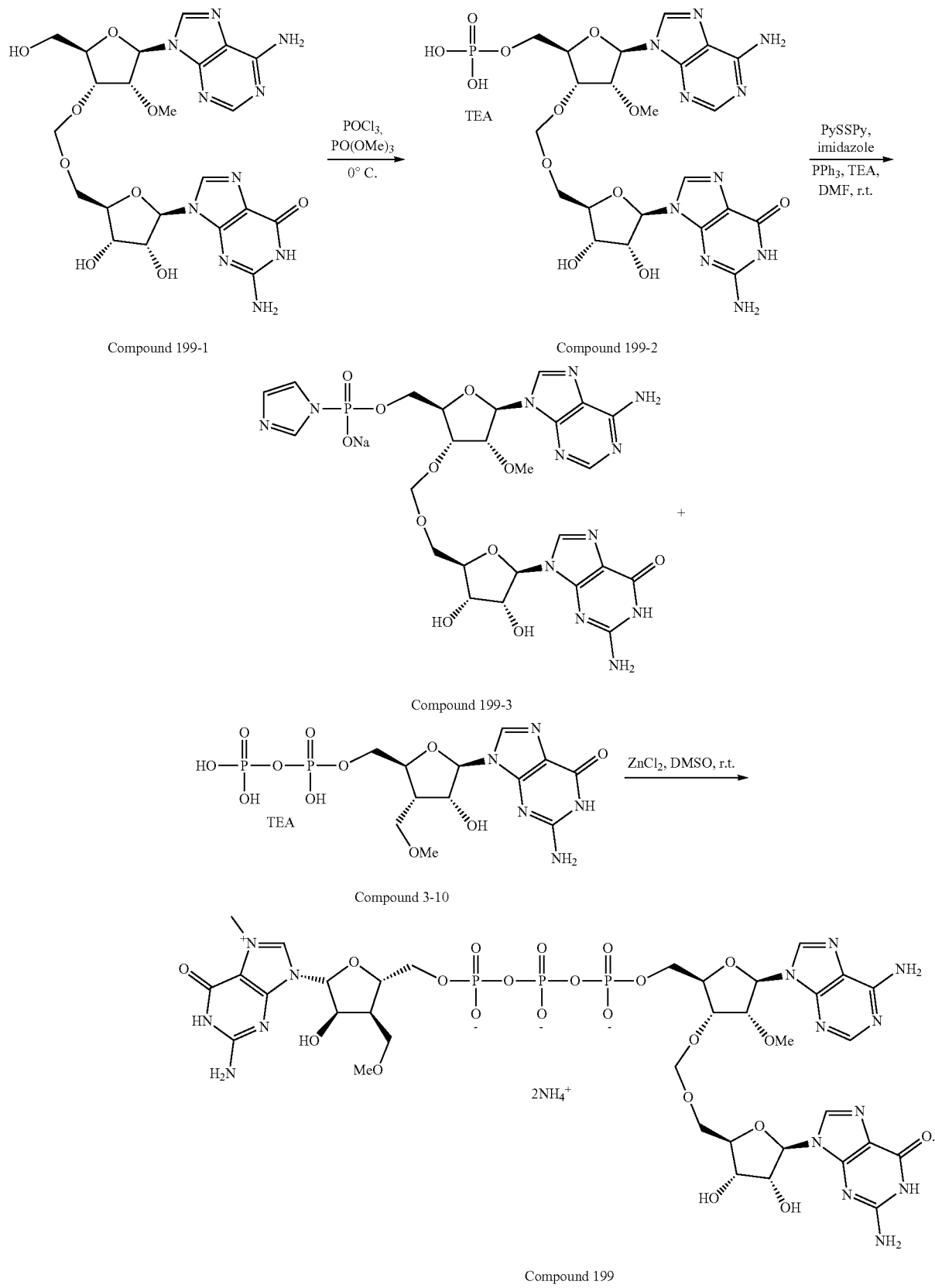

According to the above synthetic route, Compound 199-1 (250 mg, 0.43 mmol) was dissolved in trimethyl phosphate (7.5 mL), and phosphorus oxychloride (0.40 mL, 4.30 mmol) was added at 0° C. After the mixture was reacted overnight, a small amount of raw materials was remained. Water was added to quench the reaction, and the liquid was directly passed through ion exchange column to collect a peak of the desirable product. Then, the collected liquid was concentrated and passed through reversed phase column to obtain the product, which was concentrated and freeze-dried to obtain 192 mg of Compound 199-2 (triethylamine salt).

The Compound 199-2 (192 mg, 0.29 mmol), imidazole (99 mg, 1.46 mmol), 2,2'-dithiobipyridine (128 mg, 0.58 mmol), N,N-dimethylformamide (2 mL), and triethylamine (40 µL, 0.29 mmol) were added to a reaction flask, followed by addition of triphenylphosphine (152 mg, 0.58 mmol) under stirring. The mixture was stirred for 2 hours at room temperature under nitrogen atmosphere. After the reaction was completed, the reaction system was added to a mixture solution of sodium iodide (218 mg, 1.45 mmol) and acetone (5 mL), stirred for 10 min at room temperature. The liquid was filtered and the filter cake was washed with acetone. Subsequently, the filter cake was collected and dried at room temperature under reduced pressure to obtain 210 mg of Compound 199-3.

Compound 199 (ammonium salt) was prepared from Compound 3-10 and Compound 199-3 using the procedure for preparation of Compound 139.

The characteristic data of the Compound 199 was: MS (m/z): 1122.06[M−1]−. $^1$H NMR (500 MHz, D$_2$O) δ 8.22 (s, 1H), 7.91 (br, 2H), 5.98 (s, 1H), 5.86 (s, 1H), 5.75 (s, 1H), 5.13 (s, 1H), 4.92 (d, J=7.0 Hz, 1H), 4.68 (m, 1H), 4.47 (m, 2H), 4.41 (m, 1H), 4.36-4.32 (m, 6H), 4.19-4.13 (m, 4H), 4.04 (s, 3H), 3.88-3.84 (m, 1H), 3.80-3.77 (m, 1H), 3.51 (s, 3H), 3.46 (s, 3H), 2.58-2.53 (m, 1H); $^{31}$P NMR (202 MHz, D$_2$O) δ-11.13 (m, 1P), −11.70 (d, J=19.2 Hz, 1P), −23.12 (t, J=19.2 Hz, 1P).

Example 37 Synthesis of Compound 201

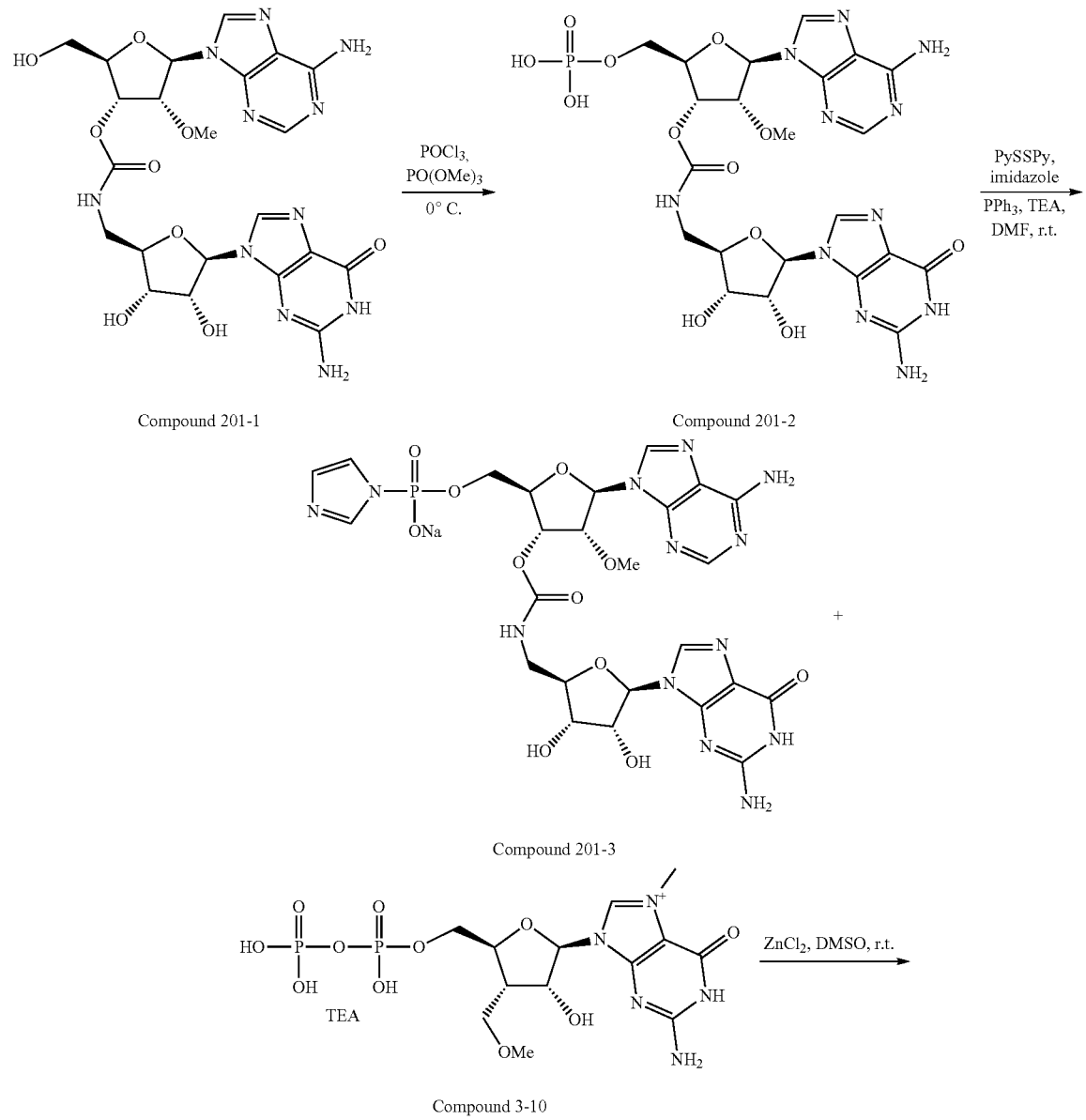

-continued
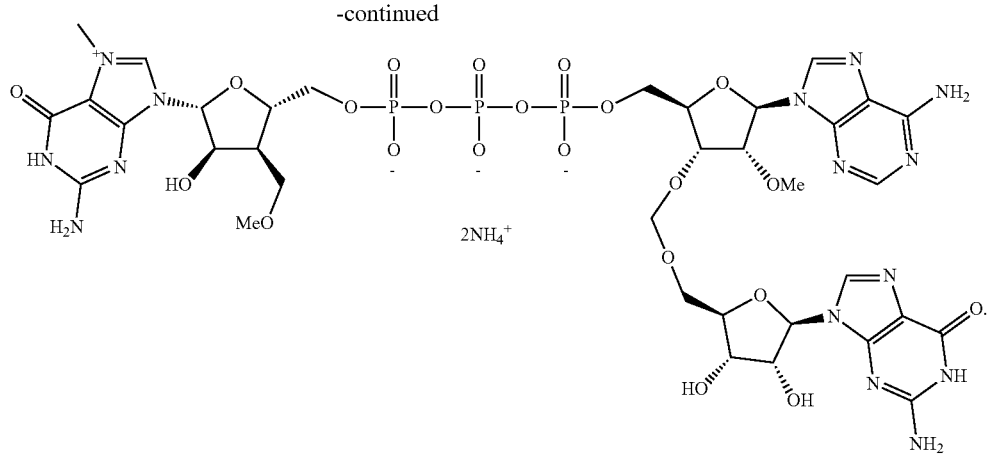
Compound 201
According to the reaction route, Compound 201 (ammonium salt) was prepared from Compound 201-1 using the procedure for preparation of Compound 139.
The characteristic data of the Compound 201 was: MS (m/z): 1133.03[M−1]⁻. ¹H NMR (500 MHz, D₂O) δ 9.14 (s, 1H), 8.42 (s, 1H), 8.24 (s, 1H), 7.82 (s, 1H), 6.18 (s, 1H), 5.82 (d, J=3.8 Hz, 1H), 5.68 (d, J=5.3 Hz, 1H), 4.72-4.71 (m, 1H), 4.56 (t, J=5.1 Hz, 1H), 4.46-4.42 (m, 3H), 4.31-4.19 (m, 4H), 4.15 (t, J=4.3 Hz, 1H), 4.04 (s, 3H), 4.00 (m, 1H), 3.73-3.69 (m, 2H), 3.58-3.53 (m, 5H), 3.50 (s, 3H), 2.89-2.87 (m, 1H), 2.61-2.53 (m, 3H); ³¹P NMR (202 MHz, D₂O) δ-11.52 (m, 2P), −22.88 (t, J=18.6 Hz, 1P).
Example 38 Synthesis of Compound 203
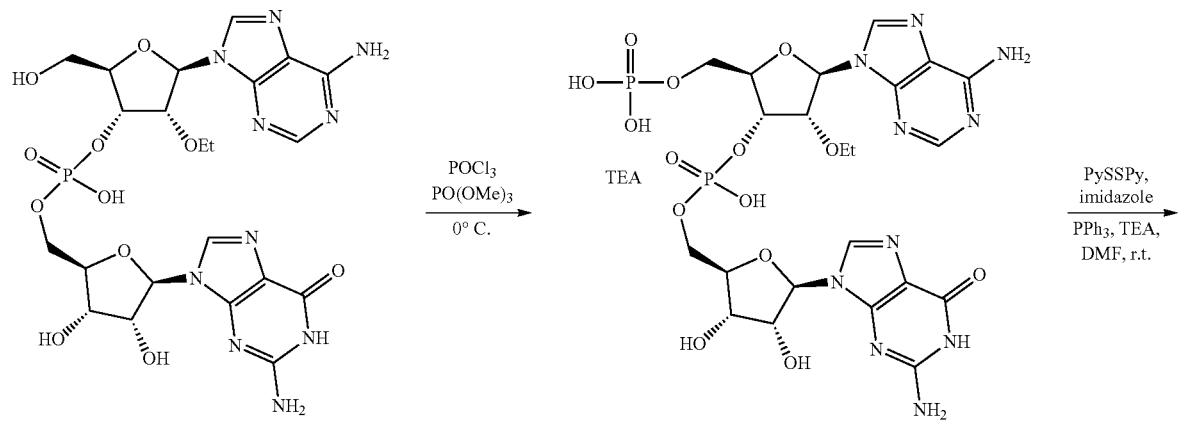
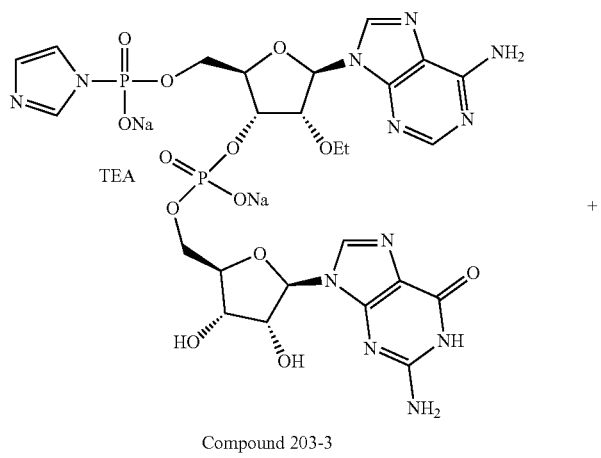
Compound 203-3

-continued

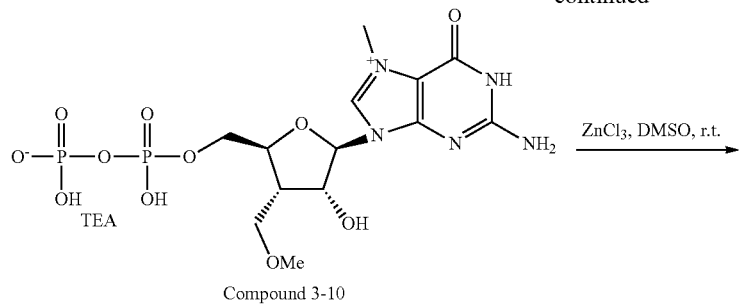

Compound 3-10

ZnCl₃, DMSO, r.t.

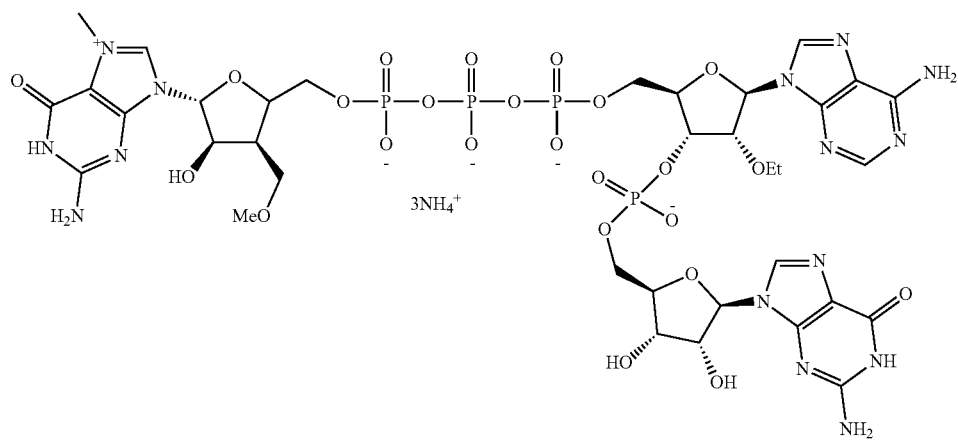

Compound 203

According to the reaction route, Compound 203 (ammonium salt) was prepared from Compound 203-1 using the procedure for preparation of Compound 139.

The characteristic data of the Compound 203 was: MS (m/z): 1186.02[M−1]⁻. ¹H NMR (500 MHz, D₂O) δ 9.05 (s, 1H), 8.40 (s, 1H), 8.13 (s, 1H), 7.93 (s, 1H), 6.01 (d, J=5.5 Hz, 1H), 5.80 (d, J=5.9 Hz, 1H), 5.78 (s, 1H), 4.93-4.90 (m, 1H), 4.76-4.75 (m, 1H), 4.63 (d, J=4.9 Hz, 1H), 4.50 (m, 1H), 4.48 (t, J=4.5 Hz, 1H), 4.43 (m, 1H), 4.41 (t, J=5.0 Hz, 1H), 4.33 (m, 1H), 4.29-4.27 (m, 2H), 4.24-4.22 (m, 1H), 4.19-4.18 (m, 2H), 4.07-4.04 (m, 1H), 3.99 (s, 3H), 3.65-3.62 (m, 1H), 3.55-3.52 (m, 1H), 3.40 (q, J=6.5 Hz, 2H), 3.32 (s, 3H), 2.61-2.52 (m, 1H), 1.18 (t, J=6.5 Hz, 3H); ³¹P NMR (202 MHz, D₂O) δ-0.93 (s, 1H), −11.65 (m, 2P), −22.90 (m, 1P).

Example 39 Synthesis of Compound 639

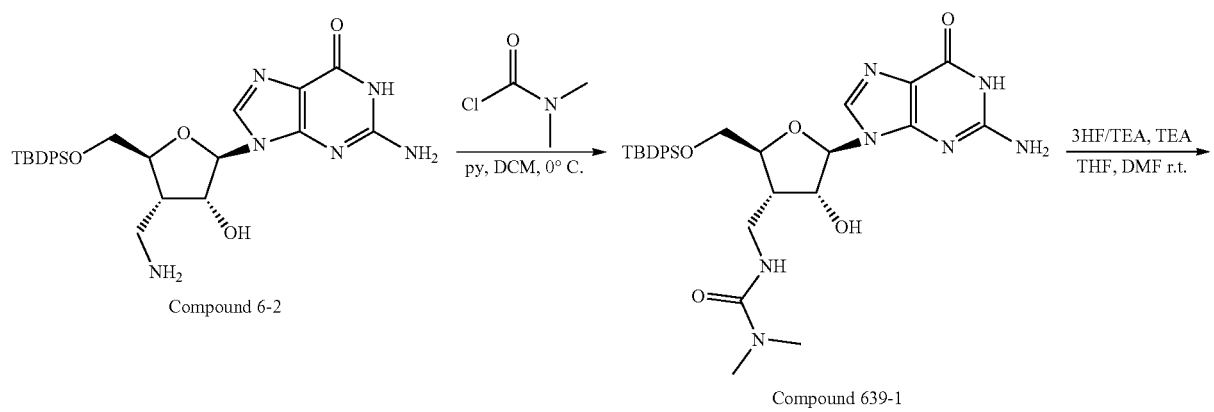

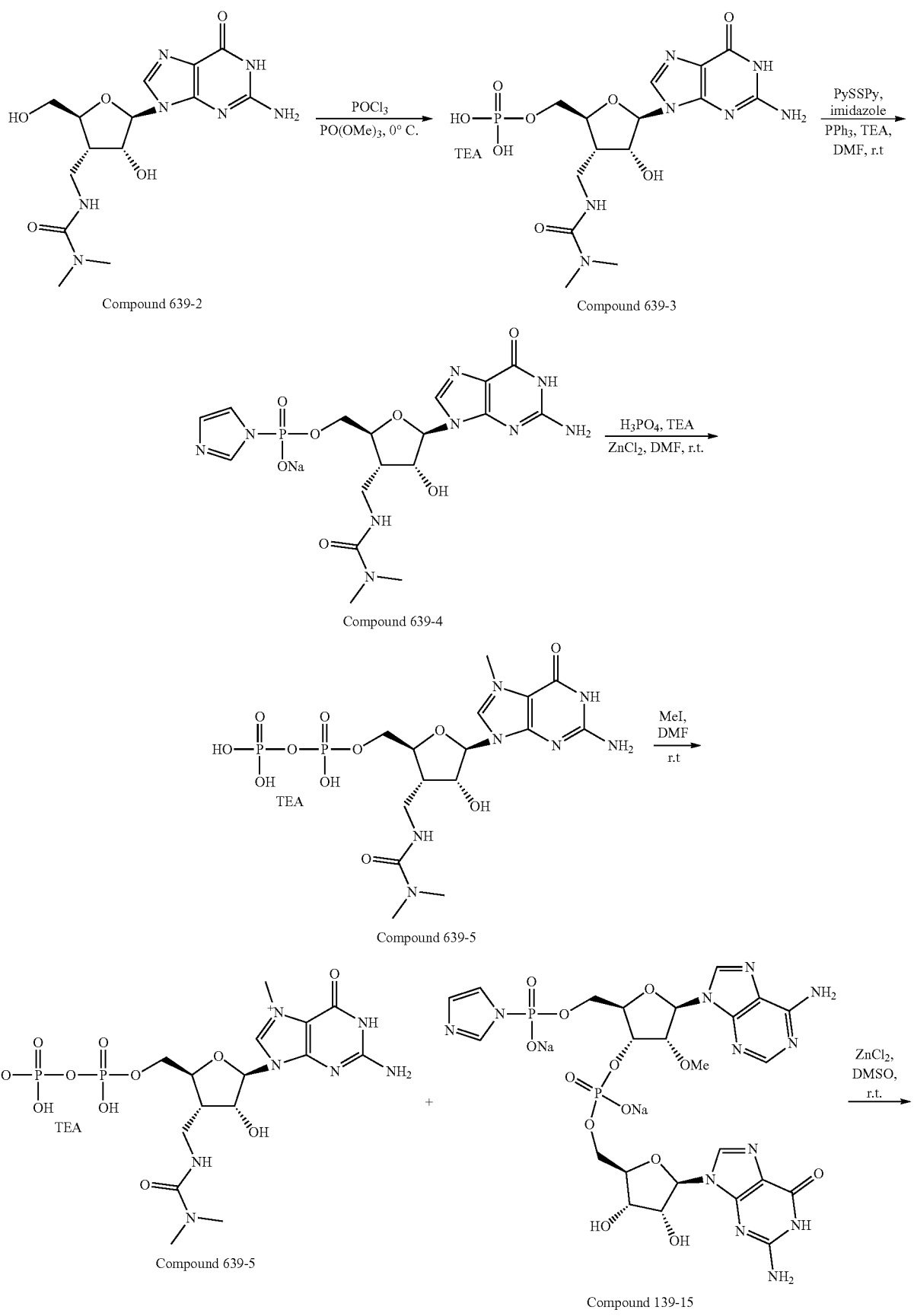

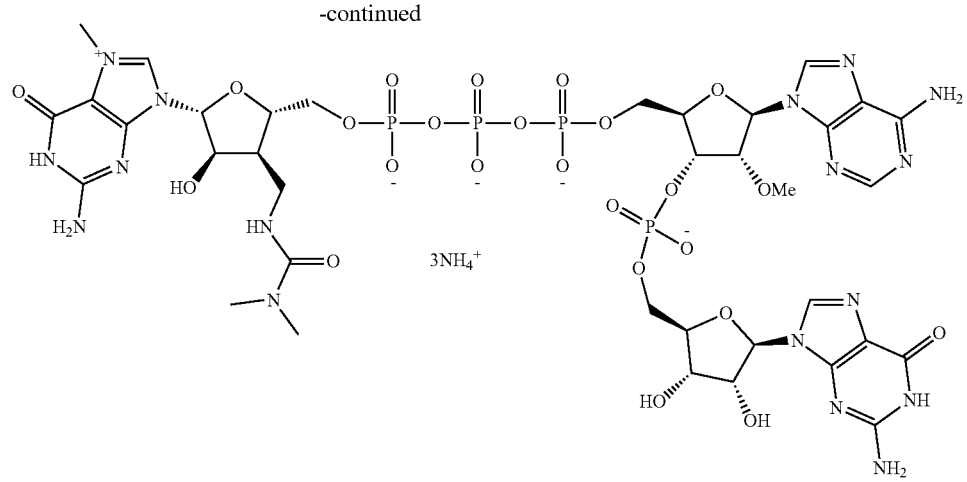

Compound 639

According to the reaction route, Compound 639-2 was prepared from Compound 6-2 using the procedure for preparation of Compound 6-4, except substituting acetyl chloride with dimethylcarbamoyl chloride.

The characteristic data of the Compound 639-2 was: $^1$H NMR (500 MHz, DMSO) δ 10.58 (s, 1H), 8.03 (s, 1H), 6.50-6.49 (m, 3H), 6.00 (d, J=3.4 Hz, 1H), 5.73 (s, 1H), 5.14 (t, J=4.8 Hz, 1H), 4.14 (s, 1H), 3.91 (d, J=9.8 Hz, 1H), 3.78-3.76 (m, 1H), 3.56-3.54 (m, 1H), 3.08-3.03 (m, 1H), 2.76 (s, 6H), 2.45-2.40 (m, 1H).

According to the reaction route, Compound 639 (ammonium salt) was prepared from Compound 639-2 using the procedure for preparation of Compound 139.

The characteristic data of the Compound 639 was: MS (m/z): 1228.06[M−1]$^-$. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.99 (s, 6H), 2.64-2.59 (m, 1H); $^{31}$P NMR (202 MHz, D$_2$O) δ-0.95 (s, 1H), −11.49 (d, J=10.9 Hz, 1P), −11.58 (d, J=12.0 Hz, 1P), −22.82 (t, J=18.2 Hz, 1P).

Example 40 Synthesis of Compound 323

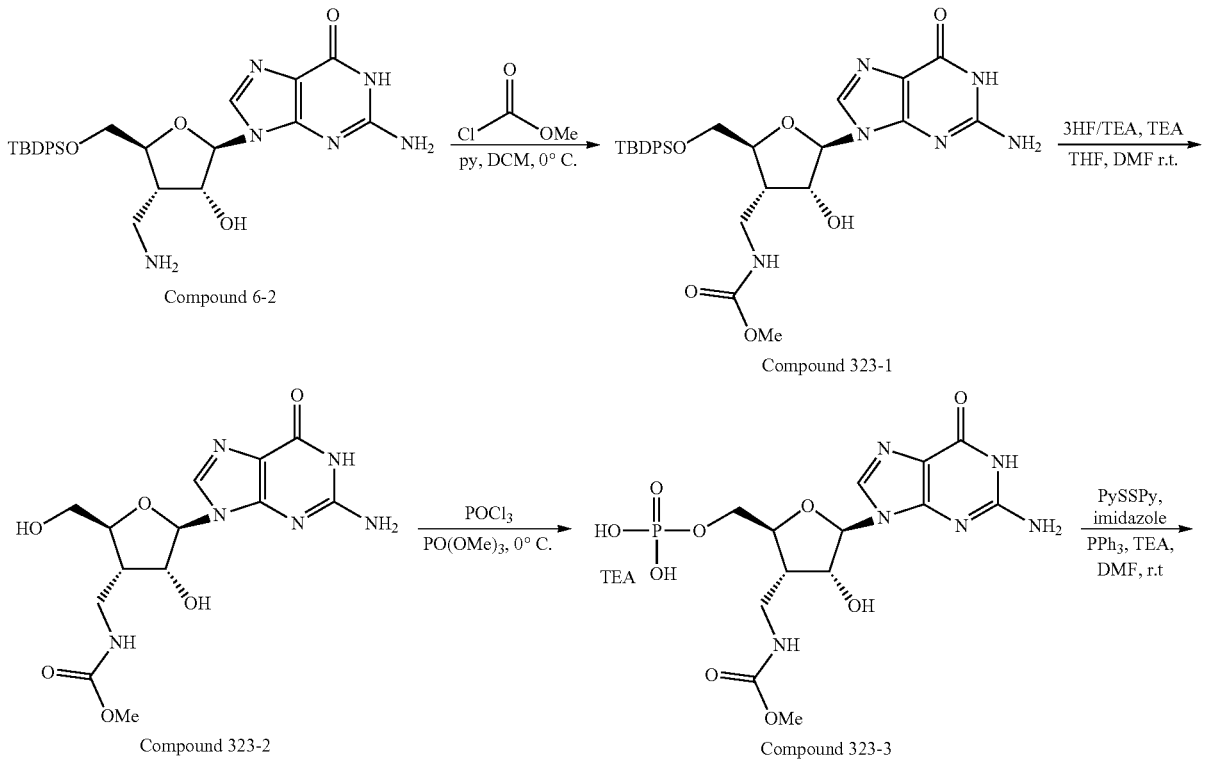

-continued
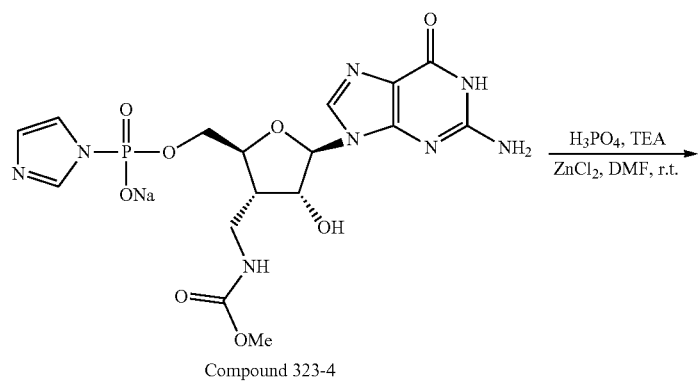
Compound 323-4
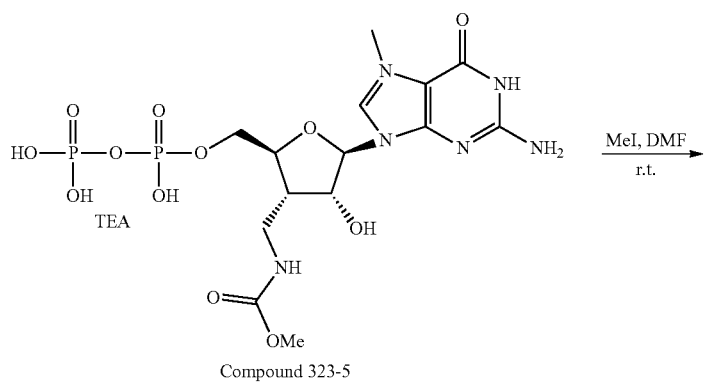
Compound 323-5
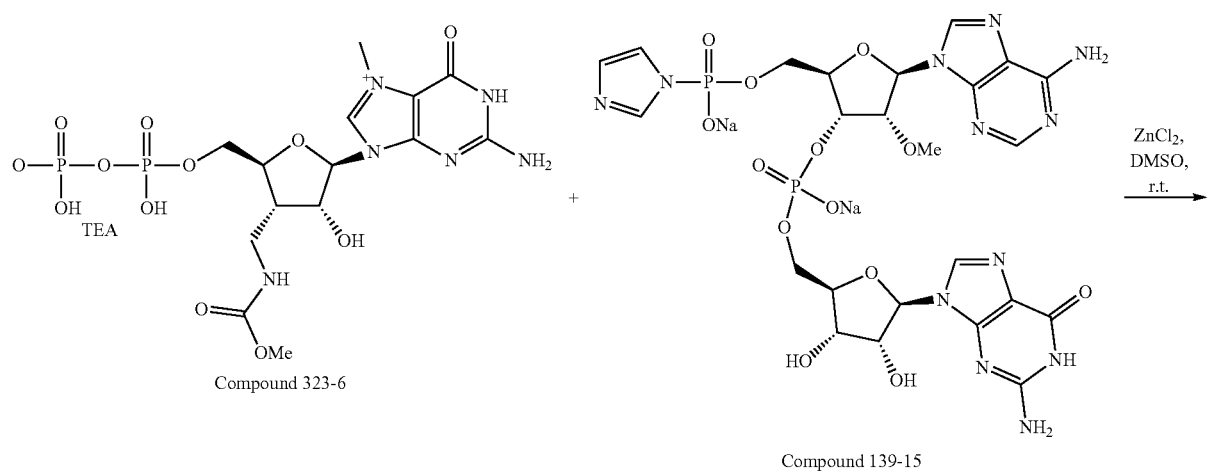
Compound 323-6
Compound 139-15

-continued

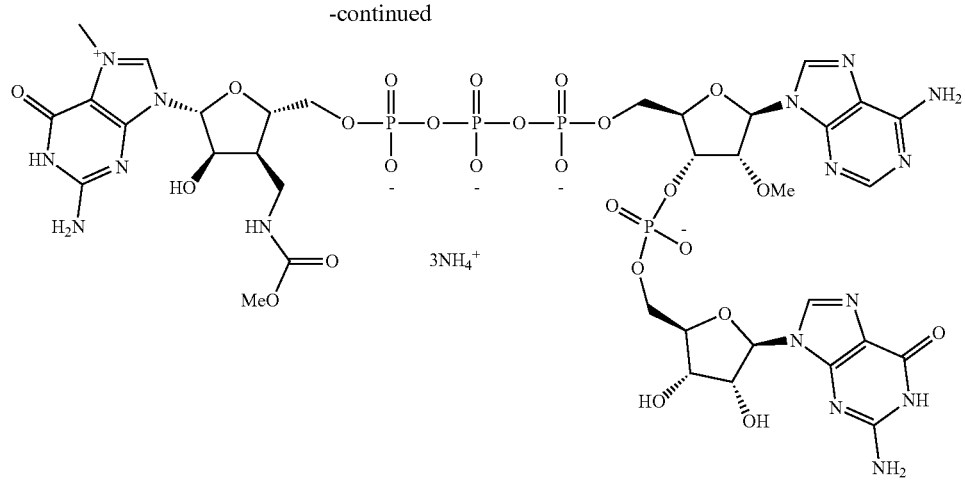

Compound 323

According to the reaction route, Compound 323-2 was prepared from Compound 6-2 using the procedure for preparation of Compound 6-4, except substituting acetyl chloride with methylclhlorofonmate.

The characteristic data of the Compound 323-2 was: $^1$H NMR (500 MHz, DMSO) δ 10.60 (s, 1H), 7.98 (s, 1H), 7.04 (s, 1H), 6.47 (s, 2H), 5.71 (s, 1H), 5.64 (d, J=4.9 Hz, 1H), 5.06 (t, J=4.8 Hz, 1H), 4.38 (s, 1H), 3.92 (d, J=8.8 Hz, 1H), 3.69 (d, J=8.8 Hz, 1H), 3.63 (s, 3H), 3.53-3.49 (m, 1H), 3.30-3.24 (m, 1H), 3.13-3.06 (m, 2H), 2.49-2.46 (m, 1H).

According to the reaction route, Compound 323 (ammonium salt) was prepared from Compound 323-2 using the procedure for preparation of Compound 139.

The characteristic data of the Compound 323 was: MS (m/z): 1215.08[M−1]$^-$. $^1$H NMR (500 MHz, D$_2$O) δ 9.00 (s, 1H), 8.38 (s, 1H), 8.10 (s, 1H), 7.95 (s, 1H), 6.01 (d, J=5.6 Hz, 1H), 5.81-5.80 (m, 2H), 4.93-4.90 (m, 1H), 4.76-4.74 (m, 1H), 4.62 (d, J=4.2 Hz, 1H), 4.50-4.46 (m, 3H), 4.40 (t, J=5.0 Hz, 1H), 4.34-4.22 (m, 4H), 4.21-4.16 (m, 2H), 4.12-4.09 (m, 1H), 3.99 (s, 3H), 3.63 (s, 3H), 3.43-3.38 (m, 4H), 3.25-3.21 (m, 1H), 2.57-2.52 (m, 1H); $^{31}$P NMR (202 MHz, D$_2$O) δ-0.98 (s, 1H), −11.55 (m, 1P), −22.73 (m, 1P).

Example 41 Synthesis of Compound 641

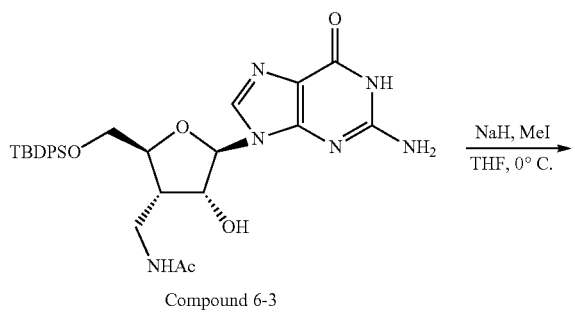

Compound 6-3

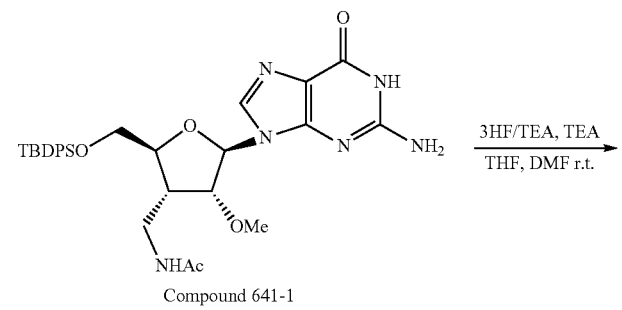

Compound 641-1

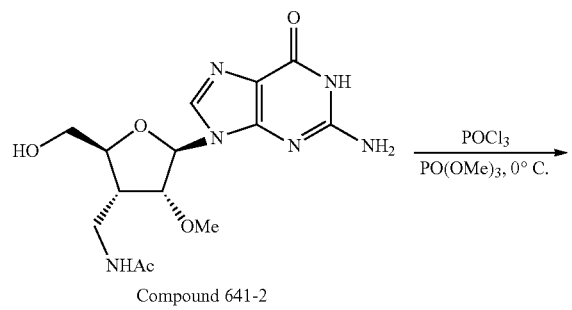

Compound 641-2

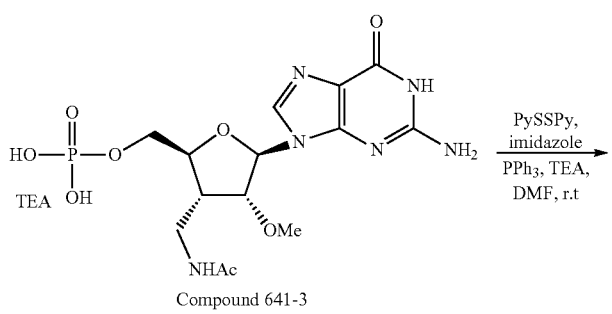

Compound 641-3

-continued
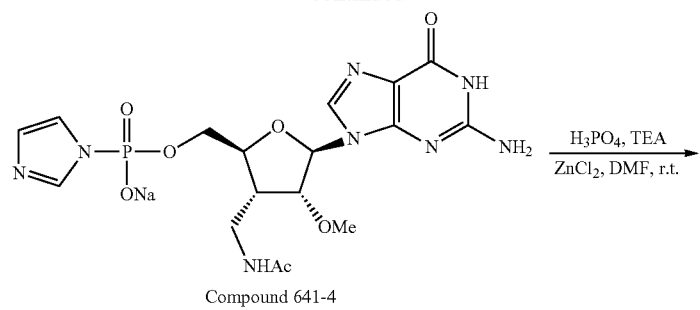
Compound 641-4
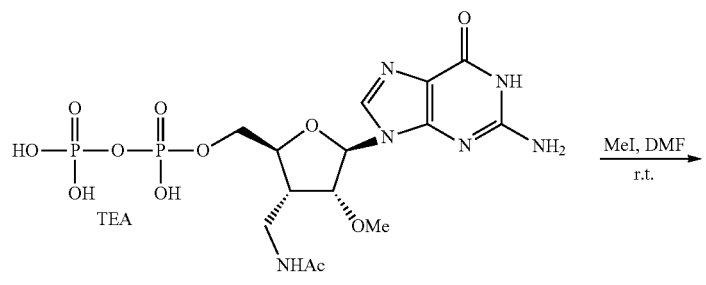
Compound 641-5
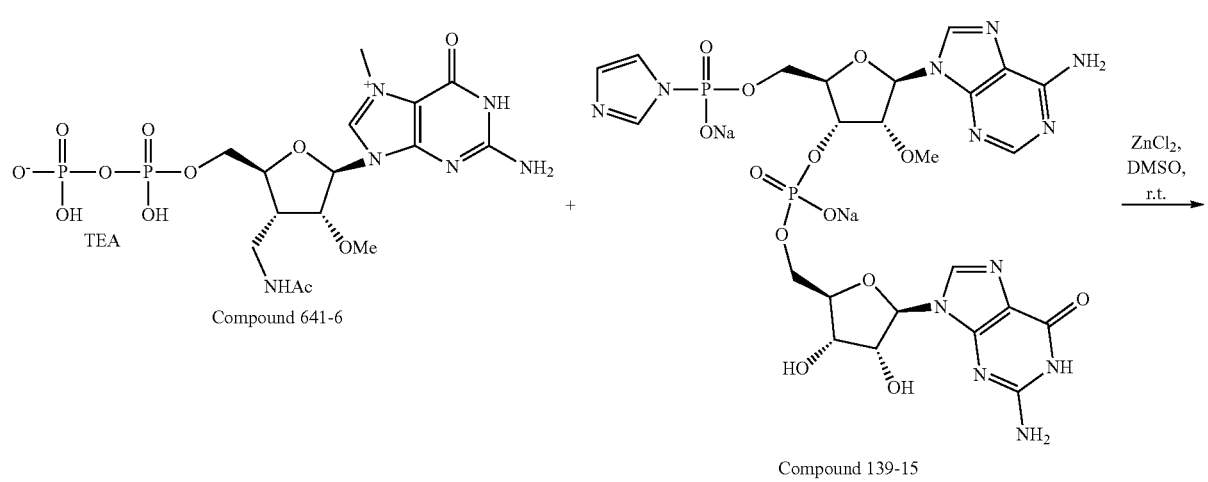
Compound 641-6 + Compound 139-15
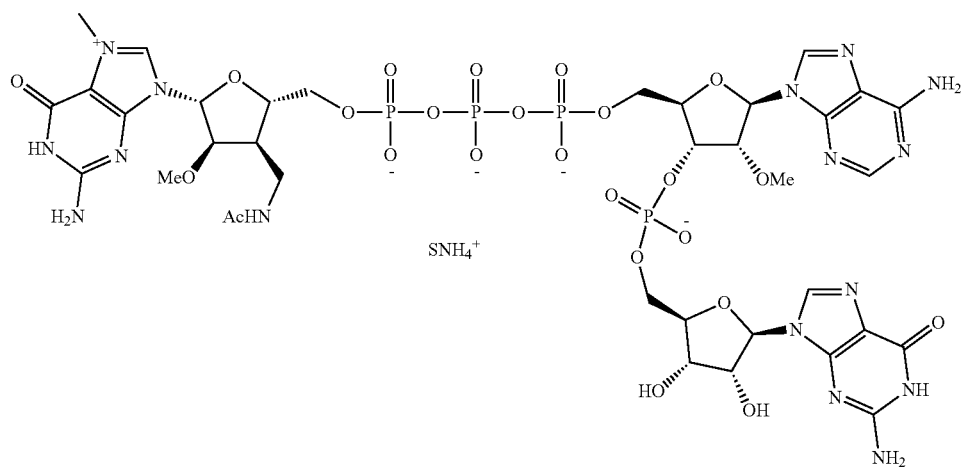
Compound 641

According to the reaction route, Compound 641-2 was prepared from Compound 6-3 using the procedure for preparation of Compound 637-3.

The characteristic data of the Compound 641-2 was: $^1$H NMR (500 MHz, D$_2$O) δ 9.07 (s, 1H), 5.99 (s, 1H), 4.64 (d, J=4.5 Hz, 1H), 4.21 (d, J=10.6 Hz, 1H), 3.96 (d, J=13.1 Hz, 1H), 3.69 (dd, J=13.2, 3.4 Hz, 1H), 3.40 (dd, J=14.2, 8.7 Hz, 1H), 3.27 (dd, J=14.1, 5.8 Hz, 1H), 3.22 (s, 3H), 2.56-2.40 (m, 1H), 1.89 (s, 3H).

According to the reaction route, Compound 641 (ammonium salt) was prepared from Compound 641-2 using the procedure for preparation of Compound 139.

The characteristic data of the ammonium salt of Compound 641 was: MS (m/z): 1213.05[M−1]$^−$. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.41 (s, 3H), 3.29 (m, dd, J$_1$=14.0 Hz, J$_2$=6.1 Hz, 1H), 2.64-2.59 (m, 1H), 2.00 (s, 3H); $^{31}$P NMR (202 MHz, D$_2$O) δ−0.95 (s, 1H), −11.49 (d, J=10.9 Hz, 1P), −11.58 (d, J=12.0 Hz, 1P), −22.82 (t, J=18.2 Hz, 1P).

Example 42 Synthesis of Compound 337

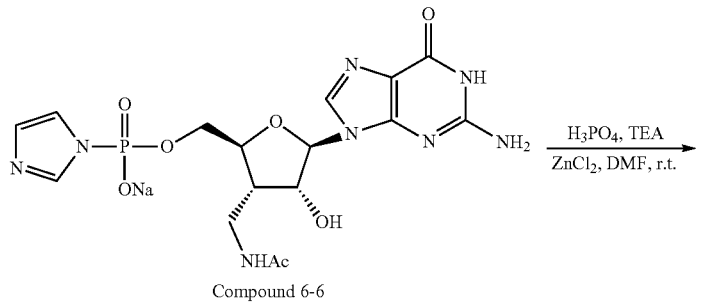

Compound 6-6

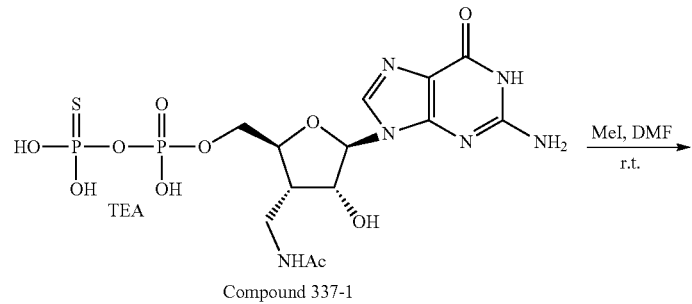

Compound 337-1

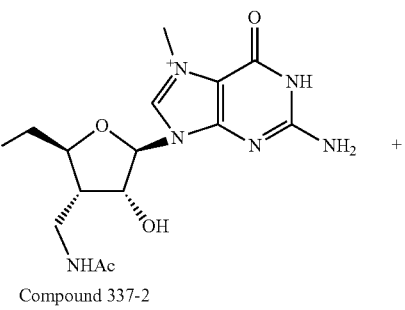

Compound 337-2

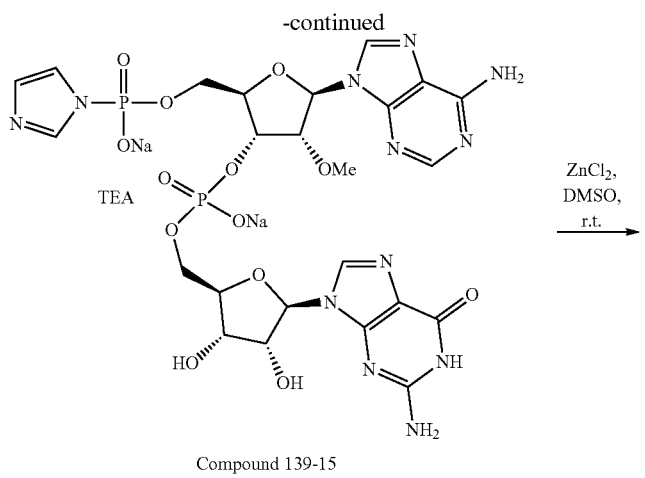

Compound 139-15

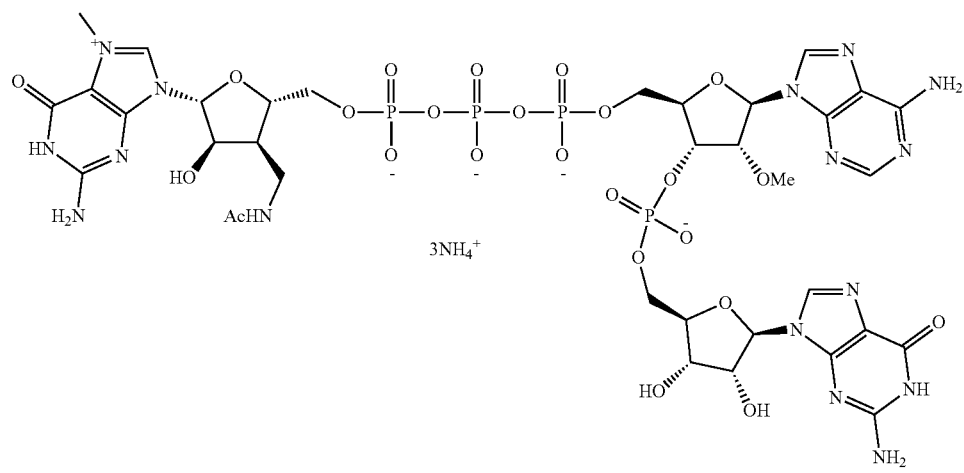

Compound 337

According to the reaction route, Compound 337 (ammonium salt) was prepared from Compound 6-6 using the procedure for preparation of Compound 139, except substituting phosphoric acid with thiophosphoric acid.

The characteristic data of the Compound 337 was: MS (m/z): 1215.05[M−1]−. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 11H), 4.76-4.75 (m, 11H), 4.63 (d, J=4.4 Hz, 11H), 4.54-4.50 (m, 31H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.64-2.59 (m, 1H), 2.00 (s, 3H); $^{31}$P NMR (202 MHz, D$_2$O) δ 28.84 (m, 1P), −0.96 (s, 1H), −11.55 (m, 2P).

Example 43 Synthesis of Compound 561

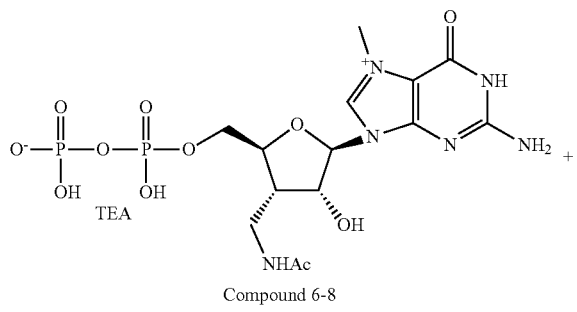

Compound 6-8

-continued

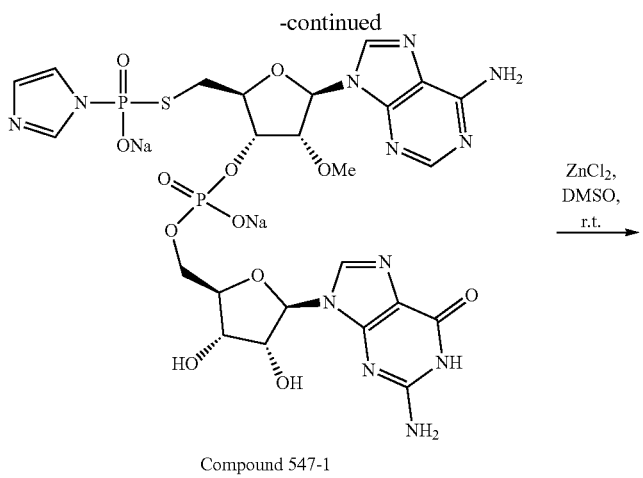

Compound 547-1

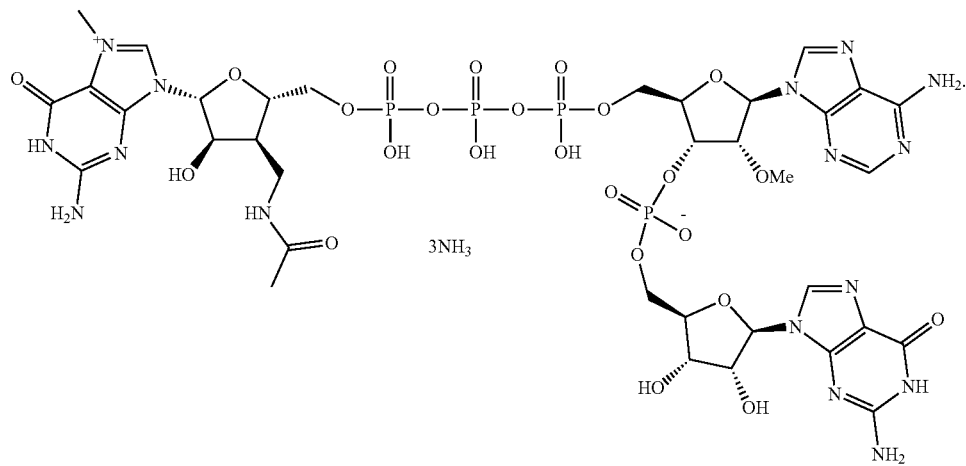

Compound 547

According to the reaction route, Compound 561 (ammonium salt) was prepared from Compound 6-8 and Compound 547-1 using the procedure for preparation of Compound 139.

The characteristic data of the Compound 561 was: MS (m/z): 1215.05[M−1]⁻. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 11H), 4.97-4.94 (m, 11H), 4.76-4.75 (m, 11H), 4.63 (d, J=4.4 Hz, 1H), 4.54-4.50 (m, 3H), 4.46 (t, J=4.9 Hz, 1H), 4.38 (m, 11H), 4.35-4.33 (m, 2H), 4.29-4.26 (m, 11H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.64-2.59 (m, 1H), 2.00 (s, 3H); $^{31}$P NMR (202 MHz, D$_2$O) δ 7.58 (m, 1P), −0.95 (s, 1H), −11.55 (d, J=10.9 Hz, 1P), −23.34 (m, 1P).

Example 44 Synthesis of Compound 118

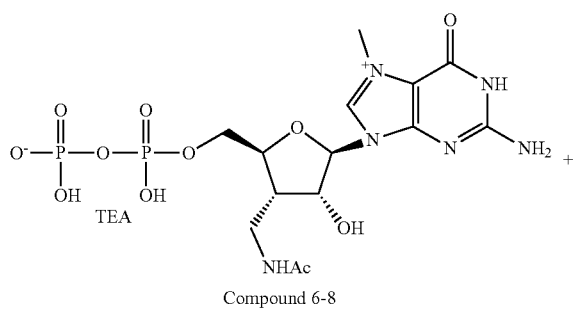

Compound 6-8

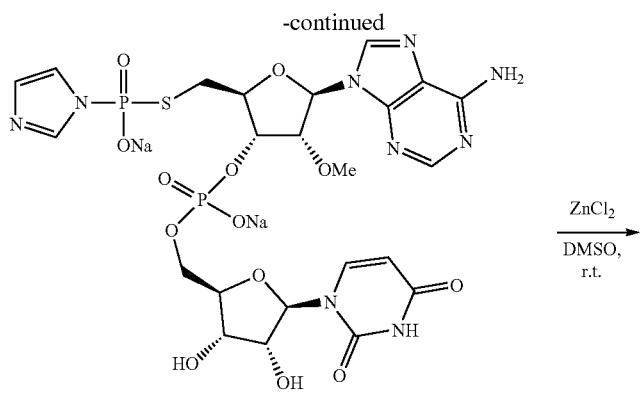

Compound 118-1

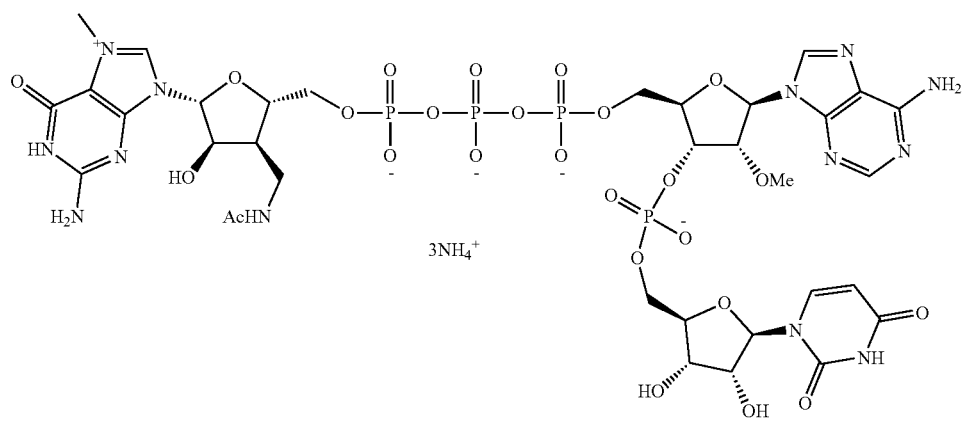

Compound 118

According to the reaction route, Compound 118 (ammonium salt) was prepared from Compound 6-8 using the procedure for preparation of Compound 139, except substituting Compound 139-15 with Compound 110-1.

The characteristic data of the Compound 118 was: MS (m/z): 1160.07[M−1]⁻. $^1$H NMR (500 MHz, D$_2$O) δ 9.08 (s, 1H), 8.46 (s, 1H), 8.20 (s, 1H), 7.86 (d, J=8.1 Hz, 1H), 6.07 (d, J=5.3 Hz, 1H), 5.86 (s, 1H), 5.83-2.80 (m, 2H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.64-2.59 (m, 1H), 2.00 (s, 3H); $^1$P NMR (202 MHz, D$_2$O) δ-0.95 (s, 1H), −11.49 (d, J=10.9 Hz, 1P), −11.58 (d, J=12.0 Hz, 1P), −22.82 (t, J=18.2 Hz, 1P).

Example 45 Synthesis of Compound 329

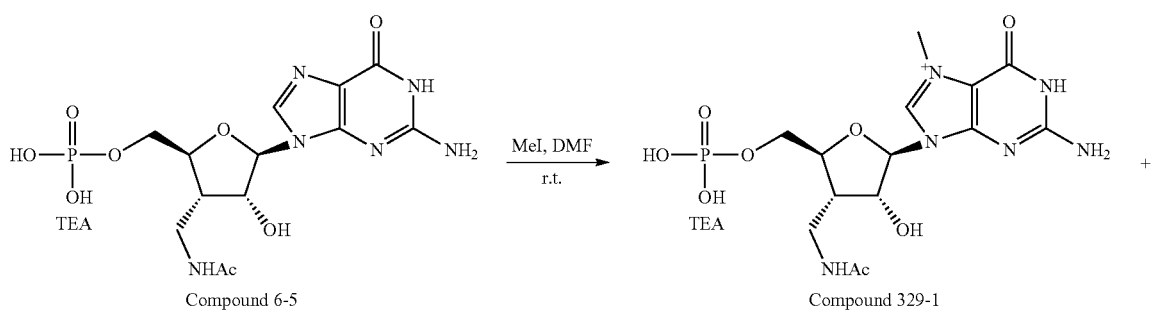

-continued

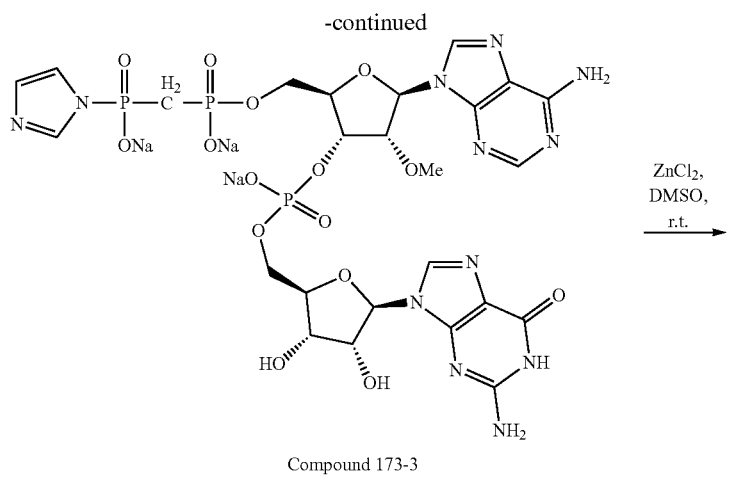

Compound 173-3

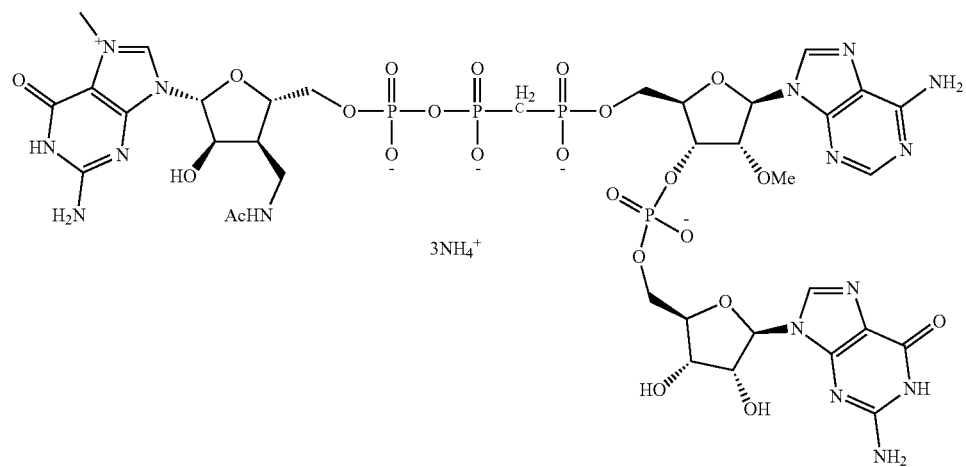

Compound 329

According to the reaction route, Compound 329 (ammonium salt) was prepared from Compound 6-5 using the procedure for preparation of Compound 173.

The characteristic data of the Compound 329 was: MS (m/z): 1197.07[M−1]⁻. ¹H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$14.0 Hz, J$_2$=6.1 Hz, 1H), 2.64-2.59 (m, 1H), 2.47 (t, J=20.4 Hz, 2H), 2.00 (s, 3H); ¹P NMR (202 MHz, D$_2$O) δ 16.79 (s, 1P), 7.80 (dd, J=25.4, 6.8 Hz, 1P), −0.95 (s, 1H), −11.49 (d, J=10.9 Hz, 1P).

Example 46 Synthesis of Compound 345

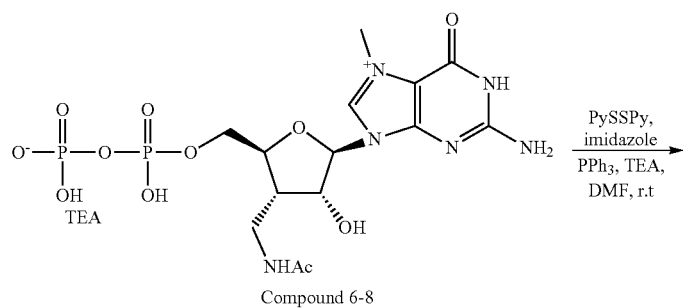

Compound 6-8

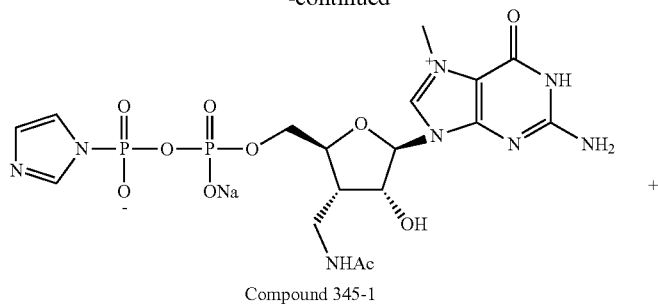

Compound 345-1

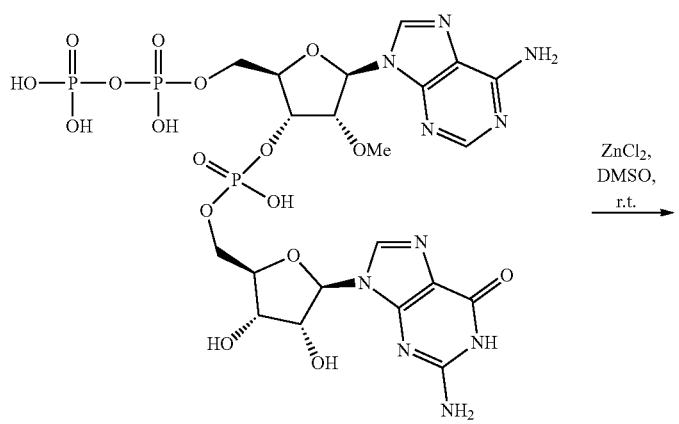

Compound 189-1

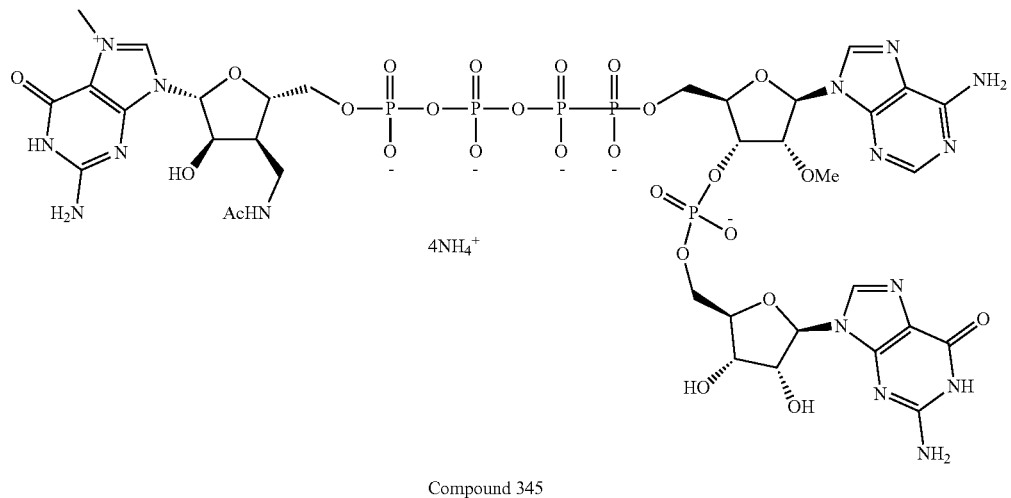

Compound 345

According to the reaction route, Compound 345 (ammonium salt) was prepared from Compound 6-8 using the procedure for preparation of Compound 189.

The characteristic data of the Compound 345 was: MS (m/z): 1279.09[M−1]$^-$. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.64-2.59 (m, 1H), 2.00 (s, 3H); $^{31}$P NMR (202 MHz, D$_2$O) δ-0.99 (s,1P), −11.65 (m, 2P), −22.91 (m, 2P).

Example 47 Synthesis of Compound 319
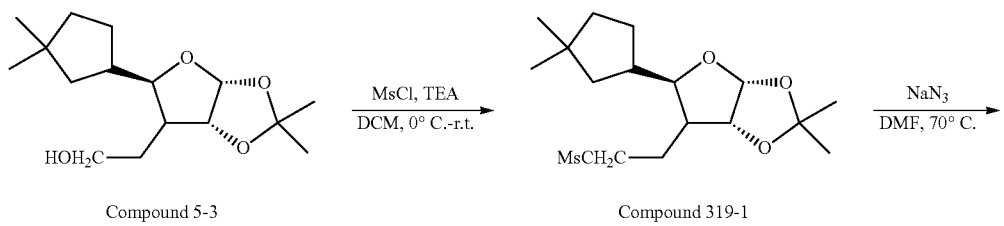
Compound 5-3 → Compound 319-1
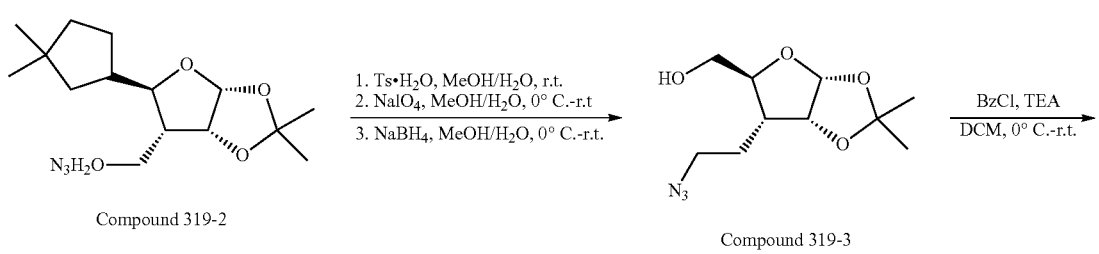
Compound 319-2 → Compound 319-3
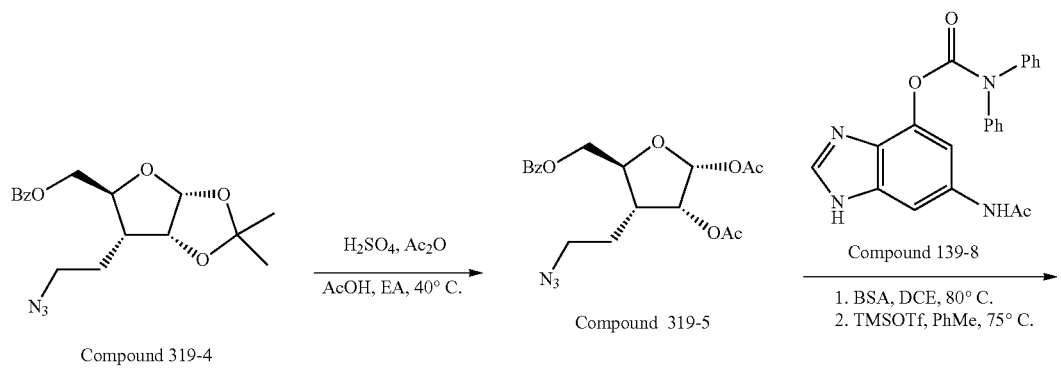
Compound 319-4 → Compound 319-5
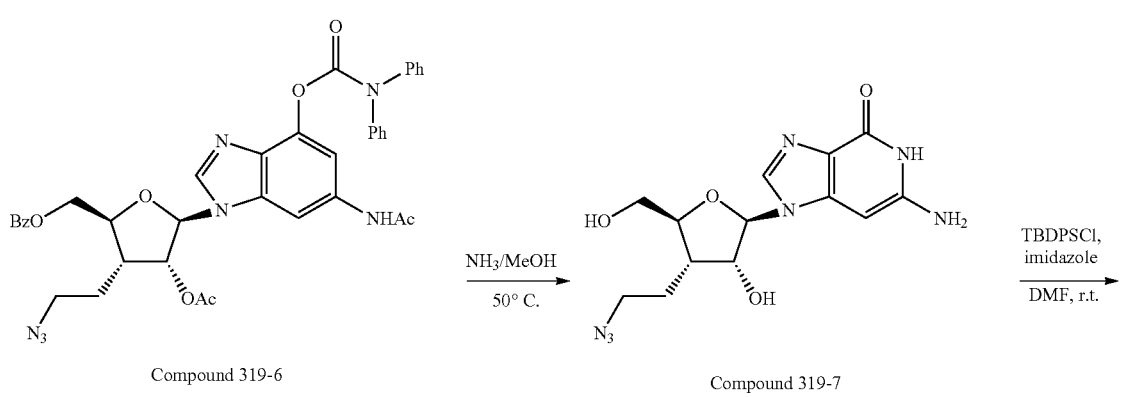
Compound 319-6 → Compound 319-7
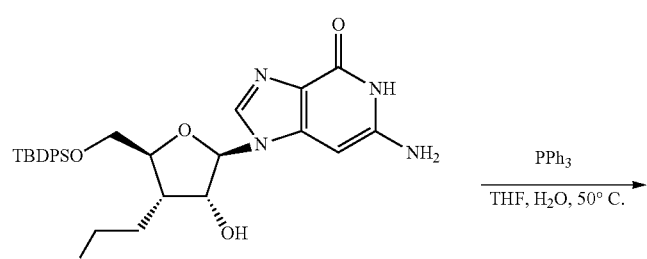
Compound 319-8

-continued
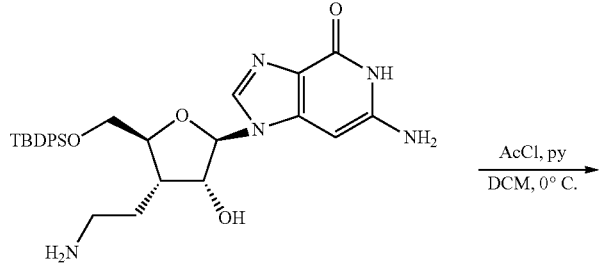
Compound 319-9
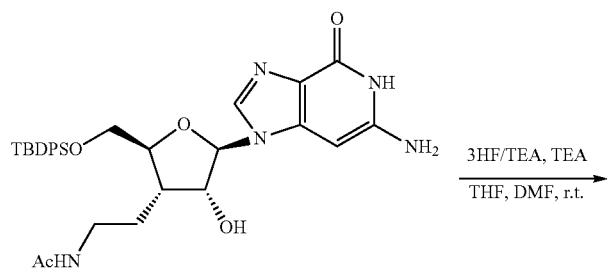
Compound 319-10
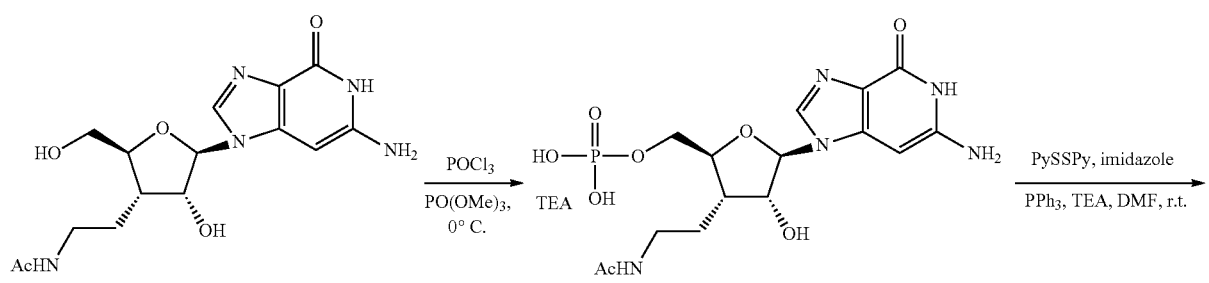
Compound 319-11                    Compound 319-12
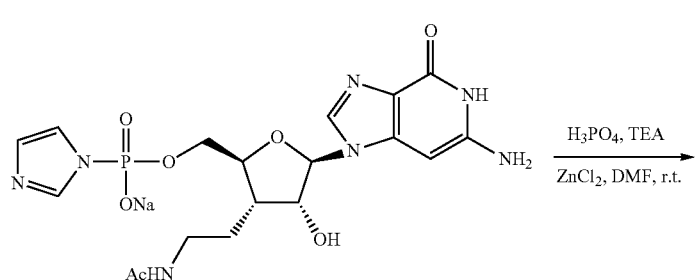
Compound 319-13
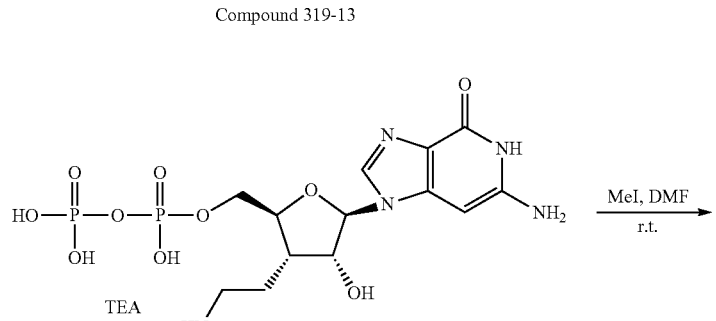
Compound 319-14

-continued

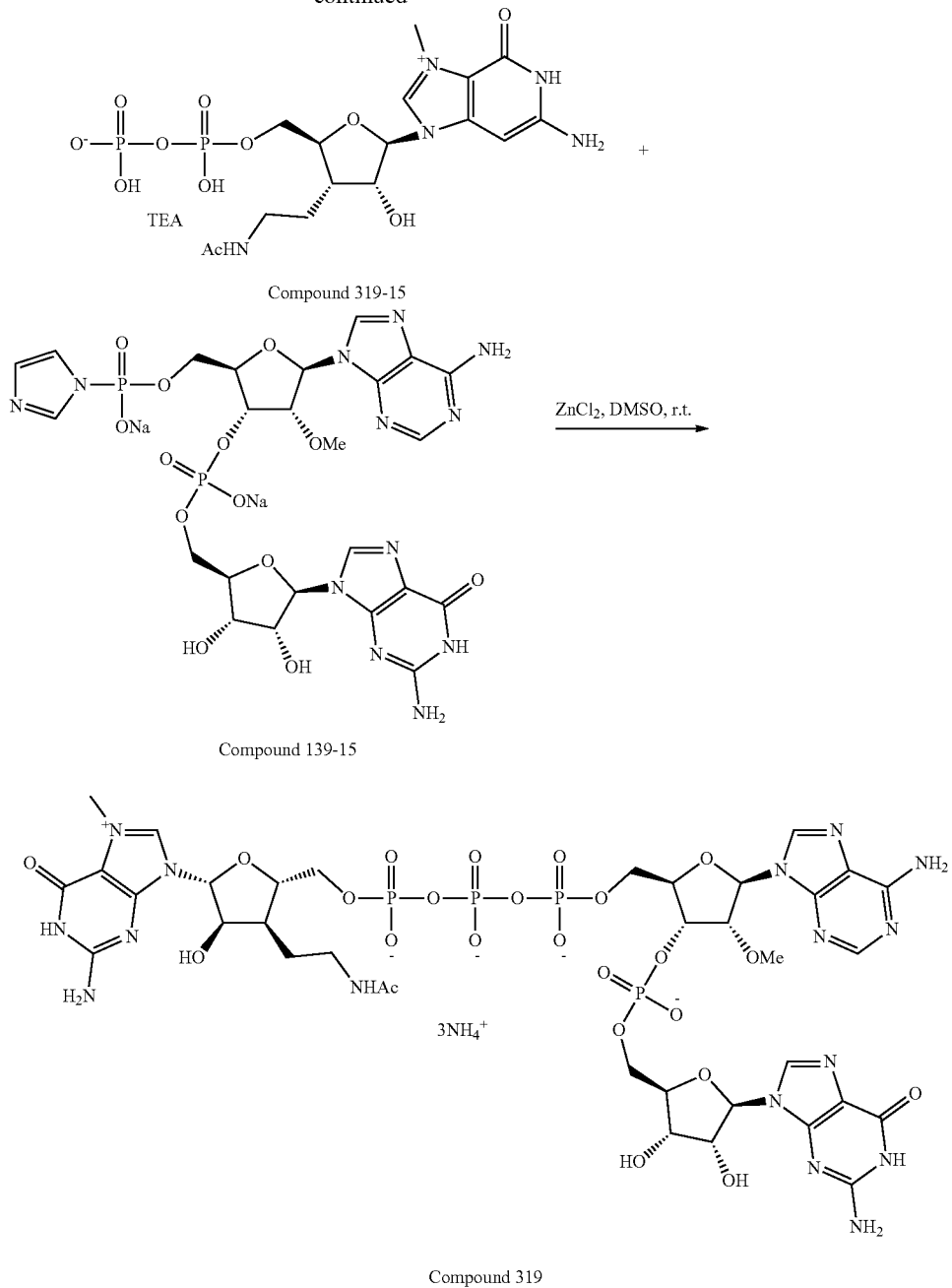

Compound 319-15

Compound 139-15

Compound 319

According to the reaction route, Compound 319-7 was prepared from Compound 5-3 using the procedure for preparation of Compound 635-7.

Compound 319-11 was prepared from Compound 319-7 using the procedure for preparation of Compound 6-4.

The characteristic data of the Compound 319-11 was: $^1$H NMR (500 MHz, D$_2$O) δ 9.07 (s, 1H), 5.99 (s, 1H), 4.64 (d, J=4.5 Hz, 1H), 4.21 (d, J=10.6 Hz, 1H), 3.96 (d, J=13.1 Hz, 1H), 3.69 (dd, J=13.2, 3.4 Hz, 1H), 3.40 (dd, J=14.2, 8.7 Hz, 1H), 3.27 (dd, J=14.1, 5.8 Hz, 1H), 1.89 (s, 3H), 1.56-1.53 (m, 1H), 1.44-1.40 (m, 2H).

According to the reaction route, Compound 319 (ammonium salt) was prepared from Compound 319-11 using the procedure for preparation of Compound 139.

The characteristic data of the Compound 319 was: MS (m/z): 1213.05[M−1]$^-$. $^1$H NMR (500 MHz, D$_2$O) δ 9.08 (s, 1H), 8.46 (s, 1H), 8.20 (s, 1H), 7.98 (s, 1H), 6.07 (d, J=5.3 Hz, 1H), 5.86 (s, 1H), 5.83 (d, J=5.9 Hz, 1H), 4.97-4.94 (m, 1H), 4.76-4.75 (m, 1H), 4.63 (d, J=4.4 Hz, 1H), 4.54-4.50 (m, 3H), 4.46 (t, J=4.9 Hz, 1H), 4.38 (m, 1H), 4.35-4.33 (m, 2H), 4.29-4.26 (m, 1H), 4.24-4.20 (m, 2H), 4.17-4.14 (m, 1H), 4.03 (s, 3H), 3.53 (dd, J$_1$=14.0 Hz, J$_2$=8.1 Hz, 1H), 3.47 (s, 3H), 3.29 (m, dd, J$_1$=14.0 Hz, J$_2$=6.1 Hz, 1H), 2.00 (s, 3H), 1.64-1.59 (m, 1H), 1.56-1.54 (m, 2H); $^{31}$P NMR (202 MHz, D$_2$O) δ−0.95 (s, 1H), −11.49 (d, J=10.9 Hz, 1P), −11.58 (d, J=12.0 Hz, 1P), −22.82 (t, J=18.2 Hz, 1P).

Example 48 Synthesis of Compound 645
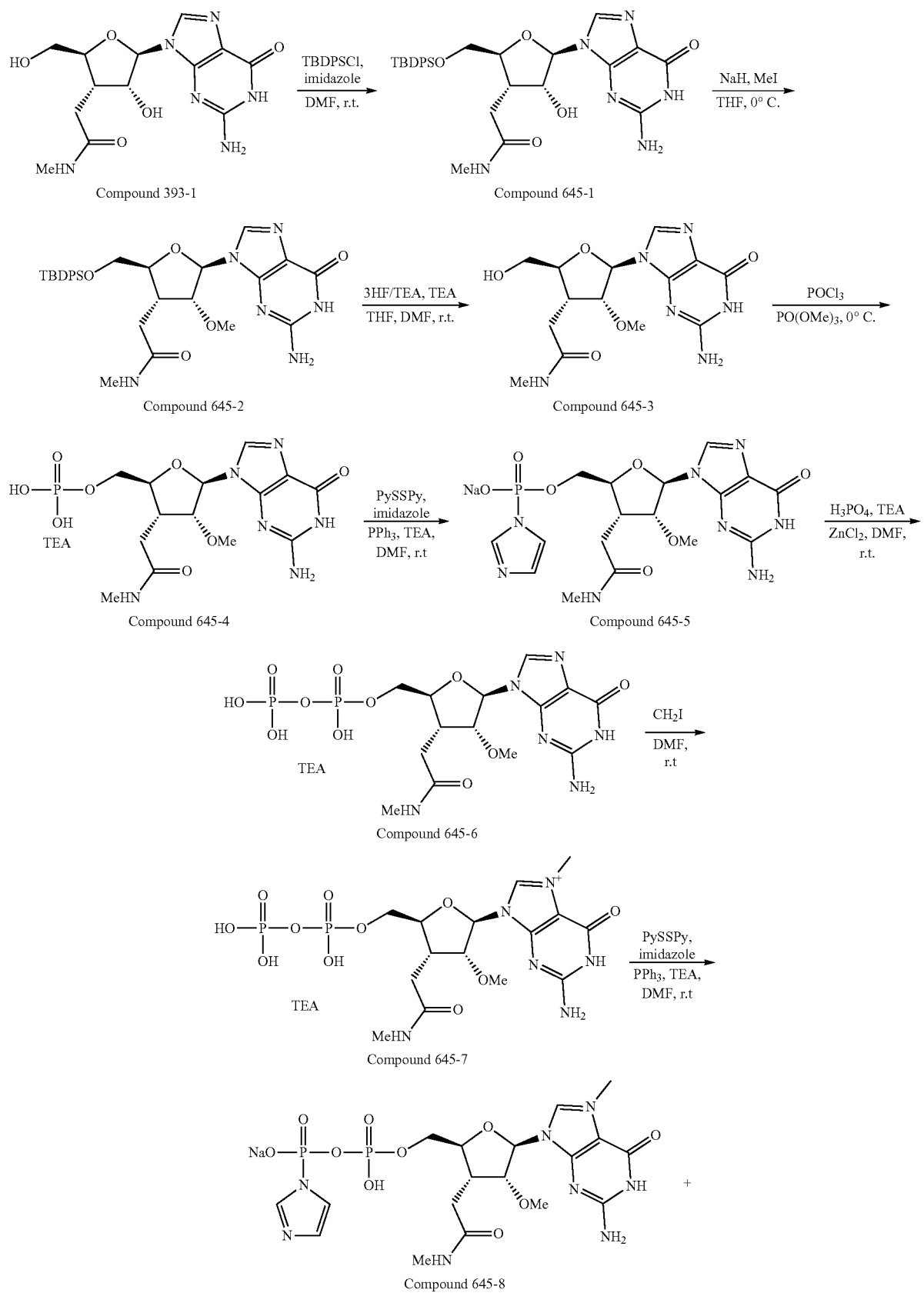

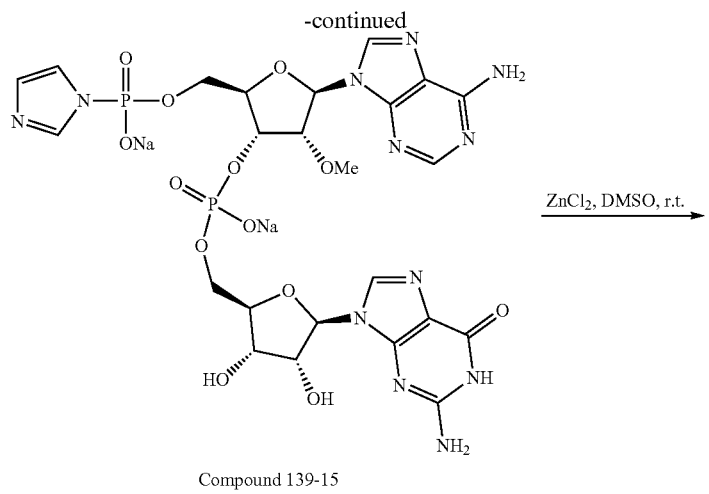

Compound 139-15

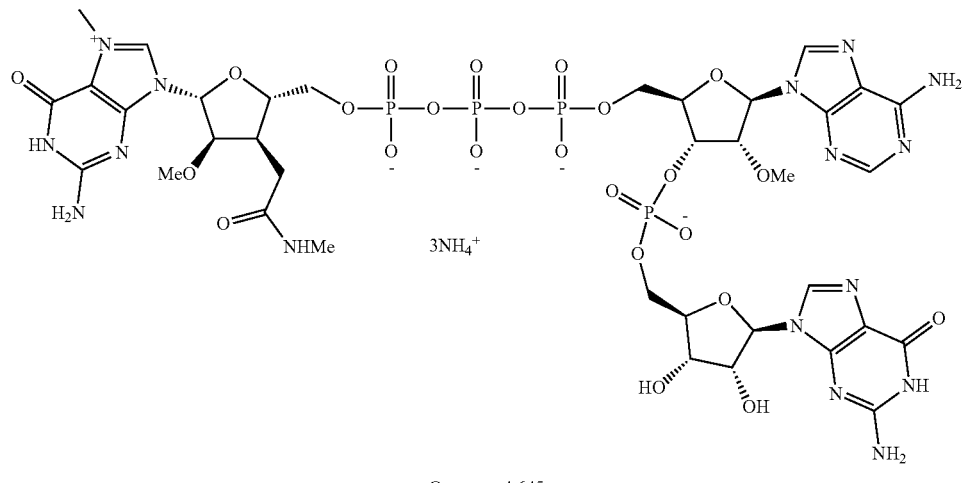

Compound 645

According to the above reaction route, Compound 645-3 was prepared from Compound 393-1 using the procedure for preparation of Compound 637-3.

The characteristic data of the Compound 645-3 was: ¹H NMR (400 MHz, DMSO) δ 10.59 (s, 1H), 8.01 (s, 1H), 7.84 (d, J=4.4 Hz, 1H), 6.46 (s, 2H), 5.74 (d, J=5.4 Hz, 1H), 5.71 (d, J=1.4 Hz, 1H), 5.02 (t, J=5.3 Hz, 1H), 4.33 (t, J=4.6 Hz, 1H), 3.88 (d, J=9.1 Hz, 1H), 3.75-3.65 (m, 1H), 3.55-3.48 (m, 1H), 3.32 (s, 3H), 2.67-2.61 (m, 1H), 2.58 (d, J=4.5 Hz, 3H), 2.43 (dd, J=15.2, 8.4 Hz, 1H), 2.19 (dd, J=15.2, 5.9 Hz, 1H).

According to the reaction route, Compound 645 (ammonium salt) was prepared from Compound 645-3 using the procedure for preparation of Compound 139.

The characteristic data of the Compound 645 was: MS (m/z): 1213.05[M−1]⁻. ¹H NMR (500 MHz, D₂O) δ 9.10 (s, 1H), 8.46 (s, 1H), 8.19 (s, 1H), 7.98 (s, 1H), 6.07 (d, J=5.5 Hz, 1H), 5.84 (d, J=5.8 Hz, 1H), 5.82 (s, 1H), 4.98-4.95 (m, 1H), 4.79 (m, 1H), 4.65 (d, J=4.1 Hz, 1H), 4.54-4.51 (m, 3H), 4.46 (t, J=5.0 Hz, 1H), 4.37-4.33 (m, 2H), 4.29-4.26 (m, 2H), 4.23-4.20 (m 2H), 4.14-4.12 (m, 1H), 4.03 (s, 3H), 3.47 (s, 3H), 3.23 (s, 3H), 3.06 (s, 3H), 2.89 (s, 3H), 2.74-2.61 (m, 2H), 2.57-2.54 (m, 1H); ³¹P NMR (202 MHz, D₂O) δ-0.88 (s, 1H), −11.52-11.70 (m, 2P), −22.82 (t, J=17.9 Hz, 1P).

Example 49 Synthesis of Compound 394

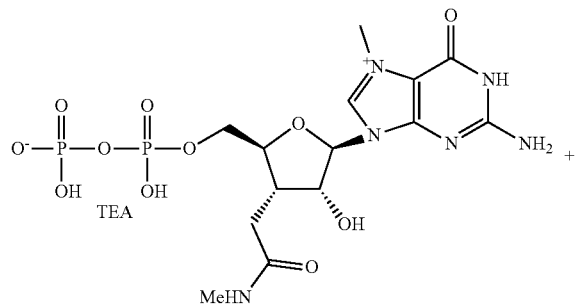

Compound 393-5

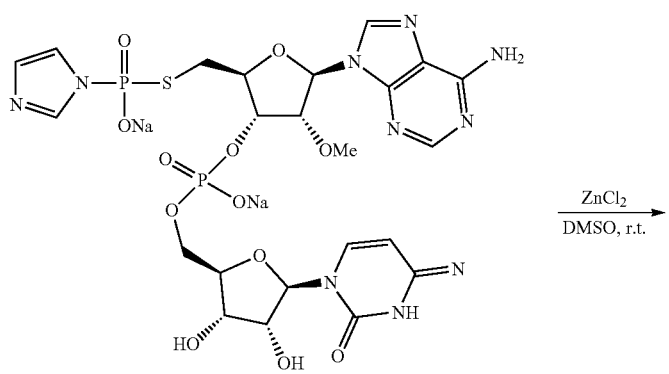

Compound 110-1

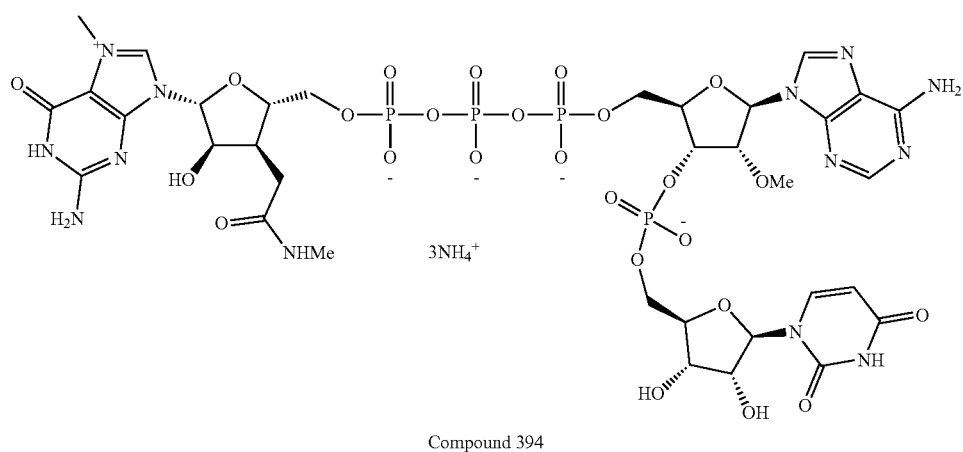

Compound 394

According to the reaction route, Compound 394 (ammonium salt) was prepared from Compound 393-5 using the procedure for preparation of Compound 139, except substituting Compound 139-15 with Compound 110-1.

The characteristic data of the Compound 394 was: MS (m/z): 1160.07[M−1]⁻. $^1$H NMR (500 MHz, D$_2$O) δ 9.05 (s, 1H), 8.44 (s, 1H), 8.17 (s, 1H), 7.86 (d, J=8.1 Hz, 1H), 6.04 (d, J=5.5 Hz, 1H), 5.82-5.81 (m, 2H), 5.78 (d, J=4.8 Hz, 1H), 4.93 (br, 1H), 4.56 (d, J=4.5 Hz, 1H), 4.51-4.46 (m, 3H), 4.43 (t, J=5.0 Hz, 1H), 4.34-4.30 (m, 2H), 4.26-4.24 (m, 2H), 4.19 (s, 2H), 4.10-4.08 (m, 1H), 4.01 (s, 3H), 3.43 (s, 3H), 2.66 (s, 3H), 2.63-2.62 (m, 1H), 2.48-2.41 (m, 2H); $^{31}$P NMR (202 MHz, D$_2$O) δ-0.91 (s, 1H), −11.61 (m, 2P), −22.88 (m, 1P).

Example 50 Synthesis of Compound 421
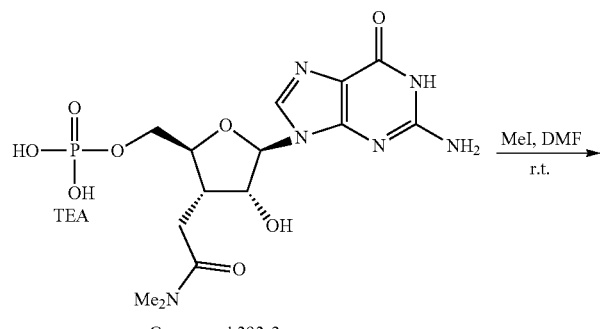
Compound 393-2
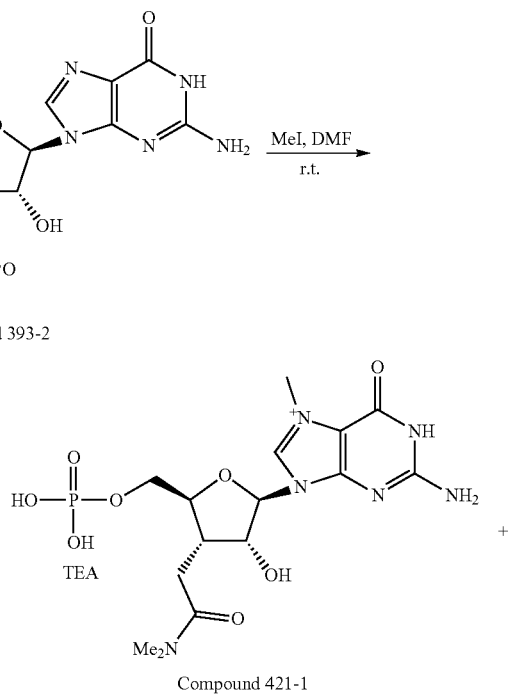
Compound 421-1
Compound 173-3
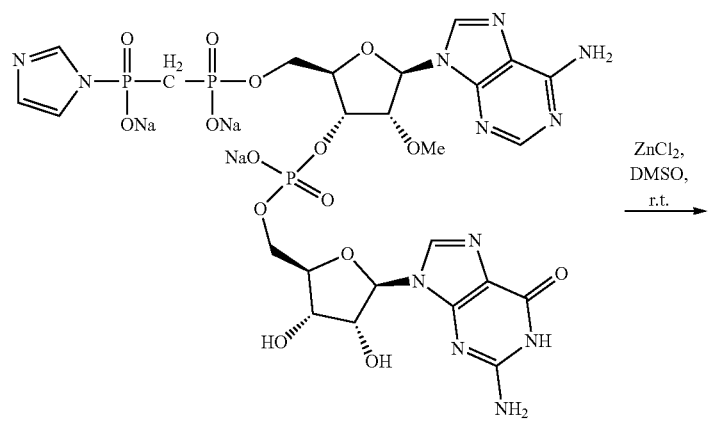
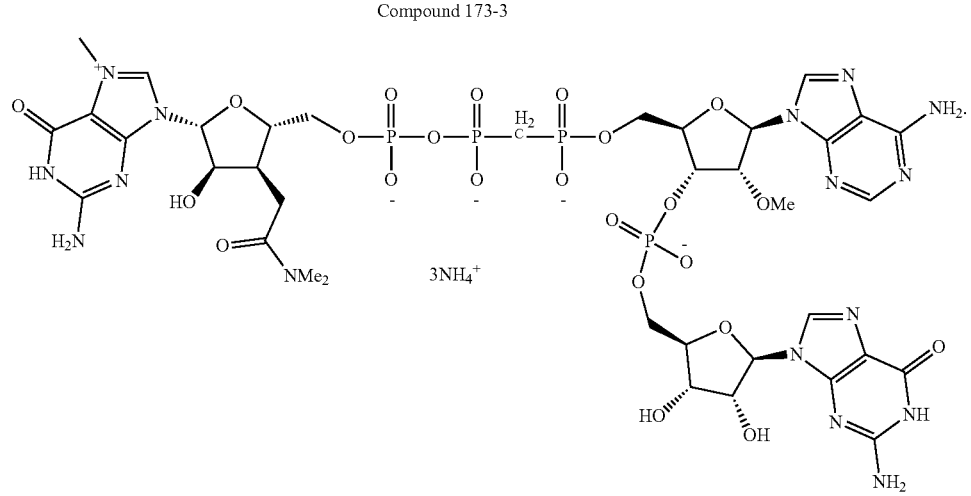
Compound 421

According to the reaction route, Compound 421 (ammonium salt) was prepared from Compound 393-2 using the procedure for preparation of Compound 173.

The characteristic data of the Compound 421 was: MS (m/z): 1211.10[M−1]⁻. ¹H NMR (500 MHz, D₂O) δ 9.10 (s, 1H), 8.46 (s, 1H), 8.19 (s, 1H), 7.98 (s, 1H), 6.07 (d J=5.5 Hz, 1H), 5.84 (d, J=5.8 Hz, 1H), 5.82 (s, 1H) 4.98-4.95 (m, 1H), 4.79 (m, 1H), 4.65 (d, J=4.1 Hz, 1H), 4.54-4.51 (m 3H) 4.46 (t, J=5.0 Hz, 1H), 4.37-4.33 (m, 2H), 4.29-4.26 (m, 2H), 4.23-4.20 (m, 2H), 4.14-4.12 (m, 1H), 4.03 (s, 3H), 3.47 (s, 3H), 3.06 (s, 3H), 2.89 (s, 3H), 2.74-2.61 (m, 2H), 2.57-2.54 (m, 1H), 2.47 (t, J=20.4 Hz, 2H); ³¹P NMR (202 MHz, D₂O) δ 16.79 (s, 1P), 7.80 (dd, J=25.4, 6.8 Hz, 1P), −0.88 (s, 1H), 11.70 (m, 1P).

Example 51 Synthesis of Compound 437

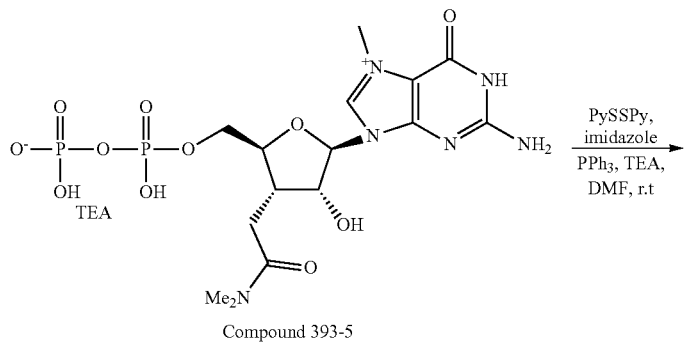

Compound 393-5

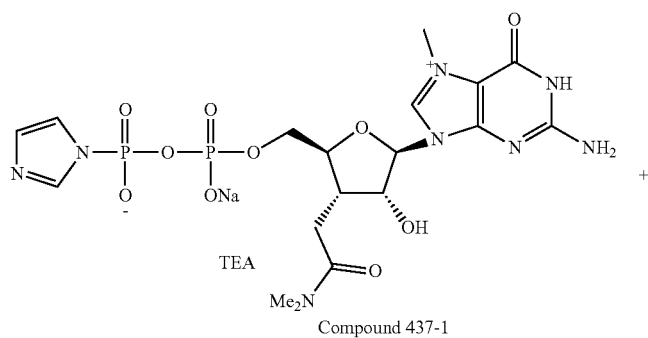

Compound 437-1

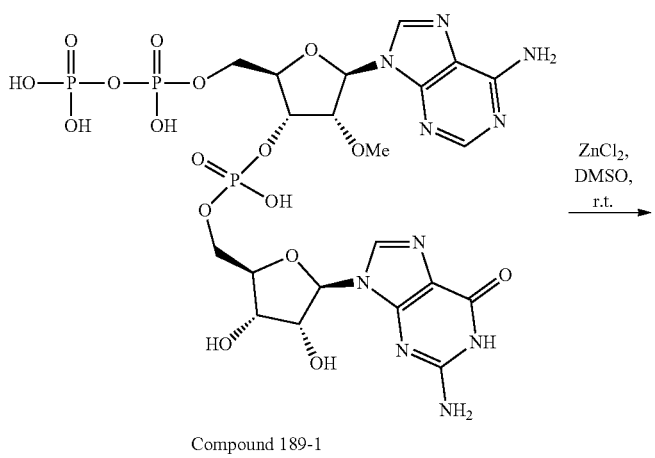

Compound 189-1

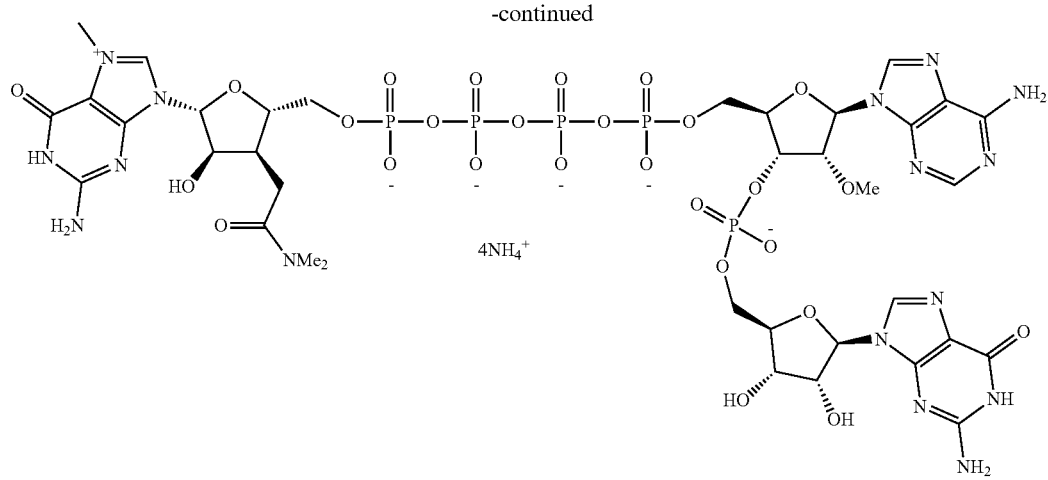
Compound 437
According to the reaction route, Compound 437 (ammonium salt) was prepared from Compound 393-5 using the procedure for preparation of Compound 189.
The characteristic data of the Compound 437 was: MS (m/z): 1293.05[M−1]⁻. $^1$H NMR (500 MHz, D$_2$O) δ 9.10 (s, 1H), 8.46 (s, 1H), 8.19 (s, 1H), 7.98 (s, 1H), 6.07 (d, J=5.5 Hz, 1H), 5.84 (d, J=5.8 Hz, 1H), 5.82 (s, 1H), 4.98-4.95 (m, 1H), 4.79 (m, 1H), 4.65 (d, J=4.1 Hz, 1H), 4.54-4.51 (m, 3H), 4.46 (t, J=5.0 Hz, 1H), 4.37-4.33 (m, 2H), 4.29-4.26 (m, 2H), 4.23-4.20 (m, 2H), 4.14-4.12 (m, 1H), 4.03 (s, 3H), 3.47 (s, 3H), 3.06 (s, 3H), 2.89 (s, 3H), 2.74-2.61 (m, 2H), 2.57-2.54 (m, 1H); $^{31}$P NMR (202 MHz, D$_2$O) δ-0.99 (s, 1P), −11.65 (m, 2P), −22.91 (m,2P).
Example 52 Synthesis of Compound 415
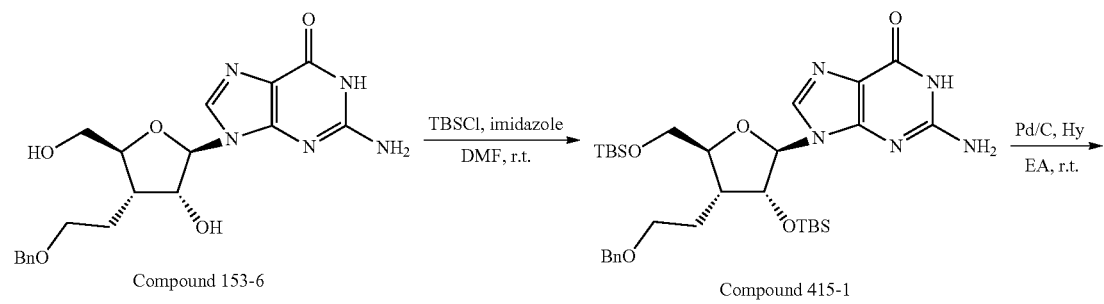
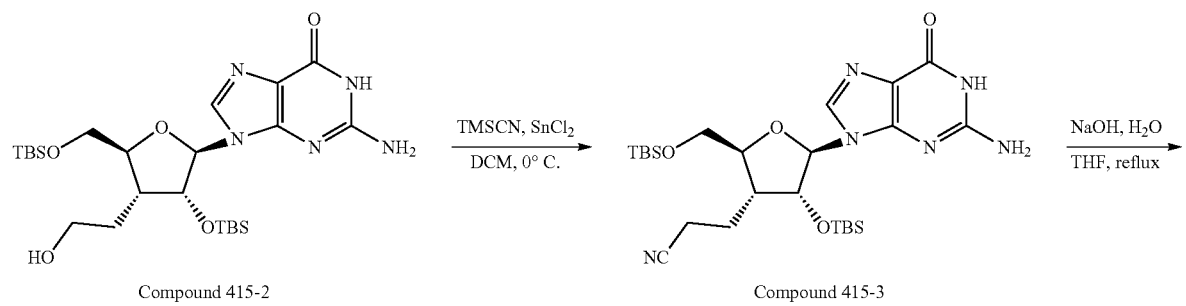

515    516
-continued
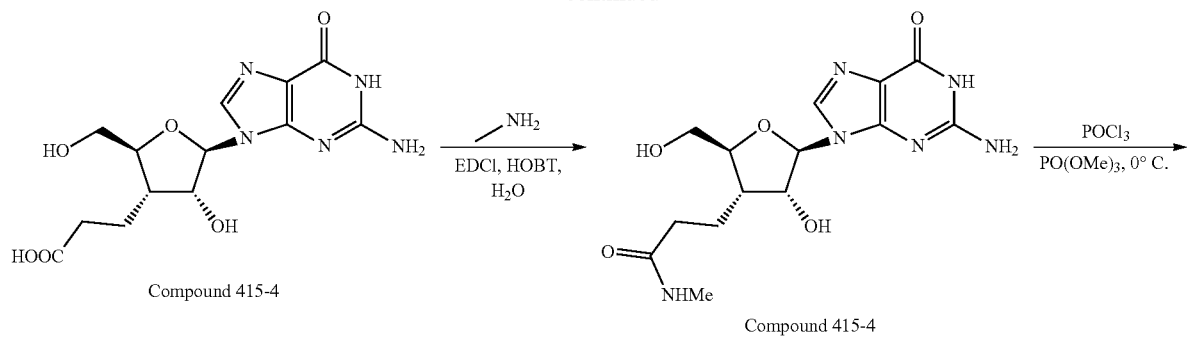
Compound 415-4 → Compound 415-4
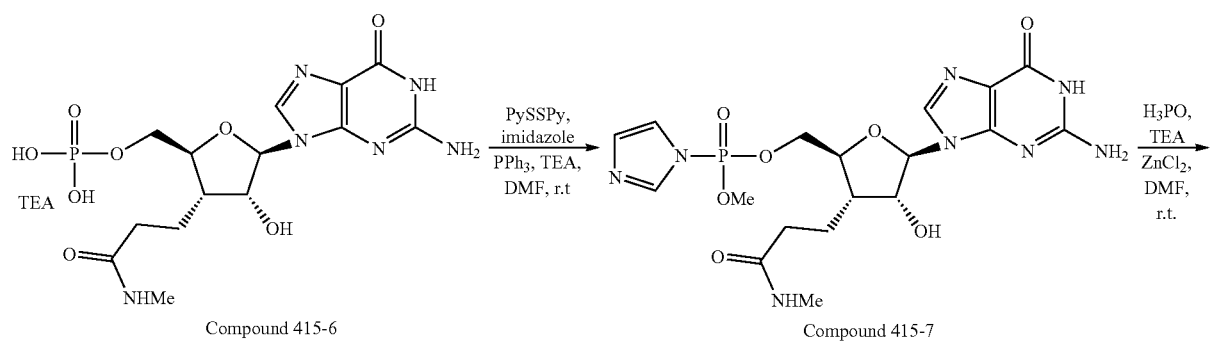
Compound 415-6 → Compound 415-7
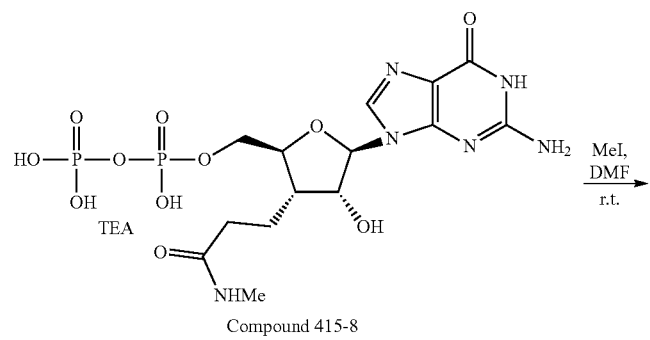
Compound 415-8
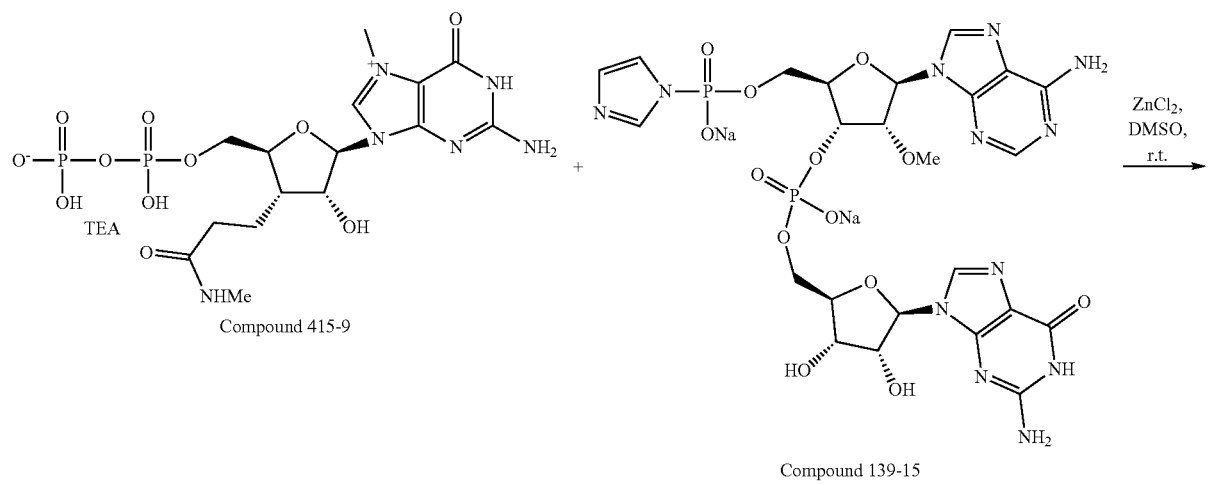
Compound 415-9 + Compound 139-15

-continued

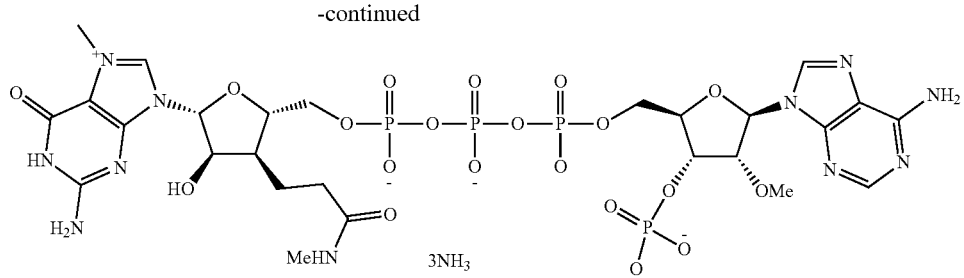
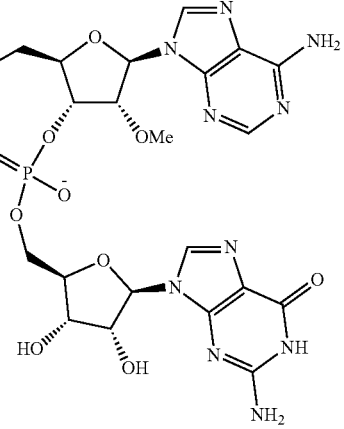

Compound 415

According to the reaction route, Compound 415-2 was prepared from Compound 153-6 using the procedure for preparation of Compound 631-2.

Under the nitrogen atmosphere and under stirring, the Compound 415-2 (8.6 g, 15.93 mmol) was dissolved in dichloromethane (100 mL); then TMSCN (10 mL, 79.66 mmol) was added and stannic chloride (5.6 mL, 47.79 mmol) was added dropwise at 0° C. After the temperature was increased to room temperature, the mixture was reacted overnight. Potassium carbonate and potassium fluoride were added to the solution, and then water was added to quench the reaction. A small amount of silica gel was added, stirred, and filtered. The filtrate was washed with saturated sodium bicarbonate, dried over anhydrous sodium sulfate, filtered, and purified by column chromatography to obtain 7.2 g of Compound 415-3.

The Compound 415-3 (7.2 g, 13.12 mmol) was dissolved in tetrahydrofuran (20 mL), followed by addition of 10% sodium hydroxide aqueous solution (50 mL). The mixture was heated to reflux overnight. After the temperature was decreased to room temperature, dilute hydrochloric acid was used for regulating pH to neutralization. Finally, the reaction liquid was purified by C18 column to obtain 3.0 g of Compound 415-4.

The Compound 415-4 (3.0 g, 8.84 mmol) was dissolved in water (10 mL), followed by addition of methylamine aqueous solution (40%, 10 mL), EDCI (3.39 g, 17.68 mmol), and HOBT (0.24 g, 1.77 mmol), and the mixture was stirred at room temperature. After the reaction was completed, the reaction liquid was purified by C18 column to obtain 2.8 g of Compound 415-5.

The characteristic data of the Compound 415-5 was: $^1$H NMR (400 MHz, DMSO) δ 10.59 (s, 1H), 8.01 (s, 1H), 7.84 (d, J=4.4 Hz, 1H), 6.46 (s, 2H), 5.74 (d, J=5.4 Hz, 1H), 5.71 (d, J=1.4 Hz, 1H), 5.02 (t, J=5.3 Hz, 1H), 4.33 (t, J=4.6 Hz, 1H), 3.88 (d, J=9.1 Hz, 1H), 3.75-3.65 (m, 1H), 3.55-3.48 (m, 1H), 2.67-2.61 (m, 1H), 2.58 (d, J=4.5 Hz, 3H), 2.43 (dd, J=15.2, 8.4 Hz, 1H), 1.92-1.89 (m, 2H), 1.68-1.66 (m, 1H).

According to the reaction route, Compound 415 (ammonium salt) was prepared from Compound 415-5 using the procedure for preparation of Compound 139.

The characteristic data of the Compound 415 was: MS (m/z): 1213.06[M−1]$^-$. $^1$H NMR (500 MHz, D$_2$O) δ 9.05 (s, 1H), 8.44 (s, 1H), 8.17 (s, 1H), 7.96 (s, 1H), 6.04 (d, J=5.5 Hz, 1H), 5.82-5.81 (m, 2H), 4.93 (br, 1H), 4.56 (d, J=4.5 Hz, 1H), 4.51-4.46 (m, 311), 4.43 (t, J=5.0 Hz, 1H), 4.34-4.30 (m, 2H), 4.26-4.24 (m, 2H), 4.19 (s, 2H), 4.10-4.08 (m, 1H), 4.01 (s, 3H), 3.43 (s, 3H), 2.66 (s, 3H), 2.48-2.41 (m, 2H), 1.98-1.95 (m, 2H), 1.65-1.62 (m, 1H); $^{31}$P NMR (202 MHz, D$_2$O) δ-0.91 (s, 1H), −11.61 (m, 2P), −22.88 (m, 1P).

Example 53 Synthesis of Compound 305

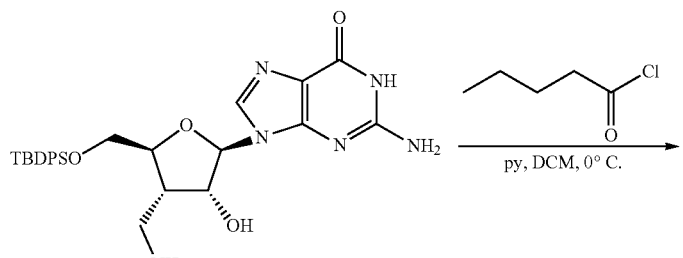

Compound 6-2

-continued
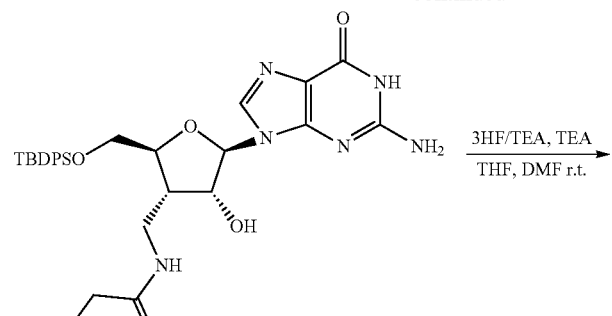
Compound 305-1
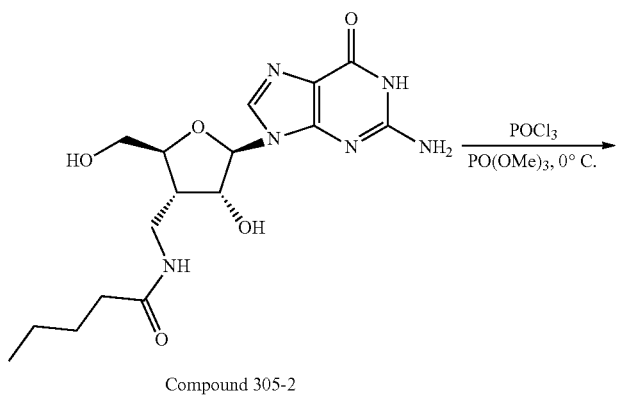
Compound 305-2
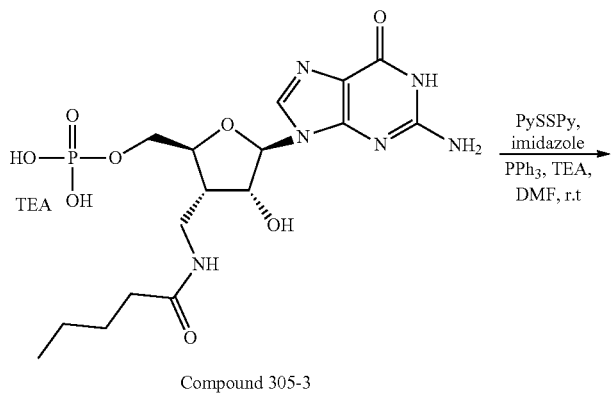
Compound 305-3
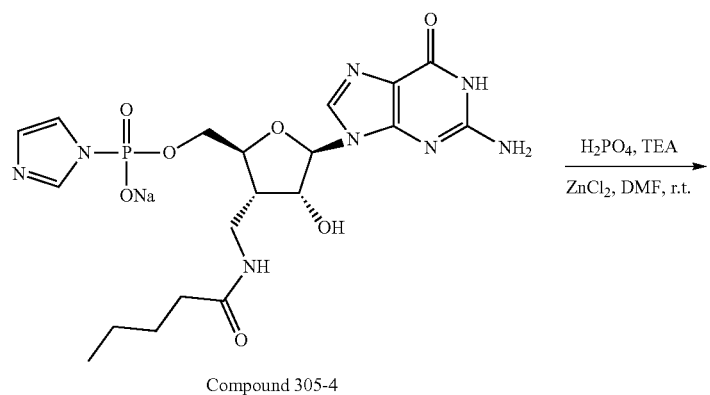
Compound 305-4

-continued
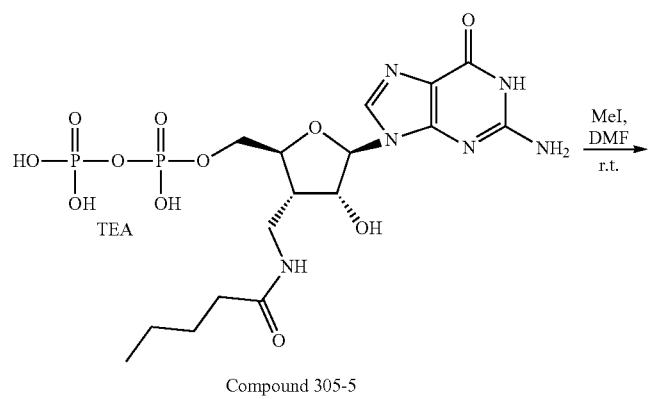
Compound 305-5
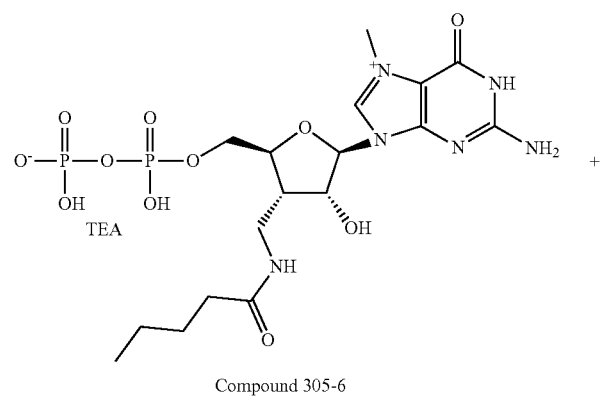
Compound 305-6
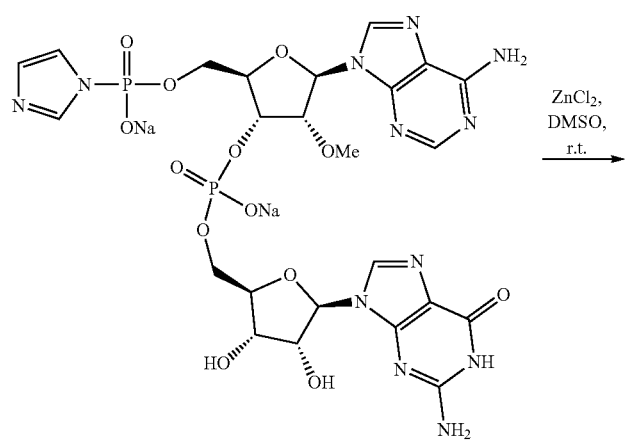
Compound 139-15

-continued

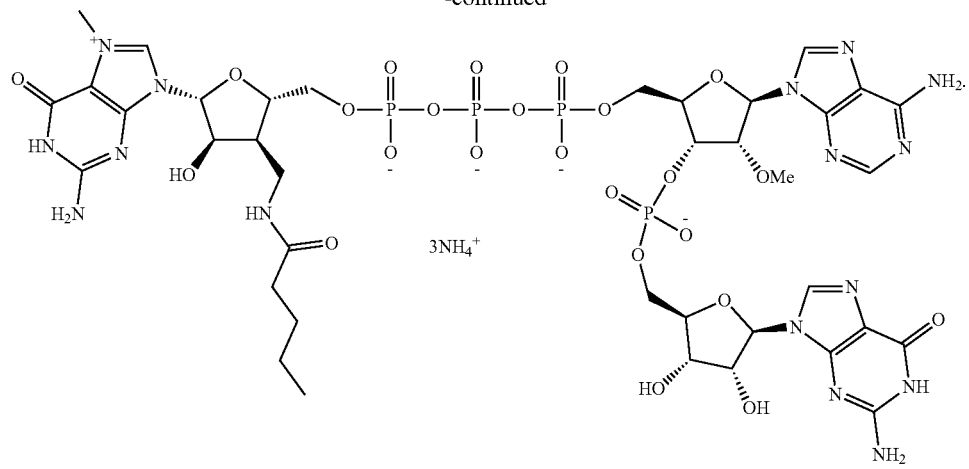

Compound 305

According to the reaction route, Compound 305-2 was prepared from Compound 6-2 using the procedure for preparation of Compound 6-4, except substituting acetyl chloride with n-pentanoyl chloride.

The characteristic data of the Compound 305-2 was: $^1$H NMR (400 MHz, DMSO) δ 10.56 (s, 1H), 8.45 (t, J=5.2 Hz, 1H), 8.04 (s, 1H), 6.47 (s, 2H), 5.82-5.79 (m, 2H), 5.15 (t, J=5.1 Hz, 1H), 4.39 (t, J=4.3 Hz, 1H), 4.03-3.98 (m, 1H), 3.80-3.75 (m, 1H), 3.65-3.52 (m, 2H), 3.42-3.38 (m, 1H), 2.63-2.57 (m, 1H), 1.92 (t, J=7.5 Hz, 2H), 1.65-1.60 (m, 2H), 1.55-1.52 (m, 2H), 0.88 (t, J=7.8 Hz, 3H).

According to the reaction route, Compound 305 (ammonium salt) was prepared from Compound 305-2 using the procedure for preparation of Compound 139.

The characteristic data of the Compound 305 was: MS (m/z): 1238.05[M−1]$^-$. $^1$H NMR (500 MHz, D$_2$O) δ 9.06 (s, 1H), 8.40 (s, 1H), 8.04 (s, 1H), 7.91 (s, 1H), 5.99 (d, J=5.6 Hz, 1H), 5.89 (s, 1H), 5.76 (d, J=5.6 Hz, 1H), 4.90-4.83 (m, 1H), 4.69 (d, J=4.2 Hz, 1H), 4.53-4.47 (m, 3H), 4.40-4.35 (m, 2H), 4.31 (s, 1H), 4.23-4.14 (m, 5H), 4.01 (s, 3H), 3.82-3.77 (m, 1H), 3.44-3.40 (m, 1H), 3.36 (s, 3H), 2.64-2.60 (m, 1H), 1.90 (t, J=7.5 Hz, 2H), 1.67-1.63 (m, 2H), 1.58-1.55 (m, 2H), 0.88 (t, J=7.8 Hz, 3H); $^{31}$P NMR (202 MHz, D$_2$O) δ-0.94 (s, 1H), −11.52 (m, 2P), −23.01 (m, 1P).

Experimental Examples

1. Capping Efficiency Analysis of mRNA
1.1 Experimental Method:
 1) A plasmid was linearized and the DNA template was purified.
 2) mRNA was synthesized in vitro with 51 types of capping structures of the present disclosure, or without any cap analogues. CleanCap®AG (3'OMe) (Trilink, N-7413) was applied as positive control group, uncapped mRNA was negative control group, and DNAase/RNase-Free water was a blank control group. The reaction system was shown in Table 1 as follow:

TABLE 1

Reaction system

| Component | Final concentration | Amount |
|---|---|---|
| DNase/RNase-Free water | | Up to 20 μL |
| ATP Solution (100 mM) | 5 mM | 1 μL |
| CTP Solution (100 mM) | 5 mM | 1 μL |

TABLE 1-continued

Reaction system

| Component | Final concentration | Amount |
|---|---|---|
| GTP Solution (100 mM) | 5 mM | 1 μL |
| UTP Solution (100 mM) | 5 mM | 1 μL |
| Cap1 Analog (100 mM) | 4 mM | 0.8 μL |
| 10× Transcription buffer | 1× | 2 μL |
| DNA template | 50 μg/mL | 1 μg |
| Murine RNase Inhibitor (40 U/μL) | 1 U/μL | 0.5 μL |
| Inorganic Pyrophosphatase (0.1 U/μL) | 0.002 U/μL | 0.4 μL |
| T7 RNA Polymerase (50 U/μL) | 8 U/μL | 3.2 μL |
| Total volume | | 20 μL |

The system was incubated for 2 to 3 hours at 37° C. and digested by TURBO DNase for 15 min LiCl was used to precipitate mRNA for at least 30 min, or overnight, mRNA precipitates were then washed with 75% ethanol. After ethanol was quickly volatilized, mRNA was re-solubilized with RNase-Free water.
 3) The transcribed products were purified and the transcription yields were calculated. The test results of some compounds were provided, as shown in Table 2.

TABLE 2

Final product mass (μg) obtained from the 20 μL of mRNA transcription system

| Example | Compound | Final product mass |
|---|---|---|
| 1 | Compound 139 | 116 |
| 2 | Compound 3 | 108 |
| 3 | Compound 135 | 104 |
| 4 | Compound 141 | 84 |
| 5 | Compound 143 | 95 |
| 6 | Compound 137 | 116 |
| 7 | Compound 635 | 118 |
| 8 | Compound 6 | 103 |
| 9 | Compound 5 | 95 |
| 10 | Compound 153 | 65 |
| 11 | Compound 4 | 78 |
| 12 | Compound 393 | 95 |
| 13 | Compound 58 | 115 |
| 14 | Compound 643 | 121 |
| 15 | Compound 633 | 100 |
| 16 | Compound 309 | 112 |
| 17 | Compound 311 | 88 |
| 18 | Compound 299 | 105 |

TABLE 2-continued

Final product mass (μg) obtained from the 20 μL of mRNA transcription system

| Example | Compound | Final product mass |
|---|---|---|
| 19 | Compound 219 | 101 |
| 20 | Compound 110 | 106 |
| 21 | Compound 197 | 121 |
| 22 | Compound 195 | 69 |
| 23 | Compound 171 | 105 |
| 24 | Compound 173 | 118 |
| 25 | Compound 189 | 92 |
| 26 | Compound 191 | 123 |
| 27 | Compound 33 | 103 |
| 28 | Compound 151 | 110 |
| 29 | Compound 51 | 114 |
| 30 | Compound 163 | 102 |
| 31 | Compound 631 | 105 |
| 32 | Compound 637 | 88 |
| 33 | Compound 215 | 95 |
| 34 | Compound 181 | 114 |
| 35 | Compound 547 | 103 |
| 36 | Compound 199 | 95 |
| 37 | Compound 201 | 108 |
| 38 | Compound 203 | 96 |
| 39 | Compound 639 | 94 |
| 40 | Compound 323 | 114 |
| 41 | Compound 641 | 89 |
| 42 | Compound 337 | 110 |
| 43 | Compound 561 | 108 |
| 44 | Compound 118 | 86 |
| 45 | Compound 329 | 110 |
| 46 | Compound 345 | 100 |
| 47 | Compound 319 | 102 |
| 48 | Compound 645 | 116 |
| 49 | Compound 394 | 107 |
| 50 | Compound 421 | 98 |
| 51 | Compound 437 | 114 |
| 52 | Compound 415 | 108 |
| 53 | Compound 305 | 92 |
|  | N-7413 | 114 |
|  | Negative control | 118 |
|  | Blank | 0 |

4) An annealing reaction was performed for the obtained mRNA and probes, and the reaction system was shown in Table 3.

TABLE 3

Annealing reaction system

| Component | Amount |
|---|---|
| RNase H probe | 100 pmol |
| mRNA | 100 pmol |
| 10* RNase H reaction buffer | 12 μL |
| DNase/RNase-Free water | Up to 120 μL |

In a PCR machine, the annealing was performed using the following gradients:
95° C. for 5 min; 65° C. for 2 min; 55° C. for 2 min; 40° C. for 2 min; 22° C. for 2 min 5) Pre-treatment of magnetic beads were bound with probes.

100 μL of magnetic beads were placed on a magnetic rack and the preservation solution was removed. 100 μL of 1*BW solution was added, mixed well, and placed on the magnetic rack, and the supernatant was then removed. The washing step was repeated three times. 100 μL of wash A buffer was added, mixed well, and placed on the magnetic rack, and the supernatant was then removed. The washing step was repeated three times. 100 μL of wash B buffer was added, mixed well, and placed on the magnetic rack, and the supernatant was then removed. The washing step was repeated three times. After 120 μL of sample was added, the sample and the magnetic beads solution were incubated for 30 min at room temperature, and they were gently mixed well while incubation.

6) mRNA was spliced to obtain 5' end mRNA single stranded sequence and binding with the probe.

20 μL of RNase H (5 U/mL) was added, incubated for 3 hours at 37° C., mixed once every half an hour. 100 μL of 1*BW solution was added, mixed well, and placed on the magnetic rack, and then the supernatant was removed. The washing step was repeated three times. Subsequently, 100 μL of deionized aqueous solution was added, mixed well, and placed on the magnetic rack, and the supernatant was then removed. The washing step was repeated three times. 100 μL of 75% methanol at 80° C. was added, and the mixture was incubated at 80° C. on a heater plate for 3 min, and placed on the magnetic rack, and the supernatant was then pipetted. The sample was dried using an evaporative centrifuge at room temperature for 45 min to 10 μL, and then resuspended in 50 μL of 100 μM EDTA solution in 1% MeOH for LC-MS analysis.

1.2 Experimental Results.

The capping efficiencies of mRNA with different cap analogs were determined by LC-MS, and some compounds of the results were shown in Table 4.

TABLE 4

Capping efficiencies (%) of mRNA with different cap analogs

| Example | Compound | Capping efficiency |
|---|---|---|
| 1 | Compound 139 | A |
| 2 | Compound 3 | A |
| 4 | Compound 141 | A |
| 5 | Compound 143 | A |
| 8 | Compound 6 | A |
| 11 | Compound 4 | A |
| 12 | Compound 393 | A |
| 15 | Compound 633 | B |
| 24 | Compound 173 | A |
| 37 | Compound 201 | C |
|  | Negative control | 0 |
|  | Blank | 0 |

Note:
Ranges of capping efficiency: 100% > A ≥ 95%, 95% > B ≥ 90%, 90% > C ≥ 80%.

From the above table, the compounds of the present disclosure showed good capping efficiencies, and some had excellent capping efficiencies (>95%).

2. Evaluation on Expression Efficiency of Different Capped Luciferase mRNAs in HEK293T Cells 2.1 Experimental Method:
1) HNE293 T cells were cultured in a DMEM culture medium with 10% FBS and penicillin/streptomycin at 37° C. in 5% $CO_2$.
2) The cultured HEK293T cells were plated into a 96-well plate, with $1.25*10^4$ cells per well.
3) After the cells were adherent, a mixture of 0.5 μg of mRNA sample and Polyplus jetMESSENGER®, was added to the cells in each well followed by incubation for 6 hours at 37° C. in 5% $CO_2$.
4) The growth medium was removed to leave the cells to be tested. The cells were washed with PBS. PBS was removed by centrifugation and 50 μL of 1× lysis buffer solution was added to the cells. The cells and all liquids were transferred into a micro centrifuge tube, then centrifuged at 12000 g for 2 min at 4° C.
5) The supernatant was transferred in to a new tube. Luminescence units were measured by using a ONE-Glo™ Luciferase Assay System kit.
3. All compounds, N-7413, negative control and blank control were tested under the same conditions, and some results of the test were shown in Table 5.

TABLE 5

Relative luminescence unit (RLU) of capped mRNA

| Example | Compound | Relative luminescence unit | Example | Compound | Relative luminescence unit | Example | Compound | Relative luminescence unit |
|---|---|---|---|---|---|---|---|---|
| 2 | Compound 3 | 1.72 | 25 | Compound 189 | 1.46 | 12 | Compound 393 | 1.74 |
| 11 | Compound 4 | 1.65 | 26 | Compound 191 | 0.93 | 52 | Compound 415 | 1.53 |
| 9 | Compound 5 | 1.26 | 22 | Compound 195 | 1.64 | 50 | Compound 421 | 1.27 |
| 8 | Compound 6 | 1.84 | 21 | Compound 197 | 1.73 | 51 | Compound 437 | 1.36 |
| 27 | Compound 33 | 1.35 | 37 | Compound 201 | 0.59 | 35 | Compound 547 | 1.43 |
| 29 | Compound 51 | 1.33 | 38 | Compound 203 | 1.65 | 43 | Compound 561 | 1.22 |
| 13 | Compound 58 | 1.48 | 36 | Compound 199 | 1.10 | 31 | Compound 631 | 1.48 |
| 3 | Compound 135 | 1.07 | 33 | Compound 215 | 1.09 | 15 | Compound 633 | 0.88 |
| 6 | Compound 137 | 1.41 | 19 | Compound 219 | 1.75 | 7 | Compound 635 | 1.34 |
| 1 | Compound 139 | 1.65 | 18 | Compound 299 | 1.67 | 32 | Compound 637 | 1.28 |
| 4 | Compound 141 | 1.46 | 53 | Compound 305 | 1.53 | 39 | Compound 639 | 1.58 |
| 5 | Compound 143 | 1.83 | 16 | Compound 309 | 1.13 | 41 | Compound 641 | 1.71 |
| 10 | Compound 153 | 1.44 | 17 | Compound 311 | 1.60 | 14 | Compound 643 | 1.61 |
| 28 | Compound 151 | 1.47 | 47 | Compound 319 | 1.52 | 48 | Compound 645 | 1.43 |
| 30 | Compound 163 | 1.10 | 40 | Compound 323 | 1.58 | | N-7413 | 1.00 |
| 23 | Compound 171 | 1.41 | 45 | Compound 329 | 1.61 | | Negative control | 0 |
| 24 | Compound 173 | 1.43 | 42 | Compound 337 | 1.78 | | Blank | 0 |
| 34 | Compound 181 | 1.51 | 46 | Compound 345 | 1.53 | | | |

Note:
The luminescence unit of N-7413 was normalized as 1, thus relative luminescence unit (RLU) was the ratio of luminescence unit of luciferase expressed by the cells transfected with other capped mRNAs to the luminescence unit of luciferase expressed by the cells transfected with N-7413.

After the capped mRNAs were transfected into 293T cells, the RLU results (6 h) were provided in Table 5. It could be seen from the table that mRNAs capped by the compounds of the present disclosure demonstrated fair expression amount, and some cap structures could provide the mRNA with a higher expression efficiency than N-7413.

In the structures of Compounds 110, 118 and 394 prepared in Examples 20, 44 and 49, $B_1$ and $B_2$ were adenine and uracil, respectively, and therefore the vectors used for these compounds were self-replicating vectors with long-lasting expression, which did not meet the comparison requirement, i.e., the above-mentioned compound should be compared under the same condition. From the Table 2, it could be seen that, when $B_1$ and $B_2$ were adenine and uracil, respectively, the capped mRNA could be transcribed normally, the transcriptional yield was good, and the self-replicating vector could be subsequently employed for long-lasting expression in cells.

3. Stability of the Capped mRNA Against the mRNA Decapping Enzymes 3.1 Experimental Method:
1) The capped mRNAs were heated at 65° C. for 10 min and their secondary structures were unfolded.
2) The concentration of mRNA Deacpping Enzyme was diluted from the original concentration (100 U/uL) to 50 U/uL, 5 U/uL, 0.5 U/uL in a 10-fold gradient dilution ratio.
3) The capped mRNAs were added to the reaction, and the amount of enzyme in the reaction was 50 U, 5 U, 0.5 U, 0 U, respectively. The mixture was mixed with a pipette, and was incubated at 37° C. for 1 hour.

| Component | 30 ul Rxn | Final Concentration |
|---|---|---|
| mRNA Decapping Enzyme Reaction Buffer (10X) | 3 µL | 1X |
| Total RNA | up to 32 µg | / |
| mRNA Decapping Enzyme at various concentrations | 1 µL | / |
| Nuclease-free water | to 30 µL | / |

4) The RNA was purified using a LiCl Precipitation method, and then diluted to 500 ng/uL*20 uL for subsequent cell transfection.
5) The cells were transfected with mRNA, and luciferase expression was detected in the same method as Experiment 2.

3.2 Some Experiment Results in the Test were Shown in FIG. 1.

Using N-7413 as reference, it can be noted from the FIG. 1, that Compound 3 had the same stability as that of N-7413, and Compound 173 at low concentration had the same stability as that of N-7413. However, when the concentration of decapping enzyme was higher, Compound 173 showed a better stability than that of N-7413; Compound 191 showed an excellent stability at different concentrations. Therefore, modification of the triphosphate in the compounds can significantly increase the stability of the capped mRNA against the decapping enzyme.

In FIG. 1, the luminescence unit of luciferase expressed by mRNA without decapping enzyme treatment (0 U) was 100%, and the percentage of the luminescence unit of luciferase expressed by capped mRNA treated with different concentrations of capping enzyme to the luminescence unit of luciferase expressed by capped mRNA without decapping enzyme treatment was calculated.

Although the present invention has been disclosed in the form of embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:
1. A compound of formula IV-A, or a pharmaceutically acceptable salt,

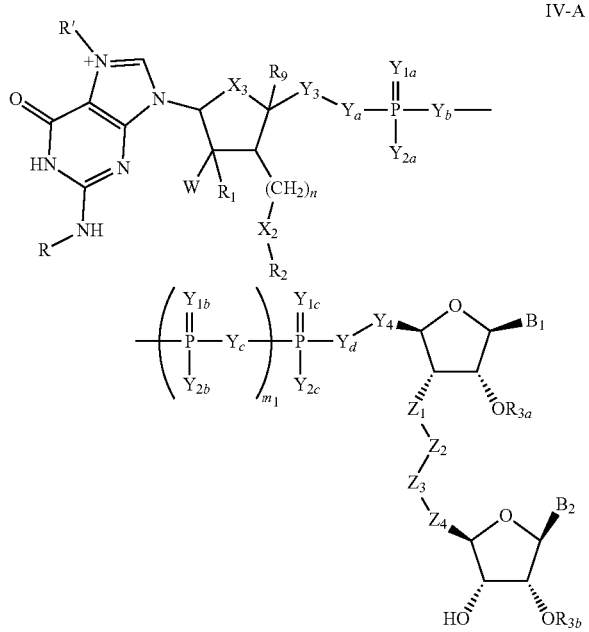

wherein:
$X_2$ is $CONR_4$, $NR_4CO$, $NR_4CO_2$, $NR_4CONR_4$, or $SO_2NR_4$;
R' is $C_1$-$C_6$ alkyl, $C_2$-$C_6$ alkenyl, $C_2$-$C_6$ alkynyl, or benzyl;
$X_3$ is O;
R is H, $C_1$-$C_6$ alkyl, $C_2$-$C_6$ alkenyl, $C_2$-$C_6$ alkynyl, or $C_3$-$C_6$ cycloalkyl;
$R_1$ is H;
$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, phenyl, benzyl, halobenzyl, CN, or $N_3$;
each of $R_{3a}$ and $R_{3b}$ is independently selected from H, $C_1$-$C_4$ alkyl, or $C_1$-$C_4$ haloalkyl;
W is $OR_4$;
each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;
each of $Y_{2a}$, $Y_{2b}$, and $Y_{2c}$ is independently selected from OH, or SH;
each of $Y_3$ and $Y_4$, is independently selected from $CH_2$, or O;
$Z_1$ is O, $CH_2$, S, or $NR_6$;
$Z_2$ is $CHR_7$, CO, PO(OH), or PO(SH);
$Z_3$ is O, $NR_6$, or $CHR_7$;
$Z_4$ is $CH_2$;
each of $B_1$ and $B_2$ is independently selected from natural pyrimidine base, or natural purine base;
$R_4$ is H, $C_1$-$C_4$ alkyl, $C_2$-$C_4$ alkenyl, or $C_2$-$C_4$ alkynyl;
$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;
$R_7$ is H, $C_1$-$C_4$ alkyl, $C_2$-$C_4$ alkenyl, or $C_2$-$C_4$ alkynyl;
$R_6$ is H, or $C_1$-$C_4$ alkyl;
$R_9$ is H;
$m_1$ is 1, 2, or 3; and
n is 1, 2, or 3.

2. The compound, or a pharmaceutically acceptable salt of claim 1, wherein the compound has a structure of formula IV:

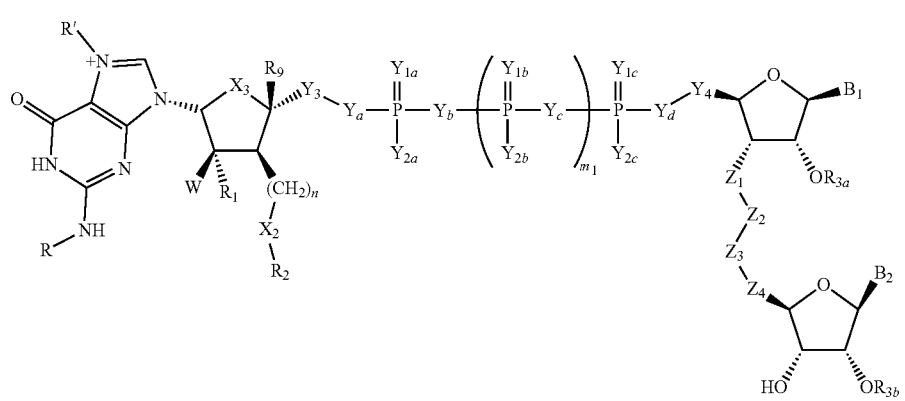

wherein, $X_2$ is $CONR_4$, $NR_4CO$, $NR_4CO_2$, $NR_4CONR_4$, or $SO_2NR_4$.

3. The compound, or a pharmaceutically acceptable salt of claim 2, wherein when $R_1$ is H, W is $OR_4$; and
$R_4$ is H, or $C_1$-$C_4$ alkyl.

4. The compound, or a pharmaceutically acceptable salt of claim 2, wherein $X_2$ is $CONR_4$, $NR_4CO$, $NR_4CO_2$, or $NR_4CONR_4$.

5. The compound, or a pharmaceutically acceptable salt of claim 4, wherein the compound has a structure of formula IV-2:

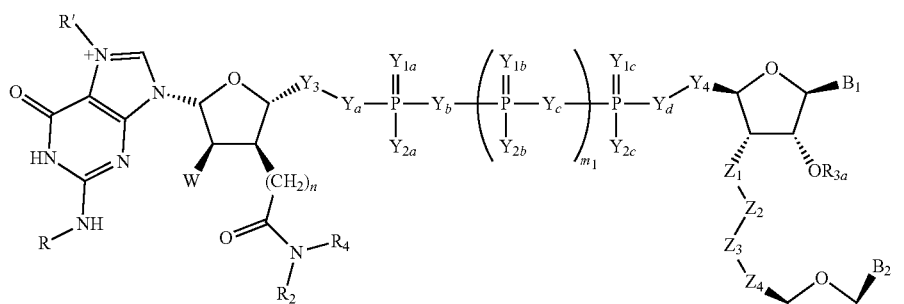

IV-2 wherein, R' is $C_1$-$C_6$ alkyl, $C_2$-$C_6$ alkenyl, $C_2$-$C_6$ alkynyl, or benzyl;

R is H, $C_1$-$C_6$ alkyl, $C_2$-$C_6$ alkenyl, $C_2$-$C_6$ alkynyl, or $C_3$-$C_6$ cycloalkyl;

$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, benzyl, halobenzyl, or CN;

each of $R_{3a}$ and $R_{3b}$ is independently selected from H, $C_1$-$C_4$ alkyl, or $C_1$-$C_4$ haloalkyl;

W is $OR_4$;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, or SH;

each of $Y_3$ and $Y_4$ is independently selected from $CH_2$, or O;

$Z_1$ is O, $CH_2$, S, or $NR_6$;

$Z_2$ is $CHR_7$, CO, P(OH), or PO(SH);

$Z_3$ is O, $NR_6$, or $CHR_7$;

$Z_4$ is $CH_2$;

each of $B_1$ and $B_2$ is independently selected from natural pyrimidine base, or natural purine base;

$R_4$ is H, $C_1$-$C_4$ alkyl, $C_2$-$C_4$ alkenyl, or $C_2$-$C_4$ alkynyl;

$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;

$R_6$ is H, or $C_1$-$C_4$ alkyl;

$R_7$ is H, $C_1$-$C_4$ alkyl, $C_2$-$C_4$ alkenyl, or $C_2$-$C_4$ alkynyl;

$m_1$ is 1, or 2; and n is 1, 2, or 3.

6. The compound, or a pharmaceutically acceptable salt of claim 4, wherein the compound has a structure of formula IV-3:

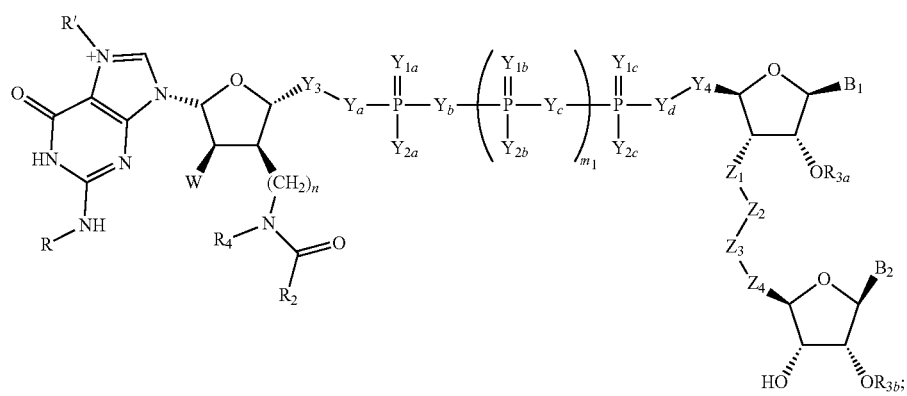

IV-3 wherein, R' is $C_1$-$C_6$ alkyl, $C_2$-$C_6$ alkenyl, $C_2$-$C_6$ alkynyl, or benzyl;

R is H, $C_1$-$C_6$ alkyl, $C_2$-$C_6$ alkenyl, $C_2$-$C_6$ alkynyl, or $C_3$-$C_6$ cycloalkyl;

$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, phenyl, benzyl, halobenzyl, or CN;

each of $R_{3a}$ and $R_{3b}$ is independently selected from H, $C_1$-$C_4$ alkyl, or $C_1$-$C_4$ haloalkyl;

W is $OR_4$;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, or SH;

each of $Y_3$ and $Y_4$ is independently selected from $CH_2$, or O;

$Z_1$ is O, $CH_2$, S, or $NR_6$;
$Z_2$ is $CHR_7$, CO, PO(OH), or PO(SH);
$Z_3$ is O, $NR_6$, or $CHR_7$;
$Z_4$ is $CH_2$;
each of $B_1$ and $B_2$ is independently selected from natural pyrimidine base, or natural purine base;
$R_4$ is H, $C_1$-$C_4$ alkyl, $C_2$-$C_4$ alkenyl, or $C_2$-$C_4$ alkynyl;
$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;
$R_6$ is H, or $C_1$-$C_4$ alkyl;
$R_7$ is H, $C_1$-$C_4$ alkyl, $C_2$-$C_4$ alkenyl, or $C_2$-$C_4$ alkynyl;
$m_1$ is 1, or 2; and
n is 1, 2, or 3.

7. The compound, or a pharmaceutically acceptable salt of claim 4,
wherein $R_2$ is H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, $R_5$-substituted $C_2$-$C_6$ alkynyl, benzyl, halobenzyl, or CN; and
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine;
W is OH, methoxy, or ethoxy;
R' is methyl, ethyl, n-propyl, or isopropyl; and
R is H, methyl, ethyl, n-propyl, or isopropyl.

8. The compound, or a pharmaceutically acceptable salt of claim 7, wherein $R_2$ is H, methyl, ethyl, n-propyl, isopropyl, butyl, hexyl, ethenyl, propenyl, butenyl, ethynyl, propynyl, butynyl, phenyl, benzyl, halomethyl, haloethyl, halopropyl, haloisopropyl, halobutyl, halohexyl, haloethenyl, halopropenyl, halobutenyl, haloethynyl, halopropynyl, halobutynyl, halobenzyl, $C_1$-$C_4$ pyridinylalkyl, $C_1$-$C_4$ pyrimidinylalkyl, $C_1$-$C_4$ alkoxy-$C_1$-$C_4$ alkyl, or $C_1$-$C_4$ alkylamio-$C_1$-$C_4$ alkyl.

9. The compound, or a pharmaceutically acceptable salt of claim 4, wherein $Z_1$ is O, $CH_2$, S, or NH;
$Z_4$ is $CH_2$;
each of $B_1$ and $B_2$ is independently selected from natural cytosine base, natural uracil base, natural adenine base, or natural guanine base;
$R_6$ is H, methyl, ethyl, propyl, or isopropyl; and
$R_7$ is H, methyl, ethyl, propyl, or isopropyl.

10. The compound, or a pharmaceutically acceptable salt of claim 4, wherein each of $Y_a$, $Y_b$, $Y_c$, and $Y_d$ is O, or at most one of $Y_a$, $Y_b$, $Y_c$, and $Y_d$ is S, $CH_2$, $CCl_2$, $CF_2$, or NH;
each of $Y_{1a}$, $Y_{1b}$, and $Y_{1c}$, is O, or at most one of $Y1_a$, $Y1_b$, or $Y1_c$ is S;
each of $Y_{2a}$, $Y_{2b}$, and $Y_{2c}$ is OH, or at most one of $Y_{2a}$, $Y_{2b}$, or $Y_{2c}$ is SH;
each of $Y_3$ and $Y_4$ is independently $CH_2$;

$Z_2$ is $CH_2$, CO, or PO(OH);
$Z_3$ is O, $CH_2$, or NH; and
$Z_4$ is $CH_2$;
R' is $C_1$-$C_4$ alkyl, $C_2$-$C_4$ alkenyl, $C_2$-$C_4$ alkynyl, or benzyl;
R is H, $C_1$-$C_4$ alkyl, $C_2$-$C_4$ alkenyl, $C_2$-$C_4$ alkynyl, or $C_3$-$C_6$ cycloalkyl;
$R_4$ is H, methyl, ethyl, n-propyl, isopropyl, butyl, ethenyl, propenyl, butenyl, ethynyl, propynyl, or butynyl;
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine; and
$R_7$ is H, methyl, ethyl, n-propyl, isopropyl, butyl, ethenyl, propenyl, butenyl, ethynyl, propynyl, or butynyl.

11. A method of synthesizing an RNA molecule, comprising steps of:
co-incubating the compound of claim 1 and polynucleotide template and transcribing the template.

12. A transcription reaction system for RNA capping, comprising polynucleotide template, the compound of claim 1, NTPs, and RNA polymerases.

13. A co-transcription reagent comprising the compound of claim 1 for capping an RNA co-transcript in vitro.

14. A compound of formula VI-5, or a pharmaceutically acceptable salt,

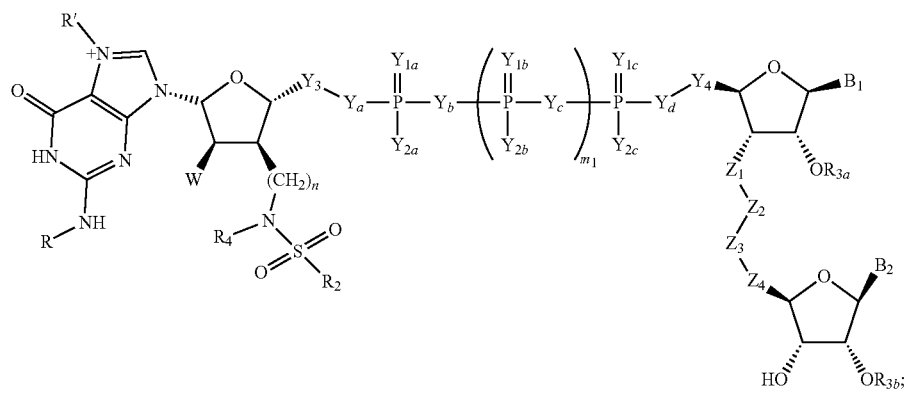

VI-5 wherein, R' is $C_1$-$C_6$ alkyl, $C_2$-$C_6$ alkenyl, $C_2$-$C_6$ alkynyl, or benzyl;
R is H, $C_1$-$C_6$ alkyl, $C_2$-$C_6$ alkenyl, $C_2$-$C_6$ alkynyl, or $C_3$-$C_6$ cycloalkyl;
$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, phenyl, benzyl, halobenzyl, or CN;
each of $R_{3a}$ and $R_{3b}$ is independently selected from H, $C_1$-$C_4$ alkyl, or $C_1$-$C_4$ haloalkyl;
W is $OR_4$;
each of $Y_a$, $Y_b$, $Y_c$, and $Y_d$ is independently selected from O, S, $CH_2$, $CCl_2$, $CF_2$, or NH;
each of $Y_{1a}$, $Y_{1b}$, and $Y_{1c}$ is independently selected from O, or S;
each of $Y_{2a}$, $Y_{2b}$, and $Y_{2c}$ is independently selected from OH, or SH;
each of $Y_3$ and $Y_4$, is independently selected from $CH_2$, or O;
$Z_1$ is O, $CH_2$, S, or $NR_6$;
$Z_2$ is $CHR_7$, CO, PO(OH), or PO(SH);
$Z_3$ is O, $NR_6$, or $CHR_7$;
$Z_4$ is $CH_2$;
each of $B_1$ and $B_2$ is independently selected from natural pyrimidine base, or natural purine base;

$R_4$ is H, $C_1$-$C_4$ alkyl, $C_2$-$C_4$ alkenyl, or $C_2$-$C_4$ alkynyl;
$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_2$, halogen, CN, pyridine, pyrimidine, or morpholine;
$R_6$ is H, or $C_1$-$C_4$ alkyl;
$R_7$ is H, $C_1$-$C_4$ alkyl, $C_2$-$C_4$ alkenyl, or $C_2$-$C_4$ alkynyl;
n is 1, or 2, or 3; and
$m_1$ is 1, or 2.

15. The compound, or a pharmaceutically acceptable salt of claim 14,
wherein $R_2$ is H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, $R_5$-substituted $C_2$-$C_6$ alkynyl, benzyl, halobenzyl, or CN; and
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine;
W is OH, methoxy, or ethoxy;
R' is methyl, ethyl, n-propyl, or isopropyl; and
R is H, methyl, ethyl, n-propyl, or isopropyl.

16. The compound, or a pharmaceutically acceptable salt of claim 15, wherein $R_2$, is H methyl, ethyl, n-propyl, isopropyl, butyl, hexyl, ethenyl, propenyl, butenyl, ethynyl, propynyl, butynyl, phenyl, benzyl, halomethyl, haloethyl, halopropyl, haloisopropyl, halobutyl, halohexyl, haloethenyl, halopropenyl, halobutenyl, haloethynyl, halopropynyl, halobutynyl, halobenzyl, $C_1$-$C_4$ pyridinylalkyl, $C_1$-$C_4$ pyrimidinylalkyl, $C_1$-$C_4$ alkoxy-$C_1$-$C_4$ alkyl, or $C_1$-$C_4$ alkylamio-$C_1$-$C_4$ alkyl.

17. The compound, or a pharmaceutically acceptable salt of claim 14, wherein $Z_1$ is O, $CH_2$, S, or NH;
$Z_4$ is $CH_2$;
each of $B_1$ and $B_2$ is independently selected from natural cytosine base, natural uracil base, natural adenine base, or natural guanine base;
$R_6$ is H, methyl, ethyl, propyl, or isopropyl; and
$R_7$ is H, methyl, ethyl, propyl, or isopropyl.

18. The compound, or a pharmaceutic ally acceptable salt of claim 14, wherein each of $Y_a$, $Y_b$, $Y_c$, and $Y_d$ is O, or at most one of $Y_a$, $Y_b$, $Y_c$, and $Y_d$ is S, $CH_2$, $CCl_2$, $CF_2$, or NH;
each of $Y_{1a}$, $Y_{1b}$, and $Y_{1c}$, is O, or at most one of $Y1_a$, $Y1_b$, or $Y1_c$ is S;
each of $Y_{2a}$, $Y_{2b}$, and $Y_{2c}$ is OH, or at most one of $Y_{2a}$, $Y_{2b}$, or $Y_{2c}$ is SH;
each of $Y_3$ and $Y_4$ is independently $CH_2$;
$Z_2$ is $CH_2$, CO, or PO(OH);
$Z_3$ is O, $CH_2$, or NH; and
$Z_4$ is $CH_2$;

R' is $C_1$-$C_4$ alkyl, $C_2$-$C_4$ alkenyl, $C_2$-$C_4$ alkynyl, or benzyl;
R is H, $C_1$-$C_4$ alkyl, $C_2$-$C_4$ alkenyl, $C_2$-$C_4$ alkynyl, or $C_3$-$C_6$ cycloalkyl;
$R_4$ is H, methyl, ethyl, n-propyl, isopropyl, butyl, ethenyl, propenyl, butenyl, ethynyl, propynyl, or butynyl;
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine; and
$R_7$ is H, methyl, ethyl, n-propyl, isopropyl, butyl, ethenyl, propenyl, butenyl, ethynyl, propynyl, or butynyl.

19. A compound of formula VI-6, or a pharmaceutically acceptable salt,

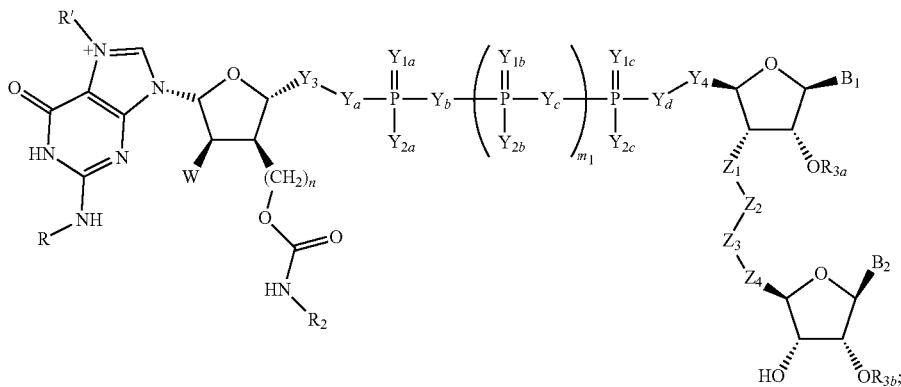

VI-6 wherein, R' is $C_1$-$C_6$ alkyl, $C_2$-$C_6$ alkenyl, $C_2$-$C_6$ alkynyl, or benzyl;
R is H, $C_1$-$C_6$ alkyl, $C_2$-$C_6$ alkenyl, $C_2$-$C_6$ alkynyl, or $C_3$-$C_6$ cycloalkyl;
$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$alkynyl, phenyl, benzyl, halobenzyl, or CN;
each of $R_{3a}$ and $R_{3b}$ is independently selected from H, $C_1$-$C_4$ alkyl, or $C_1$-$C_4$ haloalkyl;
W is $OR_4$;
each of $Y_a$, $Y_b$, $Y_c$, and $Y_d$ is independently selected from O, S, $CH_2$, $CCl_2$, $CF_2$, or NFL;
each of $Y_{1a}$, $Y_{1b}$, and $Y_{1c}$ is independently selected from O, or S;
each of $Y_{2a}$, $Y_{2b}$, and $Y_{2c}$ is independently selected from OH, or SH;
each of $Y_3$ and $Y_4$, is independently selected from $CH_2$, or O;
$Z_1$ is O, $CH_2$, S, or $NR_6$;
$Z_2$ is $CHR_7$, CO, PO(OH), or PO(SH);
$Z_3$ is O, $NR_6$, or $CHR_7$;
$Z_4$ is $CH_2$;
each of $B_1$ and $B_2$ is independently selected from natural pyrimidine base, or natural purine base;
$R_4$ is H, $C_1$-$C_4$ alkyl, $C_2$-$C_4$ alkenyl, or $C_2$-$C_4$ alkynyl;
$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;
$R_6$ is H, or $C_1$-$C_4$ alkyl;
$R_7$ is H, $C_1$-$C_4$ alkyl, $C_2$-$C_4$ alkenyl, or $C_2$-$C_4$ alkynyl;
n is 1, or 2, or 3; and
$m_1$ is 1, or 2.

20. The compound, or a pharmaceutically acceptable salt of claim 19,
wherein $R_2$ is H, $C_1$-$C_6$ alkyl, $C_2$-$C_6$ alkenyl, $C_2$-$C_6$ alkynyl, $R_5$-substituted $C_1$-$C_6$ alkyl, $R_5$-substituted $C_2$-$C_6$ alkenyl, $R_5$-substituted $C_2$-$C_6$ alkynyl, benzyl, halobenzyl, or CN; and
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine;
W is OH, methoxy, or ethoxy;
R is methyl, ethyl, n-propyl, or isopropyl; and
R is H, methyl, ethyl, n-propyl, or isopropyl.

21. The compound, or a pharmaceutically acceptable salt of claim 20, wherein $R_2$ is H, methyl, ethyl, n-propyl, isopropyl, butyl, hexyl, ethenyl, propenyl, butenyl, ethynyl, propynyl, butynyl, phenyl, benzyl, halomethyl, haloethyl, halopropyl, haloisopropyl, halobutyl, halohexyl, haloethenyl, halopropenyl, halobutenyl, haloethynyl, halopropynyl, halobutynyl, halobenzyl, $C_1$-$C_4$ pyridinylalkyl, $C_1$-$C_4$ pyrimidinylalkyl, $C_1$-$C_4$ alkoxy-$C_1$-$C_4$ alkyl, or $C_1$-$C_4$ alkylamio-$C_1$-$C_4$ alkyl.

22. The compound, or a pharmaceutically acceptable salt of claim 19, wherein $Z_1$ is O, $CH_2$, S, or NH;
$Z_4$ is $CH_2$;
each of $B_1$ and $B_2$ is independently selected from natural cytosine base, natural uracil base, natural adenine base, or natural guanine base;
$R_6$ is H, methyl, ethyl, propyl, or isopropyl; and
$R_7$ is H, methyl, ethyl, propyl, or isopropyl.

23. The compound, or a pharmaceutically acceptable salt of claim 19, wherein each of $Y_a$, $Y_b$, $Y_c$, and $Y_d$ is O, or at most one of $Y_a$, $Y_b$, $Y_c$, and $Y_d$ is S, $CH_2$, $CCl_2$, $CF_2$, or NH;
each of $Y_{1a}$, $Y_{1b}$, and $Y_{1c}$, is O, or at most one of $Y1_a$, $Y1_b$, or $Y1_c$ is S;
each of $Y_{2a}$, $Y_{2b}$, and $Y_{2c}$ is OH, or at most one of $Y_{2a}$, $Y_{2b}$, or $Y_{2c}$ is SH;
each of $Y_3$ and $Y_4$ is independently $CH_2$;
$Z_2$ is $CH_2$, CO, or PO(OH);
$Z_3$ is O, $CH_2$, or NH; and
$Z_4$ is $CH_2$;
R' is $C_1$-$C_4$ alkyl, $C_2$-$C_4$ alkenyl, $C_2$-$C_4$ alkynyl, or benzyl;
R is H, $C_1$-$C_4$ alkyl, $C_2$-$C_4$ alkenyl, $C_2$-$C_4$ alkynyl, or $C_3$-$C_6$ cycloalkyl;
$R_4$ is H, methyl, ethyl, n-propyl, isopropyl, butyl, ethenyl, propenyl, butenyl, ethynyl, propynyl, or butynyl;
$R_5$ is $C_1$-$C_4$ alkyl, $C_2$-$C_4$ alkenyl, $C_2$-$C_4$ alkynyl, $OR_7$, halogen, CN, pyridine, pyrimidine, or morpholine; and
$R_7$ is H, methyl, ethyl, n-propyl, isopropyl, butyl, ethenyl, propenyl, butenyl, ethynyl, propynyl, or butynyl.

24. A compound being selected from any one of the following compounds:

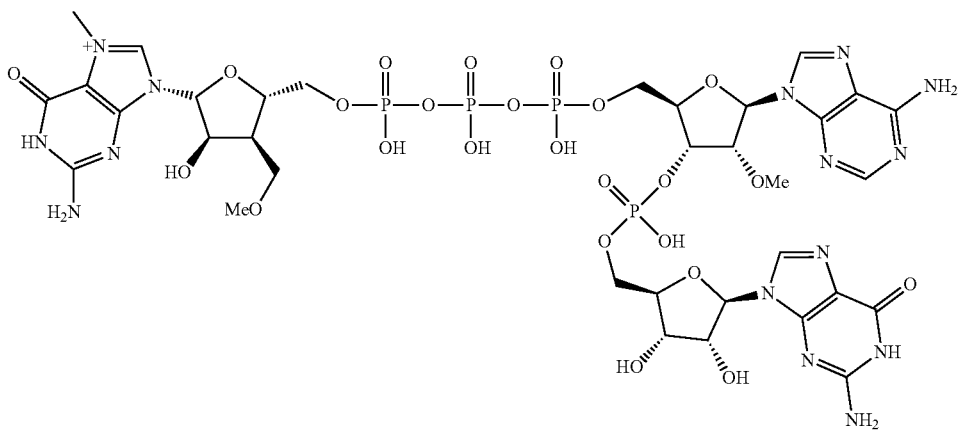

Compound 3

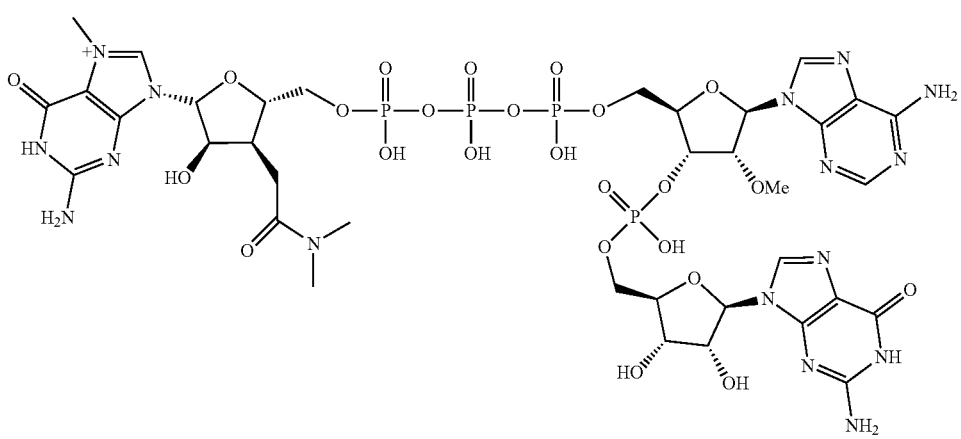

Compound 4

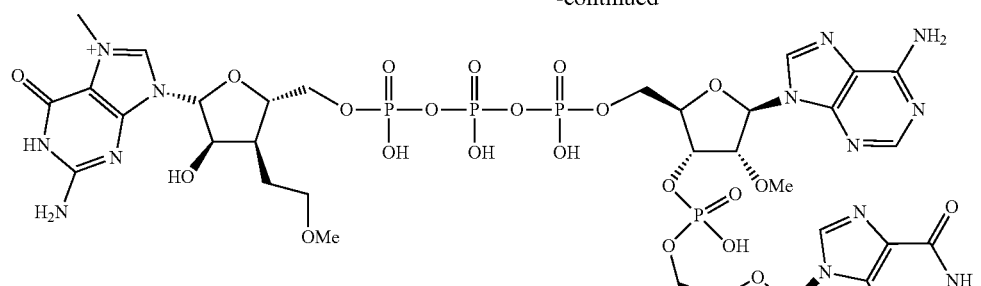
Compound 6
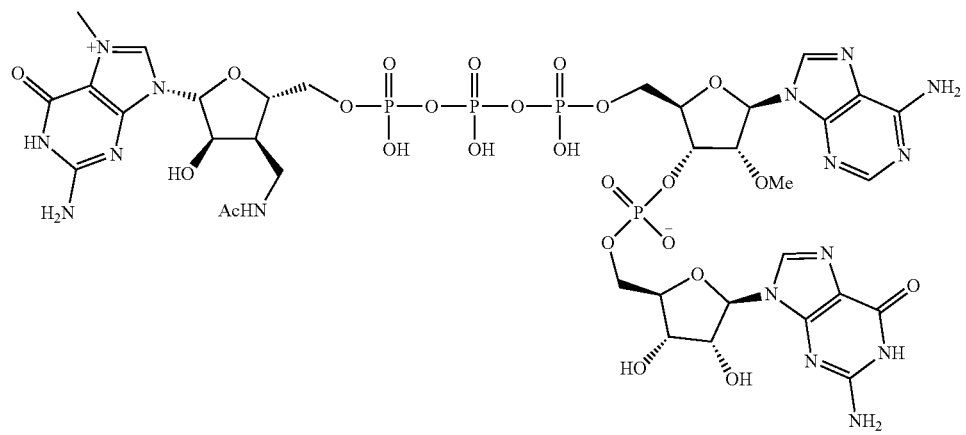
Compound 21
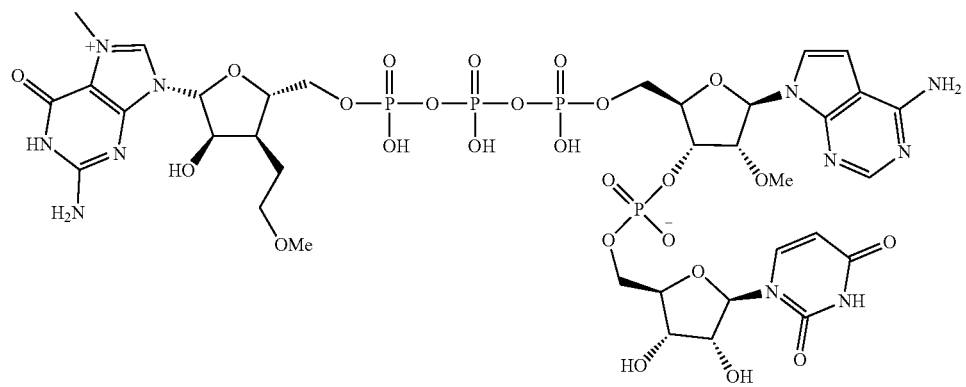
Compound 33
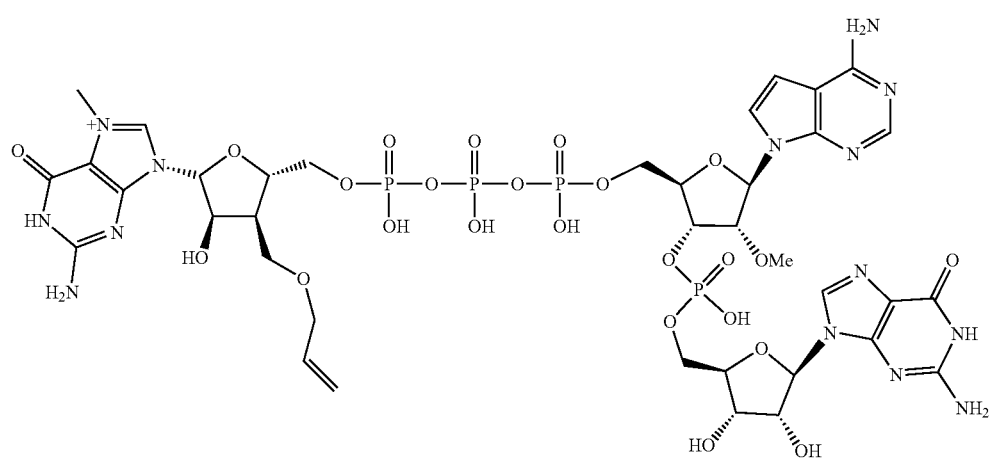

-continued
Compound 34
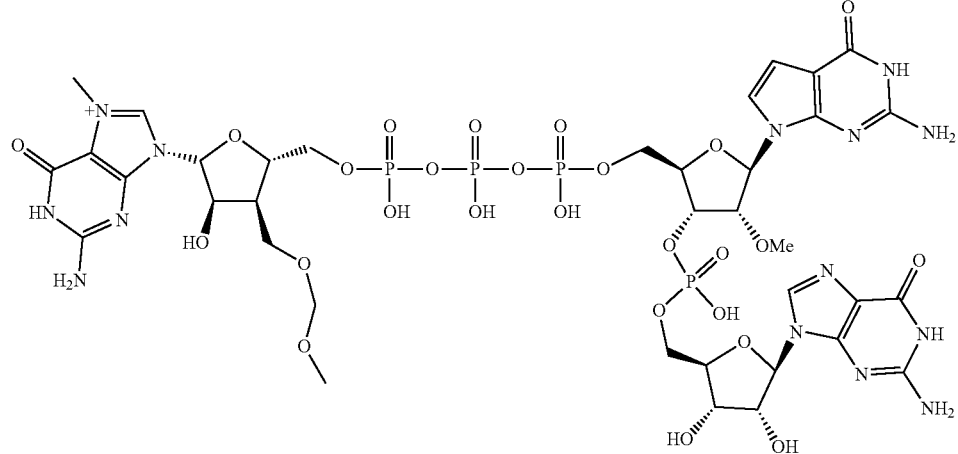
Compound 36
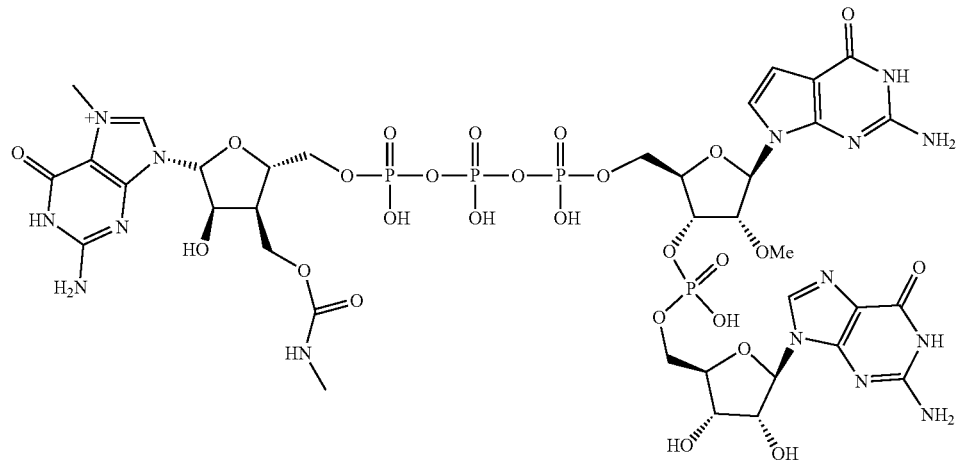
Compound 47
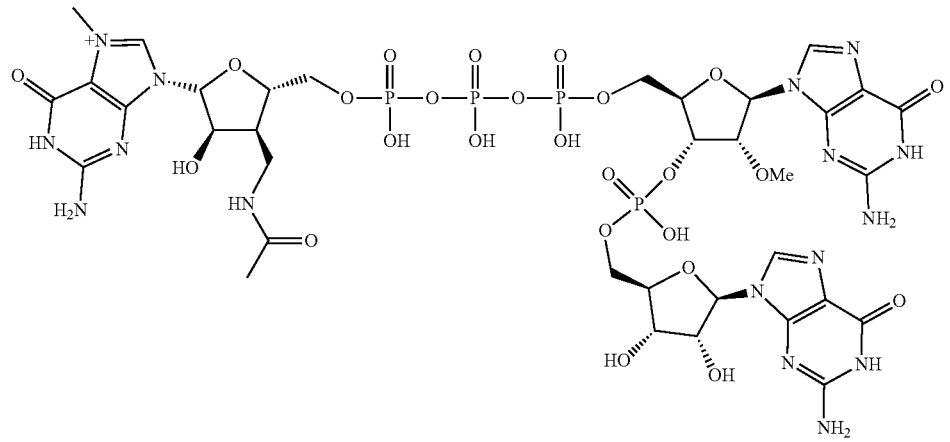

Compound 48
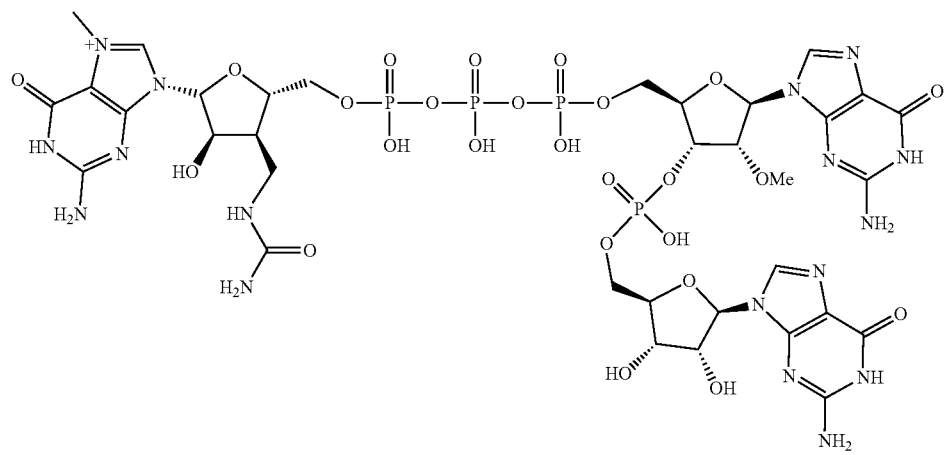
Compound 51
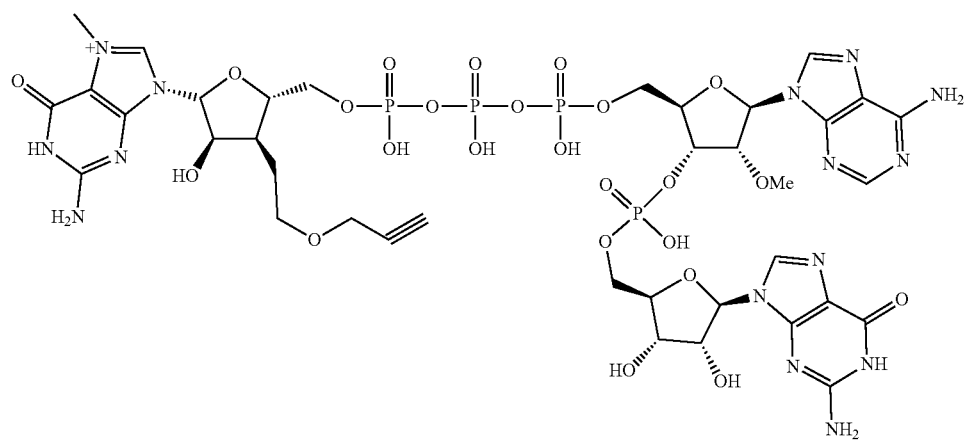
Compound 58
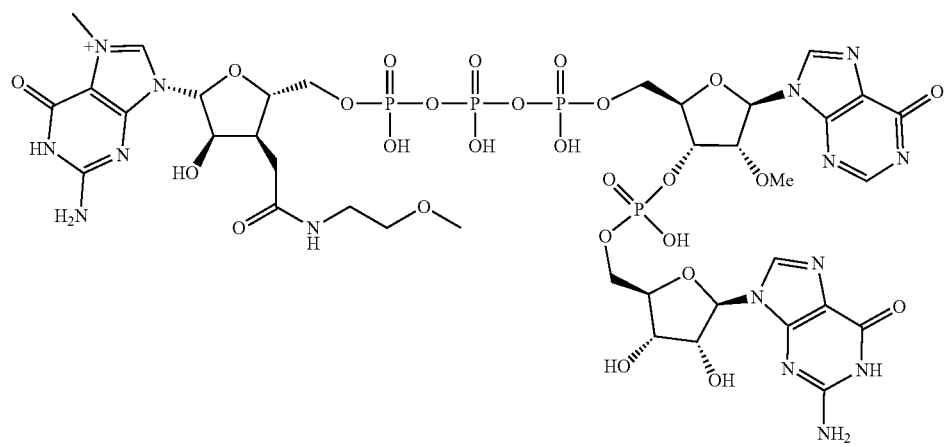

-continued
Compound 110
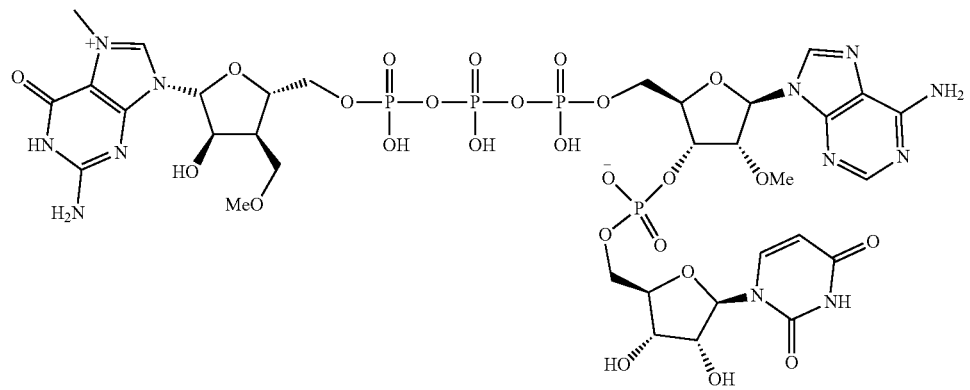
Compound 117
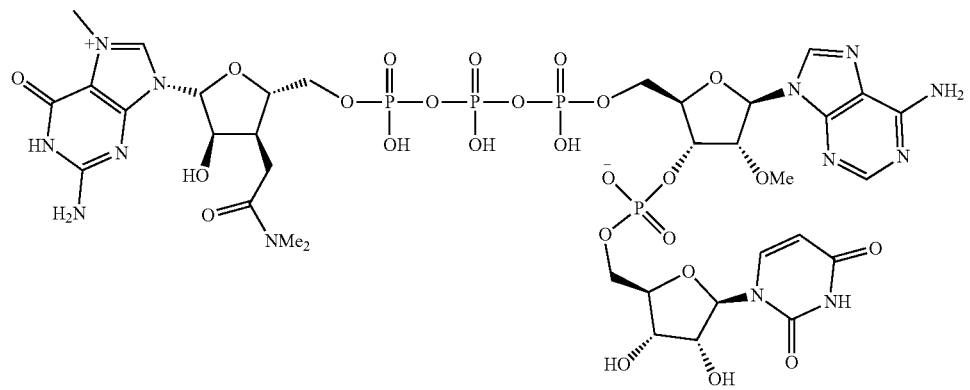
Compound 118
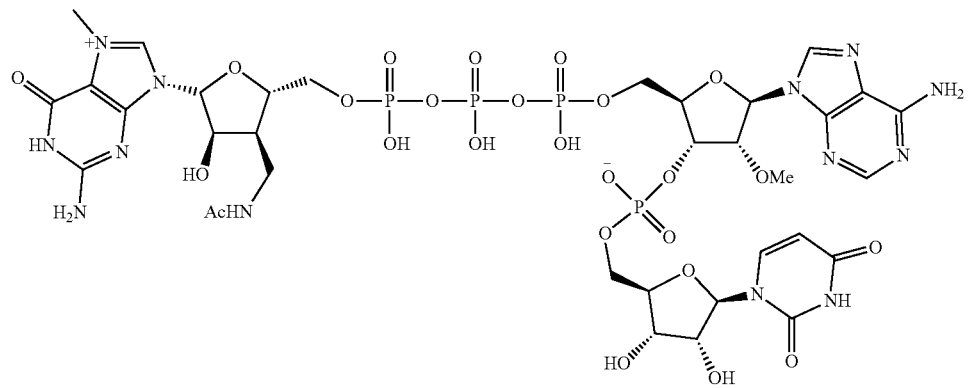
Compound 135
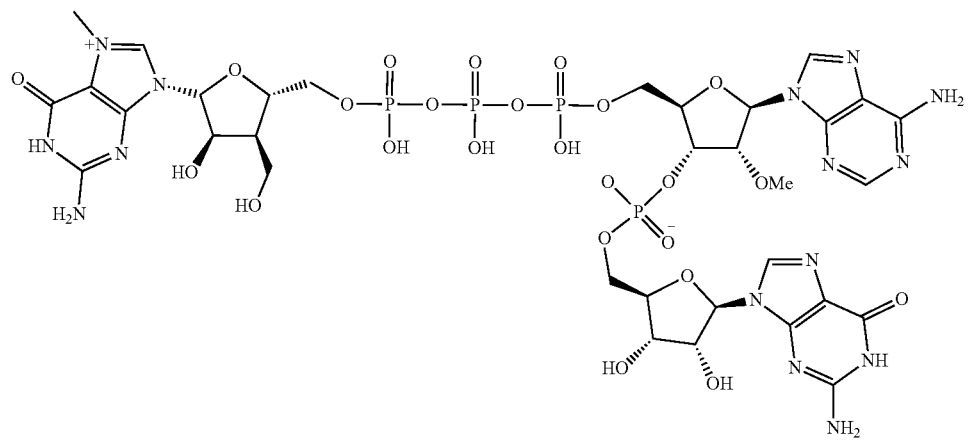

Compound 136
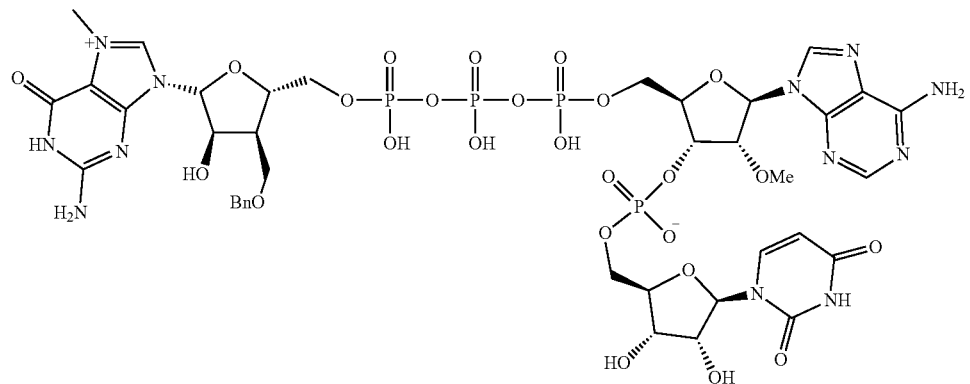
Compound 137
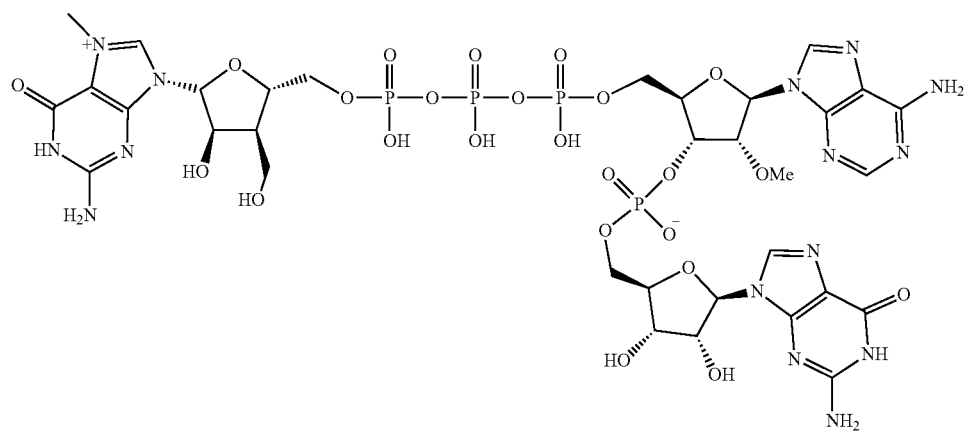
Compound 138
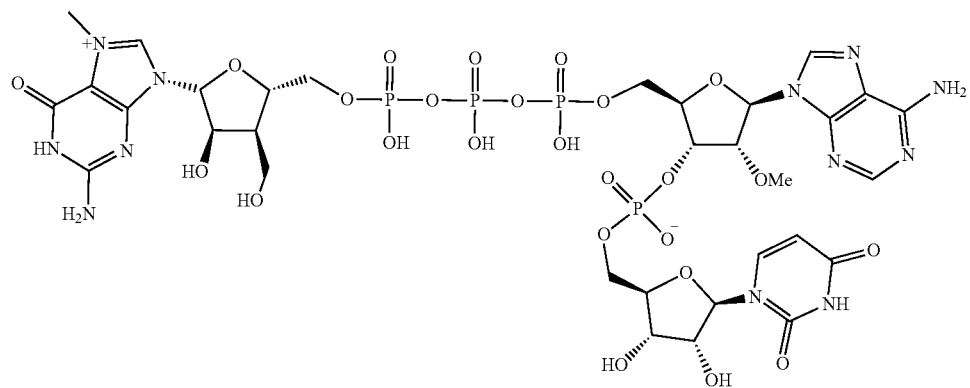
Compound 139
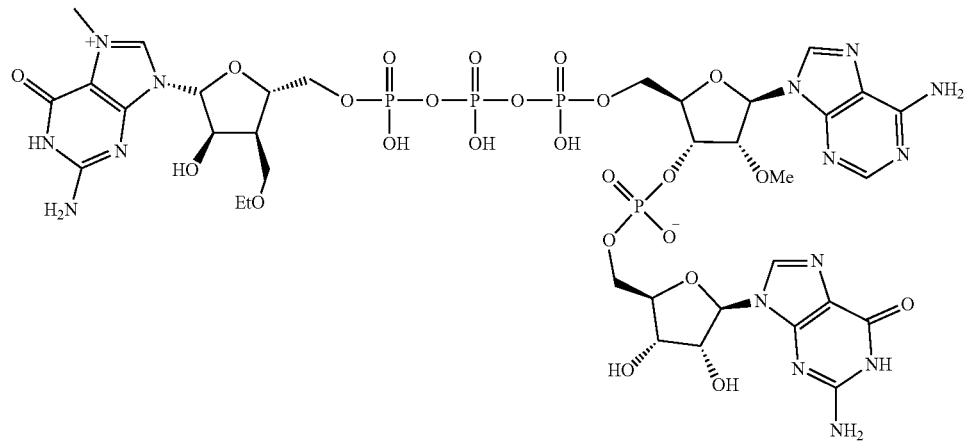

Compound 140
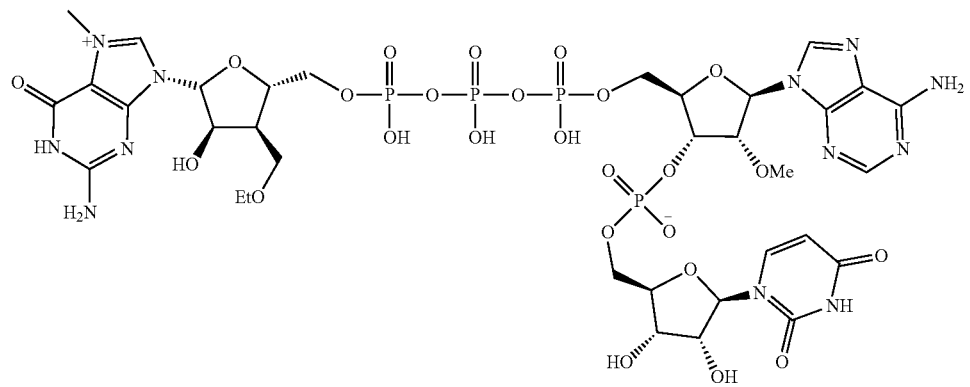
Compound 141
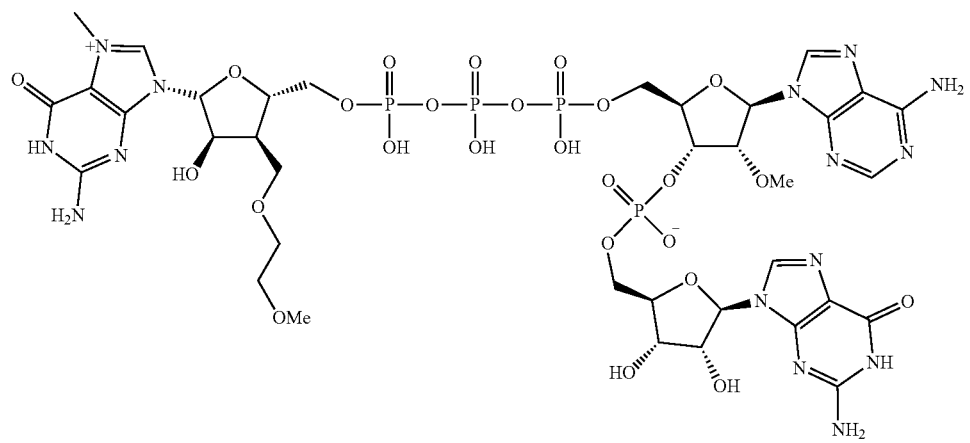
Compound 142
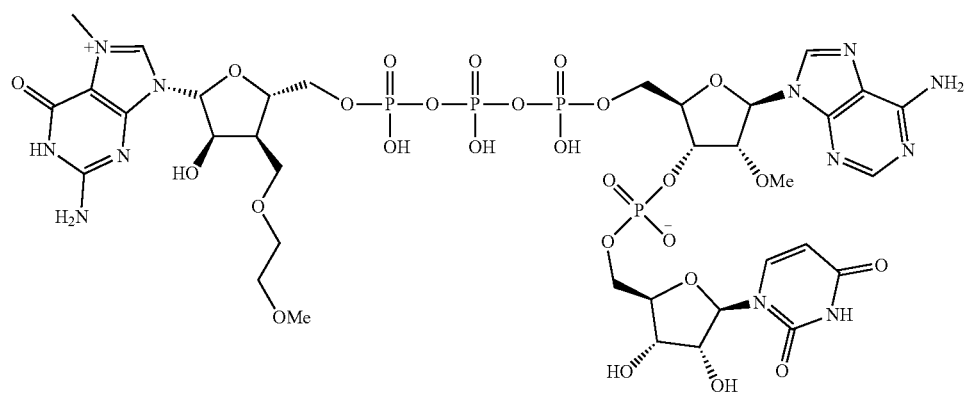
Compound 143
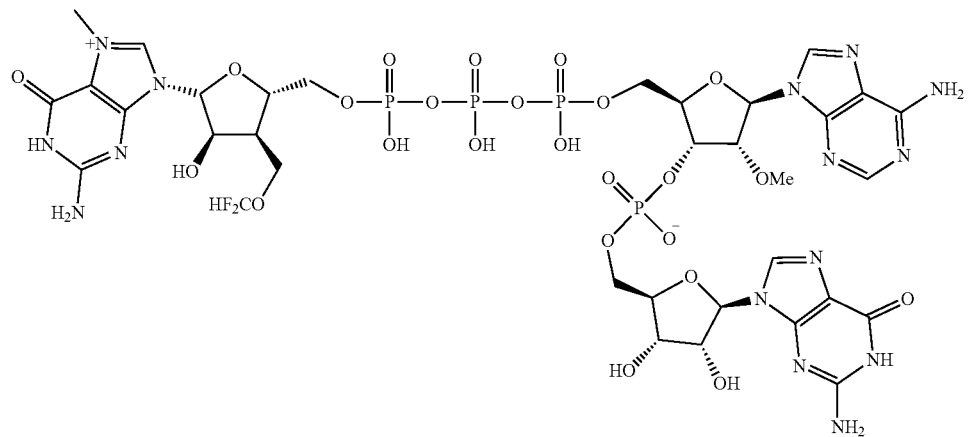

Compound 144
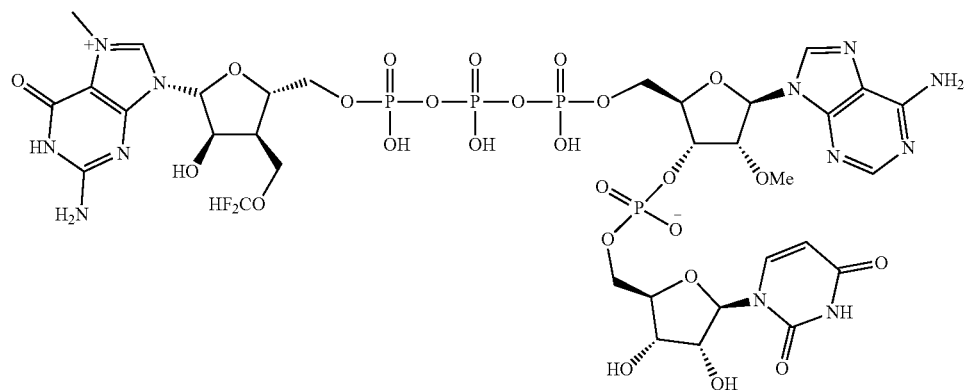
Compound 151
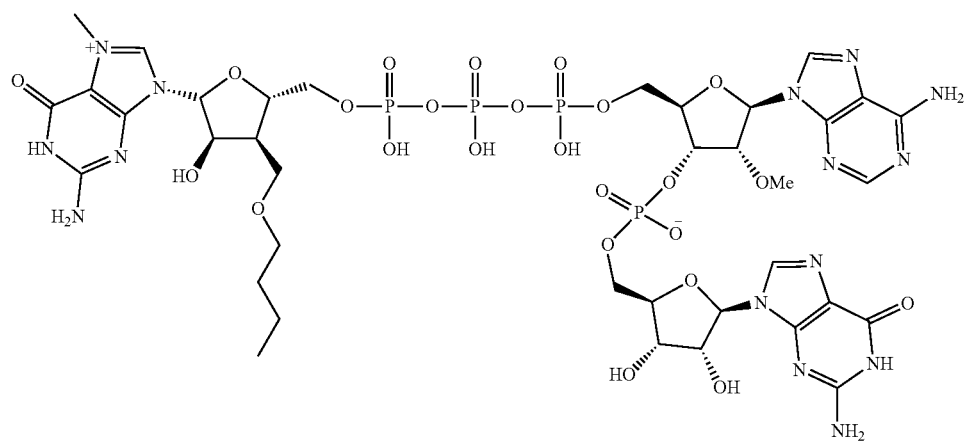
Compound 152
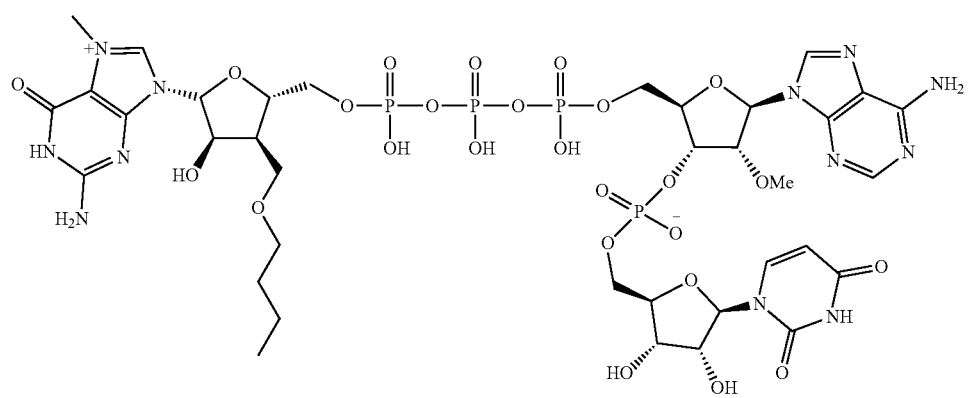
Compound 153
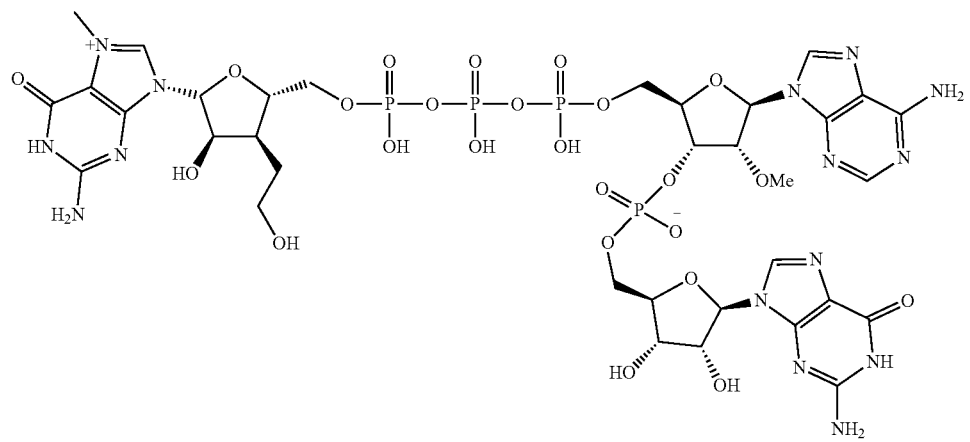

-continued
Compound 154
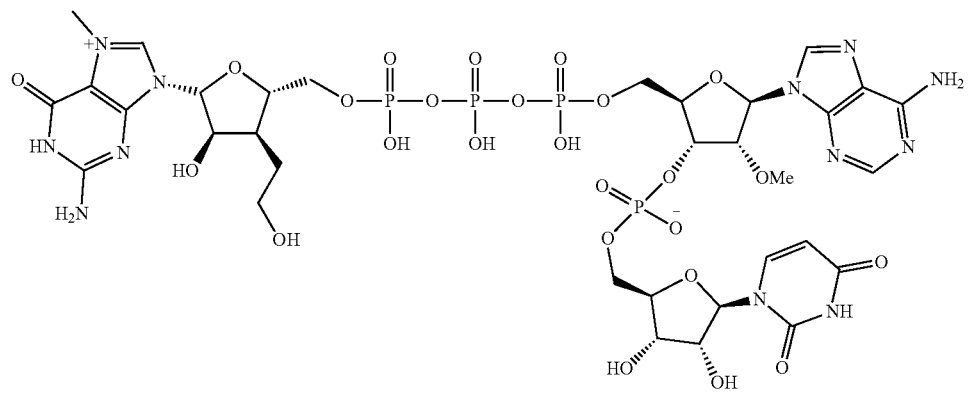
Compound 163
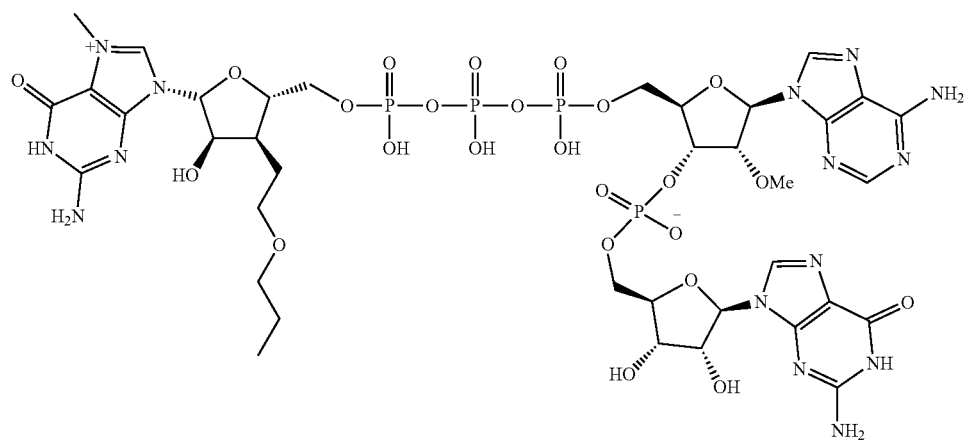
Compound 164
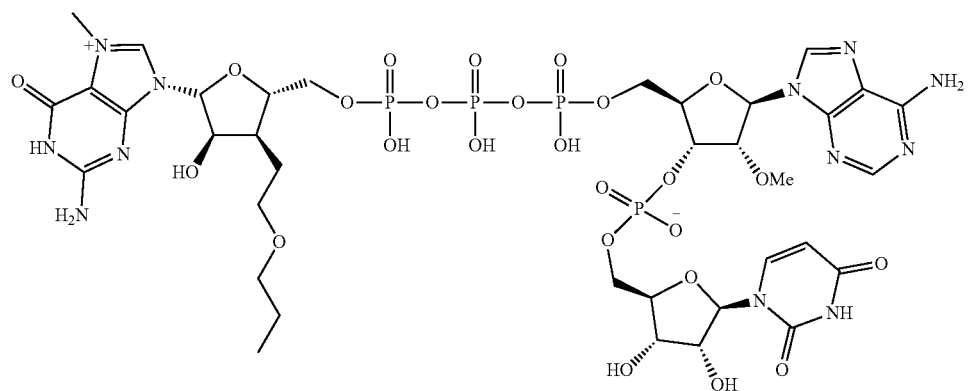

-continued
Compound 171
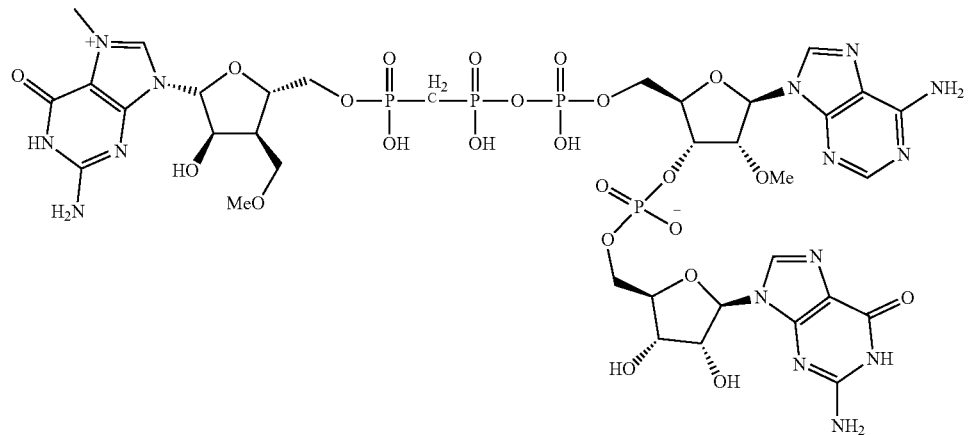
Compound 172
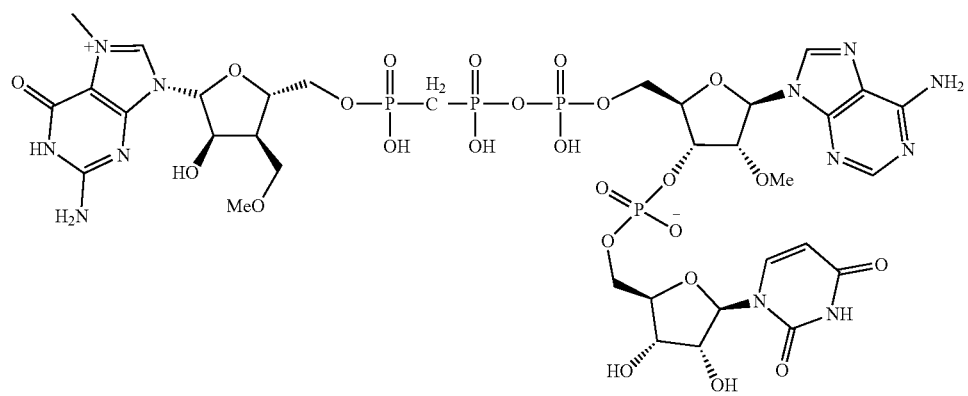
Compound 173
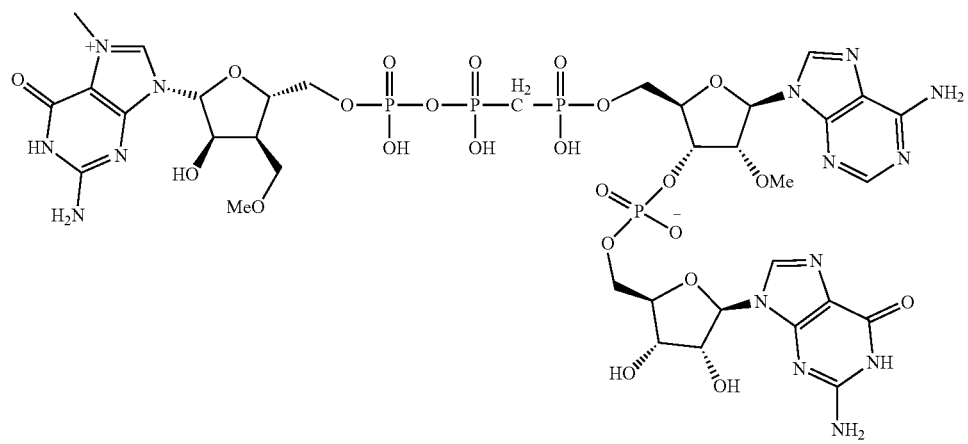

Compound 174
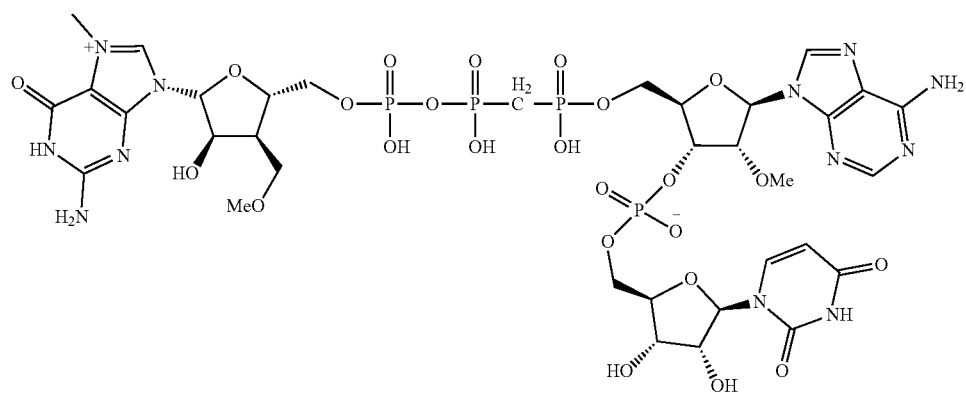
Compound 181
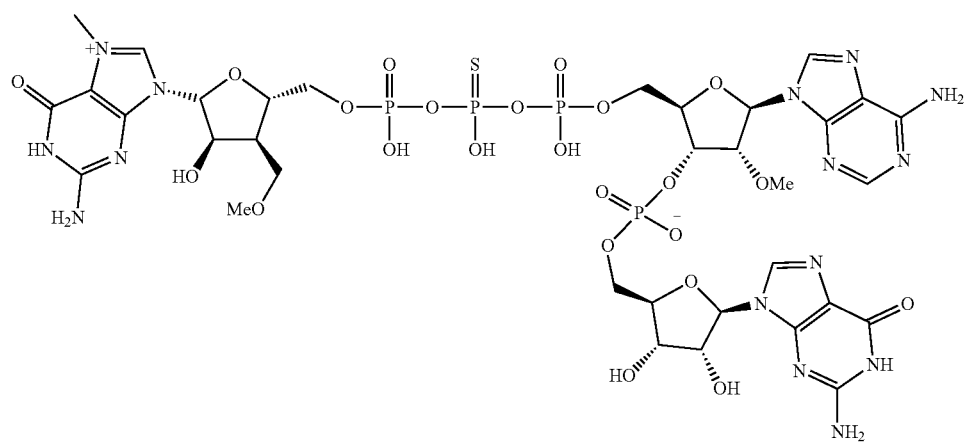
Compound 182
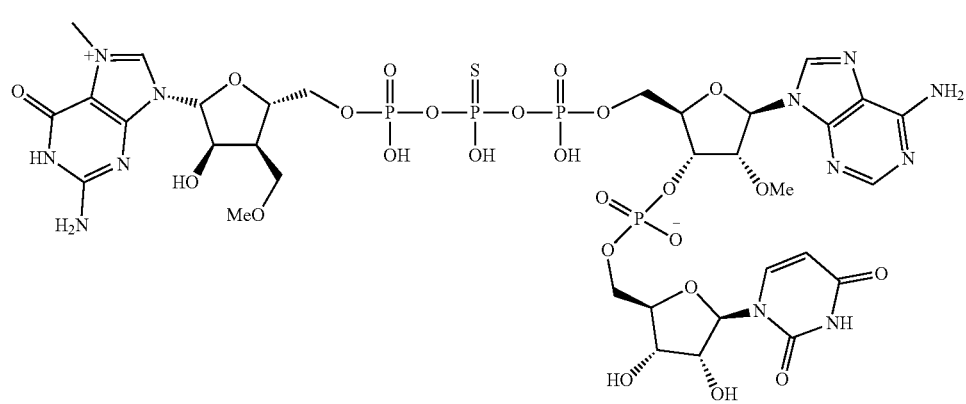

Compound 189
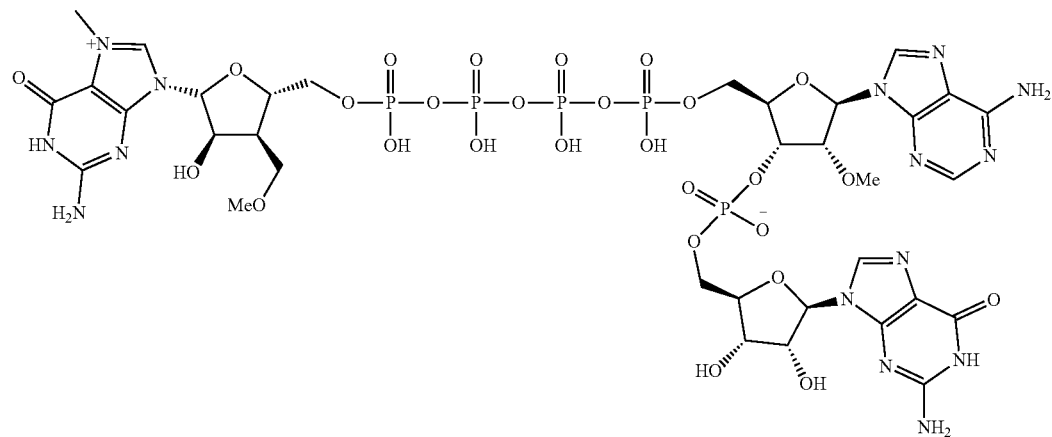
Compound 190
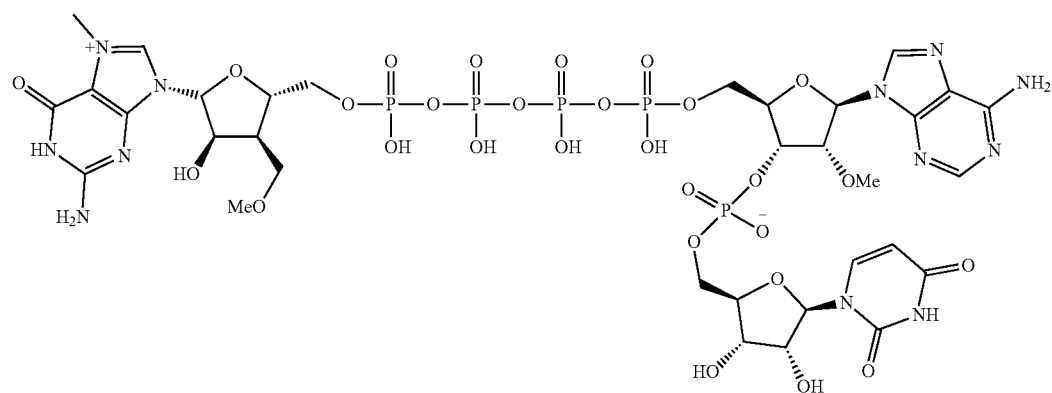
Compound 191
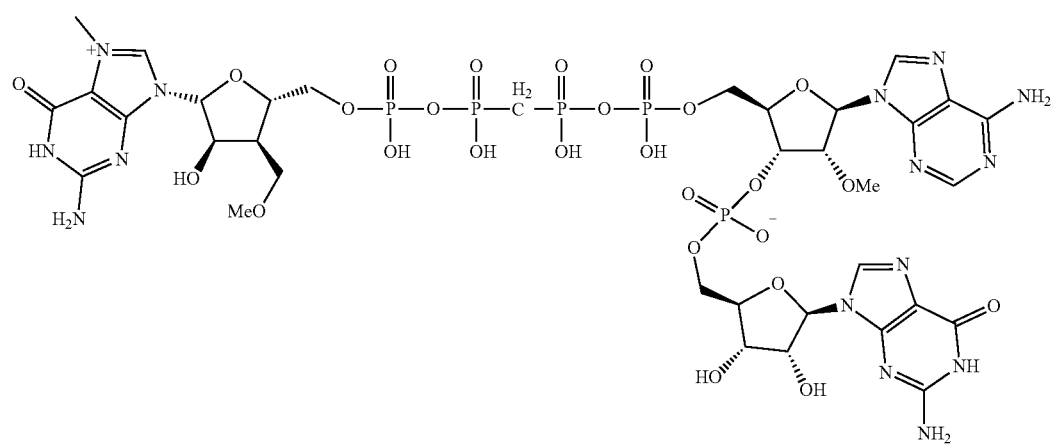

-continued
Compound 192
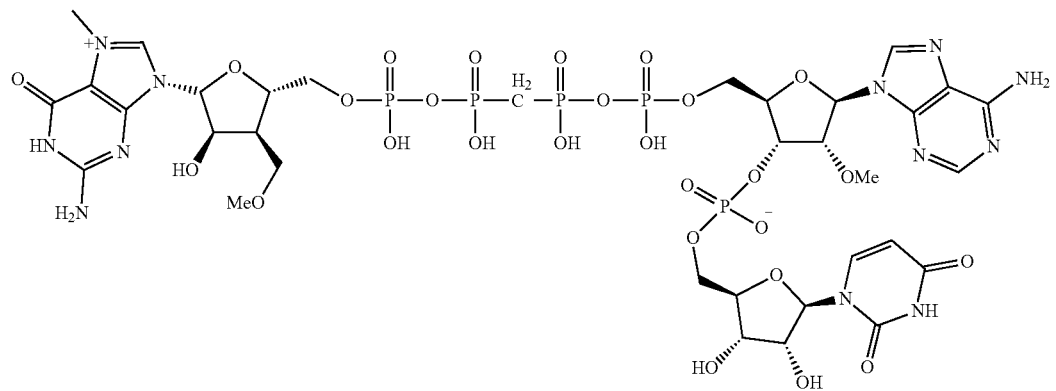
Compound 195
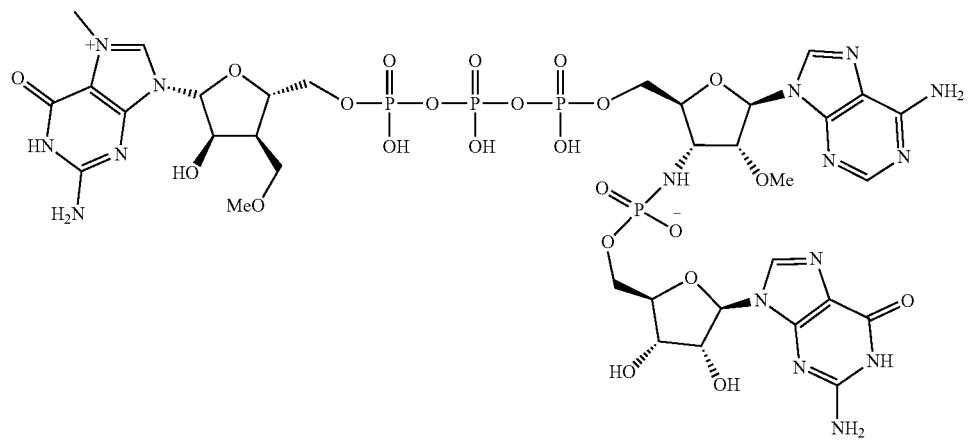
Compound 196
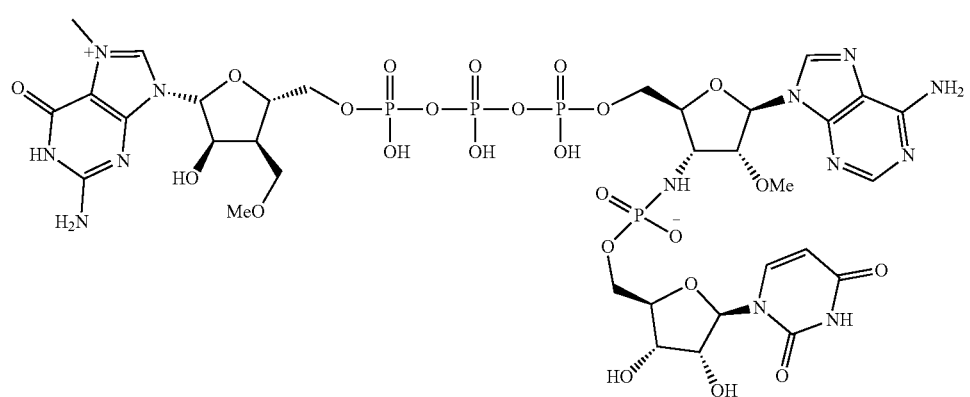

-continued
Compound 197
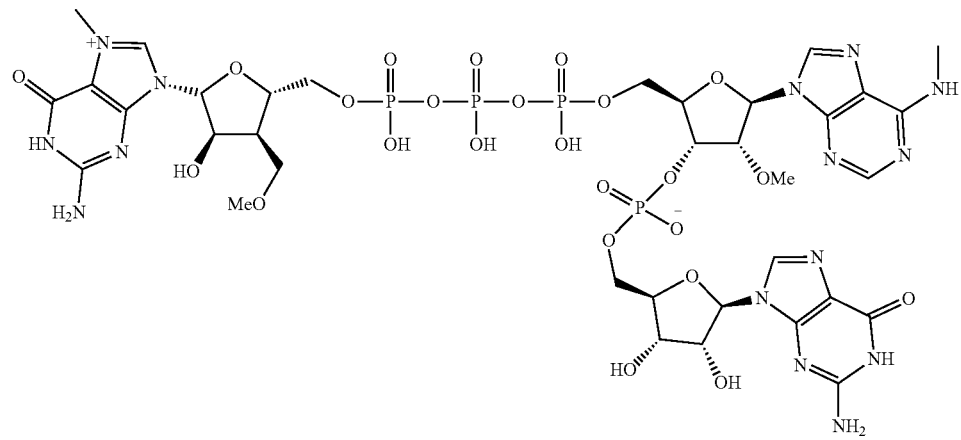
Compound 198
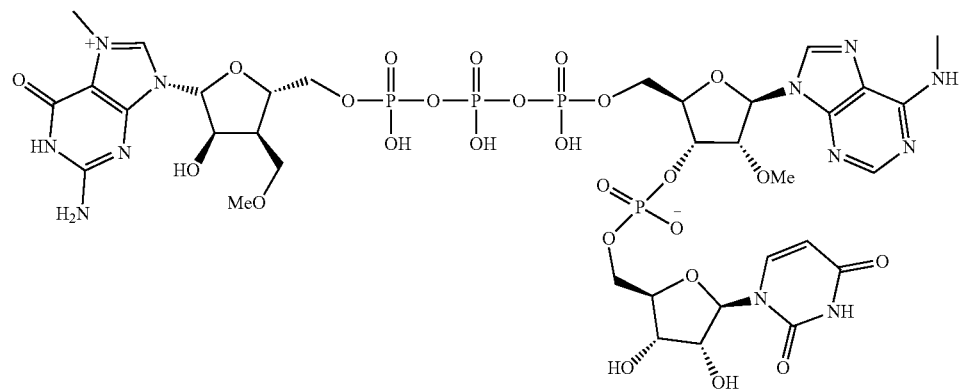
Compund 199
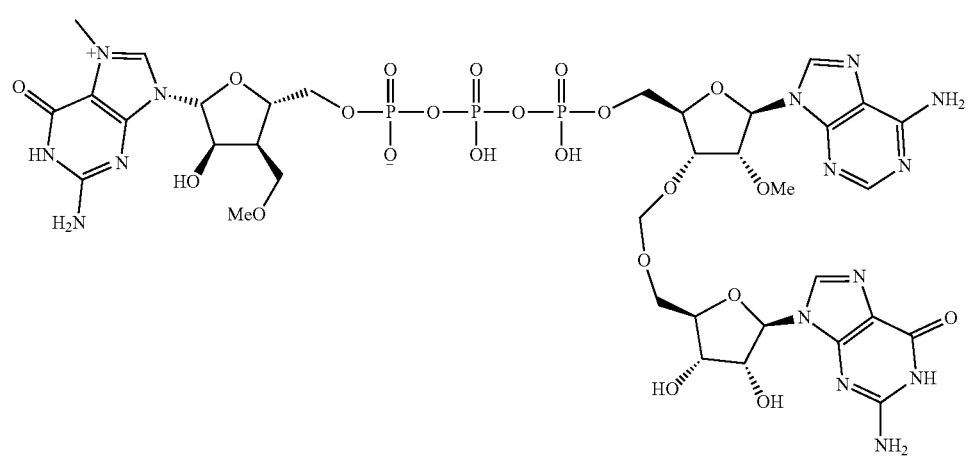

-continued
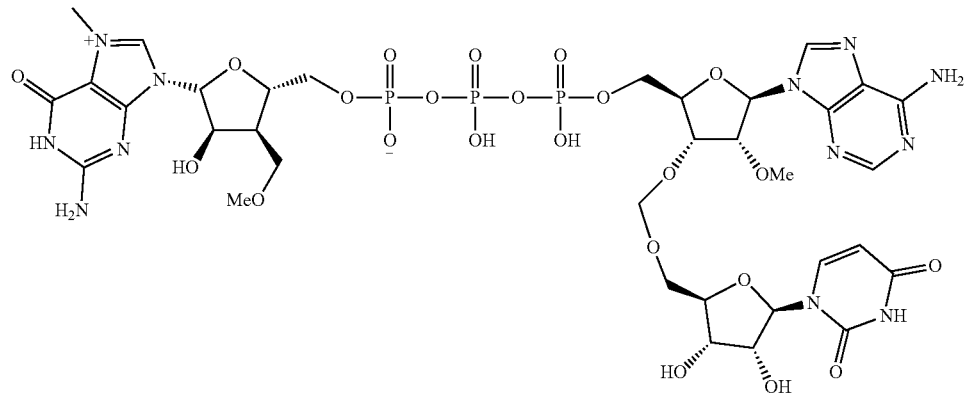
Compound 200
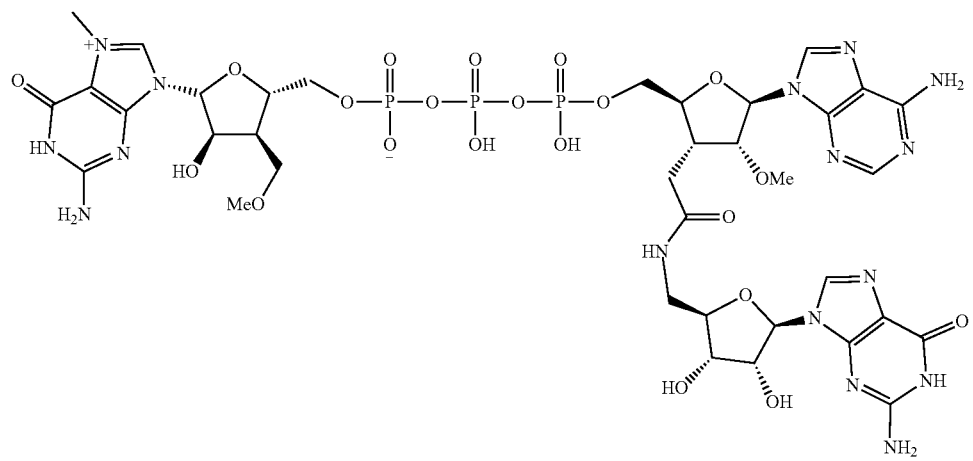
Compound 201
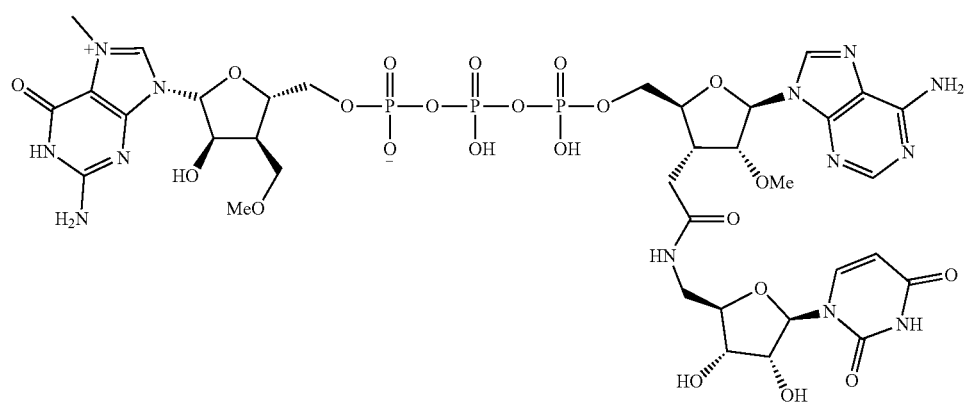
Compound 202

-continued
Compound 203
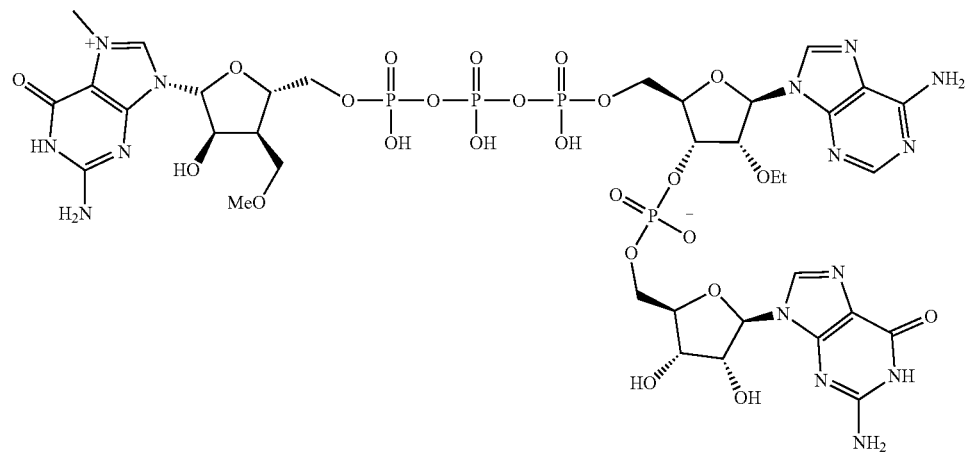
Compound 204
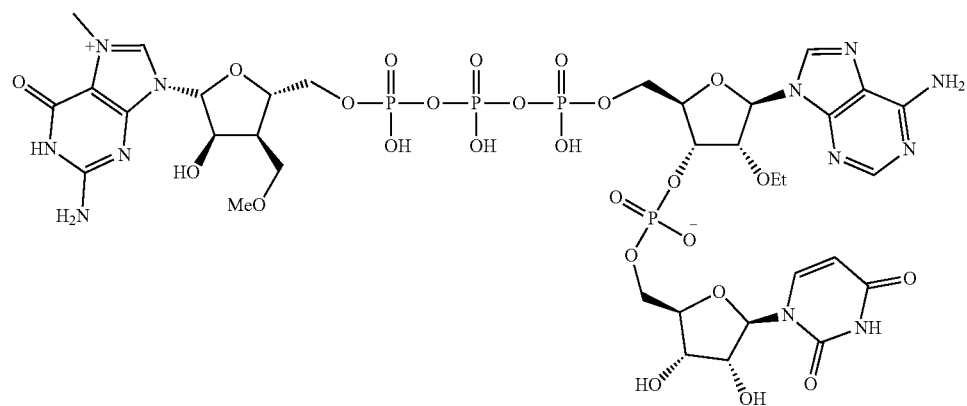
Compound 215
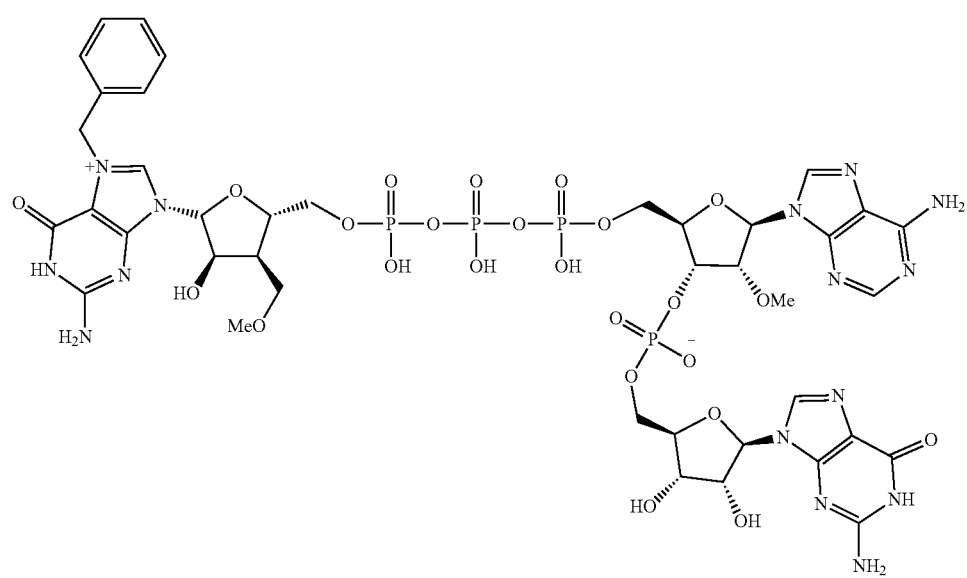

Compound 216
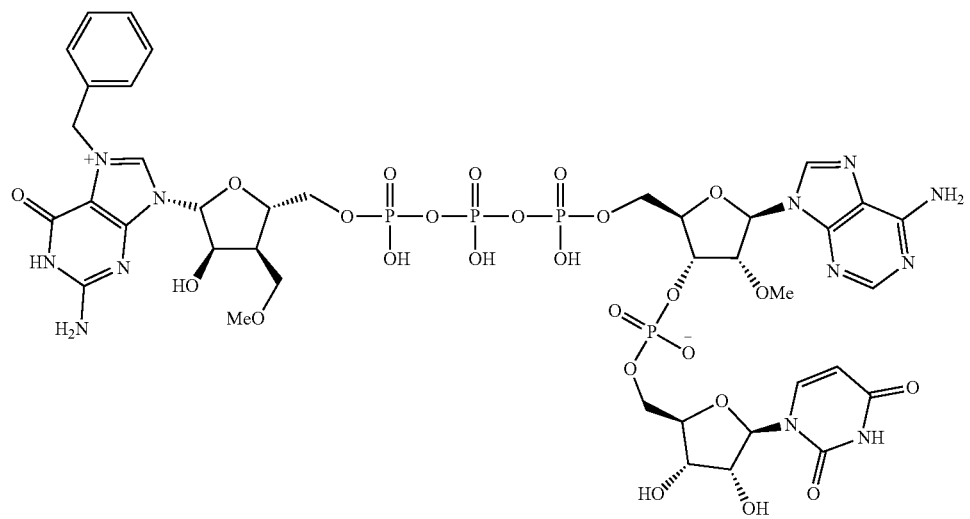
Compound 219
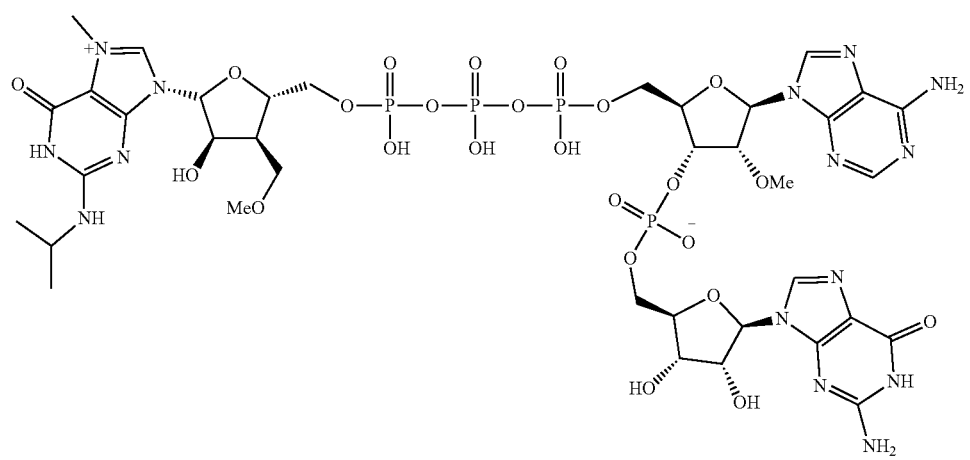
Compound 220
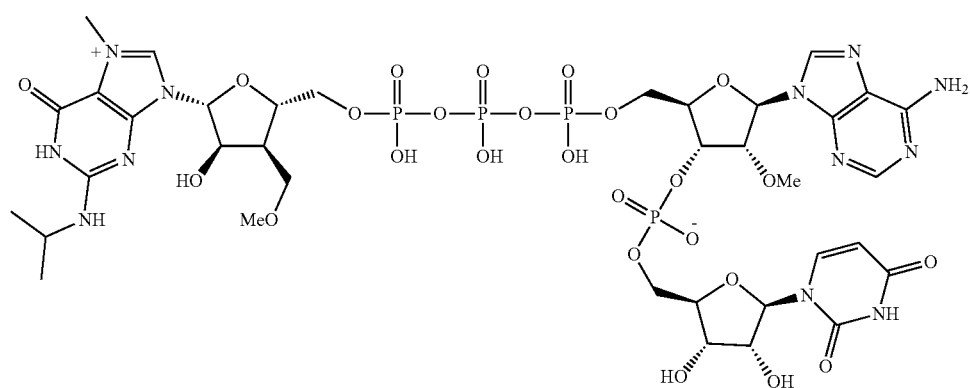

Compound 299
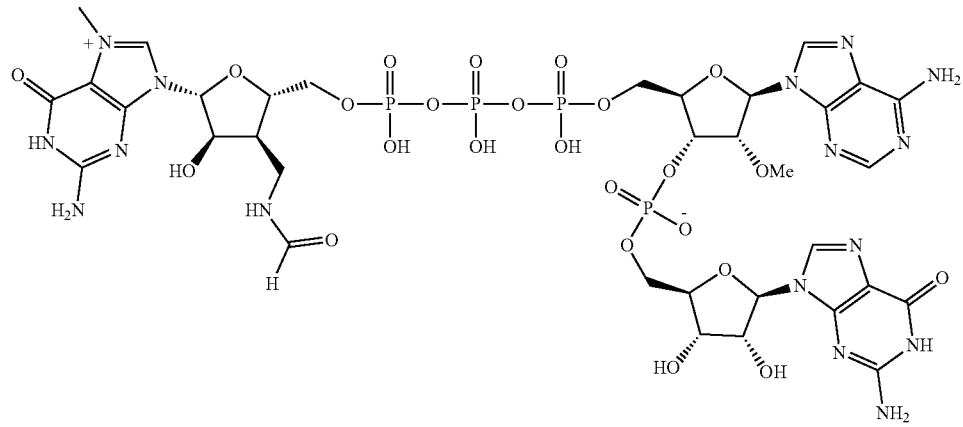
Compound 300
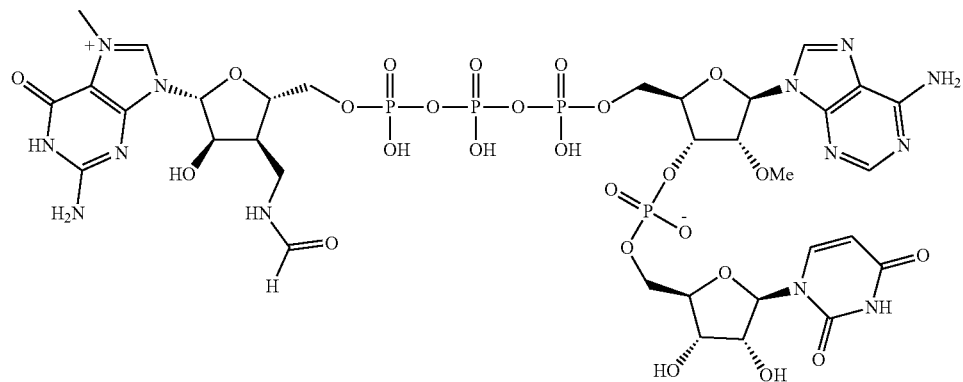
Compound 301
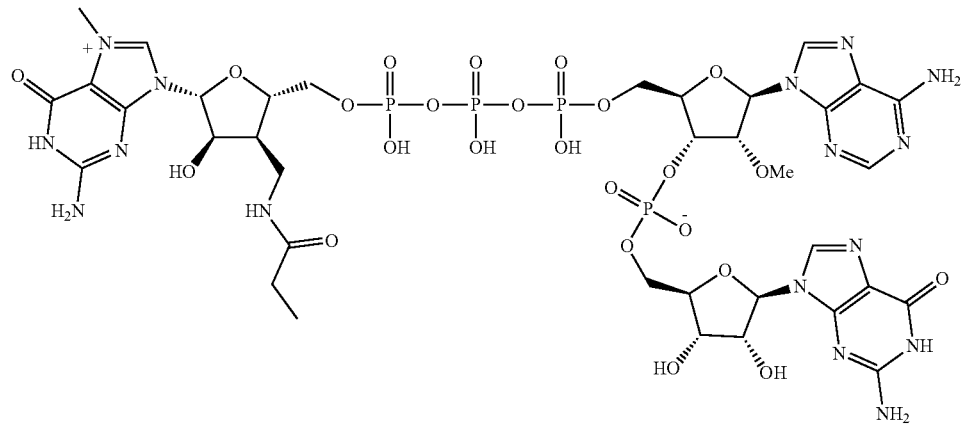
Compound 302
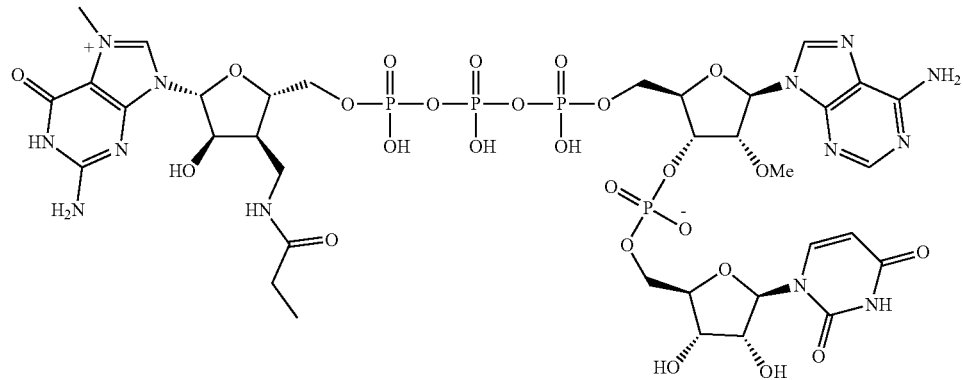

Compound 303
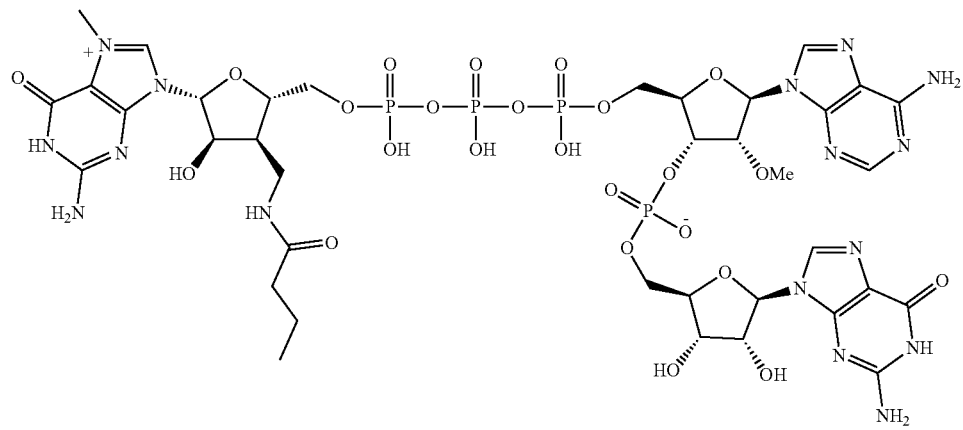
Compound 304
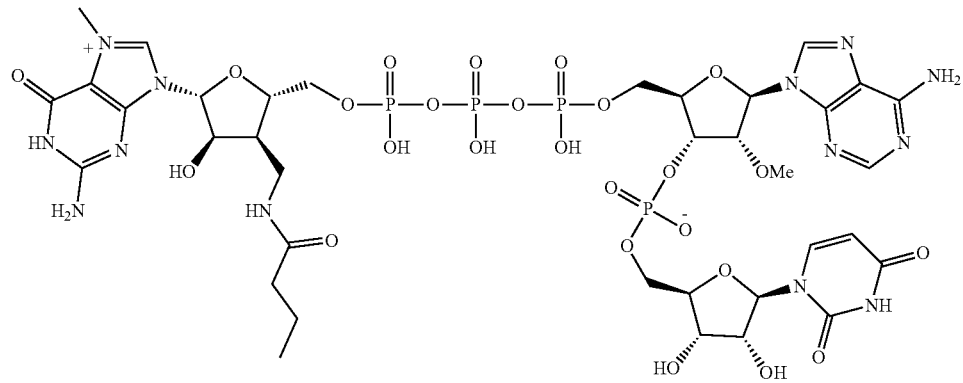
Compound 305
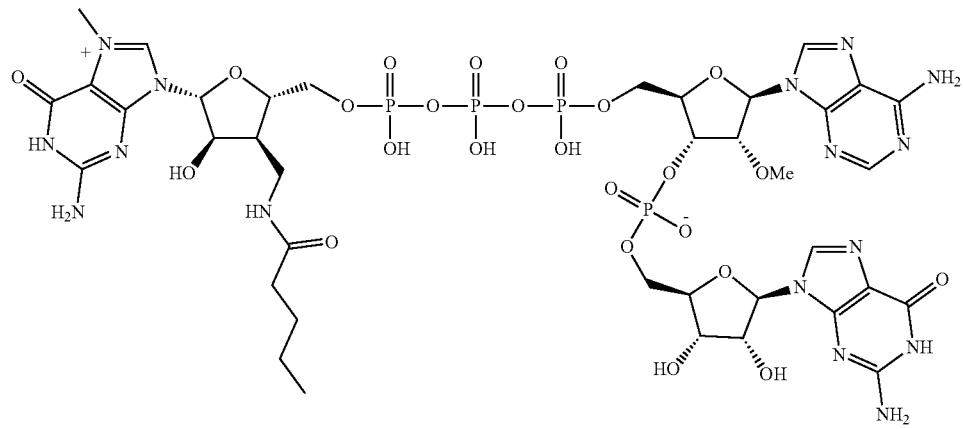
Compound 306
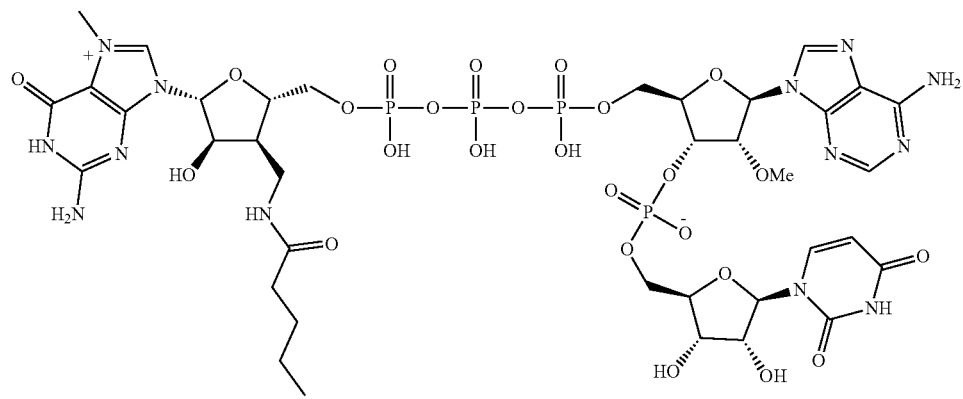

Compound 307
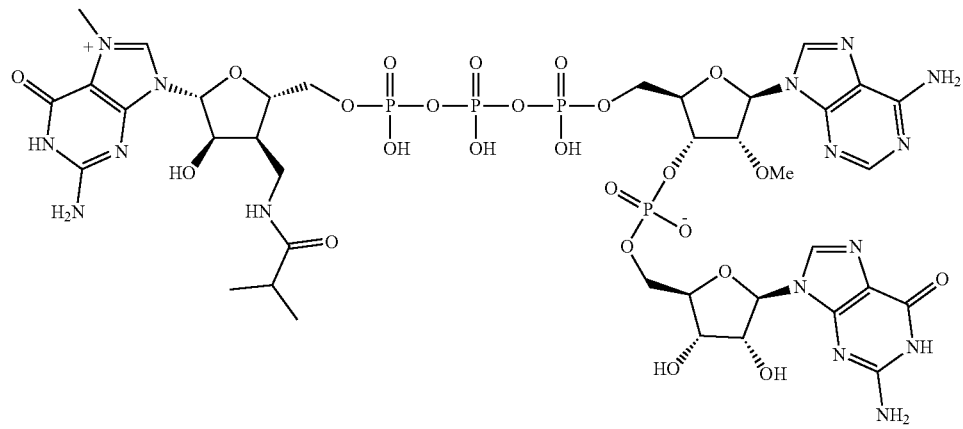
Compound 308
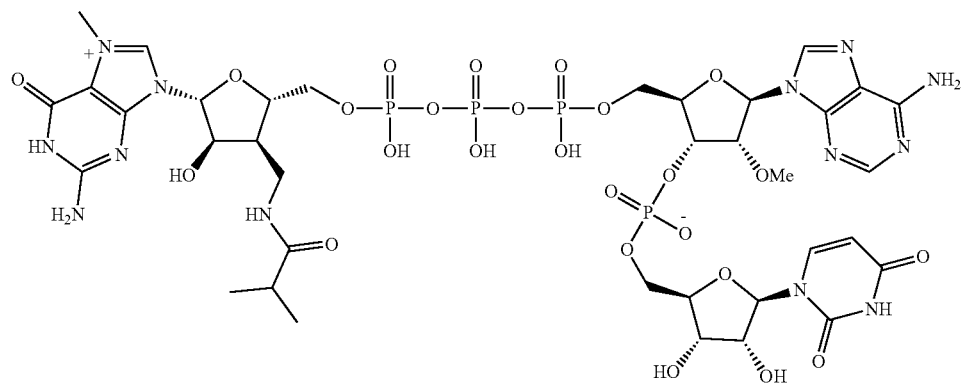
Compound 309
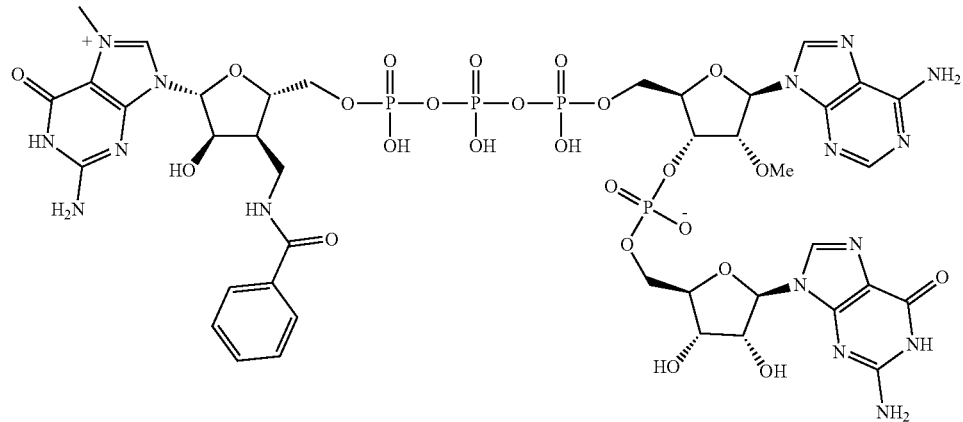
Compound 310
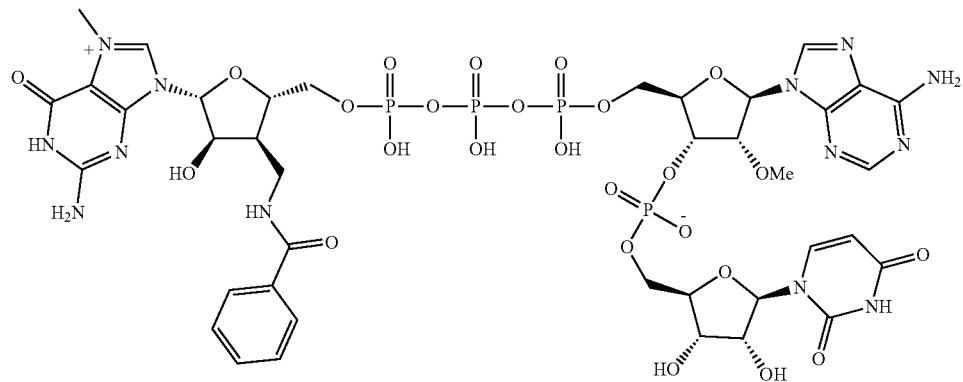

Compound 311
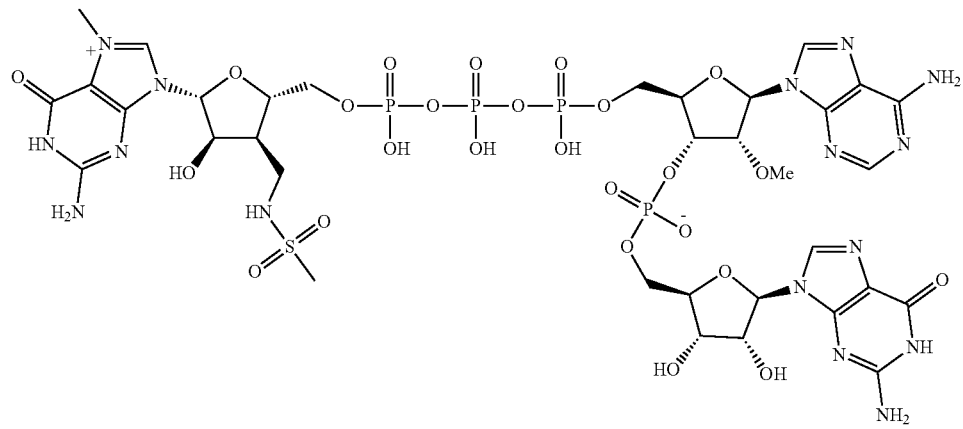
Compound 312
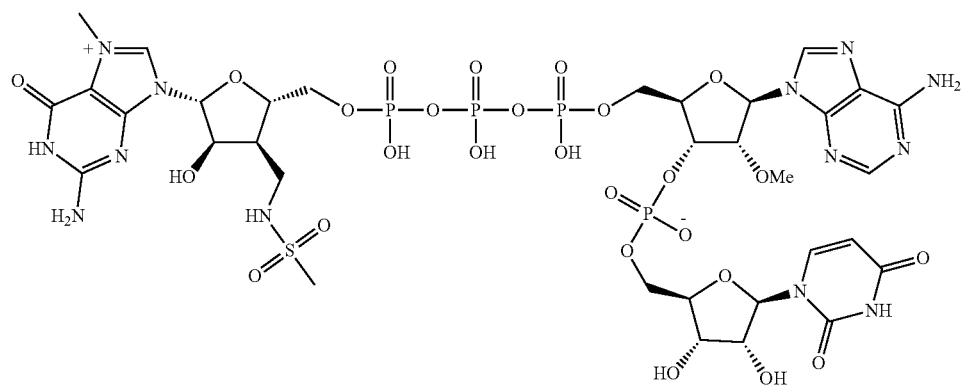
Compound 313
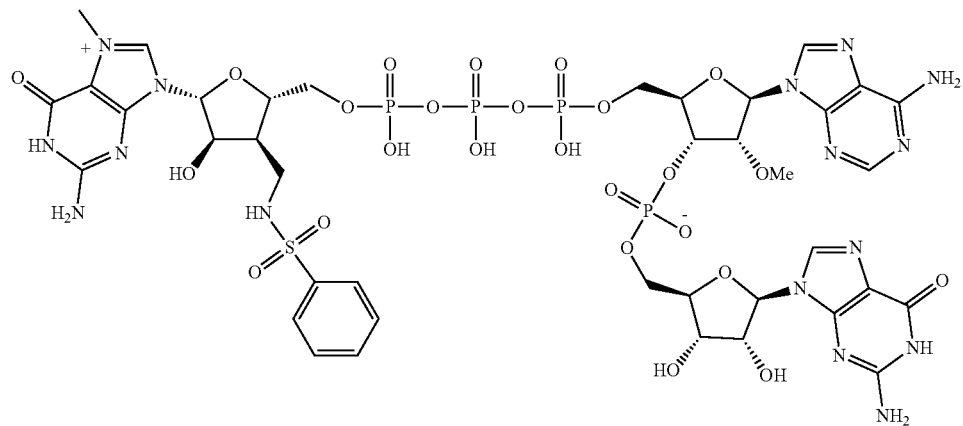
Compound 314
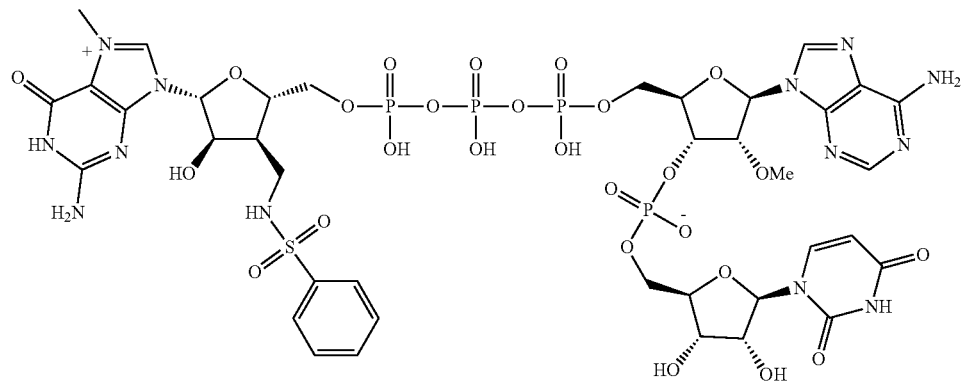

-continued
Compound 315
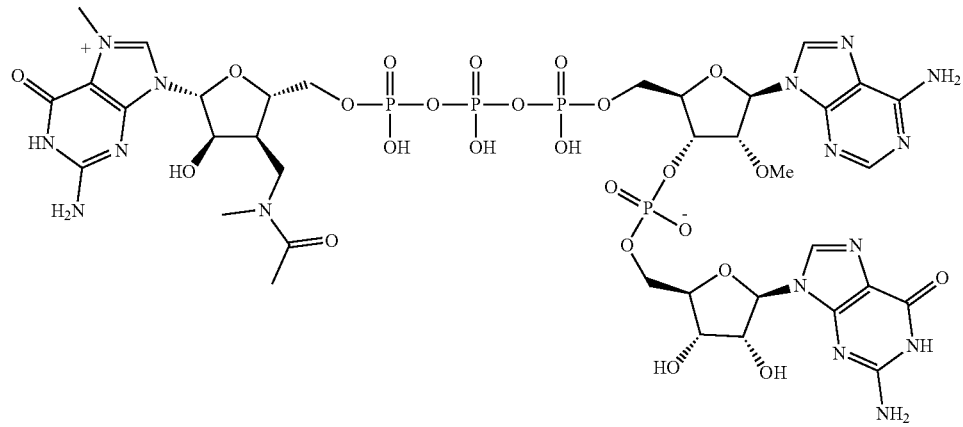
Compound 316
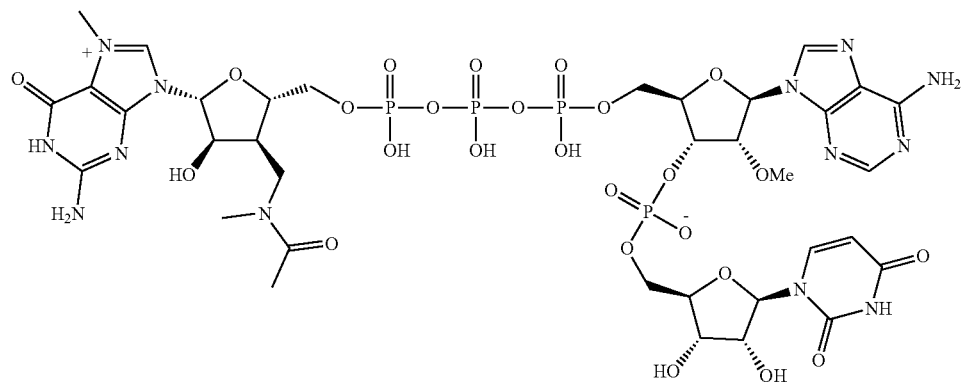
Compound 317
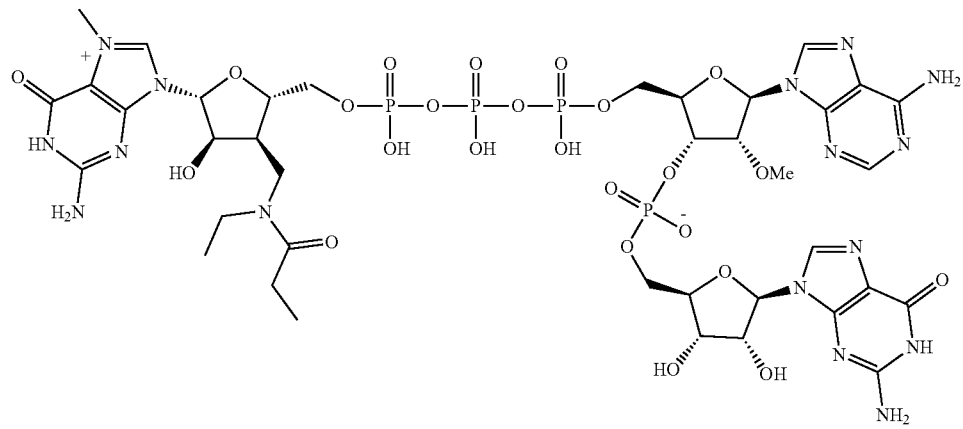
Compound 318
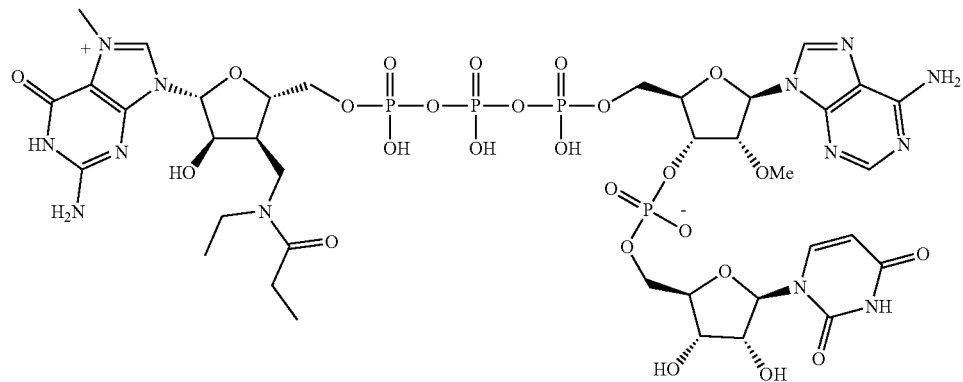

-continued
Compound 319
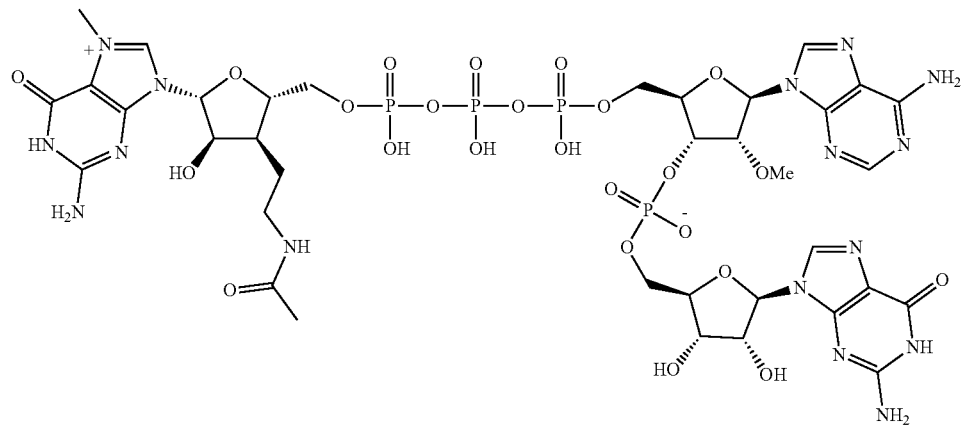
Compound 320
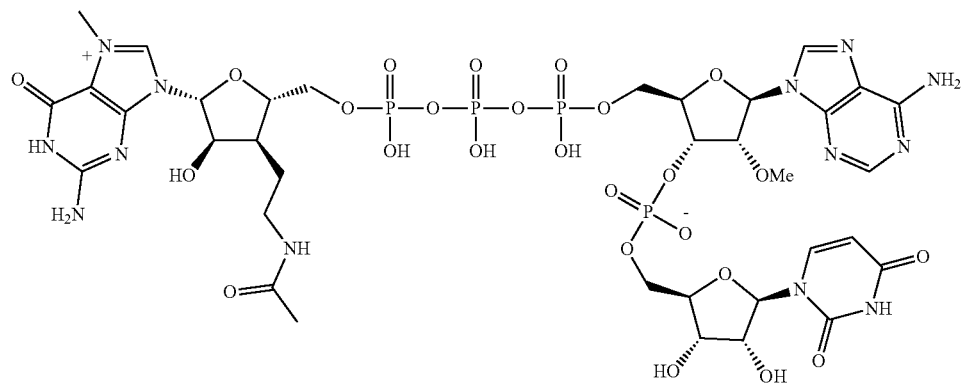
Compound 321
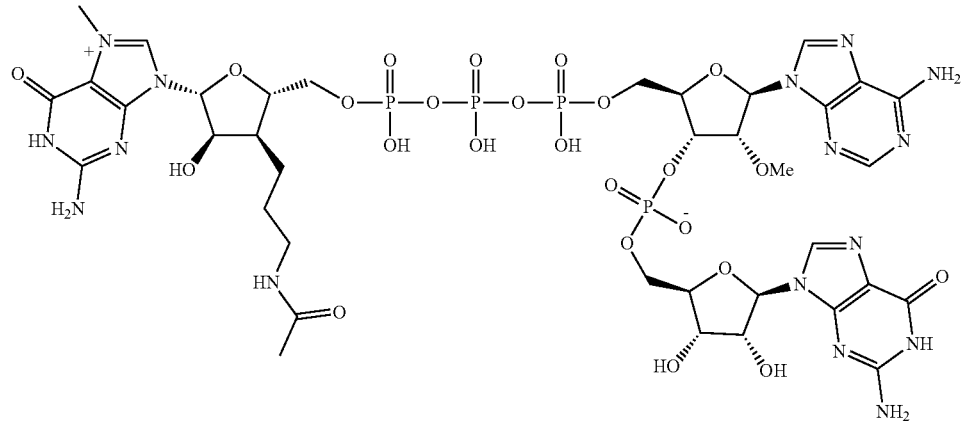
Compound 322
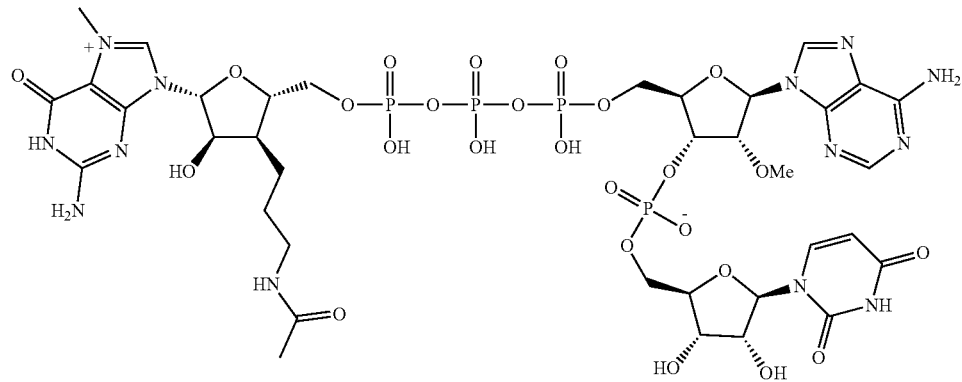

Compound 323
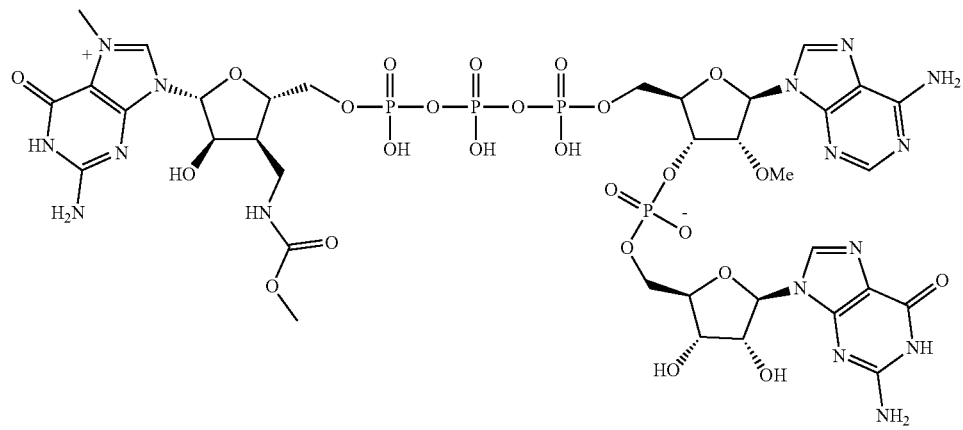
Compound 324
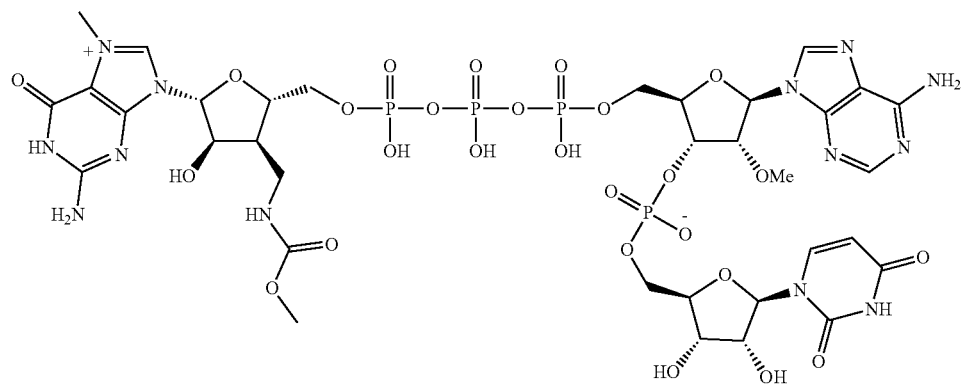
Compound 325
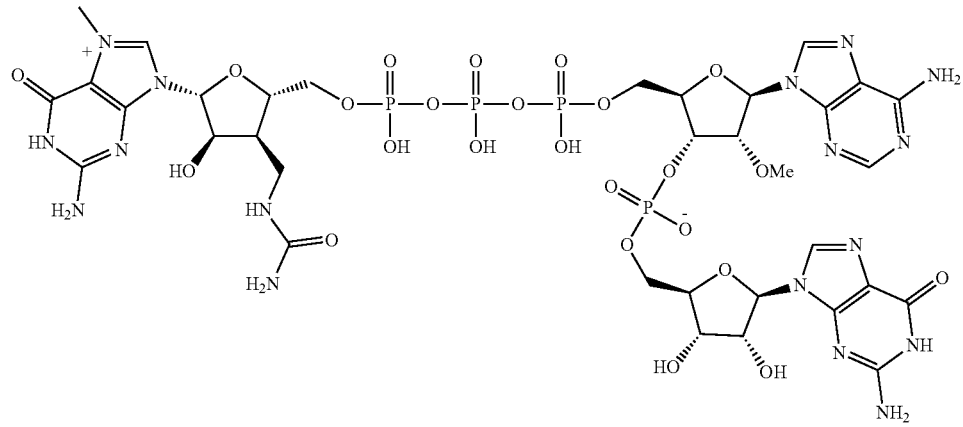
Compound 326
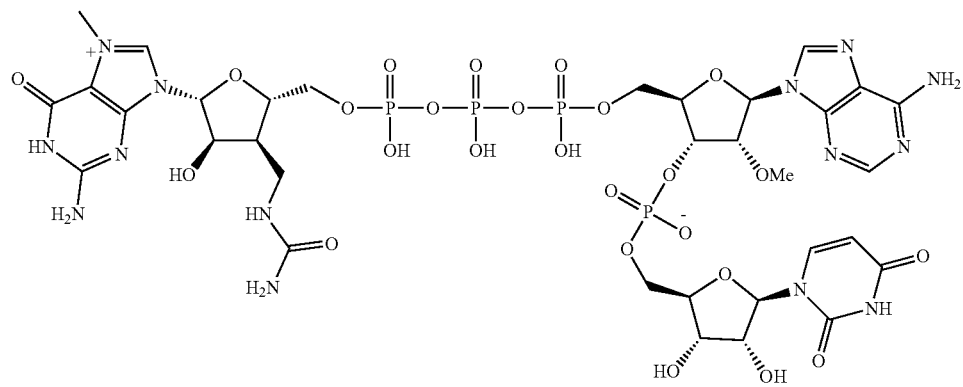

Compound 327
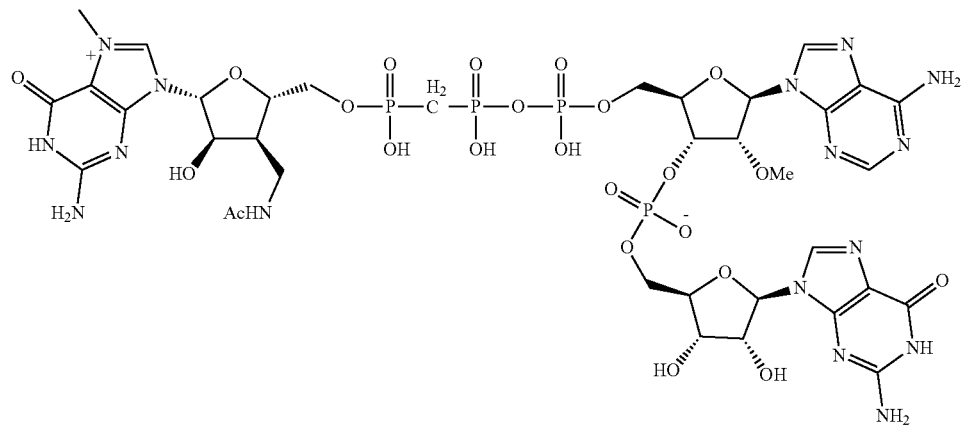
Compound 328
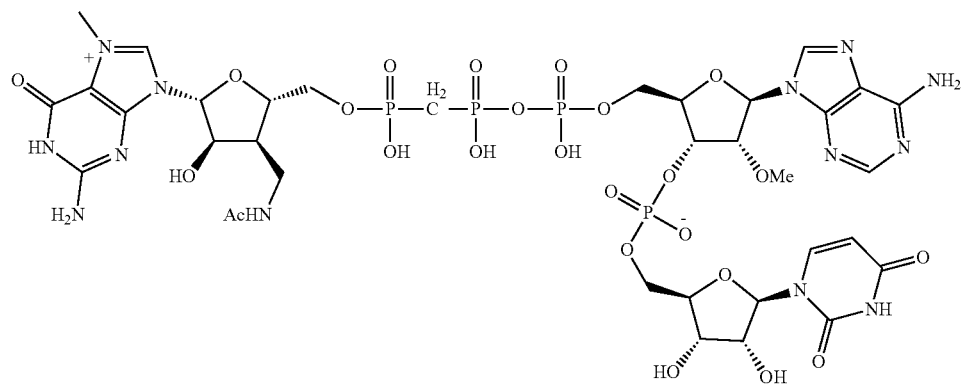
Compound 329
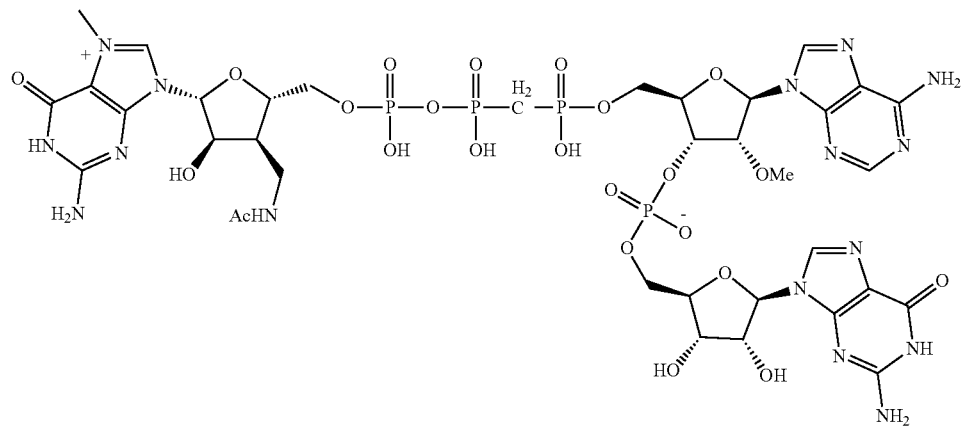
Compound 330
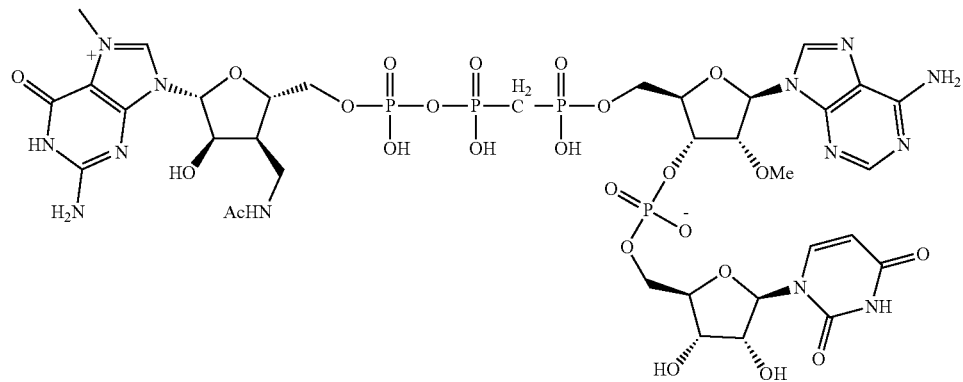

Compound 331
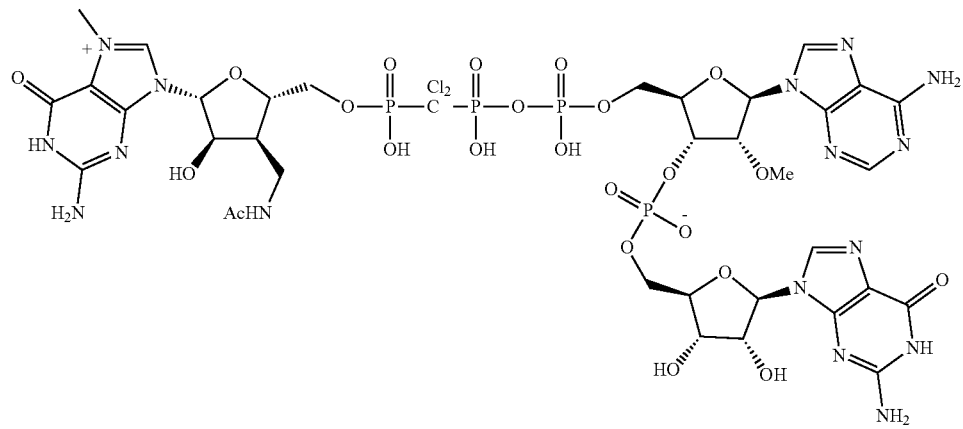
Compound 332
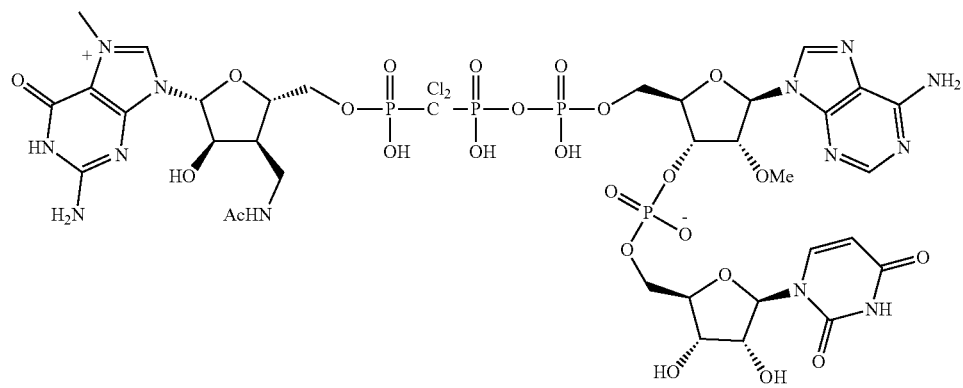
Compound 333
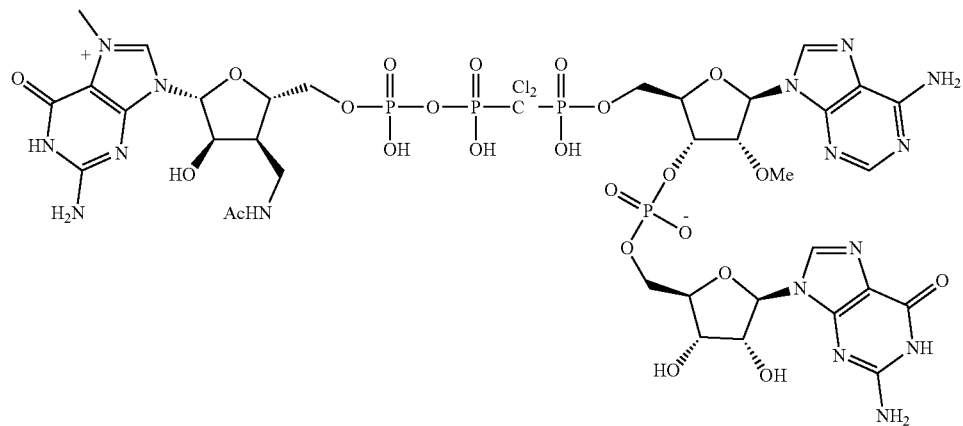
Compound 334
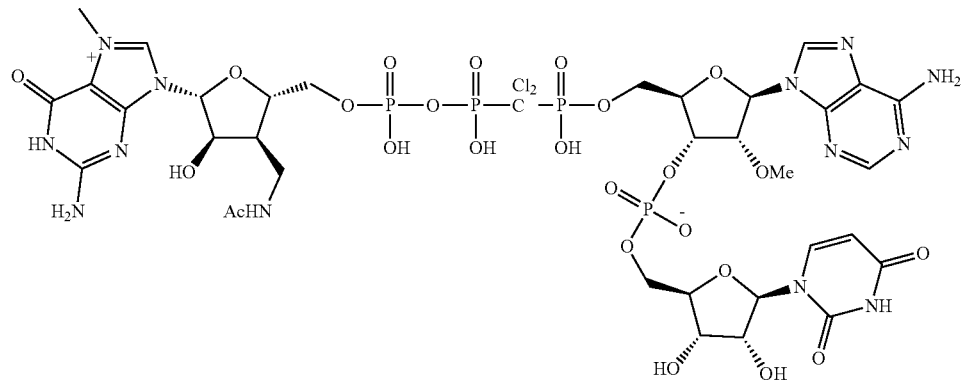

Compound 335
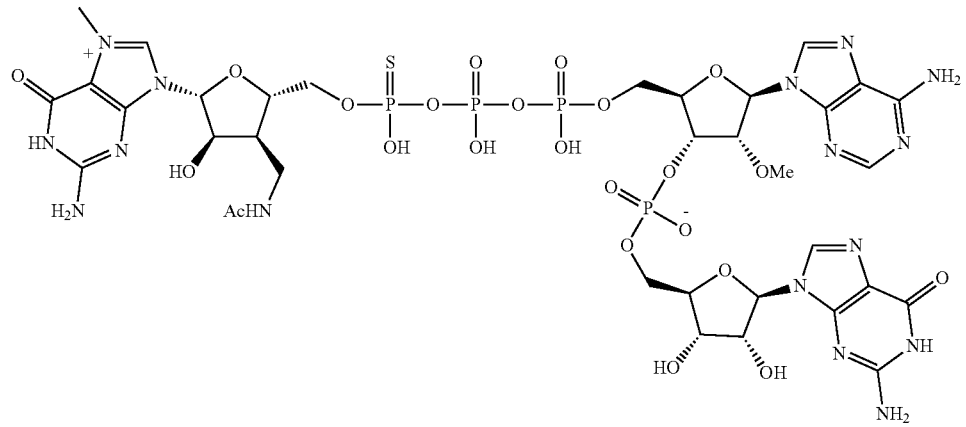
Compound 336
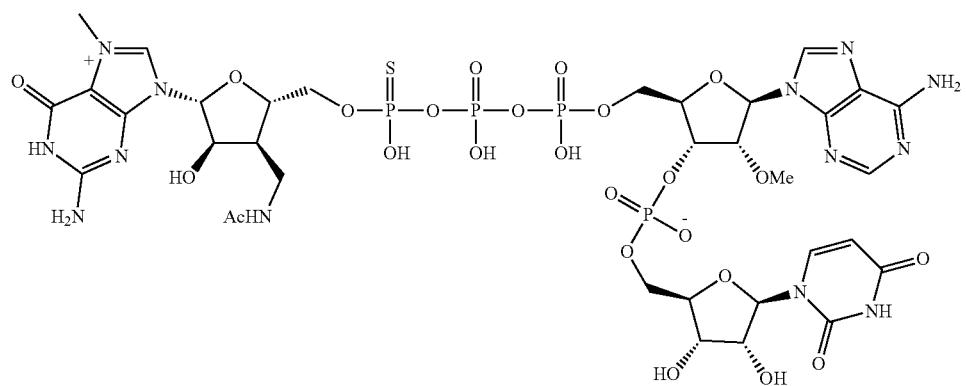
Compound 337
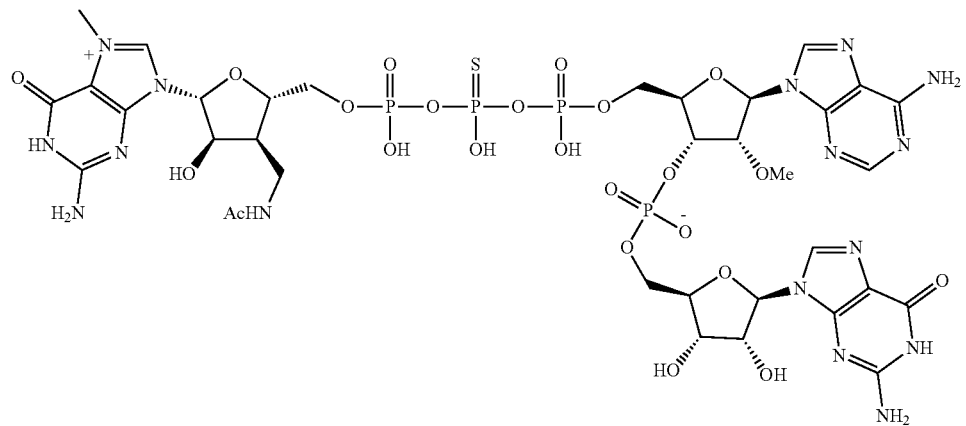
Compound 338
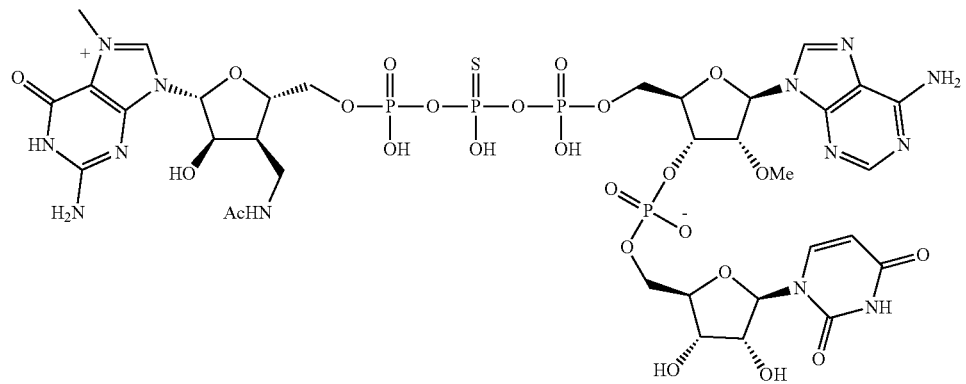

-continued
Compound 339
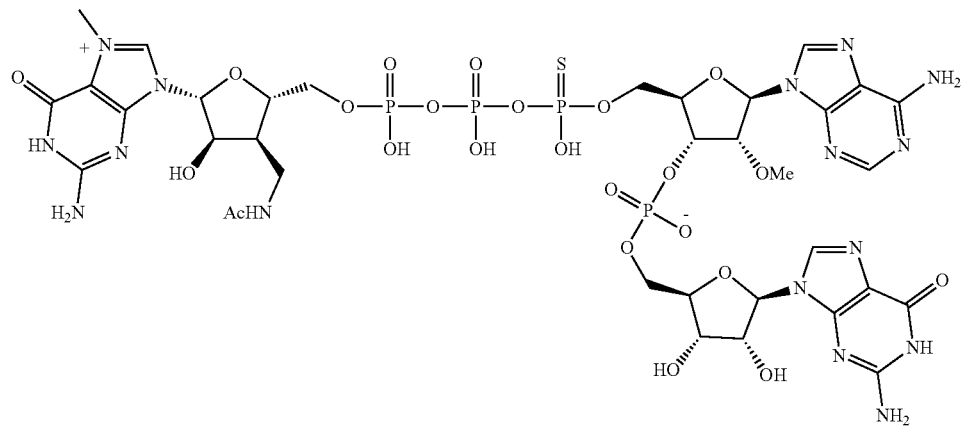
Compound 340
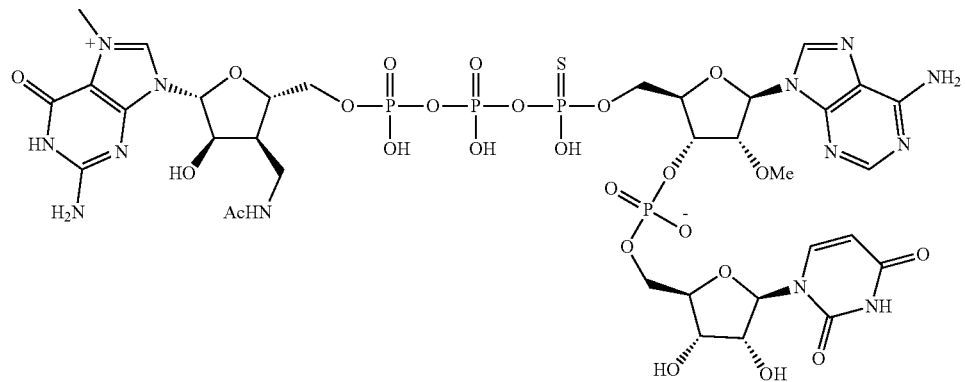
Compound 341
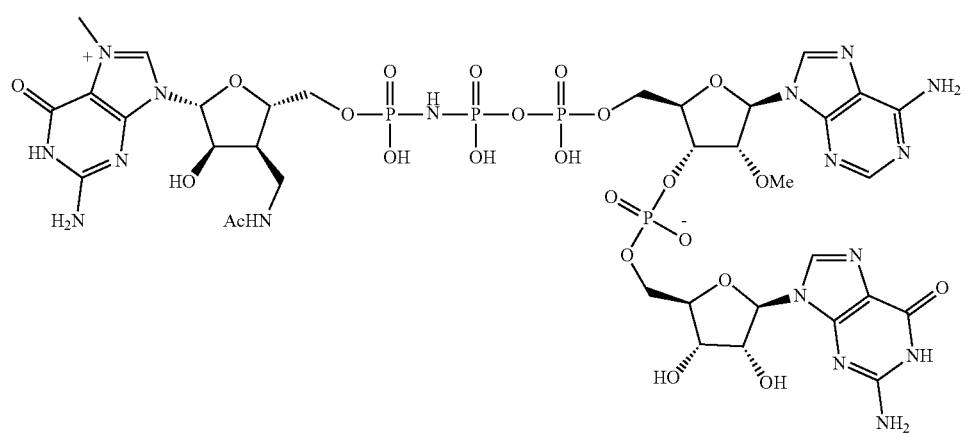

-continued
Compound 342
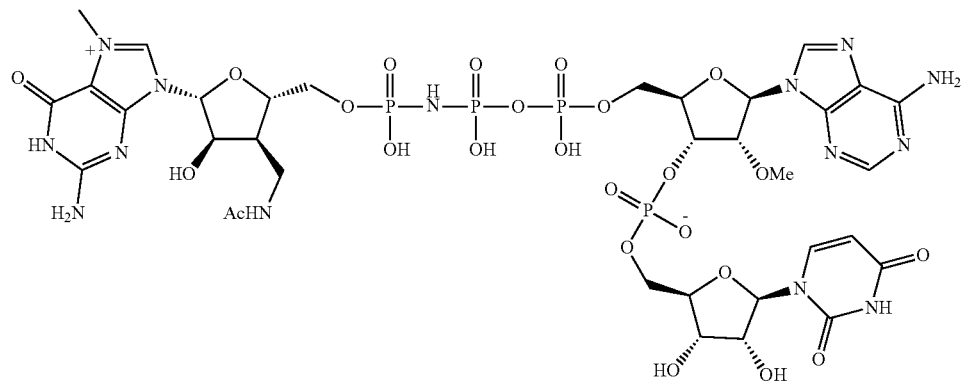
Compound 343
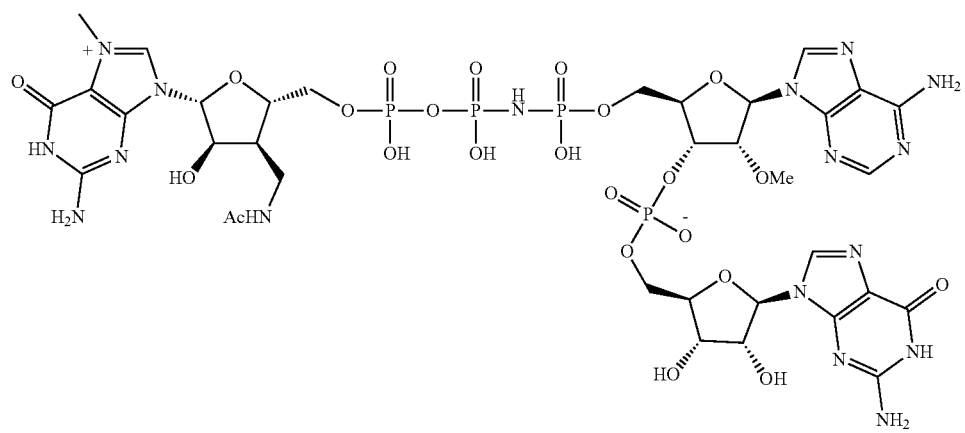
Compound 344
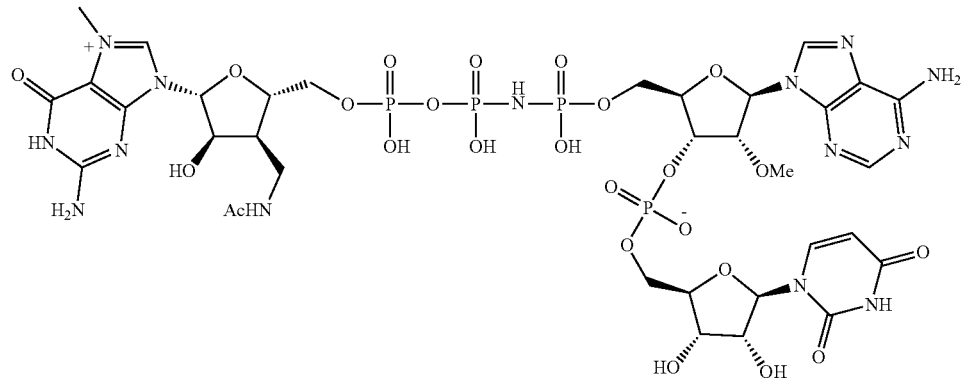
Compound 345
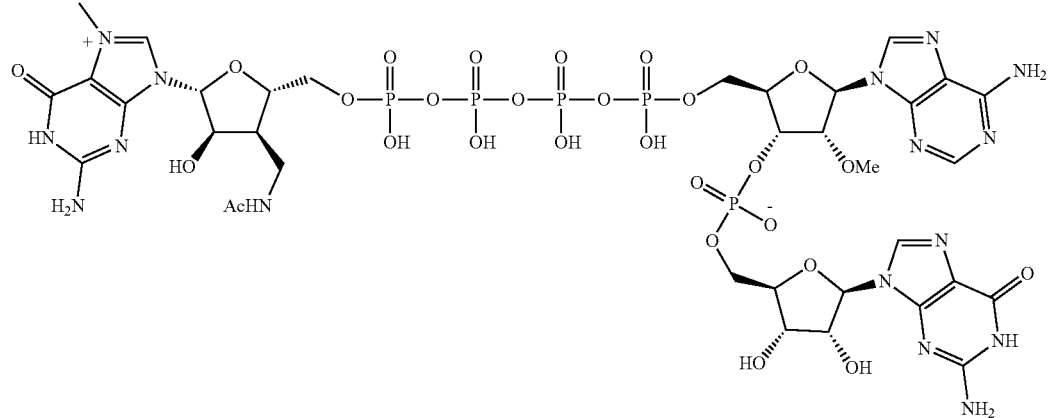

Compound 346
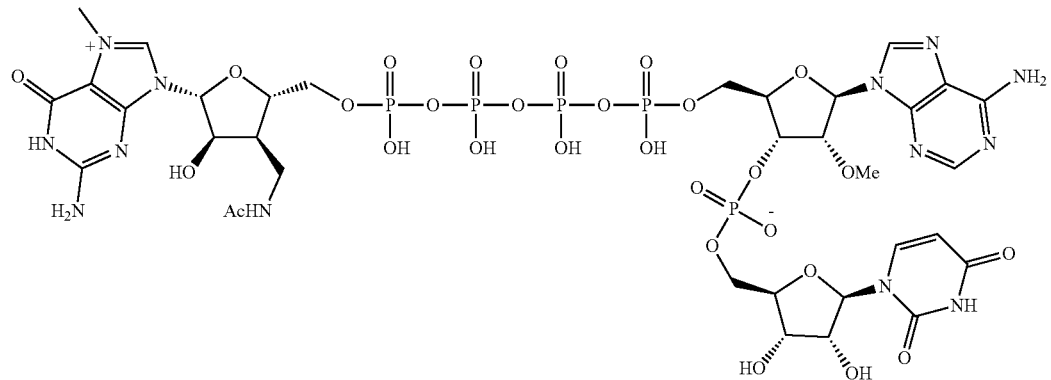
Compound 347
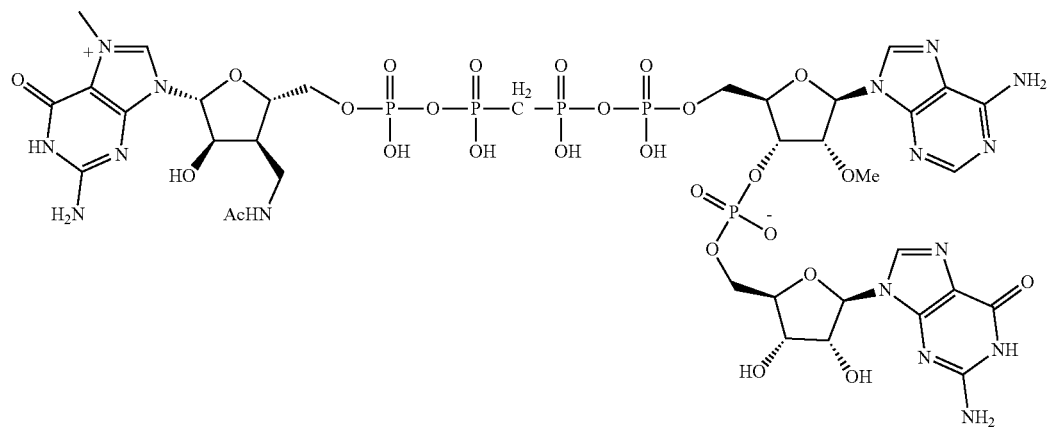
Compound 348
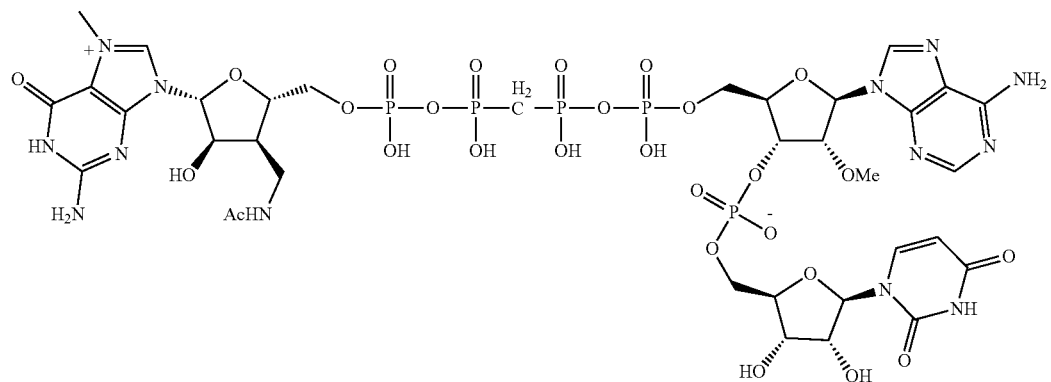
Compound 349
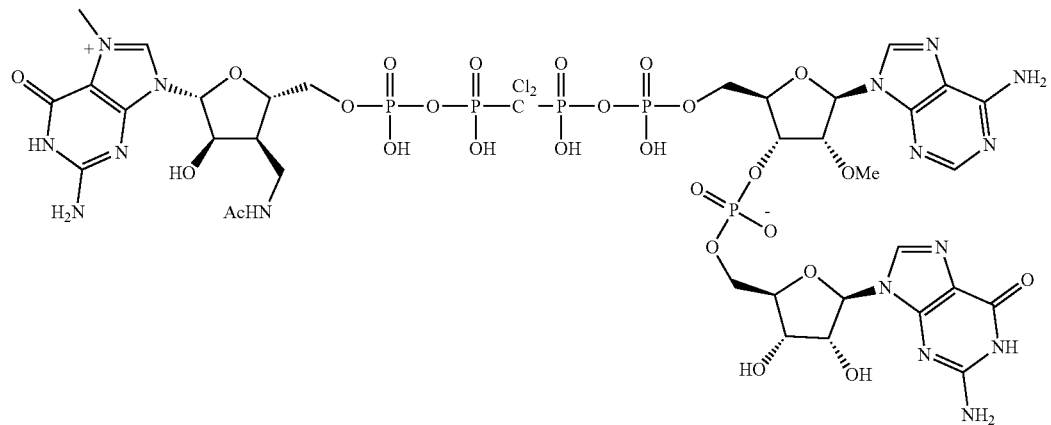

-continued
Compound 350
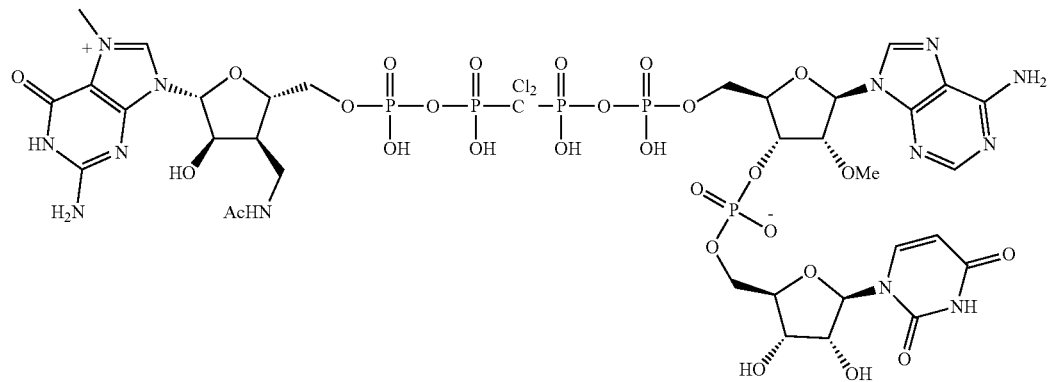
Compound 351
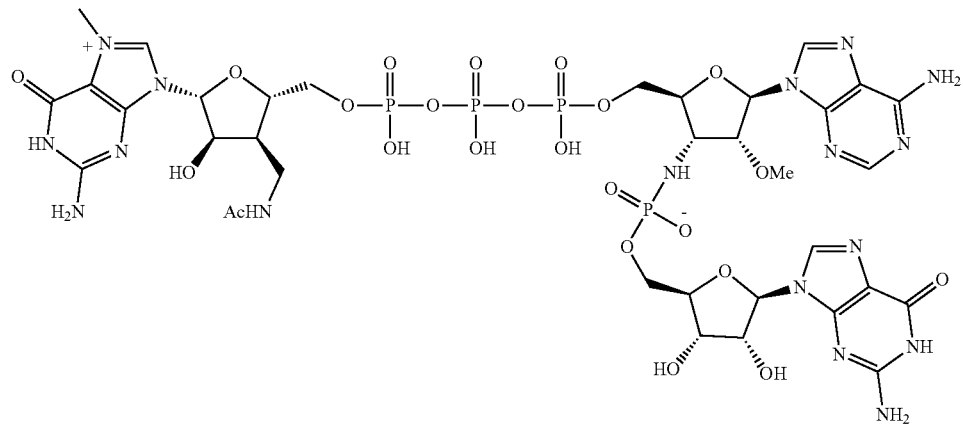
Compound 352
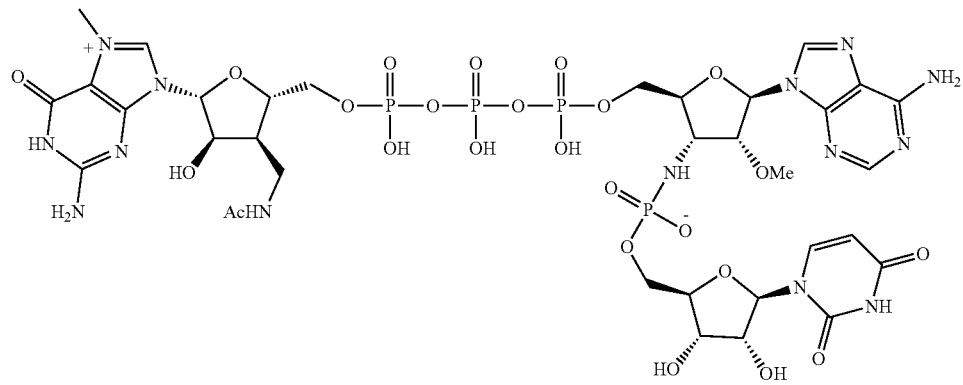
Compound 353
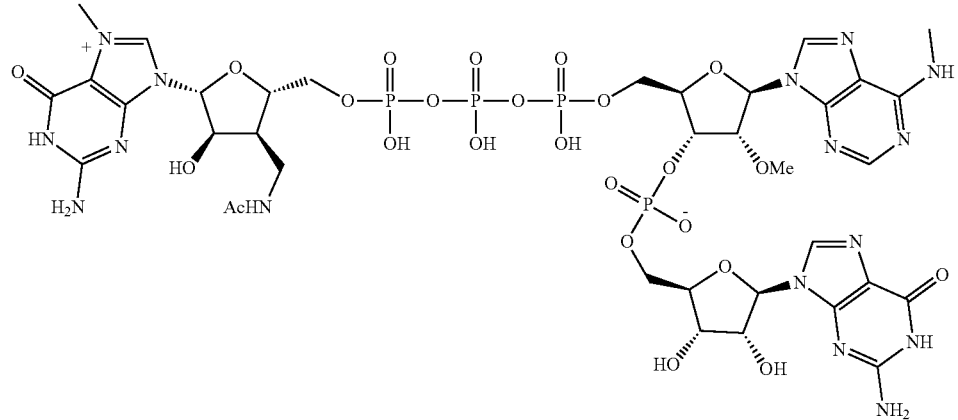

-continued
Compound 354
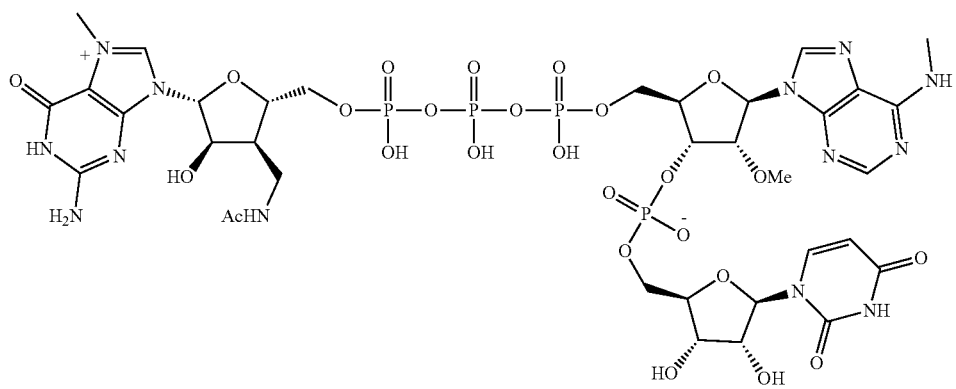
Compound 355
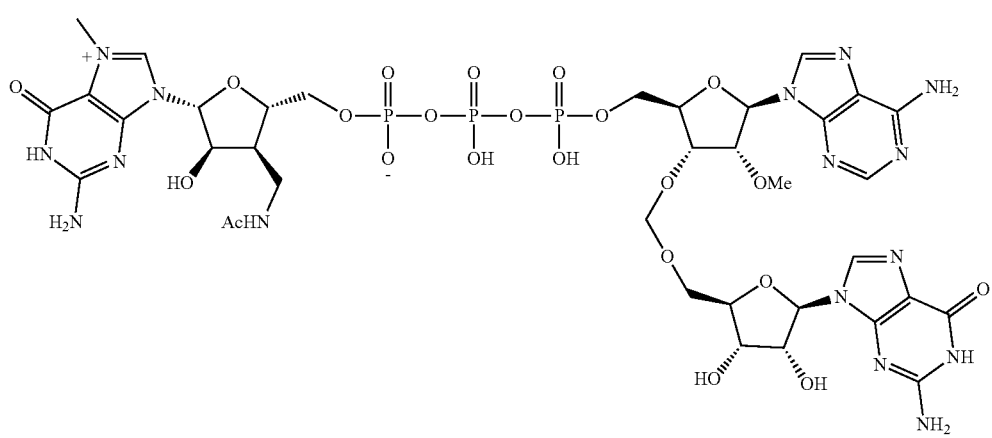
Compound 356
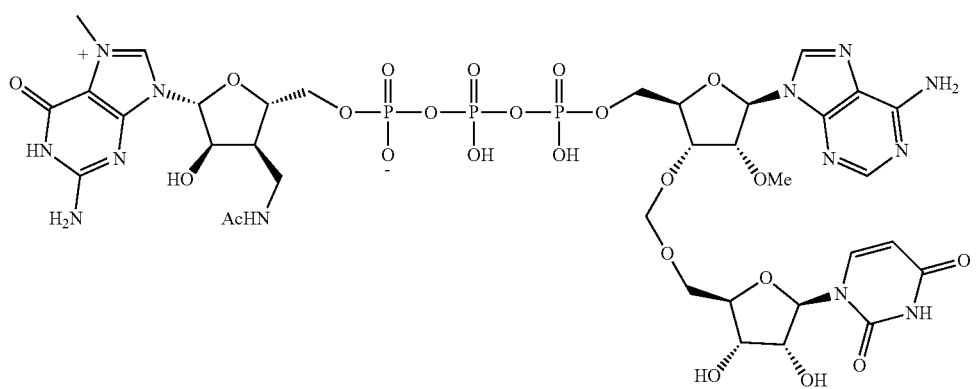
Compound 357
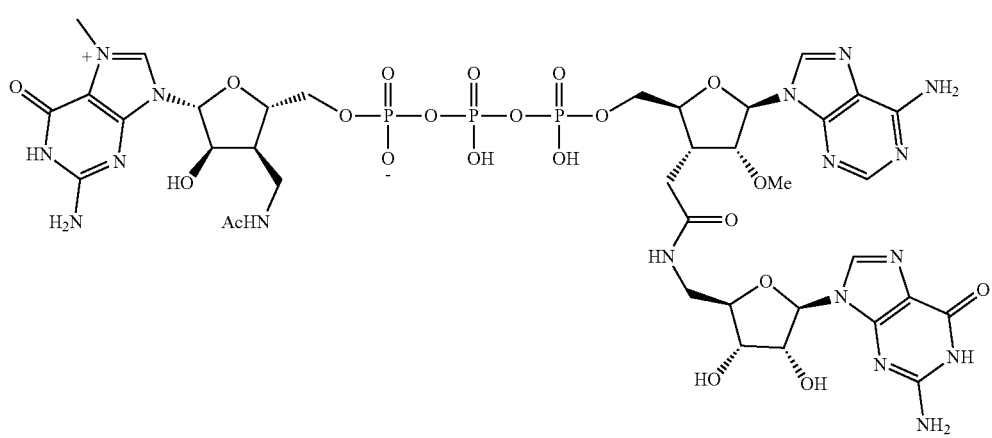

-continued
Compound 358
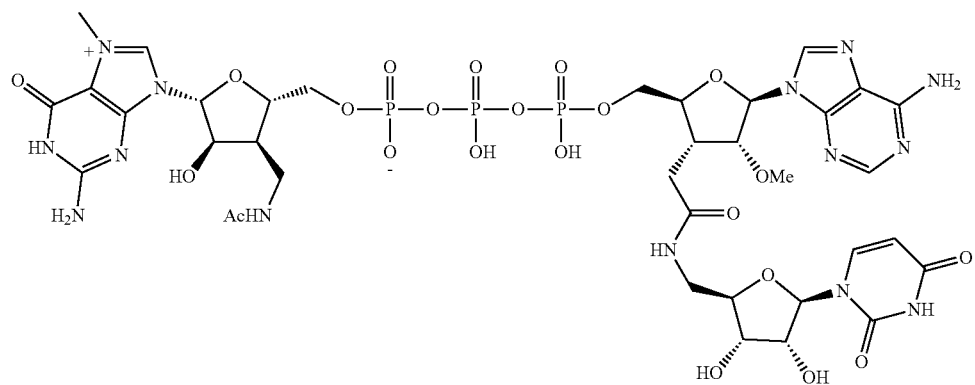
Compound 359
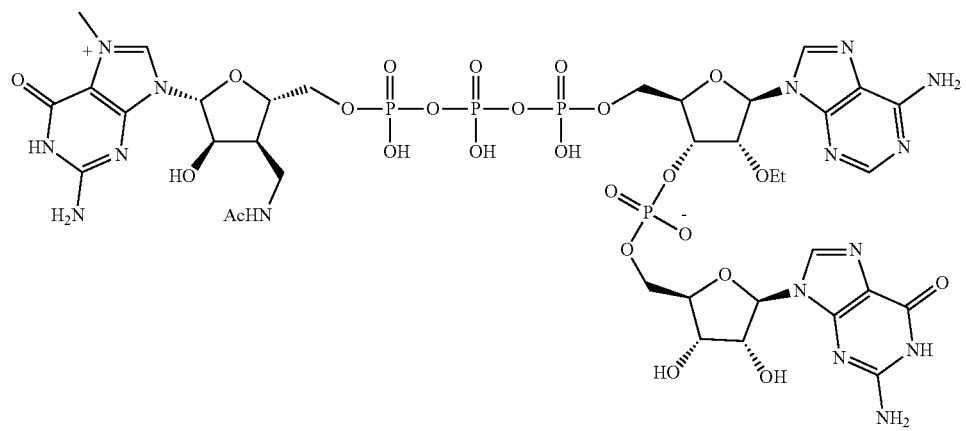
Compound 360
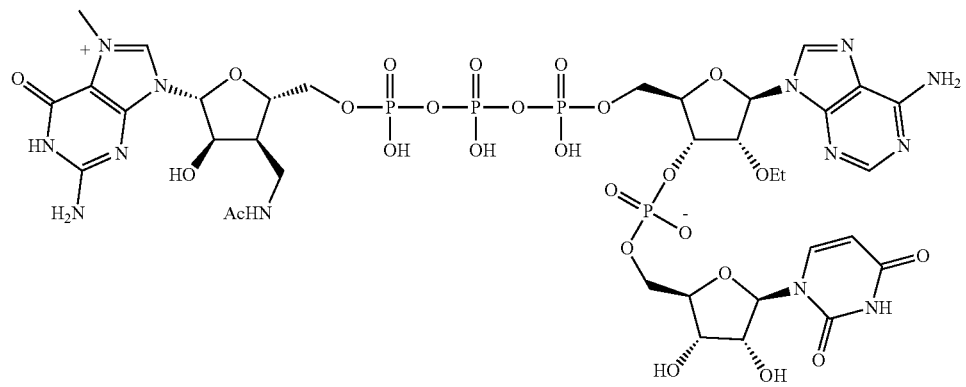
Compound 361
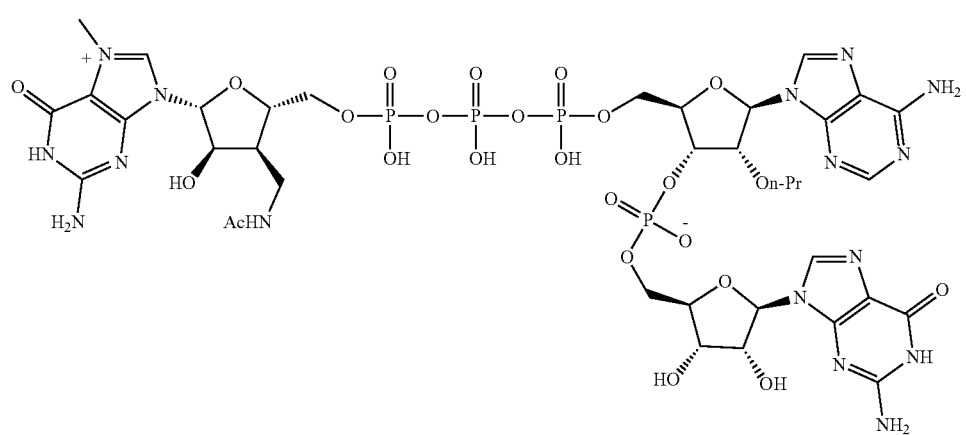

-continued
Compound 362
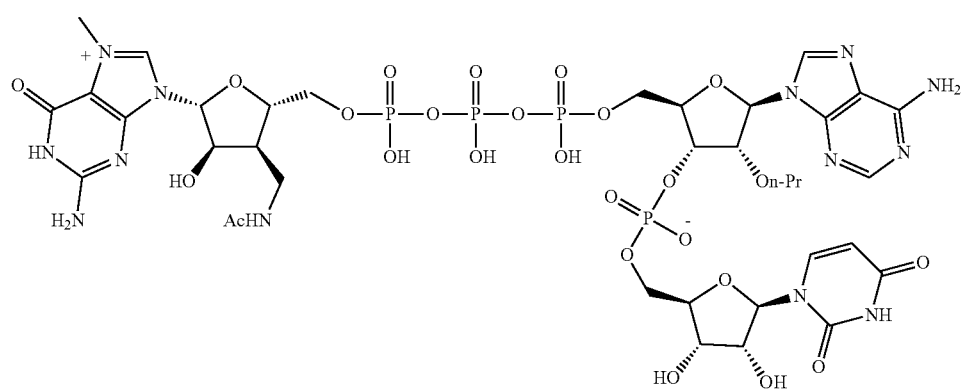
Compound 363
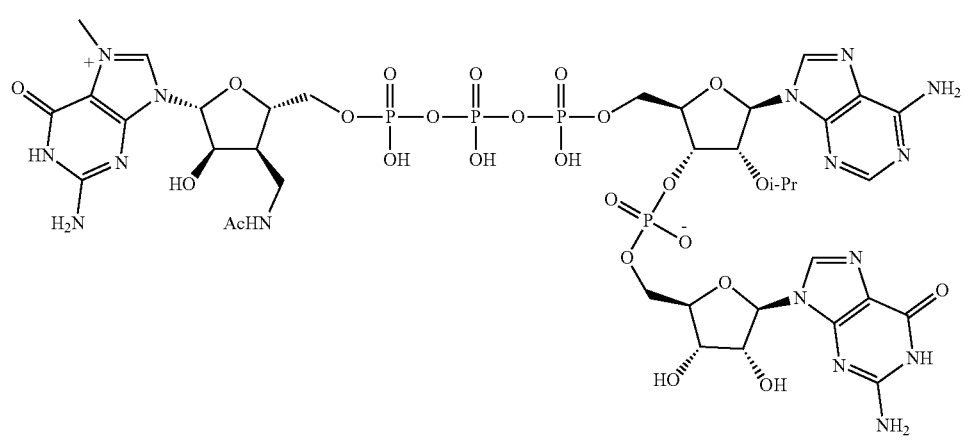
Compound 364
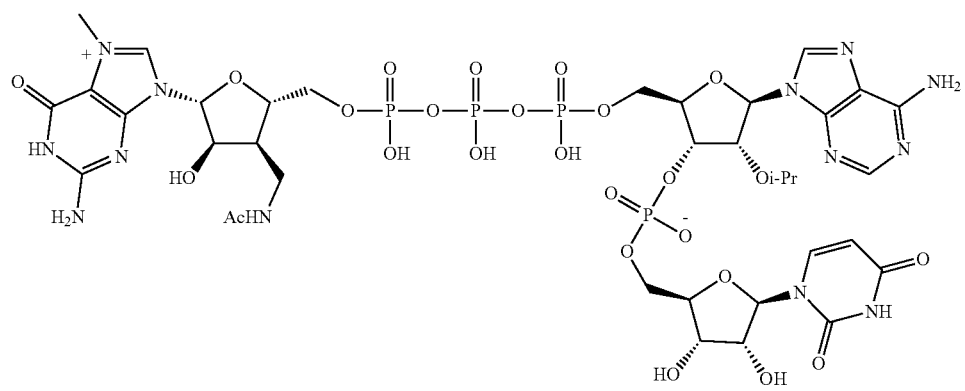
Compound 365
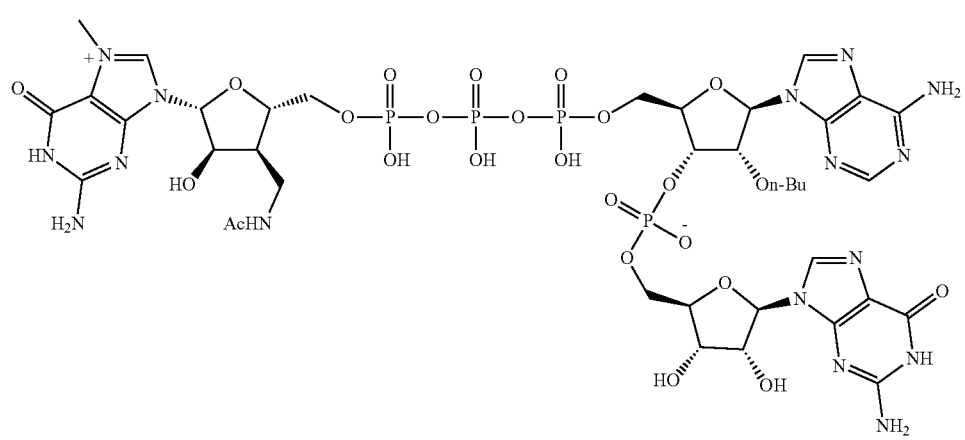

Compound 366
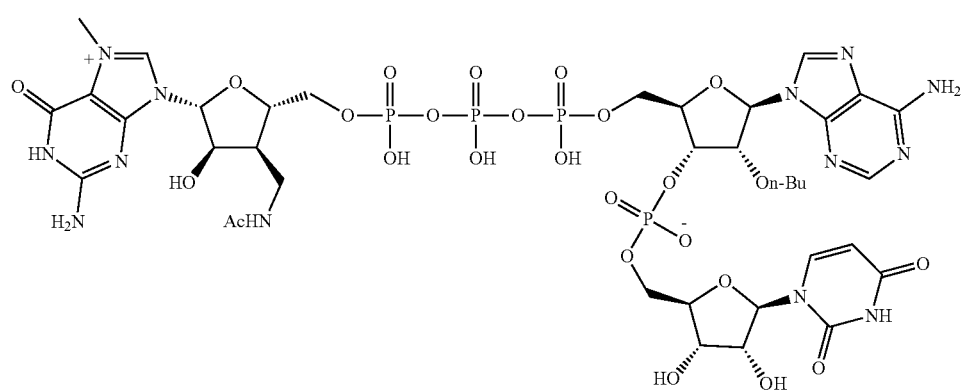
Compound 367
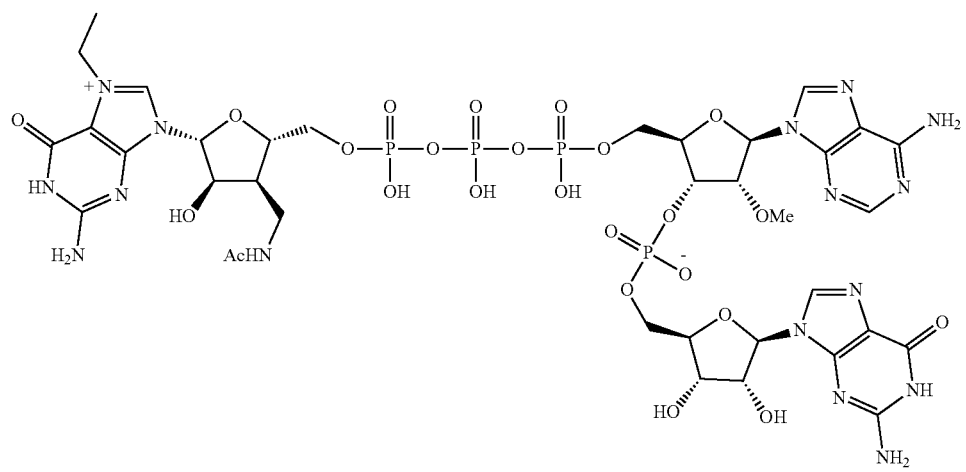
Compound 368
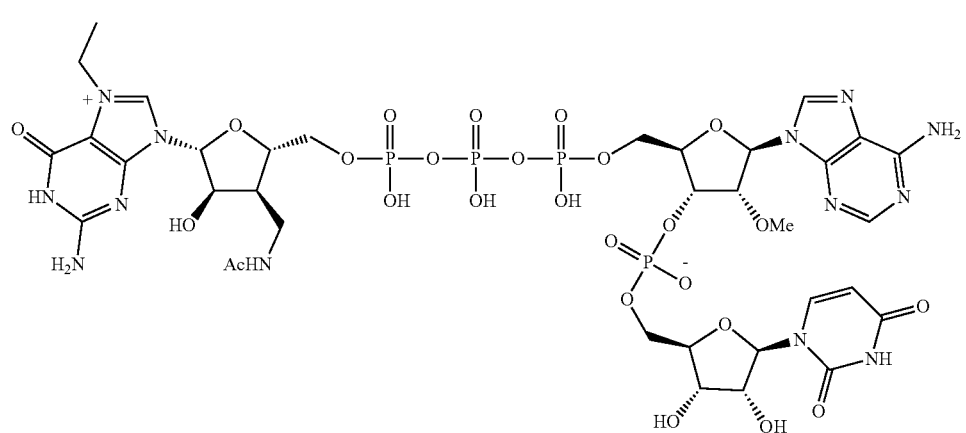

-continued
Compound 369
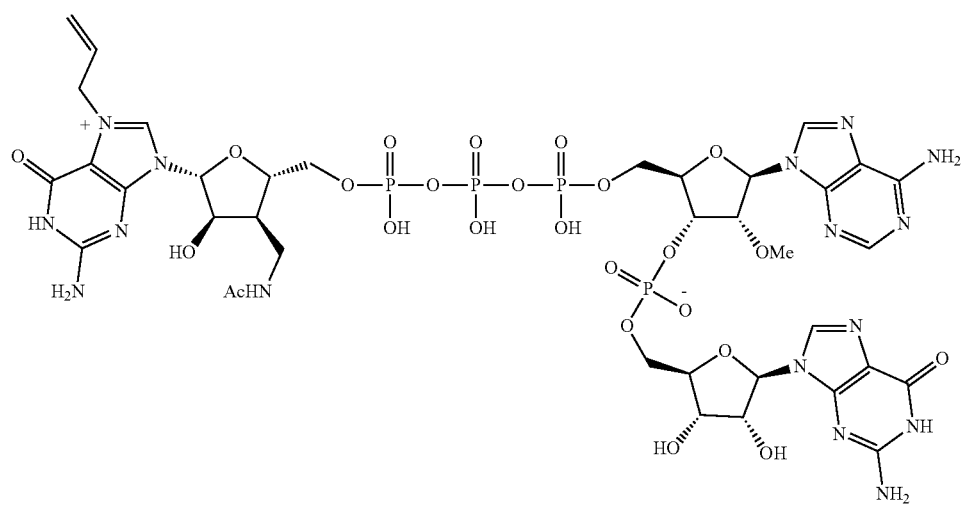
Compound 370
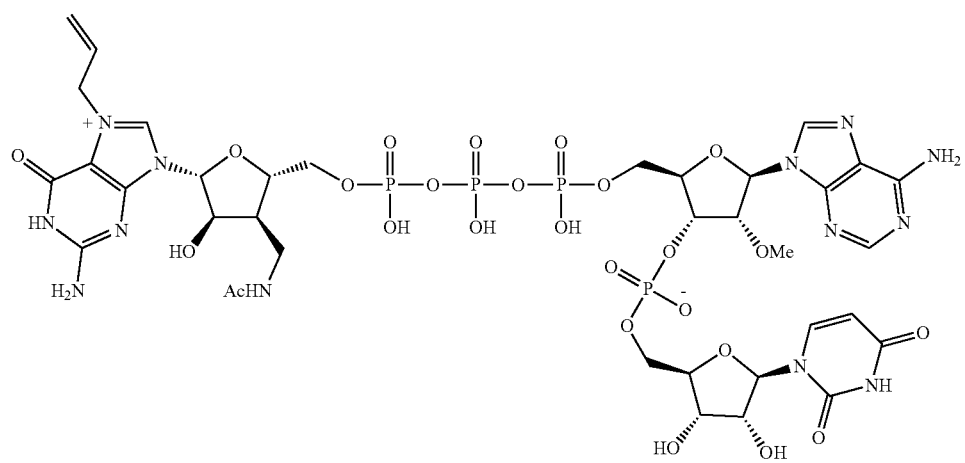
Compound 371
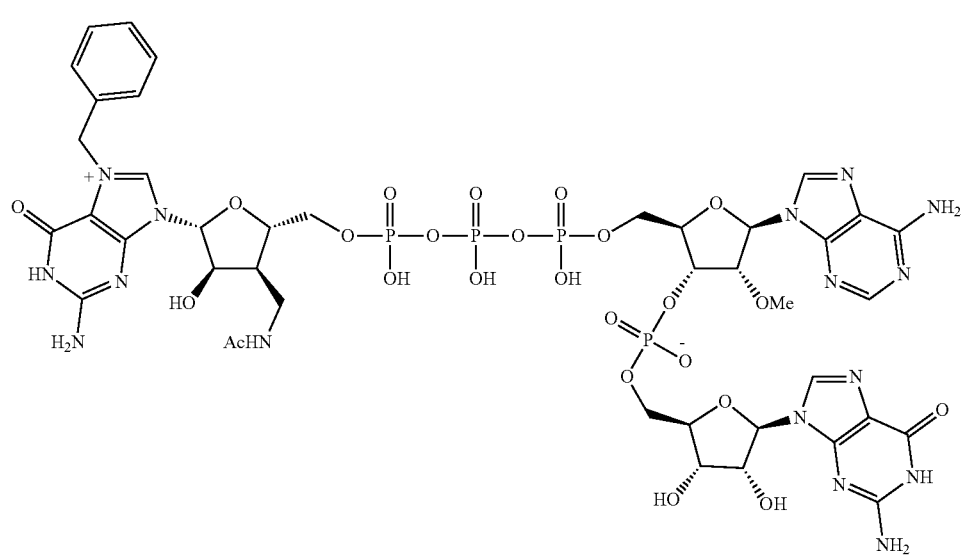

-continued
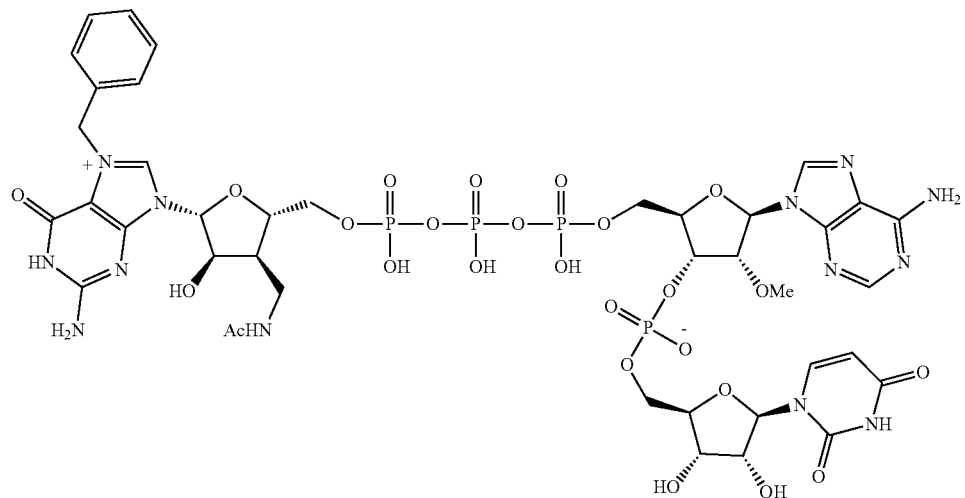
Compound 372
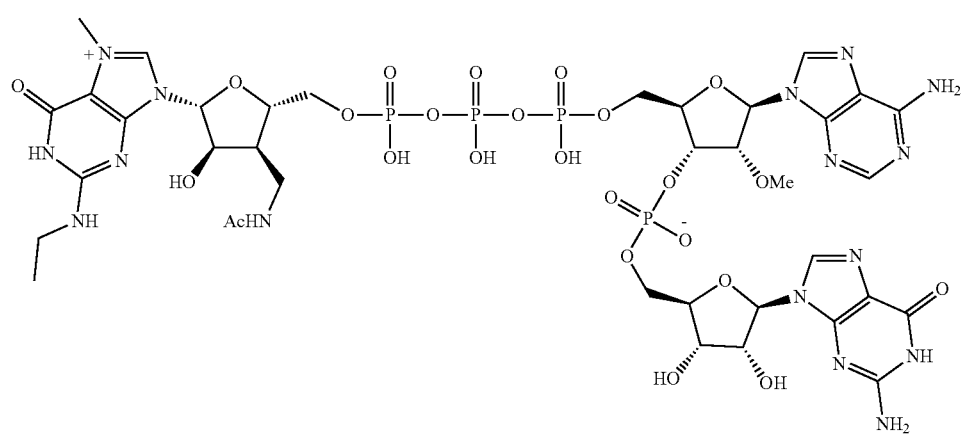
Compound 373
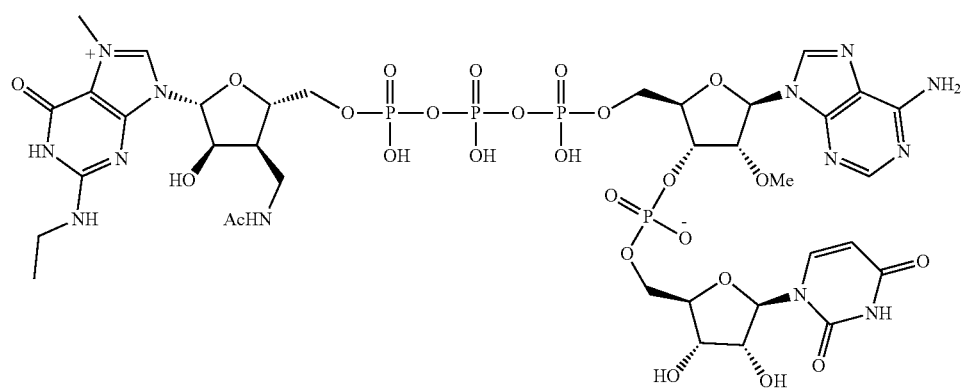
Compound 374

-continued
Compound 375
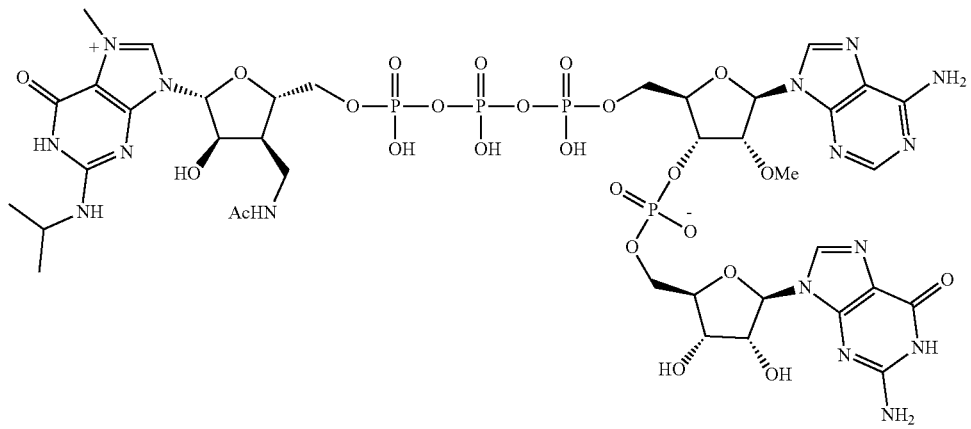
Compound 376
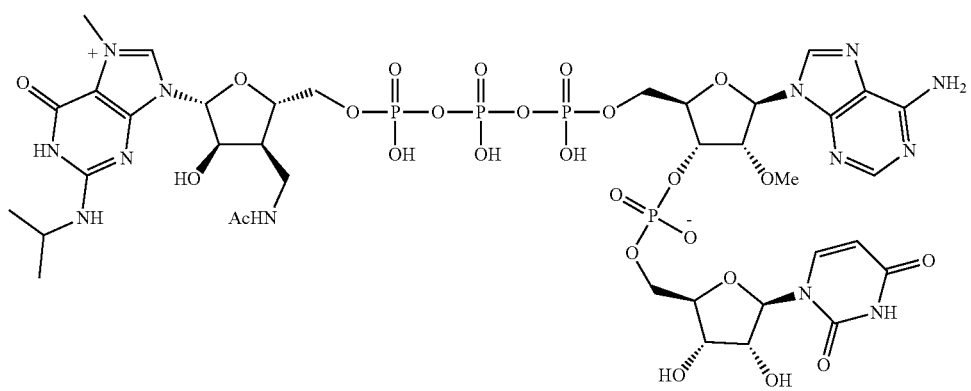
Compound 381
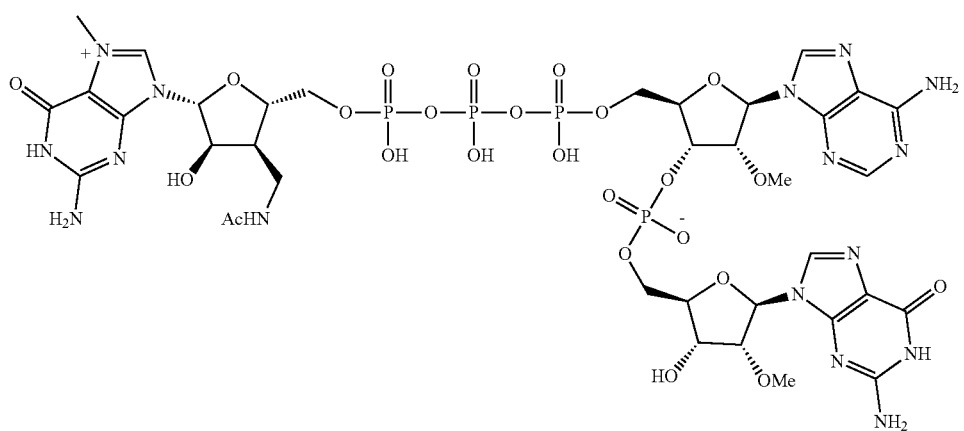
Compound 382
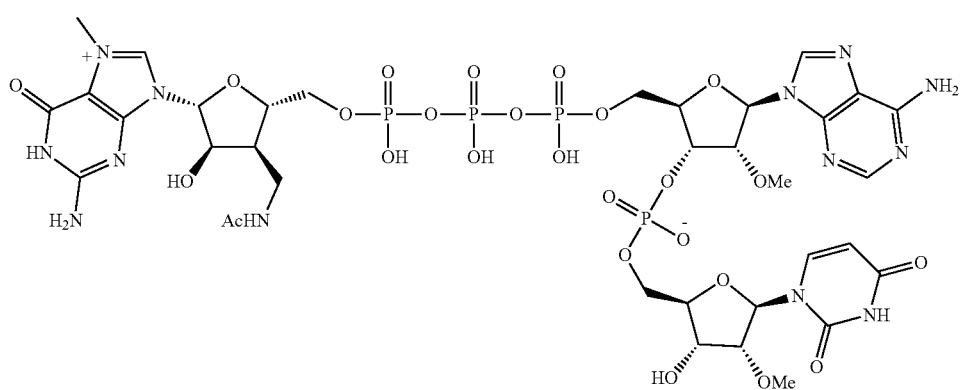

-continued
Compound 383
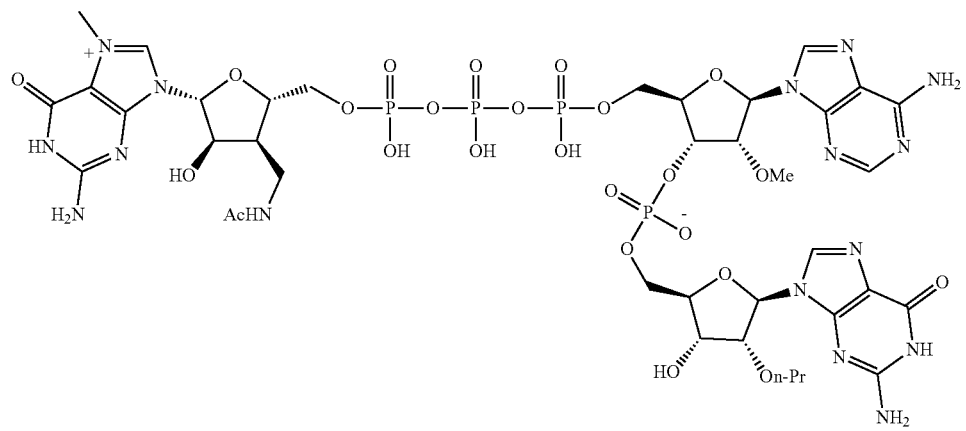
Compound 384
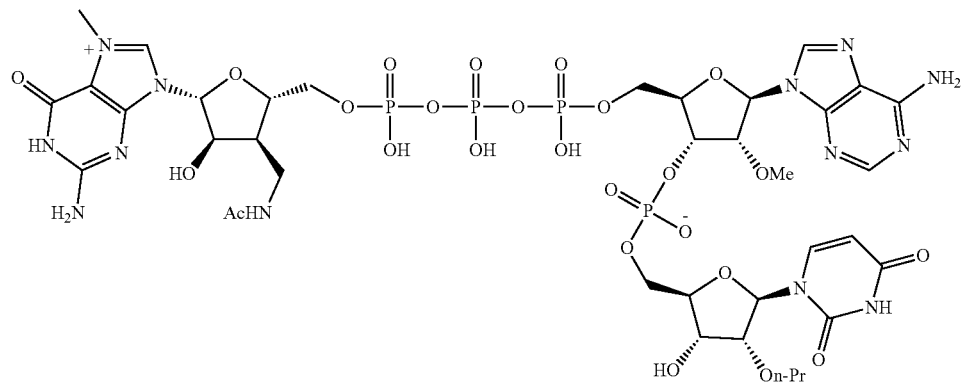
Compound 385
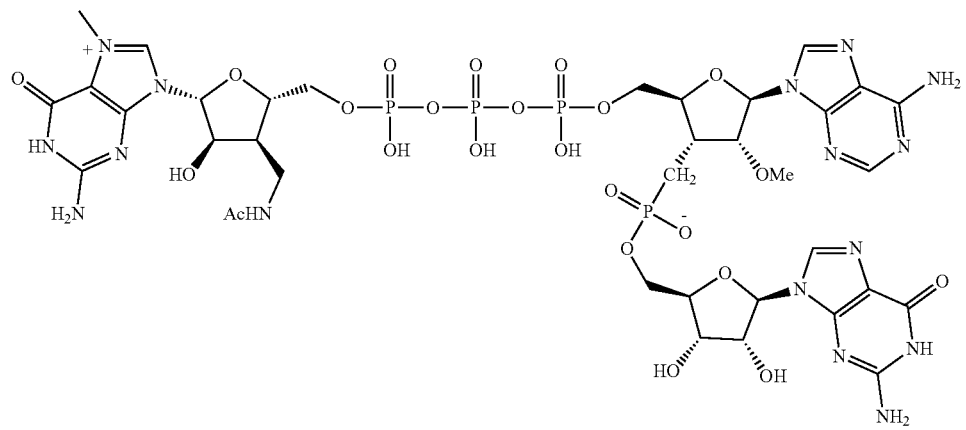
Compound 386
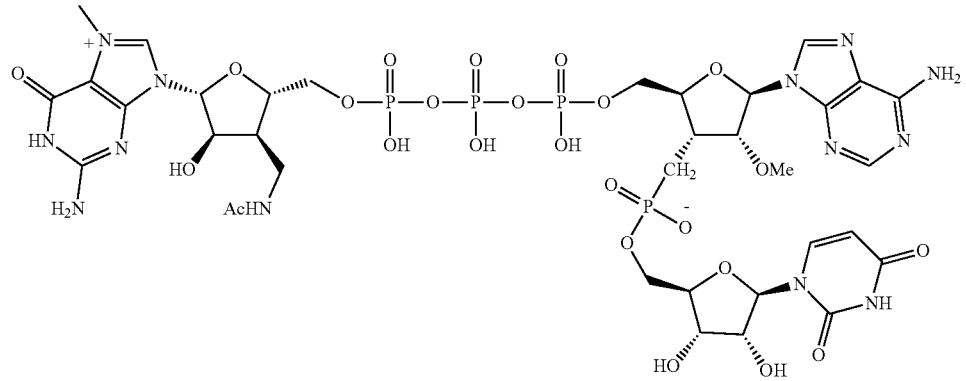

-continued
Compound 387
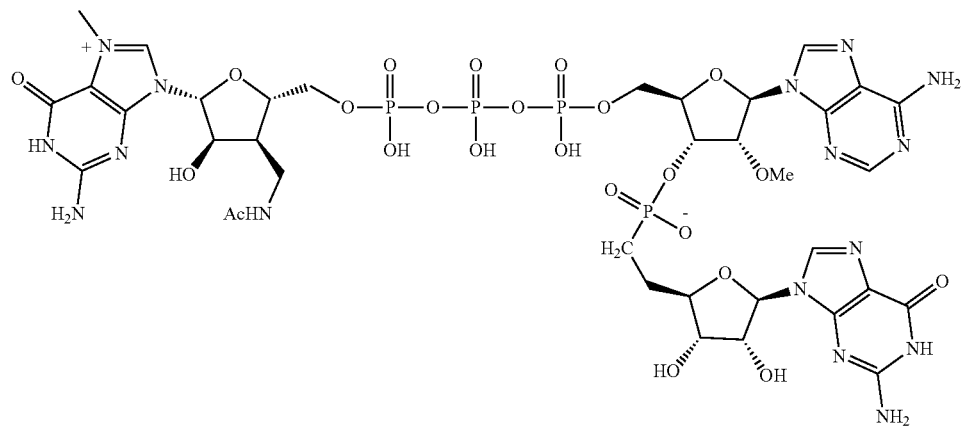
Compound 388
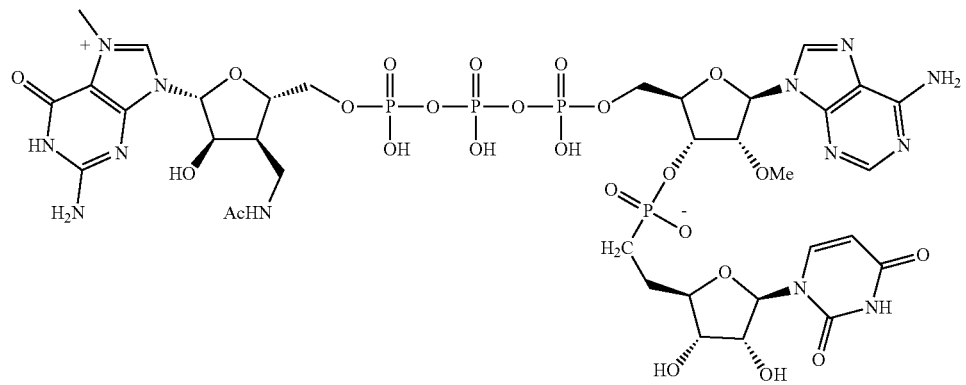
Compound 389
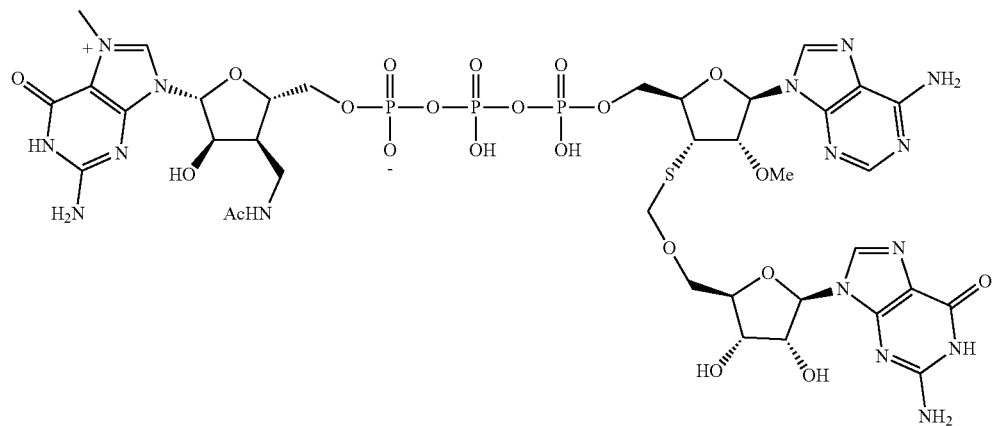
Compound 390
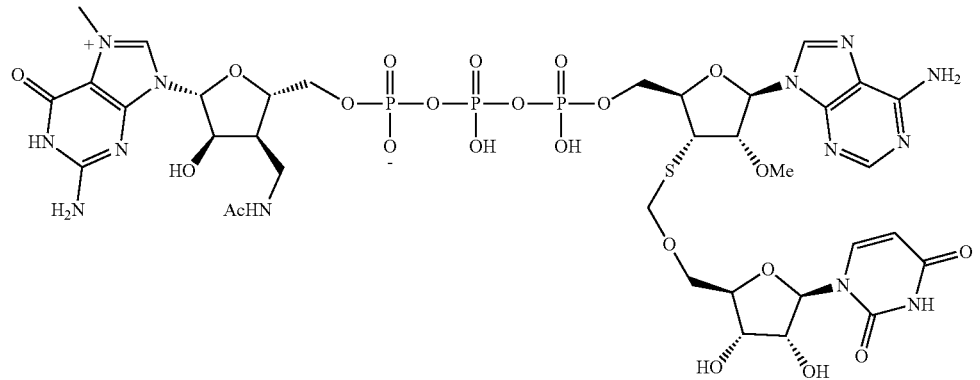

-continued
Compound 391
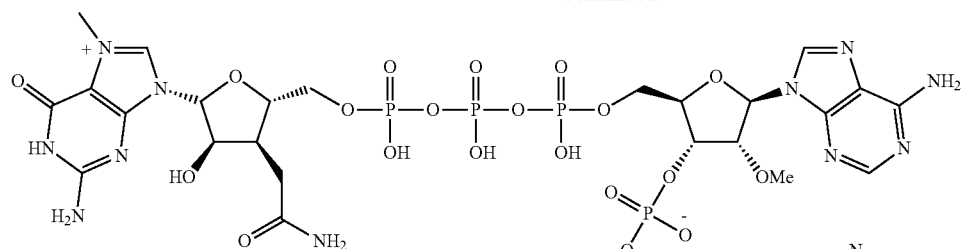
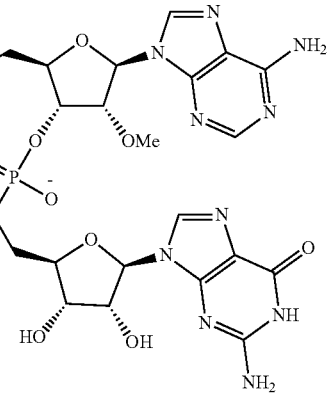
Compound 392
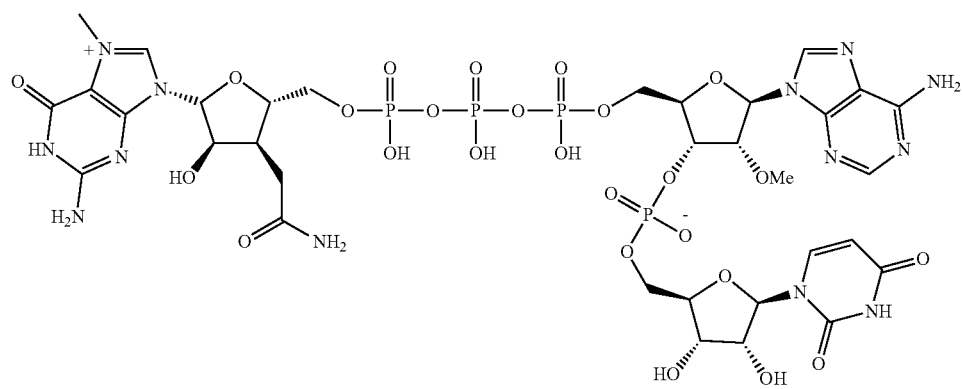
Compound 393
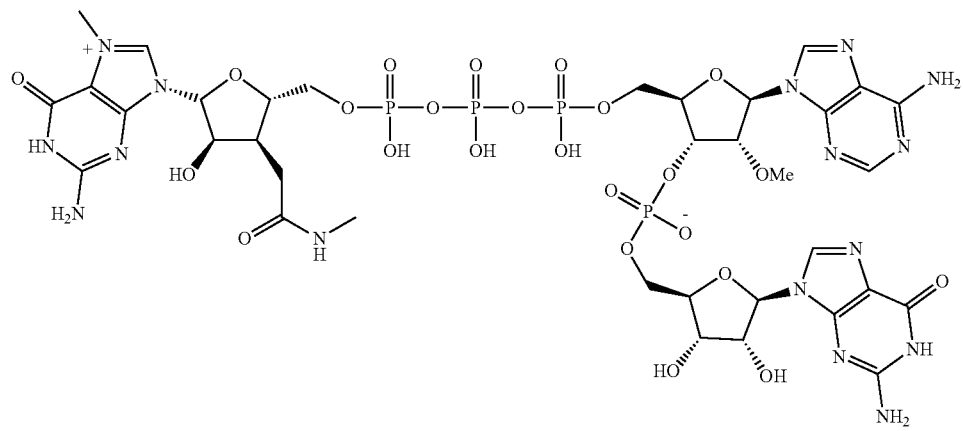
Compound 394
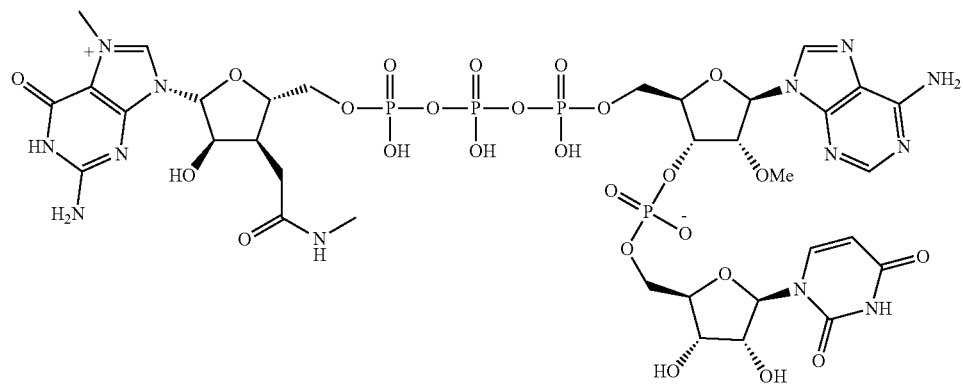

-continued
Compound 395
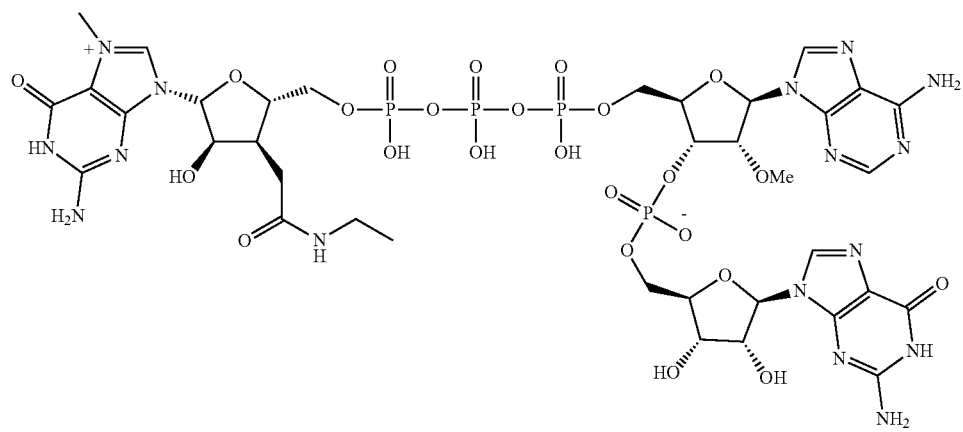
Compound 396
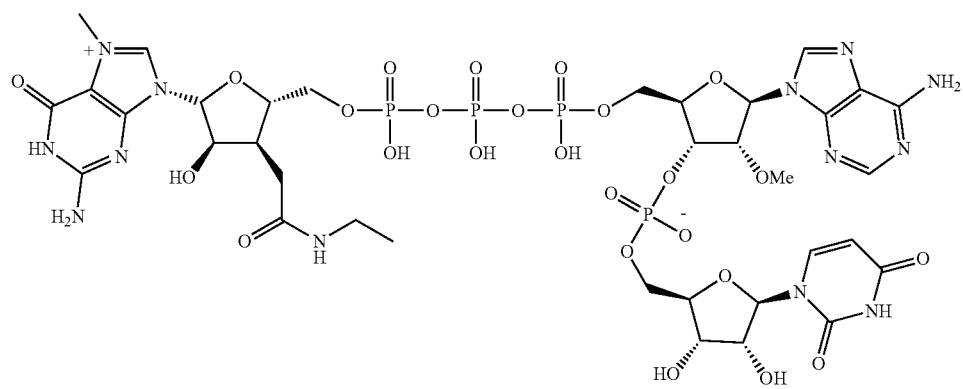
Compound 397
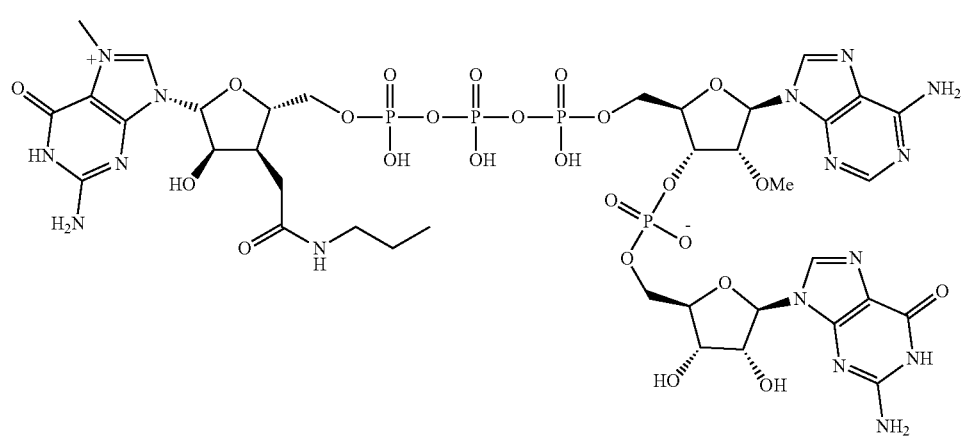
Compound 398
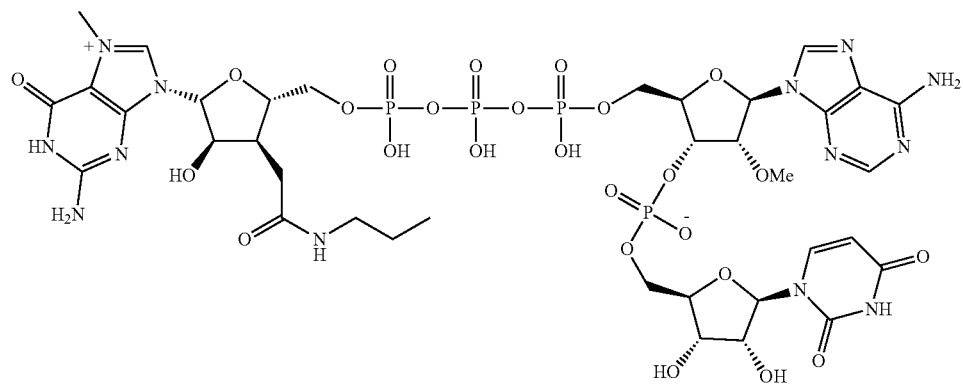

Compound 399
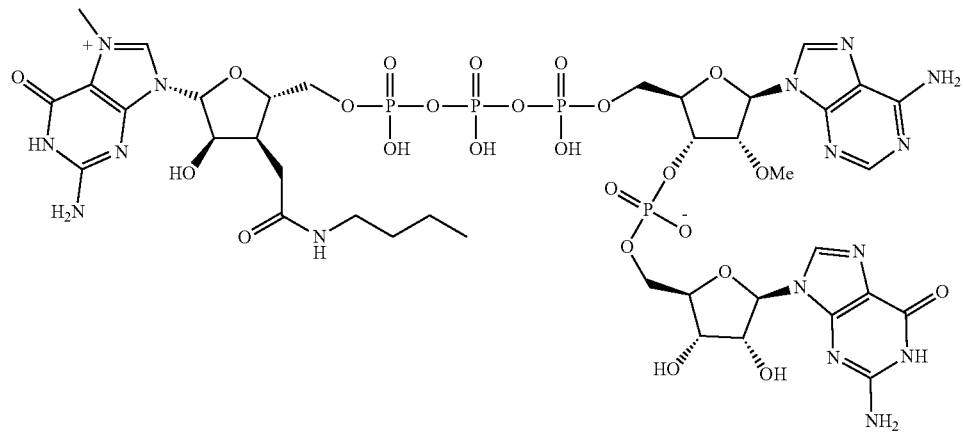
Compound 400
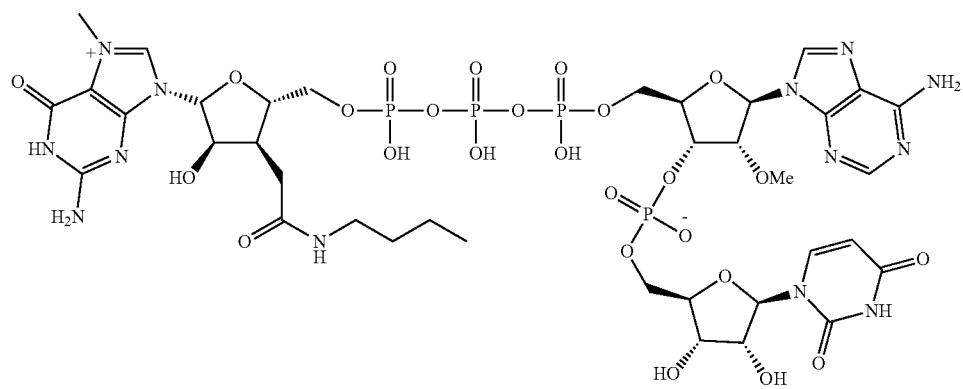
Compound 401
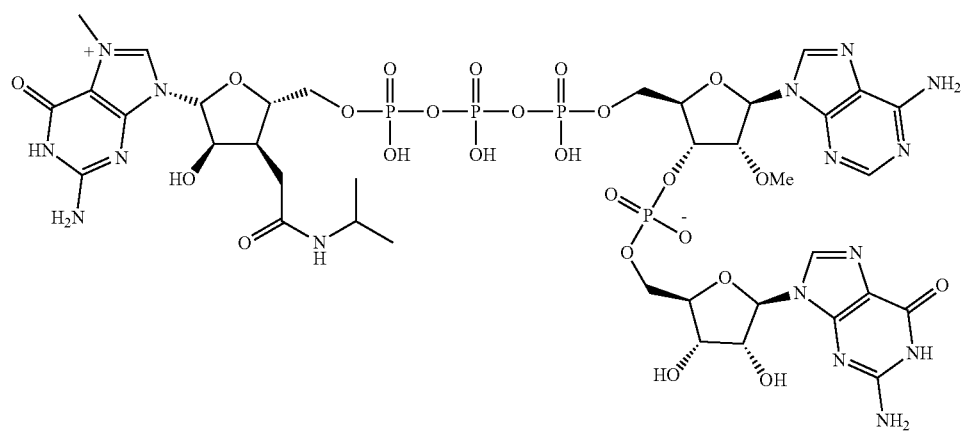
Compound 402
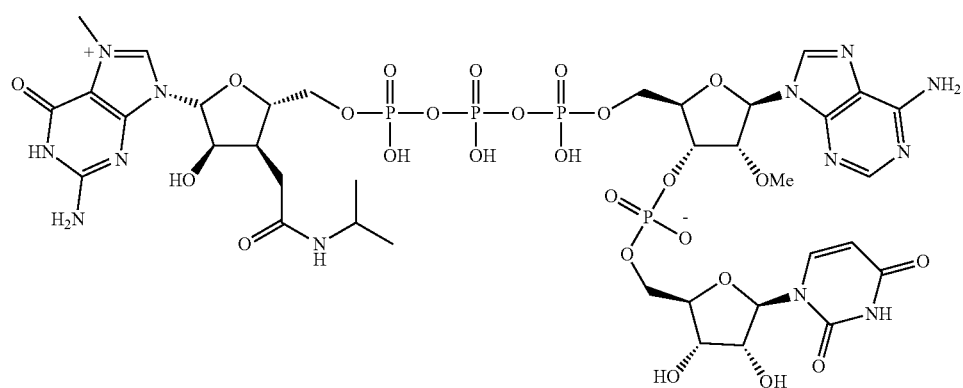

Compound 403
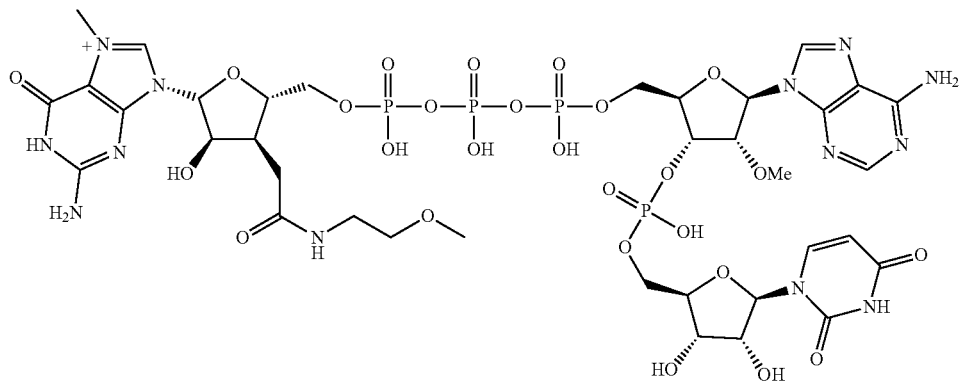
Compound 404
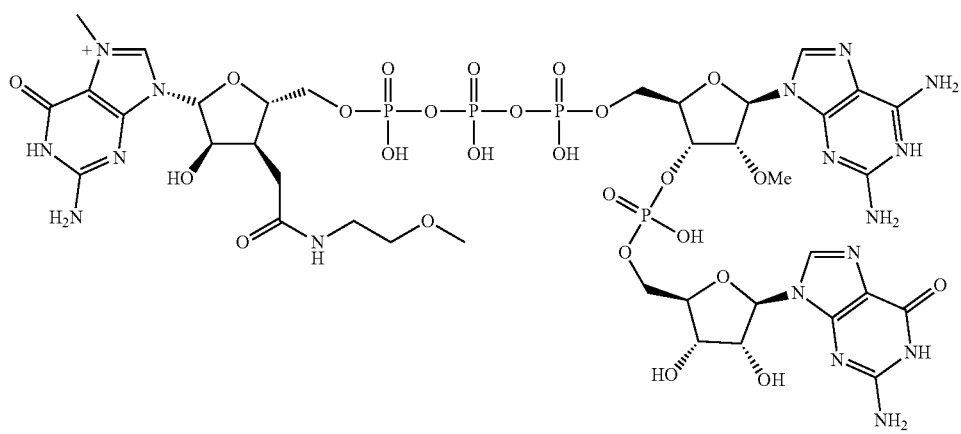
Compound 405
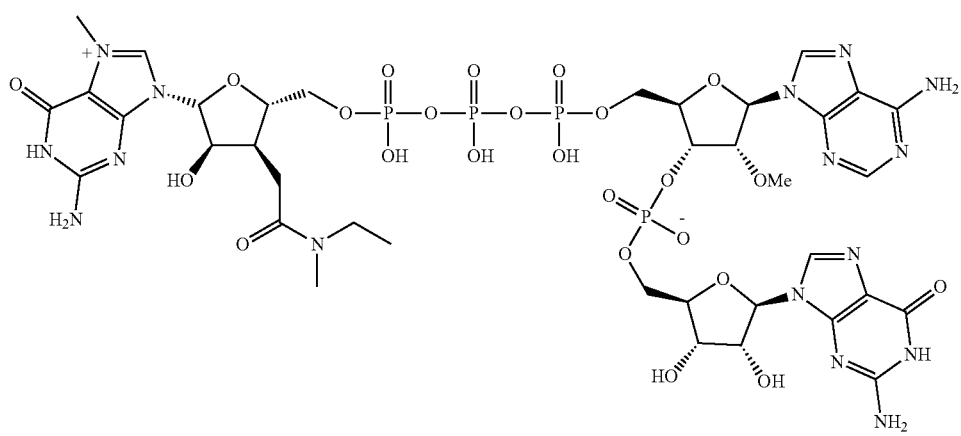
Compound 406
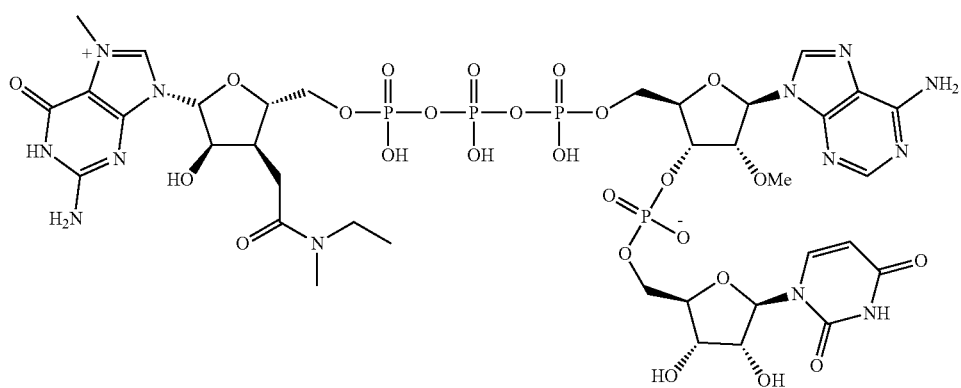

-continued
Compound 407
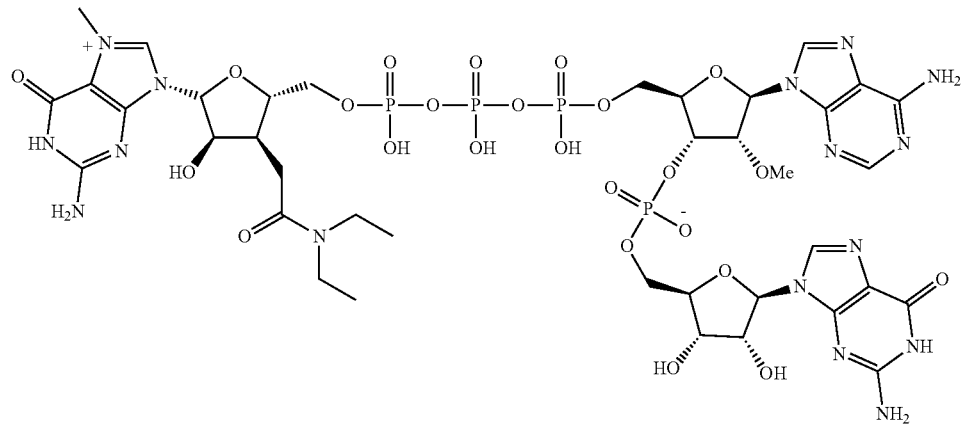
Compound 408
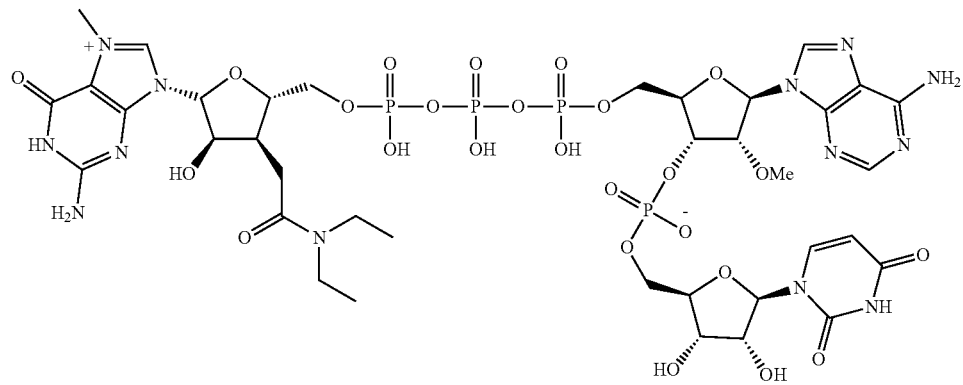
Compound 409
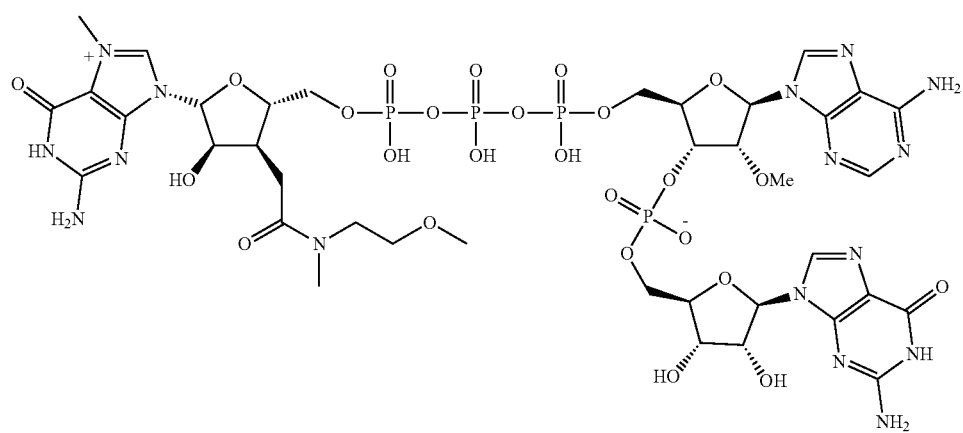
Compound 410
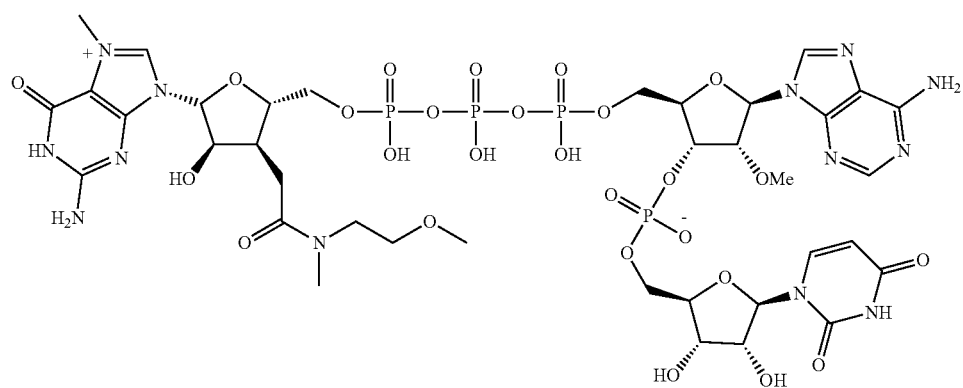

-continued
Compound 411
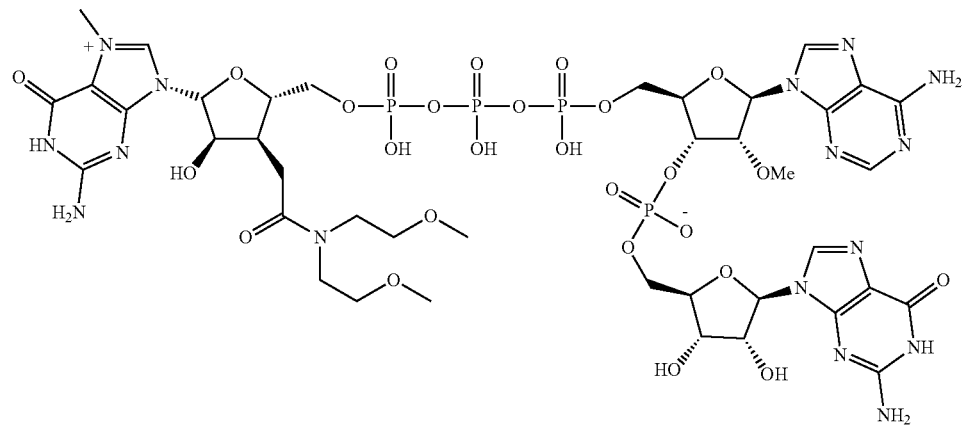
Compound 412
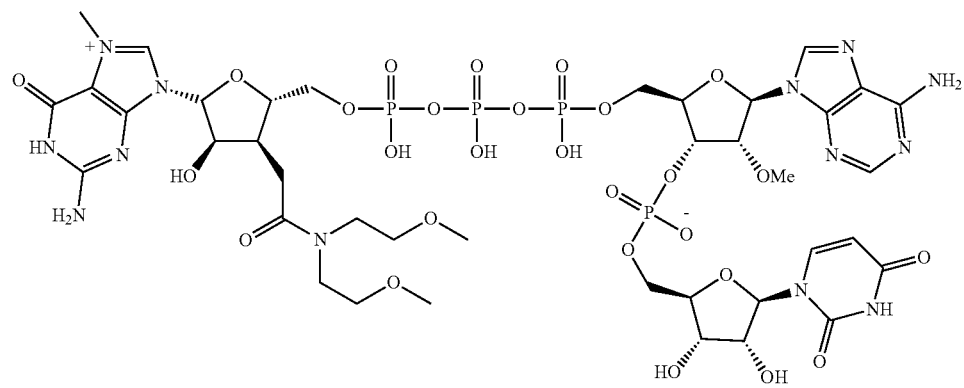
Compound 413
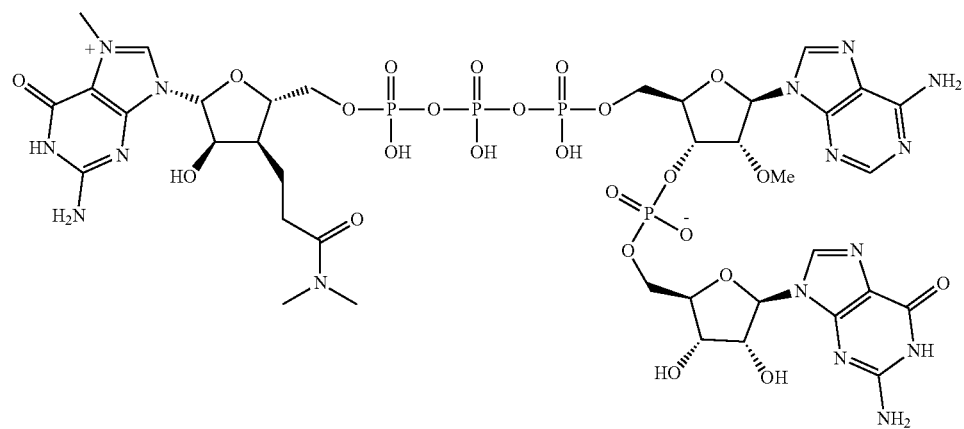
Compound 414
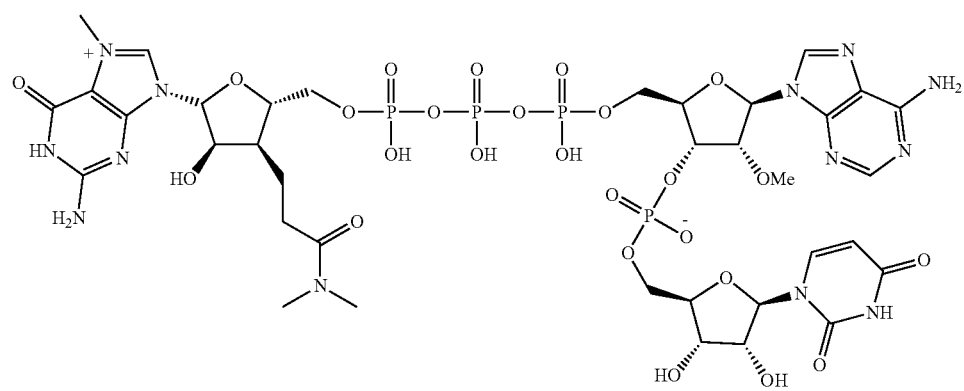

-continued
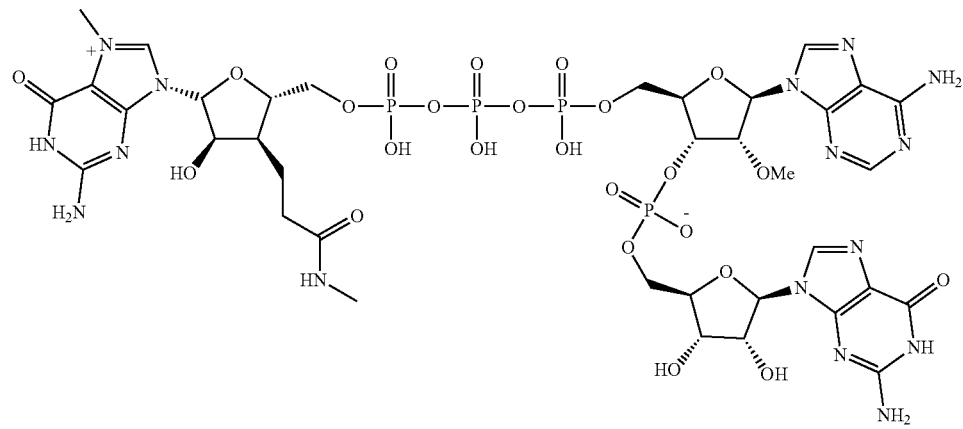
Compound 415
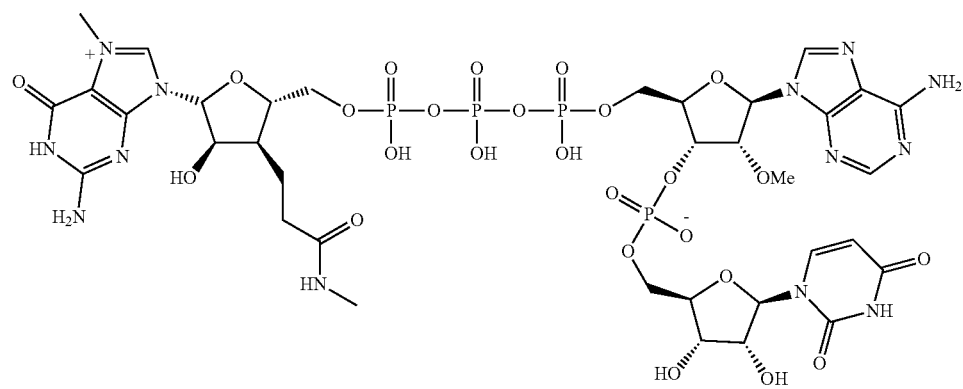
Compound 416
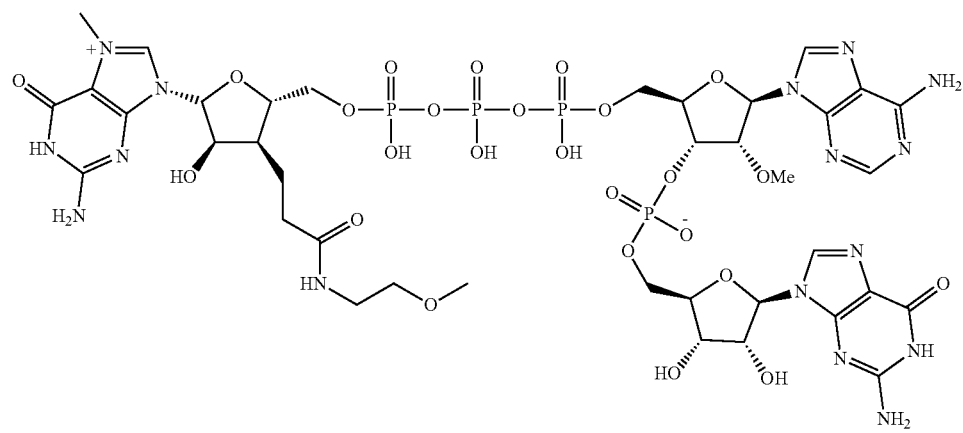
Compound 417
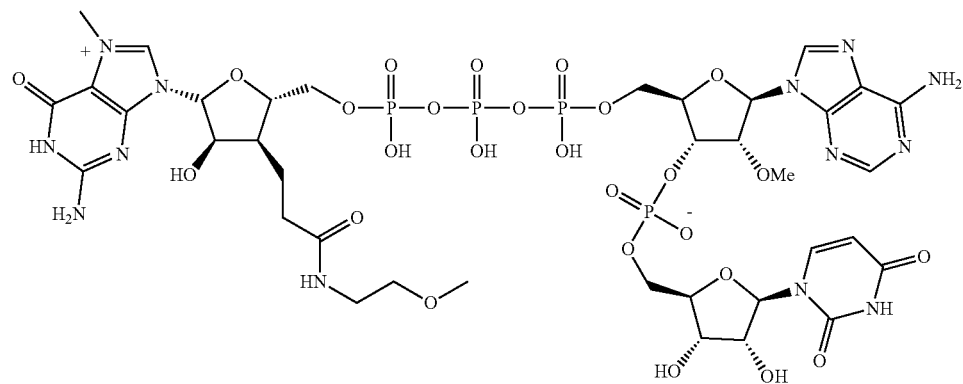
Compound 418

-continued
Compound 419
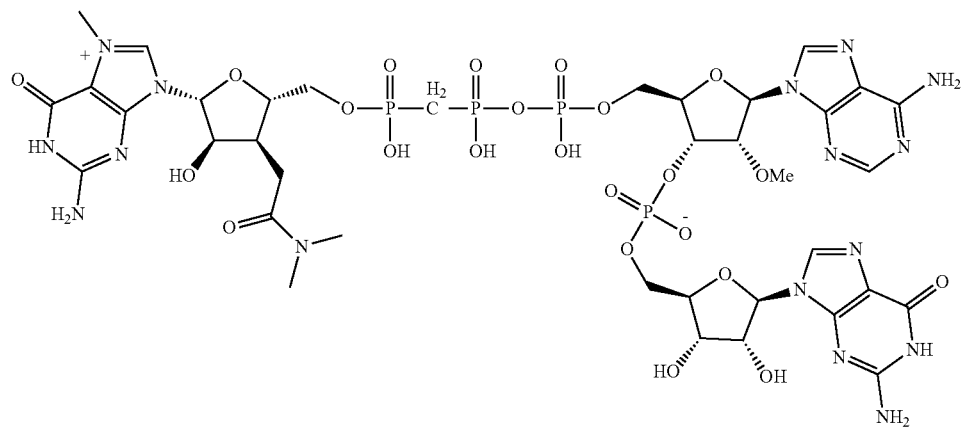
Compound 420
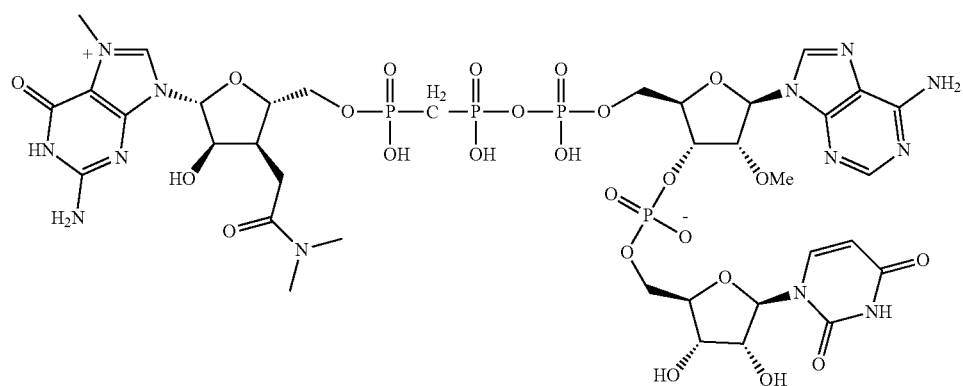
Compound 421
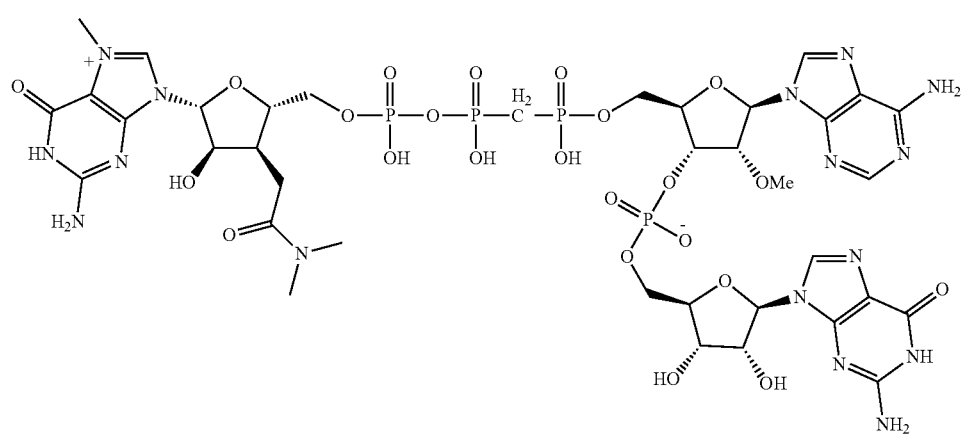
Compound 422
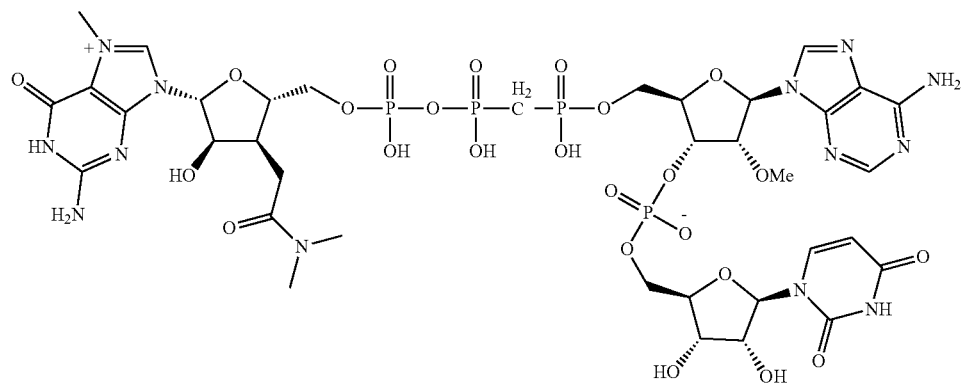

-continued
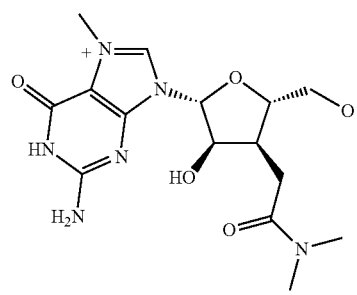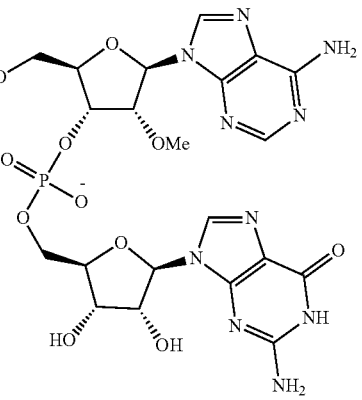
Compound 423
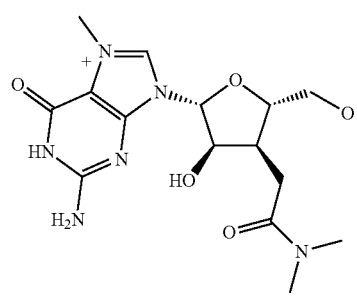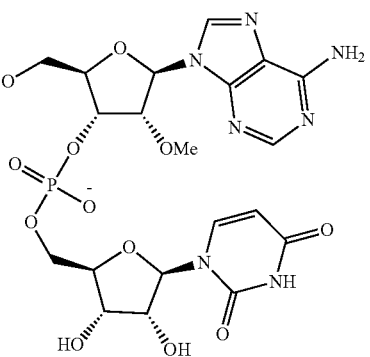
Compound 424
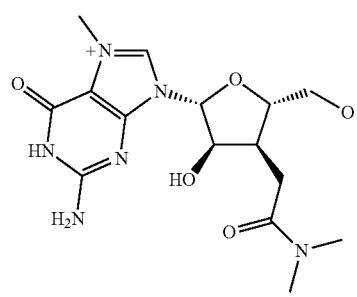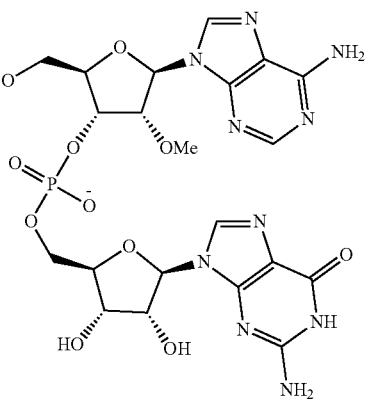
Compound 425
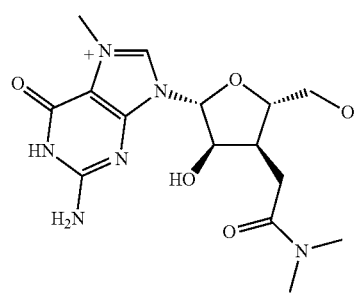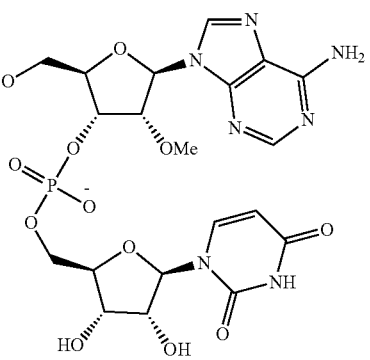
Compound 426

Compound 427
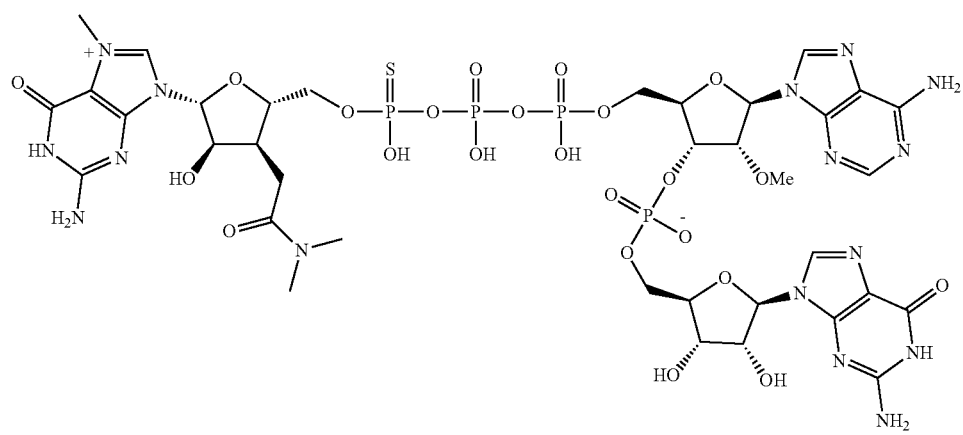
Compound 428
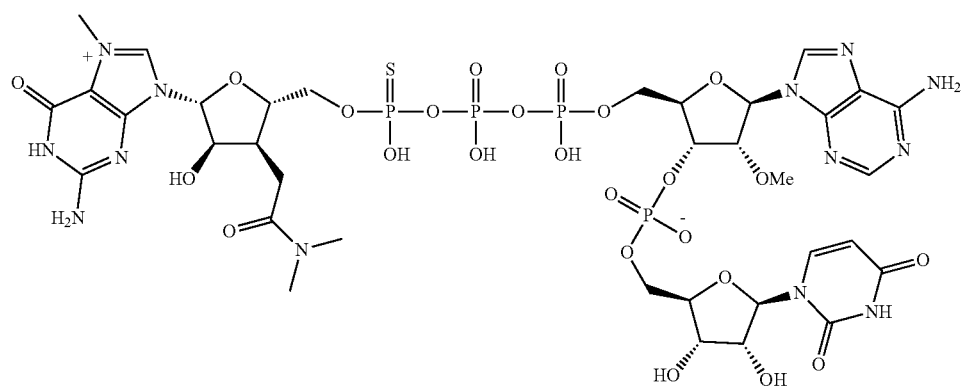
Compound 429
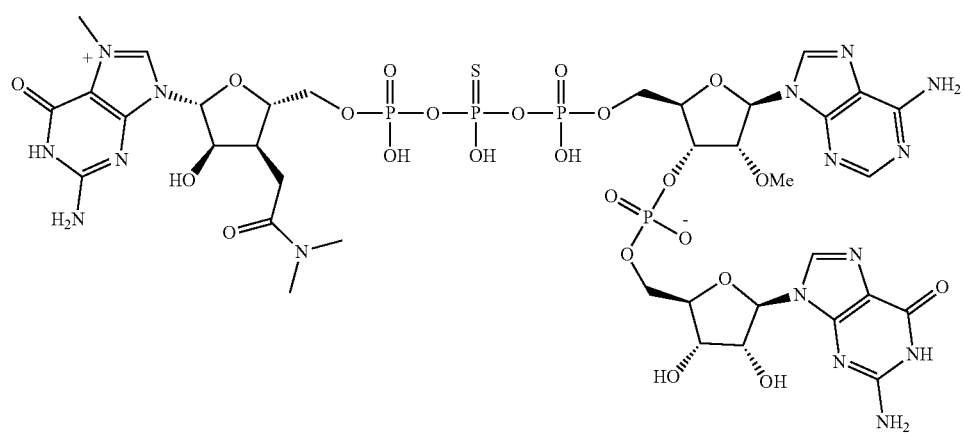
Compound 430
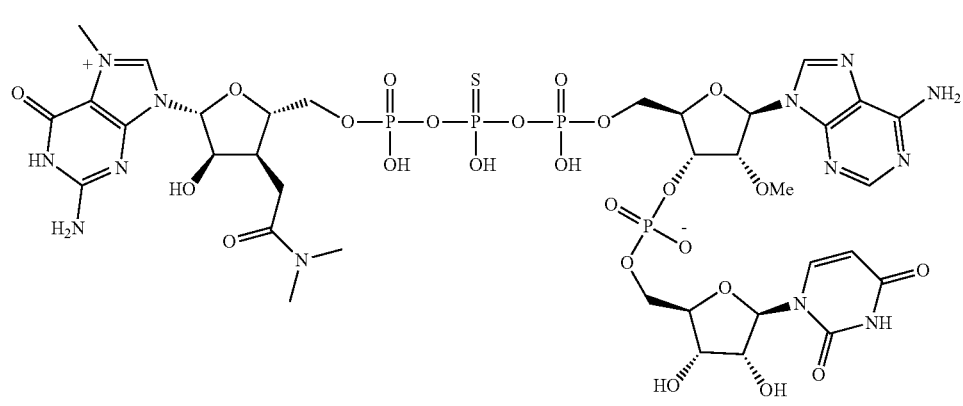

Compound 431
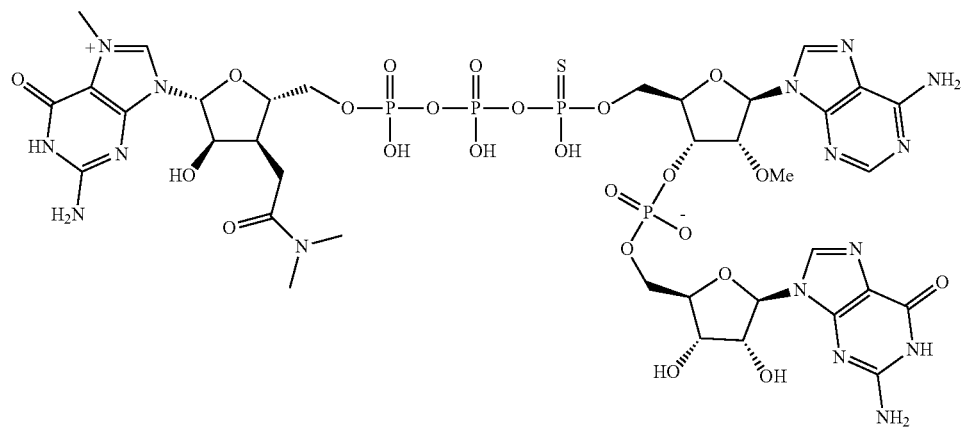
Compound 432
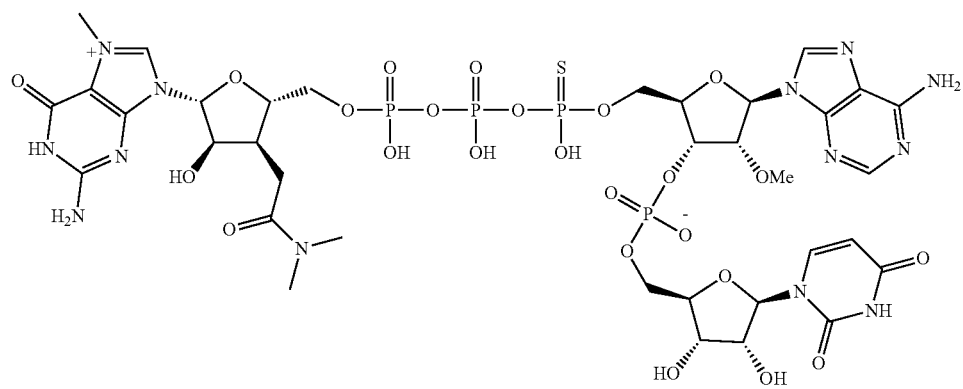
Compound 433
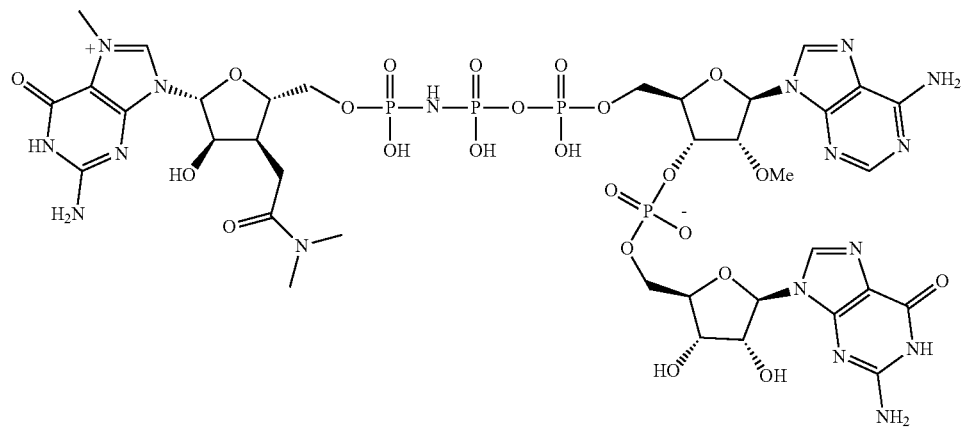
Compound 434
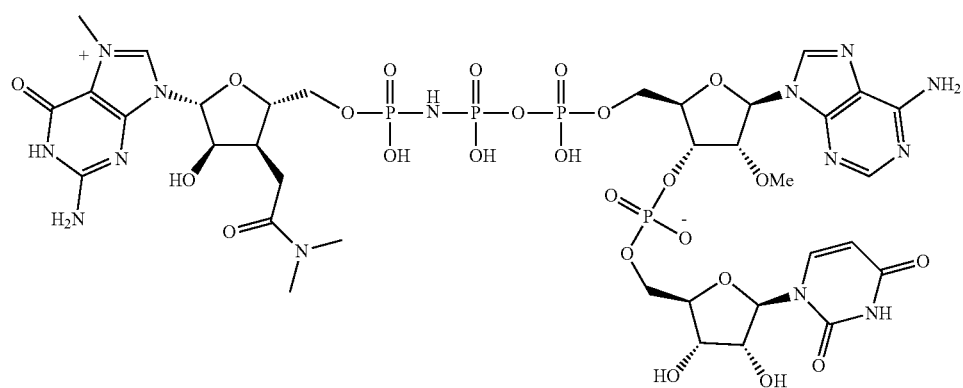

Compound 435
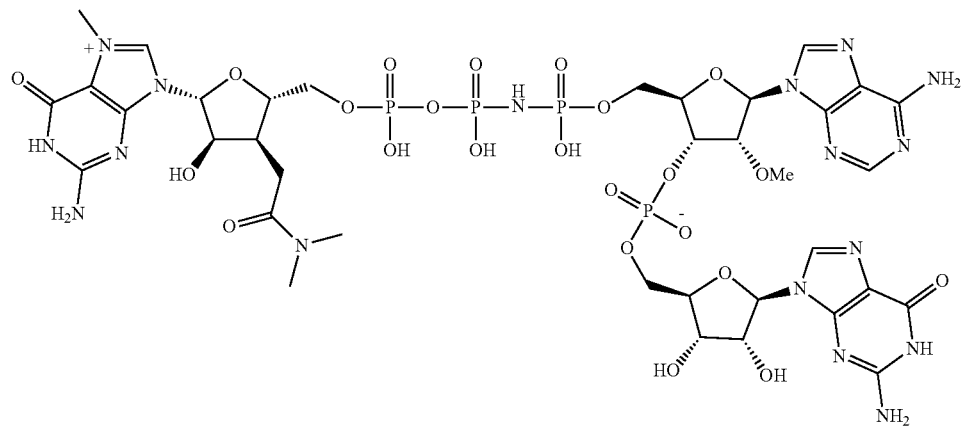
Compound 436
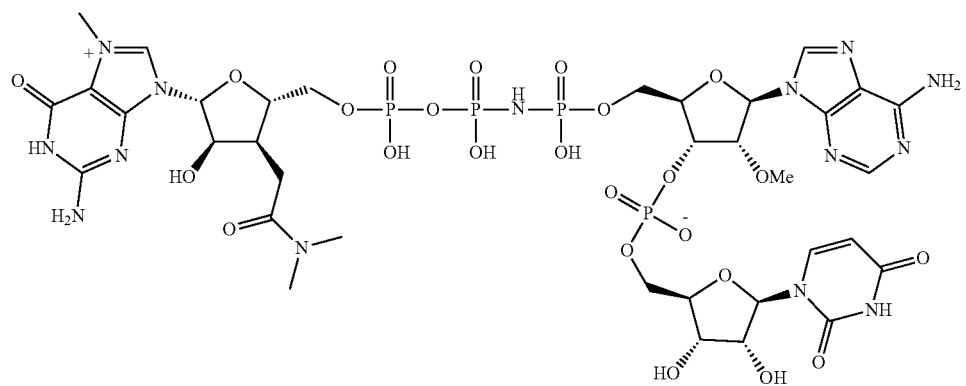
Compound 437
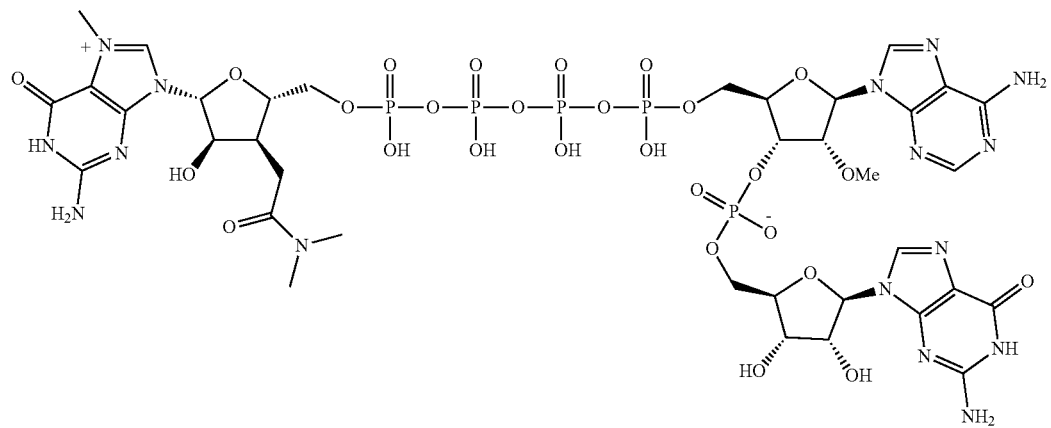
Compound 438
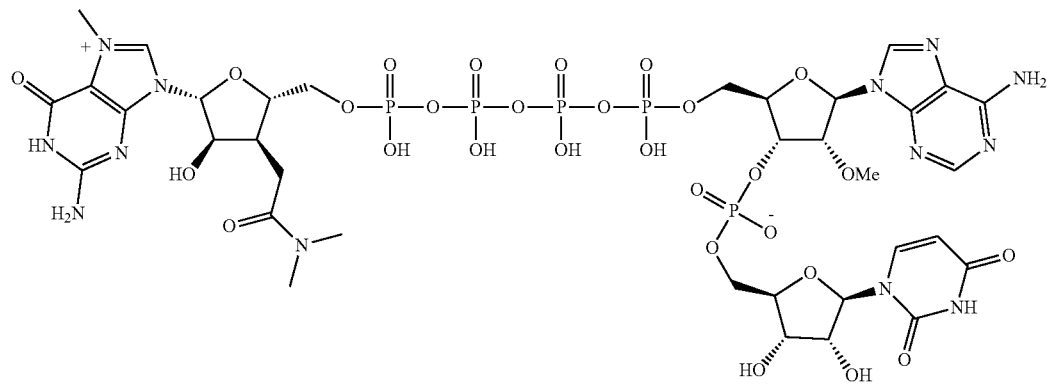

Compound 439
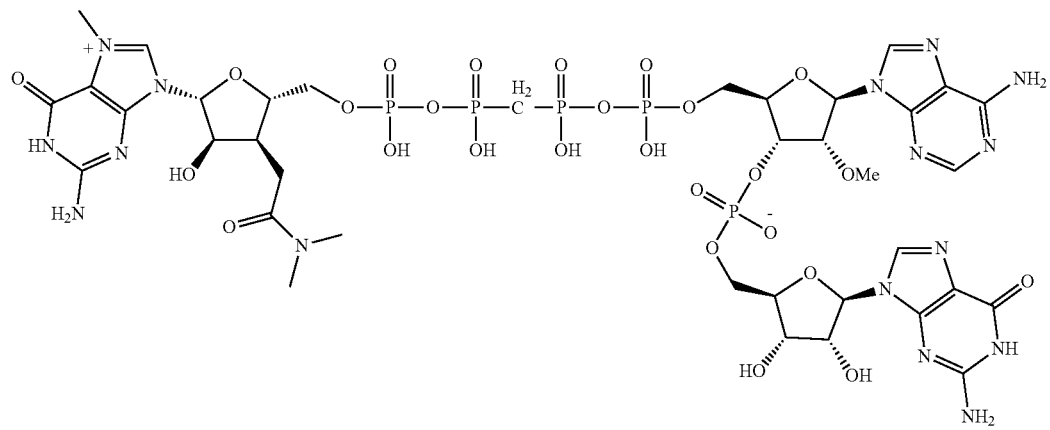
Compound 440
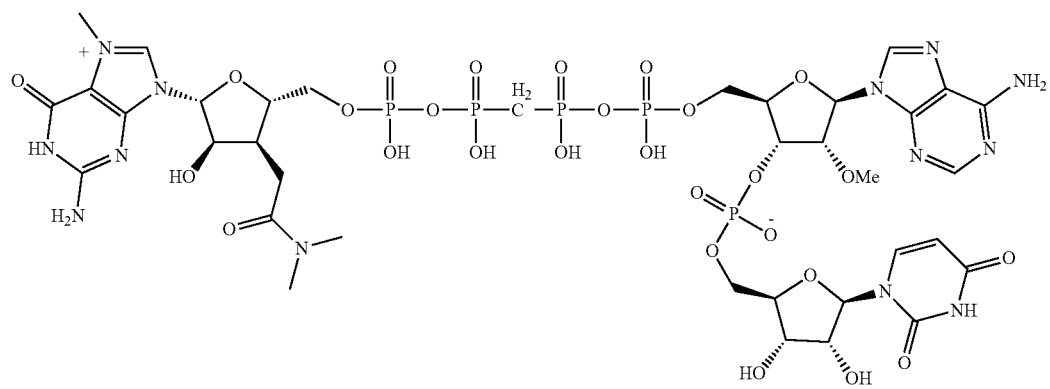
Compound 441
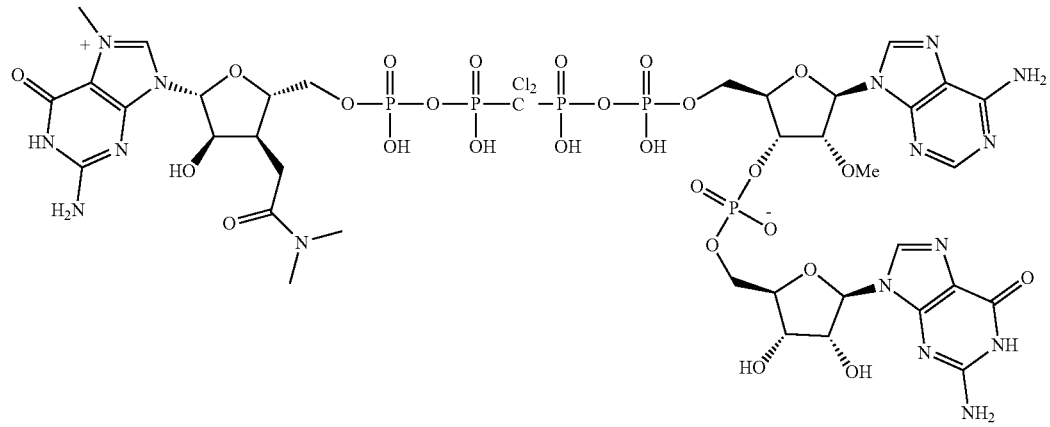
Compound 442
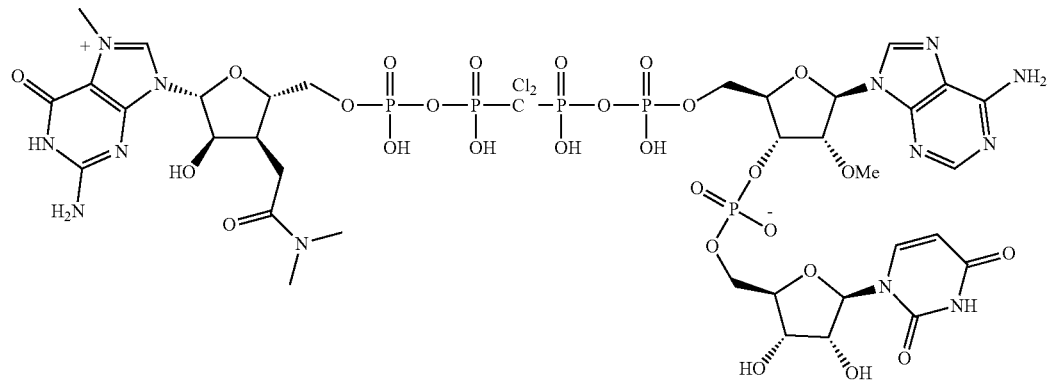

Compound 443
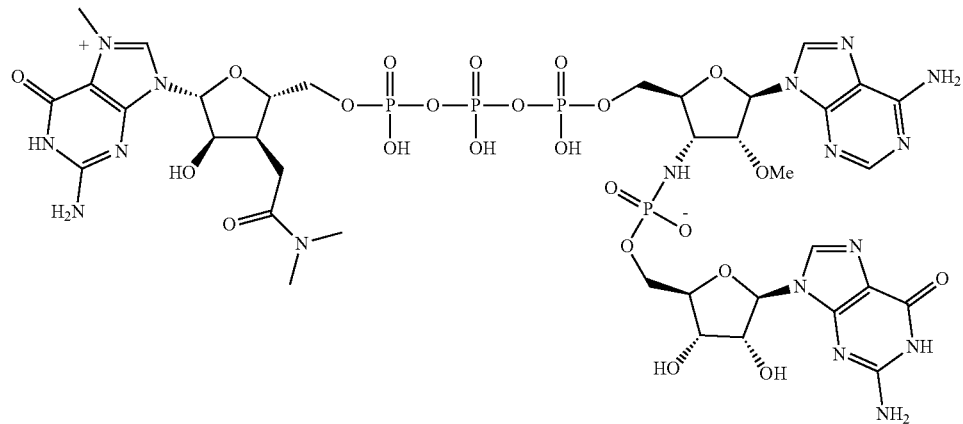
Compound 444
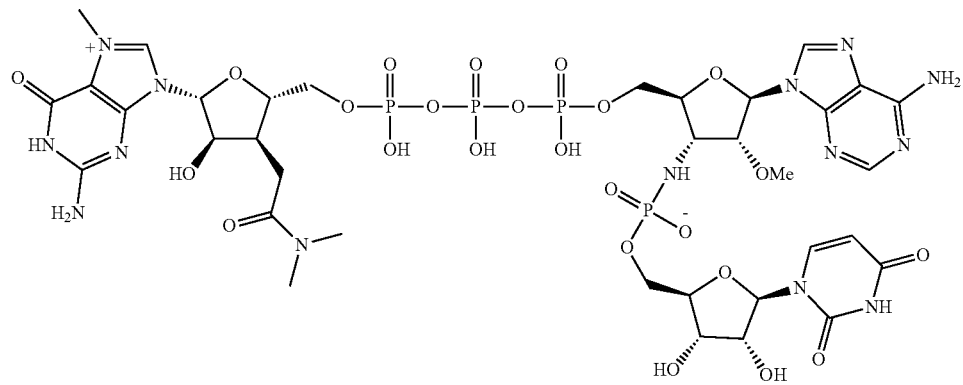
Compound 445
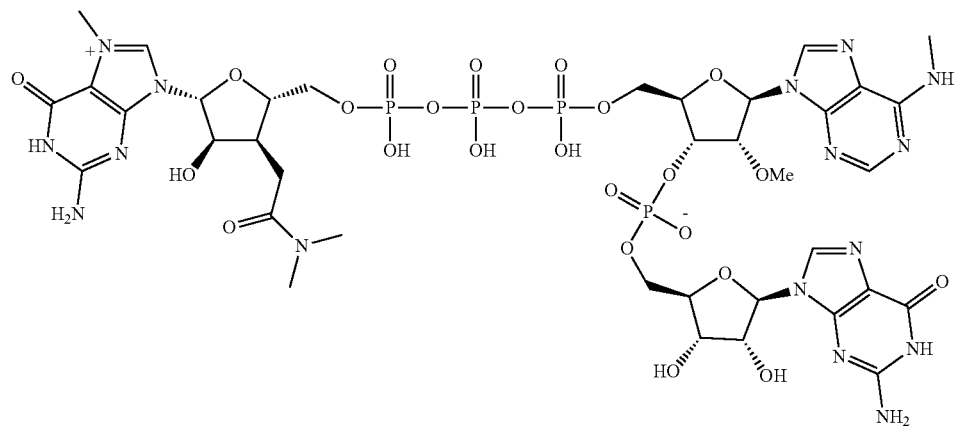
Compound 446
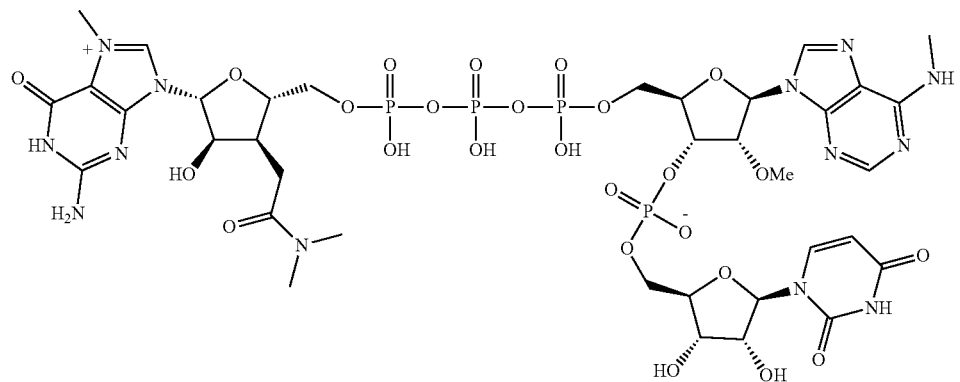

Compound 447
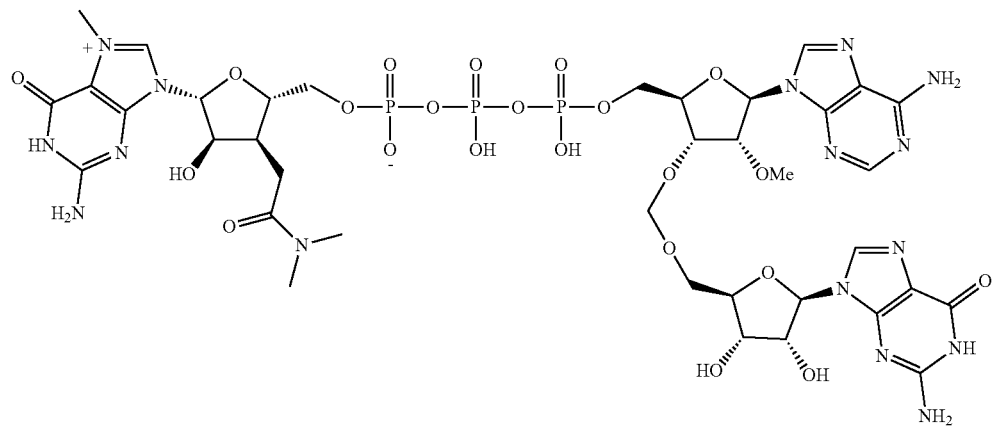
Compound 448
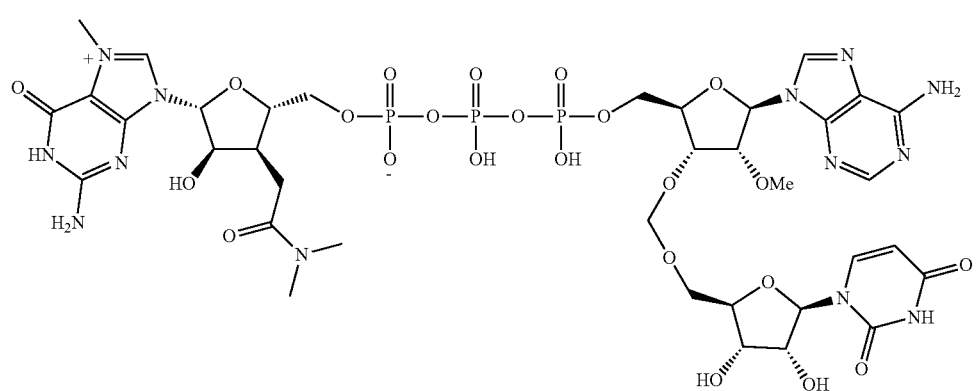
Compound 449
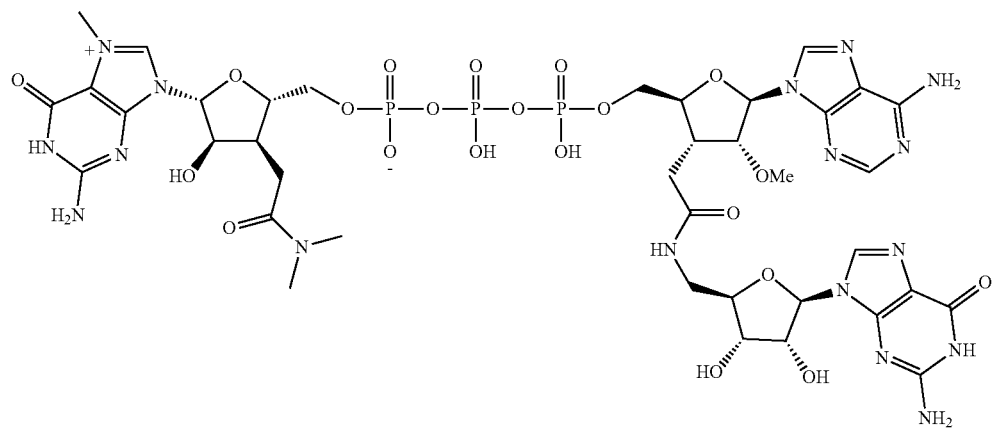
Compound 450
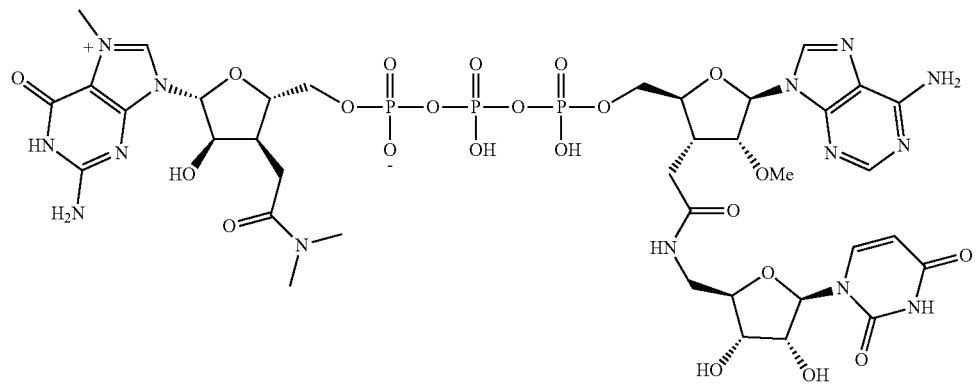

-continued
Compound 451
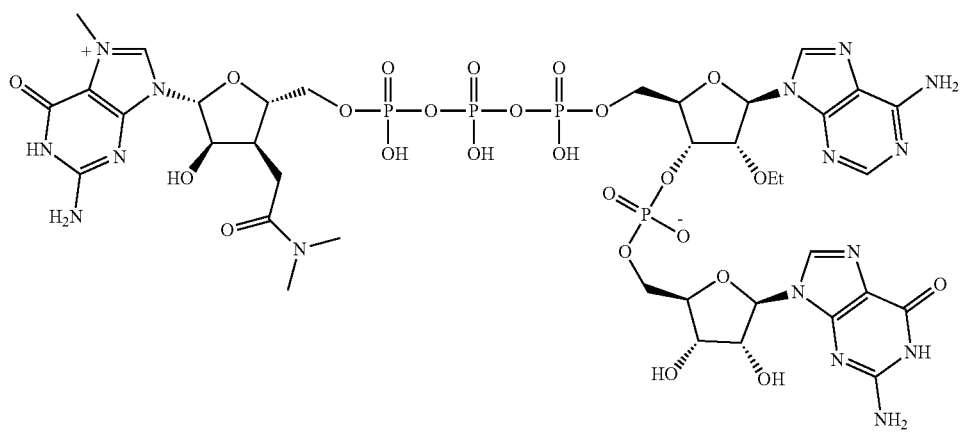
Compound 452
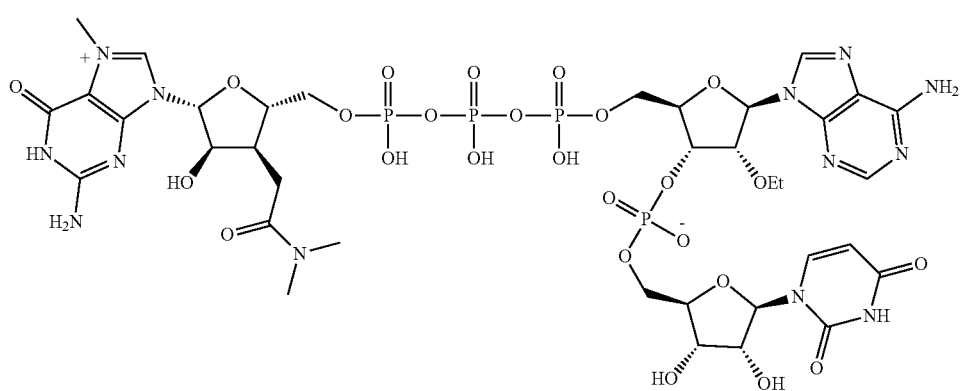
Compound 453
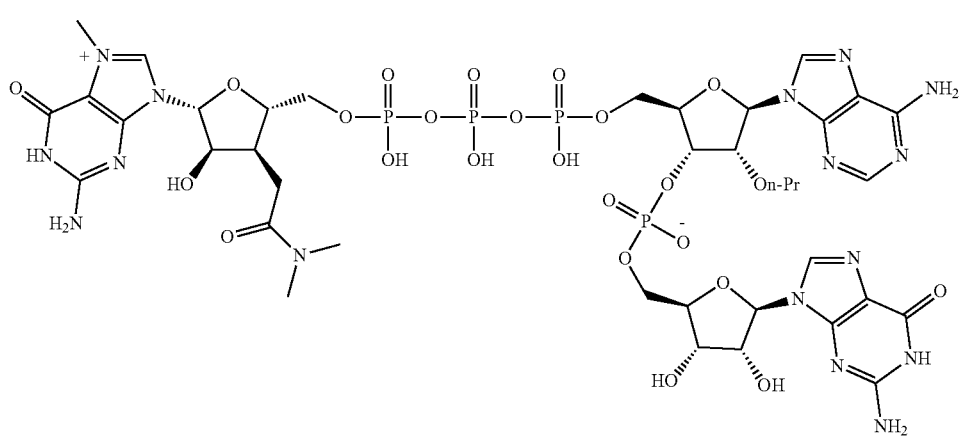
Compound 454
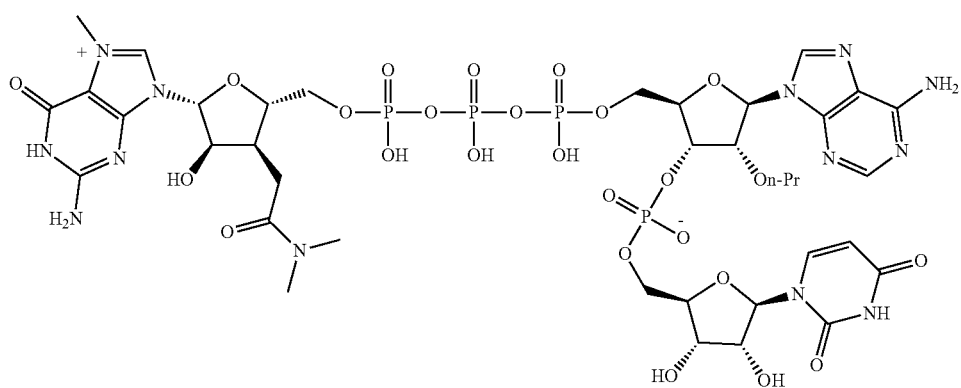

Compound 455
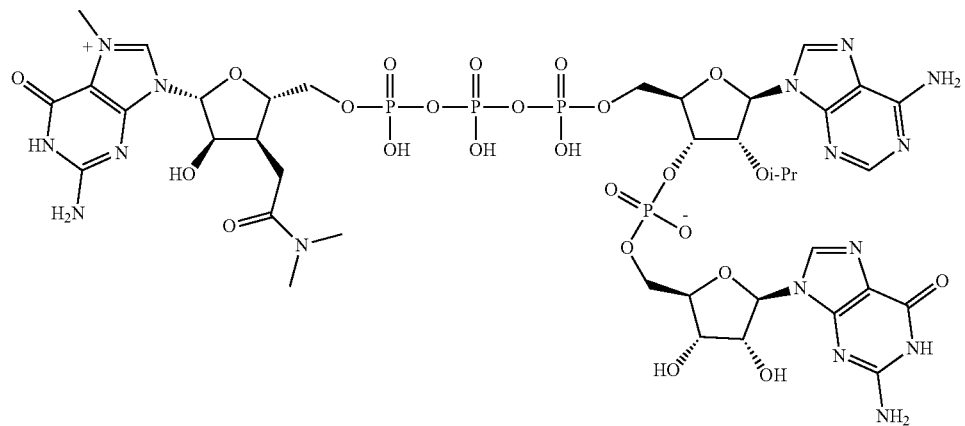
Compound 456
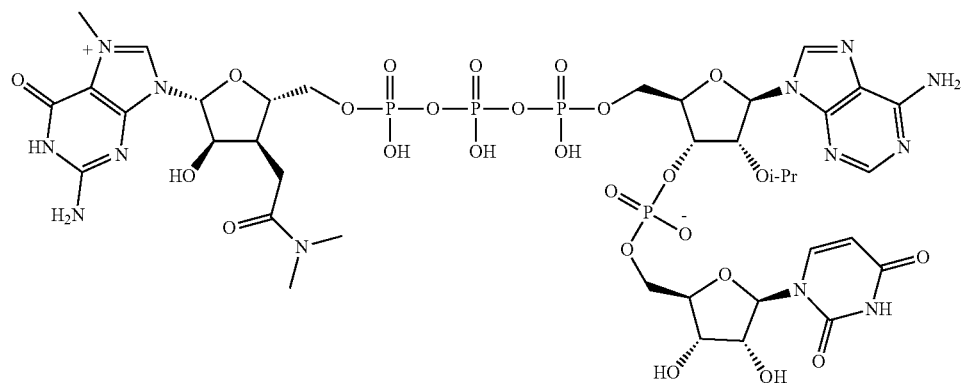
Compound 457
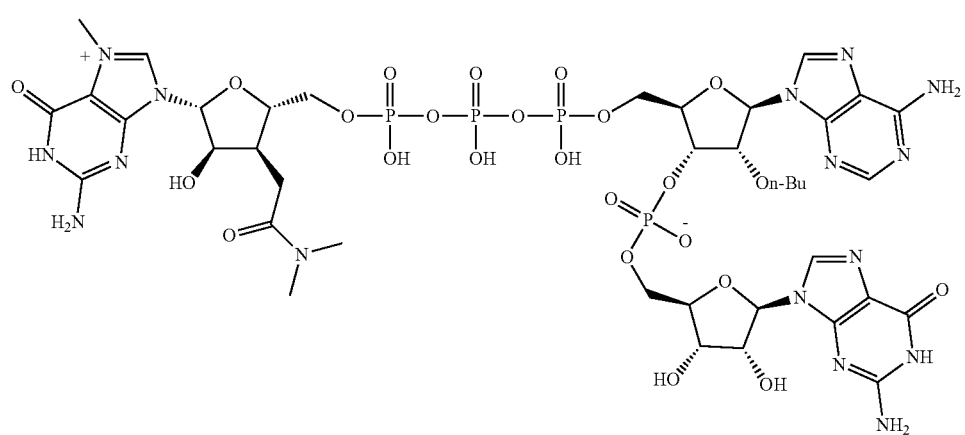

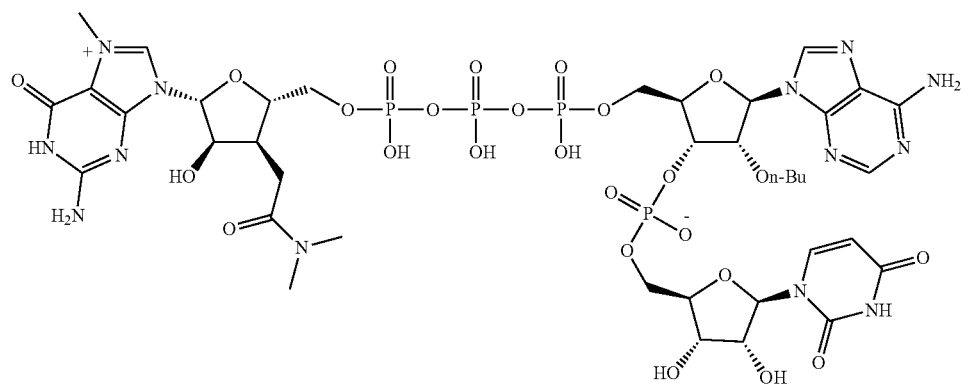
Compound 458
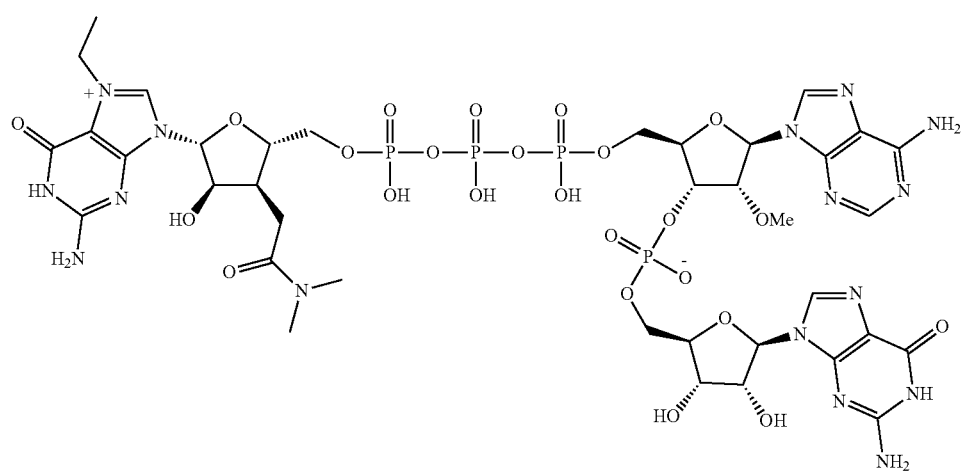
Compound 459
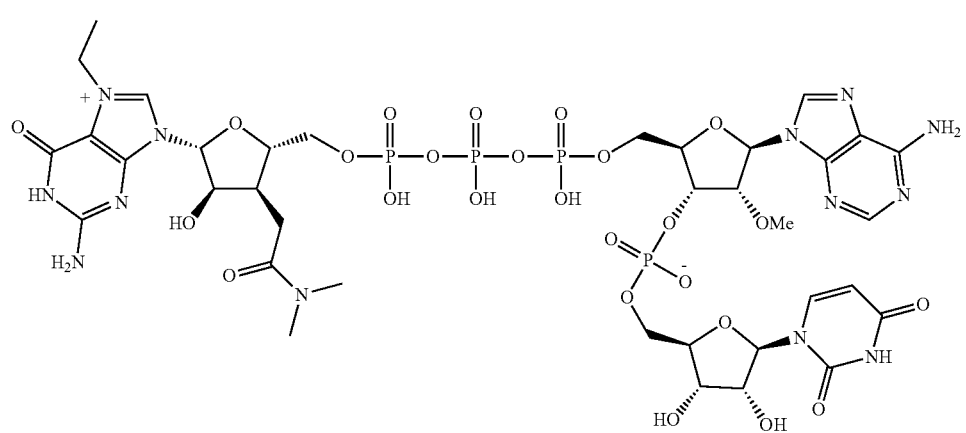
Compound 460

-continued
Compound 461
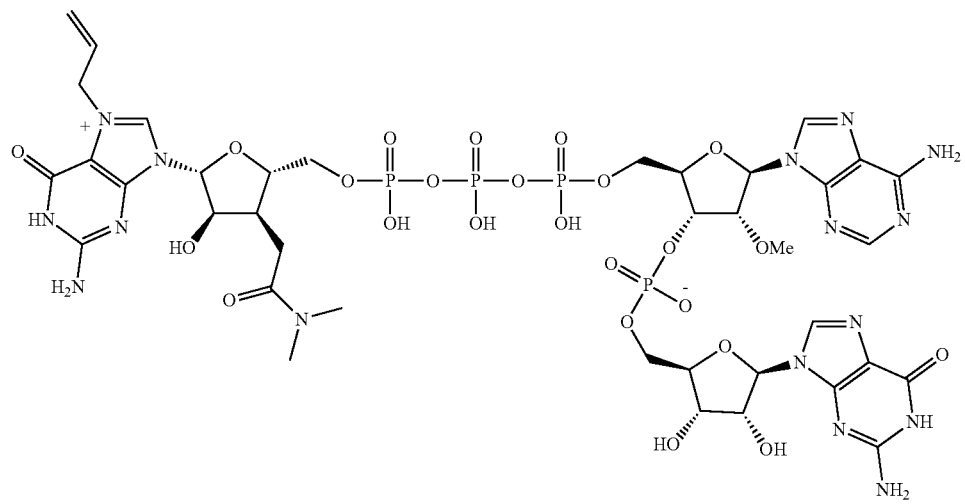
Compound 462
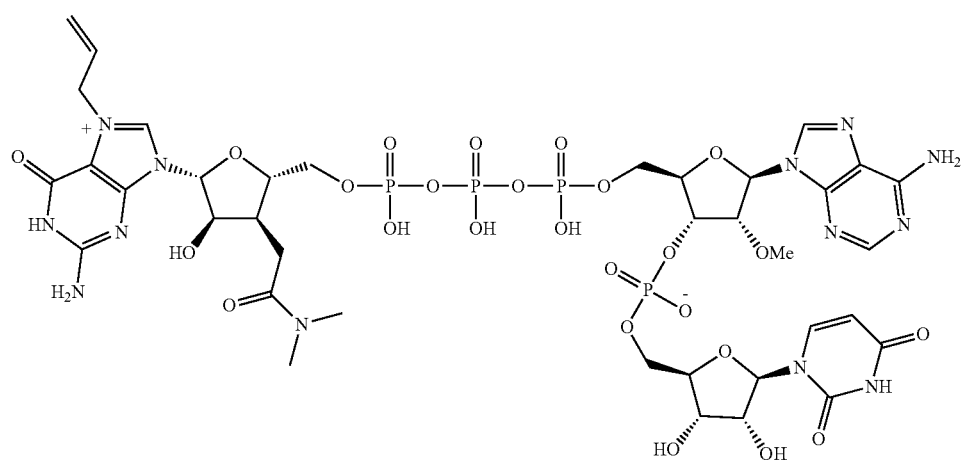
Compound 463
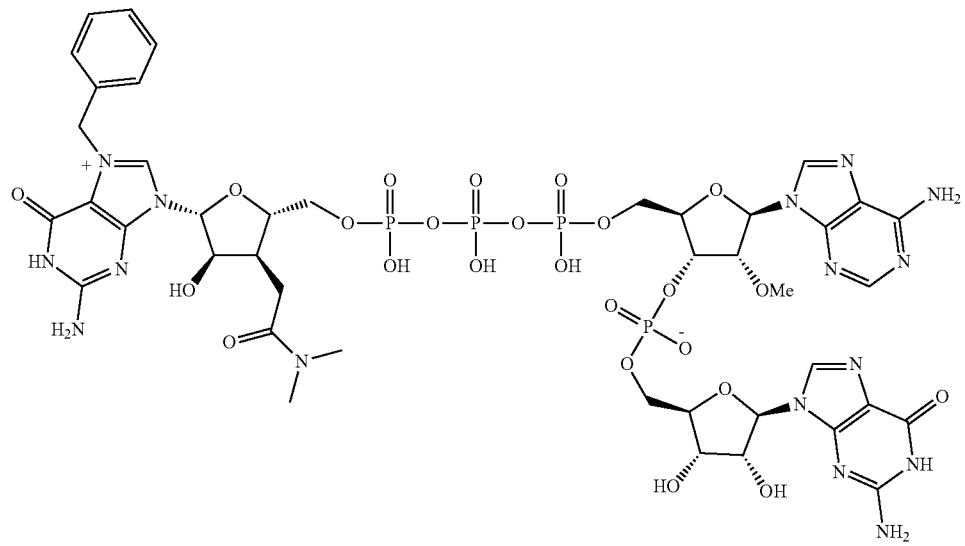

Compound 464
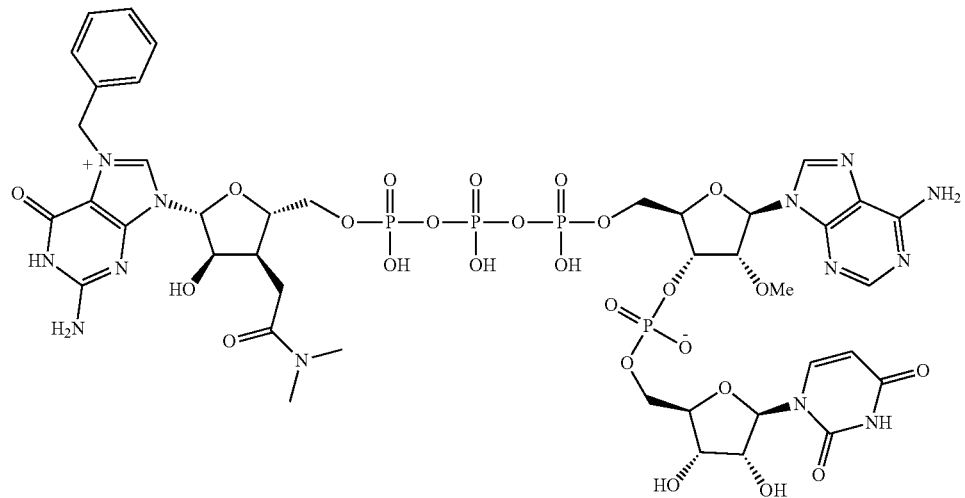
Compound 465
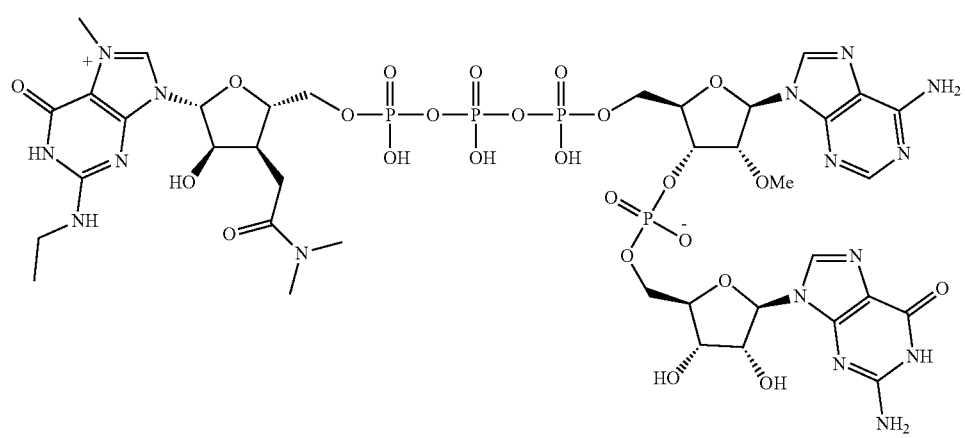
Compound 466
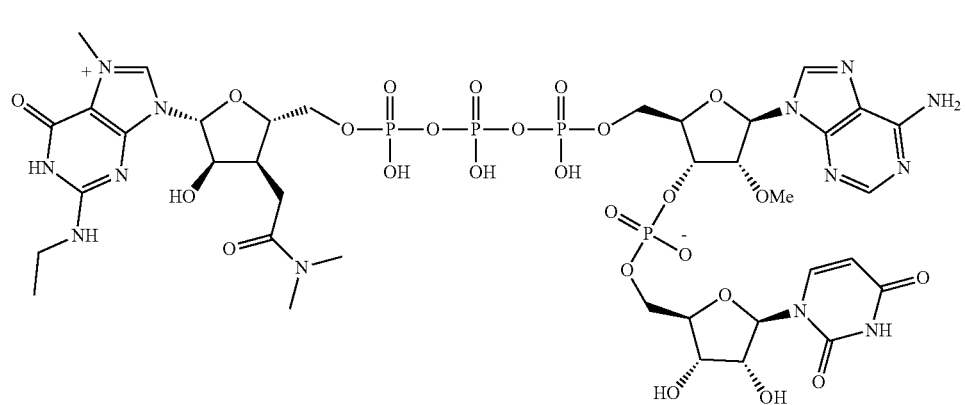

Compound 467
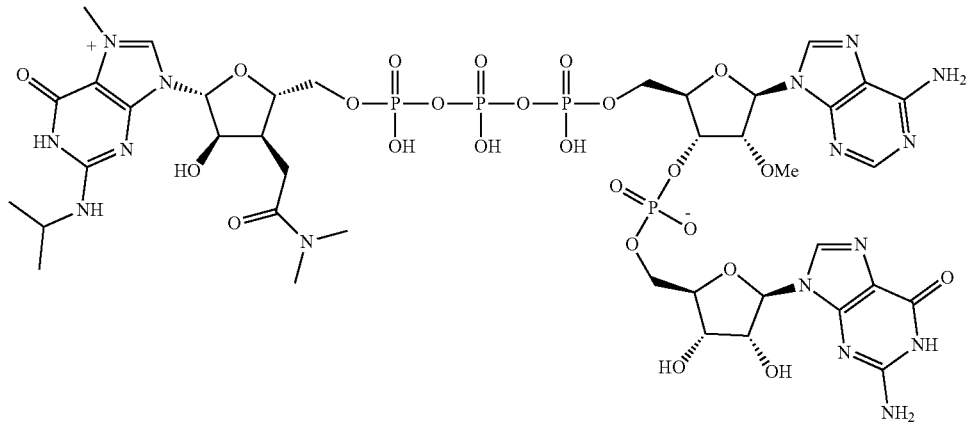
Compound 468
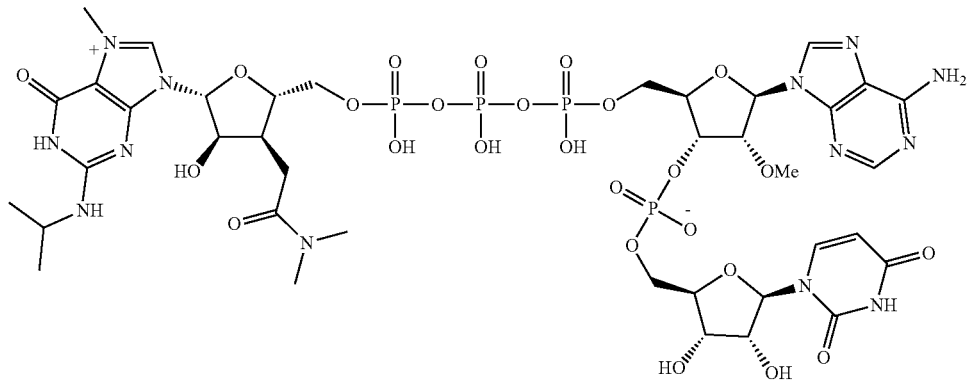
Compound 473
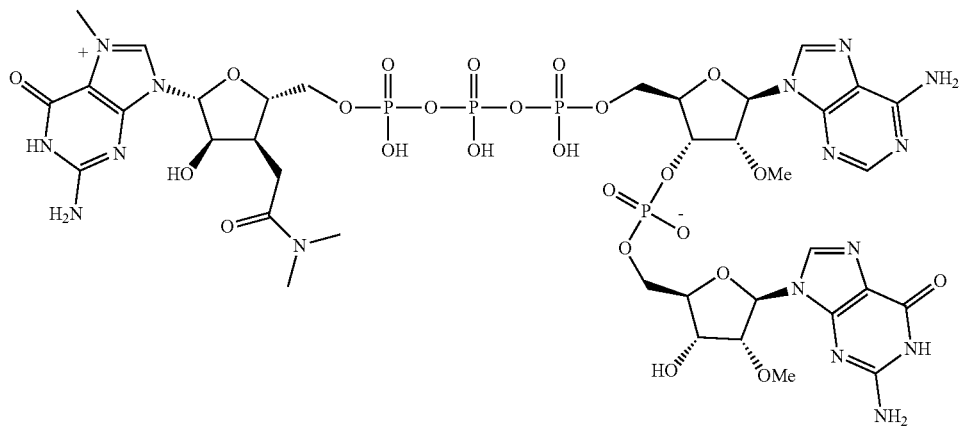
Compound 474
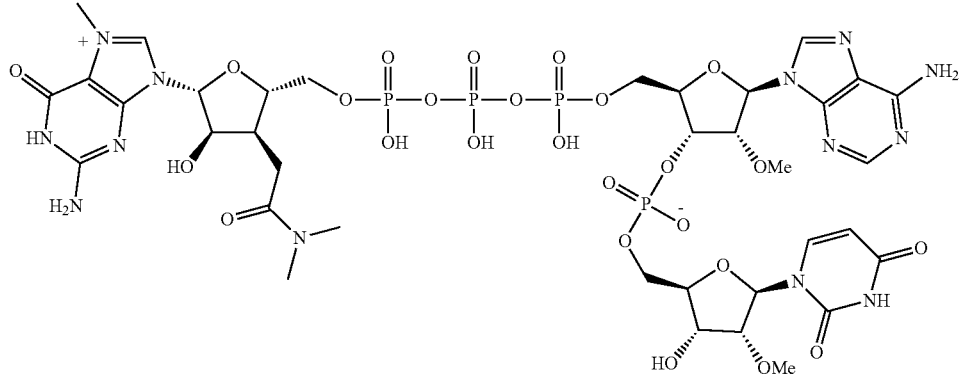

-continued
Compound 475
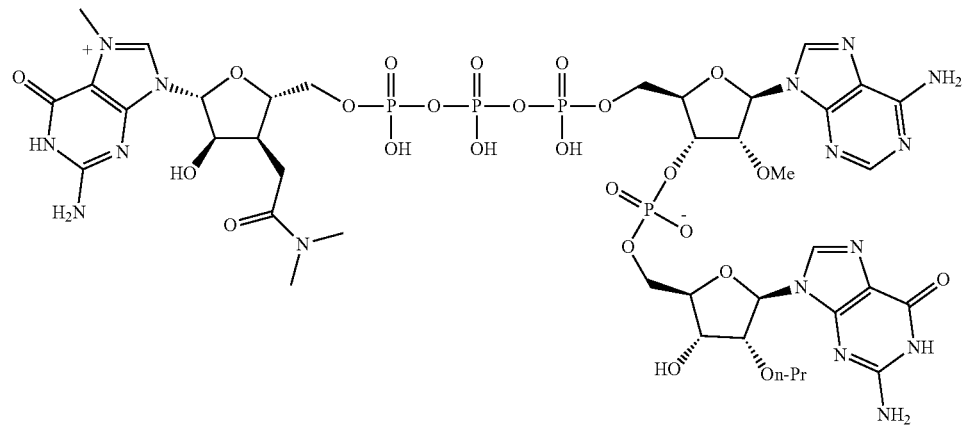
Compound 476
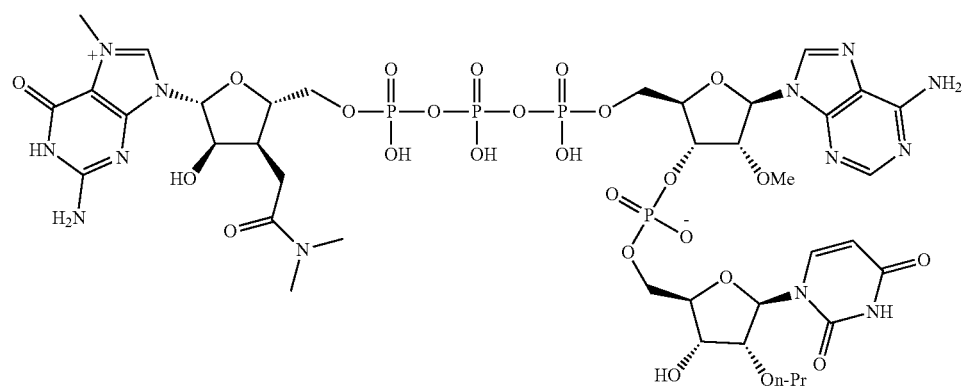
Compound 477
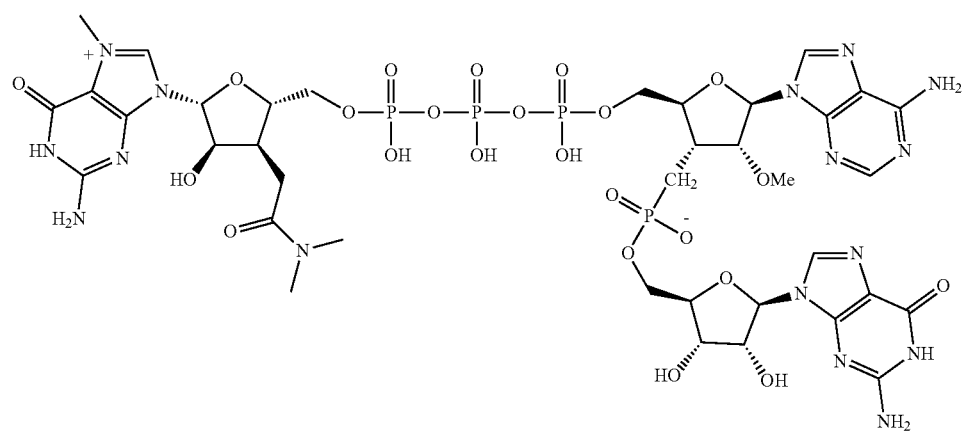
Compound 478
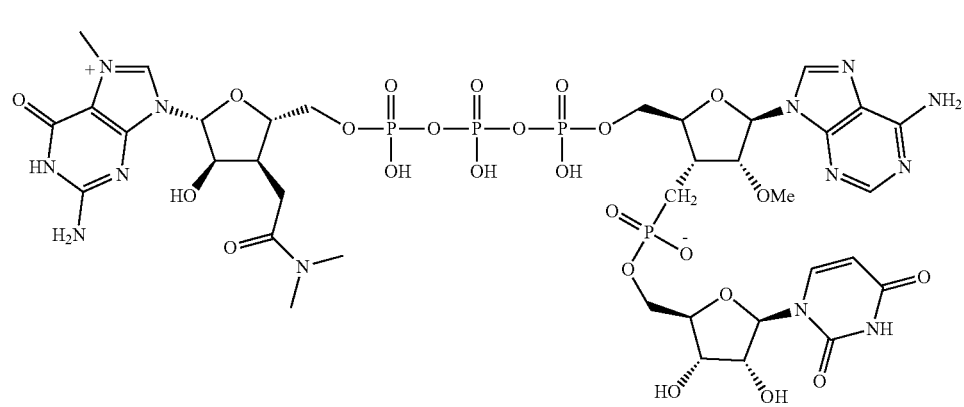

-continued
Compound 479
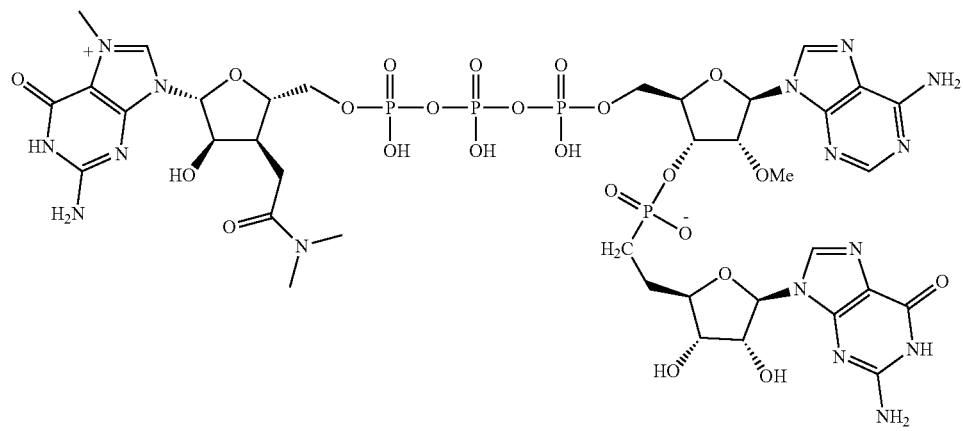
Compound 480
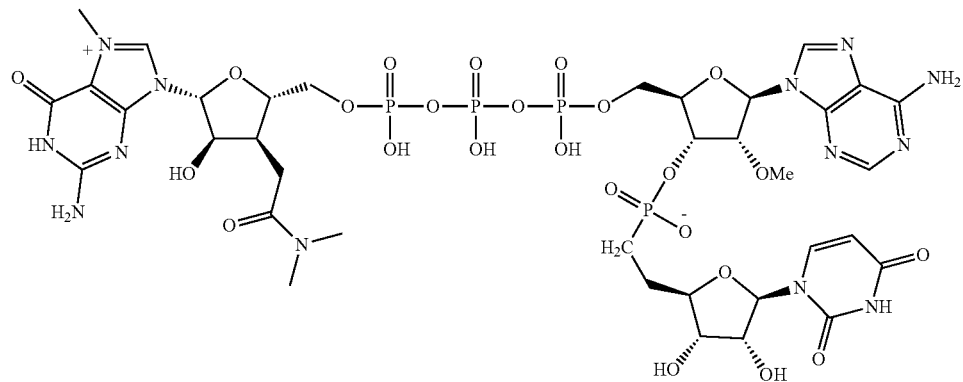
Compound 481
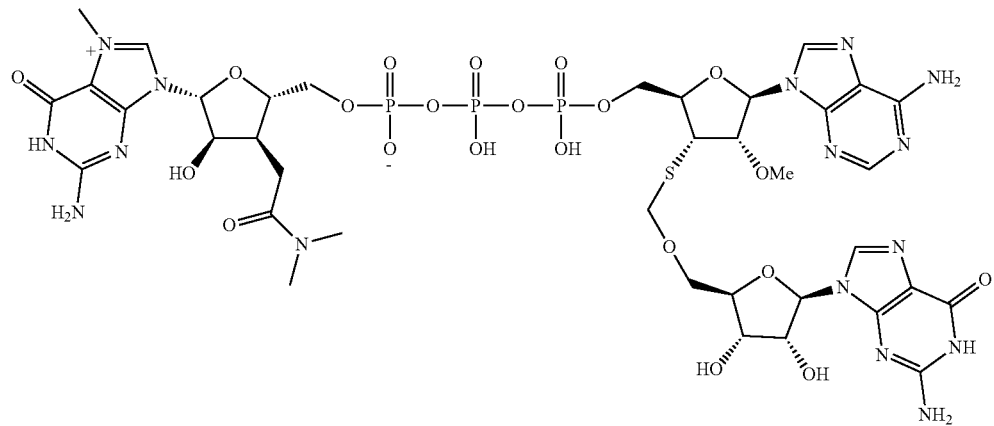
Compound 482
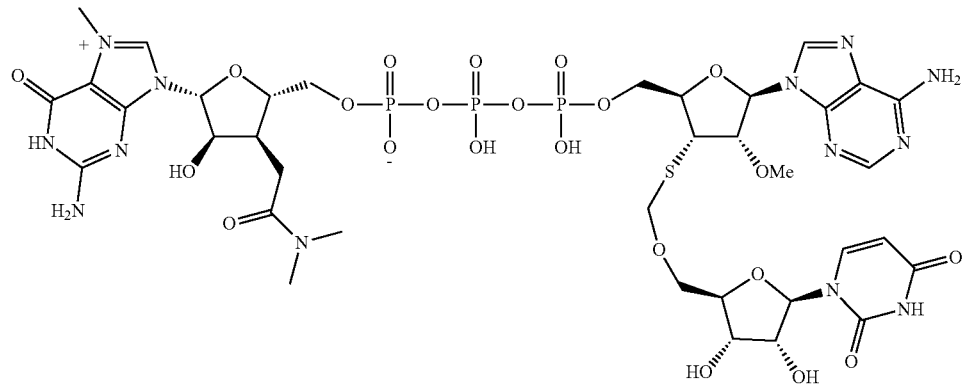

Compound 524
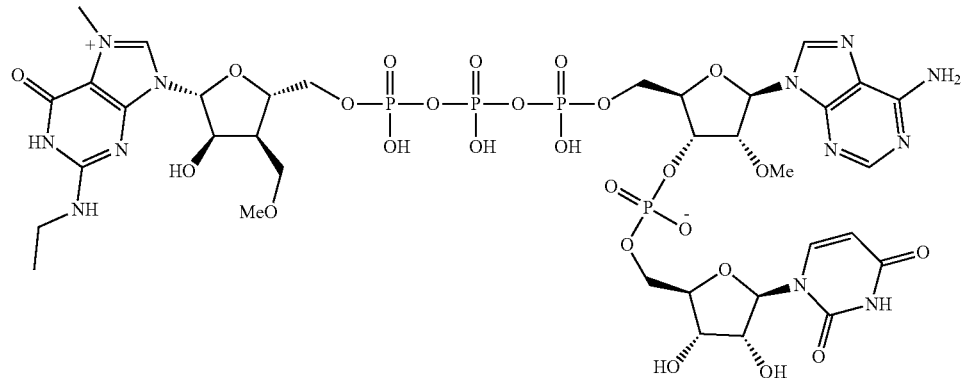
Compound 539
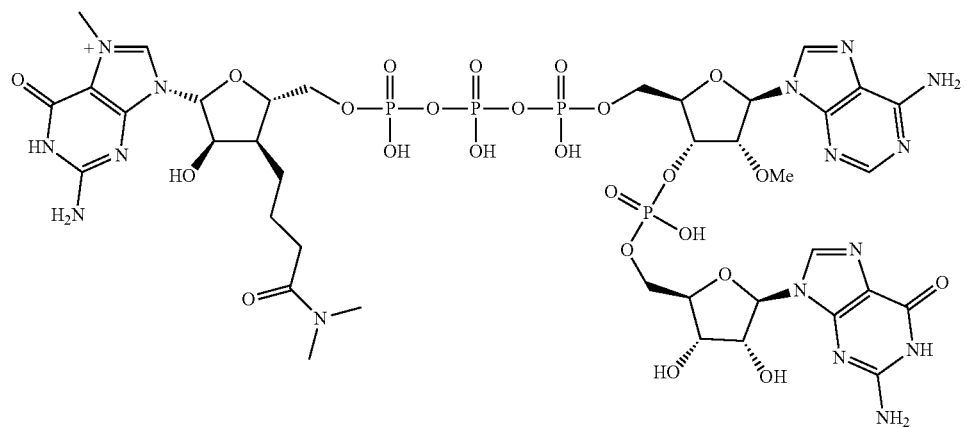
Compound 540
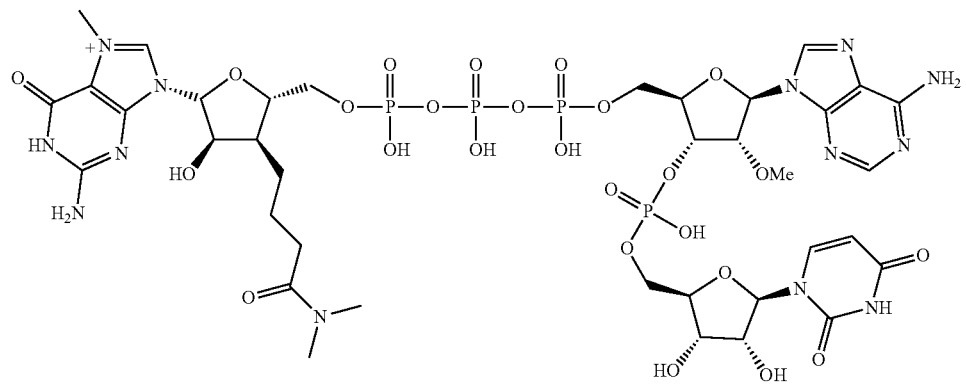
Compound 541
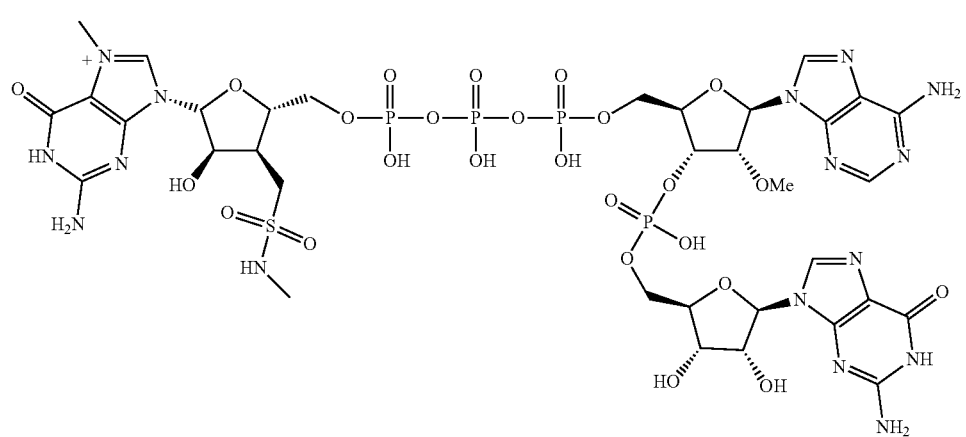

-continued
Compound 542
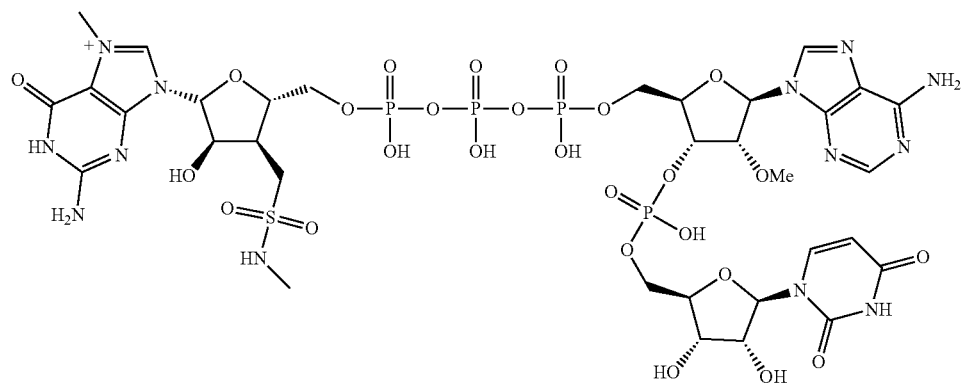
Compound 547
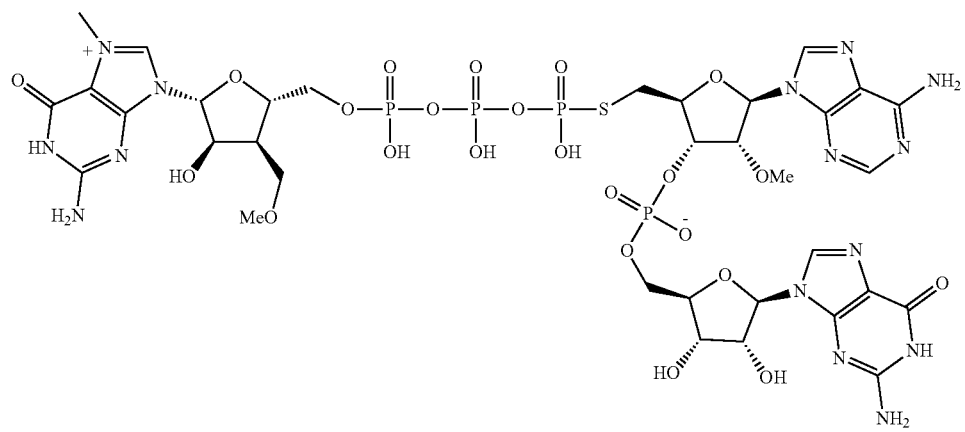
Compound 548
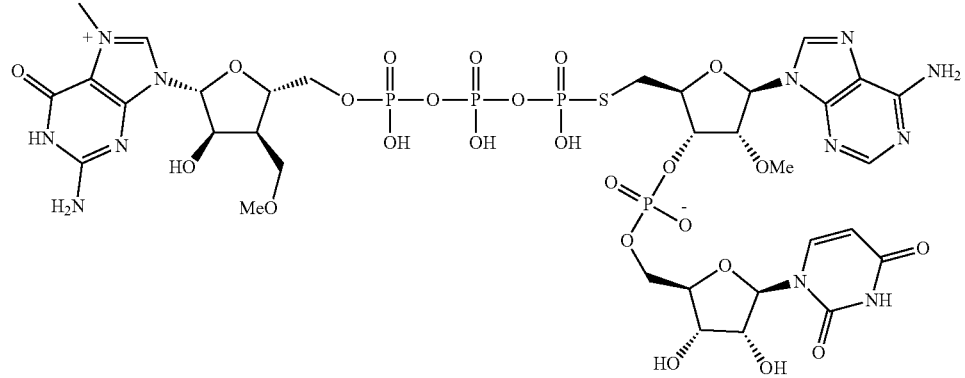
Compound 557
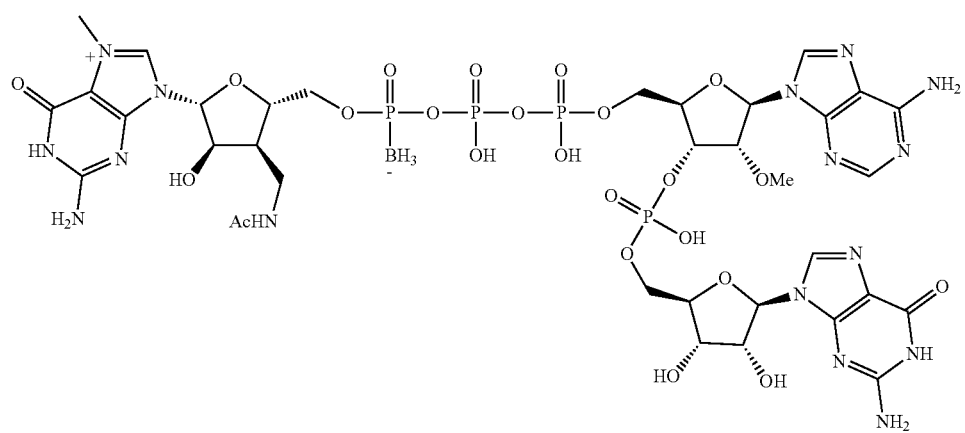

Compound 558
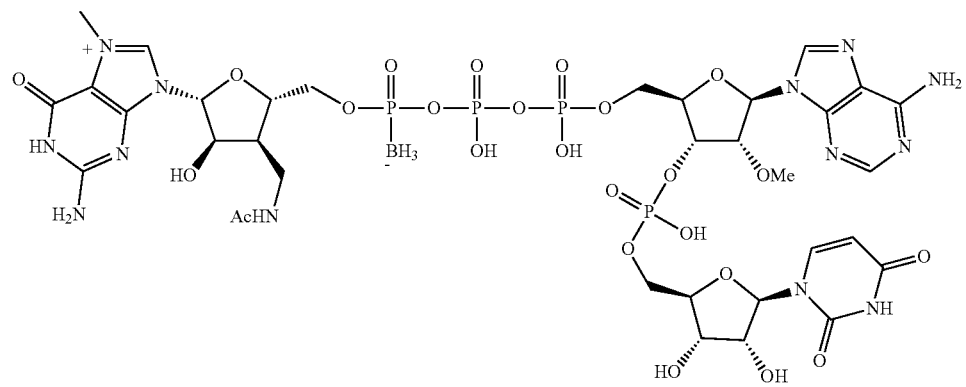
Compound 559
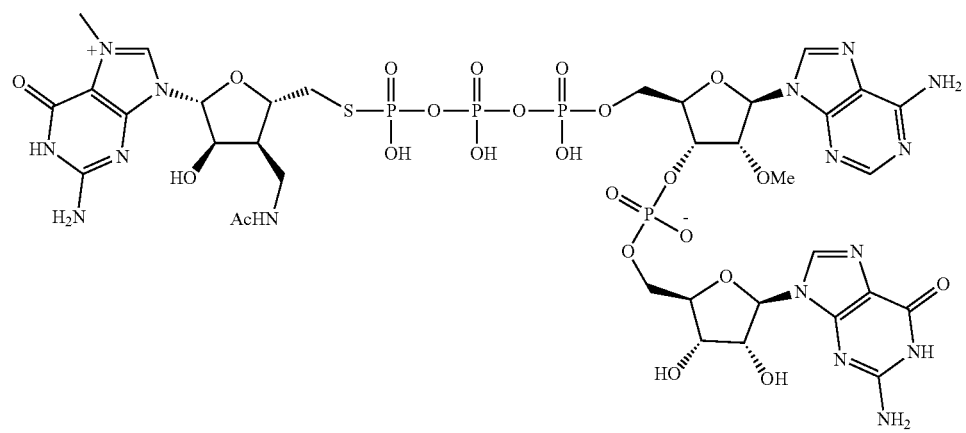
Compound 560
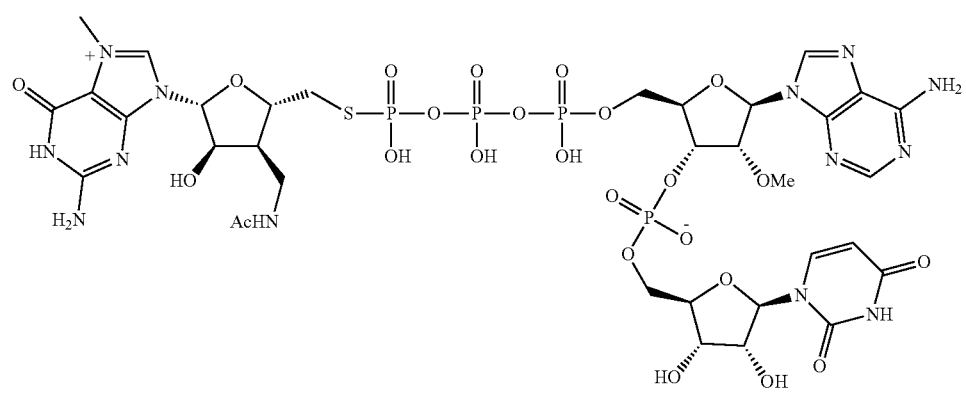
Compound 561
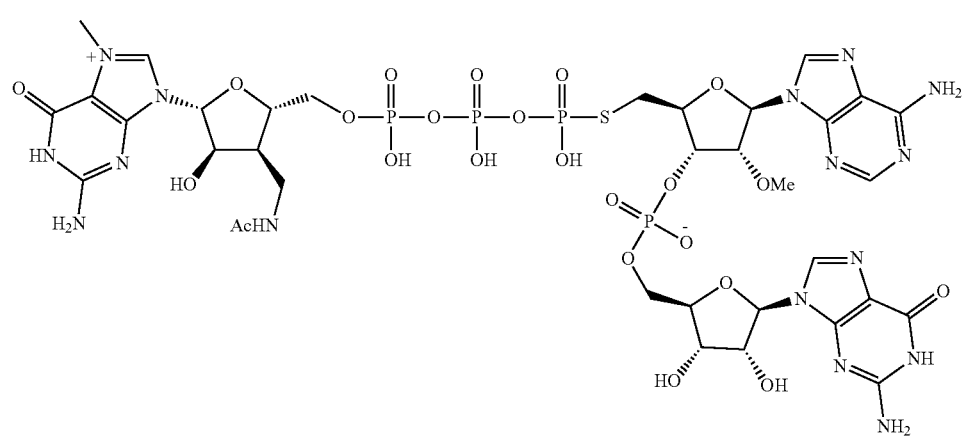

-continued
Compound 562
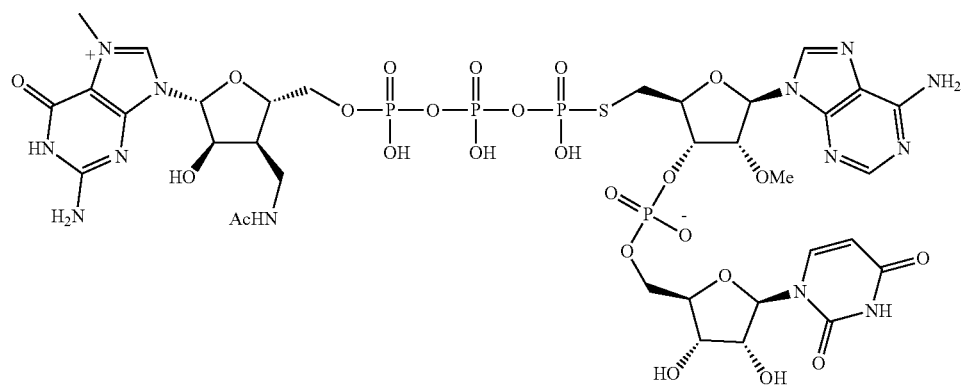
Compound 563
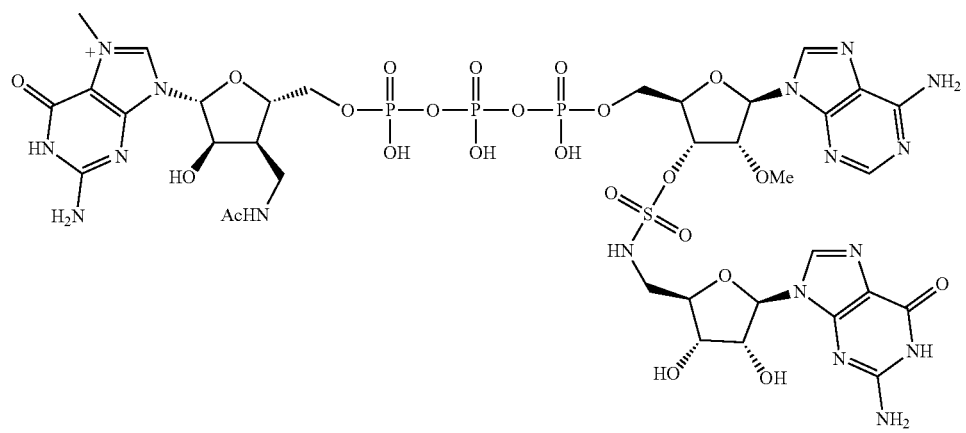
Compound 564
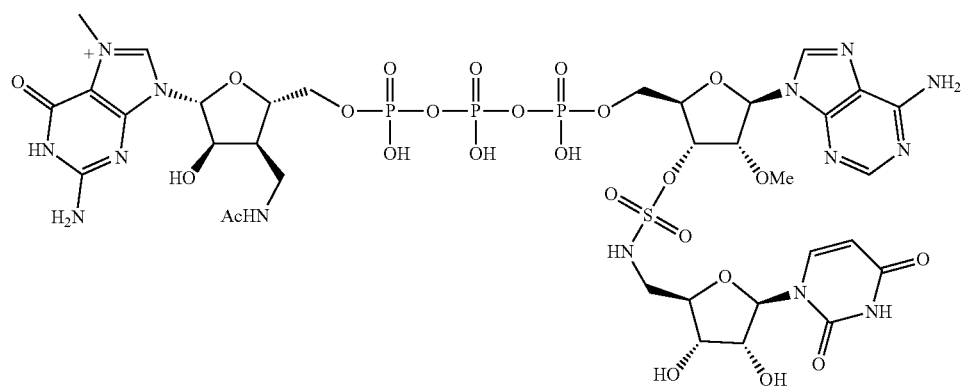
Compound 565
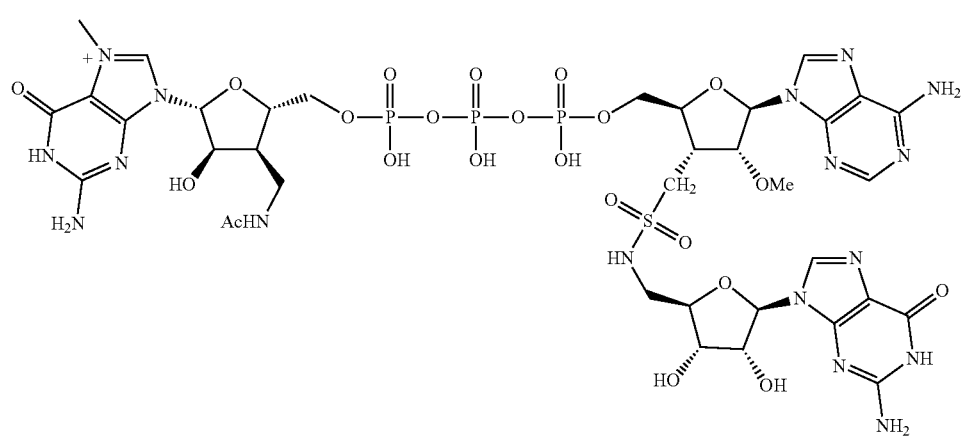

Compound 566
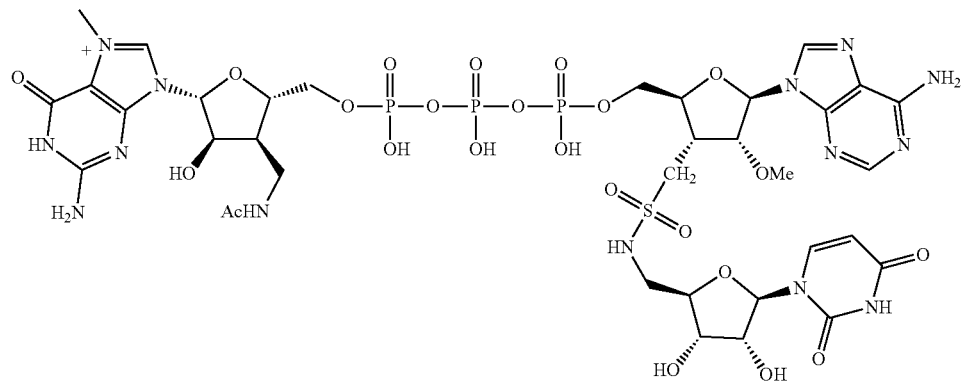
Compound 567
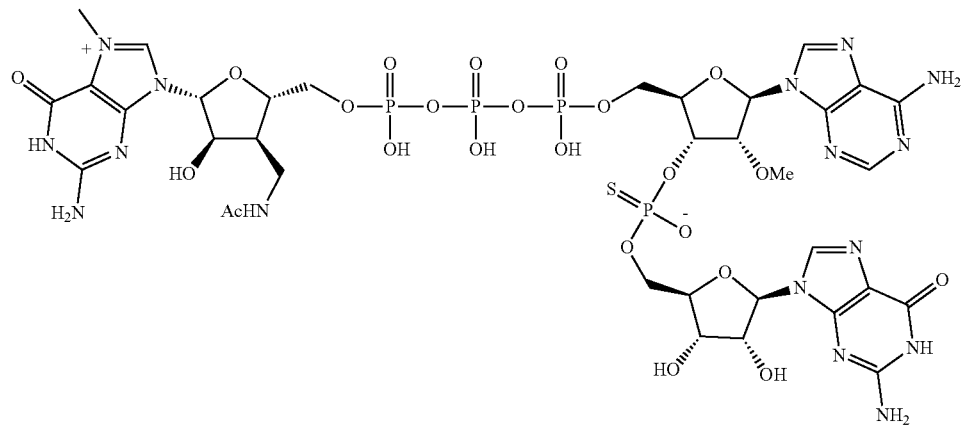
Compound 568
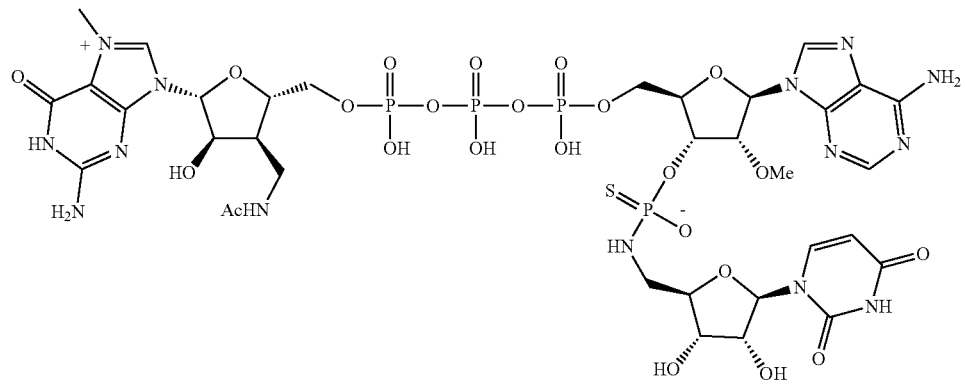
Compound 569
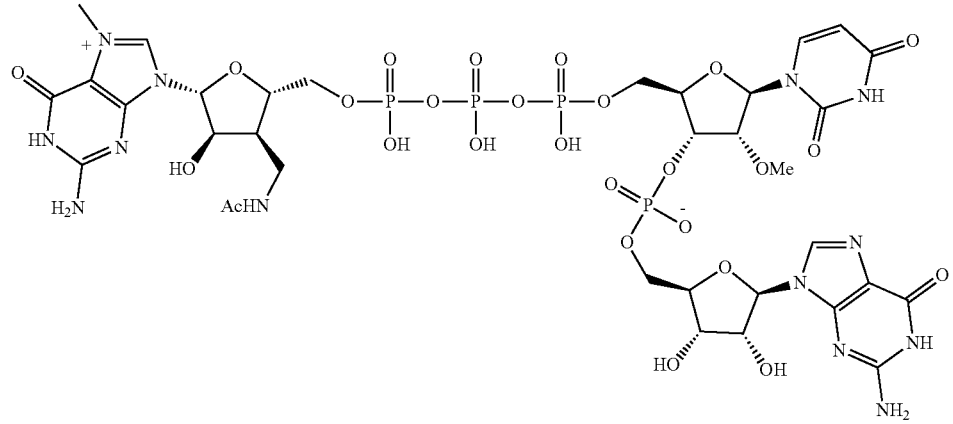

-continued
Compound 570
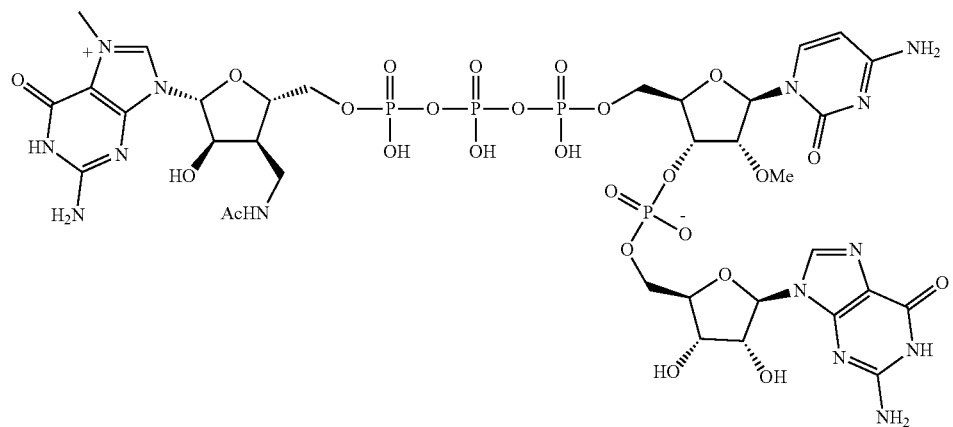
Compound 571
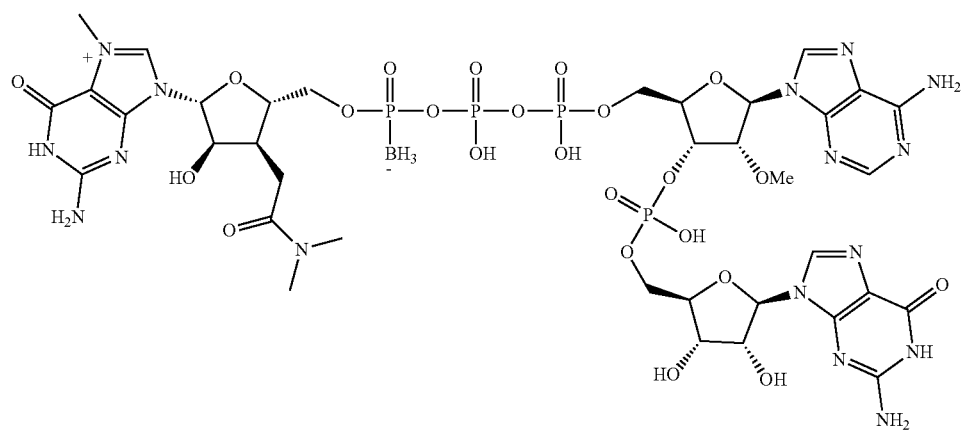
Compound 572
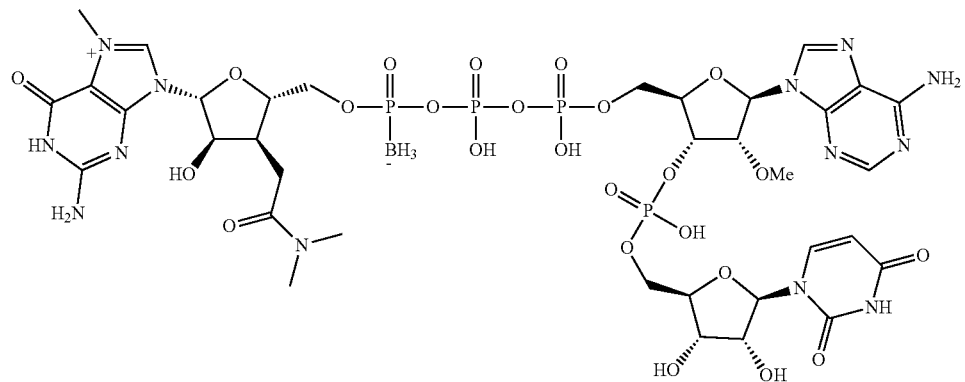

Compound 573
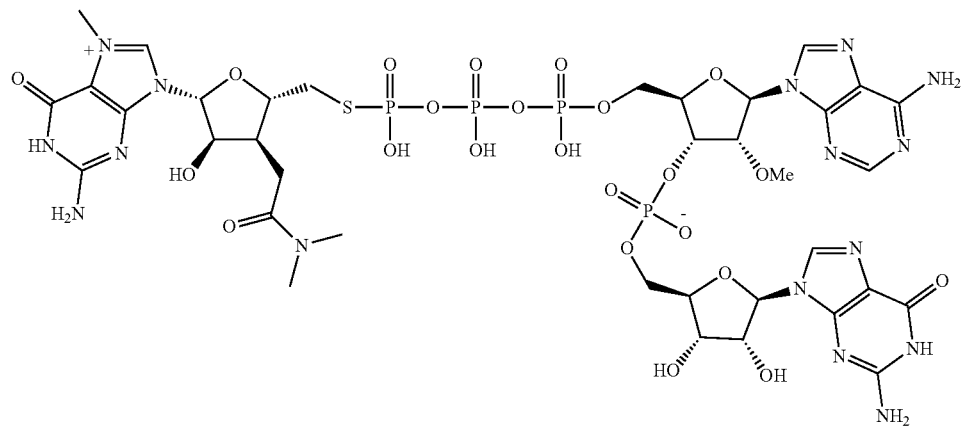
Compound 574
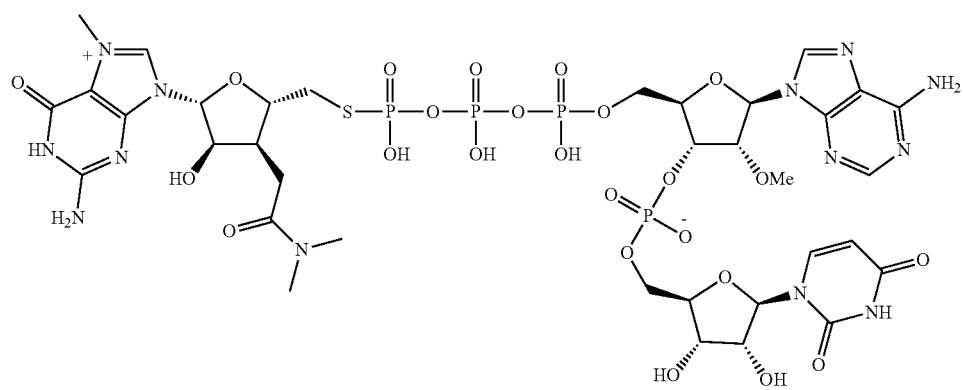
Compound 575
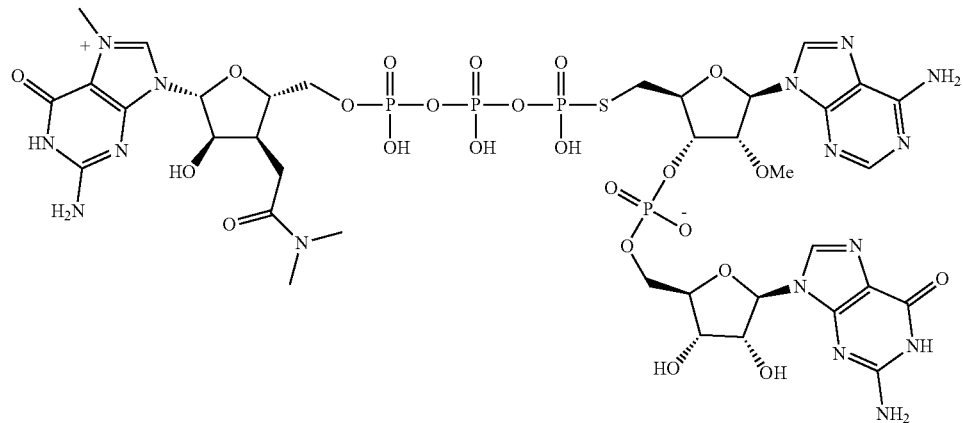
Compound 576
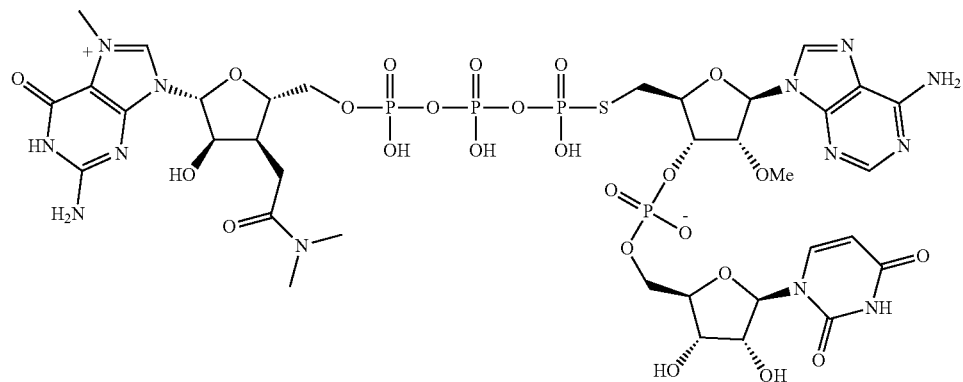

Compound 577
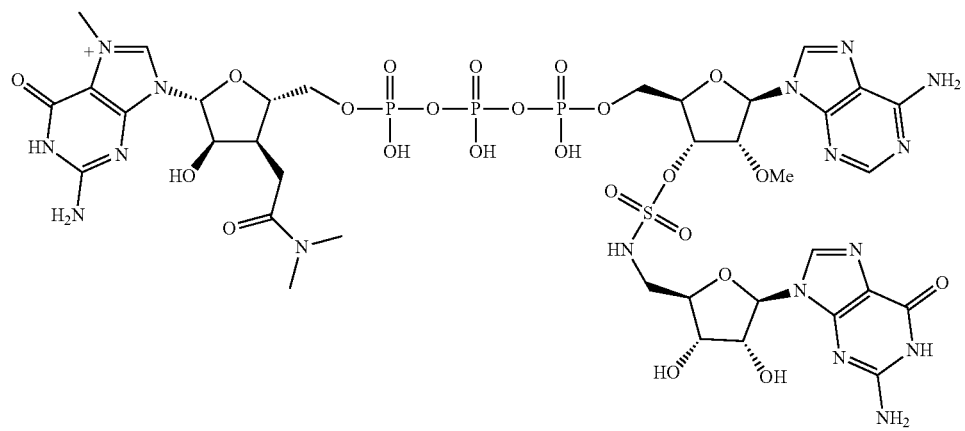
Compound 578
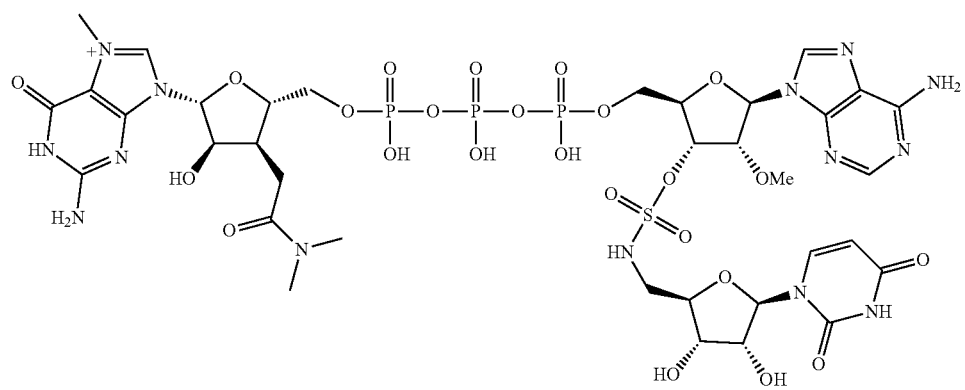
Compound 579
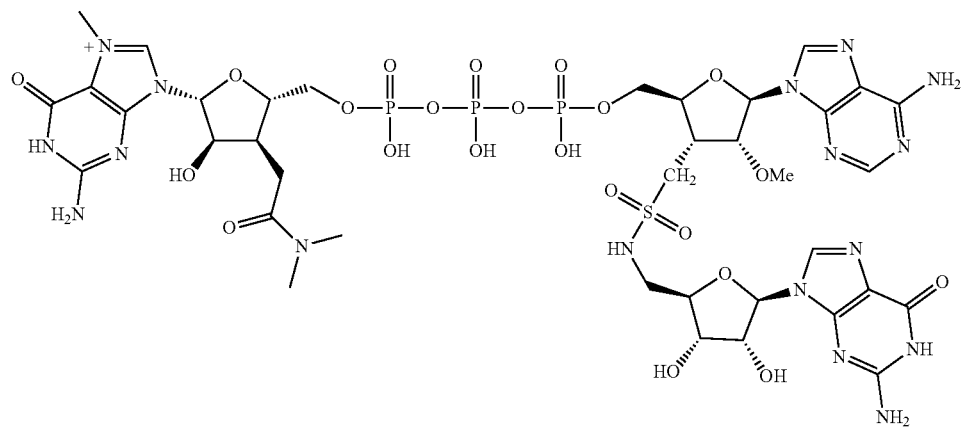
Compound 580
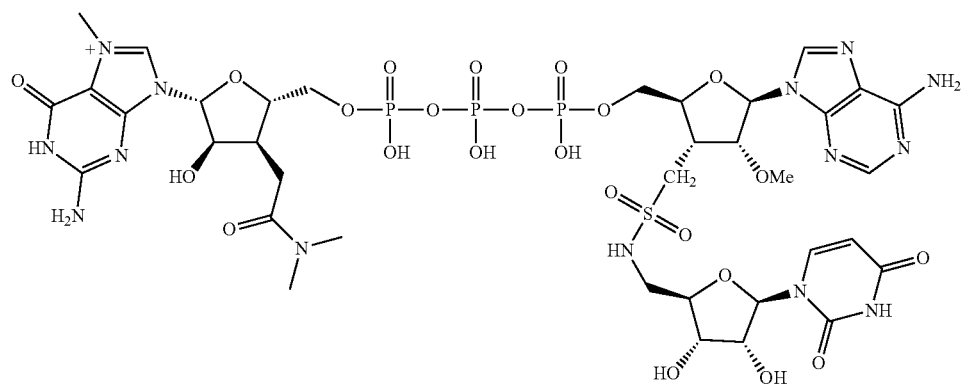

-continued
Compound 581
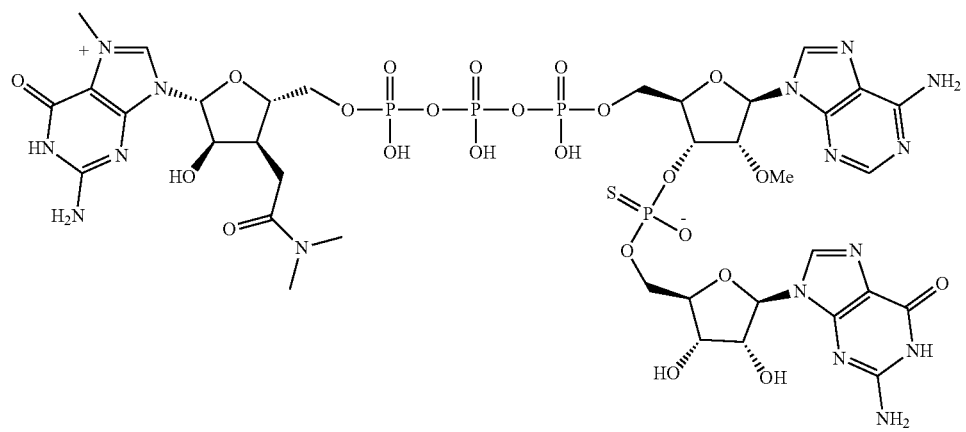
Compound 582
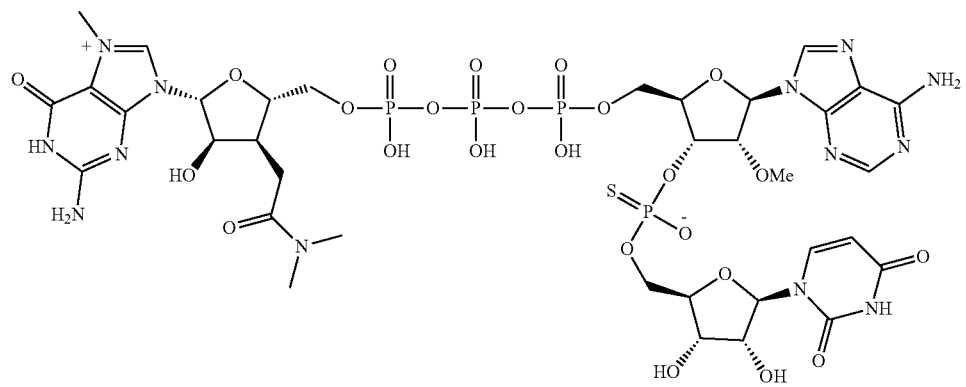
Compound 583
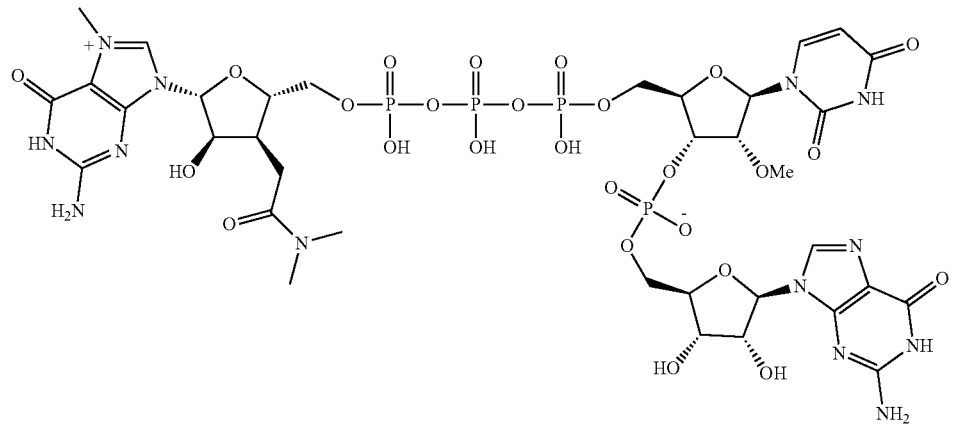
Compound 584
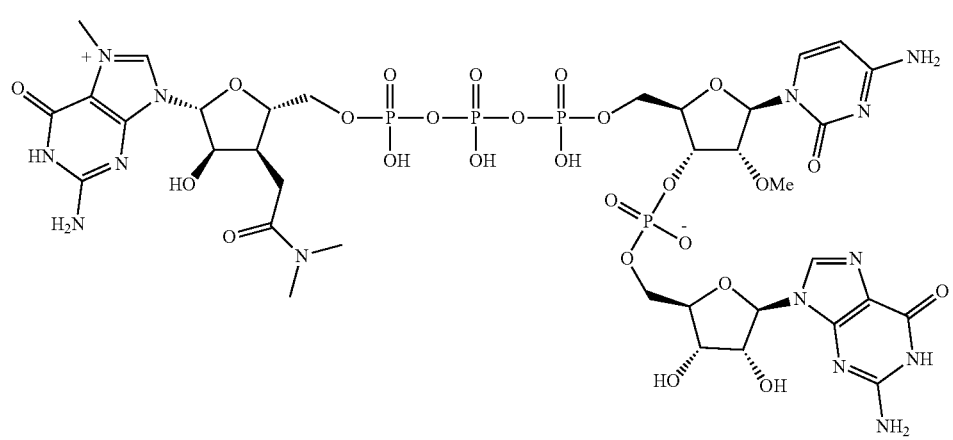

-continued
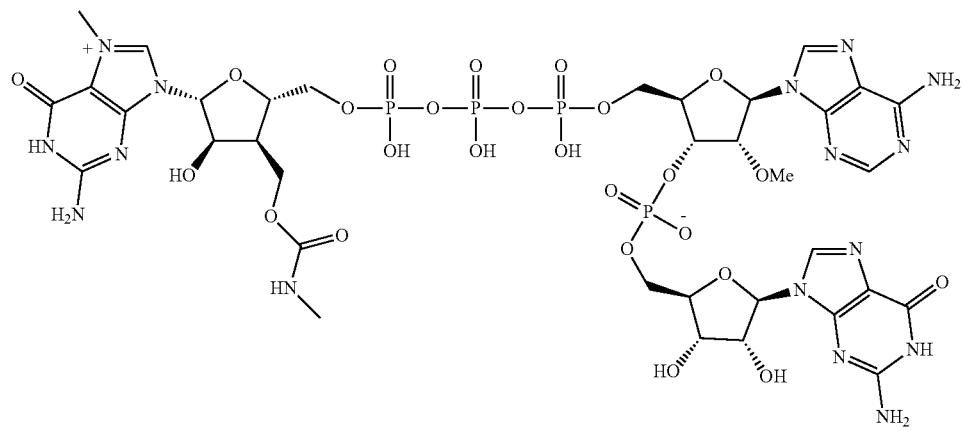
Compound 631
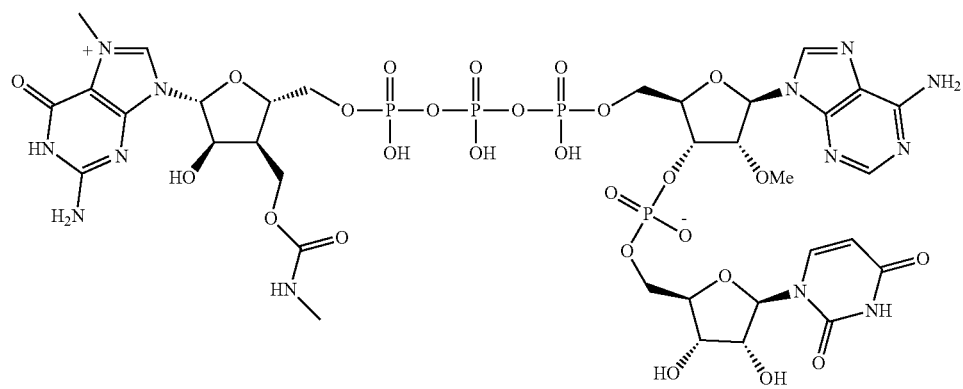
Compound 632
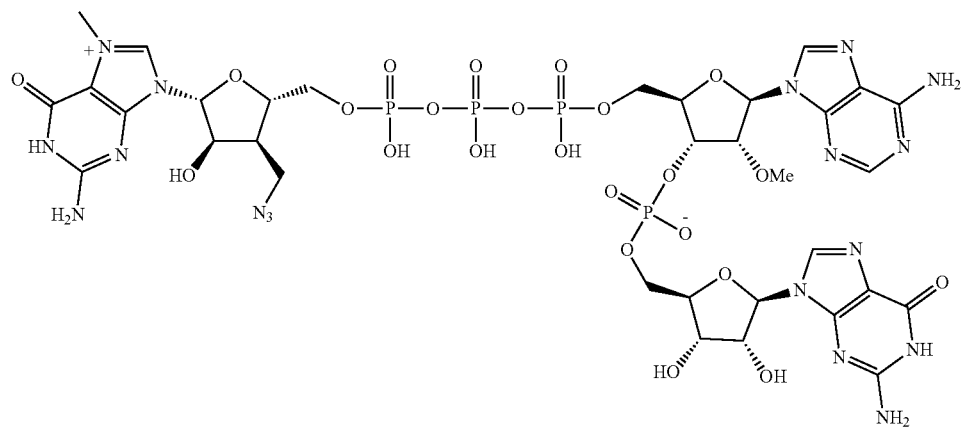
Compound 635
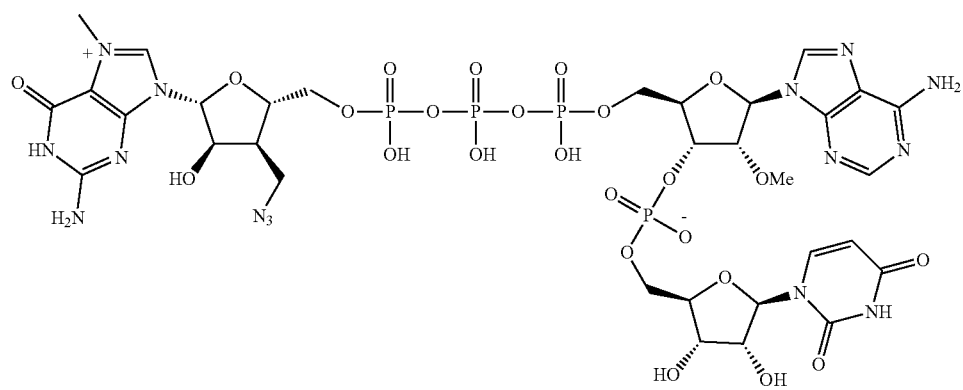
Compound 636

-continued
Compound 637
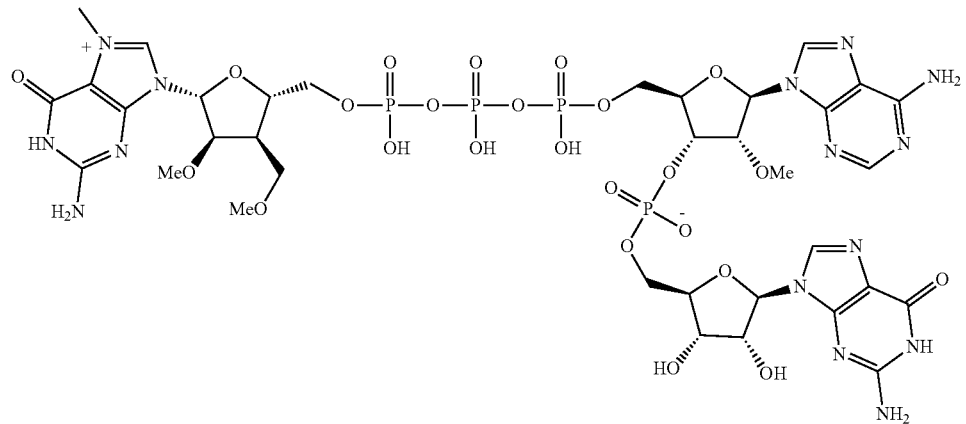
Compound 638
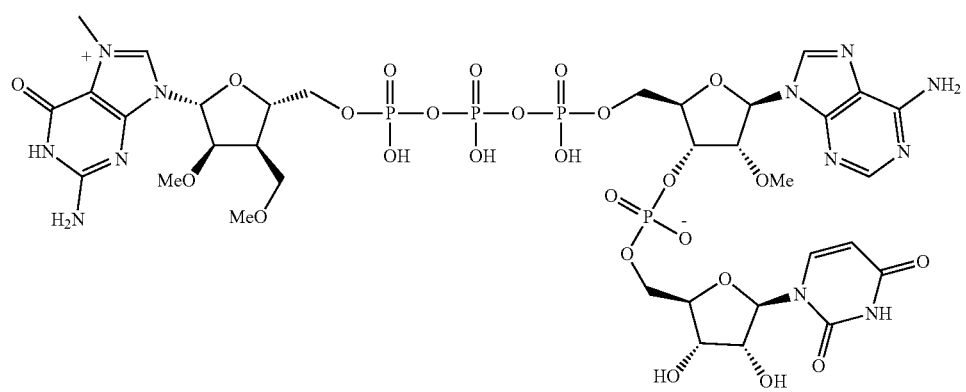
Compound 639
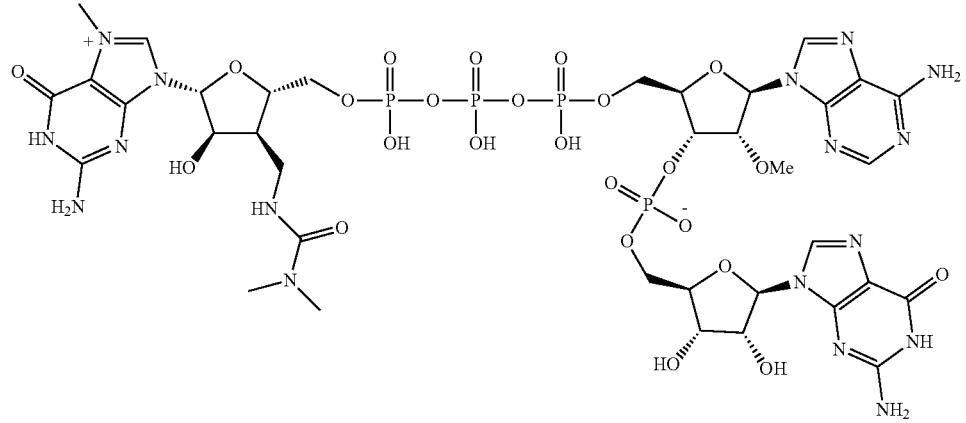
Compound 640
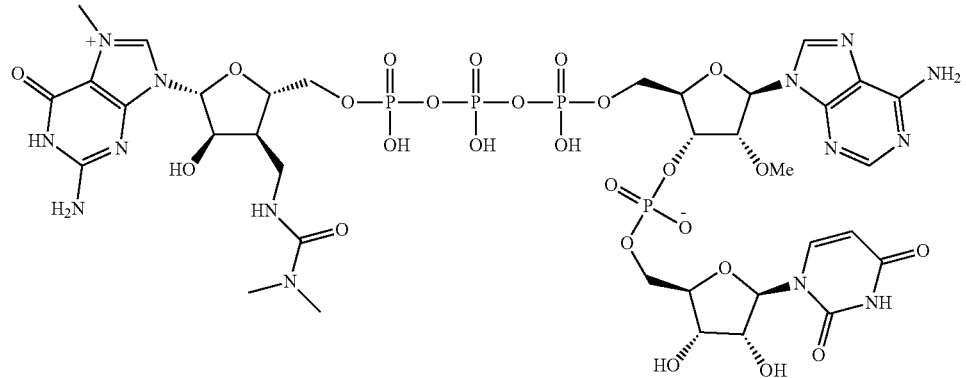

-continued
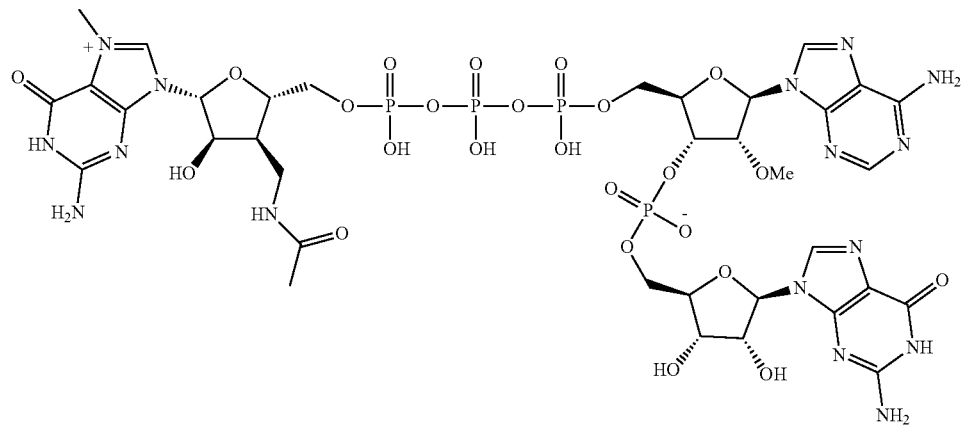
Compound 641
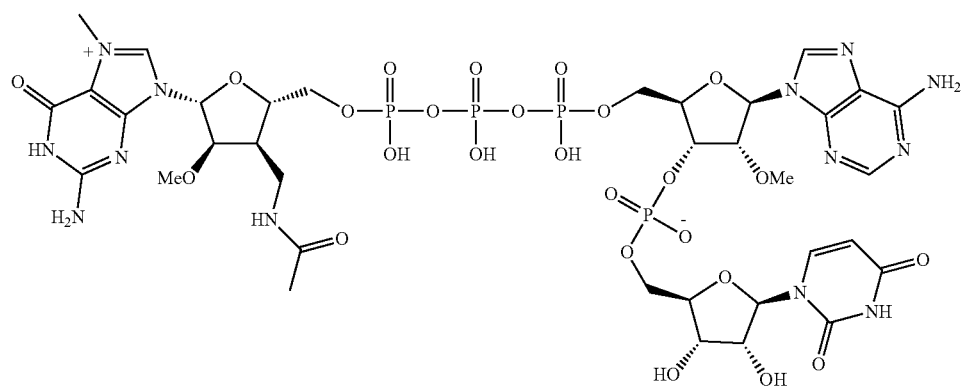
Compound 642
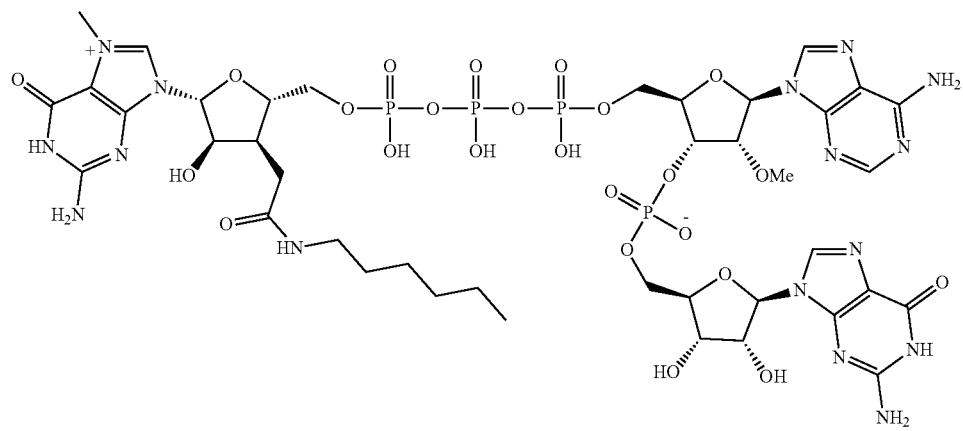
Compound 643
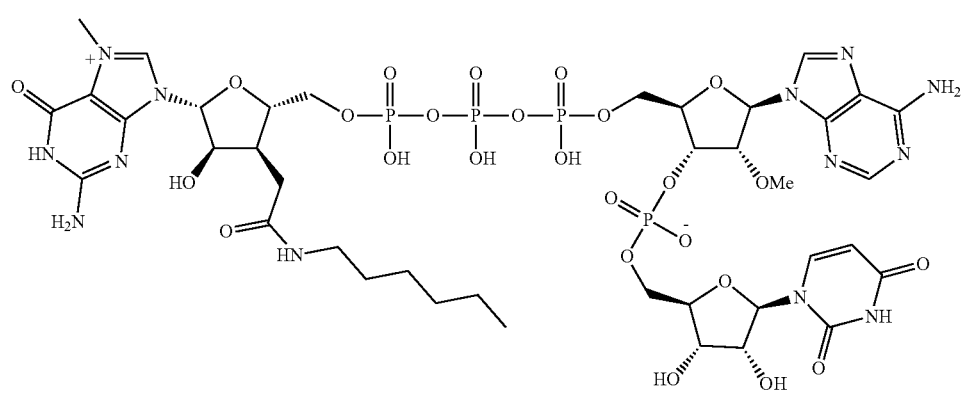
Compound 644

Compound 645
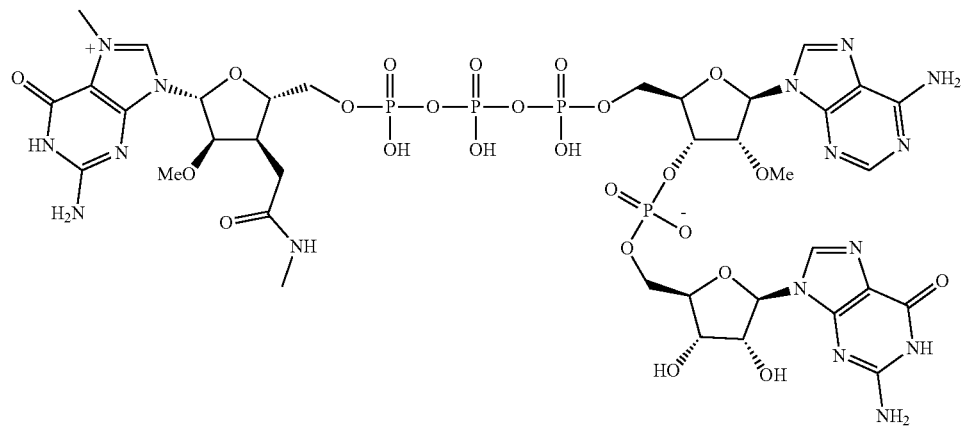
Compound 646
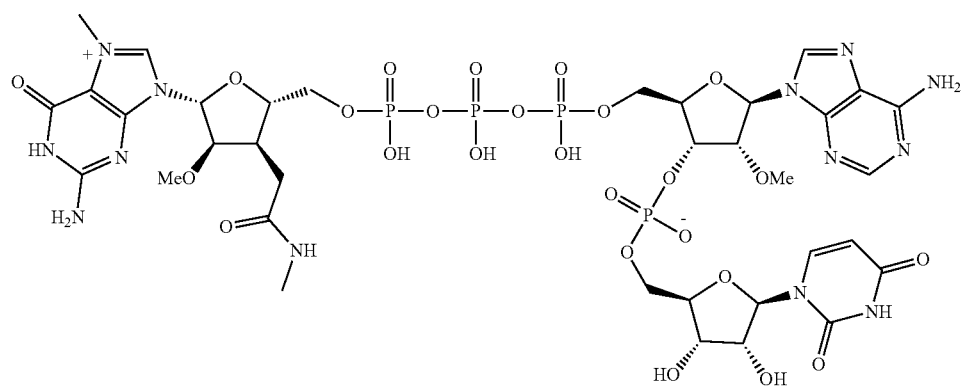
Compound 647
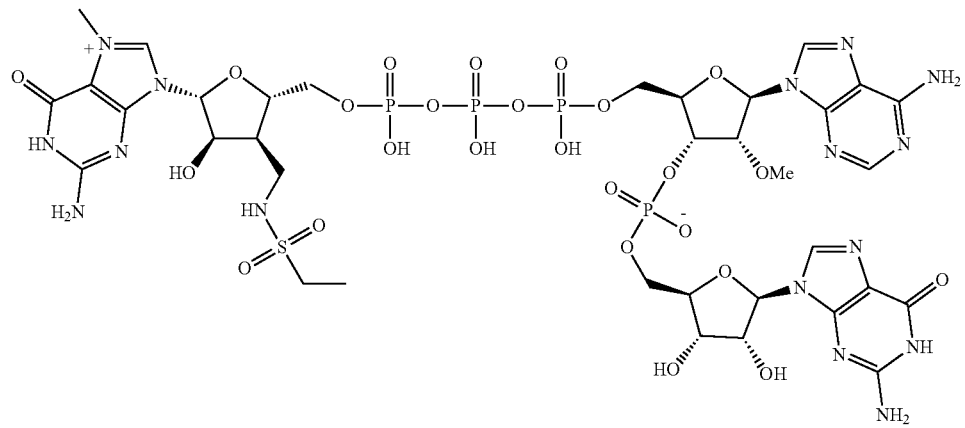
Compound 648
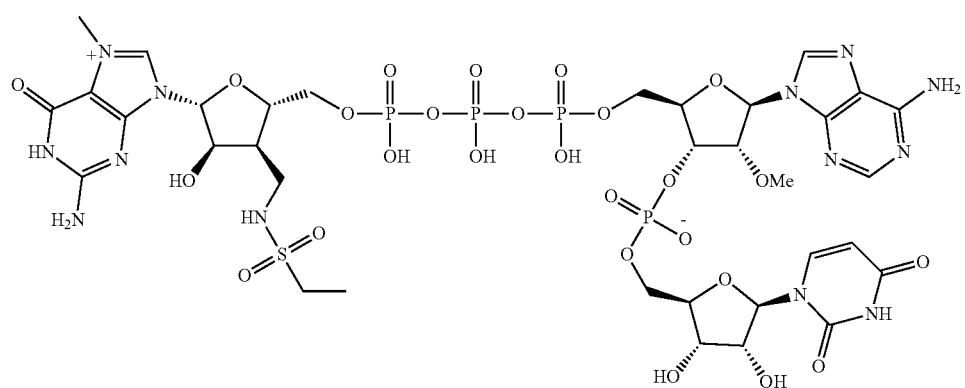

Compound 649
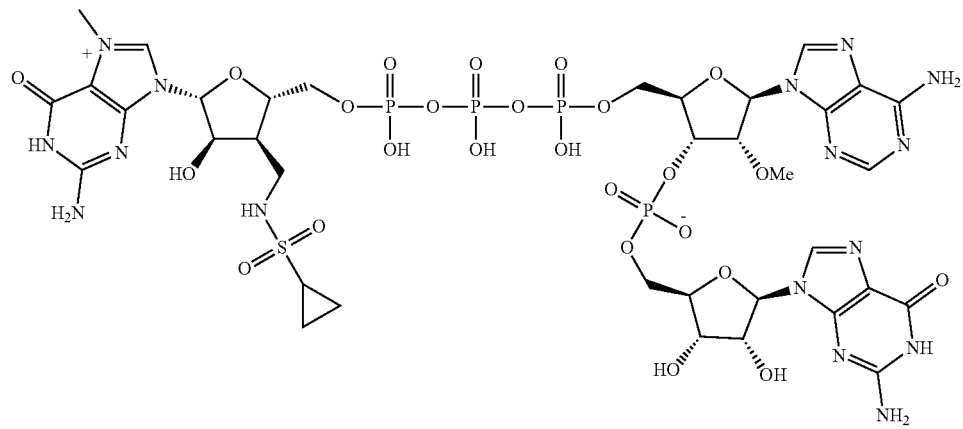
Compound 650
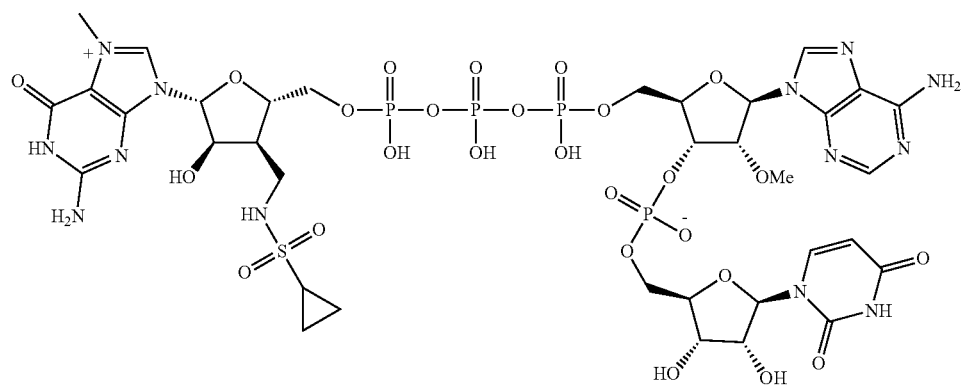
Compound 651
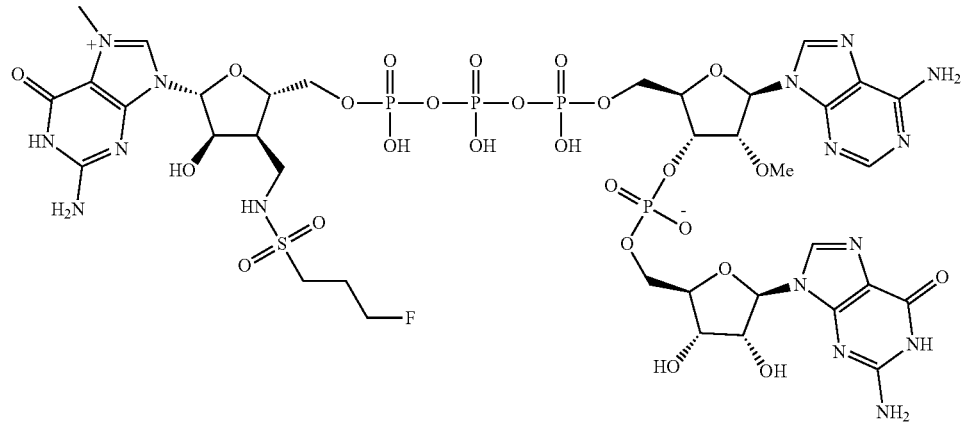
Compound 652
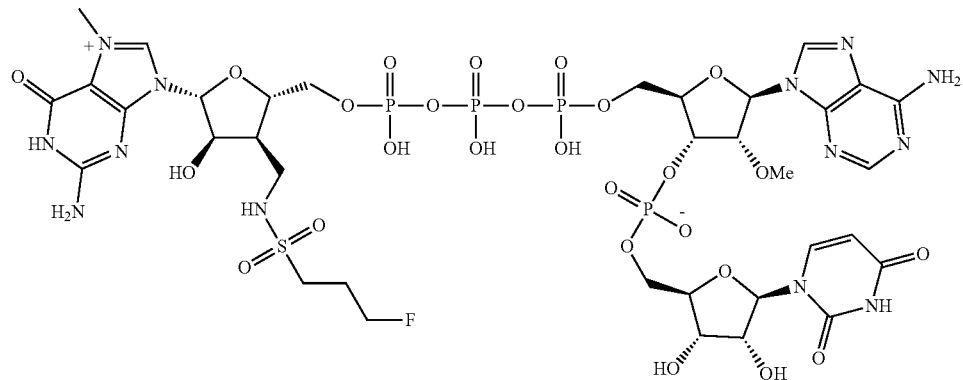

-continued
Compound 653
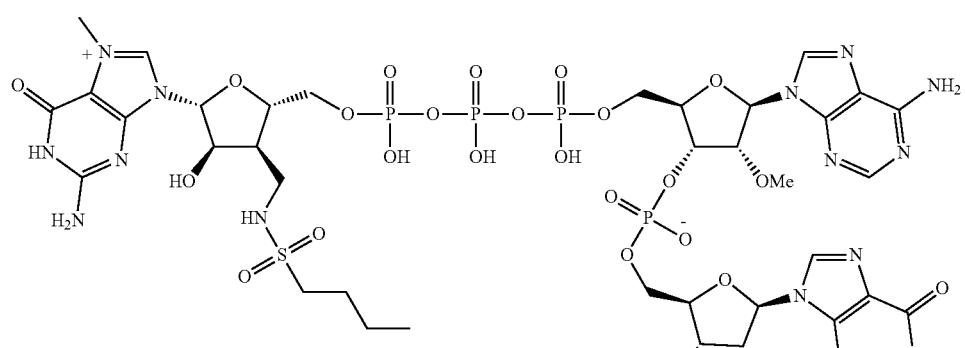
Compound 654
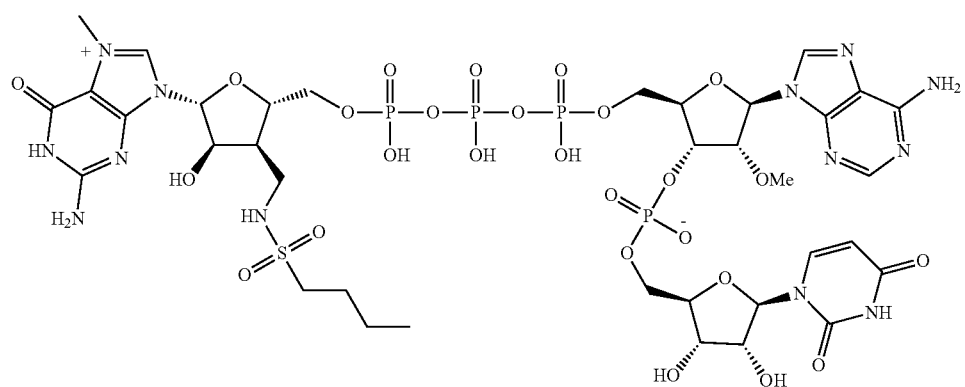
Compound 655
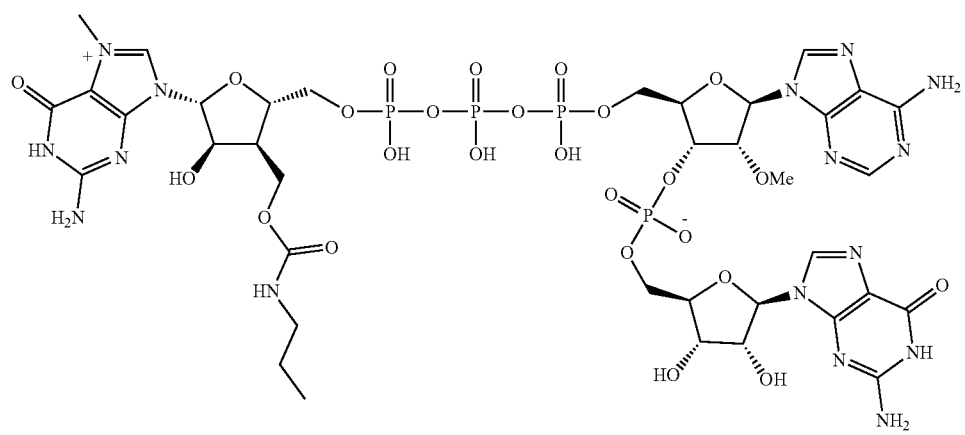
Compound 656
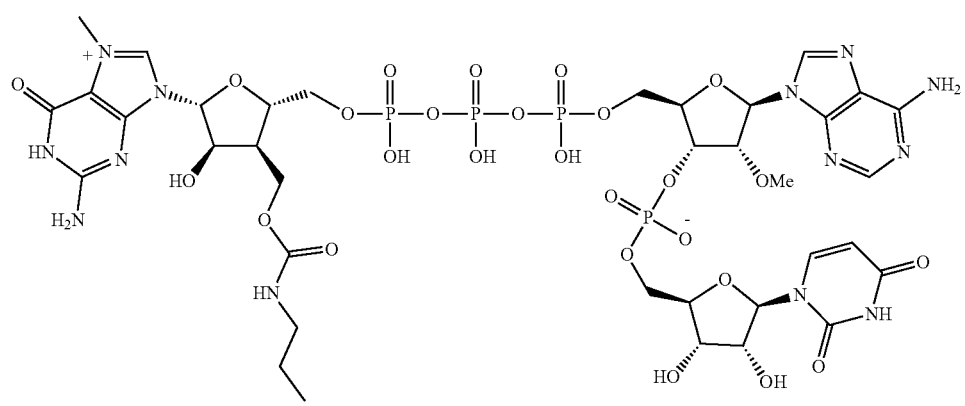

-continued
Compound 657
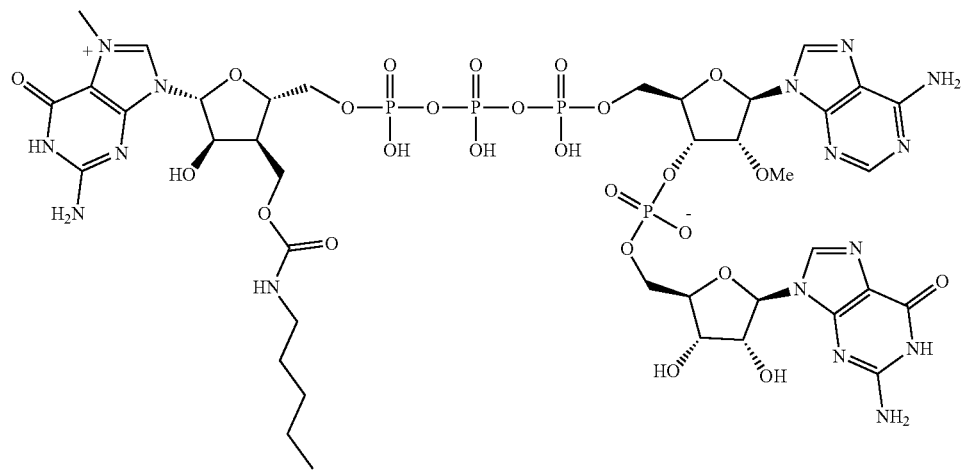
Compound 658
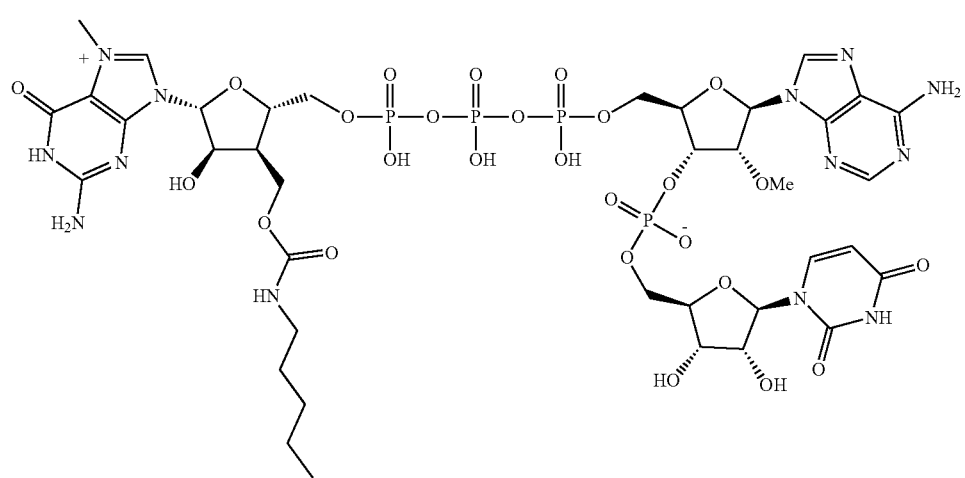
Compound 659
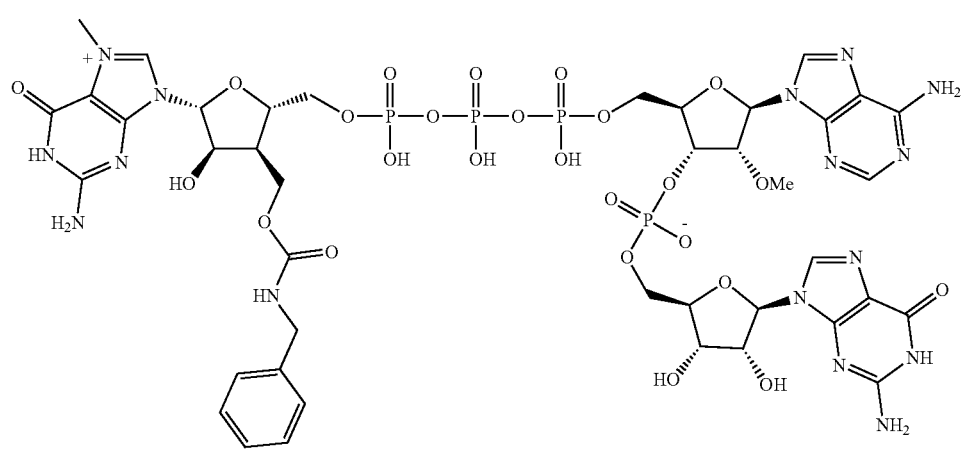

Compound 660
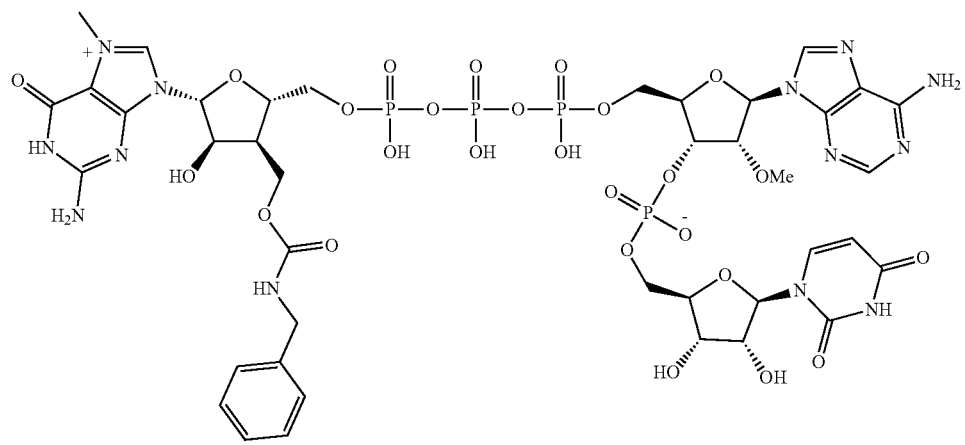
Compound 661
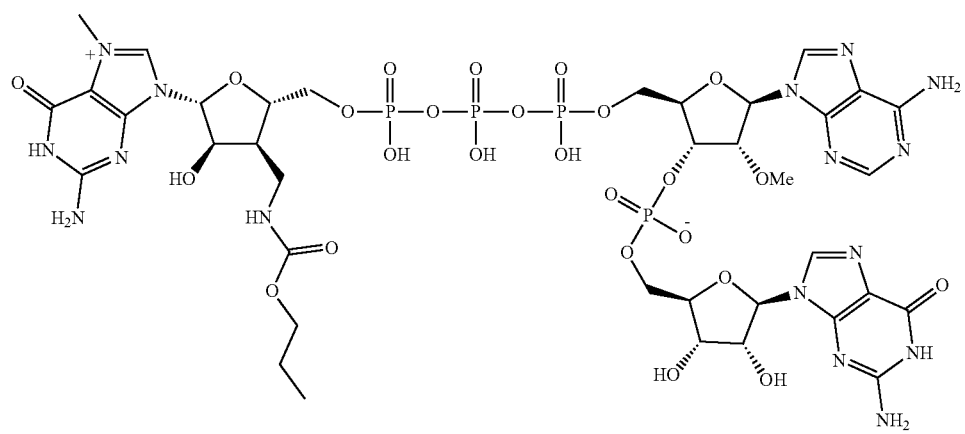
Compound 662
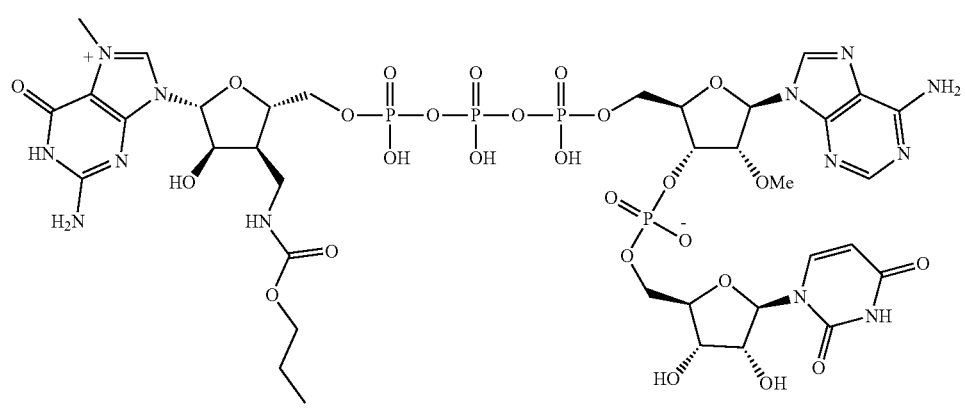

-continued
Compound 663
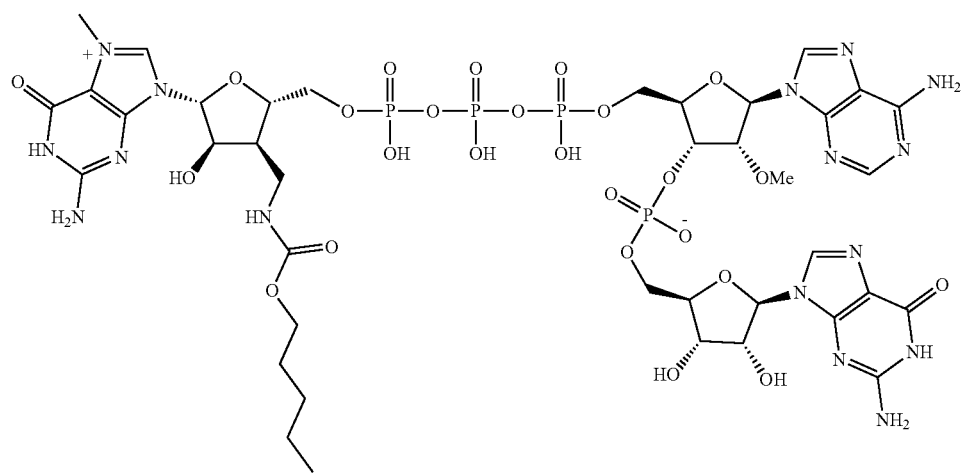
Compound 664
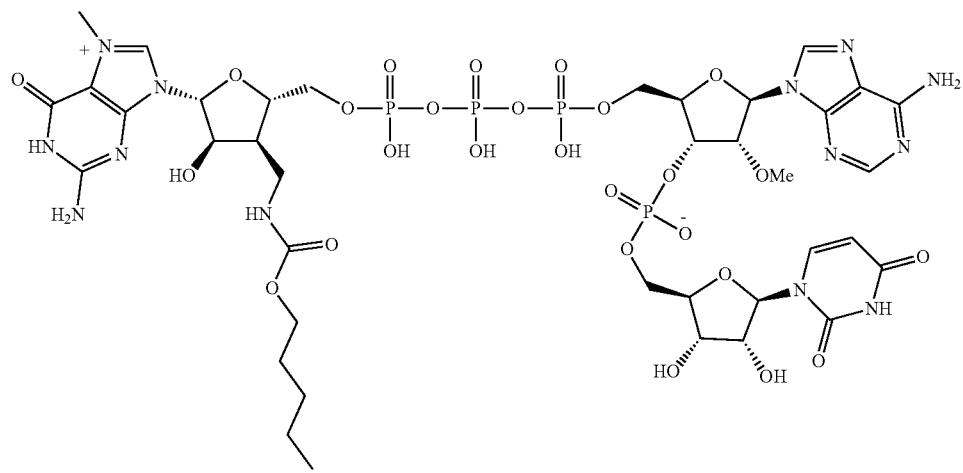
Compound 665
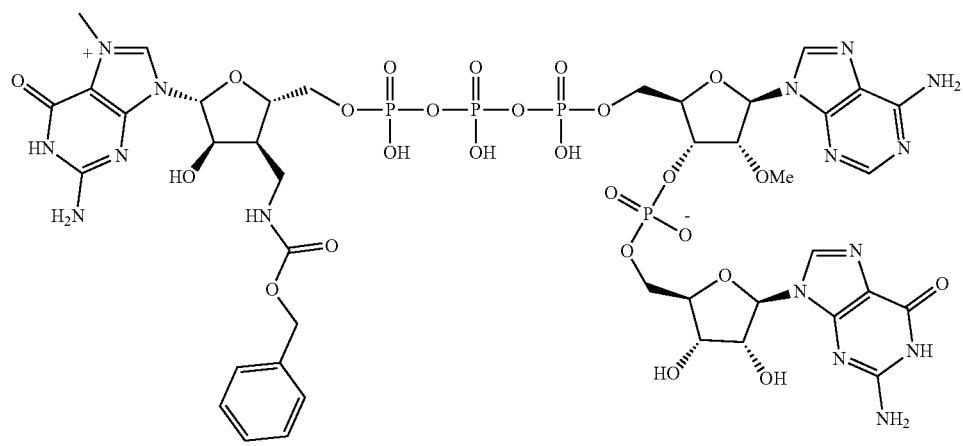

Compound 666
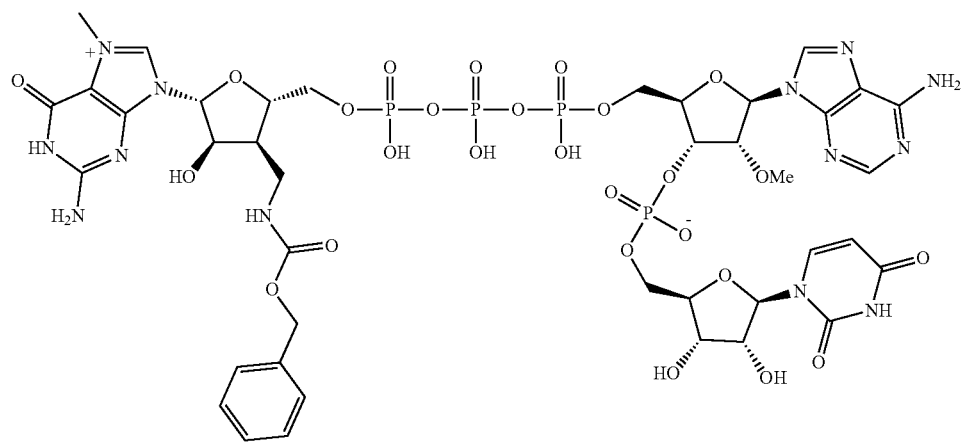
Compound 667
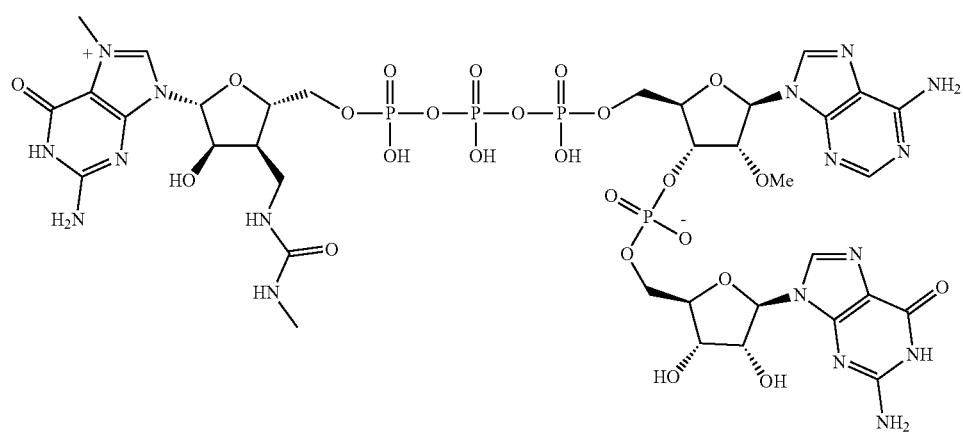
Compound 668
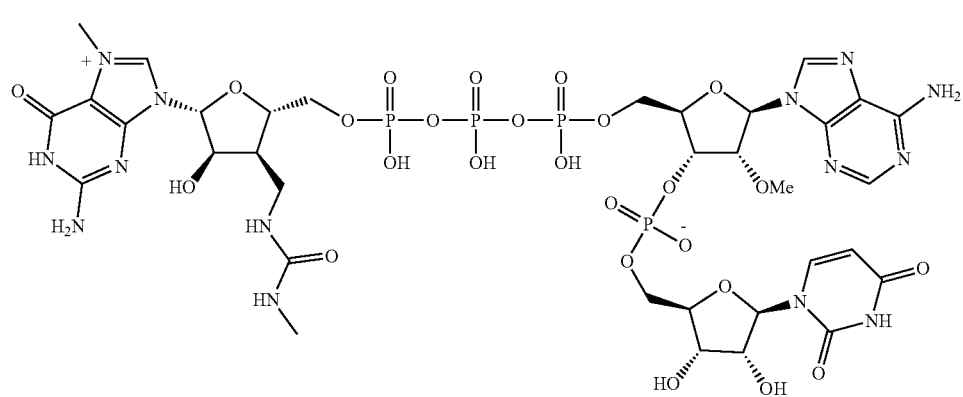

-continued
Compound 669
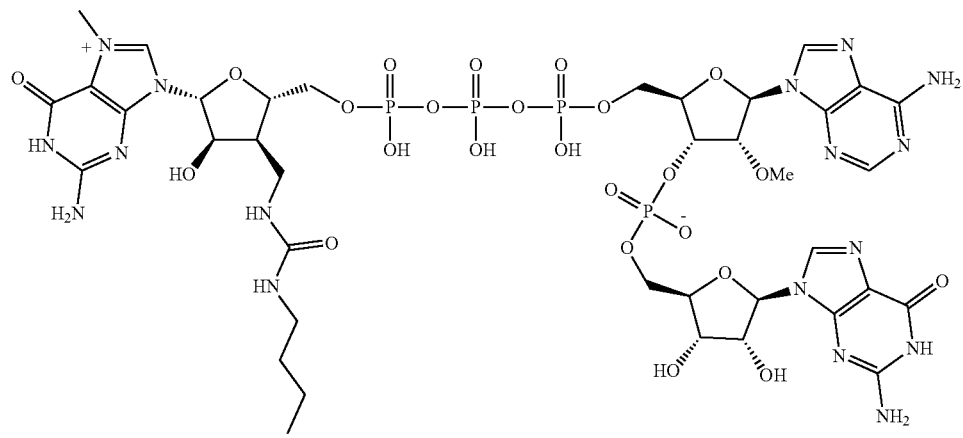
Compound 670
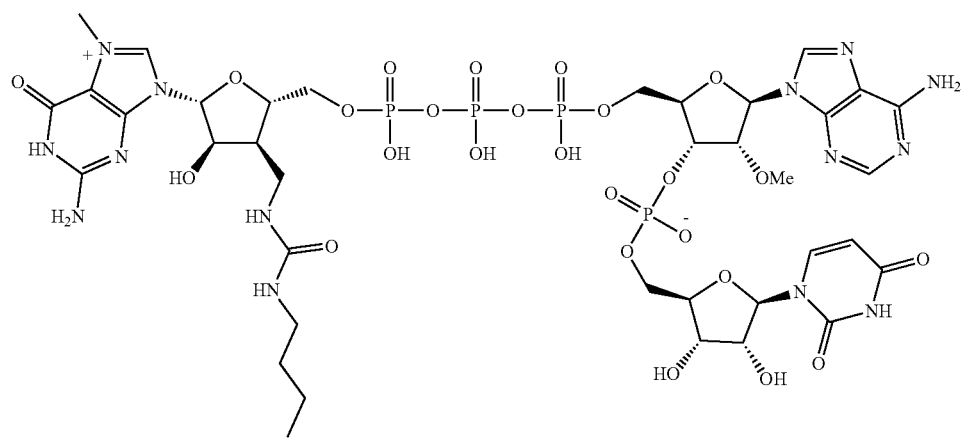
Compound 671
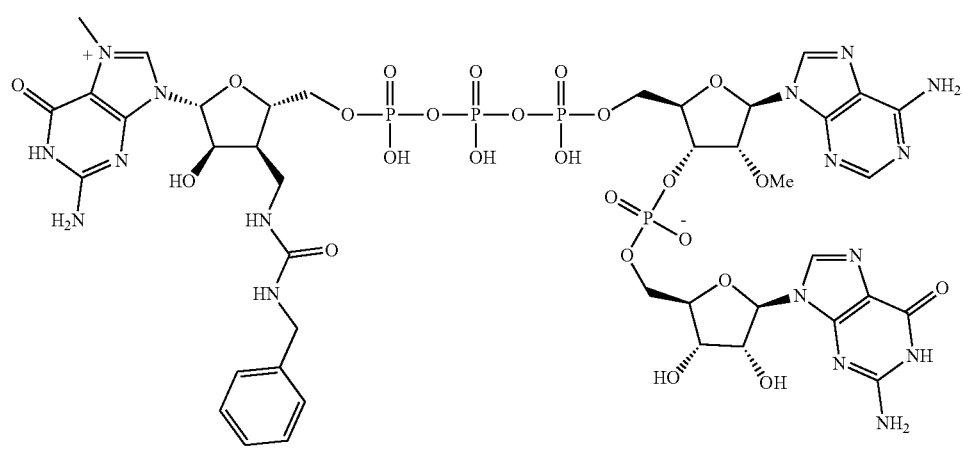

-continued

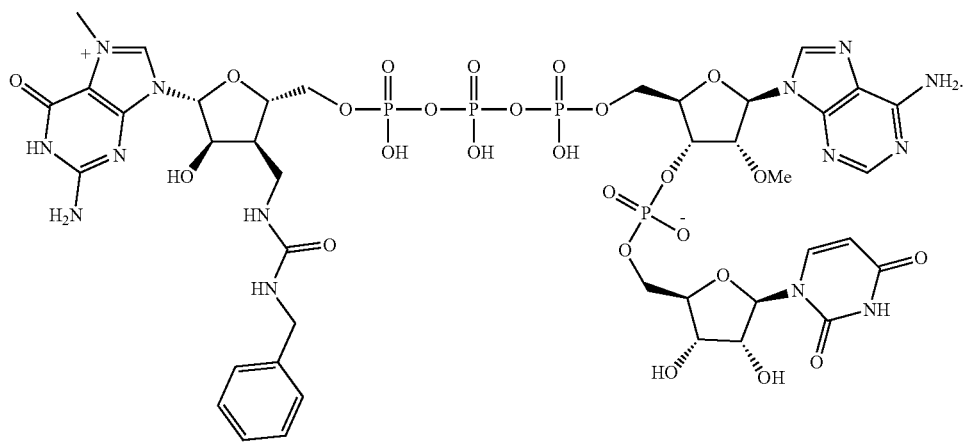

Compound 672

25. A co-transcription reagent comprising the compound of claim 24 for capping an RNA co-transcript in vitro.

26. An RNA molecule comprising a 5'-cap structure with the formula of IV-AC or a pharmaceutically acceptable salt,

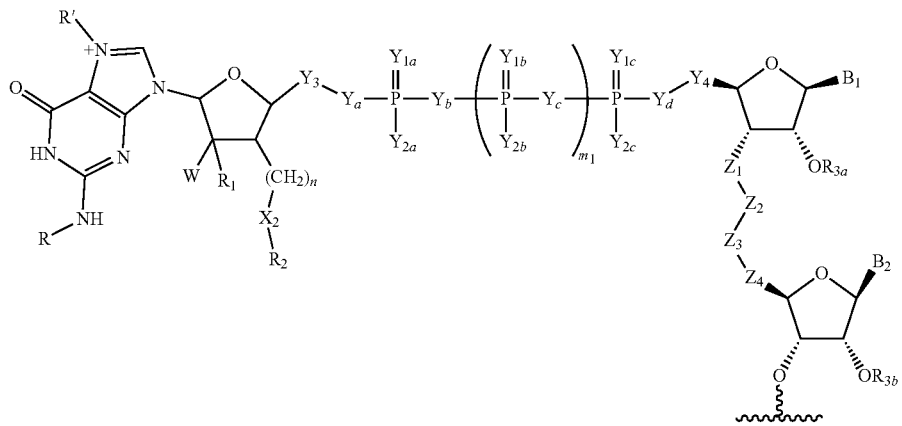

IV-AC wherein: $X_2$ is $CONR_4$, $NR_4CO$, $NR_4CO_2$, $NR_4CONR_4$, or $SO_2NR_4$;
R' is $C_1$-$C_6$ alkyl, $C_2$-$C_6$ alkenyl, $C_2$-$C_6$ alkynyl, or benzyl;
$X_3$ is O;
R is H, $C_1$-$C_6$ alkyl, $C_2$-$C_6$ alkenyl, $C_2$-$C_6$ alkynyl, or $C_3$-$C_6$ cycloalkyl;
$R_1$ is H;
$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, phenyl, benzyl, halobenzyl, CN, or $N_3$;
each of $R_{3a}$ and $R_{3b}$ is independently selected from H, $C_1$-$C_4$ alkyl, or $C_1$-$C_4$ haloalkyl;
W is $OR_4$;
each of $Y_a$, $Y_b$, $Y_c$, and $Y_d$ is independently selected from O, S, $CH_2$, $CCl_2$, $CF_2$, or NH;
each of $Y_{1a}$, $Y_{1b}$, and $Y_{1c}$ is independently selected from O, or S;
each of $Y_{2a}$, $Y_{2b}$, and $Y_{2c}$ is independently selected from OH, or SH;
each of $Y_3$ and $Y_4$, is independently selected from $CH_2$, or O;

$Z_1$ is O, $CH_2$, S, or $NR_6$;
$Z_2$ is $CHR_7$, CO, PO(OH), or PO(SH);
$Z_3$ is O, $NR_6$, or $CHR_7$;
$Z_4$ is $CH_2$;
each of $B_1$ and $B_2$ is independently selected from natural pyrimidine base, or natural purine base;
$R_4$ is H, $C_1$-$C_4$ alkyl, $C_2$-$C_4$ alkenyl, or $C_2$-$C_4$ alkynyl;
$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;
$R_7$ is H, $C_1$-$C_4$ alkyl, $C_2$-$C_4$ alkenyl, or $C_2$-$C_4$ alkynyl;
$R_6$ is H, or $C_1$-$C_4$ alkyl;
$R_9$ is H;
$m_1$ is 1, 2, or 3; and
n is 1, 2, or 3.

27. A pharmaceutical composition, comprising the RNA molecule of claim 26, and a pharmaceutically acceptable carrier.

28. An RNA molecule comprising a 5'-cap structure with the formula of VI-5C or VI-6C, or a pharmaceutically acceptable salt,

VI-5C

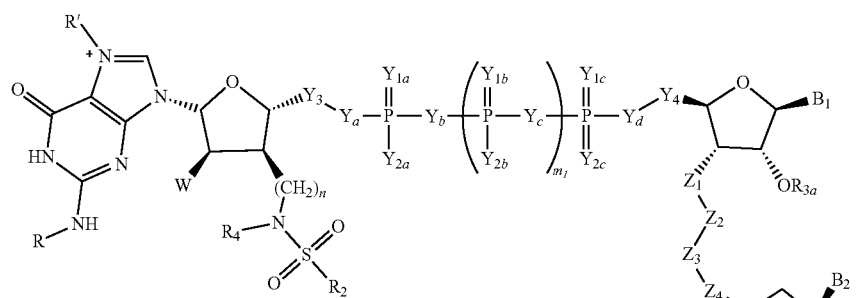

VI-6C

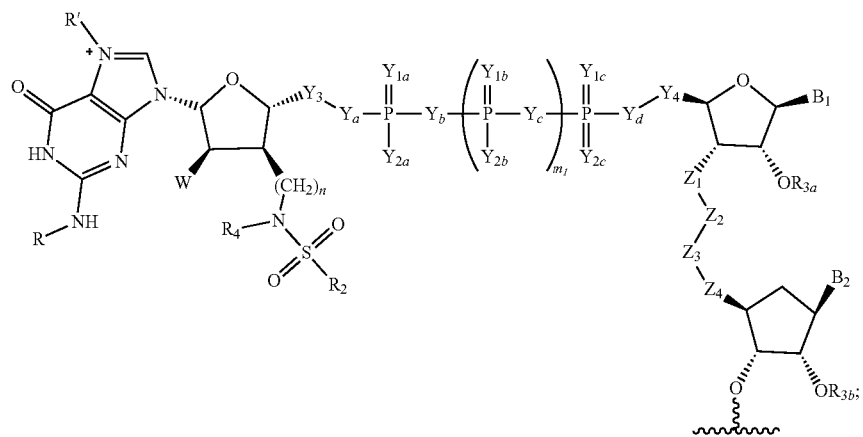

wherein, R' is $C_1$-$C_6$ alkyl, $C_2$-$C_6$ alkenyl, $C_2$-$C_6$ alkynyl, or benzyl;

R is H, $C_1$-$C_6$ alkyl, $C_2$-$C_6$ alkenyl, $C_2$-$C_6$ alkynyl, or $C_3$-$C_6$ cycloalkyl;

$R_2$ is H, $C_1$-$C_8$ alkyl, $C_2$-$C_8$ alkenyl, $C_2$-$C_8$ alkynyl, $R_5$-substituted $C_1$-$C_8$ alkyl, $R_5$-substituted $C_2$-$C_8$ alkenyl, $R_5$-substituted $C_2$-$C_8$ alkynyl, phenyl, benzyl, halobenzyl, or CN;

each of $R_{3a}$ and $R_{3b}$ is independently selected from H, $C_1$-$C_4$ alkyl, or $C_1$-$C_4$ haloalkyl;

W is $OR_4$;

each of $Y_a$, $Y_b$, $Y_c$, and $Y_d$ is independently selected from O, S, $CH_2$, $CCl_2$, $CF_2$, or NH;

each of $Y_{1a}$, $Y_{1b}$, and $Y_{1c}$ is independently selected from O, or S;

each of $Y_{2a}$, $Y_{2b}$, and $Y_{2c}$ is independently selected from OH, or SH;

each of $Y_3$ and $Y_4$, is independently selected from $CH_2$, or O;

$Z_1$ is O, $CH_2$, S, or $NR_6$;

$Z_2$ is $CHR_7$, CO, PO(OH), or PO(SH);

$Z_3$ is O, $NR_6$, or CH $R_7$;

$Z_4$ is $CH_2$;

each of $B_1$ and $B_2$ is independently selected from natural pyrimidine base, or natural purine base;

$R_4$ is H, $C_1$-$C_4$ alkyl, $C_2$-$C_4$ alkenyl, or $C_2$-$C_4$ alkynyl;

$R_5$ is $C_1$-$C_4$ alkyl, $C_2$-$C_5$ alkenyl, $C_2$-$C_5$ alkynyl, $C_1$-$C_4$ haloalkyl, $C_2$-$C_5$ haloalkenyl, $C_2$-$C_5$ haloalkynyl, $OR_7$, halogen, CN, pyridine, pyrimidine, or morpholine;

$R_6$ is H, or $C_1$-$C_4$ alkyl;

$R_7$ is H, $C_1$-$C_4$ alkyl, $C_2$-$C_4$ alkenyl, or $C_2$-$C_4$ alkynyl;

n is 1, or 2, or 3; and $m_1$ is 1, or 2.

29. A pharmaceutical composition, comprising the RNA molecule of claim 28, and a pharmaceutically acceptable carrier.

* * * * *